US012612651B2

(12) United States Patent
Gao et al.

(10) Patent No.: US 12,612,651 B2
(45) Date of Patent: Apr. 28, 2026

(54) BASE EDITOR AND THE USE THEREOF

(71) Applicants: INSTITUTE OF GENETICS AND DEVELOPMENTAL BIOLOGY, CHINESE ACADEMY OF SCIENCES, Beijing (CN); Qi Biodesign Biotechnology Company Limited, Beijing (CN)

(72) Inventors: Caixia Gao, Beijing (CN); Kevin T. Zhao, Beijing (CN); Yu Sun, Beijing (CN); Jiacheng Hu, Beijing (CN); Boshu Li, Beijing (CN)

(73) Assignees: Institute of Genetics and Developmental Biology, Chinese Academy of Sciences, Beijing (CN); Qi Biodesign Biotechnology Company Limited, Beijing (CN)

( * ) Notice: Subject to any disclaimer, the term of this patent is extended or adjusted under 35 U.S.C. 154(b) by 0 days.

(21) Appl. No.: 18/970,575

(22) Filed: Dec. 5, 2024

(65) Prior Publication Data

US 2025/0101469 A1      Mar. 27, 2025

Related U.S. Application Data

(63) Continuation of application No. PCT/CN2023/135588, filed on Nov. 30, 2023.

(30) Foreign Application Priority Data

Dec. 15, 2022  (CN) ......................... 202211613160.4
Aug. 14, 2023  (CN) ......................... 202311017698.3

(51) Int. Cl.
| | |
|---|---|
| *C12N 9/22* | (2006.01) |
| *C12N 9/78* | (2006.01) |
| *C12N 15/11* | (2006.01) |
| *C12N 15/90* | (2006.01) |

(52) U.S. Cl.
CPC ............. *C12N 15/907* (2013.01); *C12N 9/22* (2013.01); *C12N 9/78* (2013.01); *C12N 15/11* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 2008/0131962 | A1* | 6/2008 | Miller ...................... | C12N 9/22 536/23.4 |
| 2019/0169597 | A1* | 6/2019 | Astrakhan .............. | C12N 15/11 |
| 2020/0063114 | A1* | 2/2020 | Fauser ................... | C12N 15/63 |
| 2020/0140842 | A1 | 5/2020 | Young et al. | |
| 2021/0198330 | A1 | 7/2021 | Liu et al. | |
| 2022/0127622 | A1 | 4/2022 | Evans et al. | |

FOREIGN PATENT DOCUMENTS

| | | | |
|---|---|---|---|
| CN | 113151229 | A | 7/2021 |
| CN | 113774085 | A | 8/2023 |
| KR | 1020090108494 | A | 10/2010 |
| WO | 2017070633 | A2 | 4/2017 |
| WO | 2019084062 | A1 | 5/2019 |
| WO | 2020160517 | A1 | 8/2020 |
| WO | WO-2022055750 | A1 * | 3/2022 ............... A01H 1/10 |

OTHER PUBLICATIONS

Vanamee et al., FokI requires two specific DNA sites for cleavage. J. Mol. Bio. (2001), 309: 69-78 (Year: 2001).*
Rees and Liu, Base editing: precision chemistry on the genome and transcriptome of living cells. Nature Reviews Genetics (2018), 19: 770-788 (Year: 2018).*
Wray and Goddard, Multi-locus models of genetic risk of disease. Genome Medicine (2010), 2:10, pp. 1-13 (Year: 2010).*
Porto et al., Base editing: advances and therapeutic opportunities. Nature Reviews Drug Discovery (2020), 19: 839-859 (Year: 2020).*
Komor et al., Programmable editing of a target base in genomic DNA without double-stranded DNA cleavage. Nature (2016), 533: 420-424 (Year: 2016).*
Bregenhorn and Jiricny, Biochemical characterization of a cancer-associated E109K missense variant of human exonuclease 1. Nucleic Acids Research (2014), 42: 7096-7103 (Year: 2014).*
Keijzers et al., Human exonuclease 1 (EXO1) regulatory functions in DNA replication with putative roles in cancer. International Journal of Molecular Sciences (2019), 20:74, 1-15 (Year: 2019).*
Koblan et al., Efficient C• G-to-G• C base editors developed using CRISPRi screens, target-library analysis, and machine learning. Nature Biotechnology (2021), 39: 1414-1425 and Supplemental Material (Year: 2021).*
Zong et al., Precise base editing in rice, wheat and maize with a Cas9-cytidine deaminase fusion. Nature Biotechnology (2017), 35: 438-440 (Year: 2017).*

(Continued)

*Primary Examiner* — Catherine Konopka
(74) *Attorney, Agent, or Firm* — McDonnell Boehnen Hulbert & Berghoff LLP

(57) ABSTRACT

The present disclosure discloses a base editor and the use thereof. The present disclosure provides a nucleic acid base editor, specifically a base editor which is not based on CRISPR technology. The base editor comprises a sequence-specific DNA binding protein, a nickase, an exonuclease and a base-specific deaminase. This base editor is single-strand-specific, and as compared with conventional base editors, the base editor of the present disclosure has wide applicability in cells and is capable of functioning in the nucleus as well as in mitochondrial DNA and/or chloroplast DNA. This base editor has the characteristics of achieving base editing products with high purity and resulting in few indel byproducts while realizing efficient base editing, which is conducive to being used as an efficient and safe gene editing tool.

20 Claims, 81 Drawing Sheets
Specification includes a Sequence Listing.

(56)           References Cited

OTHER PUBLICATIONS

Hu et al., Strand-preferred base editing of organellar and nuclear genomes using CyDENT. Nature Biotechnology (2024), 533: 420-424 (Year: 2023).*

Hu et al., A barley stripe mosaic virus-based guide RNA delivery system for targeted mutagenesis in wheat and maize. Molecular Plant Pathology (2019), 20: 1463-1474 (Year: 2019).*

Hua et al., Improvement of base editors and prime editors advances precision genome engineering in plants. Plant Physiology (2022), 188:1795-1810 (Year: 2022).*

Mok et al., A bacterial cytidine deaminase toxin enables CRISPR-free mitochondrial base editing. Nature (2020), 583: 631-637 and Online Methods and Supplemental Material (Year: 2020).*

Kaufman and Van Houten, POLB: A new role of DNA polymerase beta in mitochondrial base excision repair. DNA Repair (2017), 60; A1-A5 (Year: 2017).*

Jinek et al., A programmable dual-RNA-guided DNA endonuclease in adaptive bacterial immunity. Science (2012), 337: 816-821 (Year: 2012).*

Mali et al., CAS9 transcriptional activators for target specificity screening and paired nickases for cooperative genome engineering. Nature Biotechnology (2013), 31: 833-838 (Year: 2013).*

NP_036037.1, three prime repair exonuclease 2 [Mus musculus], https://www.ncbi.nlm.nih.gov/protein/6755877, [retrieved Jul. 14, 2025] (Year: 2021).*

Wu et al., TALE nickase mediates high efficient targeted transgene integration at the human multi-copy ribosomal DNA locus. Biochemical and Biophysical Research Communications (2014), 446: 261-266 (Year: 2014).*

Mariano et al., Highly efficient genome editing via 2A-coupled co-expression of two TALEN monomers. BMC Research Notes (2014), 7:628 (Year: 2014).*

Wang et al., Enhanced base editing by co-expression of free uracil DNA glycosylase inhibitor. Cell Research (2017) 27:1289-1292 (Year: 2017).*

Zhang et al., The Barley stripe mosaic virus γb protein promotes chloroplast-targeted replication by enhancing unwinding of RNA duplexes. PLOS Pathogens (2017), 13(4): 31006319 (Year: 2017).*

Jiang et al., Advances in understanding multifunctionality of Barley stripe mosaic virus γb protein. PLoS Pathogens (2025), 21(7):e1013299 (Year: 2025).*

Cho et al. "Targeted A-to-G base editing in human mitochondrial DNA with programmable deaminases", Cell 185(10):1764-1776. e12, (May 2022).

Gaudelli et al. "Programmable base editing of A•T to G•C in genomic DNA without DNA cleavage", Nature 551(7681):464-471, (Nov. 2017).

Huang et al. "Discovery of deaminase functions by structurebased protein clustering", Cell 186(15):3182-3195.e14, (Jul. 2023).

Komor et al. "Programmable editing of a target base in genomic DNA without double-stranded DNA cleavage", Nature 533(7603):420-4, (May 2016).

Lei et al. "Mitochondrial base editor induces substantial nuclear off-target mutations", Nature 606: 804-811, (May 2022).

Mok et al. "A bacterial cytidine deaminase toxin enables CRISPR-free mitochondrial base editing", Nature 583(7817):631-637, (Jul. 2020).

Newby et al. "Base editing of haematopoietic stem cells rescues sickle cell disease in mice", Nature 595(7866):295-302, (Jul. 2021).

Zhao et al. "Genome editing technology and future development", Chinese Bulletin of Life Sciences 33(12):1462-1468, (Dec. 2021). [English abstract provided].

International Search Report for PCT/CN2023/135588 mailed Mar. 6, 2024. [English translation provided].

* cited by examiner

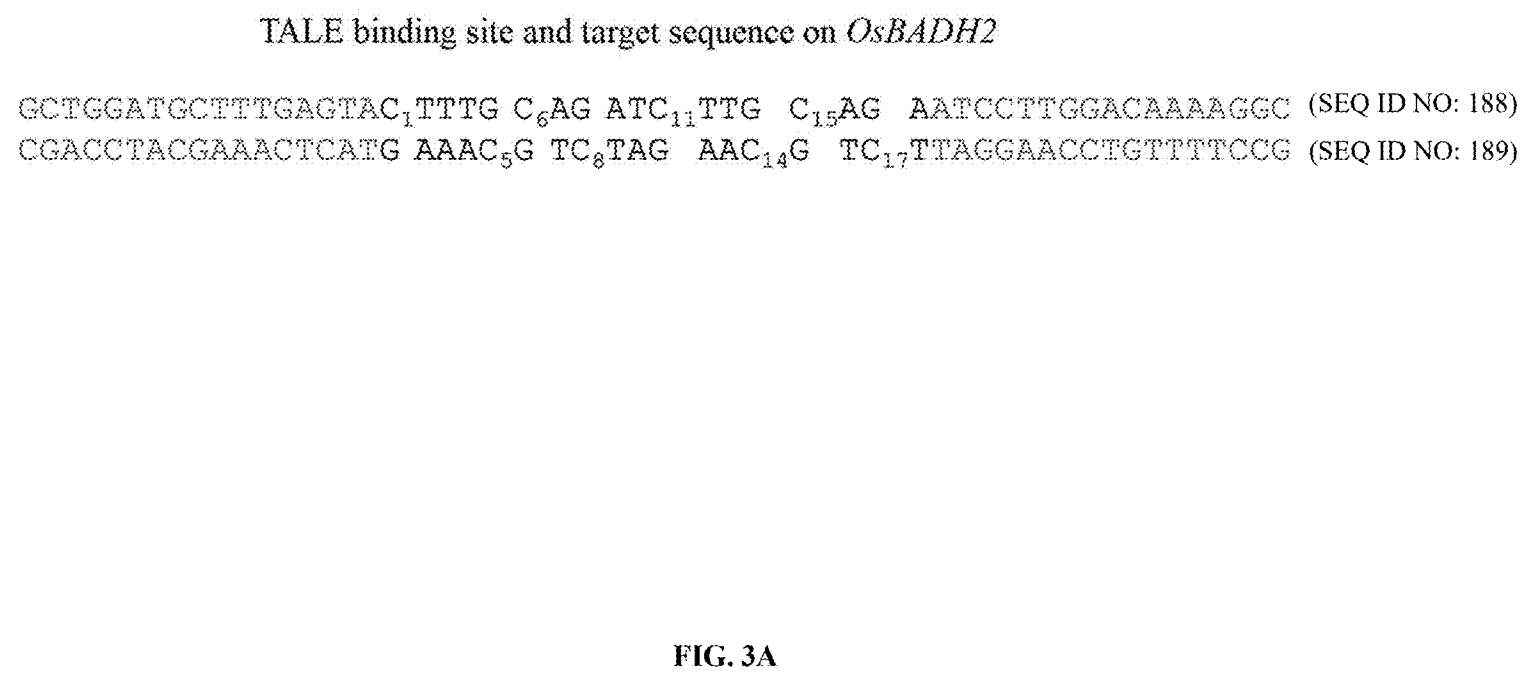

TALE binding site and target sequence on *OsBADH2*

GCTGGGATGCTTTGAGTAC$_1$TTTG C$_6$AG ATC$_{11}$TTTG C$_{15}$AG AATCCTTGGACAAAAGGC (SEQ ID NO: 188)
CGACCTACGAAACTCATG AAAC$_5$G TC$_8$TAG AAC$_{14}$G TC$_{17}$TTAGGAACCTGTTTTCCG (SEQ ID NO: 189)

FIG. 3A

OsDEP1 strand A  GCAAAAGACCAAGGTGCCTC₁AATTG₆TTC₃TTG₁₂C₁₃AG₁₅C₁₄TC₁₆ATGCTGCGACGAGCC     (SEQ ID NO: 190)

strand B  CGTTTTCTGGTTCCACGGAG TTAAC AAG AAC G TC G AG TACGACGCTGCTCGG     (SEQ ID NO: 191)

FIG. 4A

Binding sites and spacer sequences of TALE-L and TALE-R at the *OsCKX2* target site (SEQ ID NO: 192)

strand A    CCTGGACCGGTCCACGAC$C_2$GGC$_5$G AGC$_9$TC$_{11}$AAG  $C_{15}$TC$_{17}$C$_{18}$GCGCCGCCGCGGGGCTCTGGG strand B    GGACCTGGCGCAGGTGCTGC$_3$C$_4$GC$_6$TC$_8$GAG  TTC$_{14}$G  AG  G  CGCGGCGGCCCCGAGACGCC
(SEQ ID NO: 193)

FIG. 5A

OsCKX2

CCTGGACCGGCGTCCACGA$_1$CGGCGA$_7$GCT$_{10}$CA$_{12}$A$_{13}$GCTCCGGCGCCGGGGCTCTGGG (SEQ ID NO: 192)

GGACCTGGCCGCAGGTGCT GCCCGCT CGA GT T CGAGGCCGCCCCGAGACCC (SEQ ID NO: 193)

Binding sites and spacer sequences of TALE-L and TALE-R at the *OsDEP1* target site GCAAAAGACCAAGGTGCCT C$_1$AATTGTTCC$_3$TTGCC$_{13}$AGCC$_{16}$TC$_{18}$ ATCCTGCGACGAGCC (SEQ ID NO: 190)

CGTTTTCTGGTTCCACGGA  G TTAACAAG AACG TCG AG   TACGACGCTGCTCGG (SEQ ID NO: 191)

FIG. 14

Human *ND6*

TALE-L binding                                                                    (SEQ ID NO: 194)

5′ CGCCTGACCCCCATG C₁C₂TC₄AG G ATAC₁₁TC₁₃C₁₄T CAATAGCCATCGCTGTA

3′ GGGGACTGGGGGTAC G G AG TC₆C₇TATG AG G A GTTATCGGTAGCGACAT

TALE-R binding                                                                    (SEQ ID NO: 195)

*SIRT6* strand A  TACGGGGGGGGCTGTCGCCGTACGGCGGACAAGGGCAAGTGCGGCCTCCCGG  (SEQ ID NO: 198)

strand B  ATGGCCGCCCGACAGCGGCATGCCGCCTGTTCCCGTTCACGCCGGAGGGGCC  (SEQ ID NO: 199)

*SIRT6*

FIG. 21

TALE-L3

TALE-L2

TALE-L1

GACCCCCATGCCTCAGGATACTCCTCAATAG CCATCGCTGCTGTAGTATATCCAA (SEQ ID NO: 202)

CTGGGGGTACGGAGTCCTATGAGGAGTTAT GGTAGCGACATCATATAGGTT (SEQ ID NO: 203)

TALE-R1

TALE-R2

FIG. 30

BASE EDITOR AND THE USE THEREOF

CROSS-REFERENCE TO RELATED APPLICATION

The present application is a continuation of International Application. No. PCT/CN2023/135588, filed on Nov. 30, 2023, which claims priority to Chinese patent application 202211613160.4, filed on Dec. 15, 2022, and Chinese patent application 202311017698.3, filed on Aug. 14, 2023, the entire contents of which including the appendixes are each herein incorporated by reference.

SEQUENCE LISTING

The instant application contains a Sequence Listing that has been submitted electronically and is hereby incorporated by reference in its entirety. The Sequence Listing was created on Dec. 5, 2024, is named "24-1276-US-CON_SequenceListing.xml," and is 299,517 bytes in size.

TECHNICAL FIELD

The present disclosure relates to the field of gene editing, specifically relates to a nucleic acid base editor, and particularly relates to a base editor comprising a sequence-specific DNA binding protein, a nickase, an exonuclease and a base-specific deaminase, and the use thereof.

BACKGROUND

Mutations in genome and mitochondrial DNA are known to lead to various genetic diseases (Newby et al., 2021, Nature 595: 295-302), and correcting these mutations is expected to result in effective treatment or amelioration of some severe disease. In plants, some important agronomic traits are associated with the single nucleotide variation (SNV) occurring in the plant genome, plant mitochondrial genome or plant chloroplast genome; and introducing these SNVs into plants could promote plant performance, molecular breeding, restoring gene function to alleviate disease states, and the like.

Genome editing has shown great potential for genome modification; among the genome editing tools, base editing could achieve targeted base substitution without introducing DNA double-strand breaks (DSB) so as to realize more precise and more accurate editing (Gaudelli et al., 2017, Nature 551: 464-471; Komor et al., 2016, Nature 533: 420-424), thus holding great promise for disease treatment and crop improvement.

Cytosine base editor (CBE) (Komor et al., 2016, Nature 533: 420-424) and adenine base editor (ABE) (Gaudelli et al., 2017, Nature 551: 464-471) are the most widely used base editors. In the CBE system, CRISPR-Cas9 nickase (nCas9) with nicking activity on single-stranded DNA is guided to the target dsDNA by sgRNA, and the sgRNA-targeting strand is nicked by nCas9 to form an R-loop. Subsequently, the single-strand-specific cytidine deaminase converts cytosine (C) to uracil (U) within an approximately five-nucleotide window in the single-stranded DNA bubble-like structure created by nCas9, U is replaced by T after DNA repair, thereby resulting in the conversion from a C:G base pair to a T:A base pair. In addition, the addition of a uracil glycosylase inhibitor (UGI) with the function of impeding uracil excision and its downstream processes could improve the base editing efficiency and the purity of the product. Cytidine deaminases suitable for the Casmediated CBE systems include but are not limited to APOBEC1, hAID and hAPOBEC3A. Recently, some new deaminase systems have also been found to be suitable for the deaminase of the present disclosure (Huang, J. et al. Discovery of new deaminase functions by structure-based protein clustering. bioRxiv (2023).).

The ABE system is generated by fusing nCas9 to an artificially evolved single-stranded DNA adenosine deaminase TadA (Gaudelli et al., 2017, Nature 551: 464-471). The working principle of ABE is similar to that of CBE, nCas9 would nick the target strand of DNA under the guidance of sgRNA to generate a nick, and the adenosine deaminase TadA converts adenine (A) to inosine (I), which is replaced by G after DNA repair, resulting in the conversion of an A:T base pair to a G:C base pair. However, UGI is not required in the ABE system to improve its editing efficiency or the purity of the product, since no uracil intermediate is involved in the process.

ABE and CBE mentioned above are capable of working efficiently in the nucleus, but they could not work in chloroplasts or mitochondria, since the sgRNA in the CRISPR system could not be transferred into these organelles efficiently.

In 2020, researchers developed a non-CRISPR base editor system that is solely comprised of protein components. This novel base editor system was designated as DdCBE (Mok et al., 2020, Nature 583: 631-637). The core components of DdCBE include a double-stranded DNA cytidine deaminase DddA, which could convert C to U on the double-stranded DNA without the need for CRISPR-Cas9 to create a single-stranded DNA. However, intact DddA has cytotoxicity, therefore, it is split into two halves—DddA-N and DddA-C, which are fused to a pair of TALE proteins separately. DddA-N and DddA-C are guided to the target DNA sequence by the TALE pair and are recombined to restore the cytidine deaminase activity; similar to the CRISPR-based CBE system, this system is also capable of converting a C:G base pair to a T:A base pair; the addition of UGI could improve the base editing efficiency and the purity of the product of DdCBE. Due to the characteristics that the components of the DdCBE system are all protein components, the DdCBE system could not only work in the nucleus, but also could be translocated into chloroplasts and mitochondria to achieve targeted cytosine base editing in chloroplast DNA and mitochondrial DNA.

However, since DddA toxin is a cytidine deaminase, it could merely operate on a cytosine base in the CBE system, but could not operate on an adenine base as required by the ABE system, thus severely limiting its application ranges. In 2022, researchers fused an adenosine deaminase TadA-8e obtained by artificial directed evolution to DdCBE to generate the TALED system, and this system were capable of realizing the base editing of A-to-G conversion (Cho et al., 2022, Cell 185: 1764-1776). In TALED system, the adenosine deaminase TadA-8e is fused to one of the split DddAs, and this combination successfully induces C-to-T base conversion and A-to-G base conversion simultaneously in the mitochondrial DNA. In addition, when the deaminase activity of DddA is inactivated, the TadA-8e-mediated A-to-G base editing remains effective.

Although the DdCBE system and the TALED system have expanded the application range of base editing to mitochondrial DNA and/or chloroplast DNA, there are still some limitations. First, due to the intrinsic double-stranded DNA cytidine deaminase activity of DddA, deamination would occur for the cytosines in the deamination window on both strands, which means that deamination could not merely occur on a selected single strand, and thus would not be safe and precise enough to be used safely. Second, compared to the CBE-mediated base editing and ABE-mediated base editing in the nucleus, the base editing products of DddA contain a relative higher indel frequency, and the resulting products have lower purity. Third, it has been reported that a DddA-based mitochondrial base editor would induce extensive off-target mutations in the nucleus when performing mitochondrial base editing (Lei et al., 2022, Nature 606: 804-811). It is worth noting that most of the off-target mutations are TALE-independent and are caused by DddA. The substantial nuclear off-target mutations would result in significant adverse impact on the safety of using these base editors.

Therefore, there is an urgent need in the art to develop a novel base editor that is single-strand-specific and could function in the nucleus as well as in mitochondrial DNA and/or chloroplast DNA with high product purity.

SUMMARY

In order to solve the above-mentioned technical problems, the present application provides a novel base editor that does not rely on CRISPR technology. This system is single-strand-specific, is capable of functioning in the nucleus as well as in mitochondrial DNA or chloroplast DNA, and could obtain editing products with high purity.

To be specific, the present disclosure provides a novel nucleic acid base editor protein composition, a recombinant expression construct encoding a novel synthetic nucleic acid base editor protein, a genetically engineered cell comprising one or more recombinant expression constructs encoding novel synthetic nucleic acid base editor proteins, as well as the application methods of the above-mentioned novel nucleic acid base editor protein, recombinant expression construct and genetically engineered cell.

The nucleic acid base editor of the present disclosure comprises: a sequence-specific DNA binding protein; a nickase; an exonuclease and a base-specific deaminase. In certain embodiments, the nucleic acid base editor further comprises a uracil glycosylase inhibitor. In a specific embodiment, the sequence-specific DNA binding protein, the nickase, the exonuclease and the base-specific deaminase form one or more fusion proteins. In an advantageous embodiment of the nucleic acid base editor provided by the present disclosure, the sequence-specific DNA binding protein is selected from a TALE protein, a ZFA protein, a Cas protein and a meganuclease. In certain specific embodiments, the sequence-specific DNA binding protein is preferably a TALE protein. In a specific embodiment of the nucleic acid base editor of the present disclosure, the nickase is an FokI nickase. In the nucleic acid base editor of the present disclosure, the deaminase is selected from a cytidine-specific deaminase and an adenosine-specific deaminase. In an advantageous embodiment of the nucleic acid base editor of the present disclosure comprising a cytidine-specific deaminase, the cytidine deaminase is selected from hAPOBEC3A, rAPOBEC1, hAID, pmCDAT and Sdd deaminase. In an advantageous embodiment of the nucleic acid base editor of the present disclosure comprising an adenosine-specific deaminase, the adenosine deaminase is TadA-8e.

In another preferred embodiment, the composition provided by the present disclosure comprises one or more recombinant expression constructs encoding a sequence-specific DNA binding protein, a nickase, an exonuclease and a base-specific deaminase, wherein each of the sequence-specific DNA binding protein, the nickase, the exonuclease and the base-specific deaminase is capable of being expressed in a cell. In certain embodiments, these nucleic acid compositions further comprise a recombinant expression construct encoding a uracil glycosylase inhibitor. In a specific embodiment, this composition comprises one or more recombinant expression constructs encoding a sequence-specific DNA binding protein, a nickase, an exonuclease and a base-specific deaminase as a fusion protein, wherein the fusion protein comprised thereof is capable of being expressed in a cell. In an advantageous embodiment of the nucleic acid base editor provided herein, the sequence-specific DNA binding protein is selected from a TALE protein, a ZFA protein, a Cas protein and a meganuclease, and in certain specific embodiments, the sequence-specific DNA binding protein is a TALE protein. In a specific embodiment of the nucleic acid base editor of the present disclosure, the nickase is an FokI nickase. The deaminase in the nucleic acid base editor of the present disclosure is selected from a cytidine-specific deaminase and an adenosine-specific deaminase, preferably, the deaminase is selected from the deaminase as set forth in sequences SEQ ID NO. 36-59 and 80-86. In an advantageous embodiment of the above-mentioned nucleic acid base editor comprising a cytidine-specific deaminase, the cytidine deaminase is selected from hAPOBEC3A, rAPOBEC1, hAID, pmCDAT and Sdd deaminase. In an embodiment of the nucleic acid base editor of the present disclosure comprising an adenosine-specific deaminase, the adenosine deaminase is TadA-8e.

In another preferred embodiment, the present disclosure also provides a recombinant cell, which comprises one or more recombinant expression constructs encoding a sequence-specific DNA binding protein, a nickase, an exonuclease and a base-specific deaminase; wherein each of the sequence-specific DNA binding protein, the nickase, the exonuclease and the base-specific deaminase is capable of being expressed in a cell. In certain embodiments, these recombinant cells comprise nucleic acid compositions that further comprise a recombinant expression construct encoding a uracil glycosylase inhibitor. In a specific embodiment, the recombinant cell comprises one or more recombinant expression constructs encoding a sequence-specific DNA binding protein, a nickase, an exonuclease and a base-specific deaminase as a fusion protein, wherein the fusion protein comprised thereof is capable of being expressed in a cell. In an advantageous embodiment of the recombinant cell provided herein, the sequence-specific DNA binding protein is selected from a TALE protein, a ZFA protein, a Cas protein and a meganuclease, and in certain specific embodiments, the sequence-specific DNA binding protein is a TALE protein. In a specific embodiment of the recombinant cell provided herein, the nickase is FokI. Further provided are the recombinant cell of the present disclosure, comprising one or more recombinant expression constructs encoding a deaminase, wherein the deaminase is a cytidine-specific deaminase or an adenosine-specific deaminase, preferably, the deaminase is selected from the deaminase as set forth in sequences SEQ ID NO. 36-59 and 80-86. An advantageous embodiment of the recombinant cell provided herein comprises one or more recombinant expression constructs encoding a cytidine-specific deaminase, wherein the cytidine deaminase is selected from hAPOBEC3A, rAPOBEC1, hAID, pmCDAT and Sdd deaminase in an advantageous embodiment. In additional advantageous embodiments, the recombinant cell comprises one or more recombinant expression constructs encoding an adenosine-specific deaminase, wherein the adenosine deaminase is TadA-8e in non-limiting examples.

In another preferred embodiment, the present disclosure also provides a method for performing base editing in a cell, comprising the step of introducing a nucleic acid base editor, or a recombinant expression construct encoding the nucleic acid base editor of the present disclosure, or a fusion protein encoding the nucleic acid base editor of the present disclosure into the cell. In the practice of the method set forth herein, base editing is performed at a target nucleic acid recognized by the specific binding protein, and results in the change of a cytosine residue or an adenine residue.

In another preferred embodiment, the present disclosure provides a nucleic acid base editor that is specific for the base editing activity in nucleus or organelles. Further, a nucleic acid base editor for nucleus may comprise a nuclear localization signal (NLS). Further, a base editor for mitochondrion or chloroplast may comprise a mitochondrial targeting sequence (MTS) or a chloroplast translocation peptide (CTP), respectively. In these Examples, NLS, MTS or CTP may be substituted with each other depending on different specific target organelles or base editors, which will be described in further detail herein.

Exemplary technical solutions of the present disclosure are as below.

The first object of the present disclosure is to provide a nucleic acid base editor, comprising the following elements: a) a sequence-specific DNA binding protein; b) a nickase; c) an exonuclease; and d) a base-specific deaminase.

Preferably, each element of the nucleic acid base editor exists alone, or constitutes one or more fusion proteins.

Preferably, the sequence-specific DNA binding protein is one or more selected from the group consisting of a TALE protein, a ZFA protein, a Cas protein and a meganuclease.

Preferably, the sequence-specific DNA binding protein is a TALE protein.

Preferably, the nickase is a dimer of a cleavage domain monomer of FokI (Cleavage Domain monomer of FokI, FokICD) or a mutant of the dimer, the dimer of the FokICD monomer or the mutant of the dimer is composed of a pair of interacting cleavage domain monomers of FokI, and the dimer of the FokICD monomer or the mutant of the dimer has one and only one FokICD monomer which has DNA endonuclease activity.

Preferably, the cleavage domain monomer of FokI is isolated from a mutant of a wild-type FokI protein, the mutant of the wild-type FokI protein has a mutation at position 450 and/or position 467, or has an amino acid sequence which has at least 85%, at least 90%, at least 92%, at least 95%, at least 96%, at least 97%, at least 98%, at least 99%, or at least 99.5% identity with that of the cleavage domain monomer of FokI.

Further preferably, the mutation causes the FokICD monomer to lose DNA endonuclease activity.

Preferably, the cleavage domain monomer of FokI (FokICD) is isolated from a mutant of a wild-type FokI protein, the mutation prevents the FokICD monomer from the self-polymerization with a FokICD monomer containing a mutation at a same site and the formation of a dimer.

Further preferably, a sequence of the FokICD monomer is selected from SEQ ID No.87-88.

Preferably, the amino acid sequence of the cleavage domain monomer of FokI (FokICD) is selected from SEQ No. 60-63.

Preferably, the base-specific deaminase is selected from a cytidine-specific deaminase and an adenosine-specific deaminase.

Further preferably, the deaminase is selected from the deaminase as set forth in sequences SEQ ID NO. 36-59 and 80-86.

Further preferably, the base-specific deaminase is a cytidine-specific deaminase.

Further preferably, the cytidine-specific deaminase is one or more selected from the group consisting of hAPOBEC3A, rAPOBEC1, hAID, pmCDAT and Sdd deaminase.

Further, the nucleic acid base editor further comprises:
e) a uracil glycosylase inhibitor (UGI); and
the uracil glycosylase inhibitor exists alone, or constitutes at least one fusion protein with other elements of the nucleic acid base editor.

Preferably, the base-specific deaminase is an adenosine-specific deaminase.

Preferably, the adenosine-specific deaminase is TadA-8e.

Further, the nucleic acid base editor further comprises:
f) γb;
the γb constitutes at least one fusion protein with other elements of the nucleic acid base editor.

The second object of the present disclosure is to provide a fusion protein that is a nucleic acid base editor, the fusion protein comprises a protein domain of the base editor as described in the first object.

Another object of the present disclosure is to provide a fusion protein that is a nucleic acid base editor, the fusion protein comprises in linear order from the protein's amino terminus an exonuclease, an XTEN linker peptide, a base-specific deaminase, an XTEN linker peptide, a uracil glycosylase inhibitor (UGI) and a nuclear localization signal.

Another object of the present disclosure is to provide a fusion protein that is a nucleic acid base editor, the fusion protein comprises in linear order from the protein's amino terminus an exonuclease, a 48-amino acid linker peptide, a base-specific deaminase, an XTEN linker peptide, a uracil glycosylase inhibitor (UGI) and a nuclear localization signal.

Another object of the present disclosure is to provide a composition of fusion proteins having nucleic acid base editor activity, the composition comprises:
a first fusion protein comprising a nuclear localization signal (NLS), a sequence-specific DNA binding protein and a base-specific deaminase;
a second fusion protein comprising an exonuclease and a nuclear localization signal (NLS); and
a third fusion protein comprising a uracil glycosylase inhibitor (UGI) and a nuclear localization signal (NLS).

Another object of the present disclosure is to provide a composition of fusion proteins having nucleic acid base editor activity, the composition comprises:
a first fusion protein comprising in linear order from the protein's amino terminus a nuclear localization signal (NLS), a base-specific deaminase, a TALE-L protein, an FokI-L$_{D450A}$ protein, a T2A sequence, an NLS, a TALE-R protein and an FokI-R protein;
a second fusion protein comprising an exonuclease and a nuclear localization signal (NLS); and
a third fusion protein comprising a uracil glycosylase inhibitor (UGI) and a nuclear localization signal (NLS).

Another object of the present disclosure is to provide a composition of fusion proteins having nucleic acid base editor activity, the composition comprises:
a first fusion protein comprising in linear order from the protein's amino terminus a nuclear localization signal (NLS), a TALE-L protein, an FokI-L$_{D450A}$ protein, a T2A sequence, an NLS, a base-specific deaminase, a 48-amino acid linker peptide, a TALE-R protein and an FokI-R protein;

a second fusion protein comprising an exonuclease and a nuclear localization signal (NLS); and a third fusion protein comprising a uracil glycosylase inhibitor (UGI) and a nuclear localization signal (NLS).

Another object of the present disclosure is to provide a composition of fusion proteins having nucleic acid base editor activity, the composition comprises:

a first fusion protein comprising a nuclear localization signal (NLS), a sequence-specific DNA binding protein, a base-specific deaminase and a uracil glycosylase inhibitor (UGI); and a second fusion protein comprising an exonuclease and a nuclear localization signal (NLS).

Another object of the present disclosure is to provide a composition of fusion proteins having nucleic acid base editor activity, the composition comprises:

a first fusion protein comprising in linear order from the protein's amino terminus a nuclear localization signal (NLS), a base-specific deaminase, a 48-amino acid linker peptide, a TALE-L protein, an FokI-L$_{D450A}$ protein, a T2A sequence, an NLS, a TALE-R protein, an FokI-R protein, a 4-amino acid linker peptide and a uracil glycosylase inhibitor (UGI); and a second fusion protein comprising an exonuclease and a nuclear localization signal (NLS).

Another object of the present disclosure is to provide a composition of fusion proteins having nucleic acid base editor activity, the composition comprises:

a first fusion protein comprising in linear order from the protein's amino terminus a nuclear localization signal (NLS), a uracil glycosylase inhibitor (UGI), a 4-amino acid linker peptide, a base-specific deaminase, a 48-amino acid linker peptide, a TALE-L protein, an FokI-L$_{D450A}$ protein, a T2A sequence, an NLS, a TALE-R protein and an FokI-R protein; and a second fusion protein comprising an exonuclease and a nuclear localization signal (NLS).

Another object of the present disclosure is to provide a composition of fusion proteins having nucleic acid base editor activity and capable of performing base editing in mitochondria, the composition comprises:

a first fusion protein comprising in linear order from the protein's amino terminus a mitochondrial targeting sequence (MTS), a TALE-L protein and an FokI-L$_{D450A}$ protein;

a second fusion protein comprising in linear order from the protein's amino terminus a mitochondrial targeting sequence (MTS), a TALE-R protein and an FokI-R protein;

a third fusion protein comprising in linear order from the protein's amino terminus a mitochondrial targeting sequence (MTS) and an exonuclease;

a fourth fusion protein comprising in linear order from the protein's amino terminus a mitochondrial targeting sequence (MTS) and a base-specific deaminase; and a fifth fusion protein comprising in linear order from the protein's amino terminus a mitochondrial targeting sequence (MTS) and a uracil glycosylase inhibitor (UGI).

Another object of the present disclosure is to provide a composition of fusion proteins having nucleic acid base editor activity and capable of performing base editing in mitochondria, the composition comprises:

a first fusion protein comprising in linear order from the protein's amino terminus a mitochondrial targeting sequence (MTS), a TALE-L protein and an FokI-L$_{D450A}$ protein;

a second fusion protein comprising in linear order from the protein's amino terminus a mitochondrial targeting sequence (MTS), a TALE-R protein and an FokI-R protein;

a third fusion protein comprising in linear order from the protein's amino terminus a mitochondrial targeting sequence (MTS), γb and an exonuclease;

a fourth fusion protein comprising in linear order from the protein's amino terminus a mitochondrial targeting sequence (MTS) and a base-specific deaminase; and a fifth fusion protein comprising in linear order from the protein's amino terminus a mitochondrial targeting sequence (MTS), γb and a uracil glycosylase inhibitor (UGI).

Another object of the present disclosure is to provide a composition of fusion proteins having nucleic acid base editor activity, the composition comprises:

a first fusion protein comprising a nuclear localization signal (NLS)/a chloroplast translocation peptide (CTP)/a mitochondrial targeting sequence (MTS), a sequence-specific DNA binding protein and a nickase;

a second fusion protein comprising an exonuclease and a nuclear localization signal (NLS)/a chloroplast translocation peptide (CTP)/a mitochondrial targeting sequence (MTS); and a third fusion protein comprising a base-specific deaminase, a uracil glycosylase inhibitor (UGI) and a nuclear localization signal (NLS)/a chloroplast translocation peptide (CTP)/a mitochondrial targeting sequence (MTS).

Another object of the present disclosure is to provide a composition of fusion proteins having nucleic acid base editor activity, the composition comprises:

a first fusion protein comprising in linear order from the protein's amino terminus a nuclear localization signal (NLS)/a chloroplast translocation peptide (CTP)/a mitochondrial targeting sequence (MTS), a TALE-L protein, an FokI-L$_{D450A}$ protein, a T2A sequence, an NLS, a TALE-R protein and an FokI-R protein, or comprising in linear order from the protein's amino terminus a nuclear localization signal (NLS)/a chloroplast translocation peptide (CTP)/a mitochondrial targeting sequence (MTS), a TALE-L protein, an FokI-L protein, a T2A sequence, an NLS, a TALE-R protein and an FokI-R$_{D450A}$ protein;

a second fusion protein comprising in linear order from the protein's amino terminus a nuclear localization signal (NLS)/a chloroplast translocation peptide (CTP)/a mitochondrial targeting sequence (MTS) and an exonuclease; and a third fusion protein comprising in linear order from the protein's amino terminus a nuclear localization signal (NLS)/a chloroplast translocation peptide (CTP)/a mitochondrial targeting sequence (MTS), a base-specific deaminase, an XTEN linker peptide and a uracil glycosylase inhibitor (UGI).

Another object of the present disclosure is to provide a composition of fusion proteins having nucleic acid base editor activity and capable of performing base editing in mitochondria, wherein the composition comprises:

a first fusion protein comprising in linear order from the protein's amino terminus a mitochondrial targeting sequence (MTS), a base-specific deaminase, a 48-amino acid linker peptide, a TALE-L protein, an FokI-L$_{D450A}$ protein, an 11-amino acid linker peptide and a uracil glycosylase inhibitor (UGI); and a second fusion protein comprising in linear order from the protein's amino terminus a mitochondrial targeting sequence (MTS), a 48-amino acid linker peptide, a TALE-R protein, a uracil glycosylase inhibitor (UGI), a 14-amino acid linker peptide and an FokI-R protein.

Another object of the present disclosure is to provide a recombinant expression construct for nucleic acid base editing, the recombinant expression construct is used to express the nucleic acid base editor of the first object mentioned above or the fusion protein or the composition of other objects mentioned above.

Another object of the present disclosure is to provide a genetically engineered cell, and the genetically engineered cell is used for the transformation of the recombinant expression construct of the above-mentioned objects.

Another object of the present disclosure is to provide a method of performing nucleic acid base editing in a cell, the nucleic acid base editor or the recombinant expression construct of the above-mentioned objects is introduced into the cell so as to edit a target gene.

Preferably, the target gene is selected from a nuclear genomic DNA, a mitochondrial genomic DNA and a chloroplast genomic DNA.

Further preferably, the target gene is a nuclear genomic DNA, and the nucleic acid base editor further comprises a nuclear localization signal (NLS).

Further preferably, the target gene is a mitochondrial genomic DNA, and the nucleic acid base editor further comprises a mitochondrial targeting sequence (MTS).

Further preferably, the target gene is a chloroplast genomic DNA, and the nucleic acid base editor further comprises a chloroplast translocation peptide (CTP).

Another object of the present disclosure is to allow γb to be fused to the terminus of each element.

Further preferably, γb is fused to UGI and Trex2, respectively.

Another object of the present disclosure is to provide the use of base editing technique in base editing, wherein the base editor, the fusion protein, the composition, the recombinant expression construct, the genetically engineered cell or the method of the above-mentioned object is used to perform base editing on a DNA in a cell, and the cell is a mammalian cell, a bacterium, a protist, a fungus, an insect cell, a yeast, a non-conventional yeast or a plant cell.

Preferably, the plant cell is derived from a whole plant of a monocotyledon or a dicotyledon, a seedling, a meristem, a ground tissue, a vascular tissue, a dermal tissue, a seed, a leaf, a root, a bud, a stem, a flower, a fruit, a stolon, a bulb, a tuber, a corm, an asexual terminal branch, a bud, a budlet, or a tumor tissue.

Preferably, the mammalian cell is selected from a germ cell, a neuron, a muscle cell, an endocrine/exocrine cell, an epithelial cell, a muscle cell, a tumor cell, an embryonic cell, a hematopoietic cell, an osteocyte, germplasm cell, a somatic cell, a stem cell, a pluripotent stem cell, an induced pluripotent stem cell, a progenitor cell, a meiotic cell and a mitotic cell of human.

Preferably, the editor is used to perform base editing on a nuclear genome or an organellar genome.

Preferably, the organelle is mitochondrion or chloroplast.

Another object of the present disclosure is to provide the use of the base editor, the fusion protein, the composition, the recombinant expression construct or the genetically engineered cell of the above-mentioned objects in preparation of a pharmaceutical composition for treating a disease in a subject in need thereof.

Another object of the present disclosure is to provide a pharmaceutical composition for treating a disease in a subject in need thereof, the pharmaceutical composition comprises the base editor, the fusion protein, the composition, the recombinant expression construct or the genetically engineered cell of the above-mentioned objects, and optionally, a pharmaceutically acceptable carrier.

Another object of the present disclosure is to provide a method for producing a genetically modified plant, wherein the method comprises introducing the base editor, the fusion protein, the composition, the recombinant expression construct or the genetically engineered cell of the above-mentioned objects into at least one of the plants.

The present disclosure provides a base editor and the use thereof, and the beneficial effects thereof are as follow.

(1) The base editor of the present disclosure merely causes the occurrence of base editing on a selected single strand, thereby exhibiting good safety and precision.

(2) The base editor of the present disclosure achieves editing products with high purity and shows low production rate of indel byproducts, thereby having excellent editing efficiency.

(3) The base editor of the present disclosure has a low off-target rate, thereby effectively enhancing its therapeutic effects and safety.

(4) The base editor of the present disclosure is not based on CRISPR technology, has a wider range of applications and application scenarios, and all of the elements of said base editor are capable of functioning in nucleus or an organelle such as mitochondrion and chloroplast.

BRIEF DESCRIPTION OF THE DRAWINGS

In order to better understand the technical solutions described in the present disclosure, description is now made with reference to the following drawings.

FIG. 2A shows the C>T base editing efficiency for the OsBADH2 site in rice protoplast in cases where different treatment methods are adopted, and FIG. 2B shows the C>T base editing efficiency and the frequency of generating indel byproducts for the OsBADH2 site in rice protoplast in cases where different treatment methods are adopted.

FIG. 3A and FIG. 3B show the analysis of the base editing window of the base editor of the present disclosure. The rice protoplast is transformed with the nucleic acid base editor of the present disclosure, DNA is then extracted and the target site is subjected to high-throughput sequencing, so as to obtain the editing efficiency for different bases on the target sequence. FIG. 3A shows the schematic diagram of the OsBADH2 target sequence. The gray sequences on both sides are the TALE binding sites, and the black region in the middle is the spacer sequence. FIG. 3B shows the base editing window of the base editor obtained according to the analysis of the high-throughput sequencing results, wherein CK is a blank control without the transformation of any plasmid, TALEN$_{WT}$ and TALEN$_{WT}$+ExoI are those with the transformation of the wild-type TALEN or the transformation of a combination of TALEN and exonuclease ExoI, respectively, and these two treatments serve as negative control.

FIG. 13A and FIG. 13B are schematic diagrams of the base editors comprising a deaminase-TALE fusion protein of the present disclosure. In each embodiment, a fusion protein of an NLS and an exonuclease is provided in a separate vector.

In FIG. 16A to FIG. 16E, FokK-L-nickase is equivalent to FOKI-L; and FokI-R is equivalent to FOKI-R (D450A/D467A).

FIG. 16A shows the recombinant expression construct encoding the wild-type TALEN used in Example 2 and other examples (the schematic diagram of the NLS-TALEN$_{WT}$ vector, taking the TALE targeting OsBADH2 as an example). This vector could result in double-strand breaks and trigger indel mutations randomly in the target DNA, and is used as control in each example. In this construct, a stably expressed T-DNA vector having a UBI promoter derived from maize and a Nos terminator is used to drive the expression of the wild-type TALEN (including the TALE-L-FokI-L fusion protein and the TALE-R-FokI-R fusion protein, wherein FokI does not contain D450A or D467A mutation), wherein the N- and C-terminal regions of TALE comprise the corresponding truncations (ΔN152/C63), flanking the DNA-binding domain of TALE. The TALE-L-FokI-L fusion protein and the TALE-R-FokI-R fusion protein are linked via the T2A self-cleaving peptide. Other components shown in the Figure include a CaMV 35S promoter (a Cauliflower Mosaic Virus-derived promoter), the hygromycin resistance gene Hyg, the nopaline synthase terminator Nos of *Agrobacterium tumefaciens*, and the like.

FIG. 16B is a schematic representation of a recombinant expression construct comprising the sequence-specific DNA binding proteins (TALE-L, TALE-R) and the nickase (FokI nickase) (i.e., a schematic diagram of a vector containing a nickase, an exonuclease and a deaminase as parts of the vector, taking the TALE targeting OsBADH2 as an example; the corresponding coding sequence of TALE may be designed depending on the target sequence) and two additional constructs, i.e., NLS-deaminase-UGI and exonuclease-NLS. All of these constructs comprise a UBI promoter derived from maize and a Nos terminator, which drive the expression of the deaminase-UGI fusion protein and the exonuclease, respectively. UGI (a uracil-DNA glycosylase inhibitor derived from *Bacillus subtilis* bacteriophage) protects the uracil(s) in DNA by irreversibly inhibiting uracil-DNA glycosylase which is the key DNA repair enzyme. Other components shown in the Figure include a CaMV 35S promoter (a Cauliflower Mosaic Virus-derived promoter), the hygromycin resistance gene Hyg, the nopaline synthase terminator Nos of *Agrobacterium tumefaciens*, and a CaMV poly(A) signal terminator.

FIG. 16C is a schematic representation of a recombinant expression construct comprising the fusion protein of the sequence-specific DNA binding proteins (TALE-L, TALE-R), the nickase (FokI nickase) and the deaminase (i.e., a schematic diagram of a vector containing a nickase, an exonuclease, a deaminase and a uracil glycosylase inhibitor as parts of the vector, taking the TALE targeting OsBADH2 as an example; the corresponding coding sequence of TALE may be designed depending on the target sequence) and two additional constructs, i.e., UGI-NLS and exonuclease-NLS. Each of the recombinant expression constructs (UGI-NLS and exonuclease-NLS) has a UBI promoter and a CaMV terminator, which drive the expression of UGI and the exonuclease. UGI (a uracil-DNA glycosylase inhibitor derived from *Bacillus subtilis* bacteriophage) protects the uracil(s) in DNA by irreversibly inhibiting uracil-DNA glycosylase which is the key DNA repair enzyme. Other components shown in the Figure include a CaMV 35S promoter (a Cauliflower Mosaic Virus-derived promoter), the hygromycin resistance gene Hyg, the nopaline synthase terminator Nos of *Agrobacterium tumefaciens*, and a CaMV poly(A) signal terminator.

FIG. 16D is a schematic representation of a recombinant expression construct comprising the fusion protein of the sequence-specific DNA binding proteins (TALE-L, TALE-R), the nickase (FokI nickase), the deaminase and UGI (i.e., a schematic diagram of a vector containing NLS-deaminase-TALE-L-FokI-$_{nickase}$-TALEN-R-UGI and exonuclease-NLS as parts of the vector, taking the TALE targeting OsBADH2 as an example; the corresponding coding sequence of TALE may be designed depending on the target sequence) and an additional construct, i.e., exonuclease-NLS. The recombinant expression construct (exonuclease-NLS) has a UBI promoter and a CaMV terminator to drive the expression of exonuclease. UGI (a uracil-DNA glycosylase inhibitor derived from a *Bacillus subtilis* bacteriophage) protects the uracil(s) in DNA by irreversibly inhibiting uracil-DNA glycosylase which is the key DNA repair enzyme. Other components shown in the Figure include a CaMV 35S promoter (a Cauliflower Mosaic Virus-derived promoter), the hygromycin resistance gene Hyg, the nopaline synthase terminator Nos of *Agrobacterium tumefaciens*, and a CaMV poly(A) signal terminator.

FIG. 16E is a schematic representation of a recombinant expression construct comprising the fusion protein of the sequence-specific DNA binding proteins (TALE-L, TALE-R), the nickase (FokI nickase), the deaminase, the exonuclease and UGI (a schematic diagram of NLS-deaminase-TALE-L-FokI-$_{nickase}$-TALEN-R-UGI-exonuclease vector, taking the TALE targeting OsBADH2 as an example, the corresponding coding sequence of TALE may be designed depending on the target sequence), having the additional feature that UGI and exonuclease are encoded in the construct rather than being introduced into the cell in separate constructs.

FIG. 17A is a representation of the recombinant expression construct MTS-TALE-L-FokI-L for mitochondria (a schematic diagram of the MTS-TALE-L-FokI-L vector targeting mitochondrial ND6), wherein the TALE sequence could be replaced correspondingly depending on targets. The expression vector MTS-TALE-L-FokI-L has a CMV promoter and a bGH poly(A) signal terminator to drive the expression of the MTS-TALE-L-FokI-L fusion protein, wherein the N- and C-terminal regions of TALE comprise the corresponding truncations (ΔN152/C63), flanking the DNA-binding domain of TALE (see Mok et al., 2020, Nature 583: 631-637). MTS is a mitochondrial targeting sequence of *Homo sapiens* superoxide dismutase 2 that facilitates the translocation of proteins into mitochondria. The CMV promoter is a human herpesvirus 5-derived promoter, which has been demonstrated to be highly active in animal cells. The CMV enhancer is a cytomegalovirus promoter region-containing fragment capable of enhancing the transcriptional efficiency of the CMV promoter. The bGH poly(A) signal is a somatotropin poly-adenylylation signal-derived terminator.

FIG. 17B is a representation of the recombinant expression construct MTS-TALE-R-FokI-R for mitochondria (a schematic diagram of the MTS-TALE-R-FokI-R vector targeting mitochondrial ND6), wherein the TALE sequence could be replaced correspondingly depending on targets. The expression vector MTS-TALE-R-FokI-R has a CMV promoter and a bGH poly(A) signal terminator to drive the expression of the MTS-TALE-R-FokI-R fusion protein, wherein the N- and C-terminal regions of TALE comprise the corresponding truncations (ΔN152/C63), flanking the DNA-binding domain of TALE (see Mok et al., 2020, Nature 583: 631-637). In this vector, MTS is a mitochondrial targeting sequence of Cytochrome c oxidase subunit 8 that facilitates the translocation of proteins into mitochondria. The CMV promoter is a human herpesvirus 5-derived promoter, which has been demonstrated to be highly active in animal cells. The CMV enhancer is a cytomegalovirus promoter region-containing fragment capable of enhancing the transcriptional efficiency of the CMV promoter. The bGH poly(A) signal is a somatotropin poly-adenylylation signal-derived terminator.

FIG. 17C is a schematic diagram of the recombinant expression construct MTS-deaminase for mitochondria (a schematic diagram of the MTS-deaminase vector). This recombinant expression construct has a CMV promoter and a bGH poly(A) signal terminator to drive the expression of MTS-deaminase in human mitochondria. The MTS, the CMV promoter, the CMV enhancer and the bGH poly(A) signal terminator are as described in FIG. 17A.

FIG. 17D is a representation of the recombinant expression construct MTS-exonuclease for mitochondria (a schematic diagram of the MTS-exonuclease vector). This recombinant expression construct has a CMV promoter and a bGH poly(A) signal terminator to drive the expression of MTS-exonuclease in human mitochondria. The MTS, the CMV promoter, the CMV enhancer and the bGH poly(A) signal terminator are as described in FIG. 17A.

FIG. 17E is a representation of the recombinant expression construct MTS-UGI for mitochondria (a schematic diagram of the MTS-UGI vector). This recombinant expression construct has a CMV promoter and a bGH poly(A) signal terminator to drive the expression of MTS-UGI (a uracil glycosylase inhibitor derived from a *Bacillus subtilis* bacteriophage) in human mitochondria. The MTS, the CMV promoter, the CMV enhancer and the bGH poly(A) signal terminator are as described in FIG. 17A.

FIG. 17F is a schematic diagram of the recombinant expression construct MTS-deaminase-TALE-L-FokI-L for mitochondria (a schematic diagram the MTS-deaminase-TALE-L-FokI-L vector). The recombinant expression construct MTS-deaminase-TALE-L-FokI-L has a CMV promoter and a bGH poly(A) signal terminator to drive the expression of the MTS-deaminase-TALE-L fusion protein. Components such as the MTS, the CMV promoter, the CMV enhancer and the bGH poly(A) signal terminator are as described in FIG. 17A.

FIG. 17G is a schematic diagram of the recombinant expression construct MTS-exonuclease-TALE-R-FokI-R for mitochondria (a schematic diagram of the MTS-exonuclease-TALE-R-FokI-R vector). The recombinant expression construct MTS-exonuclease-TALE-R-FokI-R has a CMV promoter and a bGH poly(A) signal terminator to drive the expression of the MTS-exonuclease-TALE-R fusion protein. Components such as the MTS, the CMV promoter, the CMV enhancer and the bGH poly(A) signal terminator are as described in FIG. 17B.

FIG. 17H is a schematic diagram of the recombinant expression construct MTS-UGI-exonuclease-TALE-R-FokI-R for mitochondria (a schematic diagram of the MTS-UGI-exonuclease-TALE-R-FokI-R vector). The recombinant expression construct MTS-UGI-exonuclease-TALE-R-FokI-R has a CMV promoter and a bGH poly(A) signal terminator to drive the expression of the MTS-exonuclease-TALE-R fusion protein. Components such as the MTS, the CMV promoter, the CMV enhancer and the bGH poly(A) signal terminator are as described in FIG. 17B.

DETAILED DESCRIPTION

Terms

Figure 1:
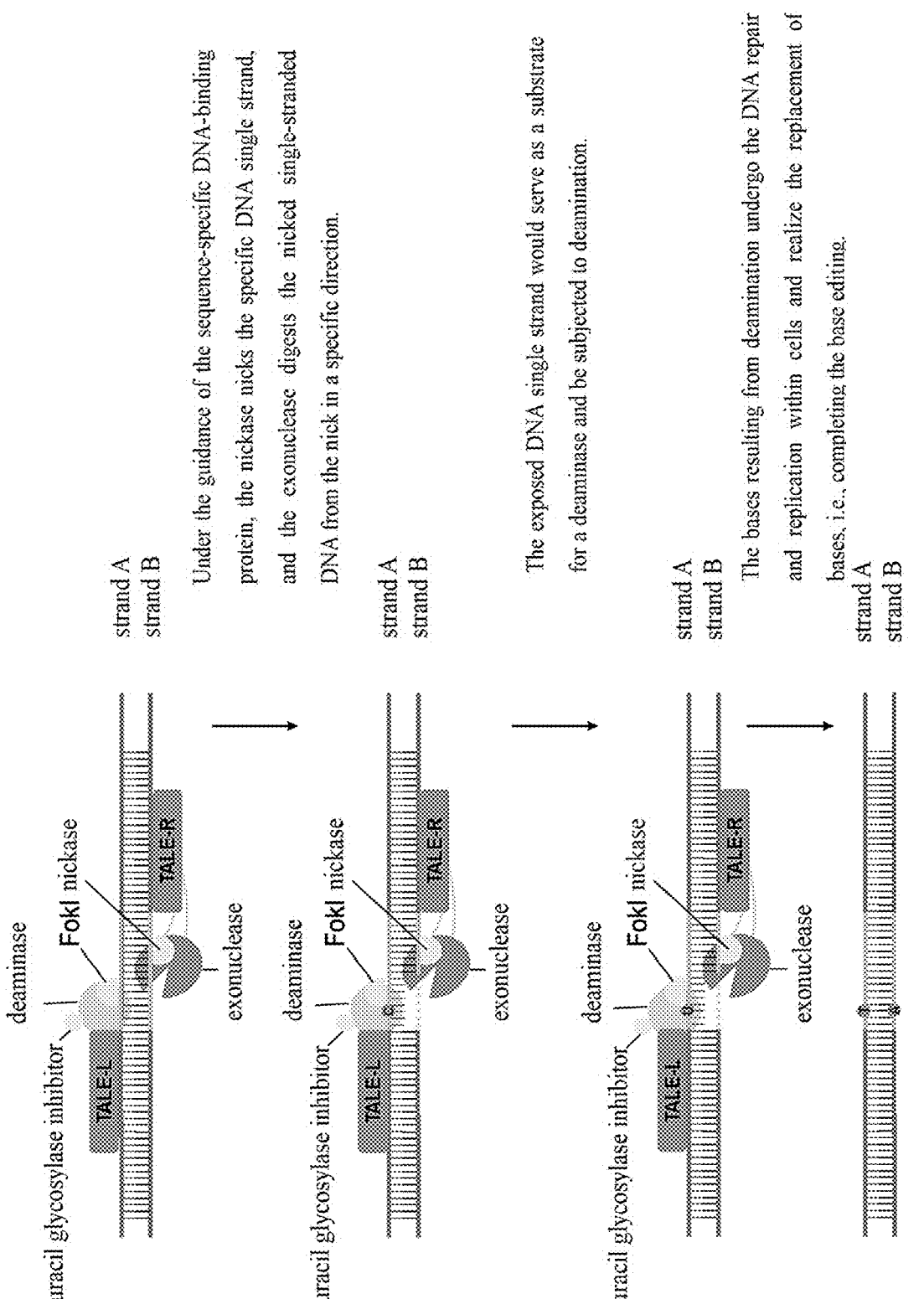
FIG. 1 is a schematic diagram of the functioning of the nucleic acid base editor of the present disclosure, wherein firstly, a sequence-specific DNA binding protein (SSDBP) locates and binds to a target DNA sequence; secondly, a nickase nicks one DNA strand preferentially at the target site and thereafter an exonuclease digests the nicked DNA strand from the nick to the SSDBP binding site. This would expose an ssDNA fragment in the complementary chain, which then becomes a substrate for a deaminase to realize deamination, thus resulting in the conversion of corresponding bases (C:G pairing to T:A pairing or A:T pairing to G:C pairing, the type of conversion depends on the deaminase used) after DNA repair.

Unless otherwise defined, all technical terms used herein have the same meaning as those commonly understood by a person skilled in the art.

A numerical range includes the number(s) defining the range, and explicitly includes each integer and non-integer fraction within the defined range. Unless otherwise indicated, all technical and scientific terms used herein have the same meaning as those commonly understood by one of ordinary skill in the art.

The terms "structure", "recombinant expression structure" or "recombinant expression construct" used in the present disclosure refers to an artificially designed DNA fragment that may be used to introduce the genetic material into a target cell (for example, a recombinant expression structure is used to produce a base editor or the components thereof). The term "express" refers to the transcription and translation of a nucleic acid encoding sequence, resulting in the production of an encoded polypeptide.

The term "genetically engineered" used in the present disclosure refers to change the genetic makeup of the cells by biotechnology, including the transfer of genes within and across species boundaries, to produce improved or non-naturally occurring cells. In particular uses of this term, the construct encodes the base editor or the components thereof, and the base editor is produced by the genetically engineered cells. A cell that contains an exogenous, recombinant, synthetic and/or otherwise modified polynucleotide is considered to be a genetically engineered cell, and thus non-naturally occurring relative to any naturally occurring counterpart. In some cases, a genetically engineered cell comprises one or more recombinant nucleic acids. In other cases, a genetically engineered cell comprises one or more synthetic or genetically engineered nucleic acids (for example, a nucleic acid containing at least one artificially created insertion, deletion, inversion or substitution relative to the sequence of its naturally occurring counterpart). Methods for producing genetically engineered cells are known in the art, for example, as described in Sambrook et al., *Molecular Cloning, A Laboratory Manual* (*Fourth Edition*), Cold Spring Harbor Press, Cold Spring Harbor, N.Y. (2012).

The term "genetically engineered cell" or "genetically engineered host cell" or "recombinant expression host cell" used in the present disclosure may be a cell that has been modified using a gene editing technique. Gene editing refers to a type of genetic engineering in which DNA is inserted, deleted, modified or replaced in the genome of a living cell. Compared with other genetic engineering techniques that may randomly insert the genetic material into a host genome, gene editing is capable of targeting an insertions to a specific location (e.g., AAVS1 alleles). Examples of gene editing techniques include but are not limited to restriction enzymes, zinc finger nucleases, TALENs and CRISPR-Cas9. The base editor disclosed herein is a specific example of gene editing that permits changes in one or more single nucleotides to result in, inter alia, the alteration of phenotype of cell.

The term "deaminase", "base-specific deaminase" or "deaminase domain" as used in the present disclosure refers to a protein or an enzyme that catalyzes a deamination reaction. In the present disclosure, "deaminase" and "base-specific deaminase" may be used interchangeably. In some embodiments, the deaminase or deaminase domain is a cytidine deaminase, which catalyzes the hydrolytic deamination of cytidine or deoxycytidine respectively to generate uridine, which is finally converted to thymidine (T) during cell modification and DNA replication. In some embodiments, the deaminase or deaminase domain is an adenosine deaminase domain, which catalyzes the hydrolytic deamination of adenosine or deoxyadenosine to generate inosine or deoxyinosine (I), which is finally converted to guanosine or deoxyguanosine (G) during cell modification and DNA replication. In some embodiments, the deaminase or deaminase domain is a naturally occurring deaminase derived from an organism, such as a microorganism, a plant, an animal, such as a human, a chimpanzee, a gorilla, a monkey, a cattle, a dog, a rat, or a mouse. In some embodiments, the deaminase or deaminase domain is a variant of a naturally occurring deaminase derived from an organism, which does not exist in nature. For example, in some embodiments, the deaminase or deaminase domain is at least 50%, at least 55%, at least 60%, at least 65%, at least 70%, at least 75%, at least 80%, at least 85%, at least 90%, at least 95%, at least 96%, at least 97%, at least 98%, at least 99%, or at least 99.5% identical to a naturally occurring deaminase derived from an organism.

The term "linker peptide" or "Linker" as used in the present disclosure refers to an element linking two molecules or moieties, for example, two domains of a fusion protein. In some embodiments, the linker peptide is an organic molecule, a group, a polymer or a chemical moiety. In some embodiments, the linker peptide is a linker peptide that is 5 to 100 amino acids in length, for example, 4, 5, 6, 7, 8, 9, 10, 11, 12, 13, 14, 15, 16, 17, 18, 19, 20, 21, 22, 23, 24, 25, 26, 27, 28, 29, 30, 30 to 35, 35 to 40, 40 to 45, 45 to 50, 50 to 60, 60 to 70, 70 to 80, 80 to 90, 90 to 100, 100 to 150, or 150 to 200 amino acids in length. Longer or shorter linker peptides have also been considered.

The term "mutation" as used in the present disclosure refers to the substitution of a residue in a sequence (for example, nucleic acid sequence or amino acid sequence) with another residue or the deletion or insertion of one or more residues in the sequence. In the present disclosure, mutations are generally described by the identification of the initial residue, followed by the identification of the position of the residue in the sequence and the identity of the newly substituted residue. Various methods for generating the amino acid substitutions (mutations) provided herein are well known in the art, and are provided in, for example, Green and Sambrook, Molecular Cloning: A Laboratory Manual (4$^{th}$ ed., Cold Spring Harbor Laboratory Press, Cold Spring Harbor, N.Y. (2012)).

The term "uracil glycosylase inhibitor" or "UGI" as used in the present disclosure refers to a protein capable of inhibiting uracil-DNA glycosylase as a base excision repair enzyme.

The terms "top strand" or "strand A" and "bottom strand" or "strand B" as used in the present disclosure are merely intended to distinguish the relative positions of the two strands at the target site of DNA in a certain example for ease of the exemplary description of the editing effect of the base editor of the present disclosure on a single-stranded DNA, and have no specific limitation on a specific double-stranded DNA structure. Among them, "top strand" and "strand A" is interchangeable, and "bottom strand" and "strand B" is interchangeable. Unless otherwise specified, the "top strand" or the "strand A" that conforms to the schematic diagram of the present application (FIG. 1) is a DNA single strand that interacts with TALE-L, and correspondingly, the "bottom strand" or the "strand B" is a DNA single strand that interacts with TALE-R.

Various examples according to the composition and the method of the present disclosure are now described in the following non-limiting examples. This example is merely for the purpose of illustration and does not limit the scope of the present disclosure in any way.

Nucleic Acid Base Editor

The base editing function of the nucleic acid base editor of the present disclosure is as shown in FIG. 1. Its components include a sequence-specific DNA binding protein (SSDBP), a nickase, an exonuclease (having 5' or 3' exonuclease activity), a cytidine deaminase or an adenosine deaminase, optionally a uracil glycosylase inhibitor (UGI), and optionally a localization sequence. These components may be expressed by separate constructs or fused in one or more constructs using appropriate linker peptides.

Sequence-Specific DNA Binding Protein

In the base editor disclosed herein, SSDBP may be a TALE protein, a zinc-finger protein (ZFA protein), a CRISPR-Cas endonuclease (Cas protein) or a meganuclease, wherein a TALE protein is selected in some specific embodiments. A transcription activator-like effector (TALE) protein is derived from the transcription activator-like effector of *Xanthomonas* spp., and is artificially modified into a sequence-specific DNA binding protein. A TALE protein comprises 1 to 33 repeating units with a length of 33~35

-continued amino acid residues, wherein each repeating unit and the half-repeating unit at the terminus are capable of specifically recognizing and binding to a specific nucleotide target site. In each repeat sequence, the type of the DNA base capable of being recognized and bound to by TALE is determined by two hypervariable residues (referred to as repeat-variable di-residues (RVDs)) at positions 12 and 13 that target a specific base pair. The code or type of DNA recognition by RVDs has been deciphered: RVDs His/Asp (HD), Asn/Gly (NG), Asn/Asn (NN) and Asn/Ile (NI) recognize cytosine (C), thymine (T), guanine (G) and adenine (A), respectively (see, Boch & Bonas, 2010, Annu. Rev. Phytopathol. 48: 419-436; Deng et al., 2012, Cell Res. 22: 1502-1504). TALE repeating units are modular, and RVDs may be artificially designed for the target binding of DNA. As disclosed in the present disclosure, a pair of TALE proteins (respectively referred to as TALE-L or TALE-L protein and TALE-R or TALE-R protein) are used to bind DNA at two adjacent sites on DNA, wherein the DNA sequence between the adjacent sites is a spacer sequence, also referred to as a target sequence, wherein the binding sites of TALE-L and TALE-R are defined as Left Binding Site and Right Binding Site. The sequence specificity of the TALE protein is used to determine the target site in the base editor disclosed in the present disclosure. In addition, in some cases, only one TALE (rather than a pair) is needed for binding and targeting the dsDNA, and the base editing function of the present disclosure may also be realized.

The structures of exemplary TALE proteins that may be used as the component of the base editor disclosed in the present disclosure are provided below, including but not limited to the N-terminal as set forth in SEQ ID NO. 1, the C-terminal as set forth in SEQ ID NO. 2 and repeating units as set forth in SEQ ID NO. 3-35.

```
TALE-NTD (Δ152):
                                    (SEQ ID NO. 1)
MVDLRTLGYSQQQQEKIKPKVRSTVAQHHEALVGHGFTHAHIVALSQHP

AALGTVAVTYQHIITALPEATHEDIVGVGKQWSGARALEALLTDAGELR

GPPLQLDTGQLVKIAKRGGVTAMEAVHASRNALTGAPLN

TALE-CTD (C63):
                                    (SEQ ID NO. 2)
SIVAQLSRPDPALAALTNDHLVALACLGGRPAMDAVKKGLPHAPELIRR

VNRRIGERTSHRVA

OsBADH2-TALE-Left repeat:
                                    (SEQ ID NO. 3)
LTPDQVVAIASNNGGKQALETVQRLLPVLCQDHG (SEQ ID NO. 4)
LTPDQVVAIASHDGGKQALETVQRLLPVLCQDHG (SEQ ID NO. 5)
LTPDQVVAIASNGGGKQALETVQRLLPVLCQDHG (SEQ ID NO. 6)
LTPDQVVAIASNNGGKQALETVQRLLPVLCQDHG (SEQ ID NO. 7)
LTPDQVVAIASNNGGKQALETVQRLLPVLCQDHG (SEQ ID NO. 8)
LTPDQVVAIASNIGGKQALETVQRLLPVLCQDHG (SEQ ID NO. 9)
LTPDQVVAIASNGGGKQALETVQRLLPVLCQDHG
```

```
                                    (SEQ ID NO. 10)
LTPDQVVAIASNNGGKQALETVQRLLPVLCQDHG (SEQ ID NO. 11)
LTPDQVVAIASHDGGKQALETVQRLLPVLCQDHG (SEQ ID NO. 12)
LTPDQVVAIASNGGGKQALETVQRLLPVLCQDHG (SEQ ID NO. 13)
LTPDQVVAIASNGGGKQALETVQRLLPVLCQDHG (SEQ ID NO. 14)
LTPDQVVAIASNGGGKQALETVQRLLPVLCQDHG (SEQ ID NO. 15)
LTPDQVVAIASNNGGKQALETVQRLLPVLCQDHG (SEQ ID NO. 16)
LTPDQVVAIASNIGGKQALETVQRLLPVLCQDHG (SEQ ID NO. 17)
LTPDQVVAIASNNGGKQALETVQRLLPVLCQDHG (SEQ ID NO. 18)
LTPDQVVAIASNGGGKQALETVQRLLPVLCQDHG (SEQ ID NO. 19)
LTPDQVVAIASNIGGKQALE

OsBADH2-TALE-Right repeat:
                                    (SEQ ID NO. 20)
LTPDQVVAIASNNGGKQALETVQRLLPVLCQDHG (SEQ ID NO. 21)
LTPDQVVAIASHDGGKQALETVQRLLPVLCQDHG (SEQ ID NO. 22)
LTPDQVVAIASHDGGKQALETVQRLLPVLCQDHG (SEQ ID NO. 23)
LTPDQVVAIASNGGGKQALETVQRLLPVLCQDHG (SEQ ID NO. 24)
LTPDQVVAIASNGGGKQALETVQRLLPVLCQDHG (SEQ ID NO. 25)
LTPDQVVAIASNGGGKQALETVQRLLPVLCQDHG (SEQ ID NO. 26)
LTPDQVVAIASNGGGKQALETVQRLLPVLCQDHG (SEQ ID NO. 27)
LTPDQVVAIASNNGGKQALETVQRLLPVLCQDHG (SEQ ID NO. 28)
LTPDQVVAIASNGGGKQALETVQRLLPVLCQDHG (SEQ ID NO. 29)
LTPDQVVAIASHDGGKQALETVQRLLPVLCQDHG (SEQ ID NO. 30)
LTPDQVVAIASHDGGKQALETVQRLLPVLCQDHG (SEQ ID NO. 31)
LTPDQVVAIASNIGGKQALETVQRLLPVLCQDHG (SEQ ID NO. 32)
LTPDQVVAIASNIGGKQALETVQRLLPVLCQDHG (SEQ ID NO. 33)
LTPDQVVAIASNNGGKQALETVQRLLPVLCQDHG (SEQ ID NO. 34)
LTPDQVVAIASNNGGKQALETVQRLLPVLCQDHG (SEQ ID NO. 35)
LTPDQVVAIASNIGGKQALETVQRLLPVLCQDHG
```

Nickase

Nickase used as the component of the base editor disclosed herein is capable of cleaving one of the double strands of a target DNA. In the base editor disclosed herein, an exemplary nickase is FokI (or referred to as FokI protein) derived from *Flavobacterium okeanokoites* and in particular amino acid sequence variants wherein the dsDNA cleavage activity is converted into a nick produced in only one strand of a target DNA, including but not limited to D450A/D467A mutant. In addition, alternative nickases comprising bacterium type IIS restriction enzymes may also be used as the component of the base editor disclosed herein.

Wild-type FokI consists of two functional domains, which are a recognition domain and a cleavage domain, respectively. The recognition domain is removed artificially so as to obtain an FokICD merely retaining the cleavage domain. When two FokICD monomers interact with each other to form a dimer, the cleavage activity of FokICD would be activated, thus being capable of cleaving both strands of a double-stranded DNA. Exemplary FokICD monomers that may be used in the present disclosure are provided below, including but not limited to those as set forth in SEQ ID NO.87-88.

```
FokI-L:
                                    (SEQ ID NO. 87)
QLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQ

ADEMQRYVKENQTRNKHINPNEWWKVYPSSVTEFKFLFVSGHFKGNYKA

QLTRLNHKTNCNGAVLSVEELLIGGEMIKAGTLTLEEVRRKFNNGEINF

FokI-R:
                                    (SEQ ID NO. 88)
QLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQ

ADEMERYVEENQTRNKHLNPNEWWKVYPSSVTEFKFLFVSGHFKGNYKA

QLTRLNHITNCNGAVLSVEELLIGGEMIKAGTLTLEEVRRKFNNGEINF
```

When the aspartic acid at position 450 (the first amino acid of the wild-type FokI comprising the recognition domain is designated as the 1st amino acid; if the first amino acid of the FokICD merely comprising the cleavage domain is designated as the 1st amino acid, then the position is position 67) and/or position 467 (the first amino acid of the wild-type FokI comprising the recognition domain is designated as the 1st amino acid; if the first amino acid of the FokICD merely comprising the cleavage domain is designated as the 1st amino acid, then the position is position 84) in an FokICD monomer of the dimer is mutated to alanine (D450A or D467A), this FokICD monomer would lose the cleavage activity, while another FokICD monomer without amino acid mutation in the dimer still retains the cleavage activity.

The FokICD dimer thus obtained could and could only cleave one strand of a double-stranded DNA and could not cleave the other strand. Such dimer of FokICD is referred to as FokI$_{nickase}$, i.e., FokI nickase. For the convenience of description, an FokICD monomer fused to TALE-L is referred to as FokI-L (for example, as set forth in SEQ ID NO.87) by the inventors, and an FokICD monomer fused to TALE-R is referred to as FokI-R (for example, as set forth in SEQ ID NO.88). Further, FokICD mutant monomers that comprise FokI D450A and/or D467A mutation and thus lose the cleavage activity are referred to as FokI-L$_{D450A/D467A}$ and FokI-R$_{D450A/D467A}$, respectively. In the present disclosure, the FokICD dimer formed by the interaction between FokI-L and FokI-R$_{D450A/D467A}$ merely retains the cleavage activity of FokI-L, and this dimer is referred to as FokI-L$_{nickase}$ (or referred to as FokI-L nickase); correspondingly, the FokICD dimer formed by the interaction between FokI-L$_{D450A/D467A}$ and FokI-R merely retains the cleavage activity of FokI-R and is referred to as FokI-R$_{nickase}$ (or referred to as FokI-R nickase).

It should be pointed out that FokI-L$_{nickase}$ and FokI-R$_{nickase}$ tend to nick different single strands in a double-stranded DNA, that is, FokI-L$_{nickase}$ and FokI-R$_{nickase}$ have single-strand specificity or preference upon nicking DNA. As shown in FIG. 1, at this target site, if FokI-R$_{nickase}$ is used, then strand B tends to be nicked, correspondingly, if FokI-L$_{nickase}$ is used, then strand A tends to be nicked (as shown in FIG. 1). The strand specificities exhibited by FokI-L$_{nickase}$ and FokI-R$_{nickase}$ are advantageous for the selection of the desired DNA single strand for the subsequent deamination step. Accompanied by the sequence-specific binding to the left binding site and the right binding site by TALE-L and TALE-R, FokI-L$_{nickase}$ or FokI-R$_{nickase}$ nicks the target sequence, leaving a nick in strand A or strand B, respectively. The strand specificity of the nickase determines the further deamination of the DNA single strand under the action of the base editor of the present disclosure.

Nickase protein monomers that may be used as the components of exemplary nucleic acid base editors of the present disclosure are provided below, including but not limited to those as set forth in SEQ ID NO.60-63.

```
FokI-L_D450A:
                                    (SEQ ID NO. 60)
QLVKSELEEKKSELRHKLKYVPHEYIELIEIARNSTQDRILEMKVMEFF

MKVYGYRGKHLGGSRKPAGAIYTVGSPIDYGVIVDTKAYSGGYNLPIGQ

ADEMQRYVKENQTRNKHINPNEWWKVYPSSVTEFKFLFVSGHFKGNYKA

QLTRLNHKTNCNGAVLSVEELLIGGEMIKAGTLTLEEVRRKFNNGEINF

FokI-L_D467A:
                                    (SEQ ID NO. 61)
QLVKSELEEKKSELRHKLKYVPHEYIELIEIARNSTQDRILEMKVMEFF

MKVYGYRGKHLGGSRKPDGAIYTVGSPIDYGVIVATKAYSGGYNLPIGQ

ADEMQRYVKENQTRNKHINPNEWWKVYPSSVTEFKFLFVSGHFKGNYKA

QLTRLNHKTNCNGAVLSVEELLIGGEMIKAGTLTLEEVRRKENNGEINF

FokI-R_D450A:
                                    (SEQ ID NO. 62)
QLVKSELEEKKSELRHKLKYVPHEYIELIEIARNSTQDRILEMKVMEFF

MKVYGYRGKHLGGSRKPAGAIYTVGSPIDYGVIVDTKAYSGGYNLPIGQ

ADEMERYVEENQTRNKHLNPNEWWKVYPSSVTEFKFLFVSGHFKGNYKA

QLTRLNHITNCNGAVLSVEELLIGGEMIKAGTLTLEEVRRKFNNGEINF

FokI-R_D467A:
                                    (SEQ ID NO. 63)
QLVKSELEEKKSELRHKLKYVPHEYIELIEIARNSTQDRILEMKVMEFF

MKVYGYRGKHLGGSRKPDGAIYTVGSPIDYGVIVATKAYSGGYNLPIGQ

ADEMERYVEENQTRNKHLNPNEWWKVYPSSVTEFKFLFVSGHFKGNYKA

QLTRLNHITNCNGAVLSVEELLIGGEMIKAGTLTLEEVRRKFNNGEINF
```

Exonuclease

Depending on the type of the exonuclease used, the exonuclease component of the nucleic acid base editor of the present disclosure digests the nicked DNA strand from the nick site in 5'→3' direction or in 3'→5' direction. After exonuclease digestion, a short ssDNA fragment is exposed at the complementary DNA strand. The type of exonuclease determines the ssDNA region (or editing window) to be deaminated. Exonucleases that may be used as the component of the nucleic acid base editor disclosed herein include but are not limited to DNA Polymerases I and III (*E. coli*), mammalian p53 protein, exonucleases I-VII (*E. coli*) (such as exonucleases I and V (having 3'→5' exonuclease activity)), bacteriophage-derived polymerases (such as T4 DNA polymerase (having 3'→5' exonuclease activity)), *Thermus aquaticus* polymerase (having 5'->3' exonuclease activity), and 3'→5' exonuclease as reported by Shevelev and Hübscher (Shevelev & Hübscher, 2002, Nat. Rev. Molec. Cell Biol. 3: 364-376).

Exonuclease proteins that may be used as the components of exemplary base editors of the present disclosure are provided below, including but not limited to the proteins as set forth in sequences SEQ ID NO.64-67 and 153.

```
Exonuclease V (ExoV):
                                        (SEQ ID NO. 153)
MAETGEEETASAEASGFSDLSDSELVEFLDLEEAKESAVSLSKPGPSAE

LPGKDDKPVSLQNWKGGLDVLSPMERFHLKYLYVTDLCTQNWCELQMVY

GKELPGSLTPEKAAVLDTGASIHLAKELELHDLVTVPIATKEDAWAVKF

LNILAMIPALQSEGRVREFPVFGEVEGIFLVGVIDELHYTSKGELELAE

LKTRRRPVLPLPAQKKKDYFQVSLYKYIFDAMVQGKVTPASLIHHTKLC

LDKPLGPSVLRHARQGGVSVKSLGDLMELVFLSLTLSDLPAIDTLKLEY

IHQETATILGTEIVAFEEKEVKSKVQHYVAYWMGHRDPQGVDVEEAWKC

RTCDYVDICEWRRGSGVLSSSWEPKAKKFK mExoI:
                                        (SEQ ID NO. 64)
MGIQGLLQFIQEASEPVNVKKYKGQAVAVDTYCWLHKGAIACAEKLAKG

EPTDRYVGFCMKFVNMLLSYGVKPILIFDGCTLPSKKEVERSRRERRQS

NLLKGKQLLREGKVSEARDCFARSINITHAMAHKVIKAARALGVDCLVA

PYEADAQLAYLNKAGIVQAVITEDSDLLAFGCKKVILKMDQFGNGLEVD

QARLGMCKQLGDVFTEEKFRYMCILSGCDYLASLRGIGLAKACKVLRLA

NNPDIVKVIKKIGHYLRMNITVPEDYITGFIRANNTFLYQLVFDPIQRK

LVPLNAYGDDVNPETLTYAGQYVGDSVALQIALGNRDVNTFEQIDDYSP

DTMPAHSRSHSWNEKAGQKPPGTNSIWHKNYCPRLEVNSVSHAPQLKEK

PSTLGLKQVISTKGLNLPRKSCVLKRPRNEALAEDDLLSQYSSVSKKIK

ENGCGDGTSPNSSKMSKSCPDSGTAHKTDAHTPSKMRNKFATFLQRRNE

ESGAVVVPGTRSRFFCSSQDFDNFIPKKESGQPLNETVATGKATTSLLG

ALDCPDTEGHKPVDANGTHNLSSQIPGNAAVSPEDEAQSSETSKLLGAM

SPPSLGTLRSCFSWSGTLREFSRTPSPSASTTLQQFRRKSDPPACLPEA

SAVVTDRCDSKSEMLGETSQPLHELGCSSRSQESMDSSCGLNTSSLSQP

SSRDSGSEESDCNNKSLDNQGEQNSKQHLPHFSKKDGLRRNKVPGLCRS

SSMDSFSTTKIKPLVPARVSGLSKKSGSMQTRKHHDVENKPGLQTKISE

LWKNFGFKKDSEKLPSCKKPLSPVKDNIQLTPETEDEIFNKPECVRAQR

AIFH
```

-continued

```
mTrex2:
                                        (SEQ ID NO. 65)
MSEPPRAETFVFLDLEATGLPNMDPEIAEISLFAVHRSSLENPERDDSG

SLVLPRVLDKLTLCMCPERPFTAKASEITGLSSESLMHCGKAGFNGAVV

RTLQGFLSRQEGPICLVAHNGFDYDFPLLCTELQRLGAHLPQDTVCLDT

LPALRGLDRAHSHGTRAQGRKSYSLASLFHRYFQAEPSAAHSAEGDVHT

LLLIFLHRAPELLAWADEQARSWAHIEPMYVPPDGPSLEA mArtimes:
                                        (SEQ ID NO. 66)
MSSGMAYTSDRDRNKARAYSHCHKDHMKGRASKRRCSKVYCSVTKTSKY

RWNRTTTSVDASGKVVVTAGHCGSVMGSNGTVYTGDRAKGASRMHSGGR

VKDSVYDTTCDRYSRCRGVRSWVTRSHHVVWNCKAAYGYYTNSGVVHVD

KDMKNMDHHTTDRNTHACRHKACWNKCGTSNKTAHTSKSTMWGRTRKTN

VVRTGSSYRACSHSSSKDSYCVNVYNVVGTVDKVMDVKCRSSVKYKGKK

RARTHDSDDDDDTRHKVYTSMKADRSGGCKASVWSSANDCSNSDSGTSG

GGSTVNADDVDWVKRRDTGCHSSTGGSSKCSDSKCSDSKCSDSDGDSTH

SSNSSSTHTDGSGWDSCDTVSSKSGGDSTSNKGAYKKKSSASDACDTHC

DKSRAVNGACVDTSGRKSKTSSTRADSSSSDSTATHCYRKATGSVVKRK

CSDS

T5 exo:
                                        (SEQ ID NO. 67)
MSKSWGKFIEEEEAEMASRRNLMIVDGTNLGFRFKHNNSKKPFASSYVS

TIQSLAKSYSARTTIVLGDKGKSVFRLEHLPEYKGNRDEKYAQRTEEEK

ALDEQFFEYLKDAFELCKTTFPTFTIRGVEADDMAAYIVKLIGHLYDHV

WLISTDGDWDTLLTDKVSRFSFTTRREYHLRDMYEHHNVDDVEQFISLK

AIMGDLGDNIRGVEGIGAKRGYNIIREFGNVLDIIDQLPLPGKQKYIQN

LNASEELLFRNLILVDLPTYCVDAIAAVGQDVLDKFTKDILEIAEQ
```

Deaminase

Deaminases that may be used as the component of the base editor of the present disclosure include cytidine deaminases and adenosine deaminases. Cytidine deaminases include but are not limited to hAPOBEC3A (Zong et al., 2018, Nat. Biotechnol. October 1. doi: 10.1038/nbt.4261), rAPOBEC1, C57 and Sdd (Huang J et al., 2023, Cell, doi: 10.1101/2023.05.21.541555), which produce a C-to-T conversion at the base site. Alternative adenosine deaminases include TadA-8e (Richter et al., 2020, Nat. Biotechnol. 38: 883-891), which produce an A-to-G conversion at the base site.

Deaminases that may be used as the components of exemplary base editors of the present disclosure are provided below, including but not limited to the deaminases set forth in Table 1 (the proteins as set forth in SEQ ID NO. 36-59 and 80-86).

TABLE 1

| Type of deaminases | | |
| --- | --- | --- |
| Name of cytidine deaminases and adenosine deaminases | SEQ ID NO. | Reference/doi |
| rAPOBEC1 | SEQ ID NO. 36 | 10.1038/nature17946 |
| hAPOBEC3A | SEQ ID NO. 37 | 10.1038/nbt.4198/10.1038/nbt.4261 |
| hAPOBEC3G-CTD | SEQ ID NO. 38 | 10.1101/658351 |
| PmCDA1 | SEQ ID NO. 39 | 10.1126/science.aaf8729 |
| tCDAIEQ | SEQ ID NO. 40 | 10.1038/s41467-022-32157-8 |
| hAID | SEQ ID NO. 41 | 10.1038/ncomms13330 |
| PpAPOBEC1 | SEQ ID NO. 42 | 10.1038/s41467-020-15887-5 |
| RrA3F | SEQ ID NO. 43 | 10.1038/s41467-020-15887-5 |
| AmAPOBEC1 | SEQ ID NO. 44 | 10.1038/s41467-020-15887-5 |
| SsAPOBEC3B | SEQ ID NO. 45 | 10.1038/s41467-020-15887-5 |
| hA3B | SEQ ID NO. 46 | 10.1016/j.molcel.2020.07.005 |
| hA3C | SEQ ID NO. 47 | 10.1016/j.molcel.2020.07.005 |
| hA3D | SEQ ID NO. 48 | 10.1016/j.molcel.2020.07.005 |
| hA3F | SEQ ID NO. 49 | 10.1016/j.molcel.2020.07.005 |
| hA3G | SEQ ID NO. 50 | 10.1016/j.molcel.2020.07.005 |
| hA3H | SEQ ID NO. 51 | 10.1016/j.molcel.2020.07.005 |
| hA3Bctd | SEQ ID NO. 52 | 10.1016/j.molcel.2020.07.005 |
| FERNY | SEQ ID NO. 53 | 10.1038/s41587-019-0193-0 |
| ecTadA | SEQ ID NO. 54 | 10.1038/nature24644 |
| mADA | SEQ ID NO. 55 | 10.1038/nature24644 |
| hADAR2 | SEQ ID NO. 56 | 10.1038/nature24644 |
| hADAT2 | SEQ ID NO. 57 | 10.1038/nature24644 |
| ecTadA*(7.10) | SEQ ID NO. 58 | 10.1038/nature24644 |
| TadA-8e | SEQ ID NO. 59 | 10.1038/s41587-020-0453-z |
| Sdd2 | SEQ ID NO. 80 | 10.1101/2023.05.21.541555 |
| Sdd3 | SEQ ID NO. 81 | 10.1101/2023.05.21.541555 |
| Sdd4 | SEQ ID NO. 82 | 10.1101/2023.05.21.541555 |
| Sdd6 | SEQ ID NO. 83 | 10.1101/2023.05.21.541555 |
| Sdd7/C57 | SEQ ID NO. 84 | 10.1101/2023.05.21.541555 |
| Sdd10 | SEQ ID NO. 85 | 10.1101/2023.05.21.541555 |
| Sdd59 | SEQ ID NO. 86 | 10.1101/2023.05.21.541555 | rAPOBEC1:
MSSETGPVAVDPTLRRRIEPHEFEVFFDPRELRKETCLLYEINWGGRHSIWRHTSQNTN
KHVEVNFIEKFTTERYFCPNTRCSITWFLSWSPCGECSRAITEFLSRYPHVTLFIYIARLY
HHADPNRQGLRDLISSGVTIQIMTEQESGYCWRNFVNYSPSNEAHWPRYPHLWVRL
YVLELYCIILGLPPCLNILRRKQPQLTFFTIALQSCHYQRLPPHILWATGLK (SEQ ID NO.
36)

hAPOBEC3A:
MEASPASGPRHLMDPHIFTSNFNNGIGRHKTYLCYEVERLDNGTSVKMDQHRGFLHN
QAKNLLCGFYGRHAELRFLDLVPSLQLDPAQIYRVTWFISWSPCFSWGCAGEVRAFLQ

TABLE 1-continued

Type of deaminases

| Name of cytidine deaminases and adenosine deaminases | SEQ ID NO. | Reference/doi |
| --- | --- | --- |

ENTHVRLRIFAARIYDYDPLYKEALQMLRDAGAQVSIMTYDEFKHCWDTFVDHQGCP
FQPWDGLDEHSQALSGRLRAILQNQGN (SEQ ID NO. 37)

hAPOBEC3G-CTD:
MDPPTFTFNFNNEPWVRGRHETYLCYEVERMHNDTWVLLNQRRGFLCNQAPHKHGF
LEGRHAELCFLDVIPFWKLDLDQDYRVTCFTSWSPCFSCAQEMAKFISKNKHVSLCIFT
ARIYDDQGRCQEGLRTLAEAGAKISIMTYSEFKHCWDTFVDHQGCPFQPWDGLDEHS
QDLSGRLRAILQNQEN (SEQ ID NO. 38)

PmCDA1:
MTDAEYVRIHEKLDIYTFKKQFFNNKKSVSHRCYVLFELKRRGERRACFWGYAVNKP
QSGTERGIHAEIFSIRKVEEYLRDNPGQFTINWYSSWSPCADCAEKILEWYNQELRGNG
HTLKIWACKLYYEKNARNQIGLWNLRDNGVGLNVMVSEHYQCCRKIFIQSSHNQLNE
NRWLEKTLKRAEKRRSELSIMIQVKILHTTKSPAVSRGSG (SEQ ID NO. 39)

tCDAIEQ:
SHRCYVLFELKRRGERRACFWGYAVNKPQSGTERGIHAEIFSIRKVEEYLRDNPGQFTI
NWYSSWSPCADCAEKILEWYNQELRGNGHTLKIEACKLYYEKNARNQIGLQNLRDNG
VGLNV (SEQ ID NO. 40)

hAID:
MDSLLMNRRKFLYQFKNVRWAKGRRETYLCYVVKRRDSATSFSLDFGYLRNKNGCH
VELLFLRYISDWDLDPGRCYRVTWFTSWSPCYDCARHVADFLRGNPNLSLRIFTARLYF
CEDRKAEPEGLRRLHRAGVQIAIMTFKDYFYCWNTFVENHERTFKAWEGLHENSVRL
SRQLRRILLPLYEVDDLRDAFRTLGL (SEQ ID NO. 41)

PpAPOBEC1:
MTSEKGPSTGDPTLRRRIESWEFDVFYDPRELRKETCLLYEIKWGMSRKIWRSSGKNT
TNHVEVNFIKKFTSERRFHSSISCSITWFLSWSPCWECSQAIREFLSQHPGVTLVIYVARL
FWHMDQRNRQGLRDLVNSGVTIQIMRASEYYHCWRNFVNYPPGDEAHWPQYPPLW
MMLYALELHCIILSLPPCLKISRRWQNHLAFFRLHLQNCHYQTIPPHILLATGLIHPSVT
WR (SEQ ID NO. 42)

RrA3F:
MKPQIRDHRPNPMEAMYPHIFYFHFENLEKAYGRNETWLCFTVEIIKQYLPVPWKKGV
FRNQVDPETHCHAEKCFLSWFCNNTLSPKKNYQVTWYTSWSPCPECAGEVAEFLAEH
SNVKLTIYTARLYYFWDTDYQEGLRSLSEEGASVEIMDYEDFQYCWENFVYDDGEPFK
RWKGLKYNFQSLTRRLREILQ (SEQ ID NO. 43)

AmAPOBEC1:
MADSSEKMRGQYISRDTFEKNYKPIDGTKEAHLLCEIKWGKYGKPWLHWCQNQRMN
IHAEDYFMNNIFKAKKHPVHCYVTWYLSWSPCADCASKIVKFLEERPYLKLTIYVAQL
YYHTEEENRKGLRLLRSKKVIIRVMDISDYNYCWKVFVSNQNGNEDYWPLQFDPWV
KENYSRLLDIFWESKCRSPNPW (SEQ ID NO. 44)

SsAPOBEC3B:
MDPQRLRQWPGPGPASRGGYGQRPRIRNPEEWFHELSPRTFSFHFRNLRFASGRNRSYI
CCQVEGKNCFFQGIFQNQVPPDPPCHAELCFLSWFQSWGLSPDEHYYVTWFISWSPCC
ECAAKVAQFLEENRNVSLSLSAARLYYFWKSESREGLRRLSDLGAQVGIMSFQDFQHC
WNNFVHNLGMPFQPWKKLHKNYQRLVTELKQILREEPATYGSPQAQGKVRIGSTAAG
LRHSHSHTRSEAHLRPNHSSRQHRILNPPREARARTCVLVDASWICYR (SEQ ID NO.
45)

hA3B:
MNPQIRNPMERMYRDTFYDNFENEPILYGRSYTWLCYEVKIKRGRSNLLWDTGVFRG
QVYFKPQYHAEMCFLSWFCGNQLPAYKCFQITWFVSWTPCPDCVAKLAEFLSEHPNV
TLTISAARLYYYWERDYRRALCRLSQAGARVKIMDYEEFAYCWENFVYNEGQQFMP
WYKFDENYAFLHRTLKEILRYLMDPDTFTFNFNNDPLVLRRRQTYLCYEVERLDNGT
WVLMDQHMGFLCNEAKNLLCGFYGRHAELRFLDLVPSLQLDPAQIYRVTWFISWSPC
FSWGCAGEVRAFLQENTHVRLRIFAARIYDYDPLYKEALQMLRDAGAQVSIMTYDEF
EYCWDTFVYRQGCPFQPWDGLEEHSQALSGRLRAILQNQGN (SEQ ID NO. 46)

hA3C:
MNPQIRNPMKAMYPGTFYFQFKNLWEANDRNETWLCFTVEGIKRRSVVSWKTGVFR
NQVDSETHCHAERCFLSWFCDDILSPNTKYQVTWYTSWSPCPDCAGEVAEFLARHSN
VNLTIFTARLYYFQYPCYQEGLRSLSQEGVAVEIMDYEDFKYCWENFVYNDNEPFKPW
KGLKTNFRLLKRRLRESLQ (SEQ ID NO. 47)

hA3D:
MNPQIRNPMERMYRDTFYDNFENEPILYGRSYTWLCYEVKIKRGRSNLLWDTGVFRG
PVLPKRQSNHRQEVYFRFENHAEMCFLSWFCGNRLPANRRFQITWFVSWNPCLPCVV
KVTKFLAEHPNVTLTISAARLYYYRDRDWRWVLLRLHKAGARVKIMDYEDFAYCWE
NFVCNEGQPFMPWYKFDDNYASLHRTLKEILRNPMEAMYPHIFYFHFKNLLKACGRN

TABLE 1-continued

<u>Type of deaminases</u>

Name of cytidine
deaminases and
adenosine
deaminases              SEQ ID NO.        Reference/doi ESWLCFTMEVTKHHSAVFRKRGVFRNQVDPETHCHAERCFLSWFCDDILSPNTNYEVT
WYTSWSPCPECAGEVAEFLARHSNVNLTIFTARLCYFWDTDYQEGLCSLSQEGASVKI
MGYKDFVSCWKNFVYSDDEPFKPWKGLQTNFRLLKRRLREILQ (SEQ ID NO. 48)

hA3F:
MKPHFRNTVERMYRDTFSYNFYNRPILSRRNTVWLCYEVKTKGPSRPRLDAKIFRGQ
VYSQPEHHAEMCFLSWFCGNQLPAYKCFQITWFVSWTPCPDCVAKLAEFLAEHPNVTL
TISAARLYYYWERDYRRALCRLSQAGARVKIMDDEEFAYCWENFVYSEGQPFMPWYK
FDDNYAFLHRTLKEILRNPMEAMYPHIFYFHFKNLRKAYGRNESWLCFTMEVVKHHSP
VSWKRGVFRNQVDPETHCHAERCFLSWFCDDILSPNTNYEVTWYTSWSPCPECAGEV
AEFLARHSNVNLTIFTARLYYFWDTDYQEGLRSLSQEGASVEIMGYKDFKYCWENFV
YNDDEPFKPWKGLKYNFLFLDSKLQEILE (SEQ ID NO. 49)
hA3G:

MKPHFRNTVERMYRDTFSYNFYNRPILSRRNTVWLCYEVKTKGPSRPPLDAKIFRGQV
YSELKYHPEMRFFHWFSKWRKLHRDQEYEVTWYISWSPCTKCTRDMATFLAEDPKV
TLTIFVARLYYFWDPDYQEALRSLCQKRDGPRATMKIMNYDEFQHCWSKFVYSQRELF
EPWNNLPKYYILLHIMLGEILRHSMDPPTFTFNFNNEPWVRGRHETYLCYEVERMHND
TWVLLNQRRGFLCNQAPHKHGFLEGRHAELCFLDVIPFWKLDLDQDYRVTCFTSWSP
CFSCAQEMAKFISKNKHVSLCIFTARIYDDQGRCQEGLRTLAEEAGAKISIMTYSEFKHC
WDTFVDHQGCPFQPWDGLDEHSQDLSGRLRAILQNQEN (SEQ ID NO. 50)

hA3H:
MALLTAETFRLQFNNKRRLRRPYYPRKALLCYQLTPQNGSTPTRGYFENKKKCHAEIC
FINEIKSMGLDETQCYQVTCYLTWSPCSSCAWELVDFIKAHDHLNLRIFASRLYYHWCK
PQQDGLRLLCGSQVPVEVMGFPEFADCWENFVDHEKPLSFNPYKMLEELDKNSRAIK
RRLDRIKS (SEQ ID NO. 51)

hA3Bctd:
MEILRYLMDPDTFTFNFNNDPLVLRRRQTYLCYEVERLDNGTWVLMDQHMGFLCNE
AKNLLCGFYGRHAELRFLDLVPSLQLDPAQIYRVTWFISWSPCFSWGCAGEVRAFLQE
NTHVRLRIFAARIYDYDPLYKEALQMLRDAGAQVSIMTYDEFEYCWDTFVYRQGCPF
QPWDGLEEHSQALSGRLRAILQNQGN (SEQ ID NO. 52)

FERNY:
FERNYDPRELRKETYLLYEIKWGKSGKLWRHWCQNNRTQHAEVYFLENIFNARRFNP
STHCSITWYLSWSPCAECSQKIVDFLKEHPNVNLEIYVARLYYHEDERNRQGLRDLVNS
GVTIRIMDLPDYNYCWKTFVSDQGGDEDYWPGHFAPWIKQYSLKL (SEQ ID NO. 53)

ecTadA:
MSEVEFSHEYWMRHALTLAKRAWDEREVPVGAVLVHNNRVIGEGWNRPIGRHDPTA
HAEIMALRQGGLVMQNYRLIDATLYVTLEPCVMCAGAMIHSRIGRVVFGARDAKTGA
AGSLMDVLHHPGMNHRVEITEGILADECAALLSDFFRMRRQEIKAQKKAQSSTD (SEQ
ID NO. 54)

mADA:
MAQTPAFNKPKVELHVHLDGAIKPETILYFGKKRGIALPADTVEELRNIIGMDKPLSLP
GFLAKFDYYMPVIAGCREAIKRIAYEFVEMKAKEGVVYVEVRYSPHLLANSKVDPMP
WNQTEGDVTPDDVVDLVNQGLQEGEQAFGIKVRSILCCMRHQPSWSLEVLELCKKYN
QKTVVAMDLAGDETIEGSSLFPGHVEAYEGAVKNGIHRTVHAGEVGSPEVVREAVDIL
KTERVGHGYHTIEDEALYNRLLKENMHFEVCPWSSYLTGAWDPKTTHAVVRFKNDKA
NYSLNTDDPLIFKSTLDTDYQMTKKDMGFTEEEFKRLNINAAKSSFLPEEEKKELLERL
YREYQ (SEQ ID NO. 55)

hADAR2:
MHLDQTPSRQPIPSEGLQLHLPQVLADAVSRLVLGKFGDLTDNFSSPHARRKVLAGVV
MTTGTDVKDAKVISVSTGTKCINGEYMSDRGLALNDCHAEIISRRSLLRFLYTQLELYL
NNKDDQKRSIFQKSERGGFRLKENVQFHLYISTSPCGDARIFSPHEPILEEPADRHPNRK
ARGQLRTKIESGEGTIPVRSNASIQTWDGVLQGERLLTMSCSDKIARWNVVGIQGSLLS
IFVEPIYFSSIILGSLYHGDHLSRAMYQRISNIEDLPPLYTLNKPLLSGISNAEARQPGKAP
NFSVNWTVGDSAIEVINATTGKDELGRASRLCKHALYCRWMRVHGKVPSHLLRSKITK
PNVYHESKLAAKEYQAAKARLFTAFIKAGLGAWVEKPTEQDQFSLTP (SEQ ID NO. 56)

hADAT2:
MEAKAAPKPAASGACSVSAEETEKWMEEAMHMAKEALENTEVPVGCLMVYNNEVV
GKGRNEVNQTKNATRHAEMVAIDQVLDWCRQSGKSPSEVFEHTVLYVTVEPCIMCAA
ALRLMKIPLVVYGCQNERFGGCGSVLNIASADLPNTGRPFQCIPGYRAEEAVEMLKTF
YKQENPNAPKSKVRKKECQKS (SEQ ID NO. 57)

ecTadA*(7.10):
MSEVEFSHEYWMRHALTLAKRARDEREVPVGAVLVLNNRVIGEGWNRAIGLHDPTAH
AEIMALRQGGLVMQNYRLIDATLYVTFEPCVMCAGAMIHSRIGRVVFGVRNAKTGAA

TABLE 1-continued

Type of deaminases

```
Name of cytidine
deaminases and
adenosine
deaminases          SEQ ID NO.      Reference/doi
```

GSLMDVLHYPGMNHRVEITEGILADECAALLCYFFRMPRQVFNAQKKAQSSTD (SEQ
ID NO. 58)

TadA*ABE8e (TadA-8e):
MSEVEFSHEYWMRHALTLAKRARDEREVPVGAVLVLNNRVIGEGWNRAIGLHDPTAH
AEIMALRQGGLVMQNYRLIDATLYVTFEPCVMCAGAMIHSRIGRVVFGVRNSKRGAA
GSLMNVLNYPGMNHRVEITEGILADECAALLCDFYRMPRQVFNAQKKAQSSIN (SEQ
ID NO. 59)

Sdd2
MAPDSLVWFDPLGLIVLQQVPYNDHPLFGAVSEFIQGKSRSDLRGRNVAAVLLDDGTVI
VRASEGGGNHAERVLMGLSEVDPAKVVAVYTERSPCTGRINCHDLLDSSLGADVPVY
YTHEMIRGQEGKTAQQIEADRNQFCRGG (SEQ ID NO. 80)

Sdd3
MSASAQLNTYLAAIGNSTTTVEAQPEAAPPPAAAESLDSTPRLPDGGIDFHALAKRLGL
LEARPTEQPPFDPRRFNPACWQGLKPYDQAGTAEGNLFIAPGKRWNTRPMQASKLEV
GPQSDLHPQWRSRKAPWHIEGKIAAYMRQKGFTDGCVYLNARPCSGPDGCARNLPDL
LPVGSTLHVHARYIDRTGETRFYYREYRGTGKALT (SEQ ID NO. 81)

Sdd4
MLDAMDAYLSEIAGGNAPARAGPKAPEPKQPGGSSSPRARDGRIDFRALLERLKAQGV
VGLEGRSDDPIPDFDPKKQNPACYQGLAPRQKGKPVRGNLFFPDGRRWNDVALESSRG
EPAFDLNIIKPEYRSLSPARGHLEGNVAAWMRSTFHQEMVLYINESPCRKHGKGCLYTL
EHFLPRGYVLHVWSRNDRGEWRGNTFRGSGEAFTEGA (SEQ ID NO. 82)

Sdd6
MVETRDKIIAAKSRSDAGLLAFQQATNGSIDSRPAEAIANLQRAKTHLDEAQRLVANSD
AAVDNYINAILGGASAATAQPSAVIPASKPSRFKPMRTDPAKADEIRPHVGKDRAVATL
WDADGNRVLGLHSADDDGPAATAAWKPPWRDYVRLRRHVEAHAAARMHQDGHKT
MVMYINLPPCKYFDGCKLNLEDILPKGSTLWMHRVFQNGGTKIYQFNGTGRAYV
(SEQ ID NO. 83)

Sdd7 (also represented as C57 in the present specification)
MLEAVRARLIGEGGGPGAVPEGGDGPPAVPAEEVERLRGELPPPVVPGTGQKTHGRWI
GPDGRVRAIVSGRDEDAALVHAQLAAKGIPDEPTRNSDVEQKLAAHMVANGIRHVTL
VINHRPCRGFDDSCDTLVPIILPEGCTLTVHGQTDKGMRVRVRYTGGARPWWS (SEQ
ID NO. 84)

Sdd10
MLDAALGAVRRIIAALGTSGAERASPGANGSERVDELAERLPPTVVPNTSAKTHGWW
FTGQGAAQELISGEGPDARAAYEALREEGYPRPGMPFVAMHVEIKLAAHMRRNDIEHA
TVVINNIPCPLVWGCENLIGVVLPEGSSLTVHGSNGYERTFTGGRKPPWPR (SEQ ID NO.
85)

Sdd59
MLLTPPPRPAAPPTTRPKPLVARTGDAYPPGTEWALPLIVQPHPPVGGTVPVEGHVRAL
RPESQISHVFHPGGGHWTEQARARLRVLPGFGWAVNLGHHVELQIAAWMTACGIHHA
ELVLNRPPCGERYGLGCHQALPVLLPRGYRLTVSSTRGGPQPYQHHYEGKA (SEQ ID
NO. 86)

Uracil Glycosylase Inhibitor (UGI)

In some embodiments, when a cytidine deaminase is used, a uracil glycosylase inhibitor (UGI) is fused to the N-terminal of the deaminase, whereas UGI is not required when an adenosine deaminase is used.

Exemplary UGI proteins that may be used as the component of the base editor of the present disclosure are disclosed below, including but not limited to the protein as set forth in SEQ ID NO.68.

TNLSDIIEKETGKQLVIQESILMLPEEVEEVI-
GNKPESDILVHTAYDESTDENVMLLT SDAPEYKP-
WALVIQDSNGENKIKML (SEQ ID NO.68)

Nuclear Localization Sequence (NLS)

In some embodiments of the present disclosure, the NLS of the fusion protein of the present disclosure may be located at N-terminal and/or C-terminal. In some embodiments of the present disclosure, the NLS of the fusion protein of the present disclosure may be located between the adenine deamination domain, the cytosine deamination domain, the nucleic acid-targeting domain and/or UGI. In some embodiments, the fusion protein comprises approximately 1, 2, 3, 4, 5, 6, 7, 8, 9, 10 or more NLS. In some embodiments, the fusion protein comprises approximately 1, 2, 3, 4, 5, 6, 7, 8, 9, 10 or more NLS at or near N-terminal. In some embodiments, the fusion protein comprises approximately 1, 2, 3, 4, 5, 6, 7, 8, 9, 10 or more NLS at or near C-terminal. In some embodiments, the polypeptide comprises a combination thereof, for example, comprising one or more NLS at N-terminal and one or more NLS at C-terminal. When more than one NLS are present, each NLS may be selected to be independent of other NLS.

Generally, NLS consists of one or more short sequences that are derived from positively charged lysine or arginine exposed on the surface of the protein, however, other types of NLS are also known. Non-limiting examples of NLS include KKRKV (SEQ ID NO. 150), PKKKRKV (SEQ ID NO. 151) or KRPAATKKAGQAKKKK (SEQ ID NO. 152).

Recombinant Expression Construct

Each component in the base editor of the present disclosure may be expressed separately, and may also be expressed as one or more fusion proteins. Alternatively, the above-mentioned elements or components are expressed separately or together by using the recombinant expression constructs used in recombinant genetic engineering technology. Exemplary recombinant expression constructs of the present disclosure are as set forth in for example, FIG. 16A to FIG. 16E and FIG. 17A to FIG. 17H.

The types, functions and references of the genes and the regulatory elements in the above-mentioned exemplary recombinant expression constructs (FIG. 16A to FIG. 16E and FIGS. 17A to 17H) are explained and exemplified below, as set forth in Table 2 below.

TABLE 2

Examples of the genes and the regulatory element in constructs

| Vector element | Function | Reference |
|---|---|---|
| MTS (Mitochondrial Targeting Sequence) | mitochondrial targeting peptide of *Homo sapiens* superoxide dismutase 2 that helps the translocation of proteins or fusion proteins including TALE, exonuclease, deaminase, UGI and the like to mitochondria. | Lei et al. Mitochondrial base editor induces substantial nuclear off-target mutations. Nature Vol. 606, 7915 (2022): 804-811. doi 10.1038/s41586-022-04836-5 |
| CTP (Chloroplast Transit Peptide) | chloroplast translocation peptide that helps the translocation of proteins or fusion proteins including TALE, exonuclease, deaminase, UGI and the like to chloroplasts. | Kang et al. Chloroplast and mitochondrial DNA editing in plants. Nature Plants Vol. 7, 2021: 899-905. doi: 10.1038/s41477-021-00943-9). |
| HA | human influenza hemagglutinin epitope tag, which is used for protein detection and purification. | Lei et al. Mitochondrial base editor induces substantial nuclear off-target mutations. Nature Vol. 606, 7915 (2022): 804-811. doi: 10.1038/s41586-022-04836-5 |
| CMV enhancer | fragment that enhances the expression of CMV promoter. | Boshart et al. A very strong enhancer is located upstream of an immediate early gene of human cytomegalovirus. Cell Vol. 41, 2 (1985): 521-30. doi: 10.1016/s0092-8674(85)80025-8 |
| CMV promoter | human cytomegalovirus 5' promoter region fragment that drives the expression of the downstream genes of interest (such as TALE, nickase and UGI). | Thomsen et al. Promoter-regulatory region of the major immediate early gene of human cytomegalovirus. PNAS Vol. 81, 3 (1984): 659-63. doi: 10.1073/pnas.81.3.659 |
| bGH poly(A) signal | bovine somatotropin polyadenylylation signal, which is used for the termination of transcription. | Pfarr et al. Differential Effects of Polyadenylation Regions on Gene Expression in Mammalian Cells. DNA Vol. 5, 2 (1986): 115-122. doi: 10.1089/dna.1986.5.115 |
| UTR | untranslated region. | Lei et al. Mitochondrial base editor induces substantial nuclear off-target mutations. Nature Vol. 606, 7915 (2022): 804-811. doi: 10.1038/s41586-022-04836-5 |
| Amp$^R$ | gene encoding β-lactamase, which confers resistance to ampicillin, carbenicillin, and related antibiotics. | Lei et al. Mitochondrial base editor induces substantial nuclear off-target mutations. Nature Vol. 606, 7915 (2022): 804-811. doi 10.1038/s41586-022-04836-5 |
| Amp$^R$ promoter | promoter that drives the expression of AmpR gene. | Lei et al. Mitochondrial base editor induces substantial nuclear off-target mutations. Nature Vol. 606, 7915 (2022): 804-811. doi 10.1038/s41586-022-04836-5 |
| T7 promoter | A promoter synthesized by bacteriophage that could be recognized by T7 RNA polymerase. | Lei et al. Mitochondrial base editor induces substantial nuclear off-target mutations. Nature Vol. 606, 7915 (2022): 804-811. doi: 10.1038/s41586-022-04836-5 |
| UGI | inhibitor of uracil-DNA glycosylase derived from a *Bacillus subtilis* bacteriophage that protects the uracil in DNA by irreversibly inhibiting uracil-DNA glycosylase which is the key DNA repair enzyme (UDG). | Mo et al. Crystal structure of human uracil-DNA glycosylase in complex with a protein inhibitor: protein mimicry of DNA. Cell Vol. 82, 5 (1995): 701-8. doi: 10.1016/0092-8674(95)90467-0 |

TABLE 2-continued

| Examples of the genes and the regulatory element in constructs | | |
|---|---|---|
| Vector element | Function | Reference |
| deaminase | including cytidine deaminases that convert C to U and adenosine deaminases that convert A to I | Komor et al. Programmable editing of a target base in genomic DNA without double-stranded DNA cleavage. Nature Vol. 533, 7603 (2016): 420-4. doi: 10.1038/nature17946; Gaudelli et al. Programmable base editing of A•T to G•C in genomic DNA without DNA cleavage. Nature Vol. 551, 7681 (2017): 464-471. doi: 10.1038/nature24644 |
| exonuclease | including 5' exonuclease such as mExoI and 3' exonuclease such as Trex2, for the digestion of the nicked DNA strand. | Lee et al. Expression specificity of the mouse exonuclease 1 (mExo1) gene. Nucleic Acids Research. Vol. 27, 20 (2022): 4114-20. doi: 10.1093/nar/27.20.4114 |
| linker | linker peptide, sequence between two protein domains of a fusion protein, for flexible linkage, wherein an XTEN linker peptide may be selected. | Komor et al. Programmable editing of a target base in genomic DNA without double-stranded DNA cleavage. Nature Vol. 533, 7603 (2016): 420-4. doi: 10.1038/nature17946 |
| CaMV 35S promoter | a constitutive promoter, which is used to drive high-level gene expression in dicotyledon. | Odell, J. T., Nagy, F. & Chua, N. H. Identification of DNA sequences required for activity of the cauliflower mosaic virus 35S promoter. Nature 313, 810-812, doi: 10.1038/313810a0 (1985). |
| Enhanced CaMV 35S promoter | a CaMV 35S promoter derivative, which is used to drive the expression of the downstream genes (Hyg, etc). | Shan, Q. et al. Rapid and efficient gene modification in rice and Brachypodium using TALENs. Mol Plant 6, 1365-1368, doi: 10.1093/mp/sss162 (2013) |
| 2 × CaMV 35S promoter | a CaMV 35S promoter derivative that drive the expression of the downstream genes. | Shan, Q. et al. Rapid and efficient gene modification in rice and Brachypodium using TALENs. Mol Plant 6, 1365-1368, doi: 10.1093/mp/sss162 (2013) |
| Ubi-promoter | a Zea mays-derived promoter that has high expression activity in monocotyledon and is used to drive the expression of the downstream genes (TALE-L, TALE-R, etc). | Shan, Q. et al. Rapid and efficient gene modification in rice and Brachypodium using TALENs. Mol Plant 6, 1365-1368, doi: 10.1093/mp/sss162 (2013) |
| CaMV poly(A) signal | poly(A) signal from CaMV, which is used for the termination of gene transcription. | Shan, Q. et al. Rapid and efficient gene modification in rice and Brachypodium using TALENs. Mol Plant 6, 1365-1368, doi: 10.1093/mp/sss162 (2013) |
| Nos terminator | NOS terminator of Agrobacterium tumefaciens, which is used for the termination of gene transcription. | Shan, Q. et al. Rapid and efficient gene modification in rice and Brachypodium using TALENs. Mol Plant 6, 1365-1368, doi: 10.1093/mp/sss162 (2013) |
| E9 terminator | terminator of pea rbcS E9 gene, which is used for the termination of gene transcription. | Xing, H. L. et al. A CRISPR/Cas9 toolkit for multiplex genome editing in plants. BMC Plant Biol 14, 327, doi: 10.1186/s12870-014-0327-y (2014) |
| pUC ori | Origin of replication of a high-copy expression plasmid in E. coli. | Shan, Q. et al. Rapid and efficient gene modification in rice and Brachypodium using TALENs. Mol Plant 6, 1365-1368, doi: 10.1093/mp/sss162 (2013) |
| CAP binding site | binding site of Catabolite activator protein, which activates transcription of the α-subunit of RNA Polymerase through the protein-protein interaction. | Shan, Q. et al. Rapid and efficient gene modification in rice and Brachypodium using TALENs. Mol Plant 6, 1365-1368, doi: 10.1093/mp/sss162 (2013) |
| bom | a structure required for plasmid transfer during bacterial conjugation. | Hajdukiewicz, P., Svab, Z. & Maliga, P. The small, versatile pPZP family of Agrobacterium binary vectors for plant transformation. Plant Mol Biol 25, 989-994, doi: 10.1007/bf00014672 (1994) |
| HygR | Hygromycin B-resistance gene, as a selection marker for Agrobacterium-mediated transformation. | Gritz, L. & Davies, J. Plasmid-encoded hygromycin B resistance: the sequence of hygromycin B phosphotransferase gene and its expression in Escherichia coli and Saccharomyces cerevisiae. Gene 25, 179-188, doi: 10.1016/0378-1119(83)90223-8 (1983) |
| Kan^R | gene encoding neomycin phosphotransferase, which | Hajdukiewicz, P., Svab, Z. & Maliga, P. The small, versatile pPZP family of |

TABLE 2-continued

| Vector element | Function | Reference |
|---|---|---|
| | confers resistance to kanamycin. | *Agrobacterium* binary vectors for plant transformation. Plant Mol Biol 25, 989-994, doi: 10.1007/bf00014672 (1994) |
| pVS1 oriV | for replication/plasmid stability in *Agrobacterium*, for *Agrobacterium*-mediated transformation. | Hajdukiewicz, P., Svab, Z. & Maliga, P. The small, versatile pPZP family of *Agrobacterium* binary vectors for plant transformation. Plant Mol Biol 25, 989-994, doi: 10.1007/bf00014672 (1994) |
| pVS1 repA | for replication/plasmid stability in *Agrobacterium*, for *Agrobacterium*-mediated transformation. | Hajdukiewicz, P., Svab, Z. & Maliga, P. The small, versatile pPZP family of *Agrobacterium* binary vectors for plant transformation. Plant Mol Biol 25, 989-994, doi: 10.1007/bf00014672 (1994) |
| pVS1 staA | for replication/plasmid stability in *Agrobacterium*, for *Agrobacterium*-mediated transformation. | Hajdukiewicz, P., Svab, Z. & Maliga, P. The small, versatile pPZP family of *Agrobacterium* binary vectors for plant transformation. Plant Mol Biol 25, 989-994, doi: 10.1007/bf00014672 (1994) |
| LB | T-DNA left border repeat sequence, which is used for the definition and delimitation of T-DNA region. | Zambryski, P., Depicker, A., Kruger, K. & Goodman, H. M. Tumor induction by *Agrobacterium tumefaciens*: analysis of the boundaries of T-DNA. J Mol Appl Genet 1, 361-370 (1982) |
| RB | T-DNA right border repeat sequence, which is used for the definition and delimitation of T-DNA region. | Zambryski, P., Depicker, A., Kruger, K. & Goodman, H. M. Tumor induction by *Agrobacterium tumefaciens*: analysis of the boundaries of T-DNA. J Mol Appl Genet 1, 361-370 (1982) |
| SV40 NLS | composed of 7-amino acid PKKKRKV, SV (simian virus) 40 nuclear localization signal as a signal fragment, mediating the transport of proteins of interest into the nucleus | Zhang et al. Transcription activator-like effector nucleases enable efficient plant genome engineering. Plant physiology vol. 161, 1 (2013): 20-7. doi: 10.1104/pp.112.205179 |
| TALEN scaffold | a modified TALEN scaffold with truncations in N-terminal region and C-terminal region respectively (ΔN152/C63) | Zhang et al. Transcription activator-like effector nucleases enable efficient plant genome engineering. Plant physiology vol. 161, 1 (2013): 20-7. doi: 10.1104/pp.112.205179 |
| TALE-L and TALE-R | synthetic repeat sequences encoding TALE-L and TALE-R protein, which are used for the targeted binding of DNA sequences of interest. | Shan, Q. et al. Rapid and efficient gene modification in rice and Brachypodium using TALENs. Mol Plant 6, 1365-1368, doi: 10.1093/mp/sss162 (2013) |
| FokI-L and FokI-R | encoding the cleavage domains of FokI enzyme, for realizing the nick of DNA strands of interest when fused to TALE, working as heterodimer. | Miller, JC et al. An improved zinc-finger nuclease architecture for highly specific genome editing. Nature biotechnology vol. 25, 7 (2007): 778-85. doi: 10.1038/nbt1319 |
| T2A | Thosea asigna virus 2A peptide separates polypeptides during the translation process in eukaryotic cells so as to express a plurality of proteins in a single ORF. | Szymczak, A. L. & Vignali, D. A. Development of 2A peptide-based strategies in the design of multicistronic vectors. Expert Opin Biol Ther 5, 627-638, doi: 10.1517/14712598.5.5.627 (2005). |

Specifically, the genes and the regulatory elements in exemplary recombinant constructs used in the present disclosure include but are not limited to the following sequences: promoter sequences as set forth in SEQ ID NO. 69-72; terminator sequences as set forth in SEQ ID NO. 73-76; mitochondrial targeting sequences (MTS) as set forth in SEQ ID NO. 77-78; and chloroplast translocation peptide (CTP) sequence as set forth in SEQ ID NO. 79.

```
UBI promoter:
                                    (SEQ ID NO. 69)
TGACCCGGTCGTGCCCCTCTCTAGAGATAATGAGCATTGCATGTCTAAGTTATAAAA

AATTACCACATATTTTTTTTGTCACACTTGTTTGAAGTGCAGTTTATCTATCTTTATAC

ATATATTTAAACTTTACTCTACGAATAATATAATCTATAGTACTACAATAATATCAGTGT

TTTAGAGAATCATATAAATGAACAGTTAGACATGGTCTAAAGGACAATTGAGTATTTT

GACAACAGGACTCTACAGTTTTATCTTTTTAGTGTGCATGTGTTCTCCTTTTTTTTTG
```

-continued

CAAATAGCTTCACCTATATAATACTTCATCCATTTTATTAGTACATCCATTTAGGGTTTA

GGGTTAATGGTTTTTATAGACTAATTTTTTTAGTACATCTATTTTATTCTATTTTAGCCT

CTAAATTAAGAAAACTAAAACTCTATTTTAGTTTTTTTATTTAATAATTTAGATATAAA

ATAGAATAAAATAAAGTGACTAAAAATTAAACAAATACCCTTTAAGAAATTAAAAAA

ACTAAGGAAACATTTTTCTTGTTTCGAGTAGATAATGCCAGCCTGTTAAACGCCGTC

GACGAGTCTAACGGACACCAACCAGCGAACCAGCAGCGTCGCGTCGGGCCAAGCG

AAGCAGACGGCACGGCATCTCTGTCGCTGCCTCTGGACCCCTCTCGATCGAGAGTT

CCGCTCCACCGTTGGACTTGCTCCGCTGTCGGCATCCAGAAATTGCGTGGCGGAGC

GGCAGACGTGAGCCGGCACGGCAGGCGGCCTCCTCCTCCTCTCACGGCACCGGCA

GCTACGGGGGATTCCTTTCCCACCGCTCCTTCGCTTTCCCTTCCTCGCCCGCCGTAAT

AAATAGACACCCCCTCCACACCCTCTTTCCCCAACCTCGTGTTGTTCGGAGCGCAC

ACACACACAACCAGATCTCCCCCAAATCCACCCGTCGGCACCTCCGCTTCAAGGTA

CGCCGCTCGTCCTCCCCCCCCCCCCCTCTCTACCTTCTCTAGATCGGCGTTCCGGTC

CATGGTTAGGGCCCGGTAGTTCTACTTCTGTTCATGTTTGTGTTAGATCCGTGTTTGT

GTTAGATCCGTGCTGCTAGCGTTCGTACACGGATGCGACCTGTACGTCAGACACGTT

CTGATTGCTAACTTGCCAGTGTTTCTCTTTGGGGAATCCTGGGATGGCTCTAGCCGT

TCCGCAGACGGGATCGATTTCATGATTTTTTTTGTTTCGTTGCATAGGGTTTGGTTTG

CCCTTTTCCTTTATTTCAATATATGCCGTGCACTTGTTTGTCGGGTCATCTTTTCATGC

TTTTTTTTGTCTTGGTTGTGATGATGTGGTCTGGTTGGGCGGTCGTTCTAGATCGGAG

TAGAATTAATTCTGTTTCAAACTACCTGGTGGATTTATTAATTTTGGATCTGTATGTGT

GTGCCATACATATTCATAGTTACGAATTGAAGATGATGGATGGAAATATCGATCTAGG

ATAGGTATACATGTTGATGCGGGTTTTACTGATGCATATACAGAGATGCTTTTTGTTC

GCTTGGTTGTGATGATGTGGTGTGGTTGGGCGGTCGTTCATTCGTTCTAGATCGGAG

TAGAATACTGTTTCAAACTACCTGGTGTATTTATTAATTTTGGAACTGTATGTGTGTG

TCATACATCTTCATAGTTACGAGTTTAAGATGGATGGAAATATCGATCTAGGATAGGT

ATACATGTTGATGTGGGTTTTACTGATGCATATACATGATGGCATATGCAGCATCTATT

CATATGCTCTAACCTTGAGTACCTATCTATTATAATAAACAAGTATGTTTTATAATTATT

TTGATCTTGATATACTTGGATGATGGCATATGCAGCAGCTATATGTGGATTTTTTTAGC

CCTGCCTTCATACGCTATTTATTTGCTTGGTACTGTTTCTTTTGTCGATGCTCACCCTG

TTGTTTGGTGTTACTTCTGCA

CaMV 35S promoter (enhanced):
                                                 (SEQ ID NO. 70)
TGAGACTTTTCAACAAAGGGTAATATCGGGAAACCTCCTCGGATTCCATTGCCCAGC

TATCTGTCACTTCATCAAAAGGACAGTAGAAAAGGAAGGTGGCACCTACAAATGCC

ATCATTGCGATAAAGGAAAGGCTATCGTTCAAGATGCCTCTGCCGACAGTGGTCCCA

AAGATGGACCCCCACCCACGAGGAGCATCGTGGAAAAAGAAGACGTTCCAACCAC

GTCTTCAAAGCAAGTGGATTGATGTGATAACATGGTGGAGCACGACACTCTCGTCT

ACTCCAAGAATATCAAAGATACAGTCTCAGAAGACCAAAGGGCTATTGAGACTTTT

CAACAAAGGGTAATATCGGGAAACCTCCTCGGATTCCATTGCCCAGCTATCTGTCAC

TTCATCAAAAGGACAGTAGAAAAGGAAGGTGGCACCTACAAATGCCATCATTGCGA

TAAAGGAAAGGCTATCGTTCAAGATGCCTCTGCCGACAGTGGTCCCAAAGATGGAC

-continued

CCCCACCCACGAGGAGCATCGTGGAAAAAGAAGACGTTCCAACCACGTCTTCAAA

GCAAGTGGATTGATGTGATATCTCCACTGACGTAAGGGATGACGCACAATCCCACTA

TCCTTCGCAAGACCTTCCTCTATATAAGGAAGTTCATTTCATTTGGAGAGGACACGC

TGA

CaMV 2 x 35S promoter (SEQ ID NO. 71)

CCTGCAGGTCAACATGGTGGAGCACGACACACTTGTCTACTCCAAAAATATCAAAG

ATACAGTCTCAGAAGACCAAAGGGCAATTGAGACTTTTCAACAAAGGGTAATATCC

GGAAACCTCCTCGGATTCCATTGCCCAGCTATCTGTCACTTTATTGTGAAGATAGTG

GAAAAGGAAGGTGGCTCCTACAAATGCCATCATTGCGATAAAGGAAAGGCCATCGT

TGAAGATGCCTCTGCCGACAGTGGTCCCAAAGATGGACCCCCACCCACGAGGAGC

ATCGTGGAAAAAGAAGACGTTCCAACCACGTCTTCAAAGCAAGTGGATTGATGTGA

TAACATGGTGGAGCACGACACACTTGTCTACTCCAAAAATATCAAAGATACAGTCTC

AGAAGACCAAAGGGCAATTGAGACTTTTCAACAAAGGGTAATATCCGGAAACCTCC

TCGGATTCCATTGCCCAGCTATCTGTCACTTTATTGTGAAGATAGTGGAAAAGGAAG

GTGGCTCCTACAAATGCCATCATTGCGATAAAGGAAAGGCCATCGTTGAAGATGCCT

CTGCCGACAGTGGTCCCAAAGATGGACCCCCACCCACGAGGAGCATCGTGGAAAA

AGAAGACGTTCCAACCACGTCTTCAAAGCAAGTGGATTGATGTGATATCTCCACTG

ACGTAAGGGATGACGCACAATCCCACTATCCTTCGCAAGACCCTTCCTCTATATAAG

GAAGTTCATTTCATTTGGAGAGGACCTCGACCTCAACACAACATATACAAAACAAA

CGAATCTCAAGCAATCAAGCATTCTACTTCTATTGCAGCAATTTAAATCATTTCTTTT

AAAGCAAAAGCAATTTTCTGAAAATTTTCACCATTTACGAACGATA

CMV promoter:

(SEQ ID NO. 72)

GTGATGCGGTTTTGGCAGTACATCAATGGGCGTGGATAGCGGTTTGACTCACGGGG

ATTTCCAAGTCTCCACCCCATTGACGTCAATGGGAGTTTGTTTTGGCACCAAAATCA

ACGGGACTTTCCAAAATGTCGTAACAACTCCGCCCCATTGACGCAAATGGGCGGTA

GGCGTGTACGGTGGGAGGTCTATATAAGCAGAGCT

Nos terminator:

(SEQ ID NO. 73)

GAATTTCCCCGATCGTTCAAACATTTGGCAATAAAGTTTCTTAAGATTGAATCCTGTT

GCCGGTCTTGCGATGATTATCATATAATTTCTGTTGAATTACGTTAAGCATGTAATAAT

TAACATGTAATGCATGACGTTATTTATGAGATGGGTTTTTATGATTAGAGTCCCGCAA

TTATACATTTAATACGCGATAGAAAACAAAATATAGCGCGCAAACTAGGATAAATTAT

CGCGCGCGGTGTCATCTATGTTACT

E9 terminator:

(SEQ ID NO. 74)

AGAGCTTTCGTTCGTATCATCGGTTTCGACAACGTTCGTCAAGTTCAATGCATCAGT

TTCATTGCGCACACACCAGAATCCTACTGAGTTTGAGTATTATGGCATTGGGAAAAC

TGTTTTTCTTGTACCATTTGTTGTGCTTGTAATTTACTGTGTTTTTTATTCGGTTTTCG

CTATCGAACTGTGAAATGGAAATGGATGGAGAAGAGTTAATGAATGATATGGTCCTT

TTGTTCATTCTCAAATTAATATTATTTGTTTTTTCTCTTATTTGTTGTGTGTTGAATTTG

AAATTATAAGAGATATGCAAACATTTTGTTTTGAGTAAAAATGTGTCAAATCGTGGC

CTCTAATGACCGAAGTTAATATGAGGAGTAAAACACTTGTAGTTGTACCATTATGCTT

ATTCACTAGGCAACAAATATATTTTTCAGACCTAGAAAAGCTGCAAATGTTACTGAAT

-continued

ACAAGTATGTCCTCTTGTGTTTTAGACATTTATGAACTTTCCTTTATGTAATTTTCCAG

AATCCTTGTCAGATTCTAATCATTGCTTTATAATTATAGTTATACTCATGGATTTGTAGT

TGAGTATGAAAATATTTTTTAATGCATTTTATGACTTGCCAATTGATTGACAAC

CaMV poly(A) signal:
                                                        (SEQ ID NO. 75)
TTTCTCCATAATAATGTGTGAGTAGTTCCCAGATAAGGGAATTAGGGTTCCTATAGGG

TTTCGCTCATGTGTTGAGCATATAAGAAACCCTTAGTATGTATTTGTATTTGTAAAATA

CTTCTATCAATAAAATTTCTAATTCCTAAAACCAAAATCCAGTACTAAAATCCAGATC bGH poly(A) signal:
                                                        (SEQ ID NO. 76)
CTGTGCCTTCTAGTTGCCAGCCATCTGTTGTTTGCCCCTCCCCCGTGCCTTCCTTGAC

CCTGGAAGGTGCCACTCCCACTGTCCTTTCCTAATAAAATGAGGAAATTGCATCGCA

TTGTCTGAGTAGGTGTCATTCTATTCTGGGGGGTGGGGTGGGGCAGGACAGCAAGG

GGGAGGATTGGGAAGACAATAGCAGGCATGCTGGGGATGCGGTGGGCTCTATGG.

SOD2 MTS:
                                                        (SEQ ID NO. 77)
MLSRAVCGTSRQLAPVLGYLGSRQKHSLPD

COX8 MTS:
                                                        (SEQ ID NO. 78)
MSVLTPLLLRGLTGSARRLPVPRAK

CTP:
                                                        (SEQ ID NO. 79)
MAPTVMMASSATAVAPFQGLKSAASLPVARRSTRSLGNVSNGGRIRCMQ

Target Cells of Interest

The recombinant expression construct provided by the present disclosure may be produced according to the genetic engineering methods known in the art. In some embodiments, a base editor or a recombinant expression construct thereof is introduced into a cell to edit a target gene and enable its expression, thereby forming an edited genetically engineered cell.

Any cell derived from any organism may be used with the nucleic acids, polypeptides, compositions and methods of the present disclosure. Cells include but are not limited to a human cell, a non-human cell, an animal cell, a mammalian cell, a bacterium, a protist, a fungus, an insect cell, a yeast, a non-conventional yeast and a plant cell, and include a monocotyledon, a dicotyledon and a plant element, as well as a plant and a seed produced by the method of the present disclosure. In some aspects, the cell of the organism is a germ cell, a somatic cell, a meiotic cell, a mitotic cell, a stem cell or a pluripotent stem cell.

In some embodiments, animal cells may include but are not limited to cells derived from the organisms of phylums including phylum Chordata, phylum Arthropoda, phylum Mollusca, phylum Annelida, phylum Coelenterata or phylum Echinodermata and the organisms of classes including mammal, insect, bird, amphibian, reptile or fish. In some aspects, the animal is a human, a mouse, a *Caenorhabditis elegans*, a rat, a fruit fly, a zebrafish, a chicken, a dog, a cattle, a sheep, a pig, a guinea pig, a hamster, a chicken, a Japanese rice fish, a sea lamprey, a puffer, a tree frog, a monkey or a chimpanzee.

Specific types of animal cell include a haploid cell, a diploid cell, a germ cell, a neuron, a muscle cell, an endocrine cell or an exocrine cell, an epithelial cell, a muscle cell, a tumor cell, an embryonic cell, a hematopoietic cell, an osteocyte, a germplasm cell, a somatic cell, a stem cell, a pluripotent stem cell, an induced pluripotent stem cell, a progenitor cell, a meiotic cell, and a mitotic cell. In some aspects, multiple cells derived from an organism may be used.

In some embodiments, plant cells include cells derived from monocotyledons and dicotyledons. Examples of monocotyledons that may be used include but are not limited to corn (*Zea mays*), rice (*Oryza sativa*), rye (*Secale cereale*), sorghum (*Sorghum bicolor, Sorghum vulgare*), millet (for example, pearl millet, *Pennisetum glaucum*), maiden cane (*Panicum miliaceum*), unhusked rice (*Setaria italica*), finger millet (*Eleusine coracana*), wheat (*Triticum* spp., for example, *Triticum aestivum, Triticum monococcum*), sugarcane (*Saccharum* spp.), oat (*Avena*), barley (*Hordeum*), switchgrass (*Panicum virgatum*), pineapple (*Ananas comosus*), banana (*Musa* spp.), palm, an ornamental plant, turfgrass, and other grasses. Examples of dicotyledons that may be used include but are not limited to soybean (*Glycine max*), *Brassica* species (such as, but not limited to oilseed rape or canola), *Brassica napus, B. campestris, Brassica rapa, Brassica. juncea*), alfalfa (*Medicago sativa*), tobacco (*Nicotiana tabacum*), Arabidopsis (*Arabidopsis thaliana*), sunflower (*Helianthus annuus*), cotton (*Gossypium arboreum, Gossypium barbadense*), peanut (*Arachis hypogaea*), tomato (*Solanum lycopersicum*), potato (*Solanum tuberosum*). Additional plants that may be used include safflower (*Carthamus tinctorius*), sweet potato (*Ipomoea batatas*), cassava (*Manihot esculenta*), coffee (*Coffea* spp.), coconut (*Cocos nucifera*), citrus tree (*Citrus* spp.), cocoa (*Theobroma cacao*), tea tree (tea, *Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugarbeet (*Beta*

*vulgaris*), vegetable, an ornamental plant, and a conifer. Vegetables that may be used include tomato (*Lycopersicon esculentum*), lettuce (for example, *Lactuca sativa*), green bean (*Phaseolus vulgaris*), lima bean (*Phaseolus limensis*), pea (*Lathyrus* spp.) and members of genus *Cucumis* such as cucumber (*C. sativus*), cantaloupe (*C. cantalupensis*), musk melon (*C. melo*). Ornamental plants include rhododendrons (*Rhododendron* spp.), hydrangea (*Macrophylla hydrangea*), Hibiscus rosasanensis, rose (*Rosa* spp.), tulip (*Tulipa* spp.), narcissus (*Narcissus* spp.), *Petunia hybrida, Dianthus caryophyllus, Euphorbia pulcherrima* and chrysanthemums. Conifers that may be used include pine trees such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglasfir (*Pseudotsuga menziesii*); Western hemlock (*Tsuga canadensis*); Sitka spruce (*Picea glauca*); redwood (*Sequoia sempervirens*); true firs, such as silver fir (*Abies amabilis*) and balsam fir (*Abies balsamea*); and cedars, such as *Thuja plicata* and *Chamaecyparis nootkatensis.*

Specific types of plant cell include but are not limited to cells derived from a whole plant, a seedling, a meristem, a ground tissue, a vascular tissue, a dermal tissue, a seed, a leaf, a root, a bud, a stem, a flower, a fruit, a stolon, a bulb, a tuber, a corm, an asexual terminal branch, a bud, a budlet, a tumor tissue, and various forms of cells and cultures (for example, a single cell, a protoplast, an embryo, a callus). They may exist in a plant or a plant organ, a tissue culture, or a cell culture.

Therapeutic Use

The present disclosure also encompasses the use of the base editor of the present disclosure in the treatment of diseases.

The up-regulation, down-regulation, inactivation, activation or mutation correction of disease-related genes, the introduction of disease-related genes to disease-related sites or the like may be achieved by modifying disease-related genes with the base editor of the present disclosure, thereby realizing the prevention and/or treatment of diseases and/or the establishment of disease-related models. For example, the target nucleic acid region as described in the present disclosure may be located in the protein coding region of a disease-related gene, or, for example, may be located in a regulatory region of gene expression such as a promoter region or an enhancer region, thereby capable of achieving the functional modification of the disease-related gene or the modification of the expression of the disease-related gene. Therefore, the modifications of a disease-related gene as described herein include the modifications of the disease-related gene itself (for example, the protein coding region), as well as the modifications of its expression regulatory regions (such as a promoter, an enhancer, an intron, etc.).

A "disease-related" gene refers to any gene that produces a transcription product or translation product at an abnormal level or in an abnormal form in cells derived from a disease-affected tissue as compared with the non-disease control tissue or cell. In a case where the modified expression is associated with the occurrence and/or progression of a disease, it may be a gene that is expressed at an abnormally high level, and it may be a gene that is expressed at an abnormally low level. A disease-related gene also refers to a genetically mutated gene that has one or more mutations, or is directly responsible for the etiology of the disease or in linkage disequilibrium with one or more genes responsible for the etiology of the disease. The mutation or genetic variation is, for example, a single nucleotide variation (SNV). The products of transcription or translation may be known or unknown, and may be at a normal level or an abnormal level.

Accordingly, the present disclosure also provides a method for treating a disease in a subject in need thereof, comprising delivering an effective amount of the base editor of the present disclosure to the subject so as to modify a gene related to the disease (for example, subjecting the mitochondrial DNA to deamination via one or more fusion proteins). The present disclosure also provides the use of the base editor in the preparation of a pharmaceutical composition for treating a disease in a subject in need thereof, wherein the base editor is used to modify a gene related to the disease. The present disclosure also provides a pharmaceutical composition for treating a disease in a subject in need thereof, comprising the base editor of the present disclosure and optionally a pharmaceutically acceptable carrier, wherein the base editor is used to modify a gene related to the disease.

In some embodiments, the fusion protein or the base editor described in the present disclosure is used to introduce a point mutation into a nucleic acid by subjecting the target nucleobase (for example, C residue) to deamination. In some embodiments, the deamination of the target nucleobase results in the correction of a genetic defect, for example, upon correcting a point mutation that leads to the loss of function in the genetic product. In some embodiments, the genetic defect is associated with a disease or condition (for example, lysosomal storage disease or a metabolic disease such as Type I diabetes). In some embodiments, the method provided herein may be used to introduce an inactivating point mutation into a gene or an allele encoding a genetic product associated with the disease or disorder.

In some embodiments, the embodiments described in the present disclosure are intended to restore the function of a dysfunctional gene via genome editing. The nucleobase editing protein provided herein may be used for in-vitro gene editing of human cells, such as the correction of a disease-related mutation in a human cell culture.

In some embodiments, the embodiments described in the present disclosure are intended for the treatment of a disease associated with or caused by a point mutation, and the point mutation may be corrected by the DNA base editing fusion protein provided herein. In some embodiments, the disease is a proliferative disease. In some embodiments, the disease is a genetic disease. In some embodiments, the disease is a de novo disease. In some embodiments, the disease is a metabolic disease. In some embodiments, the disease is lysosomal storage disease.

In some embodiments, the embodiments described in the present disclosure are intended for the treatment of mitochondrial diseases or disorders. As used herein, a "mitochondrial disease" refers to a disease caused by abnormal mitochondria, for example, a mitochondrial gene mutation, a gene mutation in enzymatic pathway, etc. Examples of the disease include but are not limited to neurological diseases, loss of motion control, muscle weakness and pain, gastrointestinal diseases and difficulty in swallowing, poor growth, heart diseases, liver diseases, diabetes, respiratory complications, epilepsy, vision/hearing problems, lactic acidosis, developmental retardation and susceptibility to infection.

Examples of the diseases described in the present disclosure include but are not limited to genetic diseases, circulatory system diseases, muscle diseases, diseases in brain, nervous centralis and immune system, Alzheimer's disease, secretase disorders, amyotrophic lateral sclerosis (ALS), autism, trinucleotide repeat expansion disorder, hearing diseases, gene-targeted therapy of non-dividing cells (neurons, muscle cells), liver and kidney diseases, diseases in epithelial cells and lung, cancer, Usher syndrome or retinitis pigmentosa-39, cystic fibrosis, HIV and AIDS, β-mediterranean anemia, sickle cell disease, herpes simplex virus, autism, drug addiction, age-related macular degeneration, and schizophrenia. Other diseases treated by correcting point mutations or introducing inactivating mutations into disease-related genes are known to a person skilled in the art, and therefore, the present disclosure is not limited in this regard. In addition to the diseases illustratively described in the present disclosure, the strategy and the fusion protein provided by the present disclosure may also be used to treat other related diseases, and this application is apparent to a person skilled in the art. For diseases or targets applicable to the present disclosure, please refer to the related diseases for which base editors are applicable as listed in WO2015089465A1 (PCT/US2014/070135), WO2016205711A1 (PCT/US2016/038181), WO2018141835A1 (PCT/EP2018/052491), WO2020191234A1 (PCT/US2020/023713), WO2020191233A1 (PCT/US2020/023712), WO2019079347A1 (PCT/US2018/056146), and WO2021155065A1 (PCT/US2021/015580).

Use in Plants

The base editing fusion protein, the base editor and the method for producing genetically modified cells of the present disclosure are particularly suitable for the genetic modification of plants. Preferably, the plant is a crop plant, including but not limited to wheat, rice, corn, soybean, sunflower, sorghum, oilseed rape, alfalfa, cotton, barley, millet, sugar cane, tomato, tobacco, cassava and potato. More preferably, the plant is rice.

In another aspect, the present disclosure provides a method for producing a genetically modified plant, comprising introducing the base editor of the present disclosure into at least one plant, thereby resulting in one or more nucleotide substitutions within the target nucleic acid region in the genome of said at least one plant.

In some embodiments, the method further comprises screening a plant having one or more nucleotide substitutions as desired from said at least one plant.

In the method of the present disclosure, the base editing composition may be introduced into a plant via various methods well known to a person skilled in the art. Methods that may be used to introduce the base editor of the present disclosure into a plant include but are not limited to biolistic method, PEG-mediated protoplast transformation, *Agrobacterium*-mediated transformation, plant virus-mediated transformation, pollen tube channel method and ovary injection method. Preferably, the base editing composition is introduced into a plant via transient transformation.

In the method of the present disclosure, the modification of the target sequence may be achieved by simply introducing the base editing fusion protein into a plant cell or producing the base editing fusion protein in a plant cell, and said modification may be stably inherited without the need of the stable transformation of the exogenous polynucleotide encoding the components of the base editor into the plant. This avoids the potential off-target effects of the stably existing (continuously produced) base editing composition, and avoids the integration of the exogenous nucleotide sequence(s) in the plant genome as well, thereby having higher biological safety.

In some preferred embodiments, said introduction is performed in the absence of selection pressure, thereby avoiding the integration of the exogenous nucleotide sequence(s) in the plant genome.

In some embodiments, said introduction include transforming the base editor of the present disclosure into an isolated plant cell or tissue and enabling the regeneration of the transformed plant cell or tissue into an intact plant. Preferably, said regeneration is performed in the absence of selection pressure, that is, any selection agent for the selection gene carried on the expression vector is not used during tissue culture. The regeneration efficiency of plant may be enhanced without the use of a selection agent, and a modified plant that does not comprise an exogenous nucleotide sequence is obtained.

In some other embodiments, the base editor of the present disclosure may be transformed into a specific part of an intact plant, such as leaf, stem tip, pollen tube, young ear, or hypocotyl. This is particularly suitable for the transformation of the plants that are difficult to regenerate by tissue culture.

Therefore, in some embodiments, a plant whose genome is free of the integration of exogenous polynucleotide, i.e., a transgene-free modified plant, may be obtained by conducting the genetic modification and breeding of plant using the method of the present disclosure.

In some embodiments of the present disclosure, the modified target nucleic acid region is associated with plant traits such as an agronomic trait. As a result, said one or more nucleotide substitutions result in the plant having altered (preferably, improved) traits such as an agronomic trait, as compared with the wild-type plant.

In some embodiments, the method further comprises a step of screening a plant having one or more nucleotide substitutions as desired and/or a desired trait such as an agronomic trait.

In some embodiments of the present disclosure, the method further comprises obtaining the progeny of the genetically modified plant. Preferably, the genetically modified plant or the progeny thereof has one or more nucleotide substitutions as desired and/or a desired trait such as an agronomic trait.

In another aspect, the present disclosure also provides a genetically modified plant, a progeny thereof or a part thereof, wherein the plant is obtained by the above-mentioned method of the present disclosure. In some embodiments, the genetically modified plant, the progeny thereof or the part thereof is non-transgenic. Preferably, the genetically modified plant or the progeny thereof has a desired genetic modification and/or a desired trait such as an agronomic trait.

In another aspect, the present disclosure also provides a method for plant breeding, comprising the hybridization of a first genetically modified plant that comprises one or more nucleotide substitutions in the target nucleic acid region and is obtained by the above-mentioned method of the present disclosure and a second plant free of said one or more nucleotide substitutions, thereby introducing said one or more nucleotide substitutions into the second plant. Preferably, the first genetically modified plant has a desired trait such as an agronomic trait.

EXAMPLES

A further understanding of the present disclosure may be obtained by referring to some specific examples given herein. These examples are merely for the illustration of the present disclosure and are not intended to impose any limitation to the scope of the present disclosure. Apparently, a variety of modifications and changes may be made to the present disclosure without departing from the essence of the present disclosure. Accordingly, these modifications and changes are also within the scope as claimed by the present application.

Partial element sequences used in subsequent examples are as set forth below.

OsBADH2 Left TALE repeat (SEQ ID NO. 89)

LTPDQVVAIASNNGGKQALETVQRLLPVLCQDHGLTPDQVVAIASHDGGKQALETVQR

LLPVLCQDHGLTPDQVVAIASNGGGKQALETVQRLLPVLCQDHGLTPDQVVAIASNNG

GKQALETVQRLLPVLCQDHGLTPDQVVAIASNNGGKQALETVQRLLPVLCQDHGLTP

DQVVAIASNIGGKQALETVQRLLPVLCQDHGLTPDQVVAIASNGGGKQALETVQRLLP

VLCQDHGLTPDQVVAIASNNGGKQALETVQRLLPVLCQDHGLTPDQVVAIASHDGGK

QALETVQRLLPVLCQDHGLTPDQVVAIASNGGGKQALETVQRLLPVLCQDHGLTPDQ

VVAIASNGGGKQALETVQRLLPVLCQDHGLTPDQVVAIASNGGGKQALETVQRLLPVL

CQDHGLTPDQVVAIASNNGGKQALETVQRLLPVLCQDHGLTPDQVVAIASNIGGKQAL

ETVQRLLPVLCQDHGLTPDQVVAIASNNGGKQALETVQRLLPVLCQDHGLTPDQVVAI

ASNGGGKQALETVQRLLPVLCQDHGLTPDQVVAIASNIGGKQALE

OsBADH2 Right TALE repeat (SEQ ID NO. 90)

LTPDQVVAIASNNGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASNGG

GKQALETVQRLLPVLCQDHGLTPDQVVAIASNGGGKQALETVQRLLPVLCQDHGLTP

DQVVAIASNGGGKQALETVQRLLPVLCQDHGLTPDQVVAIASNGGGKQALETVQRLL

PVLCQDHGLTPDQVVAIASNNGGKQALETVQRLLPVLCQDHGLTPDQVVAIASNGGG

KQALETVQRLLPVLCQDHGLTPDQVVAIASHDGGKQALETVQRLLPVLCQDHGLTPD

QVVAIASHDGGKQALETVQRLLPVLCQDHGLTPDQVVAIASNIGGKQALETVQRLLPV

LCQDHGLTPDQVVAIASNIGGKQALETVQRLLPVLCQDHGLTPDQVVAIASNNGGKQA

LETVQRLLPVLCQDHGLTPDQVVAIASNNGGKQALETVQRLLPVLCQDHGLTPDQVVA

IASNIGGKQALETVQRLLPVLCQDHGLTPDQVVAIASNGGGKQALE

OsDEP1 Left TALE repeat (SEQ ID NO. 91)

LTPDQVVAIASNNGGKQALETVQRLLPVLCQDHGLTPDQVVAIASHDGGKQALETVQR

LLPVLCQDHGLTPDQVVAIASNIGGKQALETVQRLLPVLCQDHGLTPDQVVAIASNIGG

KQALETVQRLLPVLCQDHGLTPDQVVAIASNIGGKQALETVQRLLPVLCQDHGLTPDQ

VVAIASNIGGKQALETVQRLLPVLCQDHGLTPDQVVAIASNNGGKQALETVQRLLPVL

CQDHGLTPDQVVAIASNIGGKQALETVQRLLPVLCQDHGLTPDQVVAIASHDGGKQAL

ETVQRLLPVLCQDHGLTPDQVVAIASHDGGKQALETVQRLLPVLCQDHGLTPDQVVAI

ASNIGGKQALETVQRLLPVLCQDHGLTPDQVVAIASNIGGKQALETVQRLLPVLCQDH

GLTPDQVVAIASNNGGKQALETVQRLLPVLCQDHGLTPDQVVAIASNNGGKQALETV

QRLLPVLCQDHGLTPDQVVAIASNGGGKQALETVQRLLPVLCQDHGLTPDQVVAIASN

NGGKQALETVQRLLPVLCQDHGLTPDQVVAIASHDGGKQALETVQRLLPVLCQDHGL

TPDQVVAIASHDGGKQALETVQRLLPVLCQDHGLTPDQVVAIASNGGGKQALE

OsDEP1 Right TALE repeat (SEQ ID NO. 92)

LTPDQVVAIASNNGGKQALETVQRLLPVLCQDHGLTPDQVVAIASNNGGKQALETVQR

LLPVLCQDHGLTPDQVVAIASHDGGKQALETVQRLLPVLCQDHGLTPDQVVAIASNGG

GKQALETVQRLLPVLCQDHGLTPDQVVAIASHDGGKQALETVQRLLPVLCQDHGLTP

DQVVAIASNNGGKQALETVQRLLPVLCQDHGLTPDQVVAIASNGGGKQALETVQRLL

PVLCQDHGLTPDQVVAIASHDGGKQALETVQRLLPVLCQDHGLTPDQVVAIASNNGG

KQALETVQRLLPVLCQDHGLTPDQVVAIASHDGGKQALETVQRLLPVLCQDHGLTPD

QVVAIASNIGGKQALETVQRLLPVLCQDHGLTPDQVVAIASNNGGKQALETVQRLLPV

LCQDHGLTPDQVVAIASHDGGKQALETVQRLLPVLCQDHGLTPDQVVAIASNIGGKQA

LETVQRLLPVLCQDHGLTPDQVVAIASNGGGKQALE

OsCKX2 Left TALE repeat
                                                        (SEQ ID NO. 93)
LTPDQVVAIASHDGGKQALETVQRLLPVLCQDHGLTPDQVVAIASHDGGKQALETVQR

LLPVLCQDHGLTPDQVVAIASNGGGKQALETVQRLLPVLCQDHGLTPDQVVAIASNNG

GKQALETVQRLLPVLCQDHGLTPDQVVAIASNNGGKQALETVQRLLPVLCQDHGLTP

DQVVAIASHDGGKQALETVQRLLPVLCQDHGLTPDQVVAIASHDGGKQALETVQRLL

PVLCQDHGLTPDQVVAIASNNGGKQALETVQRLLPVLCQDHGLTPDQVVAIASHDGG

KQALETVQRLLPVLCQDHGLTPDQVVAIASNNGGKQALETVQRLLPVLCQDHGLTPD

QVVAIASNGGGKQALETVQRLLPVLCQDHGLTPDQVVAIASHDGGKQALETVQRLLP

VLCQDHGLTPDQVVAIASHDGGKQALETVQRLLPVLCQDHGLTPDQVVAIASNIGGKQ

ALETVQRLLPVLCQDHGLTPDQVVAIASHDGGKQALETVQRLLPVLCQDHGLTPDQVV

AIASNNGGKQALE

OsCKX2 Right TALE repeat
                                                        (SEQ ID NO. 94)
LTPDQVVAIASHDGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASNIG

GKQALETVQRLLPVLCQDHGLTPDQVVAIASNNGGKQALETVQRLLPVLCQDHGLTP

DQVVAIASNIGGKQALETVQRLLPVLCQDHGLTPDQVVAIASNNGGKQALETVQRLLP

VLCQDHGLTPDQVVAIASHDGGKQALETVQRLLPVLCQDHGLTPDQVVAIASHDGGK

QALETVQRLLPVLCQDHGLTPDQVVAIASHDGGKQALETVQRLLPVLCQDHGLTPDQ

VVAIASHDGGKQALETVQRLLPVLCQDHGLTPDQVVAIASNNGGKQALETVQRLLPVL

CQDHGLTPDQVVAIASHDGGKQALETVQRLLPVLCQDHGLTPDQVVAIASNNGGKQA

LETVQRLLPVLCQDHGLTPDQVVAIASNNGGKQALETVQRLLPVLCQDHGLTPDQVVA

IASHDGGKQALETVQRLLPVLCQDHGLTPDQVVAIASNNGGKQALETVQRLLPVLCQ

DHGLTPDQVVAIASHDGGKQALE

OsSD1 Left TALE repeat
                                                        (SEQ ID NO. 95)
LTPDQVVAIASHDGGKQALETVQRLLPVLCQDHGLTPDQVVAIASHDGGKQALETVQR

LLPVLCQDHGLTPDQVVAIASNIGGKQALETVQRLLPVLCQDHGLTPDQVVAIASNNG

GKQALETVQRLLPVLCQDHGLTPDQVVAIASNNGGKQALETVQRLLPVLCQDHGLTP

DQVVAIASNIGGKQALETVQRLLPVLCQDHGLTPDQVVAIASHDGGKQALETVQRLLP

VLCQDHGLTPDQVVAIASNNGGKQALETVQRLLPVLCQDHGLTPDQVVAIASNIGGKQ

ALETVQRLLPVLCQDHGLTPDQVVAIASHDGGKQALETVQRLLPVLCQDHGLTPDQVV

AIASNNGGKQALETVQRLLPVLCQDHGLTPDQVVAIASNGGGKQALETVQRLLPVLC

QDHGLTPDQVVAIASHDGGKQALETVQRLLPVLCQDHGLTPDQVVAIASNNGGKQAL

ETVQRLLPVLCQDHGLTPDQVVAIASNNGGKQALETVQRLLPVLCQDHGLTPDQVVAI

ASHDGGKQALETVQRLLPVLCQDHGLTPDQVVAIASNNGGKQALETVQRLLPVLCQD

HGLTPDQVVAIASNNGGKQALE

OsSD1 Right TALE repeat
                                                        (SEQ ID NO. 96)
LTPDQVVAIASNNGGKQALETVQRLLPVLCQDHGLTPDQVVAIASNIGGKQALETVQR -continued

LLPVLCQDHGLTPDQVVAIASHDGGKQALETVQRLLPVLCQDHGLTPDQVVAIASNNG

GKQALETVQRLLPVLCQDHGLTPDQVVAIASNNGGKQALETVQRLLPVLCQDHGLTP

DQVVAIASNNGGKQALETVQRLLPVLCQDHGLTPDQVVAIASNNGGKQALETVQRLL

PVLCQDHGLTPDQVVAIASHDGGKQALETVQRLLPVLCQDHGLTPDQVVAIASNNGG

KQALETVQRLLPVLCQDHGLTPDQVVAIASHDGGKQALETVQRLLPVLCQDHGLTPD

QVVAIASHDGGKQALETVQRLLPVLCQDHGLTPDQVVAIASNIGGKQALETVQRLLPV

LCQDHGLTPDQVVAIASNGGGKQALETVQRLLPVLCQDHGLTPDQVVAIASNGGGKQ

ALETVQRLLPVLCQDHGLTPDQVVAIASHDGGKQALETVQRLLPVLCQDHGLTPDQVV

AIASNNGGKQALETVQRLLPVLCQDHGLTPDQVVAIASHDGGKQALETVQRLLPVLC

QDHGLTPDQVVAIASHDGGKQALETVQRLLPVLCQDHGLTPDQVVAIASNNGGKQAL

E

SIRT6 Left TALE repeat (SEQ ID NO. 97)
LTPDQVVAIASNGGGKQALETVQRLLPVLCQDHGLTPEQVVAIASNIGGKQALETVQR

LLPVLCQAHGLTPDQVVAIASHDGGKQALETVQRLLPVLCQAHGLTPAQVVAIANNNG

GKQALETVQRLLPVLCQDHGLTPDQVVAIASHDGGKQALETVQRLLPVLCQDHGLTPE

QVVAIANNNGGKQALETVQRLLPVLCQAHGLTPDQVVAIANNNGGKQALETVQRLLP

VLCQAHGLTPAQVVAIASHDGGKQALETVQRLLPVLCQDHGLTPDQVVAIANNNGGK

QALETVQRLLPVLCQDHGLTPEQVVAIANNNGGKQALETVQRLLPVLCQAHGLTPDQ

VVAIANNNGGKQALETVQRLLPVLCQAHGLTPAQVVAIANNNGGKQALETVQRLLPV

LCQDHGLTPDQVVAIASHDGGKQALETVQRLLPVLCQDHGLTPEQVVAIASNGGGKQ

ALETVQRLLPVLCQAHGLTPDQVVAIANNNGGKQALETVQRLLPVLCQAHGLTPAQV

VAIASNGGGKQALETVQRLLPVLCQDHGLTPEQVVAIASHDGGRPALE

SIRT6 Right TALE repeat (SEQ ID NO. 98)
LTPDQVVAIASHDGGKQALETVQRLLPVLCQDHGLTPEQVVAIASHDGGKQALETVQR

LLPVLCQAHGLTPDQVVAIANNNGGKQALETVQRLLPVLCQAHGLTPAQVVAIANNN

GGKQALETVQRLLPVLCQDHGLTPDQVVAIANNNGGKQALETVQRLLPVLCQDHGLT

PEQVVAIASNIGGKQALETVQRLLPVLCQAHGLTPDQVVAIANNNGGKQALETVQRLL

PVLCQAHGLTPAQVVAIANNNGGKQALETVQRLLPVLCQDHGLTPDQVVAIASHDGG

KQALETVQRLLPVLCQDHGLTPEQVVAIASHDGGKQALETVQRLLPVLCQAHGLTPDQ

VVAIANNNGGKQALETVQRLLPVLCQAHGLTPAQVVAIASHDGGKQALETVQRLLPV

LCQDHGLTPDQVVAIASNIGGKQALETVQRLLPVLCQDHGLTPEQVVAIASHDGGKQA

LETVQRLLPVLCQAHGLTPDQVVAIASNGGGKQALETVQRLLPVLCQAHGLTPAQVVA

IASNGGGKQALETVQRLLPVLCQDHGLTPEQVVAIASNNGGRPALE

OsRbcL Left TALE repeat (SEQ ID NO. 99)
LTPDQVVAIASNGGGKQALETVQRLLPVLCQDHGLTPDQVVAIASNGGGKQALETVQR

LLPVLCQDHGLTPDQVVAIASNIGGKQAVETVQRLLPVLCQAHGLTPAQVVAIASHDG

GKQAVETVQRLLPVLCQDHGLTPDQVVAIASHDGGKQAVETVQRLLPVLCQDHGLTP

DQVVAIASNIGGKQALETLQRLLPVLCQAHGLTPAQVVAIASNIGGKQALETVQRLLPV

LCQDHGLTPDQVVAIASNIGGKQALETVQRLLPVLCQDHGLTPDQVVAIASNNGGKQA

LETVQRLLPVLCQAHGLTPAQVVAIASNIGGKQALETVQRLLPVLCQAHGLTPDQVVAI

ASNGGGKQAVETVQRLLPVLCQAHGLTPAQVVAIASNNGGKQAVETVQRLLPVLCQA

-continued

HGLTPAQVVAIASNIGGKQAVETVQRLLPVLCQDHGLTPEQVVAIASNGGGKQALE

OsRbcL Right TALE repeat (SEQ ID NO. 100)
LTPAQVVAIASHDGGKQALETVQRLLPVLCQAHGLTPDQVVAIASHDGGKQAVETVQR

LLPVLCQDHGLTPDQVVAIASNIGGKQAVETVQRLLPVLCQAHGLTPAQVVAIASNIGG

KQAVETVQRLLPVLCQDHGLTPDQVVAIASHDGGKQALETLQRLLPVLCQDHGLTPDQ

VVAIASNNGGKQALETVQRLLPVLCQAHGLTPAQVVAIASHDGGKQALETVQRLLPVL

CQDHGLTPDQVVAIASNIGGKQALETVQRLLPVLCQDHGLTPDQVVAIASNGGGKQAL

ETVQRLLPVLCQDHGLTPDQVVAIASNIGGKQAVETVQRLLPVLCQDHGLTPDQVVAIA

SNIGGKQAVETVQRLLPVLCQDHGLTPDQVVAIASNIGGKQAVETVQRLLPVLCQDHG

LTPDQVVAIASNGGGKQALETVQRLLPVLCQDHGLTPDQVVAIASNNGGKQALETVQR

LLPVLCQDHGLTPDQVVAIASNNGGKQALETVQRLLPVLCQDHGLTPAQVVAIASNGG

GKQALETVQRLLPVLCQDHGLTPEQVVAIASNGGGKQALE

ND6 Left TALE repeat (SEQ ID NO. 101)
LTPEQVVAIASNNGGKQALETVQRLLPVLCQAHGLTPEQVVAIASNIGGKQALETVQRL

LPVLCQAHGLTPEQVVAIASHDGGKQALETVQRLLPVLCQAHGLTPEQVVAIASHDGG

KQALETVQRLLPVLCQAHGLTPEQVVAIASHDGGKQALETVQRLLPVLCQAHGLTPEQ

VVAIASHDGGKQALETVQRLLPVLCQAHGLTPEQVVAIASHDGGKQALETVQRLLPVL

CQAHGLTPEQVVAIASNIGGKQALETVQRLLPVLCQAHGLTPEQVVAIASNGGGKQAL

ETVQRLLPVLCQAHGLTPEQVVAIASNGGGRPALE

ND6 Right TALE repeat (SEQ ID NO. 102)
LTPEQVVAIASNNGGKQALETVQRLLPVLCQAHGLTPEQVVAIASNIGGKQALETVQRL

LPVLCQAHGLTPEQVVAIASNGGGKQALETVQRLLPVLCQAHGLTPEQVVAIASNNGG

KQALETVQRLLPVLCQAHGLTPEQVVAIASNNGGKQALETVQRLLPVLCQAHGLTPEQ

VVAIASHDGGKQALETVQRLLPVLCQAHGLTPEQVVAIASNGGGKQALETVQRLLPVL

CQAHGLTPEQVVAIASNIGGKQALETVQRLLPVLCQAHGLTPEQVVAIASNGGGKQAL

ETVQRLLPVLCQAHGLTPEQVVAIASNGGGKQALETVQRLLPVLCQAHGLTPEQVVAI

ASNGGGRPALE

ND5.1 Left TALE repeat (SEQ ID NO. 103)
LTPEQVVAIASNIGGKQALETVQRLLPVLCQAHGLTPEQVVAIASNNGGKQALETVQRL

LPVLCQAHGLTPEQVVAIASHDGGKQALETVQRLLPVLCQAHGLTPEQVVAIASNIGG

KQALETVQRLLPVLCQAHGLTPEQVVAIASNGGGKQALETVQRLLPVLCQAHGLTPEQ

VVAIASNGGGKQALETVQRLLPVLCQAHGLTPEQVVAIASNIGGKQALETVQRLLPVL

CQAHGLTPEQVVAIASNNGGKQALETVQRLLPVLCQAHGLTPEQVVAIASHDGGKQAL

ETVQRLLPVLCQAHGLTPEQVVAIASNIGGKQALETVQRLLPVLCQAHGLTPEQVVAIA

SNNGGKQALETVQRLLPVLCQAHGLTPEQVVAIASNNGGKQALETVQRLLPVLCQAH

GLTPEQVVAIASNIGGKQALETVQRLLPVLCQAHGLTPEQVVAIASNIGGKQALETVQR

LLPVLCQAHGLTPEQVVAIASNGGGRPALE

ND5.1 Right TALE repeat (SEQ ID NO. 104)
LTPEQVVAIASHDGGKQALETVQRLLPVLCQAHGLTPEQVVAIASNGGGKQALETVQR

LLPVLCQAHGLTPEQVVAIASNGGGKQALETVQRLLPVLCQAHGLTPEQVVAIASNGG

-continued

GKQALETVQRLLPVLCQAHGLTPEQVVAIASNNGGKQALETVQRLLPVLCQAHGLTPE

QVVAIASNNGGKQALETVQRLLPVLCQAHGLTPEQVVAIASNIGGKQALETVQRLLPV

LCQAHGLTPEQVVAIASNNGGKQALETVQRLLPVLCQAHGLTPEQVVAIASNGGGKQA

LETVQRLLPVLCQAHGLTPEQVVAIASNIGGKQALETVQRLLPVLCQAHGLTPEQVVAI

ASNNGGKQALETVQRLLPVLCQAHGLTPEQVVAIASNIGGKQALETVQRLLPVLCQAH

GLTPEQVVAIASNIGGRPALE

ND3 Left TALE repeat
                                                    (SEQ ID NO. 105)
LTPEQVVAIASNIGGKQALETVQALLPVLCQAHGLTPQQVVAIASHDGGKQALETVQR

LLPVLCQAHGLTPQQVVAIASNNGGKQALETVQRLLPVLCQAHGLTPEQVVAIASNIG

GKQALETVQALLPVLCQAHGLTPEQVVAIASNNGGKQALETVQALLPVLCQAHGLTPE

QVVAIASNGGGKQALETVQALLPVLCQAHGLTPEQVVAIASNNGGKQALETVQRLLPV

LCQAHGLTPEQVVAIASHDGGKQALETVQALLPVLCQAHGLTPEQVVAIASNNGGKQ

ALETVQRLLPVLCQAHGLTPEQVVAIASNNGGKQALETVQALLPVLCQAHGLTPEQVV

AIASHDGGKQALETVQALLPVLCQAHGLTPEQVVAIASNGGGKQALETVQALLPVLC

QAHGLTPEQVVAIASNGGGKQALETVQRLLPVLCQAHGLTPQQVVAIASHDGGKQAL

ETVQRLLPVLCQAHGLTPEQVVAIASNNGGKQALETVQALLPVLCQAHGLTPQQVVAI

ASNIGGRPALE

ND3 Right TALE repeat
                                                    (SEQ ID NO. 106)
LTPEQVVAIASNIGGKQALETVQALLPVLCQAHGLTPQQVVAIASNGGGKQALETVQR

LLPVLCQAHGLTPQQVVAIASNNGGKQALETVQRLLPVLCQAHGLTPEQVVAIASNNG

GKQALETVQALLPVLCQAHGLTPEQVVAIASNIGGKQALETVQALLPVLCQAHGLTPE

QVVAIASNNGGKQALETVQALLPVLCQAHGLTPEQVVAIASNIGGKQALETVQRLLPV

LCQAHGLTPEQVVAIASNIGGKQALETVQALLPVLCQAHGLTPEQVVAIASNIGGKQAL

ETVQRLLPVLCQAHGLTPEQVVAIASNNGGKQALETVQALLPVLCQAHGLTPEQVVAI

ASNNGGKQALETVQALLPVLCQAHGLTPEQVVAIASNNGGKQALETVQALLPVLCQA

HGLTPEQVVAIASNIGGKQLETVQRLLPVLCQAHGLTPQQVVAIASHDGGKQALETVQ

RLLPVLCQAHGLTPEQVVAIASNNGGKQALETVQALLPVLCQAHGLTPQQVVAIASHD

GGRPALE

ND1.3 Left TALE repeat
                                                    (SEQ ID NO. 107)
LTPEQVVAIASHDGGKQALETVQALLPVLCQAHGLTPQQVVAIASNGGGKQALETVQR

LLPVLCQAHGLTPQQVVAIASHDGGKQALETVQRLLPVLCQAHGLTPEQVVAIASHDG

GKQALETVQALLPVLCQAHGLTPEQVVAIASNIGGKQALETVQALLPVLCQAHGLTPE

QVVAIASHDGGKQALETVQALLPVLCQAHGLTPEQVVAIASNIGGKQALETVQRLLPV

LCQAHGLTPEQVVAIASHDGGKQALETVQALLPVLCQAHGLTPEQVVAIASNGGGKQ

ALETVQRLLPVLCQAHGLTPEQVVAIASNIGGKQALETVQALLPVLCQAHGLTPEQVV

AIASNNGGKQALETVQALLPVLCQAHGLTPEQVVAIASHDGGKQALETVQALLPVLC

QAHGLTPEQVVAIASNIGGKQALETVQRLLPVLCQAHGLTPQQVVAIASNNGGKQALE

TVQRLLPVLCQAHGLTPEQVVAIASNIGGKQALETVQALLPVLCQAHGLTPQQVVAIAS

NNGGRPALE

ND1.3 Right TALE repeat
                                                    (SEQ ID NO. 108)
LTPEQVVAIASHDGGKQALETVQALLPVLCQAHGLTPQQVVAIASHDGGKQALETVQR -continued

LLPVLCQAHGLTPQQVVAIASHDGGKQALETVQRLLPVLCQAHGLTPEQVVAIASHDG

GKQALETVQALLPVLCQAHGLTPEQVVAIASNGGGKQALETVQALLPVLCQAHGLTPE

QVVAIASNGGGKQALETVQALLPVLCQAHGLTPEQVVAIASHDGGKQALETVQRLLPV

LCQAHGLTPEQVVAIASNNGGKQALETVQALLPVLCQAHGLTPEQVVAIASNNGGKQ

ALETVQRLLPVLCQAHGLTPEQVVAIASHDGGKQALETVQALLPVLCQAHGLTPEQVV

AIASNIGGKQALETVQALLPVLCQAHGLTPEQVVAIASNIGGKQALETVQALLPVLCQA

HGLTPEQVVAIASNNGGKQALETVQRLLPVLCQAHGLTPQQVVAIASNNGGKQALETV

QRLLPVLCQAHGLTPEQVVAIASNGGGKQALETVQALLPVLCQAHGLTPEQVVAIASN

GGGKQALETVQALLPVLCQAHGLTPQQVVAIASHDGGRPALE

ND1.2 Left TALE repeat
                                          (SEQ ID NO. 109)
LTPEQVVAIASHDGGKQALETVQALLPVLCQAHGLTPQQVVAIASHDGGKQALETVQR

LLPVLCQAHGLTPQQVVAIASNGGGKQALETVQRLLPVLCQAHGLTPEQVVAIASNIG

GKQALETVQALLPVLCQAHGLTPEQVVAIASNGGGKQALETVQALLPVLCQAHGLTPE

QVVAIASNGGGKQALETVQALLPVLCQAHGLTPEQVVAIASNGGGKQALETVQRLLPV

LCQAHGLTPEQVVAIASNIGGKQALETVQALLPVLCQAHGLTPEQVVAIASNGGGKQA

LETVQRLLPVLCQAHGLTPEQVVAIASNGGGKQALETVQALLPVLCQAHGLTPEQVVA

IASHDGGKQALETVQALLPVLCQAHGLTPEQVVAIASNGGGKQALETVQALLPVLCQ

AHGLTPEQVVAIASNIGGKQALETVQALLPVLCQAHGLTPQQVVAIASNNGGRPALE

ND1.2 Right TALE repeat
                                          (SEQ ID NO. 110)
LTPEQVVAIASNGGGKQALETVQALLPVLCQAHGLTPQQVVAIASNNGGKQALETVQR

LLPVLCQAHGLTPQQVVAIASNIGGKQALETVQRLLPVLCQAHGLTPEQVVAIASNNG

GKQALETVQALLPVLCQAHGLTPEQVVAIASNGGGKQALETVQALLPVLCQAHGLTPE

QVVAIASNIGGKQALETVQALLPVLCQAHGLTPEQVVAIASNIGGKQALETVQRLLPVL

CQAHGLTPEQVVAIASNIGGKQALETVQALLPVLCQAHGLTPEQVVAIASHDGGKQAL

ETVQRLLPVLCQAHGLTPEQVVAIASNNGGKQALETVQALLPVLCQAHGLTPEQVVAI

ASNNGGKQALETVQALLPVLCQAHGLTPQQVVAIASHDGGRPALE

ND6.2 Left TALE repeat (TALE-L2)
                                          (SEQ ID NO. 111)
LTPEQVVAIASHDGGKQALETVQALLPVLCQAHGLTPQQVVAIASHDGGKQALETVQR

LLPVLCQAHGLTPQQVVAIASHDGGKQALETVQRLLPVLCQAHGLTPEQVVAIASNIG

GKQALETVQALLPVLCQAHGLTPEQVVAIASNGGGKQALETVQALLPVLCQAHGLTPE

QVVAIASNNGGKQALETVQALLPVLCQAHGLTPEQVVAIASHDGGKQALETVQRLLPV

LCQAHGLTPEQVVAIASHDGGKQALETVQALLPVLCQAHGLTPEQVVAIASNGGGKQ

ALETVQRLLPVLCQAHGLTPEQVVAIASHDGGKQALETVQALLPVLCQAHGLTPEQVV

AIASNIGGKQALETVQALLPVLCQAHGLTPEQVVAIASNNGGKQALETVQALLPVLCQ

AHGLTPEQVVAIASNNGGKQALETVQRLLPVLCQAHGLTPQQVVAIASNIGGKQALET

VQRLLPVLCQAHGLTPEQVVAIASNGGGKQALETVQALLPVLCQAHGLTPQQVVAIAS

NIGGRPALE

ND6.2 Right TALE repeat (TALE-R2)
                                          (SEQ ID NO. 112)
LTPEQVVAIASNGGGKQALETVQALLPVLCQAHGLTPQQVVAIASNGGGKQALETVQR

LLPVLCQAHGLTPQQVVAIASNNGGKQALETVQRLLPVLCQAHGLTPEQVVAIASNNG

-continued

GKQALETVQALLPVLCQAHGLTPEQVVAIASNIGGKQALETVQALLPVLCQAHGLTPE

QVVAIASNGGGKQALETVQALLPVLCQAHGLTPEQVVAIASNIGGKQALETVQRLLPV

LCQAHGLTPEQVVAIASNGGGKQALETVQALLPVLCQAHGLTPEQVVAIASNIGGKQA

LETVQRLLPVLCQAHGLTPEQVVAIASHDGGKQALETVQALLPVLCQAHGLTPEQVVA

IASNGGGKQALETVQALLPVLCQAHGLTPEQVVAIASNIGGKQALETVQALLPVLCQA

HGLTPEQVVAIASHDGGKQALETVQRLLPVLCQAHGLTPQQVVAIASNIGGKQALETV

QRLLPVLCQAHGLTPEQVVAIASNNGGKQALETVQALLPVLCQAHGLTPQQVVAIASH

DGGRPALE

ND6.2 Left TALE repeat (TALE-L1)

(SEQ ID NO. 185)

LTPDQVVAIASNNGGKQALETVQRLLPVLCQDHGLTPDQVVAIASNIGGKQALETVQR

LLPVLCQDHGLTPDQVVAIASHDGGKQALETVQRLLPVLCQDHGLTPDQVVAIASHDG

GKQALETVQRLLPVLCQDHGLTPDQVVAIASHDGGKQALETVQRLLPVLCQDHGLTP

DQVVAIASHDGGKQALETVQRLLPVLCQDHGLTPDQVVAIASHDGGKQALETVQRLL

PVLCQDHGLTPDQVVAIASNIGGKQALETVQRLLPVLCQDHGLTPDQVVAIASNGGGK

QALETVQRLLPVLCQDHGLTPDQVVAIASNNGGKQALETVQRLLPVLCQDHG

ND6.2 Left TALE repeat (TALE-L3)

(SEQ ID NO. 186)

LTPDQVVAIASNNGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASNGG

GKQALETVQRLLPVLCQDHGLTPDQVVAIASHDGGKQALETVQRLLPVLCQDHGLTP

DQVVAIASNIGGKQALETVQRLLPVLCQDHGLTPDQVVAIASNNGGKQALETVQRLLP

VLCQDHGLTPDQVVAIASNNGGKQALETVQRLLPVLCQDHGLTPDQVVAIASNIGGKQ

ALETVQRLLPVLCQDHGLTPDQVVAIASNGGGKQALETVQRLLPVLCQDHGLTPDQVV

AIASNIGGKQALETVQRLLPVLCQDHGLTPDQVVAIASHDGGKQALETVQRLLPVLCQ

DHGLTPDQVVAIASNGGGKQALETVQRLLPVLCQDHGLTPDQVVAIASHDGGKQALE

TVQRLLPVLCQDHGLTPDQVVAIASHDGGKQALETVQRLLPVLCQDHGLTPDQVVAIA

SNGGGKQALETVQRLLPVLCQDHGLTPDQVVAIASHDGGKQALETVQRLLPVLCQDH

G

ND6.2 Right TALE repeat (TALE-R1)

(SEQ ID NO. 187)

LTPDQVVAIASHDGGKQALETVQRLLPVLCQDHGLTPDQVVAIASNNGGKQALETVQR

LLPVLCQDHGLTPDQVVAIASNIGGKQALETVQRLLPVLCQDHGLTPDQVVAIASNGG

GKQALETVQRLLPVLCQDHGLTPDQVVAIASNNGGKQALETVQRLLPVLCQDHGLTP

DQVVAIASNNGGKQALETVQRLLPVLCQDHGLTPDQVVAIASHDGGKQALETVQRLL

PVLCQDHGLTPDQVVAIASNGGGKQALETVQRLLPVLCQDHGLTPDQVVAIASNIGGK

QALETVQRLLPVLCQDHGLTPDQVVAIASNGGGKQALETVQRLLPVLCQDHGLTPDQ

VVAIASNGGGKQALETVQRLLPVLCQDHGLTPDQVVAIASNNGGKQALETVQRLLPVL

CQDHG

XTEN linker peptide (SEQ ID NO. 113)

NSGSETPGTSESATPES 48-amino acid linker peptide (SEQ ID NO. 114)

SGSETPGTSESATPESSGGSSGGSSGSETPGTSESATPESSGGSSGGS

-continued 16-amino acid linker peptide
                                                    (SEQ ID NO. 115)
SGSETPGTSESATPES 14-amino acid linker peptide
                                                    (SEQ ID NO. 116)
SGGGSGGSGGSGGS 11-amino acid linker peptide
                                                    (SEQ ID NO. 117)
SGGSGGSGGSS 4-amino acid linker peptide
                                                    (SEQ ID NO. 118)
SGGS yb
                                                    (SEQ ID NO. 119)
MMATFSCVCCGTLTTSTYCGKRCERKHVYSETRNKRLELYKKYLLEPQKCALNGIVG

HSCGMPCSIAEEACDQLPIVSRFCGQKHADLYDSLLKRSEQELLLEFLQKKMQELKLS

HIVKMAKLESEVNAIRKSVASSFEDSVGCDDSSSVSK

The amino acid sequences of the vectors or elements involved in FIG. 16A to 16E and FIG. 17A to 17H are as set forth below. Unless otherwise specified in subsequent examples, corresponding fusion proteins may be constructed based on the schematic diagrams of constructs as shown in FIG. 16A to 16E and FIG. 17A to 17H and the sequences disclosed in the present specification.

OsBADH2-NLS-TALEN$_{WT}$ (FIG. 16A)
                                                    (SEQ ID NO. 120)
MDYKDHDGDYKDHDIDYKDDDDKMAPKKKRKVGIHGVPSRMVDLRTLGYSQQQQE

KIKPKVRSTVAQHHEALVGHGFTHAHIVALSQHPAALGTVAVTYQHIITALPEATHEDIV

GVGKQWSGARALEALLTDAGELRGPPLQLDTGQLVKIAKRGGVTAMEAVHASRNALT

GAPLNLTPDQVVAIASNNGGKQALETVQRLLPVLCQDHGLTPDQVVAIASHDGGKQAL

ETVQRLLPVLCQDHGLTPDQVVAIASNGGGKQALETVQRLLPVLCQDHGLTPDQVVAI

ASNNGGKQALETVQRLLPVLCQDHGLTPDQVVAIASNNGGKQALETVQRLLPVLCQD

HGLTPDQVVAIASNIGGKQALETVQRLLPVLCQDHGLTPDQVVAIASNGGGKQALETV

QRLLPVLCQDHGLTPDQVVAIASNNGGKQALETVQRLLPVLCQDHGLTPDQVVAIASH

DGGKQALETVQRLLPVLCQDHGLTPDQVVAIASNGGGKQALETVQRLLPVLCQDHGL

TPDQVVAIASNGGGKQALETVQRLLPVLCQDHGLTPDQVVAIASNGGGKQALETVQR

LLPVLCQDHGLTPDQVVAIASNNGGKQALETVQRLLPVLCQDHGLTPDQVVAIASNIG

GKQALETVQRLLPVLCQDHGLTPDQVVAIASNNGGKQALETVQRLLPVLCQDHGLTP

DQVVAIASNGGGKQALETVQRLLPVLCQDHGLTPDQVVAIASNIGGKQALESIVAQLSR

PDPALAALTNDHLVALACLGGRPAMDAVKKGLPHAPELIRRVNRRIGERTSHRVAGSQL

VKSELEEKKSELRHKLKYVPHEYIELIEIARNSTQDRILEMKVMEFFMKVYGYRGKHL

GGSRKPDGAIYTVGSPIDYGVIVDTKAYSGGYNLPIGQADEMQRYVKENQTRNKHINP

NEWWKVYPSSVTEFKFLFVSGHFKGNYKAQLTRLNHKTNCNGAVLSVEELLIGGEMI

KAGTLTLEEVRRKFNNGEINFEGRGSLLTCGDVEENPGPRMDYKDHDGDYKDHDIDY

KDDDDKMAPKKKRKVGIHGVPARMVDLRTLGYSQQQQEKIKPKVRSTVAQHHEALV

GHGFTHAHIVALSQHPAALGTVAVTYQHIITALPEATHEDIVGVGKQWSGARALEALLT

DAGELRGPPLQLDTGQLVKIAKRGGVTAMEAVHASRNALTGAPLNLTPDQVVAIASNN

-continued

```
GGKQALETVQRLLPVLCQDHGLTPDQVVAIASHDGGKQALETVQRLLPVLCQDHGLT

PDQVVAIASHDGGKQALETVQRLLPVLCQDHGLTPDQVVAIASNGGGKQALETVQRL

LPVLCQDHGLTPDQVVAIASNGGGKQALETVQRLLPVLCQDHGLTPDQVVAIASNGGG

KQALETVQRLLPVLCQDHGLTPDQVVAIASNGGGKQALETVQRLLPVLCQDHGLTPD

QVVAIASNNGGKQALETVQRLLPVLCQDHGLTPDQVVAIASNGGGKQALETVQRLLP

VLCQDHGLTPDQVVAIASHDGGKQALETVQRLLPVLCQDHGLTPDQVVAIASHDGGK

QALETVQRLLPVLCQDHGLTPDQVVAIASNIGGKQALETVQRLLPVLCQDHGLTPDQV

VAIASNIGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASNGGGKQALESIVAQLSRPDPALAALTNDHLVALA

CLGGRPAMDAVKKGLPHAPELIRRVNRRIGERTSHRVAGSQLVKSELEEKKSELRHKLK

YVPHEYIELIEIARNSTQDRILEMKVMEFFMKVYGYRGKHLGGSRKPDGAIYTVGSPID

YGVIVDTKAYSGGYNLPIGQADEMERYVEENQTRNKHLNPNEWWKVYPSSVTEFKFL

FVSGHFKGNYKAQLTRLNHITNCNGAVLSVEELLIGGEMIKAGTLTLEEVRRKENNGEI

NF

OsBADH2-NLS-TALE-L-FokI-L-T2A-TALE-R-FokI-RD450.4 (FIG. 16B)
                                              (SEQ ID NO. 121)
MDYKDHDGDYKDHDIDYKDDDDKMAPKKKRKVGIHGVPSRMVDLRTLGYSQQQQE

KIKPKVRSTVAQHHEALVGHGFTHAHIVALSQHPAALGTVAVTYQHIITALPEATHEDIV

GVGKQWSGARALEALLTDAGELRGPPLQLDTGQLVKIAKRGGVTAMEAVHASRNALT

GAPLNLTPDQVVAIASNNGGKQALETVQRLLPVLCQDHGLTPDQVVAIASHDGGKQAL

ETVQRLLPVLCQDHGLTPDQVVAIASNGGGKQALETVQRLLPVLCQDHGLTPDQVVAI

ASNNGGKQALETVQRLLPVLCQDHGLTPDQVVAIASNNGGKQALETVQRLLPVLCQD

HGLTPDQVVAIASNIGGKQALETVQRLLPVLCQDHGLTPDQVVAIASNGGGKQALETV

QRLLPVLCQDHGLTPDQVVAIASNNGGKQALETVQRLLPVLCQDHGLTPDQVVAIASH

DGGKQALETVQRLLPVLCQDHGLTPDQVVAIASNGGGKQALETVQRLLPVLCQDHGL

TPDQVVAIASNGGGKQALETVQRLLPVLCQDHGLTPDQVVAIASNGGGKQALETVQR

LLPVLCQDHGLTPDQVVAIASNNGGKQALETVQRLLPVLCQDHGLTPDQVVAIASNIG

GKQALETVQRLLPVLCQDHGLTPDQVVAIASNNGGKQALETVQRLLPVLCQDHGLTP

DQVVAIASNGGGKQALETVQRLLPVLCQDHGLTPDQVVAIASNIGGKQALESIVAQLSR

PDPALAALTNDHLVALACLGGRPAMDAVKKGLPHAPELIRRVNRRIGERTSHRVAGSQL

VKSELEEKKSELRHKLKYVPHEYIELIEIARNSTQDRILEMKVMEFFMKVYGYRGKHL

GGSRKPDGAIYTVGSPIDYGVIVDTKAYSGGYNLPIGQADEMQRYVKENQTRNKHINP

NEWWKVYPSSVTEFKFLFVSGHFKGNYKAQLTRLNHKTNCNGAVLSVEELLIGGEMI

KAGTLTLEEVRRKFNNGEINFEGRGSLLTCGDVEENPGPRMDYKDHDGDYKDHDIDY

KDDDDKMAPKKKRKVGIHGVPARMVDLRTLGYSQQQQEKIKPKVRSTVAQHHEALV

GHGFTHAHIVALSQHPAALGTVAVTYQHIITALPEATHEDIVGVGKQWSGARALEALLT

DAGELRGPPLQLDTGQLVKIAKRGGVTAMEAVHASRNALTGAPLNLTPDQVVAIASNN

GGKQALETVQRLLPVLCQDHGLTPDQVVAIASHDGGKQALETVQRLLPVLCQDHGLT

PDQVVAIASHDGGKQALETVQRLLPVLCQDHGLTPDQVVAIASNGGGKQALETVQRL

LPVLCQDHGLTPDQVVAIASNGGGKQALETVQRLLPVLCQDHGLTPDQVVAIASNGGG

KQALETVQRLLPVLCQDHGLTPDQVVAIASNGGGKQALETVQRLLPVLCQDHGLTPD
```

-continued

QVVAIASNNGGKQALETVQRLLPVLCQDHGLTPDQVVAIASNGGGKQALETVQRLLP

VLCQDHGLTPDQVVAIASHDGGKQALETVQRLLPVLCQDHGLTPDQVVAIASHDGGK

QALETVQRLLPVLCQDHGLTPDQVVAIASNIGGKQALETVQRLLPVLCQDHGLTPDQV

VAIASNIGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASNGGGKQALESIVAQLSRPDPALAALTNDHLVALA

CLGGRPAMDAVKKGLPHAPELIRRVNRRIGERTSHRVAGSQLVKSELEEKKSELRHKLK

YVPHEYIELIEIARNSTQDRILEMKVMEFFMKVYGYRGKHLGGSRKPAGAIYTVGSPID

YGVIVDTKAYSGGYNLPIGQADEMERYVEENQTRNKHLNPNEWWKVYPSSVTEFKFL

FVSGHFKGNYKAQLTRLNHITNCNGAVLSVEELLIGGEMIKAGTLTLEEVRRKFNNGEI

NF

Figure 16A:
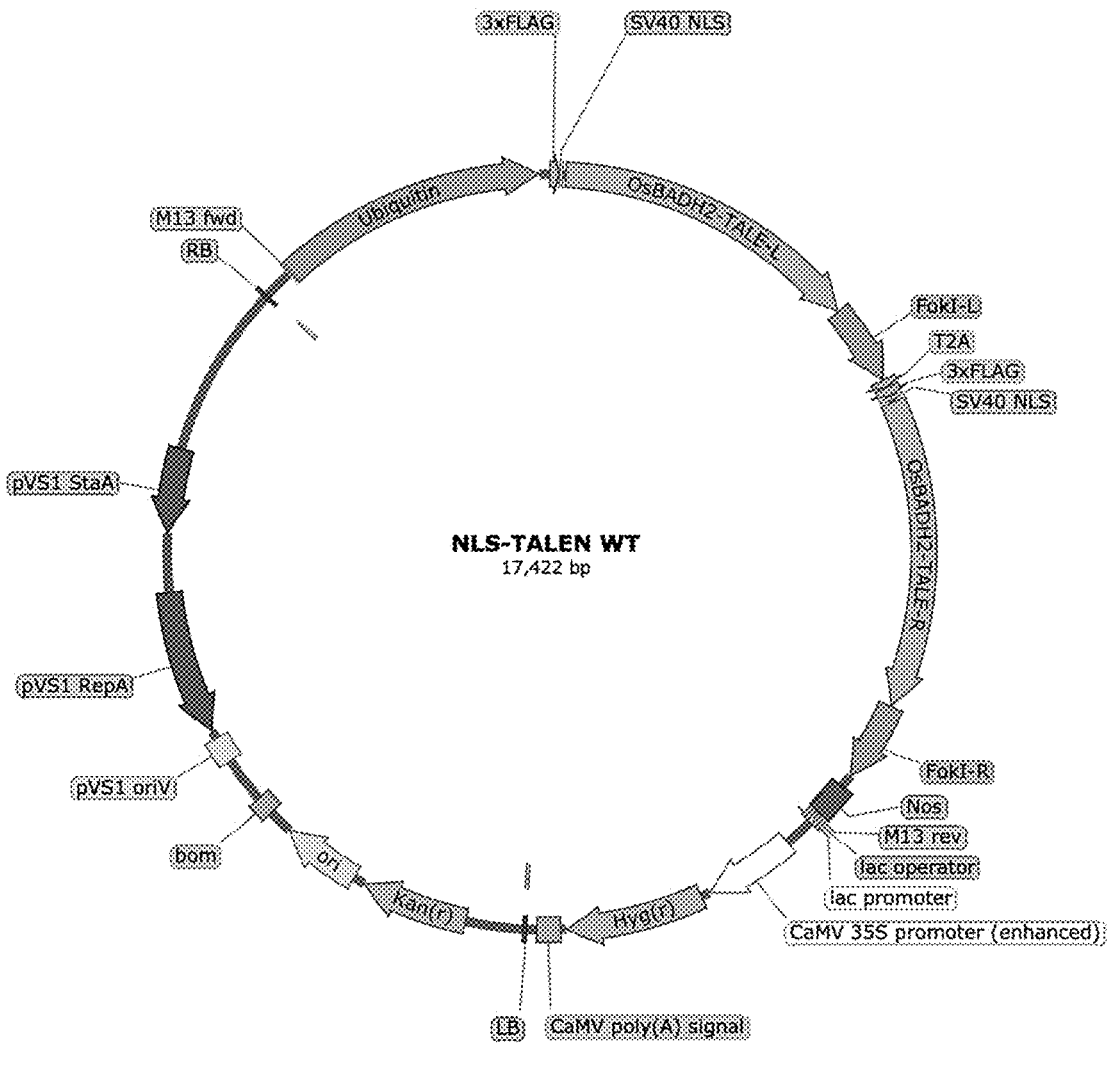
FIG. 16A to FIG. 16E are representative illustrations of the recombinant expression constructs encoding the base editors used in the Examples set forth herein in rice.
Figure 16B:
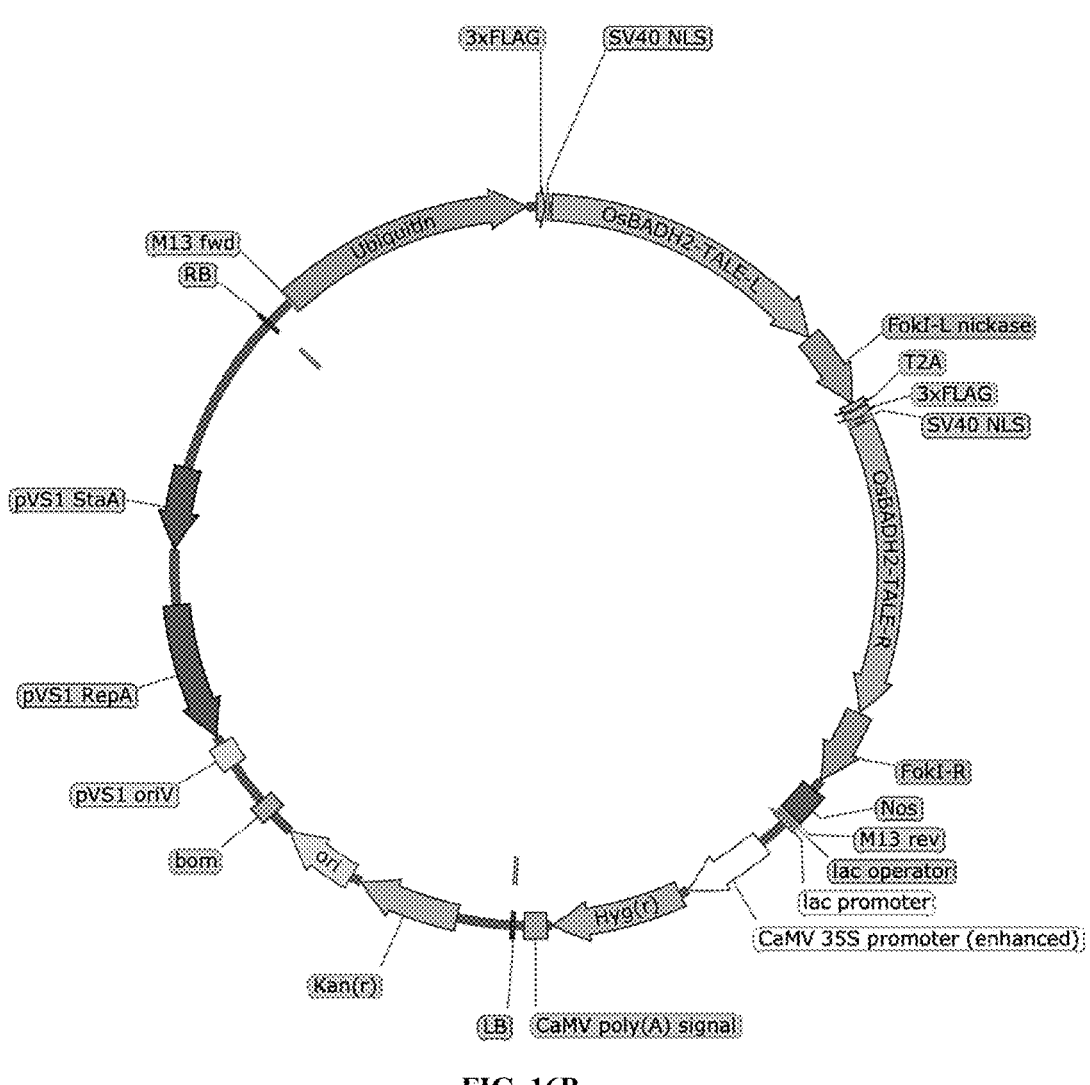
Figure 16B:
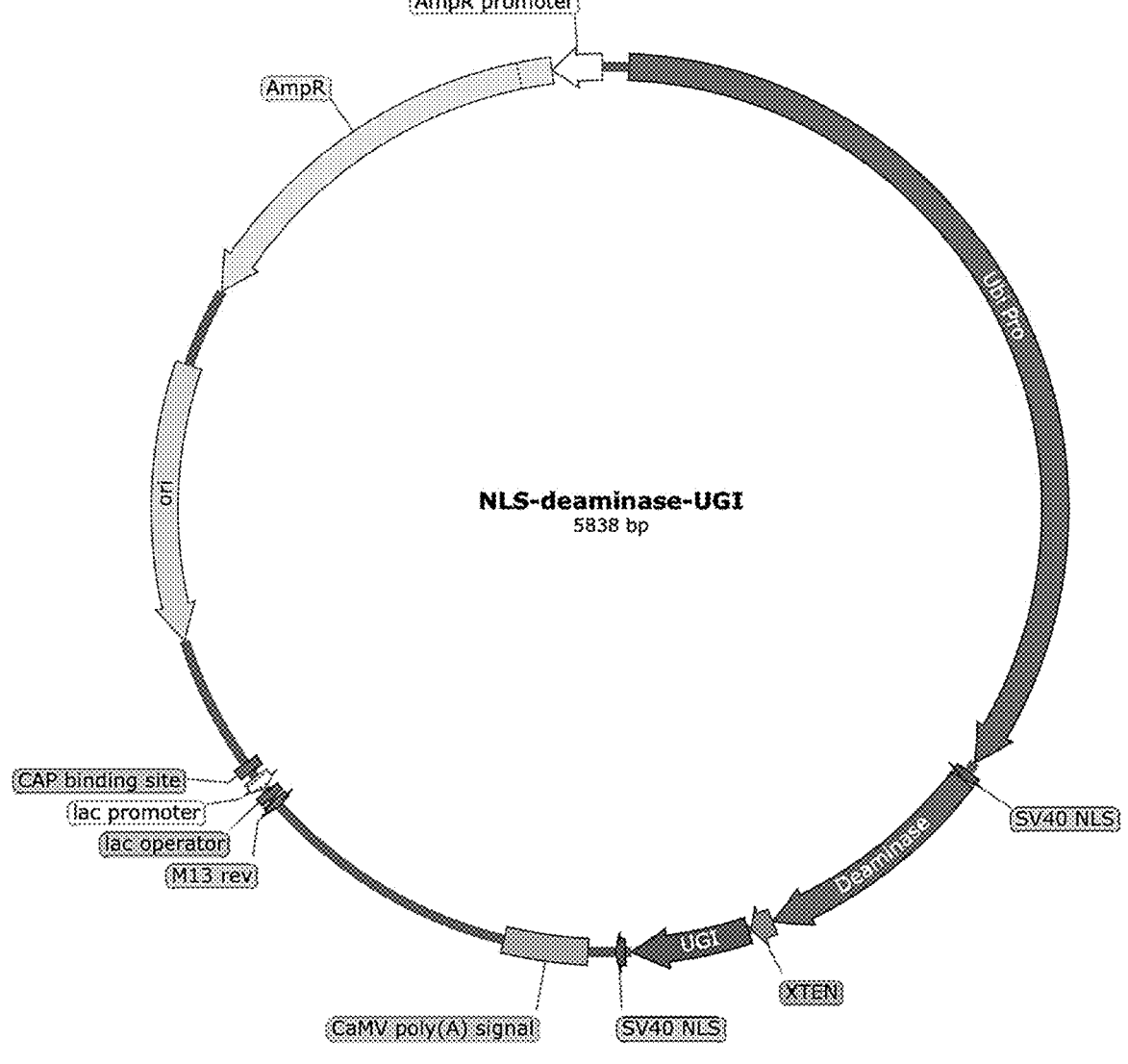
Figure 16B:
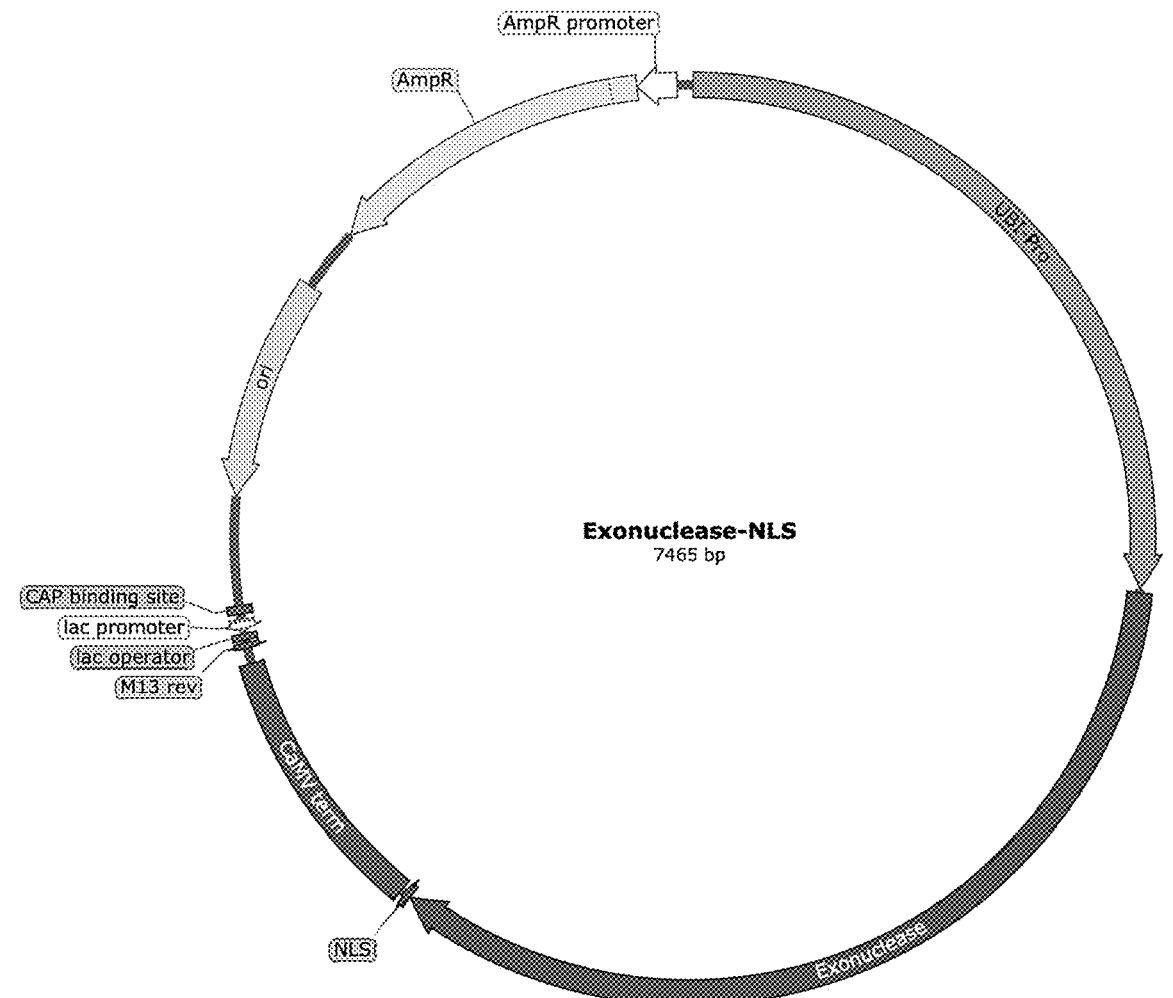

OsBADH2-NLS-TALE-L-FokI-L$_{D450A}$-T2A-TALE-R-FokI-R (FIG. 16B)

(SEQ ID NO. 122)

MDYKDHDGDYKDHDIDYKDDDDKMAPKKKRKVGIHGVPSRMVDLRTLGYSQQQQE

KIKPKVRSTVAQHHEALVGHGFTHAHIVALSQHPAALGTVAVTYQHIITALPEATHEDIV

GVGKQWSGARALEALLTDAGELRGPPLQLDTGQLVKIAKRGGVTAMEAVHASRNALT

GAPLNLTPDQVVAIASNNGGKQALETVQRLLPVLCQDHGLTPDQVVAIASHDGGKQAL

ETVQRLLPVLCQDHGLTPDQVVAIASNGGGKQALETVQRLLPVLCQDHGLTPDQVVAI

ASNNGGKQALETVQRLLPVLCQDHGLTPDQVVAIASNNGGKQALETVQRLLPVLCQD

HGLTPDQVVAIASNIGGKQALETVQRLLPVLCQDHGLTPDQVVAIASNGGGKQALETV

QRLLPVLCQDHGLTPDQVVAIASNNGGKQALETVQRLLPVLCQDHGLTPDQVVAIASH

DGGKQALETVQRLLPVLCQDHGLTPDQVVAIASNGGGKQALETVQRLLPVLCQDHGL

TPDQVVAIASNGGGKQALETVQRLLPVLCQDHGLTPDQVVAIASNGGGKQALETVQR

LLPVLCQDHGLTPDQVVAIASNNGGKQALETVQRLLPVLCQDHGLTPDQVVAIASNIG

GKQALETVQRLLPVLCQDHGLTPDQVVAIASNNGGKQALETVQRLLPVLCQDHGLTP

DQVVAIASNGGGKQALETVQRLLPVLCQDHGLTPDQVVAIASNIGGKQALESIVAQLSR

PDPALAALTNDHLVALACLGGRPAMDAVKKGLPHAPELIRRVNRRIGERTSHRVAGSQL

VKSELEEKKSELRHKLKYVPHEYIELIEIARNSTQDRILEMKVMEFFMKVYGYRGKHL

GGSRKPAGAIYTVGSPIDYGVIVDTKAYSGGYNLPIGQADEMQRYVKENQTRNKHINP

NEWWKVYPSSVTEFKFLFVSGHFKGNYKAQLTRLNHKTNCNGAVLSVEELLIGGEMI

KAGTLTLEEVRRKFNNGEINFEGRGSLLTCGDVEENPGPRMDYKDHDGDYKDHDIDY

KDDDDKMAPKKKRKVGIHGVPARMVDLRTLGYSQQQQEKIKPKVRSTVAQHHEALV

GHGFTHAHIVALSQHPAALGTVAVTYQHIITALPEATHEDIVGVGKQWSGARALEALLT

DAGELRGPPLQLDTGQLVKIAKRGGVTAMEAVHASRNALTGAPLNLTPDQVVAIASNN

GGKQALETVQRLLPVLCQDHGLTPDQVVAIASHDGGKQALETVQRLLPVLCQDHGLT

PDQVVAIASHDGGKQALETVQRLLPVLCQDHGLTPDQVVAIASNGGGKQALETVQRL

LPVLCQDHGLTPDQVVAIASNGGGKQALETVQRLLPVLCQDHGLTPDQVVAIASNGGG

KQALETVQRLLPVLCQDHGLTPDQVVAIASNGGGKQALETVQRLLPVLCQDHGLTPD

QVVAIASNNGGKQALETVQRLLPVLCQDHGLTPDQVVAIASNGGGKQALETVQRLLP

VLCQDHGLTPDQVVAIASHDGGKQALETVQRLLPVLCQDHGLTPDQVVAIASHDGGK

QALETVQRLLPVLCQDHGLTPDQVVAIASNIGGKQALETVQRLLPVLCQDHGLTPDQV

-continued

VAIASNIGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASNGGGKQALESIVAQLSRPDPALAALTNDHLVALA

CLGGRPAMDAVKKGLPHAPELIRRVNRRIGERTSHRVAGSQLVKSELEEKKSELRHKLK

YVPHEYIELIEIARNSTQDRILEMKVMEFFMKVYGYRGKHLGGSRKPDGAIYTVGSPID

YGVIVDTKAYSGGYNLPIGQADEMERYVEENQTRNKHLNPNEWWKVYPSSVTEFKFL

FVSGHFKGNYKAQLTRLNHITNCNGAVLSVEELLIGGEMIKAGTLTLEEVRRKENNGEI

NF

NLS-A3A-XTEN-UGI (FIG. 16B)

(SEQ ID NO. 123)

MKRTADGSEFESPKKKRKVMEASPASGPRHLMDPHIFTSNFNNGIGRHKTYLCYEVER

LDNGTSVKMDQHRGFLHNQAKNLLCGFYGRHAELRFLDLVPSLQLDPAQIYRVTWFIS

WSPCFSWGCAGEVRAFLQENTHVRLRIFAARIYDYDPLYKEALQMLRDAGAQVSIMT

YDEFKHCWDTFVDHQGCPFQPWDGLDEHSQALSGRLRAILQNQGNSGSETPGTSESA

TPESTNLSDIIEKETGKQLVIQESILMLPEEVEEVIGNKPESDILVHTAYDESTDENVMLL

TSDAPEYKPWALVIQDSNGENKIKML

NLS-UGI (FIG. 16B)

(SEQ ID NO. 163)

MTNLSDIIEKETGKQLVIQESILMLPEEVEEVIGNKPESDILVHTAYDESTDENVMLLTSD

APEYKPWALVIQDSNGENKIKMLMKRTADGSEFESPKKKRKV

NLS-C57-XTEN-UGI (FIG. 16B)

(SEQ ID NO. 124)

MKRTADGSEFESPKKKRKVLEAVRARLIGEGGGPGAVPEGGDGPPAVPAEEVERLRGE

LPPPVVPGTGQKTHGRWIGPDGRVRAIVSGRDEDAALVHAQLAAKGIPDEPTRNSDVE

QKLAAHMVANGIRHVTLVINHRPCRGFDDSCDTLVPIILPEGCTLTVHGQTDKGMRVR

VRYTGGARPWWSNSGSETPGTSESATPESTNLSDIIEKETGKQLVIQESILMLPEEVEEVI

GNKPESDILVHTAYDESTDENVMLLTSDAPEYKPWALVIQDSNGENKIKML

NLS-rAPOBEC1-XTEN-UGI (FIG. 16B)

(SEQ ID NO. 164)

MKRTADGSEFESPKKKRKVSSETGPVAVDPTLRRRIEPHEFEVFFDPRELRKETCLLYEI

NWGGRHSIWRHTSQNTNKHVEVNFIEKFTTERYFCPNTRCSITWFLSWSPCGECSRAIT

EFLSRYPHVTLFIYIARLYHHADPRNRQGLRDLISSGVTIQIMTEQESGYCWRNFVNYSP

SNEAHWPRYPHLWVRLYVLELYCIILGLPPCLNILRRKQPQLTFFTIALQSCHYQRLPPHI

LWATGLKNSGSETPGTSESATPESTNLSDIIEKETGKQLVIQESILMLPEEVEEVIGNKPES

DILVHTAYDESTDENVMLLTSDAPEYKPWALVIQDSNGENKIKML

TadA8e-NLS (FIG. 16B)

(SEQ ID NO. 166)

MSEVEFSHEYWMRHALTLAKRARDEREVPVGAVLVLNNRVIGEGWNRAIGLHDPTAH

AEIMALRQGGLVMQNYRLIDATLYVTFEPCVMCAGAMIHSRIGRVVFGVRNSKRGAA

GSLMNVLNYPGMNHRVEITEGILADECAALLCDFYRMPRQVFNAQKKAQSSINSGGS

MKRTADGSEFESPKKKRKV mExoI-NLS (FIG. 16B)

(SEQ ID NO. 125)

MGIQGLLQFIQEASEPVNVKKYKGQAVAVDTYCWLHKGAIACAEKLAKGEPTDRYVG

FCMKFVNMLLSYGVKPILIFDGCTLPSKKEVERSRRERRQSNLLKGKQLLREGKVSEA

RDCFARSINITHAMAHKVIKAARALGVDCLVAPYEADAQLAYLNKAGIVQAVITEDSD

LLAFGCKKVILKMDQFGNGLEVDQARLGMCKQLGDVFTEEKFRYMCILSGCDYLASL

-continued

RGIGLAKACKVLRLANNPDIVKVIKKIGHYLRMNITVPEDYITGFIRANNTFLYQLVFDP

IQRKLVPLNAYGDDVNPETLTYAGQYVGDSVALQIALGNRDVNTFEQIDDYSPDTMPA

HSRSHSWNEKAGQKPPGTNSIWHKNYCPRLEVNSVSHAPQLKEKPSTLGLKQVISTKG

LNLPRKSCVLKRPRNEALAEDDLLSQYSSVSKKIKENGCGDGTSPNSSKMSKSCPDSGT

AHKTDAHTPSKMRNKFATFLQRRNEESGAVVVPGTRSRFFCSSQDFDNFIPKKESGQPL

NETVATGKATTSLLGALDCPDTEGHKPVDANGTHNLSSQIPGNAAVSPEDEAQSSETSK

LLGAMSPPSLGTLRSCFSWSGTLREFSRTPSPSASTTLQQFRRKSDPPACLPEASAVVTD

RCDSKSEMLGETSQPLHELGCSSRSQESMDSSCGLNTSSLSQPSSRDSGSEESDCNNKS

LDNQGEQNSKQHLPHFSKKDGLRRNKVPGLCRSSSMDSFSTTKIKPLVPARVSGLSKKS

GSMQTRKHHDVENKPGLQTKISELWKNFGFKKDSEKLPSCKKPLSPVKDNIQLTPETE

DEIFNKPECVRAQRAIFHMKRTADGSEFESPKKKRKV

Trex2-NLS (FIG. 16B)
                                             (SEQ ID NO. 126)
MSEPPRAETFVFLDLEATGLPNMDPEIAEISLFAVHRSSLENPERDDSGSLVLPRVLDKLT

LCMCPERPFTAKASEITGLSSESLMHCGKAGFNGAVVRTLQGFLSRQEGPICLVAHNGF

DYDFPLLCTELQRLGAHLPQDTVCLDTLPALRGLDRAHSHGTRAQGRKSYSLASLFHR

YFQAEPSAAHSAEGDVHTLLLIFLHRAPELLAWADEQARSWAHIEPMYVPPDGPSLEA

MKRTADGSEFESPKKKRKV

OsBADH2-NLS-A3A-TALE-L-FokI-L-T2A-TALE-R-FokI-RD450A (FIG. 16C)
                                             (SEQ ID NO. 127)
MDYKDHDGDYKDHDIDYKDDDDKMAPKKKRKVEASPASGPRHLMDPHIFTSNFNNG

IGRHKTYLCYEVERLDNGTSVKMDQHRGFLHNQAKNLLCGFYGRHAELRFLDLVPSL

QLDPAQIYRVTWFISWSPCFSWGCAGEVRAFLQENTHVRLRIFAARIYDYDPLYKEALQ

MLRDAGAQVSIMTYDEFKHCWDTFVDHQGCPFQPWDGLDEHSQALSGRLRAILQNQ

GNSGSETPGTSESATPESSGGSSGGSSGSETPGTSESATPESSGGSSGGSGIHGVPSRMVD

LRTLGYSQQQQEKIKPKVRSTVAQHHEALVGHGFTHAHIVALSQHPAALGTVAVTYQHI

ITALPEATHEDIVGVGKQWSGARALEALLTDAGELRGPPLQLDTGQLVKIAKRGGVTA

MEAVHASRNALTGAPLNLTPDQVVAIASNNGGKQALETVQRLLPVLCQDHGLTPDQV

VAIASHDGGKQALETVQRLLPVLCQDHGLTPDQVVAIASNGGGKQALETVQRLLPVLC

QDHGLTPDQVVAIASNNGGKQALETVQRLLPVLCQDHGLTPDQVVAIASNNGGKQAL

ETVQRLLPVLCQDHGLTPDQVVAIASNIGGKQALETVQRLLPVLCQDHGLTPDQVVAI

ASNGGGKQALETVQRLLPVLCQDHGLTPDQVVAIASNNGGKQALETVQRLLPVLCQD

HGLTPDQVVAIASHDGGKQALETVQRLLPVLCQDHGLTPDQVVAIASNGGGKQALET

VQRLLPVLCQDHGLTPDQVVAIASNGGGKQALETVQRLLPVLCQDHGLTPDQVVAIAS

NGGGKQALETVQRLLPVLCQDHGLTPDQVVAIASNNGGKQALETVQRLLPVLCQDHG

LTPDQVVAIASNIGGKQALETVQRLLPVLCQDHGLTPDQVVAIASNNGGKQALETVQR

LLPVLCQDHGLTPDQVVAIASNGGGKQALETVQRLLPVLCQDHGLTPDQVVAIASNIG

GKQALESIVAQLSRPDPALAALTNDHLVALACLGGRPAMDAVKKGLPHAPELIRRVNR

RIGERTSHRVAGSQLVKSELEEKKSELRHKLKYVPHEYIELIEIARNSTQDRILEMKVME

FFMKVYGYRGKHLGGSRKPDGAIYTVGSPIDYGVIVDTKAYSGGYNLPIGQADEMQR

YVKENQTRNKHINPNEWWKVYPSSVTEFKFLFVSGHFKGNYKAQLTRLNHKTNCNGA

VLSVEELLIGGEMIKAGTLTLEEVRRKFNNGEINFEGRGSLLTCGDVEENPGPRMDYKD

-continued

HDGDYKDHDIDYKDDDDKMAPKKKRKVGIHGVPARMVDLRTLGYSQQQQEKIKPKV

RSTVAQHHEALVGHGFTHAHIVALSQHPAALGTVAVTYQHIITALPEATHEDIVGVGKQ

WSGARALEALLTDAGELRGPPLQLDTGQLVKIAKRGGVTAMEAVHASRNALTGAPLN

LTPDQVVAIASNNGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASNGG

GKQALETVQRLLPVLCQDHGLTPDQVVAIASNGGGKQALETVQRLLPVLCQDHGLTP

DQVVAIASNGGGKQALETVQRLLPVLCQDHGLTPDQVVAIASNGGGKQALETVQRLL

PVLCQDHGLTPDQVVAIASNNGGKQALETVQRLLPVLCQDHGLTPDQVVAIASNGGG

KQALETVQRLLPVLCQDHGLTPDQVVAIASHDGGKQALETVQRLLPVLCQDHGLTPD

QVVAIASHDGGKQALETVQRLLPVLCQDHGLTPDQVVAIASNIGGKQALETVQRLLPV

LCQDHGLTPDQVVAIASNIGGKQALETVQRLLPVLCQDHGLTPDQVVAIASNNGGKQA

LETVQRLLPVLCQDHGLTPDQVVAIASNNGGKQALETVQRLLPVLCQDHGLTPDQVVA

IASNIGGKQALETVQRLLPVLCQDHGLTPDQVVAIASNGGGKQALESIVAQLSRPDPAL

AALTNDHLVALACLGGRPAMDAVKKGLPHAPELIRRVNRRIGERTSHRVAGSQLVKSEL

EEKKSELRHKLKYVPHEYIELIEIARNSTQDRILEMKVMEFFMKVYGYRGKHLGGSRK

PAGAIYTVGSPIDYGVIVDTKAYSGGYNLPIGQADEMERYVEENQTRNKHLNPNEWW

KVYPSSVTEFKFLFVSGHFKGNYKAQLTRLNHITNCNGAVLSVEELLIGGEMIKAGTLT

LEEVRRKFNNGEINF

Figure 16C:
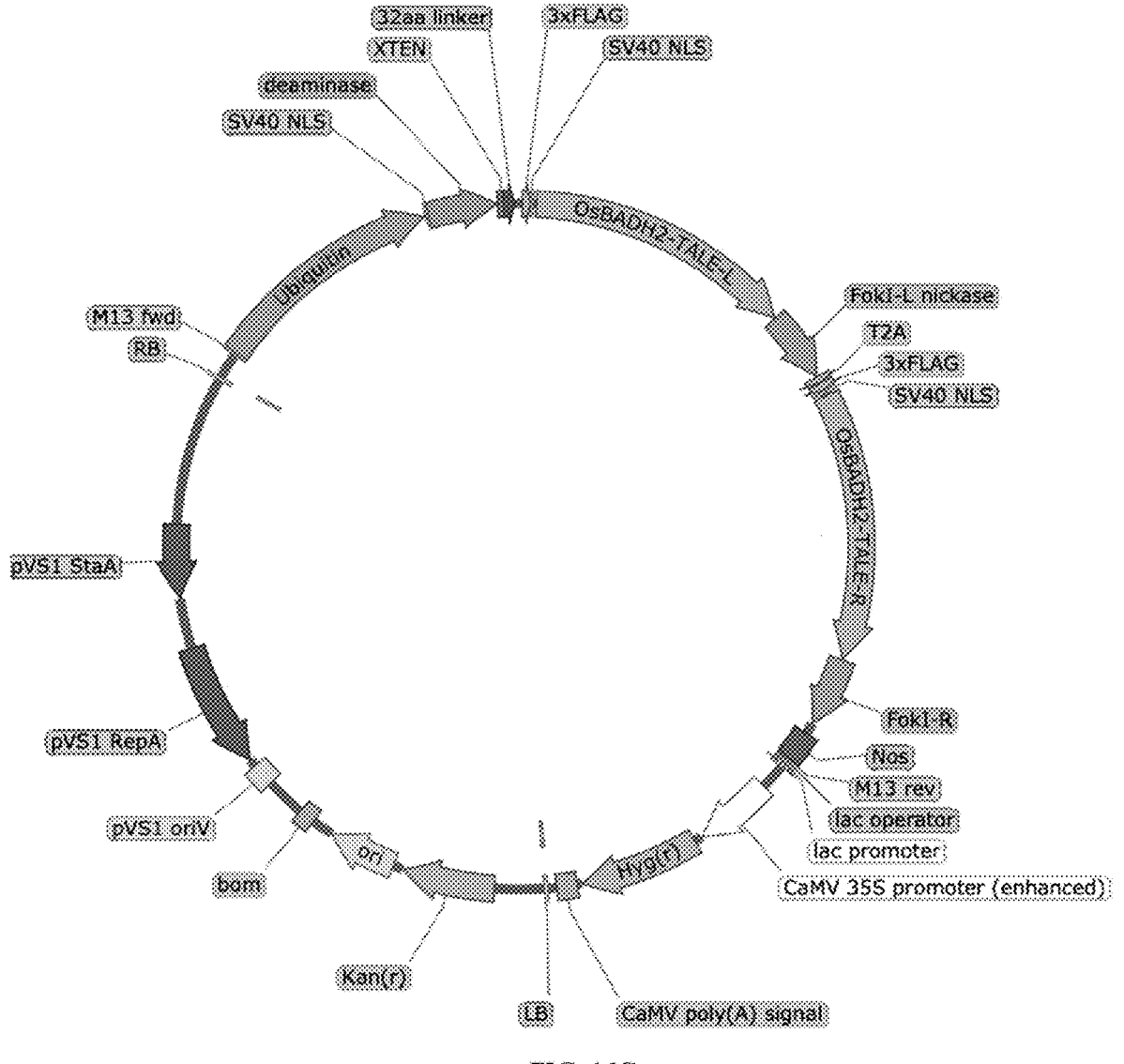
Figure 16C:
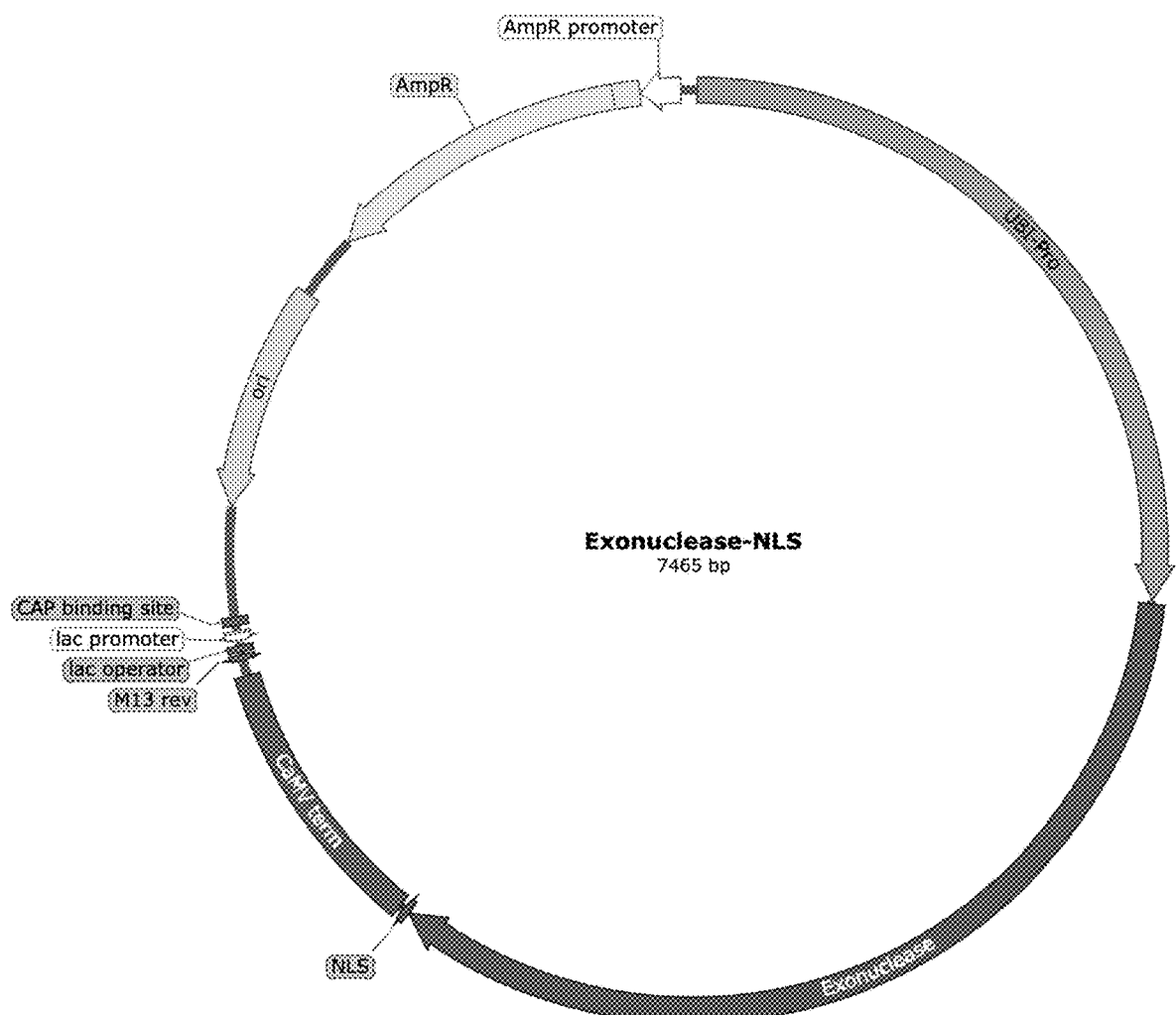
Figure 16C:
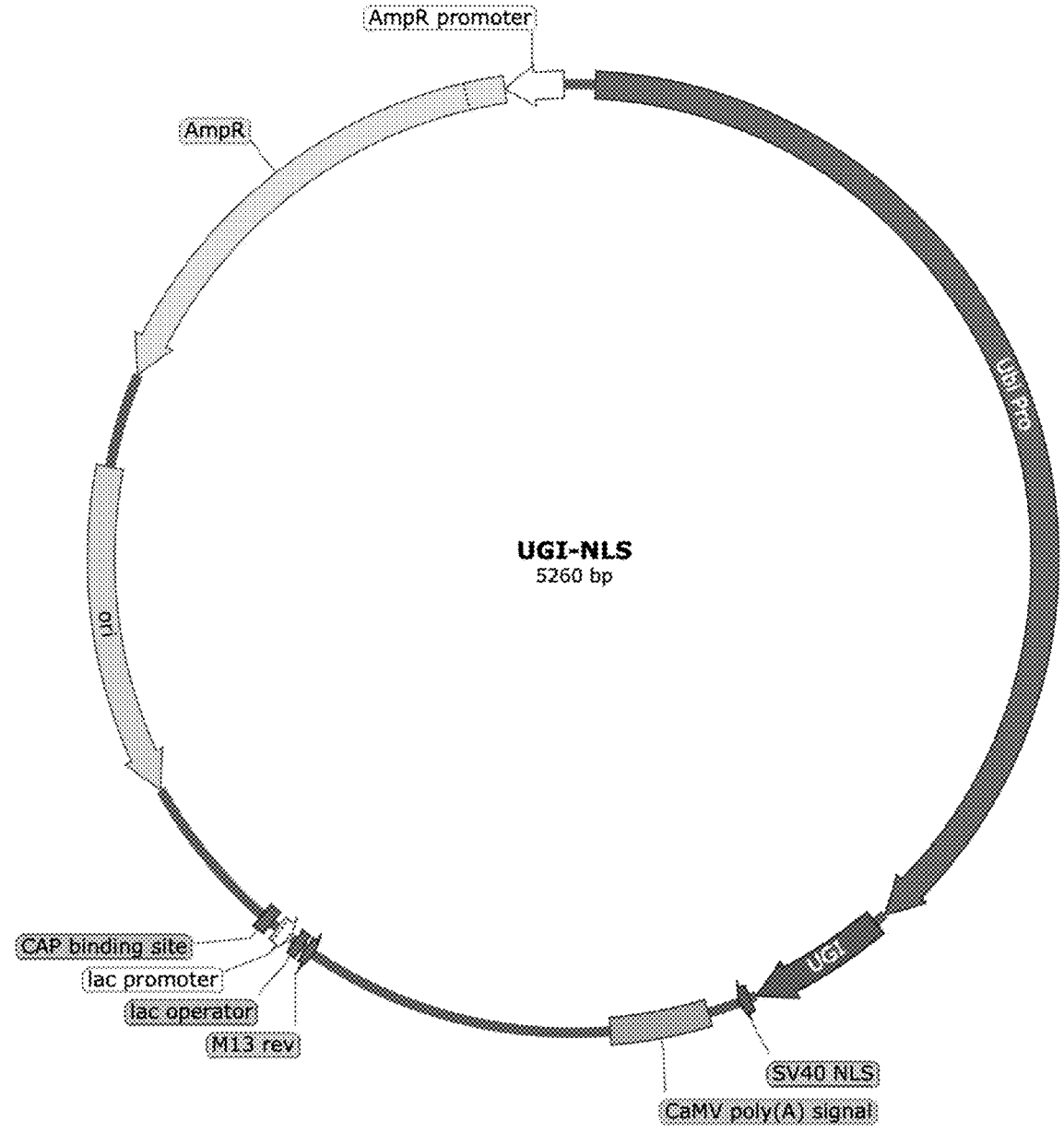

OsBADH2-NLS-A3A-TALE-L-FokI-L$_{D450A}$-T2A-TALE-R-FokI-R (FIG. 16C)

(SEQ ID NO. 128)

MDYKDHDGDYKDHDIDYKDDDDKMAPKKKRKVEASPASGPRHLMDPHIFTSNFNNG

IGRHKTYLCYEVERLDNGTSVKMDQHRGFLHNQAKNLLCGFYGRHAELRFLDLVPSL

QLDPAQIYRVTWFISWSPCFSWGCAGEVRAFLQENTHVRLRIFAARIYDYDPLYKEALQ

MLRDAGAQVSIMTYDEFKHCWDTFVDHQGCPFQPWDGLDEHSQALSGRLRAILQNQ

GNSGSETPGTSESATPESSGGSSGGSSGSETPGTSESATPESSGGSSGGSGIHGVPSRMVD

LRTLGYSQQQQEKIKPKVRSTVAQHHEALVGHGFTHAHIVALSQHPAALGTVAVTYQHI

ITALPEATHEDIVGVGKQWSGARALEALLTDAGELRGPPLQLDTGQLVKIAKRGGVTA

MEAVHASRNALTGAPLNLTPDQVVAIASNNGGKQALETVQRLLPVLCQDHGLTPDQV

VAIASHDGGKQALETVQRLLPVLCQDHGLTPDQVVAIASNGGGKQALETVQRLLPVLC

QDHGLTPDQVVAIASNNGGKQALETVQRLLPVLCQDHGLTPDQVVAIASNNGGKQAL

ETVQRLLPVLCQDHGLTPDQVVAIASNIGGKQALETVQRLLPVLCQDHGLTPDQVVAI

ASNGGGKQALETVQRLLPVLCQDHGLTPDQVVAIASNNGGKQALETVQRLLPVLCQD

HGLTPDQVVAIASHDGGKQALETVQRLLPVLCQDHGLTPDQVVAIASNGGGKQALET

VQRLLPVLCQDHGLTPDQVVAIASNGGGKQALETVQRLLPVLCQDHGLTPDQVVAIAS

NGGGKQALETVQRLLPVLCQDHGLTPDQVVAIASNNGGKQALETVQRLLPVLCQDHG

LTPDQVVAIASNIGGKQALETVQRLLPVLCQDHGLTPDQVVAIASNNGGKQALETVQR

LLPVLCQDHGLTPDQVVAIASNGGGKQALETVQRLLPVLCQDHGLTPDQVVAIASNIG

GKQALESIVAQLSRPDPALAALTNDHLVALACLGGRPAMDAVKKGLPHAPELIRRVNR

RIGERTSHRVAGSQLVKSELEEKKSELRHKLKYVPHEYIELIEIARNSTQDRILEMKVME

FFMKVYGYRGKHLGGSRKPAGAIYTVGSPIDYGVIVDTKAYSGGYNLPIGQADEMQR

YVKENQTRNKHINPNEWWKVYPSSVTEFKFLFVSGHFKGNYKAQLTRLNHKTNCNGA

VLSVEELLIGGEMIKAGTLTLEEVRRKFNNGEINFEGRGSLLTCGDVEENPGPRMDYKD

-continued

HDGDYKDHDIDYKDDDDKMAPKKKRKVGIHGVPARMVDLRTLGYSQQQQEKIKPKV

RSTVAQHHEALVGHGFTHAHIVALSQHPAALGTVAVTYQHIITALPEATHEDIVGVGKQ

WSGARALEALLTDAGELRGPPLQLDTGQLVKIAKRGGVTAMEAVHASRNALTGAPLN

LTPDQVVAIASNNGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASNGG

GKQALETVQRLLPVLCQDHGLTPDQVVAIASNGGGKQALETVQRLLPVLCQDHGLTP

DQVVAIASNGGGKQALETVQRLLPVLCQDHGLTPDQVVAIASNGGGKQALETVQRLL

PVLCQDHGLTPDQVVAIASNNGGKQALETVQRLLPVLCQDHGLTPDQVVAIASNGGG

KQALETVQRLLPVLCQDHGLTPDQVVAIASHDGGKQALETVQRLLPVLCQDHGLTPD

QVVAIASHDGGKQALETVQRLLPVLCQDHGLTPDQVVAIASNIGGKQALETVQRLLPV

LCQDHGLTPDQVVAIASNIGGKQALETVQRLLPVLCQDHGLTPDQVVAIASNNGGKQA

LETVQRLLPVLCQDHGLTPDQVVAIASNNGGKQALETVQRLLPVLCQDHGLTPDQVVA

IASNIGGKQALETVQRLLPVLCQDHGLTPDQVVAIASNGGGKQALESIVAQLSRPDPAL

AALTNDHLVALACLGGRPAMDAVKKGLPHAPELIRRVNRRIGERTSHRVAGSQLVKSEL

EEKKSELRHKLKYVPHEYIELIEIARNSTQDRILEMKVMEFFMKVYGYRGKHLGGSRK

PDGAIYTVGSPIDYGVIVDTKAYSGGYNLPIGQADEMERYVEENQTRNKHLNPNEWW

KVYPSSVTEFKFLFVSGHFKGNYKAQLTRLNHITNCNGAVLSVEELLIGGEMIKAGTLT

LEEVRRKFNNGEINF mExoI-NLS (FIG. 16C)
                                                     (SEQ ID NO. 129)
MGIQGLLQFIQEASEPVNVKKYKGQAVAVDTYCWLHKGAIACAEKLAKGEPTDRYVG

FCMKFVNMLLSYGVKPILIFDGCTLPSKKEVERSRRERRQSNLLKGKQLLREGKVSEA

RDCFARSINITHAMAHKVIKAARALGVDCLVAPYEADAQLAYLNKAGIVQAVITEDSD

LLAFGCKKVILKMDQFGNGLEVDQARLGMCKQLGDVFTEEKFRYMCILSGCDYLASL

RGIGLAKACKVLRLANNPDIVKVIKKIGHYLRMNITVPEDYITGFIRANNTFLYQLVFDP

IQRKLVPLNAYGDDVNPETLTYAGQYVGDSVALQIALGNRDVNTFEQIDDYSPDTMPA

HSRSHSWNEKAGQKPPGTNSIWHKNYCPRLEVNSVSHAPQLKEKPSTLGLKQVISTKG

LNLPRKSCVLKRPRNEALAEDDLLSQYSSVSKKIKENGCGDGTSPNSSKMSKSCPDSGT

AHKTDAHTPSKMRNKFATFLQRRNEESGAVVVPGTRSRFFCSSQDFDNFIPKKESGQPL

NETVATGKATTSLLGALDCPDTEGHKPVDANGTHNLSSQIPGNAAVSPEDEAQSSETSK

LLGAMSPPSLGTLRSCFSWSGTLREFSRTPSPSASTTLQQFRRKSDPPACLPEASAVVTD

RCDSKSEMLGETSQPLHELGCSSRSQESMDSSCGLNTSSLSQPSSRDSGSEESDCNNKS

LDNQGEQNSKQHLPHFSKKDGLRRNKVPGLCRSSSMDSFSTTKIKPLVPARVSGLSKKS

GSMQTRKHHDVENKPGLQTKISELWKNFGFKKDSEKLPSCKKPLSPVKDNIQLTPETE

DEIFNKPECVRAQRAIFHMKRTADGSEFESPKKKRKV

Trex2-NLS (FIG. 16C)
                                                     (SEQ ID NO. 130)
MSEPPRAETFVFLDLEATGLPNMDPEIAEISLFAVHRSSLENPERDDSGSLVLPRVLDKLT

LCMCPERPFTAKASEITGLSSESLMHCGKAGFNGAVVRTLQGFLSRQEGPICLVAHNGF

DYDFPLLCTELQRLGAHLPQDTVCLDTLPALRGLDRAHSHGTRAQGRKSYSLASLFHR

YFQAEPSAAHSAEGDVHTLLLIFLHRAPELLAWADEQARSWAHIEPMYVPPDGPSLEA

MKRTADGSEFESPKKKRKV

-continued

UGI-NLS (FIG. 16C)
(SEQ ID NO. 131)
MKRTADGSEFESPKKKRKVTNLSDIIEKETGKQLVIQESILMLPEEVEEVIGNKPESDILV

HTAYDESTDENVMLLTSDAPEYKPWALVIQDSNGENKIKML

OsBADH2-NLS-A3A-TALE-L-FokI-L-T2A-TALE-R-FokI-R$_{D450A}$-UGI (FIG. 16D)
(SEQ ID NO. 132)
MDYKDHDGDYKDHDIDYKDDDDKMAPKKKRKVEASPASGPRHLMDPHIFTSNFNNG

IGRHKTYLCYEVERLDNGTSVKMDQHRGFLHNQAKNLLCGFYGRHAELRFLDLVPSL

QLDPAQIYRVTWFISWSPCFSWGCAGEVRAFLQENTHVRLRIFAARIYDYDPLYKEALQ

MLRDAGAQVSIMTYDEFKHCWDTFVDHQGCPFQPWDGLDEHSQALSGRLRAILQNQ

GNSGSETPGTSESATPESSGGSSGGSSGSETPGTSESATPESSGGSSGGSGIHGVPSRMVD

LRTLGYSQQQQEKIKPKVRSTVAQHHEALVGHGFTHAHIVALSQHPAALGTVAVTYQHI

ITALPEATHEDIVGVGKQWSGARALEALLTDAGELRGPPLQLDTGQLVKIAKRGGVTA

MEAVHASRNALTGAPLNLTPDQVVAIASNNGGKQALETVQRLLPVLCQDHGLTPDQV

VAIASHDGGKQALETVQRLLPVLCQDHGLTPDQVVAIASNGGGKQALETVQRLLPVLC

QDHGLTPDQVVAIASNNGGKQALETVQRLLPVLCQDHGLTPDQVVAIASNNGGKQAL

ETVQRLLPVLCQDHGLTPDQVVAIASNIGGKQALETVQRLLPVLCQDHGLTPDQVVAI

ASNGGGKQALETVQRLLPVLCQDHGLTPDQVVAIASNNGGKQALETVQRLLPVLCQD

HGLTPDQVVAIASHDGGKQALETVQRLLPVLCQDHGLTPDQVVAIASNGGGKQALET

VQRLLPVLCQDHGLTPDQVVAIASNGGGKQALETVQRLLPVLCQDHGLTPDQVVAIAS

NGGGKQALETVQRLLPVLCQDHGLTPDQVVAIASNNGGKQALETVQRLLPVLCQDHG

LTPDQVVAIASNIGGKQALETVQRLLPVLCQDHGLTPDQVVAIASNNGGKQALETVQR

LLPVLCQDHGLTPDQVVAIASNGGGKQALETVQRLLPVLCQDHGLTPDQVVAIASNIG

GKQALESIVAQLSRPDPALAALTNDHLVALACLGGRPAMDAVKKGLPHAPELIRRVNR

RIGERTSHRVAGSQLVKSELEEKKSELRHKLKYVPHEYIELIEIARNSTQDRILEMKVME

FFMKVYGYRGKHLGGSRKPDGAIYTVGSPIDYGVIVDTKAYSGGYNLPIGQADEMQR

YVKENQTRNKHINPNEWWKVYPSSVTEFKFLFVSGHFKGNYKAQLTRLNHKTNCNGA

VLSVEELLIGGEMIKAGTLTLEEVRRKFNNGEINFEGRGSLLTCGDVEENPGPRMDYKD

HDGDYKDHDIDYKDDDDKMAPKKKRKVGIHGVPARMVDLRTLGYSQQQQEKIKPKV

RSTVAQHHEALVGHGFTHAHIVALSQHPAALGTVAVTYQHIITALPEATHEDIVGVGKQ

WSGARALEALLTDAGELRGPPLQLDTGQLVKIAKRGGVTAMEAVHASRNALTGAPLN

LTPDQVVAIASNNGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASNGG

GKQALETVQRLLPVLCQDHGLTPDQVVAIASNGGGKQALETVQRLLPVLCQDHGLTP

DQVVAIASNGGGKQALETVQRLLPVLCQDHGLTPDQVVAIASNGGGKQALETVQRLL

PVLCQDHGLTPDQVVAIASNNGGKQALETVQRLLPVLCQDHGLTPDQVVAIASNGGG

KQALETVQRLLPVLCQDHGLTPDQVVAIASHDGGKQALETVQRLLPVLCQDHGLTPD

QVVAIASHDGGKQALETVQRLLPVLCQDHGLTPDQVVAIASNIGGKQALETVQRLLPV

LCQDHGLTPDQVVAIASNIGGKQALETVQRLLPVLCQDHGLTPDQVVAIASNNGGKQA

LETVQRLLPVLCQDHGLTPDQVVAIASNNGGKQALETVQRLLPVLCQDHGLTPDQVVA

IASNIGGKQALETVQRLLPVLCQDHGLTPDQVVAIASNGGGKQALESIVAQLSRPDPAL

AALTNDHLVALACLGGRPAMDAVKKGLPHAPELIRRVNRRIGERTSHRVAGSQLVKSEL

EEKKSELRHKLKYVPHEYIELIEIARNSTQDRILEMKVMEFFMKVYGYRGKHLGGSRK

-continued

PAGAIYTVGSPIDYGVIVDTKAYSGGYNLPIGQADEMERYVEENQTRNKHLNPNEWW

KVYPSSVTEFKFLFVSGHFKGNYKAQLTRLNHITNCNGAVLSVEELLIGGEMIKAGTLT

LEEVRRKFNNGEINFSGGSGGSGGSTNLSDIIEKETGKQLVIQESILMLPEEVEEVIGNKP

ESDILVHTAYDESTDENVMLLTSDAPEYKPWALVIQDSNGENKIKML

OsBADH2-NLS-A3A-TALE-L-FokI-L$_{D450A}$-T2A-TALE-R-FokI-R-UGI (FIG. 16D)
                                                    (SEQ ID NO. 133)
MDYKDHDGDYKDHDIDYKDDDDKMAPKKKRKVEASPASGPRHLMDPHIFTSNFNNG

IGRHKTYLCYEVERLDNGTSVKMDQHRGFLHNQAKNLLCGFYGRHAELRFLDLVPSL

QLDPAQIYRVTWFISWSPCFSWGCAGEVRAFLQENTHVRLRIFAARIYDYDPLYKEALQ

MLRDAGAQVSIMTYDEFKHCWDTFVDHQGCPFQPWDGLDEHSQALSGRLRAILQNQ

GNSGSETPGTSESATPESSGGSSGGSSGSETPGTSESATPESSGGSSGGSGIHGVPSRMVD

LRTLGYSQQQQEKIKPKVRSTVAQHHEALVGHGFTHAHIVALSQHPAALGTVAVTYQHI

ITALPEATHEDIVGVGKQWSGARALEALLTDAGELRGPPLQLDTGQLVKIAKRGGVTA

MEAVHASRNALTGAPLNLTPDQVVAIASNNGGKQALETVQRLLPVLCQDHGLTPDQV

VAIASHDGGKQALETVQRLLPVLCQDHGLTPDQVVAIASNGGGKQALETVQRLLPVLC

QDHGLTPDQVVAIASNNGGKQALETVQRLLPVLCQDHGLTPDQVVAIASNNGGKQAL

ETVQRLLPVLCQDHGLTPDQVVAIASNIGGKQALETVQRLLPVLCQDHGLTPDQVVAI

ASNGGGKQALETVQRLLPVLCQDHGLTPDQVVAIASNNGGKQALETVQRLLPVLCQD

HGLTPDQVVAIASHDGGKQALETVQRLLPVLCQDHGLTPDQVVAIASNGGGKQALET

VQRLLPVLCQDHGLTPDQVVAIASNGGGKQALETVQRLLPVLCQDHGLTPDQVVAIAS

NGGGKQALETVQRLLPVLCQDHGLTPDQVVAIASNNGGKQALETVQRLLPVLCQDHG

LTPDQVVAIASNIGGKQALETVQRLLPVLCQDHGLTPDQVVAIASNNGGKQALETVQR

LLPVLCQDHGLTPDQVVAIASNGGGKQALETVQRLLPVLCQDHGLTPDQVVAIASNIG

GKQALESIVAQLSRPDPALAALTNDHLVALACLGGRPAMDAVKKGLPHAPELIRRVNR

RIGERTSHRVAGSQLVKSELEEKKSELRHKLKYVPHEYIELIEIARNSTQDRILEMKVME

FFMKVYGYRGKHLGGSRKPAGAIYTVGSPIDYGVIVDTKAYSGGYNLPIGQADEMQR

YVKENQTRNKHINPNEWWKVYPSSVTEFKFLFVSGHFKGNYKAQLTRLNHKTNCNGA

VLSVEELLIGGEMIKAGTLTLEEVRRKFNNGEINFEGRGSLLTCGDVEENPGPRMDYKD

HDGDYKDHDIDYKDDDDKMAPKKKRKVGIHGVPARMVDLRTLGYSQQQQEKIKPKV

RSTVAQHHEALVGHGFTHAHIVALSQHPAALGTVAVTYQHIITALPEATHEDIVGVGKQ

WSGARALEALLTDAGELRGPPLQLDTGQLVKIAKRGGVTAMEAVHASRNALTGAPLN

LTPDQVVAIASNNGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASNGG

GKQALETVQRLLPVLCQDHGLTPDQVVAIASNGGGKQALETVQRLLPVLCQDHGLTP

DQVVAIASNGGGKQALETVQRLLPVLCQDHGLTPDQVVAIASNGGGKQALETVQRLL

PVLCQDHGLTPDQVVAIASNNGGKQALETVQRLLPVLCQDHGLTPDQVVAIASNGGG

KQALETVQRLLPVLCQDHGLTPDQVVAIASHDGGKQALETVQRLLPVLCQDHGLTPD

QVVAIASHDGGKQALETVQRLLPVLCQDHGLTPDQVVAIASNIGGKQALETVQRLLPV

LCQDHGLTPDQVVAIASNIGGKQALETVQRLLPVLCQDHGLTPDQVVAIASNNGGKQA

LETVQRLLPVLCQDHGLTPDQVVAIASNNGGKQALETVQRLLPVLCQDHGLTPDQVVA

IASNIGGKQALETVQRLLPVLCQDHGLTPDQVVAIASNGGGKQALESIVAQLSRPDPAL

-continued
AALTNDHLVALACLGGRPAMDAVKKGLPHAPELIRRVNRRIGERTSHRVAGSQLVKSEL

EEKKSELRHKLKYVPHEYIELIEIARNSTQDRILEMKVMEFFMKVYGYRGKHLGGSRK

PDGAIYTVGSPIDYGVIVDTKAYSGGYNLPIGQADEMERYVEENQTRNKHLNPNEWW

KVYPSSVTEFKFLFVSGHFKGNYKAQLTRLNHITNCNGAVLSVEELLIGGEMIKAGTLT

LEEVRRKFNNGEINFSGGSGGSGGSTNLSDIIEKETGKQLVIQESILMLPEEVEEVIGNKP

ESDILVHTAYDESTDENVMLLTSDAPEYKPWALVIQDSNGENKIKML mExoI-NLS (FIG. 16D)
                                                    (SEQ ID NO. 134)
MGIQGLLQFIQEASEPVNVKKYKGQAVAVDTYCWLHKGAIACAEKLAKGEPTDRYVG

FCMKFVNMLLSYGVKPILIFDGCTLPSKKEVERSRRERRQSNLLKGKQLLREGKVSEA

RDCFARSINITHAMAHKVIKAARALGVDCLVAPYEADAQLAYLNKAGIVQAVITEDSD

LLAFGCKKVILKMDQFGNGLEVDQARLGMCKQLGDVFTEEKFRYMCILSGCDYLASL

RGIGLAKACKVLRLANNPDIVKVIKKIGHYLRMNITVPEDYITGFIRANNTFLYQLVFDP

IQRKLVPLNAYGDDVNPETLTYAGQYVGDSVALQIALGNRDVNTFEQIDDYSPDTMPA

HSRSHSWNEKAGQKPPGTNSIWHKNYCPRLEVNSVSHAPQLKEKPSTLGLKQVISTKG

LNLPRKSCVLKRPRNEALAEDDLLSQYSSVSKKIKENGCGDGTSPNSSKMSKSCPDSGT

AHKTDAHTPSKMRNKFATFLQRRNEESGAVVVPGTRSRFFCSSQDFDNFIPKKESGQPL

NETVATGKATTSLLGALDCPDTEGHKPVDANGTHNLSSQIPGNAAVSPEDEAQSSETSK

LLGAMSPPSLGTLRSCFSWSGTLREFSRTPSPSASTTLQQFRRKSDPPACLPEASAVVTD

RCDSKSEMLGETSQPLHELGCSSRSQESMDSSCGLNTSSLSQPSSRDSGSEESDCNNKS

LDNQGEQNSKQHLPHFSKKDGLRRNKVPGLCRSSSMDSFSTTKIKPLVPARVSGLSKKS

GSMQTRKHHDVENKPGLQTKISELWKNFGFKKDSEKLPSCKKPLSPVKDNIQLTPETE

DEIFNKPECVRAQRAIFHMKRTADGSEFESPKKKRKV

Trex2-NLS (FIG. 16D)
                                                    (SEQ ID NO. 135)
MSEPPRAETFVFLDLEATGLPNMDPEIAEISLFAVHRSSLENPERDDSGSLVLPRVLDKLT

LCMCPERPFTAKASEITGLSSESLMHCGKAGFNGAVVRTLQGFLSRQEGPICLVAHNGF

DYDFPLLCTELQRLGAHLPQDTVCLDTLPALRGLDRAHSHGTRAQGRKSYSLASLFHR

YFQAEPSAAHSAEGDVHTLLLIFLHRAPELLAWADEQARSWAHIEPMYVPPDGPSLEA

MKRTADGSEFESPKKKRKV

OsBADH2-NLS-A3A-TALE-L-FokI-L-T2A-TALE-R-FokI-R$_{D450A}$-UGI--mExoI-NLS
(FIG. 16E)
                                                    (SEQ ID NO. 136)
cassette1-[MDYKDHDGDYKDHDIDYKDDDDKMAPKKKRKVEASPASGPRHLMDPHIF

TSNFNNGIGRHKTYLCYEVERLDNGTSVKMDQHRGFLHNQAKNLLCGFYGRHAELRF

LDLVPSLQLDPAQIYRVTWFISWSPCFSWGCAGEVRAFLQENTHVRLRIFAARIYDYDP

LYKEALQMLRDAGAQVSIMTYDEFKHCWDTFVDHQGCPFQPWDGLDEHSQALSGRL

RAILQNQGNSGSETPGTSESATPESSGGSSGGSSGSETPGTSESATPESSGGSSGGSGIHG

VPSRMVDLRTLGYSQQQQEKIKPKVRSTVAQHHEALVGHGFTHAHIVALSQHPAALGT

VAVTYQHIITALPEATHEDIVGVGKQWSGARALEALLTDAGELRGPPLQLDTGQLVKIA

KRGGVTAMEAVHASRNALTGAPLNLTPDQVVAIASNNGGKQALETVQRLLPVLCQDH

GLTPDQVVAIASHDGGKQALETVQRLLPVLCQDHGLTPDQVVAIASNGGGKQALETV

QRLLPVLCQDHGLTPDQVVAIASNNGGKQALETVQRLLPVLCQDHGLTPDQVVAIASN

NGGKQALETVQRLLPVLCQDHGLTPDQVVAIASNIGGKQALETVQRLLPVLCQDHGLT

-continued

PDQVVAIASNGGGKQALETVQRLLPVLCQDHGLTPDQVVAIASNNGGKQALETVQRL

LPVLCQDHGLTPDQVVAIASHDGGKQALETVQRLLPVLCQDHGLTPDQVVAIASNGGG

KQALETVQRLLPVLCQDHGLTPDQVVAIASNGGGKQALETVQRLLPVLCQDHGLTPD

QVVAIASNGGGKQALETVQRLLPVLCQDHGLTPDQVVAIASNNGGKQALETVQRLLP

VLCQDHGLTPDQVVAIASNIGGKQALETVQRLLPVLCQDHGLTPDQVVAIASNNGGKQ

ALETVQRLLPVLCQDHGLTPDQVVAIASNGGGKQALETVQRLLPVLCQDHGLTPDQVV

AIASNIGGKQALESIVAQLSRPDPALAALTNDHLVALACLGGRPAMDAVKKGLPHAPEL

IRRVNRRIGERTSHRVAGSQLVKSELEEKKSELRHKLKYVPHEYIELIEIARNSTQDRILE

MKVMEFFMKVYGYRGKHLGGSRKPDGAIYTVGSPIDYGVIVDTKAYSGGYNLPIGQA

DEMQRYVKENQTRNKHINPNEWWKVYPSSVTEFKFLFVSGHFKGNYKAQLTRLNHK

TNCNGAVLSVEELLIGGEMIKAGTLTLEEVRRKFNNGEINFEGRGSLLTCGDVEENPGP

RMDYKDHDGDYKDHDIDYKDDDDKMAPKKKRKVGIHGVPARMVDLRTLGYSQQQQ

EKIKPKVRSTVAQHHEALVGHGFTHAHIVALSQHPAALGTVAVTYQHIITALPEATHEDI

VGVGKQWSGARALEALLTDAGELRGPPLQLDTGQLVKIAKRGGVTAMEAVHASRNAL

TGAPLNLTPDQVVAIASNNGGKQALETVQRLLPVLCQDHGLTPDQVVAIASHDGGKQA

LETVQRLLPVLCQDHGLTPDQVVAIASHDGGKQALETVQRLLPVLCQDHGLTPDQVVA

IASNGGGKQALETVQRLLPVLCQDHGLTPDQVVAIASNGGGKQALETVQRLLPVLCQ

DHGLTPDQVVAIASNGGGKQALETVQRLLPVLCQDHGLTPDQVVAIASNGGGKQALE

TVQRLLPVLCQDHGLTPDQVVAIASNNGGKQALETVQRLLPVLCQDHGLTPDQVVAIA

SNGGGKQALETVQRLLPVLCQDHGLTPDQVVAIASHDGGKQALETVQRLLPVLCQDH

GLTPDQVVAIASHDGGKQALETVQRLLPVLCQDHGLTPDQVVAIASNIGGKQALETVQ

RLLPVLCQDHGLTPDQVVAIASNIGGKQALETVQRLLPVLCQDHGLTPDQVVAIASNN

GGKQALETVQRLLPVLCQDHGLTPDQVVAIASNNGGKQALETVQRLLPVLCQDHGLT

PDQVVAIASNIGGKQALETVQRLLPVLCQDHGLTPDQVVAIASNGGGKQALESIVAQLS

RPDPALAALTNDHLVALACLGGRPAMDAVKKGLPHAPELIRRVNRRIGERTSHRVAGSQ

LVKSELEEKKSELRHKLKYVPHEYIELIEIARNSTQDRILEMKVMEFFMKVYGYRGKH

LGGSRKPAGAIYTVGSPIDYGVIVDTKAYSGGYNLPIGQADEMERYVEENQTRNKHLN

PNEWWKVYPSSVTEFKFLFVSGHFKGNYKAQLTRLNHITNCNGAVLSVEELLIGGEMI

KAGTLTLEEVRRKFNNGEINFSGGSGGSGGSTNLSDIIEKETGKQLVIQESILMLPEEVEE

VIGNKPESDILVHTAYDESTDENVMLLTSDAPEYKPWALVIQDSNGENKIKML]-cassette

2-[MGIQGLLQFIQEASEPVNVKKYKGQAVAVDTYCWLHKGAIACAEKLAKGEPTDRY

VGFCMKFVNMLLSYGVKPILIFDGCTLPSKKEVERSRRERRQSNLLKGKQLLREGKVS

EARDCFARSINITHAMAHKVIKAARALGVDCLVAPYEADAQLAYLNKAGIVQAVITED

SDLLAFGCKKVILKMDQFGNGLEVDQARLGMCKQLGDVFTEEKFRYMCILSGCDYLA

SLRGIGLAKACKVLRLANNPDIVKVIKKIGHYLRMNITVPEDYITGFIRANNTFLYQLVF

DPIQRKLVPLNAYGDDVNPETLTYAGQYVGDSVALQIALGNRDVNTFEQIDDYSPDTM

PAHSRSHSWNEKAGQKPPGTNSIWHKNYCPRLEVNSVSHAPQLKEKPSTLGLKQVIST

KGLNLPRKSCVLKRPRNEALAEDDLLSQYSSVSKKIKENGCGDGTSPNSSKMSKSCPD

SGTAHKTDAHTPSKMRNKFATFLQRRNEESGAVVVPGTRSRFFCSSQDFDNFIPKKESG

QPLNETVATGKATTSLLGALDCPDTEGHKPVDANGTHNLSSQIPGNAAVSPEDEAQSSE

TSKLLGAMSPPSLGTLRSCFSWSGTLREFSRTPSPSASTTLQQFRRKSDPPACLPEASAV

-continued

VTDRCDSKSEMLGETSQPLHELGCSSRSQESMDSSCGLNTSSLSQPSSRDSGSEESDCN

NKSLDNQGEQNSKQHLPHFSKKDGLRRNKVPGLCRSSSMDSFSTTKIKPLVPARVSGLS

KKSGSMQTRKHHDVENKPGLQTKISELWKNFGFKKDSEKLPSCKKPLSPVKDNIQLTP

ETEDEIFNKPECVRAQRAIFHMKRTADGSEFESPKKKRKV]

Figure 16D:
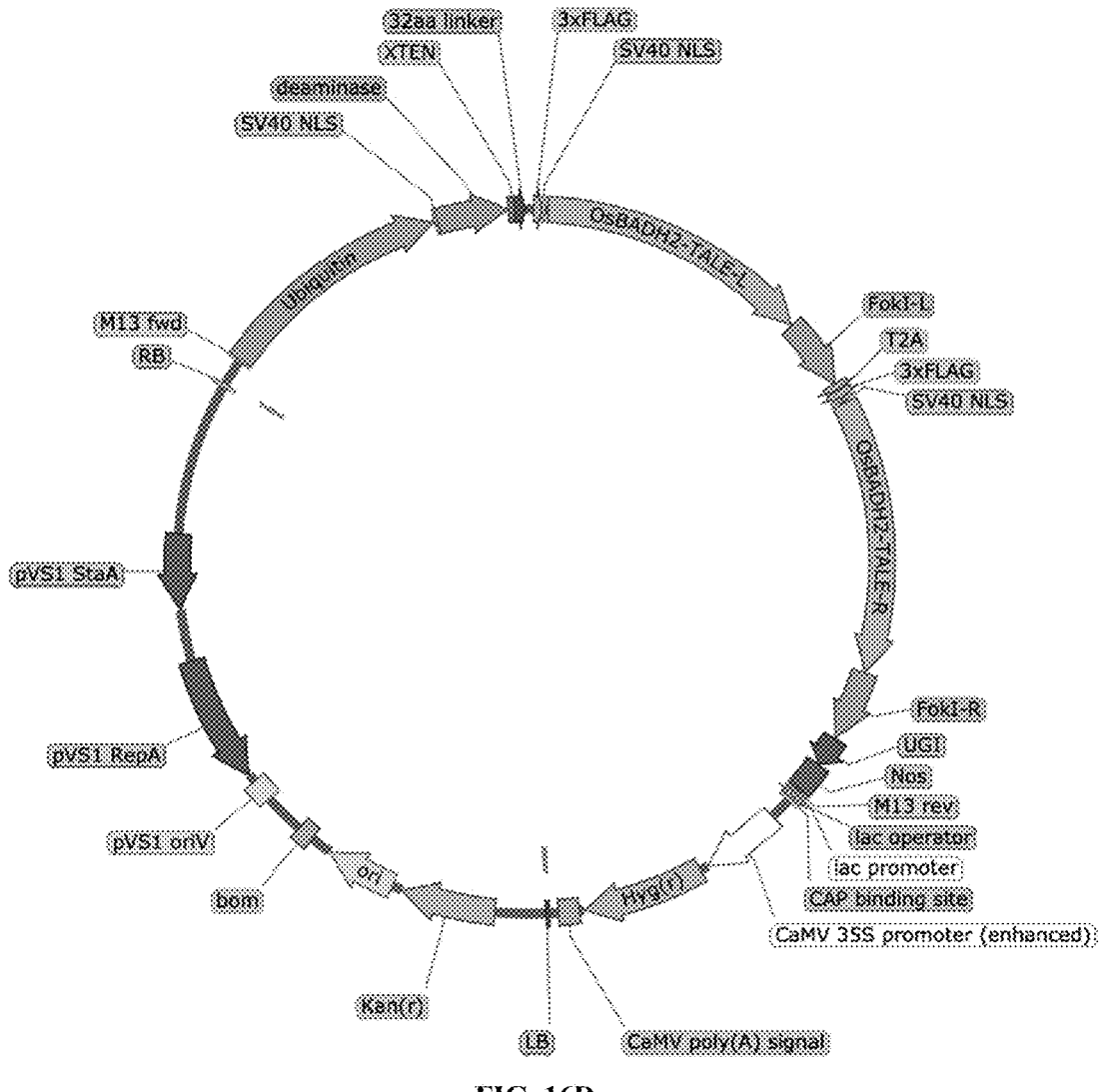
Figure 16D:
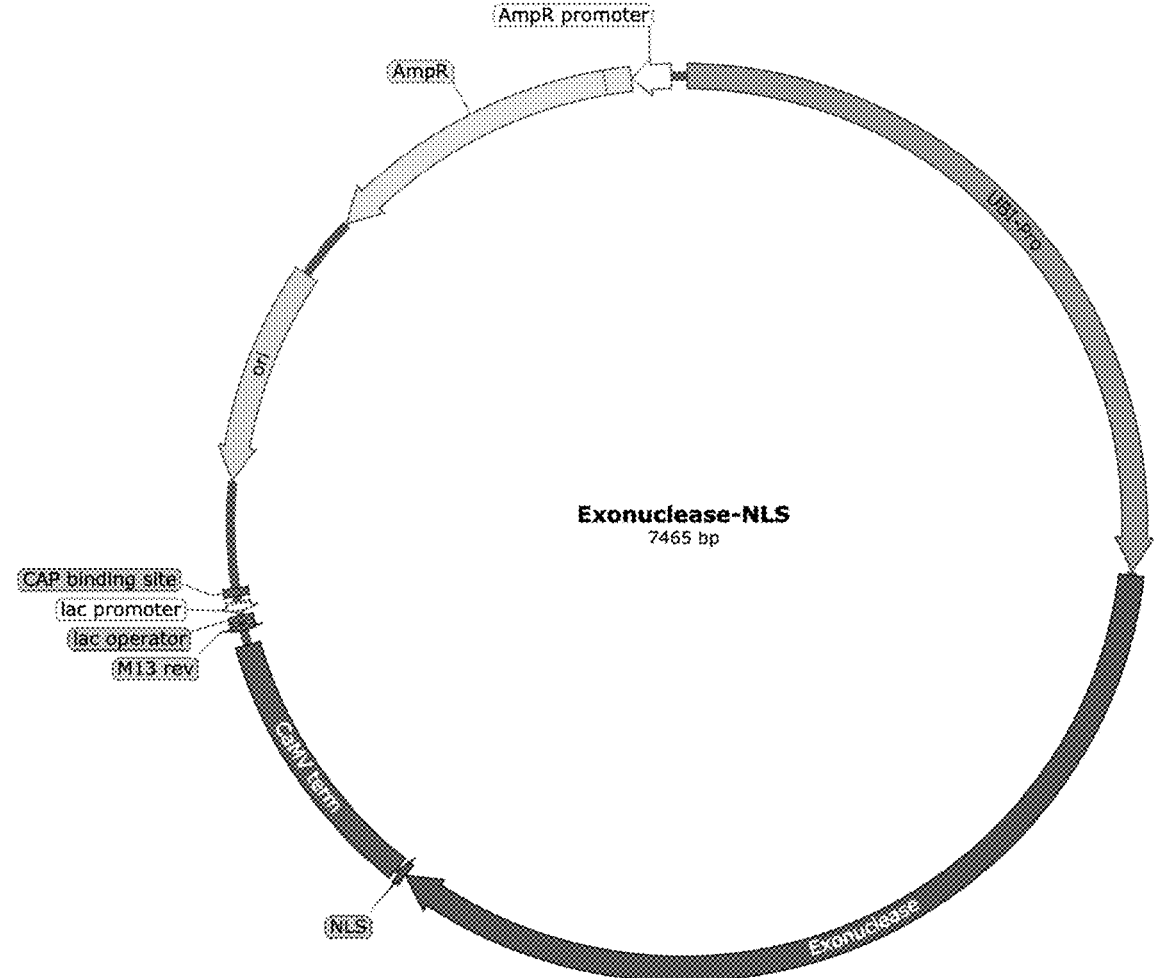
Figure 16E:
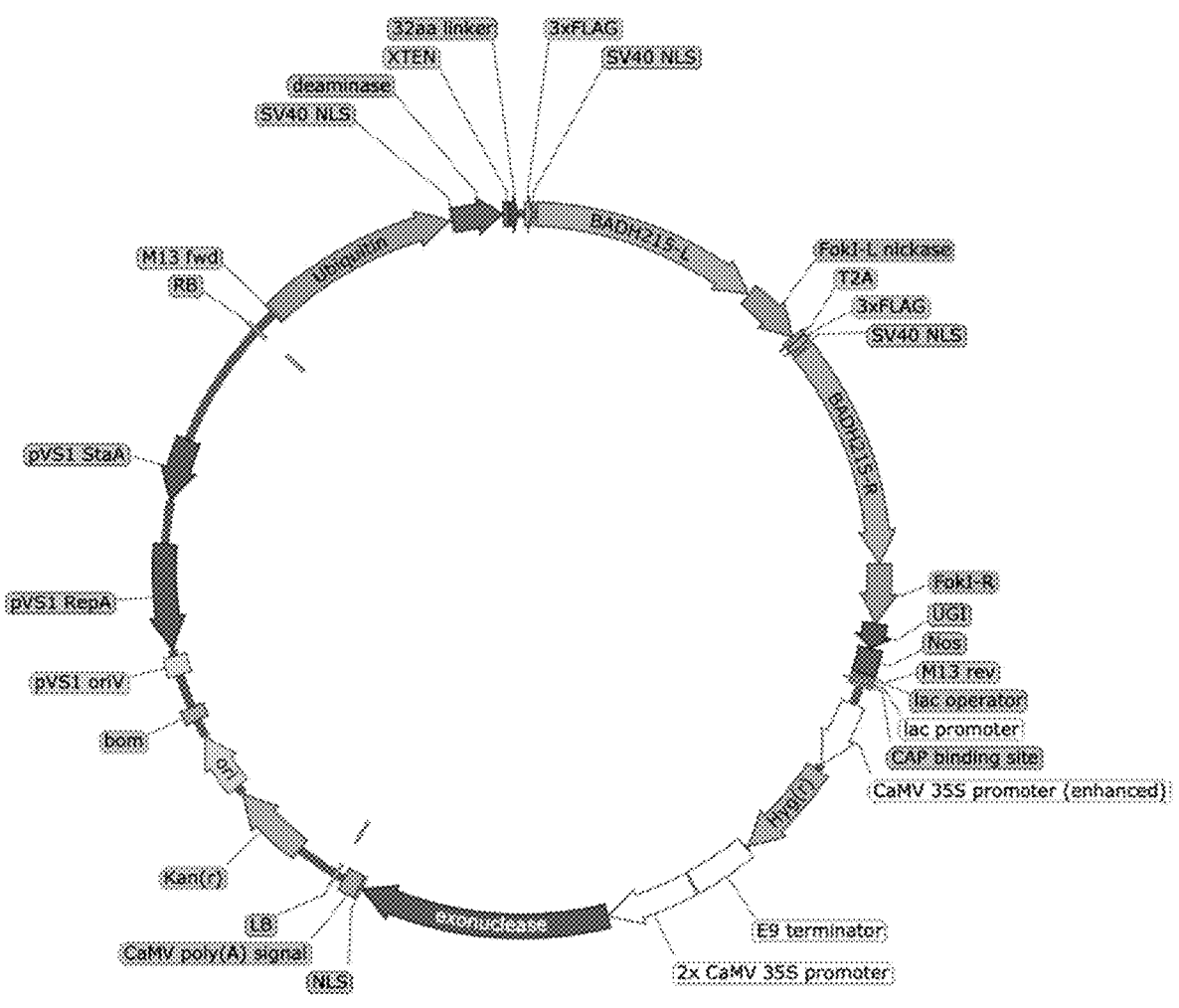

OsBADH2-NLS-A3A-TALE-L-FokI-L$_{D450A}$-T2A-TALE-R-FokI-R-UGI--mExoI-NLS
(FIG. 16E)

(SEQ ID NO. 137)

cassette1-[MDYKDHDGDYKDHDIDYKDDDDKMAPKKKRKVEASPASGPRHLMDPHIF

TSNFNNGIGRHKTYLCYEVERLDNGTSVKMDQHRGFLHNQAKNLLCGFYGRHAELRF

LDLVPSLQLDPAQIYRVTWFISWSPCFSWGCAGEVRAFLQENTHVRLRIFAARIYDYDP

LYKEALQMLRDAGAQVSIMTYDEFKHCWDTFVDHQGCPFQPWDGLDEHSQALSGRL

RAILQNQGNSGSETPGTSESATPESSGGSSGGSSGSETPGTSESATPESSGGSSGGSGIHG

VPSRMVDLRTLGYSQQQQEKIKPKVRSTVAQHHEALVGHGFTHAHIVALSQHPAALGT

VAVTYQHIITALPEATHEDIVGVGKQWSGARALEALLTDAGELRGPPLQLDTGQLVKIA

KRGGVTAMEAVHASRNALTGAPLNLTPDQVVAIASNNGGKQALETVQRLLPVLCQDH

GLTPDQVVAIASHDGGKQALETVQRLLPVLCQDHGLTPDQVVAIASNGGGKQALETV

QRLLPVLCQDHGLTPDQVVAIASNNGGKQALETVQRLLPVLCQDHGLTPDQVVAIASN

NGGKQALETVQRLLPVLCQDHGLTPDQVVAIASNIGGKQALETVQRLLPVLCQDHGLT

PDQVVAIASNGGGKQALETVQRLLPVLCQDHGLTPDQVVAIASNNGGKQALETVQRL

LPVLCQDHGLTPDQVVAIASHDGGKQALETVQRLLPVLCQDHGLTPDQVVAIASNGGG

KQALETVQRLLPVLCQDHGLTPDQVVAIASNGGGKQALETVQRLLPVLCQDHGLTPD

QVVAIASNGGGKQALETVQRLLPVLCQDHGLTPDQVVAIASNNGGKQALETVQRLLP

VLCQDHGLTPDQVVAIASNIGGKQALETVQRLLPVLCQDHGLTPDQVVAIASNNGGKQ

ALETVQRLLPVLCQDHGLTPDQVVAIASNGGGKQALETVQRLLPVLCQDHGLTPDQVV

AIASNIGGKQALESIVAQLSRPDPALAALTNDHLVALACLGGRPAMDAVKKGLPHAPEL

IRRVNRRIGERTSHRVAGSQLVKSELEEKKSELRHKLKYVPHEYIELIEIARNSTQDRILE

MKVMEFFMKVYGYRGKHLGGSRKPAGAIYTVGSPIDYGVIVDTKAYSGGYNLPIGQA

DEMQRYVKENQTRNKHINPNEWWKVYPSSVTEFKFLFVSGHFKGNYKAQLTRLNHK

TNCNGAVLSVEELLIGGEMIKAGTLTLEEVRRKFNNGEINFEGRGSLLTCGDVEENPGP

RMDYKDHDGDYKDHDIDYKDDDDKMAPKKKRKVGIHGVPARMVDLRTLGYSQQQQ

EKIKPKVRSTVAQHHEALVGHGFTHAHIVALSQHPAALGTVAVTYQHIITALPEATHEDI

VGVGKQWSGARALEALLTDAGELRGPPLQLDTGQLVKIAKRGGVTAMEAVHASRNAL

TGAPLNLTPDQVVAIASNNGGKQALETVQRLLPVLCQDHGLTPDQVVAIASHDGGKQA

LETVQRLLPVLCQDHGLTPDQVVAIASHDGGKQALETVQRLLPVLCQDHGLTPDQVVA

IASNGGGKQALETVQRLLPVLCQDHGLTPDQVVAIASNGGGKQALETVQRLLPVLCQ

DHGLTPDQVVAIASNGGGKQALETVQRLLPVLCQDHGLTPDQVVAIASNGGGKQALE

TVQRLLPVLCQDHGLTPDQVVAIASNNGGKQALETVQRLLPVLCQDHGLTPDQVVAIA

SNGGGKQALETVQRLLPVLCQDHGLTPDQVVAIASHDGGKQALETVQRLLPVLCQDH

GLTPDQVVAIASHDGGKQALETVQRLLPVLCQDHGLTPDQVVAIASNIGGKQALETVQ

RLLPVLCQDHGLTPDQVVAIASNIGGKQALETVQRLLPVLCQDHGLTPDQVVAIASNN

GGKQALETVQRLLPVLCQDHGLTPDQVVAIASNNGGKQALETVQRLLPVLCQDHGLT

-continued

PDQVVAIASNIGGKQALETVQRLLPVLCQDHGLTPDQVVAIASNGGGKQALESIVAQLS

RPDPALAALTNDHLVALACLGGRPAMDAVKKGLPHAPELIRRVNRRIGERTSHRVAGSQ

LVKSELEEKKSELRHKLKYVPHEYIELIEIARNSTQDRILEMKVMEFFMKVYGYRGKH

LGGSRKPDGAIYTVGSPIDYGVIVDTKAYSGGYNLPIGQADEMERYVEENQTRNKHLN

PNEWWKVYPSSVTEFKFLFVSGHFKGNYKAQLTRLNHITNCNGAVLSVEELLIGGEMI

KAGTLTLEEVRRKFNNGEINFSGGSGGSGGSTNLSDIIEKETGKQLVIQESILMLPEEVEE

VIGNKPESDILVHTAYDESTDENVMLLTSDAPEYKPWALVIQDSNGENKIKML]-cassette

2-[MGIQGLLQFIQEASEPVNVKKYKGQAVAVDTYCWLHKGAIACAEKLAKGEPTDRY

VGFCMKFVNMLLSYGVKPILIFDGCTLPSKKEVERSRRERRQSNLLKGKQLLREGKVS

EARDCFARSINITHAMAHKVIKAARALGVDCLVAPYEADAQLAYLNKAGIVQAVITED

SDLLAFGCKKVILKMDQFGNGLEVDQARLGMCKQLGDVFTEEKFRYMCILSGCDYLA

SLRGIGLAKACKVLRLANNPDIVKVIKKIGHYLRMNITVPEDYITGFIRANNTFLYQLVF

DPIQRKLVPLNAYGDDVNPETLTYAGQYVGDSVALQIALGNRDVNTFEQIDDYSPDTM

PAHSRSHSWNEKAGQKPPGTNSIWHKNYCPRLEVNSVSHAPQLKEKPSTLGLKQVIST

KGLNLPRKSCVLKRPRNEALAEDDLLSQYSSVSKKIKENGCGDGTSPNSSKMSKSCPD

SGTAHKTDAHTPSKMRNKFATFLQRRNEESGAVVVPGTRSRFFCSSQDFDNFIPKKESG

QPLNETVATGKATTSLLGALDCPDTEGHKPVDANGTHNLSSQIPGNAAVSPEDEAQSSE

TSKLLGAMSPPSLGTLRSCFSWSGTLREFSRTPSPSASTTLQQFRRKSDPPACLPEASAV

VTDRCDSKSEMLGETSQPLHELGCSSRSQESMDSSCGLNTSSLSQPSSRDSGSEESDCN

NKSLDNQGEQNSKQHLPHFSKKDGLRRNKVPGLCRSSSMDSFSTTKIKPLVPARVSGLS

KKSGSMQTRKHHDVENKPGLQTKISELWKNFGFKKDSEKLPSCKKPLSPVKDNIQLTP

ETEDEIFNKPECVRAQRAIFHMKRTADGSEFESPKKKRKV]

ND6-MTS-TALE-L-FokI-L (FIG. 17A)
                                                                  (SEQ ID NO. 138)
MALSRAVCGTSRQLAPVLGYLGSRQKHSLPDYPYDVPDYAGYPYDVPDYAGYPYDVP

DYAMDIADLRTLGYSQQQQEKIKPKVRSTVAQHHEALVGHGFTHAHIVALSQHPAALG

TVAVKYQDMIAALPEATHEAIVGVGKQWSGARALEALLTVAGELRGPPLQLDTGQLLK

IAKRGGVTAVEAVHAWRNALTGAPLNLTPEQVVAIASNNGGKQALETVQRLLPVLCQA

HGLTPEQVVAIASNIGGKQALETVQRLLPVLCQAHGLTPEQVVAIASHDGGKQALETV

QRLLPVLCQAHGLTPEQVVAIASHDGGKQALETVQRLLPVLCQAHGLTPEQVVAIASH

DGGKQALETVQRLLPVLCQAHGLTPEQVVAIASHDGGKQALETVQRLLPVLCQAHGL

TPEQVVAIASHDGGKQALETVQRLLPVLCQAHGLTPEQVVAIASNIGGKQALETVQRL

LPVLCQAHGLTPEQVVAIASNGGGKQALETVQRLLPVLCQAHGLTPEQVVAIASNGGG

RPALESIVAQLSRPDPALAALTNDHLVALACLGGRPALDAVKKGLGGSQLVKSELEEKK

SELRHKLKYVPHEYIELIEIARNSTQDRILEMKVMEFFMKVYGYRGKHLGGSRKPDGA

IYTVGSPIDYGVIVDTKAYSGGYNLPIGQADEMQRYVKENQTRNKHINPNEWWKVYP

SSVTEFKFLFVSGHFKGNYKAQLTRLNHKTNCNGAVLSVEELLIGGEMIKAGTLTLEEV

RRKFNNGEINF

ND6-MTS-TALE-R-FokI-R$_{D450A}$ (FIG. 17B)
                                                                  (SEQ ID NO. 139)
MASVLTPLLLRGLTGSARRLPVPRAKIHSLDYKDHDGDYKDHDIDYKDDDDKMDIAD

LRTLGYSQQQQEKIKPKVRSTVAQHHEALVGHGFTHAHIVALSQHPAALGTVAVKYQD

MIAALPEATHEAIVGVGKRGAGARALEALLTVAGELRGPPLQLDTGQLLKIAKRGGVT

-continued

AVEAVHAWRNALTGAPLNLTPEQVVAIASNNGGKQALETVQRLLPVLCQAHGLTPEQV

VAIASNIGGKQALETVQRLLPVLCQAHGLTPEQVVAIASNGGGKQALETVQRLLPVLC

QAHGLTPEQVVAIASNNGGKQALETVQRLLPVLCQAHGLTPEQVVAIASNNGGKQALE

TVQRLLPVLCQAHGLTPEQVVAIASHDGGKQALETVQRLLPVLCQAHGLTPEQVVAIA

SNGGGKQALETVQRLLPVLCQAHGLTPEQVVAIASNIGGKQALETVQRLLPVLCQAHG

LTPEQVVAIASNGGGKQALETVQRLLPVLCQAHGLTPEQVVAIASNGGGKQALETVQR

LLPVLCQAHGLTPEQVVAIASNGGGRPALESIVAQLSRPDPALAALTNDHLVALACLGG

RPALDAVKKGLGGSQLVKSELEEKKSELRHKLKYVPHEYIELIEIARNSTQDRILEMKV

MEFFMKVYGYRGKHLGGSRKPAGAIYTVGSPIDYGVIVDTKAYSGGYNLPIGQADEM

ERYVEENQTRNKHLNPNEWWKVYPSSVTEFKFLFVSGHFKGNYKAQLTRLNHITNCN

GAVLSVEELLIGGEMIKAGTLTLEEVRRKFNNGEINF

Figure 17A:
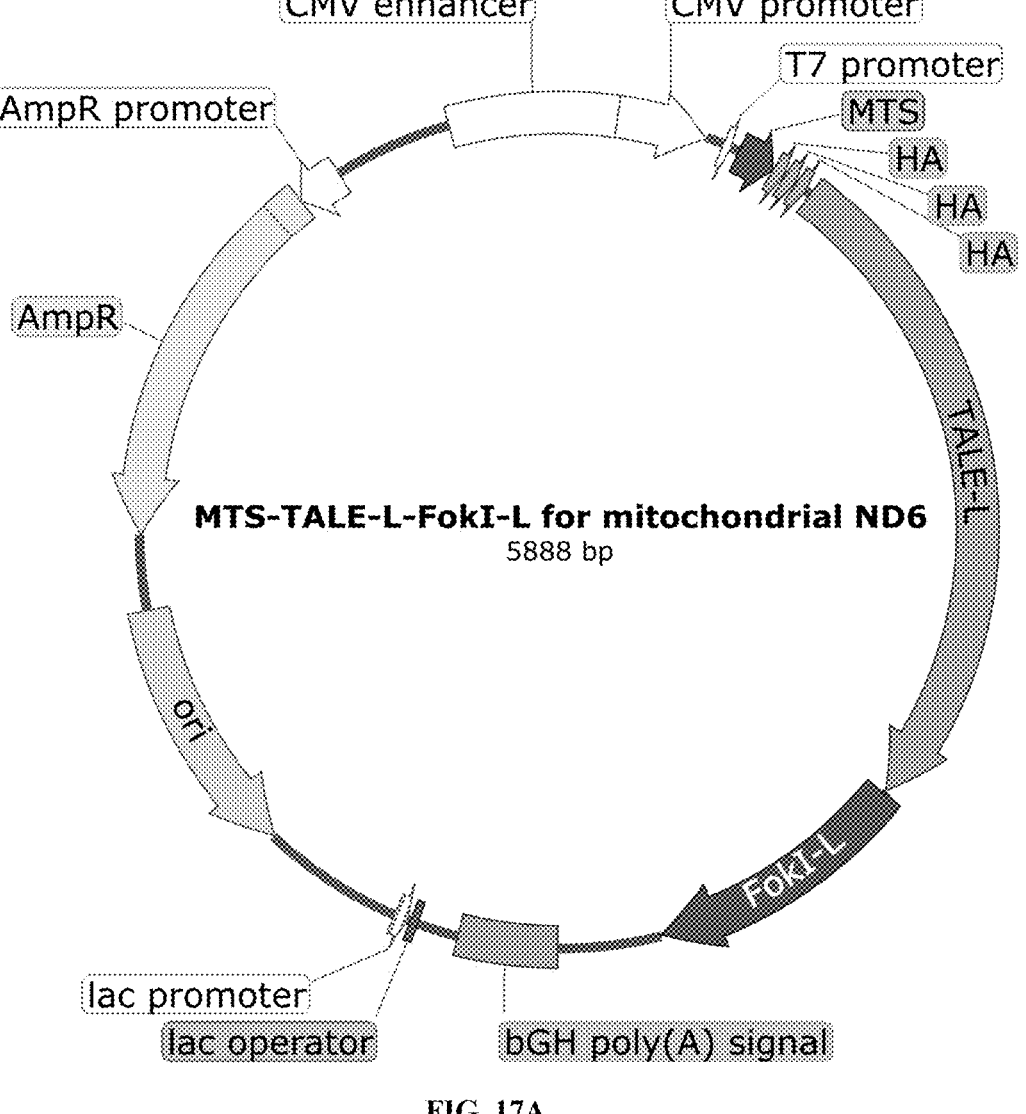
FIG. 17A to FIG. 17H are representative illustrations of the recombinant expression constructs encoding the base editors used in the Examples set forth herein for mitochondrial editing in human cells.

ND6-MTS-TALE-L-FokI-L$_{D450A}$ (FIG. 17A)

(SEQ ID NO. 140)

MALSRAVCGTSRQLAPVLGYLGSRQKHSLPDYPYDVPDYAGYPYDVPDYAGYPYDVP

DYAMDIADLRTLGYSQQQQEKIKPKVRSTVAQHHEALVGHGFTHAHIVALSQHPAALG

TVAVKYQDMIAALPEATHEAIVGVGKQWSGARALEALLTVAGELRGPPLQLDTGQLLK

IAKRGGVTAVEAVHAWRNALTGAPLNLTPEQVVAIASNNGGKQALETVQRLLPVLCQA

HGLTPEQVVAIASNIGGKQALETVQRLLPVLCQAHGLTPEQVVAIASHDGGKQALETV

QRLLPVLCQAHGLTPEQVVAIASHDGGKQALETVQRLLPVLCQAHGLTPEQVVAIASH

DGGKQALETVQRLLPVLCQAHGLTPEQVVAIASHDGGKQALETVQRLLPVLCQAHGL

TPEQVVAIASHDGGKQALETVQRLLPVLCQAHGLTPEQVVAIASNIGGKQALETVQRL

LPVLCQAHGLTPEQVVAIASNGGGKQALETVQRLLPVLCQAHGLTPEQVVAIASNGGG

RPALESIVAQLSRPDPALAALTNDHLVALACLGGRPALDAVKKGLGGSQLVKSELEEKK

SELRHKLKYVPHEYIELIEIARNSTQDRILEMKVMEFFMKVYGYRGKHLGGSRKPAGA

IYTVGSPIDYGVIVDTKAYSGGYNLPIGQADEMQRYVKENQTRNKHINPNEWWKVYP

SSVTEFKFLFVSGHFKGNYKAQLTRLNHKTNCNGAVLSVEELLIGGEMIKAGTLTLEEV

RRKFNNGEINF

Figure 17B:
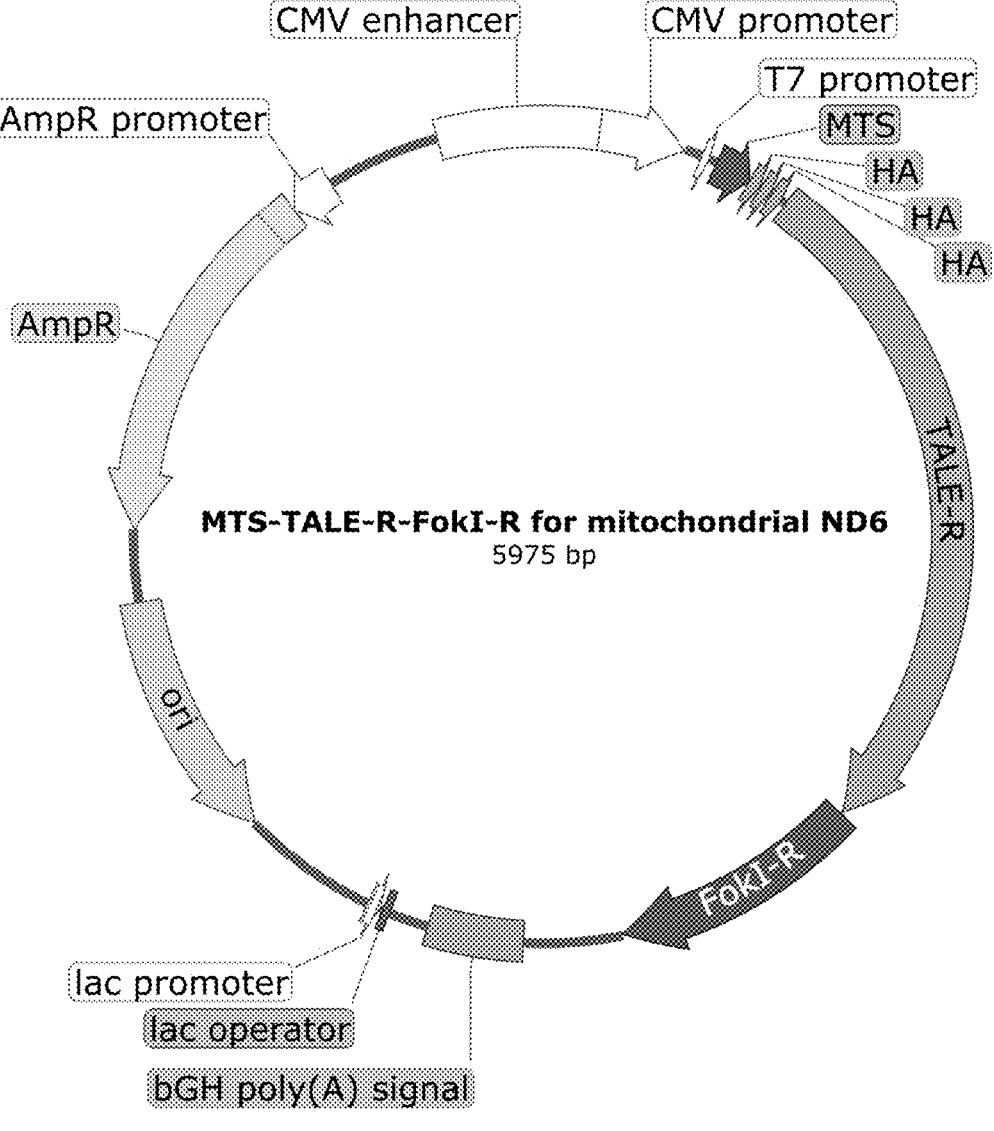
Figure 17C:
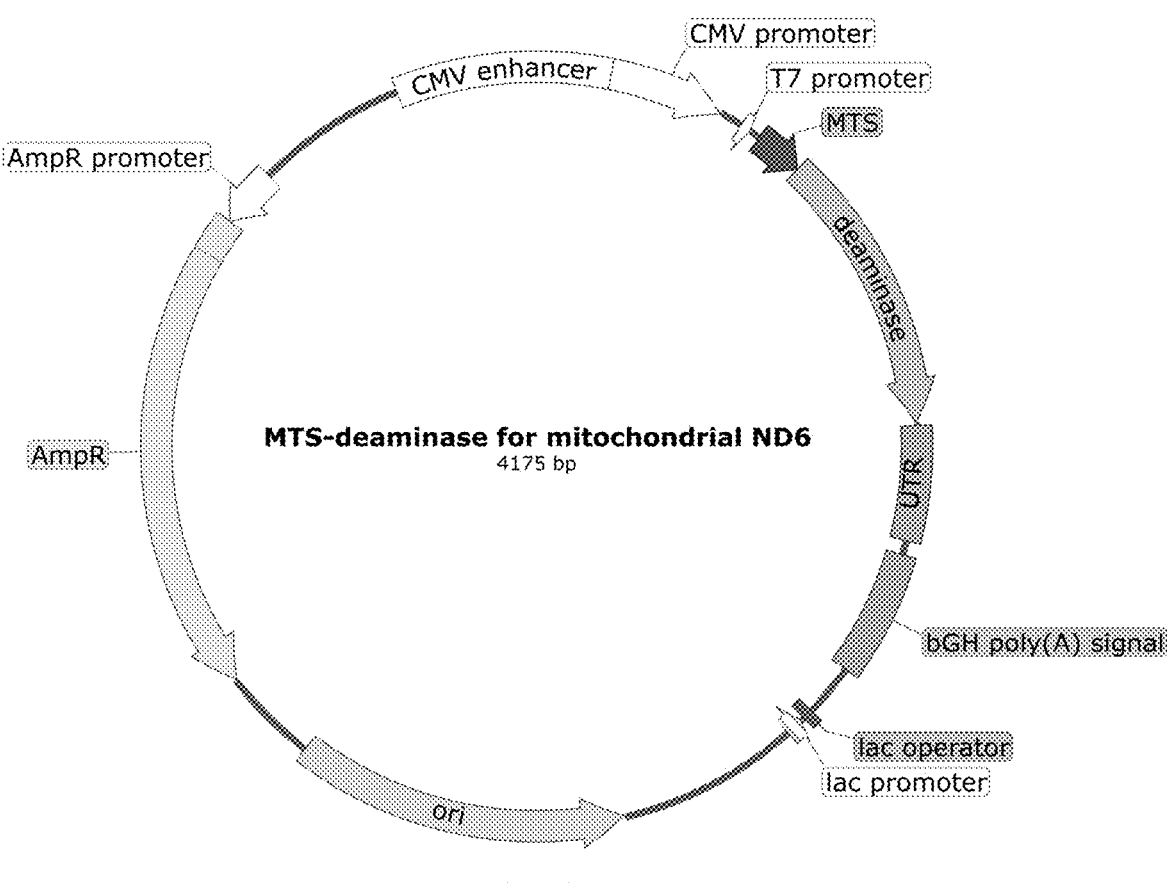
Figure 17D:
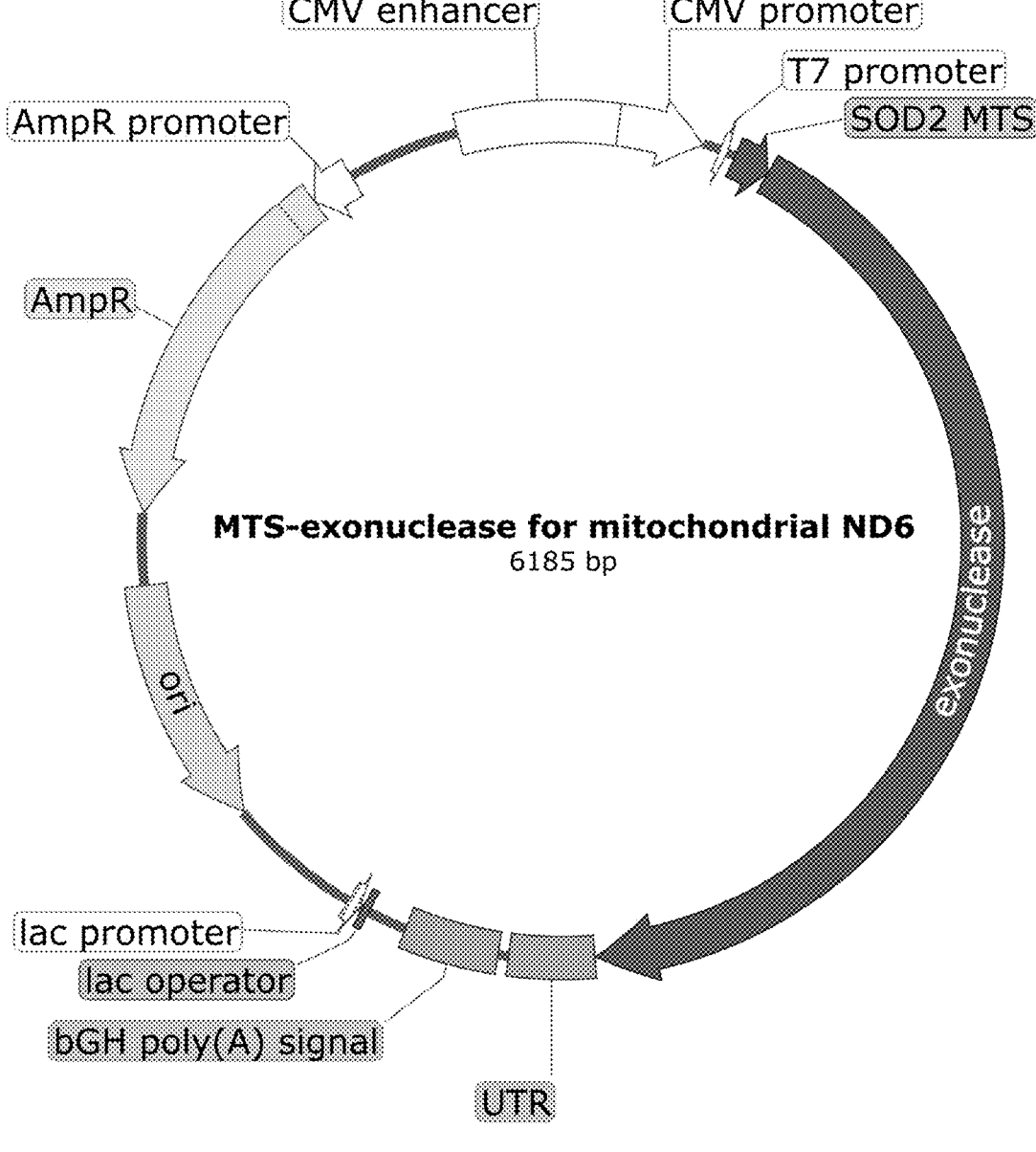
Figure 17E:
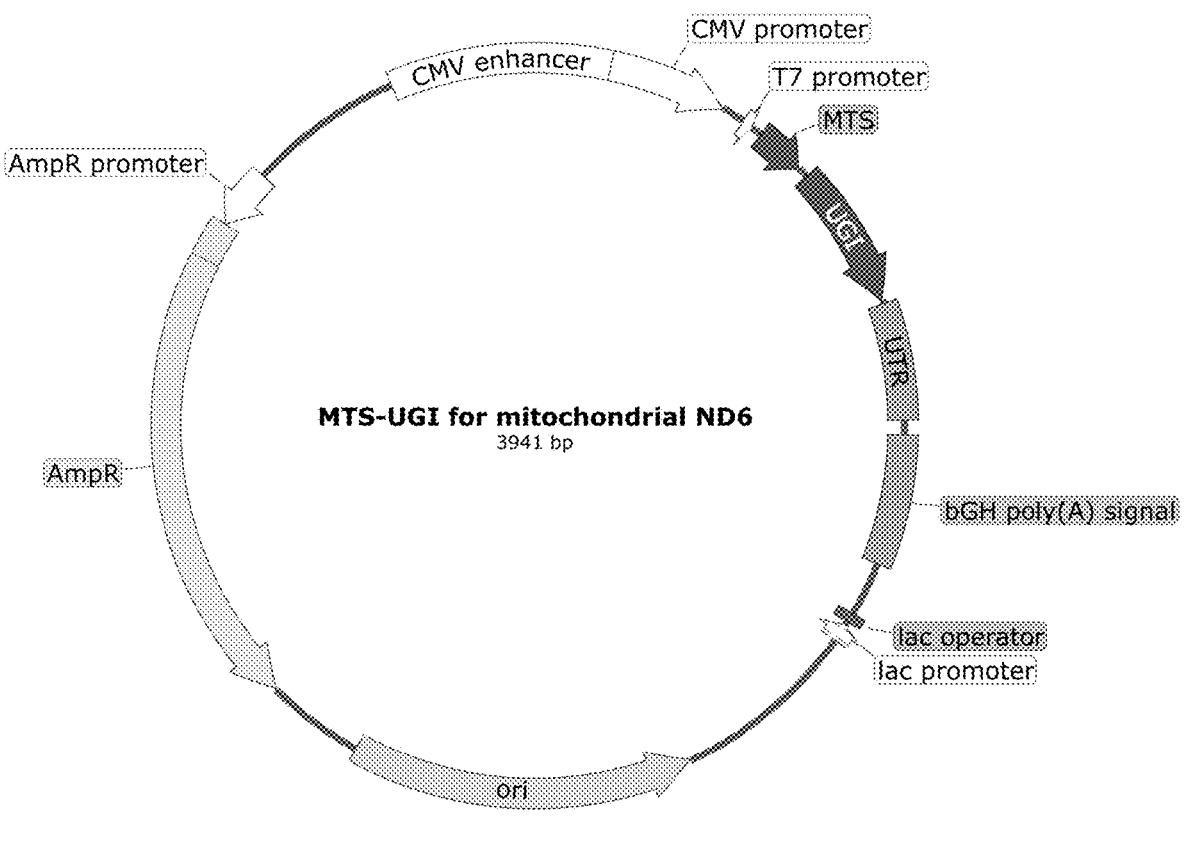
Figure 17F:
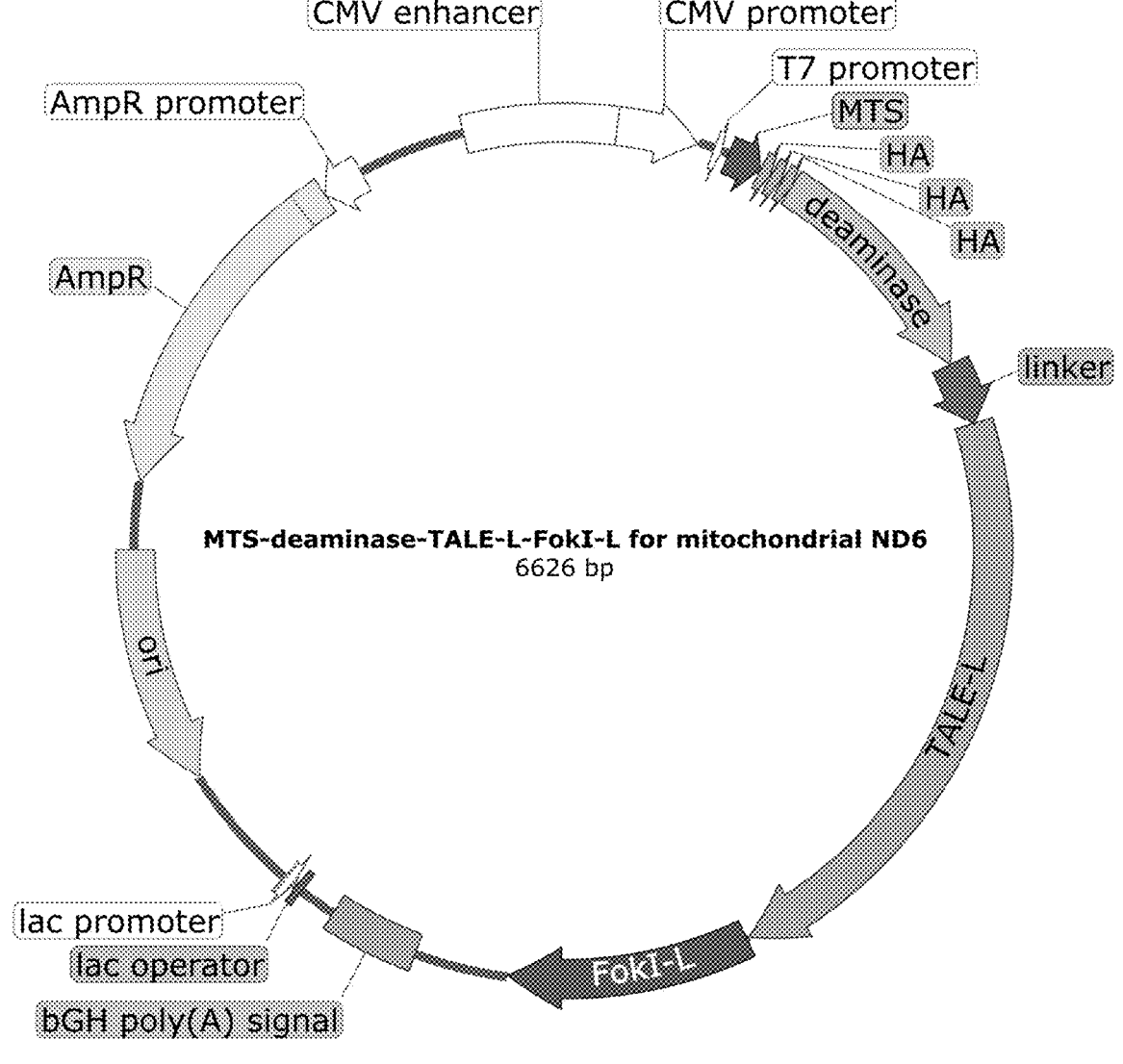

ND6-MTS-TALE-R-FokI-R (FIG. 17B)

(SEQ ID NO. 141)

MASVLTPLLLRGLTGSARRLPVPRAKIHSLDYKDHDGDYKDHDIDYKDDDDKMDIAD

LRTLGYSQQQQEKIKPKVRSTVAQHHEALVGHGFTHAHIVALSQHPAALGTVAVKYQD

MIAALPEATHEAIVGVGKRGAGARALEALLTVAGELRGPPLQLDTGQLLKIAKRGGVT

AVEAVHAWRNALTGAPLNLTPEQVVAIASNNGGKQALETVQRLLPVLCQAHGLTPEQV

VAIASNIGGKQALETVQRLLPVLCQAHGLTPEQVVAIASNGGGKQALETVQRLLPVLC

QAHGLTPEQVVAIASNNGGKQALETVQRLLPVLCQAHGLTPEQVVAIASNNGGKQALE

TVQRLLPVLCQAHGLTPEQVVAIASHDGGKQALETVQRLLPVLCQAHGLTPEQVVAIA

SNGGGKQALETVQRLLPVLCQAHGLTPEQVVAIASNIGGKQALETVQRLLPVLCQAHG

LTPEQVVAIASNGGGKQALETVQRLLPVLCQAHGLTPEQVVAIASNGGGKQALETVQR

LLPVLCQAHGLTPEQVVAIASNGGGRPALESIVAQLSRPDPALAALTNDHLVALACLGG

RPALDAVKKGLGGSQLVKSELEEKKSELRHKLKYVPHEYIELIEIARNSTQDRILEMKV

MEFFMKVYGYRGKHLGGSRKPDGAIYTVGSPIDYGVIVDTKAYSGGYNLPIGQADEM

ERYVEENQTRNKHLNPNEWWKVYPSSVTEFKFLFVSGHFKGNYKAQLTRLNHITNCN

GAVLSVEELLIGGEMIKAGTLTLEEVRRKFNNGEINF

MTS-mExoI (FIG. 17D)
                                                                              (SEQ ID NO. 142)
MALSRAVCGTSRQLAPVLGYLGSRQKHSLPDMGIQGLLQFIQEASEPVNVKKYKGQAV

AVDTYCWLHKGAIACAEKLAKGEPTDRYVGFCMKFVNMLLSYGVKPILIFDGCTLPSK

KEVERSRRERRQSNLLKGKQLLREGKVSEARDCFARSINITHAMAHKVIKAARALGVD

CLVAPYEADAQLAYLNKAGIVQAVITEDSDLLAFGCKKVILKMDQFGNGLEVDQARL

GMCKQLGDVFTEEKFRYMCILSGCDYLASLRGIGLAKACKVLRLANNPDIVKVIKKIG

HYLRMNITVPEDYITGFIRANNTFLYQLVFDPIQRKLVPLNAYGDDVNPETLTYAGQYV

GDSVALQIALGNRDVNTFEQIDDYSPDTMPAHSRSHSWNEKAGQKPPGTNSIWHKNY

CPRLEVNSVSHAPQLKEKPSTLGLKQVISTKGLNLPRKSCVLKRPRNEALAEDDLLSQ

YSSVSKKIKENGCGDGTSPNSSKMSKSCPDSGTAHKTDAHTPSKMRNKFATFLQRRNE

ESGAVVVPGTRSRFFCSSQDFDNFIPKKESGQPLNETVATGKATTSLLGALDCPDTEGH

KPVDANGTHNLSSQIPGNAAVSPEDEAQSSETSKLLGAMSPPSLGTLRSCFSWSGTLRE

FSRTPSPSASTTLQQFRRKSDPPACLPEASAVVTDRCDSKSEMLGETSQPLHELGCSSRS

QESMDSSCGLNTSSLSQPSSRDSGSEESDCNNKSLDNQGEQNSKQHLPHFSKKDGLRR

NKVPGLCRSSSMDSFSTTKIKPLVPARVSGLSKKSGSMQTRKHHDVENKPGLQTKISEL

WKNFGFKKDSEKLPSCKKPLSPVKDNIQLTPETEDEIFNKPECVRAQRAIFH

MTS-Trex2 (FIG. 17D)
                                                                              (SEQ ID NO. 143)
MALSRAVCGTSRQLAPVLGYLGSRQKHSLPDMSEPPRAETFVFLDLEATGLPNMDPEI

AEISLFAVHRSSLENPERDDSGSLVLPRVLDKLTLCMCPERPFTAKASEITGLSSESLMHC

GKAGFNGAVVRTLQGFLSRQEGPICLVAHNGFDYDFPLLCTELQRLGAHLPQDTVCLD

TLPALRGLDRAHSHGTRAQGRKSYSLASLFHRYFQAEPSAAHSAEGDVHTLLLIFLHR

APELLAWADEQARSWAHIEPMYVPPDGPSLEA

MTS-A3A (FIG. 17C)
                                                                              (SEQ ID NO. 144)
MALSRAVCGTSRQLAPVLGYLGSRQKHSLPDEASPASGPRHLMDPHIFTSNFNNGIGR

HKTYLCYEVERLDNGTSVKMDQHRGFLHNQAKNLLCGFYGRHAELRFLDLVPSLQLD

PAQIYRVTWFISWSPCFSWGCAGEVRAFLQENTHVRLRIFAARIYDYDPLYKEALQML

RDAGAQVSIMTYDEFKHCWDTFVDHQGCPFQPWDGLDEHSQALSGRLRAILQNQGN

MTS-C57/Sdd7 (FIG. 17C)
                                                                              (SEQ ID NO. 145)
MALSRAVCGTSRQLAPVLGYLGSRQKHSLPDLEAVRARLIGEGGGPGAVPEGGDGPPA

VPAEEVERLRGELPPPVVPGTGQKTHGRWIGPDGRVRAIVSGRDEDAALVHAQLAAK

GIPDEPTRNSDVEQKLAAHMVANGIRHVTLVINHRPCRGFDDSCDTLVPIILPEGCTLTV

HGQTDKGMRVRVRYTGGARPWWS

MTS-UGI (FIG. 17E)
                                                                              (SEQ ID NO. 146)
MALSRAVCGTSRQLAPVLGYLGSRQKHSLPDGSSGGSTNLSDIIEKETGKQLVIQESIL

MLPEEVEEVIGNKPESDILVHTAYDESTDENVMLLTSDAPEYKPWALVIQDSNGENKIK

ML

ND6-MTS-A3A-TALE-L-FokI-L (FIG. 17F)
                                                                              (SEQ ID NO. 147)
MALSRAVCGTSRQLAPVLGYLGSRQKHSLPDYPYDVPDYAGYPYDVPDYAGYPYDVP

-continued

DYAEASPASGPRHLMDPHIFTSNFNNGIGRHKTYLCYEVERLDNGTSVKMDQHRGFLH

NQAKNLLCGFYGRHAELRFLDLVPSLQLDPAQIYRVTWFISWSPCFSWGCAGEVRAFL

QENTHVRLRIFAARIYDYDPLYKEALQMLRDAGAQVSIMTYDEFKHCWDTFVDHQGC

PFQPWDGLDEHSQALSGRLRAILQNQGNSGSETPGTSESATPESSGGSSGGSSGSETPGT

SESATPESSGGSSGGSMDIADLRTLGYSQQQQEKIKPKVRSTVAQHHEALVGHGFTHA

HIVALSQHPAALGTVAVKYQDMIAALPEATHEAIVGVGKQWSGARALEALLTVAGELR

GPPLQLDTGQLLKIAKRGGVTAVEAVHAWRNALTGAPLNLTPEQVVAIASNNGGKQAL

ETVQRLLPVLCQAHGLTPEQVVAIASNIGGKQALETVQRLLPVLCQAHGLTPEQVVAIA

SHDGGKQALETVQRLLPVLCQAHGLTPEQVVAIASHDGGKQALETVQRLLPVLCQAH

GLTPEQVVAIASHDGGKQALETVQRLLPVLCQAHGLTPEQVVAIASHDGGKQALETVQ

RLLPVLCQAHGLTPEQVVAIASHDGGKQALETVQRLLPVLCQAHGLTPEQVVAIASNIG

GKQALETVQRLLPVLCQAHGLTPEQVVAIASNGGGKQALETVQRLLPVLCQAHGLTPE

QVVAIASNGGGRPALESIVAQLSRPDPALAALTNDHLVALACLGGRPALDAVKKGLGGS

QLVKSELEEKKSELRHKLKYVPHEYIELIEIARNSTQDRILEMKVMEFFMKVYGYRGK

HLGGSRKPDGAIYTVGSPIDYGVIVDTKAYSGGYNLPIGQADEMQRYVKENQTRNKHI

NPNEWWKVYPSSVTEFKFLFVSGHFKGNYKAQLTRLNHKTNCNGAVLSVEELLIGGE

MIKAGTLTLEEVRRKFNNGEINF

Figure 17G:
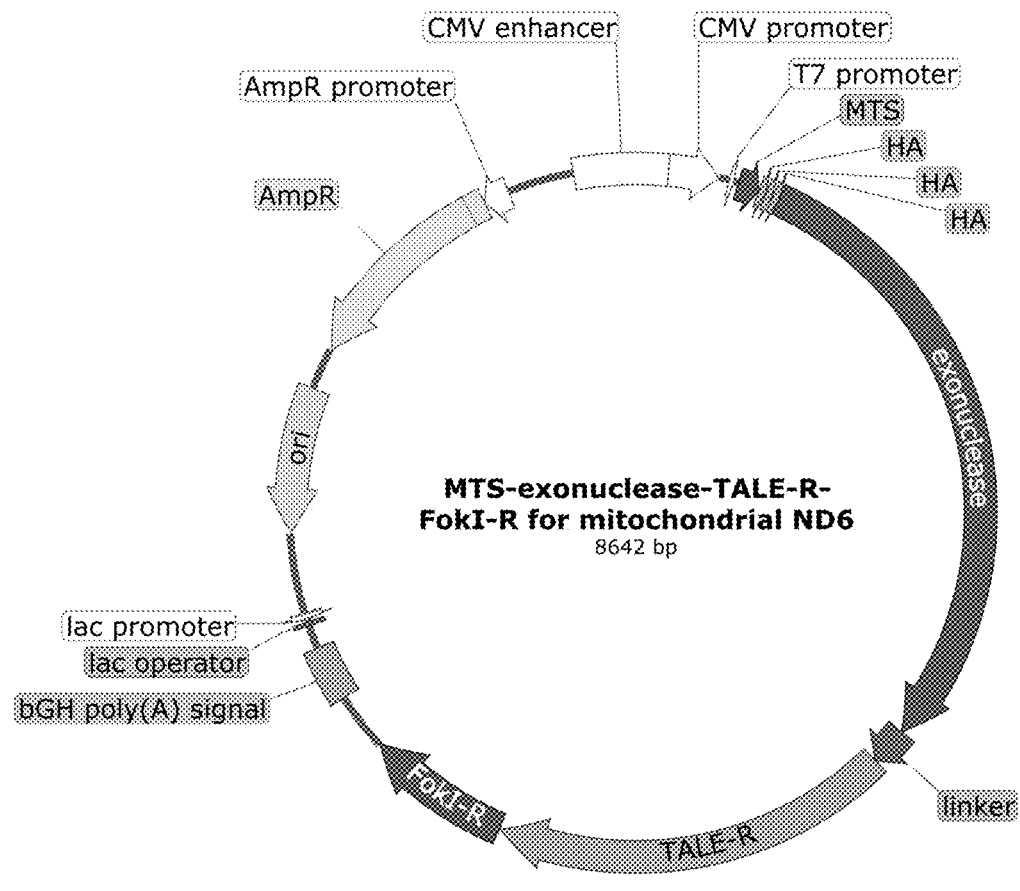

ND6-MTS-Trex2-TALE-R-FokI-R$_{D450A}$ (FIG. 17G)

(SEQ ID NO. 148)

MASVLTPLLLRGLTGSARRLPVPRAKIHSLDYKDHDGDYKDHDIDYKDDDDKMSEPP

RAETFVFLDLEATGLPNMDPEIAEISLFAVHRSSLENPERDDSGSLVLPRVLDKLTLCMC

PERPFTAKASEITGLSSESLMHCGKAGFNGAVVRTLQGFLSRQEGPICLVAHNGFDYDF

PLLCTELQRLGAHLPQDTVCLDTLPALRGLDRAHSHGTRAQGRKSYSLASLFHRYFQA

EPSAAHSAEGDVHTLLLIFLHRAPELLAWADEQARSWAHIEPMYVPPDGPSLEASGSET

PGTSESATPESSGGSSGGSSGSETPGTSESATPESSGGSSGGSMDIADLRTLGYSQQQQE

KIKPKVRSTVAQHHEALVGHGFTHAHIVALSQHPAALGTVAVKYQDMIAALPEATHEAI

VGVGKRGAGARALEALLTVAGELRGPPLQLDTGQLLKIAKRGGVTAVEAVHAWRNAL

TGAPLNLTPEQVVAIASNNGGKQALETVQRLLPVLCQAHGLTPEQVVAIASNIGGKQAL

ETVQRLLPVLCQAHGLTPEQVVAIASNGGGKQALETVQRLLPVLCQAHGLTPEQVVAI

ASNNGGKQALETVQRLLPVLCQAHGLTPEQVVAIASNNGGKQALETVQRLLPVLCQA

HGLTPEQVVAIASHDGGKQALETVQRLLPVLCQAHGLTPEQVVAIASNGGGKQALETV

QRLLPVLCQAHGLTPEQVVAIASNIGGKQALETVQRLLPVLCQAHGLTPEQVVAIASNG

GGKQALETVQRLLPVLCQAHGLTPEQVVAIASNGGGKQALETVQRLLPVLCQAHGLTP

EQVVAIASNGGGRPALESIVAQLSRPDPALAALTNDHLVALACLGGRPALDAVKKGLGG

SQLVKSELEEKKSELRHKLKYVPHEYIELIEIARNSTQDRILEMKVMEFFMKVYGYRG

KHLGGSRKPAGAIYTVGSPIDYGVIVDTKAYSGGYNLPIGQADEMERYVEENQTRNKH

LNPNEWWKVYPSSVTEFKFLFVSGHFKGNYKAQLTRLNHITNCNGAVLSVEELLIGGE

MIKAGTLTLEEVRRKFNNGEINF

Figure 17H:
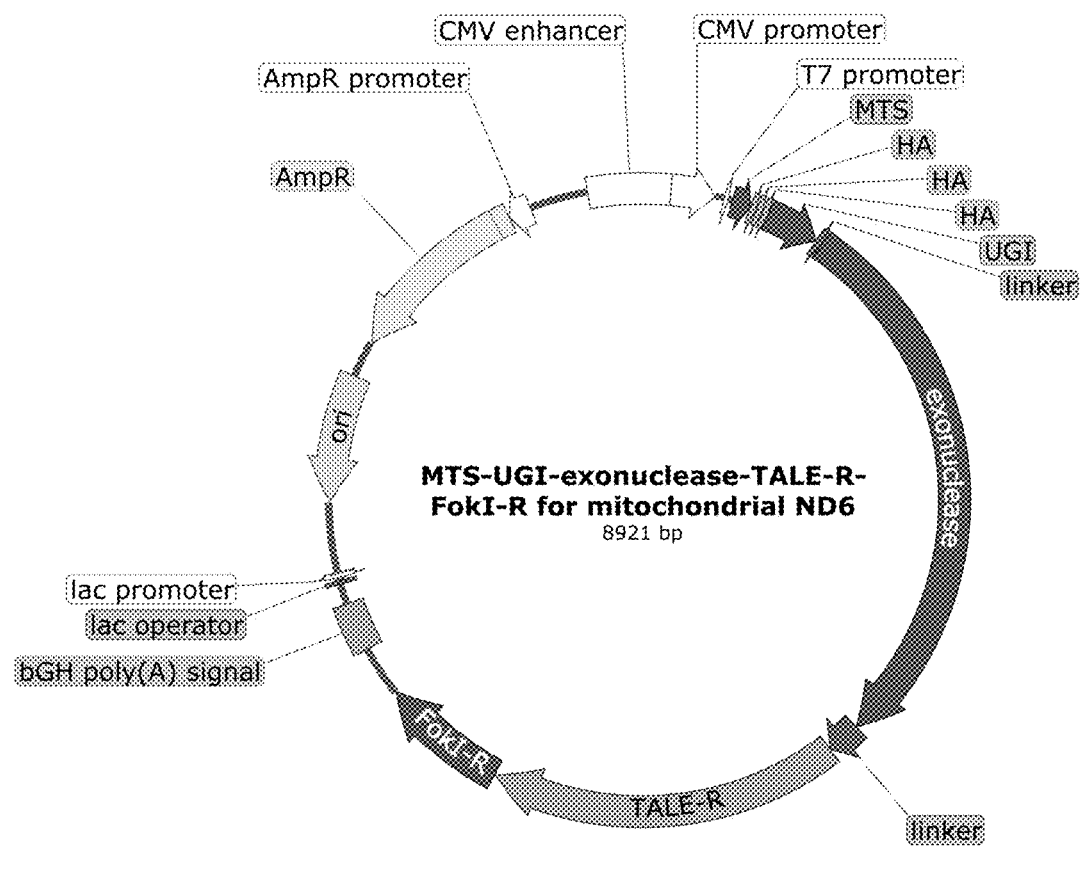

ND6-MTS-UGI-Trex2-TALE-R-FokI-R$_{D450A}$ (FIG. 17H)

(SEQ ID NO. 149)

MASVLTPLLLRGLTGSARRLPVPRAKIHSLDYKDHDGDYKDHDIDYKDDDDKTNLSDI

IEKETGKQLVIQESILMLPEEVEEVIGNKPESDILVHTAYDESTDENVMLLTSDAPEYKP

WALVIQDSNGENKIKMLSGGSGGSGGSMSEPPRAETFVFLDLEATGLPNMDPEIAEISLF

-continued

AVHRSSLENPERDDSGSLVLPRVLDKLTLCMCPERPFTAKASEITGLSSESLMHCGKAG

FNGAVVRTLQGFLSRQEGPICLVAHNGFDYDFPLLCTELQRLGAHLPQDTVCLDTLPAL

RGLDRAHSHGTRAQGRKSYSLASLFHRYFQAEPSAAHSAEGDVHTLLLIFLHRAPELL

AWADEQARSWAHIEPMYVPPDGPSLEASGSETPGTSESATPESSGGSSGGSSGSETPGTS

ESATPESSGGSSGGSMDIADLRTLGYSQQQQEKIKPKVRSTVAQHHEALVGHGFTHAHI

VALSQHPAALGTVAVKYQDMIAALPEATHEAIVGVGKRGAGARALEALLTVAGELRGP

PLQLDTGQLLKIAKRGGVTAVEAVHAWRNALTGAPLNLTPEQVVAIASNNGGKQALET

VQRLLPVLCQAHGLTPEQVVAIASNIGGKQALETVQRLLPVLCQAHGLTPEQVVAIASN

GGGKQALETVQRLLPVLCQAHGLTPEQVVAIASNNGGKQALETVQRLLPVLCQAHGL

TPEQVVAIASNNGGKQALETVQRLLPVLCQAHGLTPEQVVAIASHDGGKQALETVQRL

LPVLCQAHGLTPEQVVAIASNGGGKQALETVQRLLPVLCQAHGLTPEQVVAIASNIGG

KQALETVQRLLPVLCQAHGLTPEQVVAIASNGGGKQALETVQRLLPVLCQAHGLTPEQ

VVAIASNGGGKQALETVQRLLPVLCQAHGLTPEQVVAIASNGGGRPALESIVAQLSRPD

PALAALTNDHLVALACLGGRPALDAVKKGLGGSQLVKSELEEKKSELRHKLKYVPHEY

IELIEIARNSTQDRILEMKVMEFFMKVYGYRGKHLGGSRKPAGAIYTVGSPIDYGVIVD

TKAYSGGYNLPIGQADEMERYVEENQTRNKHLNPNEWWKVYPSSVTEFKFLFVSGHF

KGNYKAQLTRLNHITNCNGAVLSVEELLIGGEMIKAGTLTLEEVRRKENNGEINF

In Examples, the exemplary amino acid sequences of the elements or fusion proteins are as set forth below. Unless otherwise specified in the subsequent Examples, corresponding fusion proteins may be constructed in accordance with the schematic diagrams of the constructs shown in FIG. 16A to 16E and FIG. 17A to 17H, based on the exemplary sequences as set forth below and the sequence disclosed in the present specification.

In subsequent Examples, the nickases used in the experiments for editing OsBADH2 were set forth below.

TALEN_{WT}

(SEQ ID NO. 154)

MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASNNGGKQ

ALETVQRLLPVLCQDHGLTPDQVVAIASHDGGKQALETVQRLLPVLCQDHGLTPDQVV

AIASNGGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASNGGGKQALETVQRLLPVLCQDHGLTPDQVVAIA

SNNGGKQALETVQRLLPVLCQDHGLTPDQVVAIASHDGGKQALETVQRLLPVLCQDH

GLTPDQVVAIASNGGGKQALETVQRLLPVLCQDHGLTPDQVVAIASNGGGKQALETV

QRLLPVLCQDHGLTPDQVVAIASNGGGKQALETVQRLLPVLCQDHGLTPDQVVAIASN

NGGKQALETVQRLLPVLCQDHGLTPDQVVAIASNIGGKQALETVQRLLPVLCQDHGLT

PDQVVAIASNNGGKQALETVQRLLPVLCQDHGLTPDQVVAIASNGGGKQALETVQRL

LPVLCQDHGLTPDQVVAIASNIGGKQALESIVAQLSRPDPALAALTNDHLVALACLGGR

PAMDAVKKGLPHAPELIRRVNRRIGERTSHRVAGSQLVKSELEEKKSELRHKLKYVPHE

YIELIEIARNSTQDRILEMKVMEFFMKVYGYRGKHLGGSRKPDGAIYTVGSPIDYGVIV

DTKAYSGGYNLPIGQADEMQRYVKENQTRNKHINPNEWWKVYPSSVTEFKFLFVSGH

FKGNYKAQLTRLNHKTNCNGAVLSVEELLIGGEMIKAGTLTLEEVRRKENNGEINFRS

GGGEGRGSLLTCGDVEENPGPRMDYKDHDGDYKDHDIDYKDDDDKMAPKKKRKVG

-continued

IHGVPARMVDLRTLGYSQQQQEKIKPKVRSTVAQHHEALVGHGFTHAHIVALSQHPAA

LGTVAVTYQHIITALPEATHEDIVGVGKQWSGARALEALLTDAGELRGPPLQLDTGQLV

KIAKRGGVTAMEAVHASRNALTGAPLNLTPDQVVAIASNNGGKQALETVQRLLPVLCQ

DHGLTPDQVVAIASHDGGKQALETVQRLLPVLCQDHGLTPDQVVAIASHDGGKQALE

TVQRLLPVLCQDHGLTPDQVVAIASNGGGKQALETVQRLLPVLCQDHGLTPDQVVAIA

SNGGGKQALETVQRLLPVLCQDHGLTPDQVVAIASNGGGKQALETVQRLLPVLCQDH

GLTPDQVVAIASNGGGKQALETVQRLLPVLCQDHGLTPDQVVAIASNNGGKQALETV

QRLLPVLCQDHGLTPDQVVAIASNGGGKQALETVQRLLPVLCQDHGLTPDQVVAIASH

DGGKQALETVQRLLPVLCQDHGLTPDQVVAIASHDGGKQALETVQRLLPVLCQDHGL

TPDQVVAIASNIGGKQALETVQRLLPVLCQDHGLTPDQVVAIASNIGGKQALETVQRLL

PVLCQDHGLTPDQVVAIASNNGGKQALETVQRLLPVLCQDHGLTPDQVVAIASNNGG

KQALETVQRLLPVLCQDHGLTPDQVVAIASNIGGKQALETVQRLLPVLCQDHGLTPDQ

VVAIASNGGGKQALESIVAQLSRPDPALAALTNDHLVALACLGGRPAMDAVKKGLPHA

PELIRRVNRRIGERTSHRVAGSQLVKSELEEKKSELRHKLKYVPHEYIELIEIARNSTQDR

ILEMKVMEFFMKVYGYRGKHLGGSRKPDGAIYTVGSPIDYGVIVDTKAYSGGYNLPIG

QADEMERYVEENQTRNKHLNPNEWWKVYPSSVTEFKFLFVSGHFKGNYKAQLTRLN

HITNCNGAVLSVEELLIGGEMIKAGTLTLEEVRRKFNNGEINF

TALE-FokI-R$_{nickase (D450A)}$ or referred to as TALE-FokI-R$_{nickase}$
(SEQ ID NO. 155)
MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASNNGGKQ

ALETVQRLLPVLCQDHGLTPDQVVAIASHDGGKQALETVQRLLPVLCQDHGLTPDQVV

AIASNGGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASNGGGKQALETVQRLLPVLCQDHGLTPDQVVAIA

SNNGGKQALETVQRLLPVLCQDHGLTPDQVVAIASHDGGKQALETVQRLLPVLCQDH

GLTPDQVVAIASNGGGKQALETVQRLLPVLCQDHGLTPDQVVAIASNGGGKQALETV

QRLLPVLCQDHGLTPDQVVAIASNGGGKQALETVQRLLPVLCQDHGLTPDQVVAIASN

NGGKQALETVQRLLPVLCQDHGLTPDQVVAIASNIGGKQALETVQRLLPVLCQDHGLT

PDQVVAIASNNGGKQALETVQRLLPVLCQDHGLTPDQVVAIASNGGGKQALETVQRL

LPVLCQDHGLTPDQVVAIASNIGGKQALESIVAQLSRPDPALAALTNDHLVALACLGGR

PAMDAVKKGLPHAPELIRRVNRRIGERTSHRVAGSQLVKSELEEKKSELRHKLKYVPHE

YIELIEIARNSTQDRILEMKVMEFFMKVYGYRGKHLGGSRKPAGAIYTVGSPIDYGVIV

DTKAYSGGYNLPIGQADEMQRYVKENQTRNKHINPNEWWKVYPSSVTEFKFLFVSGH

FKGNYKAQLTRLNHKTNCNGAVLSVEELLIGGEMIKAGTLTLEEVRRKFNNGEINFRS

GGGEGRGSLLTCGDVEENPGPRMDYKDHDGDYKDHDIDYKDDDDKMAPKKKRKVG

IHGVPARMVDLRTLGYSQQQQEKIKPKVRSTVAQHHEALVGHGFTHAHIVALSQHPAA

LGTVAVTYQHIITALPEATHEDIVGVGKQWSGARALEALLTDAGELRGPPLQLDTGQLV

KIAKRGGVTAMEAVHASRNALTGAPLNLTPDQVVAIASNNGGKQALETVQRLLPVLCQ

DHGLTPDQVVAIASHDGGKQALETVQRLLPVLCQDHGLTPDQVVAIASHDGGKQALE

TVQRLLPVLCQDHGLTPDQVVAIASNGGGKQALETVQRLLPVLCQDHGLTPDQVVAIA

SNGGGKQALETVQRLLPVLCQDHGLTPDQVVAIASNGGGKQALETVQRLLPVLCQDH

GLTPDQVVAIASNGGGKQALETVQRLLPVLCQDHGLTPDQVVAIASNNGGKQALETV

QRLLPVLCQDHGLTPDQVVAIASNGGGKQALETVQRLLPVLCQDHGLTPDQVVAIASH

DGGKQALETVQRLLPVLCQDHGLTPDQVVAIASHDGGKQALETVQRLLPVLCQDHGL

TPDQVVAIASNIGGKQALETVQRLLPVLCQDHGLTPDQVVAIASNIGGKQALETVQRLL

PVLCQDHGLTPDQVVAIASNNGGKQALETVQRLLPVLCQDHGLTPDQVVAIASNNGG

KQALETVQRLLPVLCQDHGLTPDQVVAIASNIGGKQALETVQRLLPVLCQDHGLTPDQ

VVAIASNGGGKQALESIVAQLSRPDPALAALTNDHLVALACLGGRPAMDAVKKGLPHA

PELIRRVNRRIGERTSHRVAGSQLVKSELEEKKSELRHKLKYVPHEYIELIEIARNSTQDR

ILEMKVMEFFMKVYGYRGKHLGGSRKPDGAIYTVGSPIDYGVIVDTKAYSGGYNLPIG

QADEMERYVEENQTRNKHLNPNEWWKVYPSSVTEFKFLFVSGHFKGNYKAQLTRLN

HITNCNGAVLSVEELLIGGEMIKAGTLTLEEVRRKFNNGEINF

TALE-FokI-R*nickase (D467A)*
                                                              (SEQ ID NO. 156)
MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASNNGGKQ

ALETVQRLLPVLCQDHGLTPDQVVAIASHDGGKQALETVQRLLPVLCQDHGLTPDQVV

AIASNGGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASNGGGKQALETVQRLLPVLCQDHGLTPDQVVAIA

SNNGGKQALETVQRLLPVLCQDHGLTPDQVVAIASHDGGKQALETVQRLLPVLCQDH

GLTPDQVVAIASNGGGKQALETVQRLLPVLCQDHGLTPDQVVAIASNGGGKQALETV

QRLLPVLCQDHGLTPDQVVAIASNGGGKQALETVQRLLPVLCQDHGLTPDQVVAIASN

NGGKQALETVQRLLPVLCQDHGLTPDQVVAIASNIGGKQALETVQRLLPVLCQDHGLT

PDQVVAIASNNGGKQALETVQRLLPVLCQDHGLTPDQVVAIASNGGGKQALETVQRL

LPVLCQDHGLTPDQVVAIASNIGGKQALESIVAQLSRPDPALAALTNDHLVALACLGGR

PAMDAVKKGLPHAPELIRRVNRRIGERTSHRVAGSQLVKSELEEKKSELRHKLKYVPHE

YIELIEIARNSTQDRILEMKVMEFFMKVYGYRGKHLGGSRKPDGAIYTVGSPIDYGVIV

ATKAYSGGYNLPIGQADEMQRYVKENQTRNKHINPNEWWKVYPSSVTEFKFLFVSGH

FKGNYKAQLTRLNHKTNCNGAVLSVEELLIGGEMIKAGTLTLEEVRRKFNNGEINFRS

GGGEGRGSLLTCGDVEENPGPRMDYKDHDGDYKDHDIDYKDDDDKMAPKKKRKVG

IHGVPARMVDLRTLGYSQQQQEKIKPKVRSTVAQHHEALVGHGFTHAHIVALSQHPAA

LGTVAVTYQHIITALPEATHEDIVGVGKQWSGARALEALLTDAGELRGPPLQLDTGQLV

KIAKRGGVTAMEAVHASRNALTGAPLNLTPDQVVAIASNNGGKQALETVQRLLPVLCQ

DHGLTPDQVVAIASHDGGKQALETVQRLLPVLCQDHGLTPDQVVAIASHDGGKQALE

TVQRLLPVLCQDHGLTPDQVVAIASNGGGKQALETVQRLLPVLCQDHGLTPDQVVAIA

SNGGGKQALETVQRLLPVLCQDHGLTPDQVVAIASNGGGKQALETVQRLLPVLCQDH

GLTPDQVVAIASNGGGKQALETVQRLLPVLCQDHGLTPDQVVAIASNNGGKQALETV

QRLLPVLCQDHGLTPDQVVAIASNGGGKQALETVQRLLPVLCQDHGLTPDQVVAIASH

DGGKQALETVQRLLPVLCQDHGLTPDQVVAIASHDGGKQALETVQRLLPVLCQDHGL

-continued

TPDQVVAIASNIGGKQALETVQRLLPVLCQDHGLTPDQVVAIASNIGGKQALETVQRLL

PVLCQDHGLTPDQVVAIASNNGGKQALETVQRLLPVLCQDHGLTPDQVVAIASNNGG

KQALETVQRLLPVLCQDHGLTPDQVVAIASNIGGKQALETVQRLLPVLCQDHGLTPDQ

VVAIASNGGGKQALESIVAQLSRPDPALAALTNDHLVALACLGGRPAMDAVKKGLPHA

PELIRRVNRRIGERTSHRVAGSQLVKSELEEKKSELRHKLKYVPHEYIELIEIARNSTQDR

ILEMKVMEFFMKVYGYRGKHLGGSRKPDGAIYTVGSPIDYGVIVDTKAYSGGYNLPIG

QADEMERYVEENQTRNKHLNPNEWWKVYPSSVTEFKFLFVSGHFKGNYKAQLTRLN

HITNCNGAVLSVEELLIGGEMIKAGTLTLEEVRRKFNNGEINF

15

Nickases used in the experiments for editing OsDEP1:

TALEN$_{WT}$ (SEQ ID NO. 157)
MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASNNGGKQ

ALETVQRLLPVLCQDHGLTPDQVVAIASHDGGKQALETVQRLLPVLCQDHGLTPDQVV

AIASNIGGKQALETVQRLLPVLCQDHGLTPDQVVAIASNIGGKQALETVQRLLPVLCQD

HGLTPDQVVAIASNIGGKQALETVQRLLPVLCQDHGLTPDQVVAIASNIGGKQALETVQ

RLLPVLCQDHGLTPDQVVAIASNNGGKQALETVQRLLPVLCQDHGLTPDQVVAIASNI

GGKQALETVQRLLPVLCQDHGLTPDQVVAIASHDGGKQALETVQRLLPVLCQDHGLT

PDQVVAIASHDGGKQALETVQRLLPVLCQDHGLTPDQVVAIASNIGGKQALETVQRLL

PVLCQDHGLTPDQVVAIASNIGGKQALETVQRLLPVLCQDHGLTPDQVVAIASNNGGK

QALETVQRLLPVLCQDHGLTPDQVVAIASNNGGKQALETVQRLLPVLCQDHGLTPDQ

VVAIASNGGGKQALETVQRLLPVLCQDHGLTPDQVVAIASNNGGKQALETVQRLLPVL

CQDHGLTPDQVVAIASHDGGKQALETVQRLLPVLCQDHGLTPDQVVAIASHDGGKQA

LETVQRLLPVLCQDHGLTPDQVVAIASNGGGKQALESIVAQLSRPDPALAALTNDHLVA

LACLGGRPAMDAVKKGLPHAPELIRRVNRRIGERTSHRVAGSQLVKSELEEKKSELRHK

LKYVPHEYIELIEIARNSTQDRILEMKVMEFFMKVYGYRGKHLGGSRKPDGAIYTVGS

PIDYGVIVDTKAYSGGYNLPIGQADEMQRYVKENQTRNKHINPNEWWKVYPSSVTEF

KFLFVSGHFKGNYKAQLTRLNHKTNCNGAVLSVEELLIGGEMIKAGTLTLEEVRRKFN

NGEINFRSGGGEGRGSLLTCGDVEENPGPRMDYKDHDGDYKDHDIDYKDDDDKMAP

KKKRKVGIHGVPARMVDLRTLGYSQQQQEKIKPKVRSTVAQHHEALVGHGFTHAHIV

ALSQHPAALGTVAVTYQHIITALPEATHEDIVGVGKQWSGARALEALLTDAGELRGPPL

QLDTGQLVKIAKRGGVTAMEAVHASRNALTGAPLNLTPDQVVAIASNNGGKQALETV

QRLLPVLCQDHGLTPDQVVAIASNNGGKQALETVQRLLPVLCQDHGLTPDQVVAIASH

DGGKQALETVQRLLPVLCQDHGLTPDQVVAIASNGGGKQALETVQRLLPVLCQDHGL

TPDQVVAIASHDGGKQALETVQRLLPVLCQDHGLTPDQVVAIASNNGGKQALETVQR

LLPVLCQDHGLTPDQVVAIASNGGGKQALETVQRLLPVLCQDHGLTPDQVVAIASHDG

GKQALETVQRLLPVLCQDHGLTPDQVVAIASNNGGKQALETVQRLLPVLCQDHGLTP

DQVVAIASHDGGKQALETVQRLLPVLCQDHGLTPDQVVAIASNIGGKQALETVQRLLP

VLCQDHGLTPDQVVAIASNNGGKQALETVQRLLPVLCQDHGLTPDQVVAIASHDGGK

-continued

```
QALETVQRLLPVLCQDHGLTPDQVVAIASNIGGKQALETVQRLLPVLCQDHGLTPDQV

VAIASNGGGKQALESIVAQLSRPDPALAALTNDHLVALACLGGRPAMDAVKKGLPHAP

ELIRRVNRRIGERTSHRVAGSQLVKSELEEKKSELRHKLKYVPHEYIELIEIARNSTQDRI

LEMKVMEFFMKVYGYRGKHLGGSRKPDGAIYTVGSPIDYGVIVDTKAYSGGYNLPIG

QADEMERYVEENQTRNKHLNPNEWWKVYPSSVTEFKFLFVSGHFKGNYKAQLTRLN

HITNCNGAVLSVEELLIGGEMIKAGTLTLEEVRRKFNNGEINF
```

TALE-FokI-R$_{nickase\,(D450A)}$ or referred to as TALE-FokI-R$_{nickase}$ (SEQ ID NO. 158)

```
MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASNNGGKQ

ALETVQRLLPVLCQDHGLTPDQVVAIASHDGGKQALETVQRLLPVLCQDHGLTPDQVV

AIASNIGGKQALETVQRLLPVLCQDHGLTPDQVVAIASNIGGKQALETVQRLLPVLCQD

HGLTPDQVVAIASNIGGKQALETVQRLLPVLCQDHGLTPDQVVAIASNIGGKQALETVQ

RLLPVLCQDHGLTPDQVVAIASNNGGKQALETVQRLLPVLCQDHGLTPDQVVAIASNI

GGKQALETVQRLLPVLCQDHGLTPDQVVAIASHDGGKQALETVQRLLPVLCQDHGLT

PDQVVAIASHDGGKQALETVQRLLPVLCQDHGLTPDQVVAIASNIGGKQALETVQRLL

PVLCQDHGLTPDQVVAIASNIGGKQALETVQRLLPVLCQDHGLTPDQVVAIASNNGGK

QALETVQRLLPVLCQDHGLTPDQVVAIASNNGGKQALETVQRLLPVLCQDHGLTPDQ

VVAIASNGGGKQALETVQRLLPVLCQDHGLTPDQVVAIASNNGGKQALETVQRLLPVL

CQDHGLTPDQVVAIASHDGGKQALETVQRLLPVLCQDHGLTPDQVVAIASHDGGKQA

LETVQRLLPVLCQDHGLTPDQVVAIASNGGGKQALESIVAQLSRPDPALAALTNDHLVA

LACLGGRPAMDAVKKGLPHAPELIRRVNRRIGERTSHRVAGSQLVKSELEEKKSELRHK

LKYVPHEYIELIEIARNSTQDRILEMKVMEFFMKVYGYRGKHLGGSRKPAGAIYTVGS

PIDYGVIVDTKAYSGGYNLPIGQADEMQRYVKENQTRNKHINPNEWWKVYPSSVTEF

KFLFVSGHFKGNYKAQLTRLNHKTNCNGAVLSVEELLIGGEMIKAGTLTLEEVRRKFN

NGEINFRSGGGEGRGSLLTCGDVEENPGPRMDYKDHDGDYKDHDIDYKDDDDKMAP

KKKRKVGIHGVPARMVDLRTLGYSQQQQEKIKPKVRSTVAQHHEALVGHGFTHAHIV

ALSQHPAALGTVAVTYQHIITALPEATHEDIVGVGKQWSGARALEALLTDAGELRGPPL

QLDTGQLVKIAKRGGVTAMEAVHASRNALTGAPLNLTPDQVVAIASNNGGKQALETV

QRLLPVLCQDHGLTPDQVVAIASNNGGKQALETVQRLLPVLCQDHGLTPDQVVAIASH

DGGKQALETVQRLLPVLCQDHGLTPDQVVAIASNGGGKQALETVQRLLPVLCQDHGL

TPDQVVAIASHDGGKQALETVQRLLPVLCQDHGLTPDQVVAIASNNGGKQALETVQR

LLPVLCQDHGLTPDQVVAIASNGGGKQALETVQRLLPVLCQDHGLTPDQVVAIASHDG

GKQALETVQRLLPVLCQDHGLTPDQVVAIASNNGGKQALETVQRLLPVLCQDHGLTP

DQVVAIASHDGGKQALETVQRLLPVLCQDHGLTPDQVVAIASNIGGKQALETVQRLLP

VLCQDHGLTPDQVVAIASNNGGKQALETVQRLLPVLCQDHGLTPDQVVAIASHDGGK

QALETVQRLLPVLCQDHGLTPDQVVAIASNIGGKQALETVQRLLPVLCQDHGLTPDQV

VAIASNGGGKQALESIVAQLSRPDPALAALTNDHLVALACLGGRPAMDAVKKGLPHAP

ELIRRVNRRIGERTSHRVAGSQLVKSELEEKKSELRHKLKYVPHEYIELIEIARNSTQDRI
```

-continued

LEMKVMEFFMKVYGYRGKHLGGSRKPDGAIYTVGSPIDYGVIVDTKAYSGGYNLPIG

QADEMERYVEENQTRNKHLNPNEWWKVYPSSVTEFKFLFVSGHFKGNYKAQLTRLN

HITNCNGAVLSVEELLIGGEMIKAGTLTLEEVRRKFNNGEINF

TALE-FokI-R$_{nickase\,(D467A)}$ (SEQ ID NO. 159)

MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASNNGGKQ

ALETVQRLLPVLCQDHGLTPDQVVAIASHDGGKQALETVQRLLPVLCQDHGLTPDQVV

AIASNIGGKQALETVQRLLPVLCQDHGLTPDQVVAIASNIGGKQALETVQRLLPVLCQD

HGLTPDQVVAIASNIGGKQALETVQRLLPVLCQDHGLTPDQVVAIASNIGGKQALETVQ

RLLPVLCQDHGLTPDQVVAIASNNGGKQALETVQRLLPVLCQDHGLTPDQVVAIASNI

GGKQALETVQRLLPVLCQDHGLTPDQVVAIASHDGGKQALETVQRLLPVLCQDHGLT

PDQVVAIASHDGGKQALETVQRLLPVLCQDHGLTPDQVVAIASNIGGKQALETVQRLL

PVLCQDHGLTPDQVVAIASNIGGKQALETVQRLLPVLCQDHGLTPDQVVAIASNNGGK

QALETVQRLLPVLCQDHGLTPDQVVAIASNNGGKQALETVQRLLPVLCQDHGLTPDQ

VVAIASNGGGKQALETVQRLLPVLCQDHGLTPDQVVAIASNNGGKQALETVQRLLPVL

CQDHGLTPDQVVAIASHDGGKQALETVQRLLPVLCQDHGLTPDQVVAIASHDGGKQA

LETVQRLLPVLCQDHGLTPDQVVAIASNGGGKQALESIVAQLSRPDPALAALTNDHLVA

LACLGGRPAMDAVKKGLPHAPELIRRVNRRIGERTSHRVAGSQLVKSELEEKKSELRHK

LKYVPHEYIELIEIARNSTQDRILEMKVMEFFMKVYGYRGKHLGGSRKPDGAIYTVGS

PIDYGVIVATKAYSGGYNLPIGQADEMQRYVKENQTRNKHINPNEWWKVYPSSVTEFK

FLFVSGHFKGNYKAQLTRLNHKTNCNGAVLSVEELLIGGEMIKAGTLTLEEVRRKENN

GEINFRSGGGEGRGSLLTCGDVEENPGPRMDYKDHDGDYKDHDIDYKDDDDKMAPK

KKRKVGIHGVPARMVDLRTLGYSQQQQEKIKPKVRSTVAQHHEALVGHGFTHAHIVA

LSQHPAALGTVAVTYQHIITALPEATHEDIVGVGKQWSGARALEALLTDAGELRGPPLQ

LDTGQLVKIAKRGGVTAMEAVHASRNALTGAPLNLTPDQVVAIASNNGGKQALETVQ

RLLPVLCQDHGLTPDQVVAIASNNGGKQALETVQRLLPVLCQDHGLTPDQVVAIASHD

GGKQALETVQRLLPVLCQDHGLTPDQVVAIASNGGGKQALETVQRLLPVLCQDHGLT

PDQVVAIASHDGGKQALETVQRLLPVLCQDHGLTPDQVVAIASNNGGKQALETVQRL

LPVLCQDHGLTPDQVVAIASNGGGKQALETVQRLLPVLCQDHGLTPDQVVAIASHDGG

KQALETVQRLLPVLCQDHGLTPDQVVAIASNNGGKQALETVQRLLPVLCQDHGLTPD

QVVAIASHDGGKQALETVQRLLPVLCQDHGLTPDQVVAIASNIGGKQALETVQRLLPV

LCQDHGLTPDQVVAIASNNGGKQALETVQRLLPVLCQDHGLTPDQVVAIASHDGGKQ

ALETVQRLLPVLCQDHGLTPDQVVAIASNIGGKQALETVQRLLPVLCQDHGLTPDQVV

AIASNGGGKQALESIVAQLSRPDPALAALTNDHLVALACLGGRPAMDAVKKGLPHAPE

LIRRVNRRIGERTSHRVAGSQLVKSELEEKKSELRHKLKYVPHEYIELIEIARNSTQDRIL

EMKVMEFFMKVYGYRGKHLGGSRKPDGAIYTVGSPIDYGVIVDTKAYSGGYNLPIGQ

ADEMERYVEENQTRNKHLNPNEWWKVYPSSVTEFKFLFVSGHFKGNYKAQLTRLNHI

TNCNGAVLSVEELLIGGEMIKAGTLTLEEVRRKFNNGEINF

Nickases used in the experiments for editing OsCKX2:

TALEN$_{WT}$ (SEQ ID NO. 160)

MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASHDGGKQ

ALETVQRLLPVLCQDHGLTPDQVVAIASHDGGKQALETVQRLLPVLCQDHGLTPDQVV

AIASNGGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASHDGGKQALETVQRLLPVLCQDHGLTPDQVVAIA

SHDGGKQALETVQRLLPVLCQDHGLTPDQVVAIASNNGGKQALETVQRLLPVLCQDH

GLTPDQVVAIASHDGGKQALETVQRLLPVLCQDHGLTPDQVVAIASNNGGKQALETV

QRLLPVLCQDHGLTPDQVVAIASNIGGKQALETVQRLLPVLCQDHGLTPDQVVAIASNI

GGKQALETVQRLLPVLCQDHGLTPDQVVAIASNIGGKQALETVQRLLPVLCQDHGLTP

DQVVAIASNNGGKQALETVQRLLPVLCQDHGLTPDQVVAIASNIGGKQALETVQRLLP

VLCQDHGLTPDQVVAIASHDGGKQALETVQRLLPVLCQDHGLTPDQVVAIASHDGGK

QALETVQRLLPVLCQDHGLTPDQVVAIASNIGGKQALETVQRLLPVLCQDHGLTPDQV

VAIASNGGGKQALETVQRLLPVLCQDHGLTPDQVVAIASHDGGKQALETVQRLLPVLC

QDHGLTPDQVVAIASHDGGKQALETVQRLLPVLCQDHGLTPDQVVAIASNIGGKQALE

TVQRLLPVLCQDHGLTPDQVVAIASHDGGKQALETVQRLLPVLCQDHGLTPDQVVAIA

SNNGGKQALESIVAQLSRPDPALAALTNDHLVALACLGGRPAMDAVKKGLPHAPELIRR

VNRRIGERTSHRVAGSQLVKSELEEKKSELRHKLKYVPHEYIELIEIARNSTQDRILEMK

VMEFFMKVYGYRGKHLGGSRKPDGAIYTVGSPIDYGVIVDTKAYSGGYNLPIGQADE

MQRYVKENQTRNKHINPNEWWKVYPSSVTEFKFLFVSGHFKGNYKAQLTRLNHKTN

CNGAVLSVEELLIGGEMIKAGTLTLEEVRRKFNNGEINFRSGGGEGRGSLLTCGDVEEN

PGPRMDYKDHDGDYKDHDIDYKDDDDKMAPKKKRKVGIHGVPARMVDLRTLGYSQ

QQQEKIKPKVRSTVAQHHEALVGHGFTHAHIVALSQHPAALGTVAVTYQHIITALPEAT

HEDIVGVGKQWSGARALEALLTDAGELRGPPLQLDTGQLVKIAKRGGVTAMEAVHAS

RNALTGAPLNLTPDQVVAIASHDGGKQALETVQRLLPVLCQDHGLTPDQVVAIASHDG

GKQALETVQRLLPVLCQDHGLTPDQVVAIASHDGGKQALETVQRLLPVLCQDHGLTP

DQVVAIASNIGGKQALETVQRLLPVLCQDHGLTPDQVVAIASNNGGKQALETVQRLLP

VLCQDHGLTPDQVVAIASNIGGKQALETVQRLLPVLCQDHGLTPDQVVAIASNNGGKQ

ALETVQRLLPVLCQDHGLTPDQVVAIASHDGGKQALETVQRLLPVLCQDHGLTPDQVV

AIASHDGGKQALETVQRLLPVLCQDHGLTPDQVVAIASHDGGKQALETVQRLLPVLC

QDHGLTPDQVVAIASHDGGKQALETVQRLLPVLCQDHGLTPDQVVAIASNNGGKQAL

ETVQRLLPVLCQDHGLTPDQVVAIASHDGGKQALETVQRLLPVLCQDHGLTPDQVVAI

ASNNGGKQALETVQRLLPVLCQDHGLTPDQVVAIASNNGGKQALETVQRLLPVLCQD

HGLTPDQVVAIASHDGGKQALETVQRLLPVLCQDHGLTPDQVVAIASNNGGKQALET

VQRLLPVLCQDHGLTPDQVVAIASHDGGKQALESIVAQLSRPDPALAALTNDHLVALAC

LGGRPAMDAVKKGLPHAPELIRRVNRRIGERTSHRVAGSQLVKSELEEKKSELRHKLKY

VPHEYIELIEIARNSTQDRILEMKVMEFFMKVYGYRGKHLGGSRKPDGAIYTVGSPIDY

GVIVDTKAYSGGYNLPIGQADEMERYVEENQTRNKHLNPNEWWKVYPSSVTEFKFLF

-continued

VSGHFKGNYKAQLTRLNHITNCNGAVLSVEELLIGGEMIKAGTLTLEEVRRKENNGEIN

F

TALE-FokI-R_{nickase}

(SEQ ID NO. 161)

MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASHDGGKQ

ALETVQRLLPVLCQDHGLTPDQVVAIASHDGGKQALETVQRLLPVLCQDHGLTPDQVV

AIASNGGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASHDGGKQALETVQRLLPVLCQDHGLTPDQVVAIA

SHDGGKQALETVQRLLPVLCQDHGLTPDQVVAIASNNGGKQALETVQRLLPVLCQDH

GLTPDQVVAIASHDGGKQALETVQRLLPVLCQDHGLTPDQVVAIASNNGGKQALETV

QRLLPVLCQDHGLTPDQVVAIASNIGGKQALETVQRLLPVLCQDHGLTPDQVVAIASNI

GGKQALETVQRLLPVLCQDHGLTPDQVVAIASNIGGKQALETVQRLLPVLCQDHGLTP

DQVVAIASNNGGKQALETVQRLLPVLCQDHGLTPDQVVAIASNIGGKQALETVQRLLP

VLCQDHGLTPDQVVAIASHDGGKQALETVQRLLPVLCQDHGLTPDQVVAIASHDGGK

QALETVQRLLPVLCQDHGLTPDQVVAIASNIGGKQALETVQRLLPVLCQDHGLTPDQV

VAIASNGGGKQALETVQRLLPVLCQDHGLTPDQVVAIASHDGGKQALETVQRLLPVLC

QDHGLTPDQVVAIASHDGGKQALETVQRLLPVLCQDHGLTPDQVVAIASNIGGKQALE

TVQRLLPVLCQDHGLTPDQVVAIASHDGGKQALETVQRLLPVLCQDHGLTPDQVVAIA

SNNGGKQALESIVAQLSRPDPALAALTNDHLVALACLGGRPAMDAVKKGLPHAPELIRR

VNRRIGERTSHRVAGSQLVKSELEEKKSELRHKLKYVPHEYIELIEIARNSTQDRILEMK

VMEFFMKVYGYRGKHLGGSRKPAGAIYTVGSPIDYGVIVDTKAYSGGYNLPIGQADE

MQRYVKENQTRNKHINPNEWWKVYPSSVTEFKFLFVSGHFKGNYKAQLTRLNHKTN

CNGAVLSVEELLIGGEMIKAGTLTLEEVRRKFNNGEINFRSGGGEGRGSLLTCGDVEEN

PGPRMDYKDHDGDYKDHDIDYKDDDDKMAPKKKRKVGIHGVPARMVDLRTLGYSQ

QQQEKIKPKVRSTVAQHHEALVGHGFTHAHIVALSQHPAALGTVAVTYQHIITALPEAT

HEDIVGVGKQWSGARALEALLTDAGELRGPPLQLDTGQLVKIAKRGGVTAMEAVHAS

RNALTGAPLNLTPDQVVAIASHDGGKQALETVQRLLPVLCQDHGLTPDQVVAIASHDG

GKQALETVQRLLPVLCQDHGLTPDQVVAIASHDGGKQALETVQRLLPVLCQDHGLTP

DQVVAIASNIGGKQALETVQRLLPVLCQDHGLTPDQVVAIASNNGGKQALETVQRLLP

VLCQDHGLTPDQVVAIASNIGGKQALETVQRLLPVLCQDHGLTPDQVVAIASNNGGKQ

ALETVQRLLPVLCQDHGLTPDQVVAIASHDGGKQALETVQRLLPVLCQDHGLTPDQVV

AIASHDGGKQALETVQRLLPVLCQDHGLTPDQVVAIASHDGGKQALETVQRLLPVLC

QDHGLTPDQVVAIASHDGGKQALETVQRLLPVLCQDHGLTPDQVVAIASNNGGKQAL

ETVQRLLPVLCQDHGLTPDQVVAIASHDGGKQALETVQRLLPVLCQDHGLTPDQVVAI

ASNNGGKQALETVQRLLPVLCQDHGLTPDQVVAIASNNGGKQALETVQRLLPVLCQD

HGLTPDQVVAIASHDGGKQALETVQRLLPVLCQDHGLTPDQVVAIASNNGGKQALET

VQRLLPVLCQDHGLTPDQVVAIASHDGGKQALESIVAQLSRPDPALAALTNDHLVALAC

LGGRPAMDAVKKGLPHAPELIRRVNRRIGERTSHRVAGSQLVKSELEEKKSELRHKLKY

-continued

VPHEYIELIEIARNSTQDRILEMKVMEFFMKVYGYRGKHLGGSRKPDGAIYTVGSPIDY

GVIVDTKAYSGGYNLPIGQADEMERYVEENQTRNKHLNPNEWWKVYPSSVTEFKFLF

VSGHFKGNYKAQLTRLNHITNCNGAVLSVEELLIGGEMIKAGTLTLEEVRRKFNNGEIN

F

TALE-FokI-L$_{nickase}$ (SEQ ID NO. 162)

MAPKKKRKVGIHGVPSRMVDLRTLGYSQQQQEKIKPKVRSTVAQHHEALVGHGF

THAHIVALSQHPAALGTVAVTYQHIITALPEATHEDIVGVGKQWSGARALEALLTDAGE

LRGPPLQLDTGQLVKIAKRGGVTAMEAVHASRNALTGAPLNLTPDQVVAIASHDGGKQ

ALETVQRLLPVLCQDHGLTPDQVVAIASHDGGKQALETVQRLLPVLCQDHGLTPDQVV

AIASNGGGKQALETVQRLLPVLCQDHGLTPDQVVAIASNNGGKQALETVQRLLPVLC

QDHGLTPDQVVAIASNNGGKQALETVQRLLPVLCQDHGLTPDQVVAIASNIGGKQALE

TVQRLLPVLCQDHGLTPDQVVAIASHDGGKQALETVQRLLPVLCQDHGLTPDQVVAIA

SHDGGKQALETVQRLLPVLCQDHGLTPDQVVAIASNNGGKQALETVQRLLPVLCQDH

GLTPDQVVAIASHDGGKQALETVQRLLPVLCQDHGLTPDQVVAIASNNGGKQALETV

QRLLPVLCQDHGLTPDQVVAIASNIGGKQALETVQRLLPVLCQDHGLTPDQVVAIASNI

GGKQALETVQRLLPVLCQDHGLTPDQVVAIASNIGGKQALETVQRLLPVLCQDHGLTP

DQVVAIASNNGGKQALETVQRLLPVLCQDHGLTPDQVVAIASNIGGKQALETVQRLLP

VLCQDHGLTPDQVVAIASHDGGKQALETVQRLLPVLCQDHGLTPDQVVAIASHDGGK

QALETVQRLLPVLCQDHGLTPDQVVAIASNIGGKQALETVQRLLPVLCQDHGLTPDQV

VAIASNGGGKQALETVQRLLPVLCQDHGLTPDQVVAIASHDGGKQALETVQRLLPVLC

QDHGLTPDQVVAIASHDGGKQALETVQRLLPVLCQDHGLTPDQVVAIASNIGGKQALE

TVQRLLPVLCQDHGLTPDQVVAIASHDGGKQALETVQRLLPVLCQDHGLTPDQVVAIA

SNNGGKQALESIVAQLSRPDPALAALTNDHLVALACLGGRPAMDAVKKGLPHAPELIRR

VNRRIGERTSHRVAGSQLVKSELEEKKSELRHKLKYVPHEYIELIEIARNSTQDRILEMK

VMEFFMKVYGYRGKHLGGSRKPDGAIYTVGSPIDYGVIVDTKAYSGGYNLPIGQADE

MQRYVKENQTRNKHINPNEWWKVYPSSVTEFKFLFVSGHFKGNYKAQLTRLNHKTN

CNGAVLSVEELLIGGEMIKAGTLTLEEVRRKFNNGEINFRSGGGEGRGSLLTCGDVEEN

PGPRMDYKDHDGDYKDHDIDYKDDDDKMAPKKKRKVGIHGVPARMVDLRTLGYSQ

QQQEKIKPKVRSTVAQHHEALVGHGFTHAHIVALSQHPAALGTVAVTYQHIITALPEAT

HEDIVGVGKQWSGARALEALLTDAGELRGPPLQLDTGQLVKIAKRGGVTAMEAVHAS

RNALTGAPLNLTPDQVVAIASHDGGKQALETVQRLLPVLCQDHGLTPDQVVAIASHDG

GKQALETVQRLLPVLCQDHGLTPDQVVAIASHDGGKQALETVQRLLPVLCQDHGLTP

DQVVAIASNIGGKQALETVQRLLPVLCQDHGLTPDQVVAIASNNGGKQALETVQRLLP

VLCQDHGLTPDQVVAIASNIGGKQALETVQRLLPVLCQDHGLTPDQVVAIASNNGGKQ

ALETVQRLLPVLCQDHGLTPDQVVAIASHDGGKQALETVQRLLPVLCQDHGLTPDQVV

AIASHDGGKQALETVQRLLPVLCQDHGLTPDQVVAIASHDGGKQALETVQRLLPVLC

QDHGLTPDQVVAIASHDGGKQALETVQRLLPVLCQDHGLTPDQVVAIASNNGGKQAL

ETVQRLLPVLCQDHGLTPDQVVAIASHDGGKQALETVQRLLPVLCQDHGLTPDQVVAI

ASNNGGKQALETVQRLLPVLCQDHGLTPDQVVAIASNNGGKQALETVQRLLPVLCQD

HGLTPDQVVAIASHDGGKQALETVQRLLPVLCQDHGLTPDQVVAIASNNGGKQALET

VQRLLPVLCQDHGLTPDQVVAIASHDGGKQALESIVAQLSRPDPALAALTNDHLVALAC

-continued

```
LGGRPAMDAVKKGLPHAPELIRRVNRRIGERTSHRVAGSQLVKSELEEKKSELRHKLKY

VPHEYIELIEIARNSTQDRILEMKVMEFFMKVYGYRGKHLGGSRKPAGAIYTVGSPIDY

GVIVDTKAYSGGYNLPIGQADEMERYVEENQTRNKHLNPNEWWKVYPSSVTEFKFLF

VSGHFKGNYKAQLTRLNHITNCNGAVLSVEELLIGGEMIKAGTLTLEEVRRKFNNGEIN

F
```

In Examples 1 to 6, mExoI is the aforementioned mExoI-NLS (FIG. 16B), SEQ ID NO. 125; A3A-UGI is the aforementioned NLS-A3A-XTEN-UGI (FIG. 16B), SEQ ID NO. 123; Trex2 is the aforementioned Trex2-NLS (FIG. 16B), SEQ ID NO. 126.

In Examples 1 to 6, the amino acid sequence of UGI is the aforementioned NLS-UGI (FIG. 16B) (SEQ ID NO. 163).

The amino acid sequence of APOBEC1-UGI in Example 4 is the aforementioned NLS-rAPOBEC1-XTEN-UGI (FIG. 16B) (SEQ ID NO. 164).

```
Amino acid sequence of ExoV (ExoV-NLS) in
Example 1 (SEQ ID NO. 165):
MAETGEEETASAEASGFSDLSDSELVEFLDLEEAKESAVSLSKPGPSAE

LPGKDDKPVSLQNWKGGLDVLSPMERFHLKYLYVTDLCTQNWCELQMVY
```

-continued

```
GKELPGSLTPEKAAVLDTGASIHLAKELELHDLVTVPIATKEDAWAVKF

LNILAMIPALQSEGRVREFPVFGEVEGIFLVGVIDELHYTSKGELELAE

LKTRRRPVLPLPAQKKKDYFQVSLYKYIFDAMVQGKVTPASLIHHTKLC

LDKPLGPSVLRHARQGGVSVKSLGDLMELVFLSLTLSDLPAIDTLKLEY

IHQETATILGTEIVAFEEKEVKSKVQHYVAYWMGHRDPQGVDVEEAWKC

RTCDYVDICEWRRGSGVLSSSWEPKAKKFKMKRTADGSEFESPKKKRKV
```

The amino acid sequence of TadA-8e in Example 5 is the aforementioned TadA8e-NLS (FIG. 16B) (SEQ ID NO. 166).

In Example 6

```
Amino acid sequence of mExoI-16 aa-A3A-UGI (SEQ ID NO. 167):
MKRTADGSEFESPKKKRKVMGIQGLLQFIQEASEPVNVKKYKGQAVAVDTYCWL

HKGAIACAEKLAKGEPTDRYVGFCMKFVNMLLSYGVKPILIFDGCTLPSKKEVERSRR

ERRQSNLLKGKQLLREGKVSEARDCFARSINITHAMAHKVIKAARALGVDCLVAPYEA

DAQLAYLNKAGIVQAVITEDSDLLAFGCKKVILKMDQFGNGLEVDQARLGMCKQLGD

VFTEEKFRYMCILSGCDYLASLRGIGLAKACKVLRLANNPDIVKVIKKIGHYLRMNITV

PEDYITGFIRANNTFLYQLVFDPIQRKLVPLNAYGDDVNPETLTYAGQYVGDSVALQIAL

GNRDVNTFEQIDDYSPDTMPAHSRSHSWNEKAGQKPPGTNSIWHKNYCPRLEVNSVS

HAPQLKEKPSTLGLKQVISTKGLNLPRKSCVLKRPRNEALAEDDLLSQYSSVSKKIKEN

GCGDGTSPNSSKMSKSCPDSGTAHKTDAHTPSKMRNKFATFLQRRNEESGAVVVPGTR

SRFFCSSQDFDNFIPKKESGQPLNETVATGKATTSLLGALDCPDTEGHKPVDANGTHNL

SSQIPGNAAVSPEDEAQSSETSKLLGAMSPPSLGTLRSCFSWSGTLREFSRTPSPSASTTL

QQFRRKSDPPACLPEASAVVTDRCDSKSEMLGETSQPLHELGCSSRSQESMDSSCGLNT

SSLSQPSSRDSGSEESDCNNKSLDNQGEQNSKQHLPHFSKKDGLRRNKVPGLCRSSSM

DSFSTTKIKPLVPARVSGLSKKSGSMQTRKHHDVENKPGLQTKISELWKNFGFKKDSEK

LPSCKKPLSPVKDNIQLTPETEDEIFNKPECVRAQRAIFHSGSETPGTSESATPESMKRTA

DGSEFESPKKKRKVMEASPASGPRHLMDPHIFTSNFNNGIGRHKTYLCYEVERLDNGT

SVKMDQHRGFLHNQAKNLLCGFYGRHAELRFLDLVPSLQLDPAQIYRVTWFISWSPCF

SWGCAGEVRAFLQENTHVRLRIFAARIYDYDPLYKEALQMLRDAGAQVSIMTYDEFK

HCWDTFVDHQGCPFQPWDGLDEHSQALSGRLRAILQNQGNSGSETPGTSESATPESTN

LSDIIEKETGKQLVIQESILMLPEEVEEVIGNKPESDILVHTAYDESTDENVMLLTSDAPE

YKPWALVIQDSNGENKIKML

Amino acid sequence of mExoI-48 aa-A3A-UGI (SEQ ID NO. 168):
MKRTADGSEFESPKKKRKVMGIQGLLQFIQEASEPVNVKKYKGQAVAVDTYCWL
```

-continued

HKGAIACAEKLAKGEPTDRYVGFCMKFVNMLLSYGVKPILIFDGCTLPSKKEVERSRR

ERRQSNLLKGKQLLREGKVSEARDCFARSINITHAMAHKVIKAARALGVDCLVAPYEA

DAQLAYLNKAGIVQAVITEDSDLLAFGCKKVILKMDQFGNGLEVDQARLGMCKQLGD

VFTEEKFRYMCILSGCDYLASLRGIGLAKACKVLRLANNPDIVKVIKKIGHYLRMNITV

PEDYITGFIRANNTFLYQLVFDPIQRKLVPLNAYGDDVNPETLTYAGQYVGDSVALQIAL

GNRDVNTFEQIDDYSPDTMPAHSRSHSWNEKAGQKPPGTNSIWHKNYCPRLEVNSVS

HAPQLKEKPSTLGLKQVISTKGLNLPRKSCVLKRPRNEALAEDDLLSQYSSVSKKIKEN

GCGDGTSPNSSKMSKSCPDSGTAHKTDAHTPSKMRNKFATFLQRRNEESGAVVVPGTR

SRFFCSSQDFDNFIPKKESGQPLNETVATGKATTSLLGALDCPDTEGHKPVDANGTHNL

SSQIPGNAAVSPEDEAQSSETSKLLGAMSPPSLGTLRSCFSWSGTLREFSRTPSPSASTTL

QQFRRKSDPPACLPEASAVVTDRCDSKSEMLGETSQPLHELGCSSRSQESMDSSCGLNT

SSLSQPSSRDSGSEESDCNNKSLDNQGEQNSKQHLPHFSKKDGLRRNKVPGLCRSSSM

DSFSTTKIKPLVPARVSGLSKKSGSMQTRKHHDVENKPGLQTKISELWKNFGFKKDSEK

LPSCKKPLSPVKDNIQLTPETEDEIFNKPECVRAQRAIFHSGSETPGTSESATPESSGGSS

GGSSGSETPGTSESATPESSGGSSGGSMKRTADGSEFESPKKKRKVMEASPASGPRHLM

DPHIFTSNFNNGIGRHKTYLCYEVERLDNGTSVKMDQHRGFLHNQAKNLLCGFYGRH

AELRFLDLVPSLQLDPAQIYRVTWFISWSPCFSWGCAGEVRAFLQENTHVRLRIFAARI

YDYDPLYKEALQMLRDAGAQVSIMTYDEFKHCWDTFVDHQGCPFQPWDGLDEHSQA

LSGRLRAILQNQGNSGSETPGTSESATPESTNLSDIIEKETGKQLVIQESILMLPEEVEEVI

GNKPESDILVHTAYDESTDENVMLLTSDAPEYKPWALVIQDSNGENKIKML

A3A-TALE-FokI-R$_{nickase}$ (SEQ ID NO. 169)

MAPKKKRKVMEASPASGPRHLMDPHIFTSNFNNGIGRHKTYLCYEVERLDNGTSV

KMDQHRGFLHNQAKNLLCGFYGRHAELRFLDLVPSLQLDPAQIYRVTWFISWSPCFSW

GCAGEVRAFLQENTHVRLRIFAARIYDYDPLYKEALQMLRDAGAQVSIMTYDEFKHC

WDTFVDHQGCPFQPWDGLDEHSQALSGRLRAILQNQGSGSETPGTSESATPESSGGSS

GGSSGSETPGTSESATPESSGGSSGGSGIHGVPSRMVDLRTLGYSQQQQEKIKPKVRSTV

AQHHEALVGHGFTHAHIVALSQHPAALGTVAVTYQHIITALPEATHEDIVGVGKQWSG

ARALEALLTDAGELRGPPLQLDTGQLVKIAKRGGVTAMEAVHASRNALTGAPLNLTPD

QVVAIASNNGGKQALETVQRLLPVLCQDHGLTPDQVVAIASHDGGKQALETVQRLLP

VLCQDHGLTPDQVVAIASNIGGKQALETVQRLLPVLCQDHGLTPDQVVAIASNIGGKQ

ALETVQRLLPVLCQDHGLTPDQVVAIASNIGGKQALETVQRLLPVLCQDHGLTPDQVV

AIASNIGGKQALETVQRLLPVLCQDHGLTPDQVVAIASNNGGKQALETVQRLLPVLCQ

DHGLTPDQVVAIASNIGGKQALETVQRLLPVLCQDHGLTPDQVVAIASHDGGKQALET

VQRLLPVLCQDHGLTPDQVVAIASHDGGKQALETVQRLLPVLCQDHGLTPDQVVAIAS

NIGGKQALETVQRLLPVLCQDHGLTPDQVVAIASNIGGKQALETVQRLLPVLCQDHGL

TPDQVVAIASNNGGKQALETVQRLLPVLCQDHGLTPDQVVAIASNNGGKQALETVQR

LLPVLCQDHGLTPDQVVAIASNGGGKQALETVQRLLPVLCQDHGLTPDQVVAIASNNG

GKQALETVQRLLPVLCQDHGLTPDQVVAIASHDGGKQALETVQRLLPVLCQDHGLTP

DQVVAIASHDGGKQALETVQRLLPVLCQDHGLTPDQVVAIASNGGGKQALESIVAQLS

RPDPALAALTNDHLVALACLGGRPAMDAVKKGLPHAPELIRRVNRRIGERTSHRVAGSQ

LVKSELEEKKSELRHKLKYVPHEYIELIEIARNSTQDRILEMKVMEFFMKVYGYRGKH

LGGSRKPAGAIYTVGSPIDYGVIVDTKAYSGGYNLPIGQADEMQRYVKENQTRNKHIN

PNEWWKVYPSSVTEFKFLFVSGHFKGNYKAQLTRLNHKTNCNGAVLSVEELLIGGEMI

KAGTLTLEEVRRKFNNGEINFRSGGGEGRGSLLTCGDVEENPGPRMDYKDHDGDYKD

HDIDYKDDDDKMAPKKKRKVGIHGVPARMVDLRTLGYSQQQQEKIKPKVRSTVAQH

HEALVGHGFTHAHIVALSQHPAALGTVAVTYQHIITALPEATHEDIVGVGKQWSGARAL

EALLTDAGELRGPPLQLDTGQLVKIAKRGGVTAMEAVHASRNALTGAPLNLTPDQVVA

IASNNGGKQALETVQRLLPVLCQDHGLTPDQVVAIASNNGGKQALETVQRLLPVLCQ

DHGLTPDQVVAIASHDGGKQALETVQRLLPVLCQDHGLTPDQVVAIASNGGGKQALE

TVQRLLPVLCQDHGLTPDQVVAIASHDGGKQALETVQRLLPVLCQDHGLTPDQVVAIA

SNNGGKQALETVQRLLPVLCQDHGLTPDQVVAIASNGGGKQALETVQRLLPVLCQDH

GLTPDQVVAIASHDGGKQALETVQRLLPVLCQDHGLTPDQVVAIASNNGGKQALETV

QRLLPVLCQDHGLTPDQVVAIASHDGGKQALETVQRLLPVLCQDHGLTPDQVVAIASN

IGGKQALETVQRLLPVLCQDHGLTPDQVVAIASNNGGKQALETVQRLLPVLCQDHGLT

PDQVVAIASHDGGKQALETVQRLLPVLCQDHGLTPDQVVAIASNIGGKQALETVQRLL

PVLCQDHGLTPDQVVAIASNGGGKQALESIVAQLSRPDPALAALTNDHLVALACLGGRP

AMDAVKKGLPHAPELIRRVNRRIGERTSHRVAGSQLVKSELEEKKSELRHKLKYVPHE

YIELIEIARNSTQDRILEMKVMEFFMKVYGYRGKHLGGSRKPDGAIYTVGSPIDYGVIV

DTKAYSGGYNLPIGQADEMERYVEENQTRNKHLNPNEWWKVYPSSVTEFKFLFVSGH

FKGNYKAQLTRLNHITNCNGAVLSVEELLIGGEMIKAGTLTLEEVRRKENNGEINF

APOBEC1-TALE-FokI-R$_{nickase}$ (SEQ ID NO. 170)
MAPKKKRKVSSETGPVAVDPTLRRRIEPHEFEVFFDPRELRKETCLLYEINWGGRH

SIWRHTSQNTNKHVEVNFIEKFTTERYFCPNTRCSITWFLSWSPCGECSRAITEFLSRYP

HVTLFIYIARLYHHADPRNRQGLRDLISSGVTIQIMTEQESGYCWRNFVNYSPSNEAHW

PRYPHLWVRLYVLELYCIILGLPPCLNILRRKQPQLTFFTIALQSCHYQRLPPHILWATGL

KSGSETPGTSESATPESSGGSSGGSSGSETPGTSESATPESSGGSSGGSGIHGVPSRMVDL

RTLGYSQQQQEKIKPKVRSTVAQHHEALVGHGFTHAHIVALSQHPAALGTVAVTYQHII

TALPEATHEDIVGVGKQWSGARALEALLTDAGELRGPPLQLDTGQLVKIAKRGGVTA

MEAVHASRNALTGAPLNLTPDQVVAIASNNGGKQALETVQRLLPVLCQDHGLTPDQV

VAIASHDGGKQALETVQRLLPVLCQDHGLTPDQVVAIASNIGGKQALETVQRLLPVLC

QDHGLTPDQVVAIASNIGGKQALETVQRLLPVLCQDHGLTPDQVVAIASNIGGKQALET

VQRLLPVLCQDHGLTPDQVVAIASNIGGKQALETVQRLLPVLCQDHGLTPDQVVAIAS

NNGGKQALETVQRLLPVLCQDHGLTPDQVVAIASNIGGKQALETVQRLLPVLCQDHGL

TPDQVVAIASHDGGKQALETVQRLLPVLCQDHGLTPDQVVAIASHDGGKQALETVQR

LLPVLCQDHGLTPDQVVAIASNIGGKQALETVQRLLPVLCQDHGLTPDQVVAIASNIGG

KQALETVQRLLPVLCQDHGLTPDQVVAIASNNGGKQALETVQRLLPVLCQDHGLTPD

QVVAIASNNGGKQALETVQRLLPVLCQDHGLTPDQVVAIASNGGGKQALETVQRLLP

VLCQDHGLTPDQVVAIASNNGGKQALETVQRLLPVLCQDHGLTPDQVVAIASHDGGK

QALETVQRLLPVLCQDHGLTPDQVVAIASHDGGKQALETVQRLLPVLCQDHGLTPDQ

VVAIASNGGGKQALESIVAQLSRPDPALAALTNDHLVALACLGGRPAMDAVKKGLPHA

PELIRRVNRRIGERTSHRVAGSQLVKSELEEKKSELRHKLKYVPHEYIELIEIARNSTQDR

-continued

```
ILEMKVMEFFMKVYGYRGKHLGGSRKPAGAIYTVGSPIDYGVIVDTKAYSGGYNLPIG

QADEMQRYVKENQTRNKHINPNEWWKVYPSSVTEFKFLFVSGHFKGNYKAQLTRLN

HKTNCNGAVLSVEELLIGGEMIKAGTLTLEEVRRKFNNGEINFRSGGGEGRGSLLTCGD

VEENPGPRMDYKDHDGDYKDHDIDYKDDDDKMAPKKKRKVGIHGVPARMVDLRTL

GYSQQQQEKIKPKVRSTVAQHHEALVGHGFTHAHIVALSQHPAALGTVAVTYQHIITAL

PEATHEDIVGVGKQWSGARALEALLTDAGELRGPPLQLDTGQLVKIAKRGGVTAMEA

VHASRNALTGAPLNLTPDQVVAIASNNGGKQALETVQRLLPVLCQDHGLTPDQVVAIA

SNNGGKQALETVQRLLPVLCQDHGLTPDQVVAIASHDGGKQALETVQRLLPVLCQDH

GLTPDQVVAIASNGGGKQALETVQRLLPVLCQDHGLTPDQVVAIASHDGGKQALETV

QRLLPVLCQDHGLTPDQVVAIASNNGGKQALETVQRLLPVLCQDHGLTPDQVVAIASN

GGGKQALETVQRLLPVLCQDHGLTPDQVVAIASHDGGKQALETVQRLLPVLCQDHGL

TPDQVVAIASNNGGKQALETVQRLLPVLCQDHGLTPDQVVAIASHDGGKQALETVQR

LLPVLCQDHGLTPDQVVAIASNIGGKQALETVQRLLPVLCQDHGLTPDQVVAIASNNG

GKQALETVQRLLPVLCQDHGLTPDQVVAIASHDGGKQALETVQRLLPVLCQDHGLTP

DQVVAIASNIGGKQALETVQRLLPVLCQDHGLTPDQVVAIASNGGGKQALESIVAQLSR

PDPALAALTNDHLVALACLGGRPAMDAVKKGLPHAPELIRRVNRRIGERTSHRVAGSQL

VKSELEEKKSELRHKLKYVPHEYIELIEIARNSTQDRILEMKVMEFFMKVYGYRGKHL

GGSRKPDGAIYTVGSPIDYGVIVDTKAYSGGYNLPIGQADEMERYVEENQTRNKHLNP

NEWWKVYPSSVTEFKFLFVSGHFKGNYKAQLTRLNHITNCNGAVLSVEELLIGGEMIK

AGTLTLEEVRRKFNNGEINF
```

A3A-TALE-FokI-L<sub>nickase</sub>

(SEQ ID NO. 171)
```
MAPKKKRKVMEASPASGPRHLMDPHIFTSNFNNGIGRHKTYLCYEVERLDNGTSV

KMDQHRGFLHNQAKNLLCGFYGRHAELRFLDLVPSLQLDPAQIYRVTWFISWSPCFSW

GCAGEVRAFLQENTHVRLRIFAARIYDYDPLYKEALQMLRDAGAQVSIMTYDEFKHC

WDTFVDHQGCPFQPWDGLDEHSQALSGRLRAILQNQGSGSETPGTSESATPESSGGSS

GGSSGSETPGTSESATPESSGGSSGGSGIHGVPSRMVDLRTLGYSQQQQEKIKPKVRSTV

AQHHEALVGHGFTHAHIVALSQHPAALGTVAVTYQHIITALPEATHEDIVGVGKQWSG

ARALEALLTDAGELRGPPLQLDTGQLVKIAKRGGVTAMEAVHASRNALTGAPLNLTPD

QVVAIASHDGGKQALETVQRLLPVLCQDHGLTPDQVVAIASHDGGKQALETVQRLLP

VLCQDHGLTPDQVVAIASNGGGKQALETVQRLLPVLCQDHGLTPDQVVAIASNNGGK

QALETVQRLLPVLCQDHGLTPDQVVAIASNNGGKQALETVQRLLPVLCQDHGLTPDQ

VVAIASNIGGKQALETVQRLLPVLCQDHGLTPDQVVAIASHDGGKQALETVQRLLPVL

CQDHGLTPDQVVAIASHDGGKQALETVQRLLPVLCQDHGLTPDQVVAIASNNGGKQA

LETVQRLLPVLCQDHGLTPDQVVAIASHDGGKQALETVQRLLPVLCQDHGLTPDQVVA

IASNNGGKQALETVQRLLPVLCQDHGLTPDQVVAIASNIGGKQALETVQRLLPVLCQD

HGLTPDQVVAIASNIGGKQALETVQRLLPVLCQDHGLTPDQVVAIASNIGGKQALETVQ

RLLPVLCQDHGLTPDQVVAIASNNGGKQALETVQRLLPVLCQDHGLTPDQVVAIASNI

GGKQALETVQRLLPVLCQDHGLTPDQVVAIASHDGGKQALETVQRLLPVLCQDHGLT

PDQVVAIASHDGGKQALETVQRLLPVLCQDHGLTPDQVVAIASNIGGKQALETVQRLL

PVLCQDHGLTPDQVVAIASNGGGKQALETVQRLLPVLCQDHGLTPDQVVAIASHDGG
```

-continued

KQALETVQRLLPVLCQDHGLTPDQVVAIASHDGGKQALETVQRLLPVLCQDHGLTPD

QVVAIASNIGGKQALETVQRLLPVLCQDHGLTPDQVVAIASHDGGKQALETVQRLLPV

LCQDHGLTPDQVVAIASNNGGKQALESIVAQLSRPDPALAALTINDHLVALACLGGRPA

MDAVKKGLPHAPELIRRVNRRIGERTSHRVAGSQLVKSELEEKKSELRHKLKYVPHEYI

ELIEIARNSTQDRILEMKVMEFFMKVYGYRGKHLGGSRKPDGAIYTVGSPIDYGVIVD

TKAYSGGYNLPIGQADEMQRYVKENQTRNKHINPNEWWKVYPSSVTEFKFLFVSGHF

KGNYKAQLTRLNHKTNCNGAVLSVEELLIGGEMIKAGTLTLEEVRRKFNNGEINFRSG

GGEGRGSLLTCGDVEENPGPRMDYKDHDGDYKDHDIDYKDDDDKMAPKKKRKVGI

HGVPARMVDLRTLGYSQQQQEKIKPKVRSTVAQHHEALVGHGFTHAHIVALSQHPAAL

GTVAVTYQHIITALPEATHEDIVGVGKQWSGARALEALLTDAGELRGPPLQLDTGQLVK

IAKRGGVTAMEAVHASRNALTGAPLNLTPDQVVAIASHDGGKQALETVQRLLPVLCQD

HGLTPDQVVAIASHDGGKQALETVQRLLPVLCQDHGLTPDQVVAIASHDGGKQALET

VQRLLPVLCQDHGLTPDQVVAIASNIGGKQALETVQRLLPVLCQDHGLTPDQVVAIAS

NNGGKQALETVQRLLPVLCQDHGLTPDQVVAIASNIGGKQALETVQRLLPVLCQDHGL

TPDQVVAIASNNGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASHDG

GKQALETVQRLLPVLCQDHGLTPDQVVAIASHDGGKQALETVQRLLPVLCQDHGLTP

DQVVAIASNNGGKQALETVQRLLPVLCQDHGLTPDQVVAIASHDGGKQALETVQRLL

PVLCQDHGLTPDQVVAIASNNGGKQALETVQRLLPVLCQDHGLTPDQVVAIASNNGG

KQALETVQRLLPVLCQDHGLTPDQVVAIASHDGGKQALETVQRLLPVLCQDHGLTPD

QVVAIASNNGGKQALETVQRLLPVLCQDHGLTPDQVVAIASHDGGKQALESIVAQLSR

PDPALAALTNDHLVALACLGGRPAMDAVKKGLPHAPELIRRVNRRIGERTSHRVAGSQL

VKSELEEKKSELRHKLKYVPHEYIELIEIARNSTQDRILEMKVMEFFMKVYGYRGKHL

GGSRKPAGAIYTVGSPIDYGVIVDTKAYSGGYNLPIGQADEMERYVEENQTRNKHLNP

NEWWKVYPSSVTEFKFLFVSGHFKGNYKAQLTRLNHITNCNGAVLSVEELLIGGEMIK

AGTLTLEEVRRKFNNGEINF

APOBEC1-TALE-FokI-L*nickase*

(SEQ ID NO. 172)

MAPKKKRKVSSETGPVAVDPTLRRRIEPHEFEVFFDPRELRKETCLLYEINWGGRH

SIWRHTSQNTNKHVEVNFIEKFTTERYFCPNTRCSITWFLSWSPCGECSRAITEFLSRYP

HVTLFIYIARLYHHADPRNRQGLRDLISSGVTIQIMTEQESGYCWRNFVNYSPSNEAHW

PRYPHLWVRLYVLELYCIILGLPPCLNILRRKQPQLTFFTIALQSCHYQRLPPHILWATGL

KSGSETPGTSESATPESSGGSSGGSSGSETPGTSESATPESSGGSSGGSGIHGVPSRMVDL

RTLGYSQQQQEKIKPKVRSTVAQHHEALVGHGFTHAHIVALSQHPAALGTVAVTYQHII

TALPEATHEDIVGVGKQWSGARALEALLTDAGELRGPPLQLDTGQLVKIAKRGGVTA

MEAVHASRNALTGAPLNLTPDQVVAIASHDGGKQALETVQRLLPVLCQDHGLTPDQV

VAIASHDGGKQALETVQRLLPVLCQDHGLTPDQVVAIASNGGGKQALETVQRLLPVLC

QDHGLTPDQVVAIASNNGGKQALETVQRLLPVLCQDHGLTPDQVVAIASNNGGKQAL

ETVQRLLPVLCQDHGLTPDQVVAIASNIGGKQALETVQRLLPVLCQDHGLTPDQVVAI

ASHDGGKQALETVQRLLPVLCQDHGLTPDQVVAIASHDGGKQALETVQRLLPVLCQD

HGLTPDQVVAIASNNGGKQALETVQRLLPVLCQDHGLTPDQVVAIASHDGGKQALET

VQRLLPVLCQDHGLTPDQVVAIASNNGGKQALETVQRLLPVLCQDHGLTPDQVVAIAS

-continued

NIGGKQALETVQRLLPVLCQDHGLTPDQVVAIASNIGGKQALETVQRLLPVLCQDHGL

TPDQVVAIASNIGGKQALETVQRLLPVLCQDHGLTPDQVVAIASNNGGKQALETVQRL

LPVLCQDHGLTPDQVVAIASNIGGKQALETVQRLLPVLCQDHGLTPDQVVAIASHDGG

KQALETVQRLLPVLCQDHGLTPDQVVAIASHDGGKQALETVQRLLPVLCQDHGLTPD

QVVAIASNIGGKQALETVQRLLPVLCQDHGLTPDQVVAIASNGGGKQALETVQRLLPV

LCQDHGLTPDQVVAIASHDGGKQALETVQRLLPVLCQDHGLTPDQVVAIASHDGGKQ

ALETVQRLLPVLCQDHGLTPDQVVAIASNIGGKQALETVQRLLPVLCQDHGLTPDQVV

AIASHDGGKQALETVQRLLPVLCQDHGLTPDQVVAIASNNGGKQALESIVAQLSRPDP

ALAALTNDHLVALACLGGRPAMDAVKKGLPHAPELIRRVNRRIGERTSHRVAGSQLVKS

ELEEKKSELRHKLKYVPHEYIELIEIARNSTQDRILEMKVMEFFMKVYGYRGKHLGGS

RKPDGAIYTVGSPIDYGVIVDTKAYSGGYNLPIGQADEMQRYVKENQTRNKHINPNEW

WKVYPSSVTEFKFLFVSGHFKGNYKAQLTRLNHKTNCNGAVLSVEELLIGGEMIKAGT

LTLEEVRRKFNNGEINFRSGGGEGRGSLLTCGDVEENPGPRMDYKDHDGDYKDHDID

YKDDDDKMAPKKKRKVGIHGVPARMVDLRTLGYSQQQQEKIKPKVRSTVAQHHEAL

VGHGFTHAHIVALSQHPAALGTVAVTYQHIITALPEATHEDIVGVGKQWSGARALEALL

TDAGELRGPPLQLDTGQLVKIAKRGGVTAMEAVHASRNALTGAPLNLTPDQVVAIASH

DGGKQALETVQRLLPVLCQDHGLTPDQVVAIASHDGGKQALETVQRLLPVLCQDHGL

TPDQVVAIASHDGGKQALETVQRLLPVLCQDHGLTPDQVVAIASNIGGKQALETVQRL

LPVLCQDHGLTPDQVVAIASNNGGKQALETVQRLLPVLCQDHGLTPDQVVAIASNIGG

KQALETVQRLLPVLCQDHGLTPDQVVAIASNNGGKQALETVQRLLPVLCQDHGLTPD

QVVAIASHDGGKQALETVQRLLPVLCQDHGLTPDQVVAIASHDGGKQALETVQRLLP

VLCQDHGLTPDQVVAIASHDGGKQALETVQRLLPVLCQDHGLTPDQVVAIASHDGGK

QALETVQRLLPVLCQDHGLTPDQVVAIASNNGGKQALETVQRLLPVLCQDHGLTPDQ

VVAIASHDGGKQALETVQRLLPVLCQDHGLTPDQVVAIASNNGGKQALETVQRLLPVL

CQDHGLTPDQVVAIASNNGGKQALETVQRLLPVLCQDHGLTPDQVVAIASHDGGKQA

LETVQRLLPVLCQDHGLTPDQVVAIASNNGGKQALETVQRLLPVLCQDHGLTPDQVVA

IASHDGGKQALESIVAQLSRPDPALAALTNDHLVALACLGGRPAMDAVKKGLPHAPELI

RRVNRRIGERTSHRVAGSQLVKSELEEKKSELRHKLKYVPHEYIELIEIARNSTQDRILE

MKVMEFFMKVYGYRGKHLGGSRKPAGAIYTVGSPIDYGVIVDTKAYSGGYNLPIGQA

DEMERYVEENQTRNKHLNPNEWWKVYPSSVTEFKFLFVSGHFKGNYKAQLTRLNHIT

NCNGAVLSVEELLIGGEMIKAGTLTLEEVRRKFNNGEINF

SIRT6-NLS-TALE-L-DddAN-UGI (SEQ ID NO. 173)
MALSRAVCGTSRQLAPVLGYLGSRQKHSLPDYPYDVPDYAGYPYDVPDYAGYPY

DVPDYAMDIADLRTLGYSQQQQEKIKPKVRSTVAQHHEALVGHGFTHAHIVALSQHPA

ALGTVAVKYQDMIAALPEATHEAIVGVGKQWSGARALEALLTVAGELRGPPLQLDTG

QLLKIAKRGGVTAVEAVHAWRNALTGAPLNLTPDQVVAIASNGGGKQALETVQRLLPV

LCQDHGLTPEQVVAIASNIGGKQALETVQRLLPVLCQAHGLTPDQVVAIASHDGGKQA

LETVQRLLPVLCQAHGLTPAQVVAIANNNGGKQALETVQRLLPVLCQDHGLTPDQVV

AIASHDGGKQALETVQRLLPVLCQDHGLTPEQVVAIANNNGGKQALETVQRLLPVLC

QAHGLTPDQVVAIANNNGGKQALETVQRLLPVLCQAHGLTPAQVVAIASHDGGKQAL

-continued

ETVQRLLPVLCQDHGLTPDQVVAIANNNGGKQALETVQRLLPVLCQDHGLTPEQVVAI

ANNNGGKQALETVQRLLPVLCQAHGLTPDQVVAIANNNGGKQALETVQRLLPVLCQ

AHGLTPAQVVAIANNNGGKQALETVQRLLPVLCQDHGLTPDQVVAIASHDGGKQALE

TVQRLLPVLCQDHGLTPEQVVAIASNGGGKQALETVQRLLPVLCQAHGLTPDQVVAIA

NNNGGKQALETVQRLLPVLCQAHGLTPAQVVAIASNGGGKQALETVQRLLPVLCQDH

GLTPEQVVAIASHDGGRPALESIVAQLSRPDPALAALTNDHLVALACLGGRPALDAVKK

GLGGSGSYALGPYQISAPQLPAYNGQTVGTFYYVNDAGGLESKVFSSGGPTPYPNYAN

AGHVEGQSALFMRDNGISEGLVFHNNPEGTCGFCVNMTETLLPENAKMTVVPPEGSG

GSTNLSDIIEKETGKQLVIQESILMLPEEVEEVIGNKPESDILVHTAYDESTDENVMLLTS

DAPEYKPWALVIQDSNGENKIKML

SIRT6-NLS-TALE-R-DddAc-UGI (SEQ ID NO. 174)

MASVLTPLLLRGLTGSARRLPVPRAKIHSLDYKDHDGDYKDHDIDYKDDDDKMDI

ADLRTLGYSQQQQEKIKPKVRSTVAQHHEALVGHGFTHAHIVALSQHPAALGTVAVKY

QDMIAALPEATHEAIVGVGKRGAGARALEALLTVAGELRGPPLQLDTGQLLKIAKRGG

VTAVEAVHAWRNALTGAPLNLTPDQVVAIASHDGGKQALETVQRLLPVLCQDHGLTPE

QVVAIASHDGGKQALETVQRLLPVLCQAHGLTPDQVVAIANNNGGKQALETVQRLLP

VLCQAHGLTPAQVVAIANNNGGKQALETVQRLLPVLCQDHGLTPDQVVAIANNNGGK

QALETVQRLLPVLCQDHGLTPEQVVAIASNIGGKQALETVQRLLPVLCQAHGLTPDQV

VAIANNNGGKQALETVQRLLPVLCQAHGLTPAQVVAIANNNGGKQALETVQRLLPVL

CQDHGLTPDQVVAIASHDGGKQALETVQRLLPVLCQDHGLTPEQVVAIASHDGGKQA

LETVQRLLPVLCQAHGLTPDQVVAIANNNGGKQALETVQRLLPVLCQAHGLTPAQVV

AIASHDGGKQALETVQRLLPVLCQDHGLTPDQVVAIASNIGGKQALETVQRLLPVLCQ

DHGLTPEQVVAIASHDGGKQALETVQRLLPVLCQAHGLTPDQVVAIASNGGGKQALET

VQRLLPVLCQAHGLTPAQVVAIASNGGGKQALETVQRLLPVLCQDHGLTPEQVVAIAS

NNGGRPALESIVAQLSRPDPALAALTNDHLVALACLGGRPALDAVKKGLGGSAIPVKRG

ATGETKVFTGNSNSPKSPTKGGCSGGSTNLSDIIEKETGKQLVIQESILMLPEEVEEVIGN

KPESDILVHTAYDESTDENVMLLTSDAPEYKPWALVIQDSNGENKIKML

45

In Examples 11, 14 and 15

ND6-MTS-TALE-L-DddA$_N$-UGI (SEQ ID NO. 175)

MALSRAVCGTSRQLAPVLGYLGSRQKHSLPDYPYDVPDYAGYPYDVPDYAGYPY

DVPDYAMDIADLRTLGYSQQQQEKIKPKVRSTVAQHHEALVGHGFTHAHIVALSQHPA

ALGTVAVKYQDMIAALPEATHEAIVGVGKQWSGARALEALLTVAGELRGPPLQLDTG

QLLKIAKRGGVTAVEAVHAWRNALTGAPLNLTPEQVVAIASNNGGKQALETVQRLLPV

LCQAHGLTPEQVVAIASNIGGKQALETVQRLLPVLCQAHGLTPEQVVAIASHDGGKQA

LETVQRLLPVLCQAHGLTPEQVVAIASHDGGKQALETVQRLLPVLCQAHGLTPEQVVA

IASHDGGKQALETVQRLLPVLCQAHGLTPEQVVAIASHDGGKQALETVQRLLPVLCQA

HGLTPEQVVAIASHDGGKQALETVQRLLPVLCQAHGLTPEQVVAIASNIGGKQALETV

QRLLPVLCQAHGLTPEQVVAIASNGGGKQALETVQRLLPVLCQAHGLTPEQVVAIASN

GGGRPALESIVAQLSRPDPALAALTNDHLVALACLGGRPALDAVKKGLGGSGSYALGPY

-continued

QISAPQLPAYNGQTVGTFYYVNDAGGLESKVFSSGGPTPYPNYANAGHVEGQSALFMR

DNGISEGLVFHNNPEGTCGFCVNMTETLLPENAKMTVVPPEGSGGSTNLSDIIEKETGK

QLVIQESILMLPEEVEEVIGNKPESDILVHTAYDESTDENVMLLTSDAPEYKPWALVIQD

SNGENKIKML

ND6-MTS-TALE-R-DddA$_C$-UGI (SEQ ID NO. 176)

MASVLTPLLLRGLTGSARRLPVPRAKIHSLDYKDHDGDYKDHDIDYKDDDDKMDI

ADLRTLGYSQQQQEKIKPKVRSTVAQHHEALVGHGFTHAHIVALSQHPAALGTVAVKY

QDMIAALPEATHEAIVGVGKRGAGARALEALLTVAGELRGPPLQLDTGQLLKIAKRGG

VTAVEAVHAWRNALTGAPLNLTPEQVVAIASNNGGKQALETVQRLLPVLCQAHGLTPE

QVVAIASNIGGKQALETVQRLLPVLCQAHGLTPEQVVAIASNGGGKQALETVQRLLPV

LCQAHGLTPEQVVAIASNNGGKQALETVQRLLPVLCQAHGLTPEQVVAIASNNGGKQA

LETVQRLLPVLCQAHGLTPEQVVAIASHDGGKQALETVQRLLPVLCQAHGLTPEQVVA

IASNGGGKQALETVQRLLPVLCQAHGLTPEQVVAIASNIGGKQALETVQRLLPVLCQA

HGLTPEQVVAIASNGGGKQALETVQRLLPVLCQAHGLTPEQVVAIASNGGGKQALETV

QRLLPVLCQAHGLTPEQVVAIASNGGGRPALESIVAQLSRPDPALAALTNDHLVALACL

GGRPALDAVKKGLGGSAIPVKRGATGETKVFTGNSNSPKSPTKGGCSGGSTNLSDIIEK

ETGKQLVIQESILMLPEEVEEVIGNKPESDILVHTAYDESTDENVMLLTSDAPEYKPWAL

VIQDSNGENKIKML

ND1.2-MTS-TALE-L-DddA$_N$-UGI (SEQ ID NO. 177)

MALSRAVCGTSRQLAPVLGYLGSRQKHSLPDYPYDVPDYAGYPYDVPDYAGYPY

DVPDYAMDIADLRTLGYSQQQQEKIKPKVRSTVAQHHEALVGHGFTHAHIVALSQHPA

ALGTVAVKYQDMIAALPEATHEAIVGVGKQWSGARALEALLTVAGELRGPPLQLDTG

QLLKIAKRGGVTAVEAVHAWRNALTGAPLNLTPEQVVAIASHDGGKQALETVQALLPV

LCQAHGLTPQQVVAIASHDGGKQALETVQRLLPVLCQAHGLTPQQVVAIASNGGGKQ

ALETVQRLLPVLCQAHGLTPEQVVAIASNIGGKQALETVQALLPVLCQAHGLTPEQVV

AIASNGGGKQALETVQALLPVLCQAHGLTPEQVVAIASNGGGKQALETVQALLPVLC

QAHGLTPEQVVAIASNGGGKQALETVQRLLPVLCQAHGLTPEQVVAIASNIGGKQALE

TVQALLPVLCQAHGLTPEQVVAIASNGGGKQALETVQRLLPVLCQAHGLTPEQVVAIA

SNGGGKQALETVQALLPVLCQAHGLTPEQVVAIASHDGGKQALETVQALLPVLCQAH

GLTPEQVVAIASNGGGKQALETVQALLPVLCQAHGLTPEQVVAIASNIGGKQALETVQ

ALLPVLCQAHGLTPQQVVAIASNNGGRPALESIVAQLSRPDPALAALTNDHLVALACLG

GRPALDAVKKGLGGSGSYALGPYQISAPQLPAYNGQTVGTFYYVNDAGGLESKVFSSG

GPTPYPNYANAGHVEGQSALFMRDNGISEGLVFHNNPEGTCGFCVNMTETLLPENAK

MTVVPPEGSGGSTNLSDIIEKETGKQLVIQESILMLPEEVEEVIGNKPESDILVHTAYDES

TDENVMLLTSDAPEYKPWALVIQDSNGENKIKML

ND1.2-MTS-TALE-R-DddA$_C$-UGI (SEQ ID NO. 178)

MASVLTPLLLRGLTGSARRLPVPRAKIHSLDYKDHDGDYKDHDIDYKDDDDKMDI

ADLRTLGYSQQQQEKIKPKVRSTVAQHHEALVGHGFTHAHIVALSQHPAALGTVAVKY

QDMIAALPEATHEAIVGVGKRGAGARALEALLTVAGELRGPPLQLDTGQLLKIAKRGG

VTAVEAVHAWRNALTGAPLNLTPEQVVAIASNGGGKQALETVQALLPVLCQAHGLTPQ

-continued

QVVAIASNNGGKQALETVQRLLPVLCQAHGLTPQQVVAIASNIGGKQALETVQRLLPV

LCQAHGLTPEQVVAIASNNGGKQALETVQALLPVLCQAHGLTPEQVVAIASNGGGKQ

ALETVQALLPVLCQAHGLTPEQVVAIASNIGGKQALETVQALLPVLCQAHGLTPEQVV

AIASNIGGKQALETVQRLLPVLCQAHGLTPEQVVAIASNIGGKQALETVQALLPVLCQA

HGLTPEQVVAIASHDGGKQALETVQRLLPVLCQAHGLTPEQVVAIASNNGGKQALETV

QALLPVLCQAHGLTPEQVVAIASNNGGKQALETVQALLPVLCQAHGSIVAQLSRPDPA

LAALTNDHLVALACLGGRPALDAVKKGLGGSAIPVKRGATGETKVFTGNSNSPKSPTK

GGCSGGSTNLSDIIEKETGKQLVIQESILMLPEEVEEVIGNKPESDILVHTAYDESTDENV

MLLTSDAPEYKPWALVIQDSNGENKIKML

ND1.3-MTS-TALE-L-DddA$_N$-UGI (SEQ ID NO. 179)

MALSRAVCGTSRQLAPVLGYLGSRQKHSLPDYPYDVPDYAGYPYDVPDYAGYPY

DVPDYAMDIADLRTLGYSQQQQEKIKPKVRSTVAQHHEALVGHGFTHAHIVALSQHPA

ALGTVAVKYQDMIAALPEATHEAIVGVGKQWSGARALEALLTVAGELRGPPLQLDTG

QLLKIAKRGGVTAVEAVHAWRNALTGAPLNLTPEQVVAIASHDGGKQALETVQALLPV

LCQAHGLTPQQVVAIASNGGGKQALETVQRLLPVLCQAHGLTPQQVVAIASHDGGKQ

ALETVQRLLPVLCQAHGLTPEQVVAIASHDGGKQALETVQALLPVLCQAHGLTPEQVV

AIASNIGGKQALETVQALLPVLCQAHGLTPEQVVAIASHDGGKQALETVQALLPVLCQ

AHGLTPEQVVAIASNIGGKQALETVQRLLPVLCQAHGLTPEQVVAIASHDGGKQALET

VQALLPVLCQAHGLTPEQVVAIASNGGGKQALETVQRLLPVLCQAHGLTPEQVVAIAS

NIGGKQALETVQALLPVLCQAHGLTPEQVVAIASNNGGKQALETVQALLPVLCQAHGL

TPEQVVAIASHDGGKQALETVQALLPVLCQAHGLTPEQVVAIASNIGGKQALETVQRL

LPVLCQAHGLTPQQVVAIASNNGGKQALETVQRLLPVLCQAHGLTPEQVVAIASNIGG

KQALETVQALLPVLCQAHGLTPQQVVAIASNNGGRPALESIVAQLSRPDPALAALTNDH

LVALACLGGRPALDAVKKGLGGSGSYALGPYQISAPQLPAYNGQTVGTFYYVNDAGGL

ESKVFSSGGPTPYPNYANAGHVEGQSALFMRDNGISEGLVFHNNPEGTCGFCVNMTET

LLPENAKMTVVPPEGSGGSTNLSDIIEKETGKQLVIQESILMLPEEVEEVIGNKPESDILV

HTAYDESTDENVMLLTSDAPEYKPWALVIQDSNGENKIKML

ND1.3-MTS-TALE-R-DddA$_C$-UGI (SEQ ID NO. 180)

MASVLTPLLLRGLTGSARRLPVPRAKIHSLDYKDHDGDYKDHDIDYKDDDDKMDI

ADLRTLGYSQQQQEKIKPKVRSTVAQHHEALVGHGFTHAHIVALSQHPAALGTVAVKY

QDMIAALPEATHEAIVGVGKRGAGARALEALLTVAGELRGPPLQLDTGQLLKIAKRGG

VTAVEAVHAWRNALTGAPLNLTPEQVVAIASHDGGKQALETVQALLPVLCQAHGLTPQ

QVVAIASHDGGKQALETVQRLLPVLCQAHGLTPQQVVAIASHDGGKQALETVQRLLP

VLCQAHGLTPEQVVAIASHDGGKQALETVQALLPVLCQAHGLTPEQVVAIASNGGGK

QALETVQALLPVLCQAHGLTPEQVVAIASNGGGKQALETVQALLPVLCQAHGLTPEQV

VAIASHDGGKQALETVQRLLPVLCQAHGLTPEQVVAIASNNGGKQALETVQALLPVLC

QAHGLTPEQVVAIASNNGGKQALETVQRLLPVLCQAHGLTPEQVVAIASHDGGKQALE

TVQALLPVLCQAHGLTPEQVVAIASNIGGKQALETVQALLPVLCQAHGLTPEQVVAIAS

NIGGKQALETVQALLPVLCQAHGLTPEQVVAIASNNGGKQALETVQRLLPVLCQAHGL

TPQQVVAIASNNGGKQALETVQRLLPVLCQAHGLTPEQVVAIASNGGGKQALETVQAL

LPVLCQAHGLTPEQVVAIASNGGGKQALETVQALLPVLCQAHGLTPQQVVAIASHDGG

RPALESIVAQLSRPDPALAALTNDHLVALACLGGRPALDAVKKGLGGSAIPVKRGATGE

TKVFTGNSNSPKSPTKGGCSGGSTNLSDIIEKETGKQLVIQESILMLPEEVEEVIGNKPES

DILVHTAYDESTDENVMLLTSDAPEYKPWALVIQDSNGENKIKML

ND6.2-MTS-TALE-L-DddA$_N$-UGI (SEQ ID NO. 181)

MALSRAVCGTSRQLAPVLGYLGSRQKHSLPDYPYDVPDYAGYPYDVPDYAGYPY

DVPDYAMDIADLRTLGYSQQQQEKIKPKVRSTVAQHHEALVGHGFTHAHIVALSQHPA

ALGTVAVKYQDMIAALPEATHEAIVGVGKQWSGARALEALLTVAGELRGPPLQLDTG

QLLKIAKRGGVTAVEAVHAWRNALTGAPLNLTPEQVVAIASHDGGKQALETVQALLPV

LCQAHGLTPQQVVAIASHDGGKQALETVQRLLPVLCQAHGLTPQQVVAIASHDGGKQ

ALETVQRLLPVLCQAHGLTPEQVVAIASNIGGKQALETVQALLPVLCQAHGLTPEQVV

AIASNGGGKQALETVQALLPVLCQAHGLTPEQVVAIASNNGGKQALETVQALLPVLC

QAHGLTPEQVVAIASHDGGKQALETVQRLLPVLCQAHGLTPEQVVAIASHDGGKQALE

TVQALLPVLCQAHGLTPEQVVAIASNGGGKQALETVQRLLPVLCQAHGLTPEQVVAIA

SHDGGKQALETVQALLPVLCQAHGLTPEQVVAIASNIGGKQALETVQALLPVLCQAH

GLTPEQVVAIASNNGGKQALETVQALLPVLCQAHGLTPEQVVAIASNNGGKQALETVQ

RLLPVLCQAHGLTPQQVVAIASNIGGKQALETVQRLLPVLCQAHGLTPEQVVAIASNGG

GKQALETVQALLPVLCQAHGLTPQQVVAIASNIGGRPALESIVAQLSRPDPALAALTND

HLVALACLGGRPALDAVKKGLGGSGSYALGPYQISAPQLPAYNGQTVGTFYYVNDAG

GLESKVFSSGGPTPYPNYANAGHVEGQSALFMRDNGISEGLVFHNNPEGTCGFCVNMT

ETLLPENAKMTVVPPEGSGGSTNLSDIIEKETGKQLVIQESILMLPEEVEEVIGNKPESDI

LVHTAYDESTDENVMLLTSDAPEYKPWALVIQDSNGENKIKML

ND6.2-MTS-TALE-R-DddA$_C$-UGI (SEQ ID NO. 182)

MASVLTPLLLRGLTGSARRLPVPRAKIHSLDYKDHDGDYKDHDIDYKDDDDKMDI

ADLRTLGYSQQQQEKIKPKVRSTVAQHHEALVGHGFTHAHIVALSQHPAALGTVAVKY

QDMIAALPEATHEAIVGVGKRGAGARALEALLTVAGELRGPPLQLDTGQLLKIAKRGG

VTAVEAVHAWRNALTGAPLNLTPEQVVAIASNGGGKQALETVQALLPVLCQAHGLTPQ

QVVAIASNGGGKQALETVQRLLPVLCQAHGLTPQQVVAIASNNGGKQALETVQRLLP

VLCQAHGLTPEQVVAIASNNGGKQALETVQALLPVLCQAHGLTPEQVVAIASNIGGKQ

ALETVQALLPVLCQAHGLTPEQVVAIASNGGGKQALETVQALLPVLCQAHGLTPEQVV

AIASNIGGKQALETVQRLLPVLCQAHGLTPEQVVAIASNGGGKQALETVQALLPVLCQ

AHGLTPEQVVAIASNIGGKQALETVQRLLPVLCQAHGLTPEQVVAIASHDGGKQALET

VQALLPVLCQAHGLTPEQVVAIASNGGGKQALETVQALLPVLCQAHGLTPEQVVAIAS

NIGGKQALETVQALLPVLCQAHGLTPEQVVAIASHDGGKQALETVQRLLPVLCQAHGL

TPQQVVAIASNIGGKQALETVQRLLPVLCQAHGLTPEQVVAIASNNGGKQALETVQAL

LPVLCQAHGLTPQQVVAIASHDGGRPALESIVAQLSRPDPALAALTNDHLVALACLGGR

PALDAVKKGLGGSAIPVKRGATGETKVFTGNSNSPKSPTKGGCSGGSTNLSDIIEKETG

KQLVIQESILMLPEEVEEVIGNKPESDILVHTAYDESTDENVMLLTSDAPEYKPWALVIQ

DSNGENKIKML

ND3-MTS-TALE-L-DddA$_N$-UGI (SEQ ID NO. 183)

MALSRAVCGTSRQLAPVLGYLGSRQKHSLPDYPYDVPDYAGYPYDVPDYAGYPY

-continued

DVPDYAMDIADLRTLGYSQQQQEKIKPKVRSTVAQHHEALVGHGFTHAHIVALSQHPA

ALGTVAVKYQDMIAALPEATHEAIVGVGKQWSGARALEALLTVAGELRGPPLQLDTG

QLLKIAKRGGVTAVEAVHAWRNALTGAPLNLTPEQVVAIASNIGGKQALETVQALLPV

LCQAHGLTPQQVVAIASHDGGKQALETVQRLLPVLCQAHGLTPQQVVAIASNNGGKQ

ALETVQRLLPVLCQAHGLTPEQVVAIASNIGGKQALETVQALLPVLCQAHGLTPEQVV

AIASNNGGKQALETVQALLPVLCQAHGLTPEQVVAIASNGGGKQALETVQALLPVLC

QAHGLTPEQVVAIASNNGGKQALETVQRLLPVLCQAHGLTPEQVVAIASHDGGKQALE

TVQALLPVLCQAHGLTPEQVVAIASNNGGKQALETVQRLLPVLCQAHGLTPEQVVAIA

SNNGGKQALETVQALLPVLCQAHGLTPEQVVAIASHDGGKQALETVQALLPVLCQAH

GLTPEQVVAIASNGGGKQALETVQALLPVLCQAHGLTPEQVVAIASNGGGKQALETVQ

RLLPVLCQAHGLTPQQVVAIASHDGGKQALETVQRLLPVLCQAHGLTPEQVVAIASNN

GGKQALETVQALLPVLCQAHGLTPQQVVAIASNIGGRPALESIVAQLSRPDPALAALTN

DHLVALACLGGRPALDAVKKGLGGSGSYALGPYQISAPQLPAYNGQTVGTFYYVNDA

GGLESKVFSSGGPTPYPNYANAGHVEGQSALFMRDNGISEGLVFHNNPEGTCGFCVN

MTETLLPENAKMTVVPPEGSGGSTNLSDIIEKETGKQLVIQESILMLPEEVEEVIGNKPE

SDILVHTAYDESTDENVMLLTSDAPEYKPWALVIQDSNGENKIKML

ND3-MTS-TALE-R-DddA_C-UGI (SEQ ID NO. 184)

MASVLTPLLLRGLTGSARRLPVPRAKIHSLDYKDHDGDYKDHDIDYKDDDDKMDI

ADLRTLGYSQQQQEKIKPKVRSTVAQHHEALVGHGFTHAHIVALSQHPAALGTVAVKY

QDMIAALPEATHEAIVGVGKRGAGARALEALLTVAGELRGPPLQLDTGQLLKIAKRGG

VTAVEAVHAWRNALTGAPLNLTPEQVVAIASNIGGKQALETVQALLPVLCQAHGLTPQ

QVVAIASNGGGKQALETVQRLLPVLCQAHGLTPQQVVAIASNNGGKQALETVQRLLP

VLCQAHGLTPEQVVAIASNNGGKQALETVQALLPVLCQAHGLTPEQVVAIASNIGGKQ

ALETVQALLPVLCQAHGLTPEQVVAIASNNGGKQALETVQALLPVLCQAHGLTPEQVV

AIASNIGGKQALETVQRLLPVLCQAHGLTPEQVVAIASNIGGKQALETVQALLPVLCQA

HGLTPEQVVAIASNIGGKQALETVQRLLPVLCQAHGLTPEQVVAIASNNGGKQALETV

QALLPVLCQAHGLTPEQVVAIASNNGGKQALETVQALLPVLCQAHGLTPEQVVAIASN

NGGKQALETVQALLPVLCQAHGLTPEQVVAIASNIGGKQLETVQRLLPVLCQAHGLTP

QQVVAIASHDGGKQALETVQRLLPVLCQAHGLTPEQVVAIASNNGGKQALETVQALLP

VLCQAHGLTPQQVVAIASHDGGRPALESIVAQLSRPDPALAALTNDHLVALACLGGRPA

LDAVKKGLGGSAIPVKRGATGETKVFTGNSNSPKSPTKGGCSGGSTNLSDIIEKETGKQ

LVIQESILMLPEEVEEVIGNKPESDILVHTAYDESTDENVMLLTSDAPEYKPWALVIQDS

NGENKIKML

The target sequences in the following Examples and the accompanying drawings involved therein are set forth below.

A strand of the OsBADH2 target site in the figure

SEQ ID NO. 188

GCTGGATGCTTTGAGTACTTTGCAGATCTTGCAGAATCCTTGGACAAAA

GGC

B strand of the OsBADH2 target site in the figure

SEQ ID NO. 189

CGACCTACGAAACTCATGAAACGTCTAGAACGTCTTAGGAACCTGTTTT

CCG

A strand of the OsDEP1 target site in the figure

SEQ ID NO. 190

GCAAAAGACCAAGGTGCCTCAATTGTTCTTGCAGCTCATGCTGCGACGA

GCC

B strand of the OsDEP1 target site in the figure

SEQ ID NO. 191
CGTTTTCTGGTTCCACGGAGTTAACAAGAACGTCGAGTACGACGCTGCT
CGG

A strand of the OsCKX2 target site in the figure

SEQ ID NO. 192
CCTGGACCGCGTCCACGACGGCGAGCTCAAGCTCCGCGCCGCGGGGCTC
TGGG

B strand of the OsCKX2 target site in the figure

SEQ ID NO. 193
GGACCTGGCGCAGGTGCTGCCGCTCGAGTTCGAGGCGCGGCGCCCCGAG
ACCC

A strand of the Human ND6 target site in the figure

SEQ ID NO. 194
CCCCTGACCCCCATGCCTCAGGATACTCCTCAATAGCCATCGCTGTA

B strand of the Human ND6 target site in the figure

SEQ ID NO. 195
GGGGACTGGGGGTACGGAGTCCTATGAGGAGTTATCGGTAGCGACAT

A strand of the OsSD1 target site in the figure

SEQ ID NO. 196
CCAGGACGACGTCGGCGGCCTCGAGGTCCTCGTCGACGGCGAATGGCGC
CCCGTC

B strand of the OsSD1 target site in the figure

SEQ ID NO. 197
GGTCCTGCTGCAGCCGCCGGAGCTCCAGGAGCAGCTGCCGCTTACCGCG
GGGCAG

A strand of the SIRT6 target site in the figure

SEQ ID NO. 198
TACGCGGGGGGCTGTCGCCGTACGCGGACAAGGGCAAGTGCGGCCTCCC
GG

B strand of the SIRT6 target site in the figure

SEQ ID NO. 199
ATGCGCCGCCCCGACAGCGGCATGCGCCTGTTCCCGTTCACGCCGGAGG
GCC

A strand of the OsRbcL target site in the figure

SEQ ID NO. 200
TTACCAAAGATGATGAAAACGTAAACTCACAACCATTTATGCGTTGG

B strand of the OsRbcL target site in the figure

SEQ ID NO. 201
AATGGTTTCTACTACTTTTGCATTTGAGTGTTGGTAAATACGCAACC

A strand of the ND6.2 target site in the figure

SEQ ID NO. 202
GACCCCCATGCCTCAGGATACTCCTCAATAGCCATCGCTGTAGTATAT
CCAA

B strand of the ND6.2 target site in the figure

SEQ ID NO. 203
CTGGGGGTACGGAGTCCTATGAGGAGTTATCGGTAGCGACATCATATA
GGTT

A strand of the ND1.2 target site in the figure

SEQ ID NO. 204
CCTATTTATTCTAGCCACCTCTAGCCTAGCCGTTTACTCA

B strand of the ND1.2 target site in the figure

SEQ ID NO. 205
GGATAAATAAGATCGGTGGAGATCGGATCGGCAAATGAGT

A strand of the ND1.3 target site in the figure

SEQ ID NO. 206
TCTCCACACTAGCAGAGACCAACCGAACCCCCTTCGACCTTGCCGAAG
GGG

B strand of the ND1.3 target site in the figure

SEQ ID NO. 207
AGAGGTGTGATCGTCTCTGGTTGGCTTGGGGGAAGCTGGAACGGCTTC
CCC

A strand of the ND3 target site in the figure

SEQ ID NO. 208
ACGAGTGCGGCTTCGACCCTATATCCCCCGCCCGCGTCCCTTTCTCCA
T

B strand of the ND3 target site in the figure

SEQ ID NO. 209
TGCTCACGCCGAAGCTGGGATATAGGGGGGGGCGCAGGGAAAGAGGT
A

A strand of the ND1 target site in the figure

SEQ ID NO. 210
CTAGCCTAGCCGTTTACTCAATCCTCTCATCAGGGTGAGCATCAAACT
C

B strand of the ND1 target site in the figure

SEQ ID NO. 211
GATCGGATCGGCAAATGAGTTAGGAGACTAGTCCCACTCGTAGTTTGA
G

A strand of the ND4 target site in the figure

SEQ ID NO. 212
GCTAGTAACCACGTTCTCCTGATCAAATATCACTCTCCTACTTACAG
G

B strand of the ND4 target site in the figure

```
                                      SEQ ID NO. 213
CGATCATTGGTGCAAGAGGACTAGTTTATAGTGAGAGGATGAATGTC
C
```

A strand of the ND5.1 target site in the figure

```
                                      SEQ ID NO. 214
AGCATTAGCAGGAATACCTTTCCTCACAGGTTTCTACTCCAAAG
```

B strand of the ND5.1 target site in the figure

```
                                      SEQ ID NO. 215
TCGTAATCGTCCTTATGGAAAGGAGTGTCCAAAGATGAGGTTTC

SEQ ID NO. 216
GACCCCCATGCCTCAGGATACTCCTCAATAGCCATC
```

```
                                      SEQ ID NO. 217
CTGGGGGTACGGAGTCCTATGAGGAGTTATCGGTAG

SEQ ID NO. 218
CCCCATGCCTCAGGATACTCCTCAATAGCCATCGCTGTAGTATATCCAA

SEQ ID NO. 219
GGGGTACGGAGTCCTATGAGGAGTTATCGGTAGCGACATCATATAGGTT
```

Example 1: Synthesis and Determination of Base Editor

The synthesis strategy of the base editor of the present disclosure was as shown in FIG. 1.

In order to verify the above-mentioned strategy, a target site in OsBADH2 gene of rice was selected, two set of TALE encoding vectors modified to target the site were constructed, and the above-mentioned elements were listed in Table 3.

TABLE 3

Special examples of the combinations of base editors in Examples

| Construct | Fusion protein of sequence-specific DNA binding protein and nickase | Exonuclease | Fusion protein of deaminase and UGI |
|---|---|---|---|
| TALEN$_{WT}$ | TALE-L-FokI-L and | Exonuclease I | hAPOBEC3A-UGI |
| | TALE-R-FokI-R | Exonuclease V | hAPOBEC3A-UGI |
| TALE-FokI-R$_{nickase(D450A)}$ | TALE-L-FokI-L$_{D450A}$ and | Exonuclease I | hAPOBEC3A-UGI |
| | TALE-R-FokI-R | Exonuclease V | hAPOBEC3A-UGI |
| TALE-FokI-R$_{nickase(D467A)}$ | TALE-L-FokI-L$_{D467A}$ and | Exonuclease I | hAPOBEC3A-UGI |
| | TALE-R-FokI-R | Exonuclease V | hAPOBEC3A-UGI |

An FokICD (or mutant) monomer was fused to the C-terminal of TALE-L and TALE-R, respectively, and wild-type FokI (without D450A or D467A mutation) was used as a control group (FIG. 16A). The application of two exonucleases (Exonuclease I (rat exonuclease I, simply referred to as mExoI) and Exonuclease V (simply referred to as ExoV)) and one deaminase (hAPOBEC3A, simply referred to as hA3A or A3A) in the novel base editor was evaluated, wherein UGI was fused to the carboxy terminal of the deaminase with an XTEN linker peptide in each group (FIG. 16B). The nuclear localization signal (NLS, i.e., SV40 NLS in Table 2) was fused to the terminal of the protein.

Recombinant expression constructs encoding these components were transformed into rice protoplasts via PEG-mediated transformation. Said constructs were as shown by FIGS. 16A-16B. Rice protoplasts were transformed with different construct combinations to target the OsBADH2 site, and next-generation sequencing (NGS) was used to determine C>T base editing frequency. Sequencing results (FIG. 2A) indicated that, for the combination comprising FokI nickase, deaminase, exonuclease and UGI, targeted cytosine base editing was achieved with a frequency up to about 10%. Importantly, the results of determination also indicated that the novel nucleic acid base editor merely resulted in indel byproducts at a very low level (as shown in FIG. 2B). The above-mentioned results indicated that the novel base editor had the characteristics of achieving high product purity, which was important for precise genome editing.

Figure 2A:
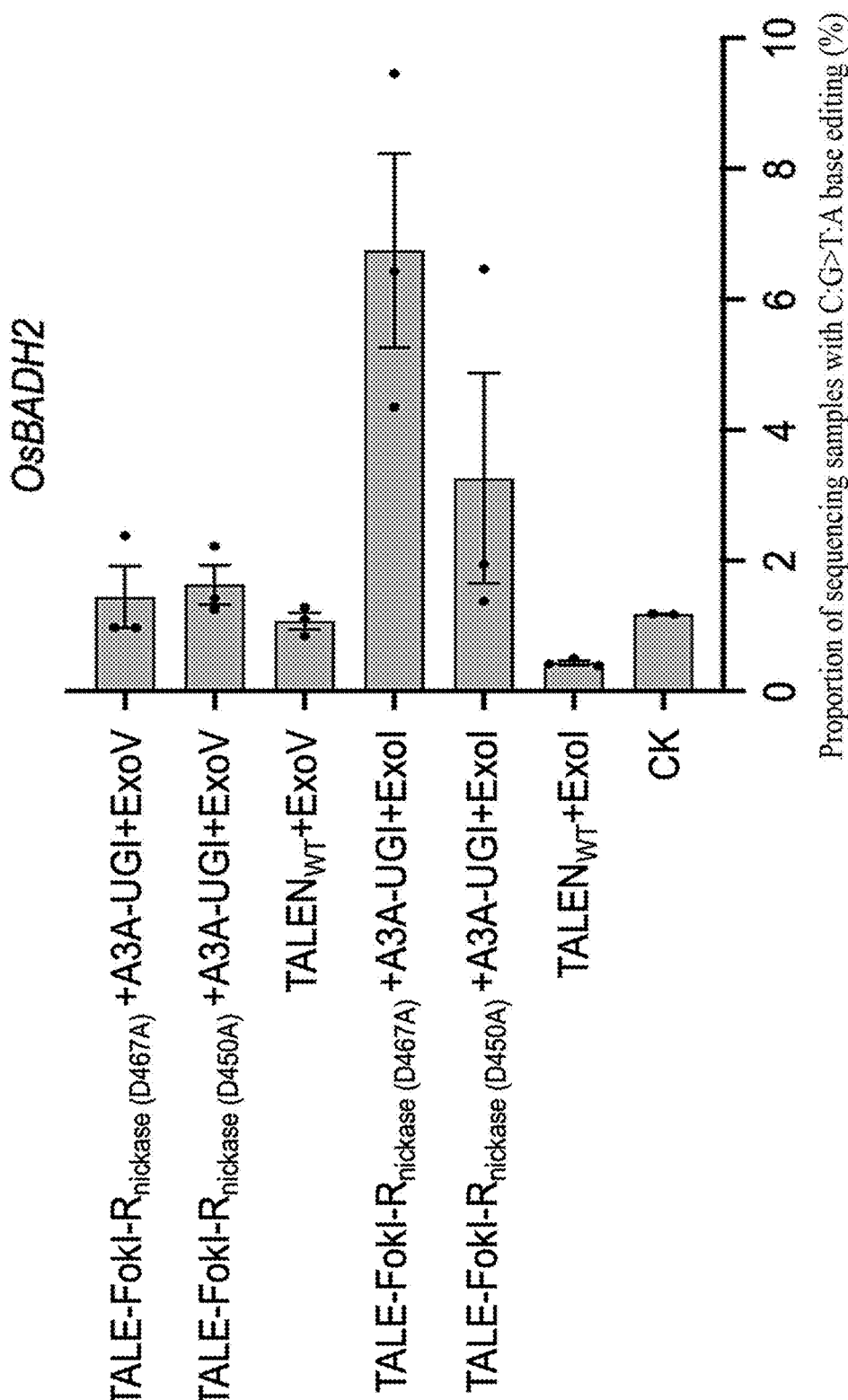
FIG. 2A and FIG. 2B show the application effects of the high-purity base editing of the nucleic acid base editor of the present disclosure in rice nuclear base editing. Among them.
Figure 2B:
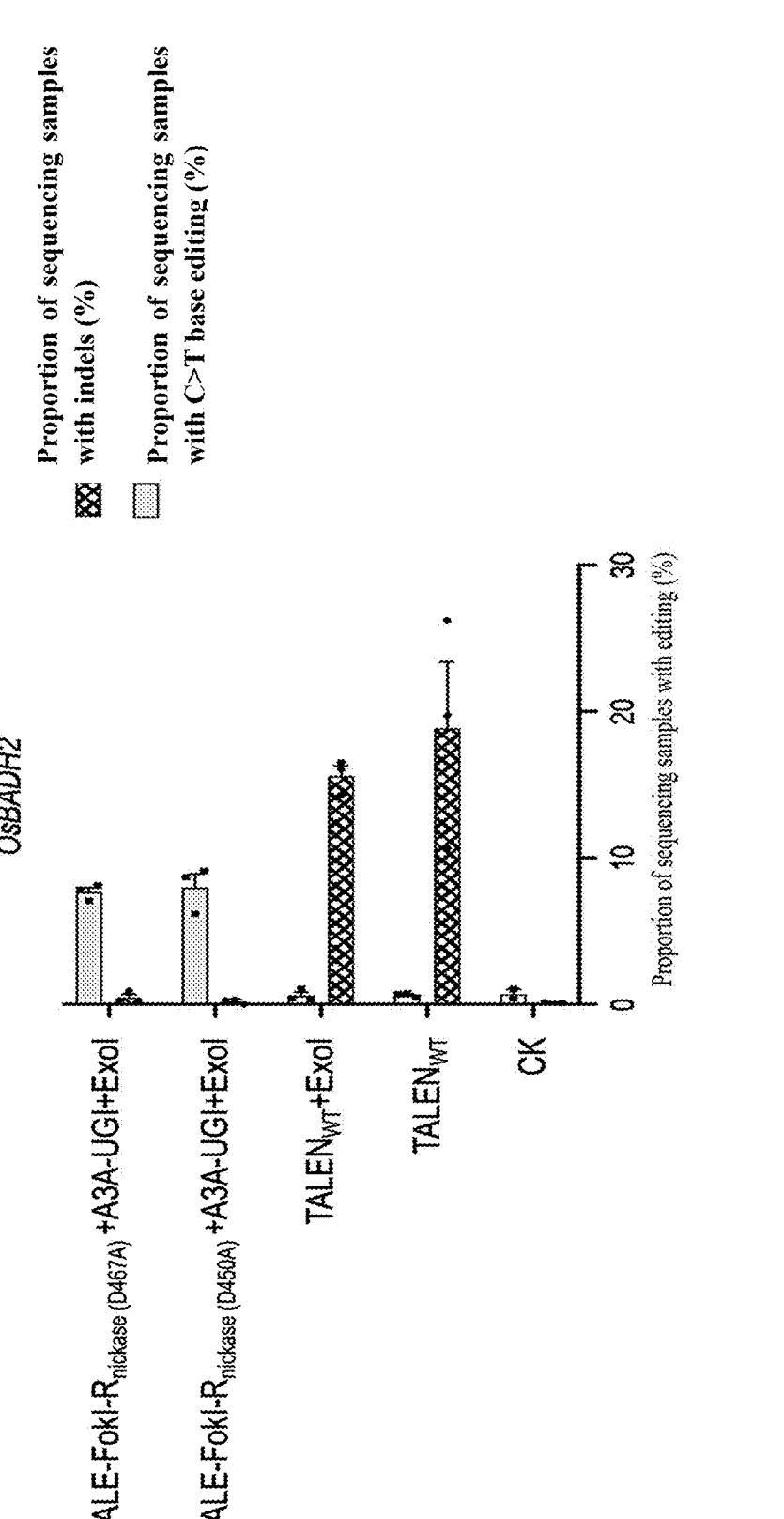

In FIG. 2A and FIG. 2B, the experimental treatments or construct combinations involved in figures and the schematic diagrams of related vectors were as shown below.

| Experimental treatments or construct combinations involved in figures | Schematic diagrams of related vectors |
|---|---|
| CK | None |
| $TALEN_{WT}$ + mExoI | Exonuclease (mExoI) - nuclear localization signal fusion protein vector in FIG. 16A and Fig. 16C |
| TALE-FokI-$R_{nickase\ (D450A)}$ + A3A-UGI + mExoI | FIG. 16B, wherein the corresponding nickase was FokI-$R_{nickase\ (D450A)}$, the corresponding deaminase was hAPOBEC3A, and the corresponding exonuclease was mExoI. |
| TALE-FokI-$R_{nickase\ (D467A)}$ + A3A-UGI + mExoI | FIG. 16B, wherein the corresponding nickase was FokI-$R_{nickase\ (D467A)}$, the corresponding deaminase was hAPOBEC3A, and the corresponding exonuclease was mExoI. |
| $TALEN_{WT}$ + ExoV | Exonuclease (ExoV) - nuclear localization signal fusion protein vector in FIG. 16A and Fig. 16C |
| TALE-FokI-$R_{nickase\ (D450A)}$ + A3A-UGI + ExoV | FIG. 16B, wherein the corresponding nickase was FokI-$R_{nickase\ (D450A)}$, the corresponding deaminase was hAPOBEC3A, and the corresponding exonuclease was ExoV. |
| TALE-FokI-$R_{nickase\ (D467A)}$ + A3A-UGI + ExoV | FIG. 16B, wherein the corresponding nickase was FokI-$R_{nickase\ (D467A)}$, the corresponding deaminase was hAPOBEC3A, and the corresponding exonuclease was ExoV. |

Example 2: Characterization of Cleavage Performance of Base Editor on Single Strand The base editing windows of the base editors tested in Example 1 were analyzed. Among the four C sites (C1, C6, C11 and C15, in the spacer sequence between two TALEs, the first base adjacent to TALE-L was counted as 1) present in strand A of the target gene (as shown in FIG. 3A), the C6 and C11 cytosines were efficiently edited (FIG. 3B).

Figure 3B:
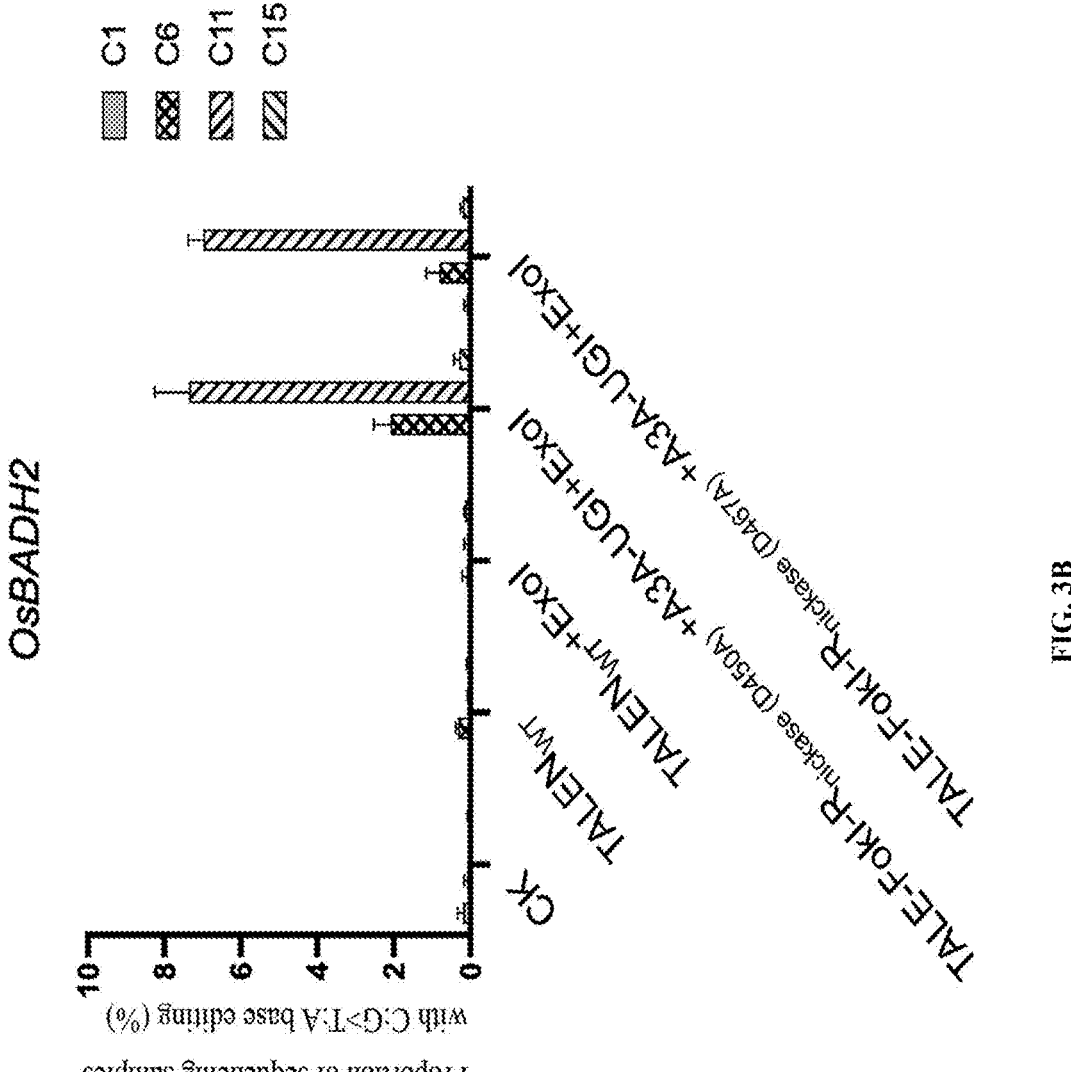

In FIG. 3B, the experimental treatments or construct combinations involved in figures and the schematic diagrams of related vectors were as shown below.

| Experimental treatments or construct combinations involved in figures | Schematic diagrams of related vectors |
|---|---|
| CK | None |
| $TALEN_{WT}$ + mExoI | Exonuclease (mExoI) - nuclear localization signal fusion protein vector in FIG. 16A and FIG. 16C |
| TALE-FokI-$R_{nickase\ (D450A)}$ + A3A-UGI + mExoI | FIG. 16B, wherein the corresponding nickase was FokI-$R_{nickase\ (D450A)}$, the corresponding deaminase was hAPOBEC3A, and the corresponding exonuclease was mExoI. |
| TALE-FokI-$R_{nickase\ (D467A)}$ + A3A-UGI + mExoI | FIG. 16B, wherein the corresponding nickase was FokI-$R_{nickase\ (D467A)}$, the corresponding deaminase was hAPOBEC3A, and the corresponding exonuclease was mExoI. |
| $TALEN_{WT}$ | FIG. 16A |

These results indicated that the base editor comprising FokI-$R_{nickase}$ (FokI-L in the dimeric nickase composed of FokI-L and FokI-R had a D450A or D467A mutation) tended to nick strand B by nickase, and the nicked single strand was subsequently digested by exonuclease, leaving a short fragment of ssDNA in strand A. The direction of digestion depended on the enzymatic direction (5' to 3' or 3 to 5') of the exonuclease.

Figure 4A:
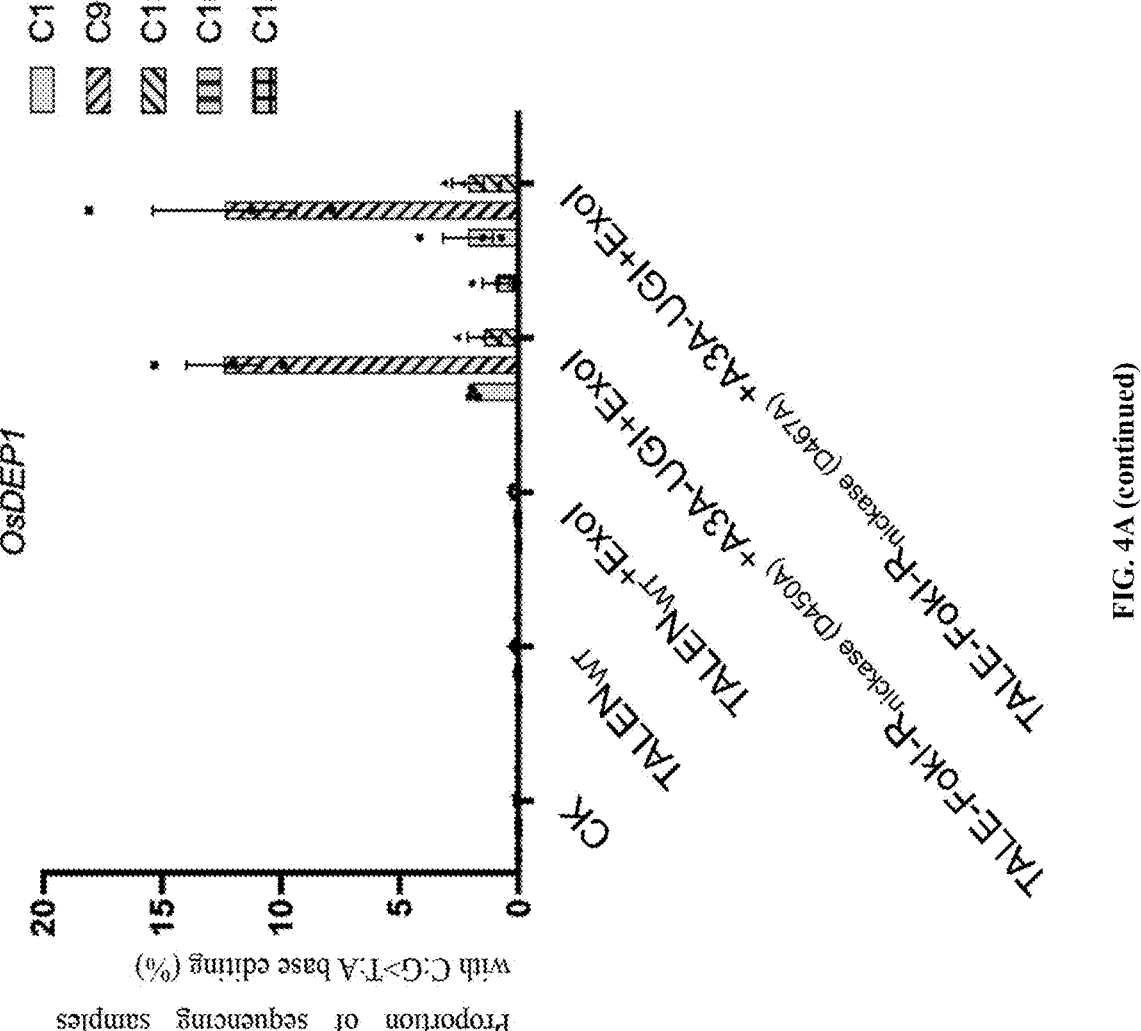
FIG. 4A and FIG. 4B show the editing efficiency of cytosine nucleotide at the target site (FIG. 4A) and the frequency of generating indel byproducts (FIG. 4B) analyzed by high-throughput sequencing after the rice protoplast is transformed with the base editor of the present disclosure to target OsDEP1, wherein CK is a blank control without the transformation of any plasmid, TALEN$_{WT}$ and TALEN$_{WT}$+ExoI are those with the transformation of the wild-type TALEN or the transformation of a combination of TALEN and exonuclease ExoI, respectively, and these two treatments serve as negative control.
Figure 4B:
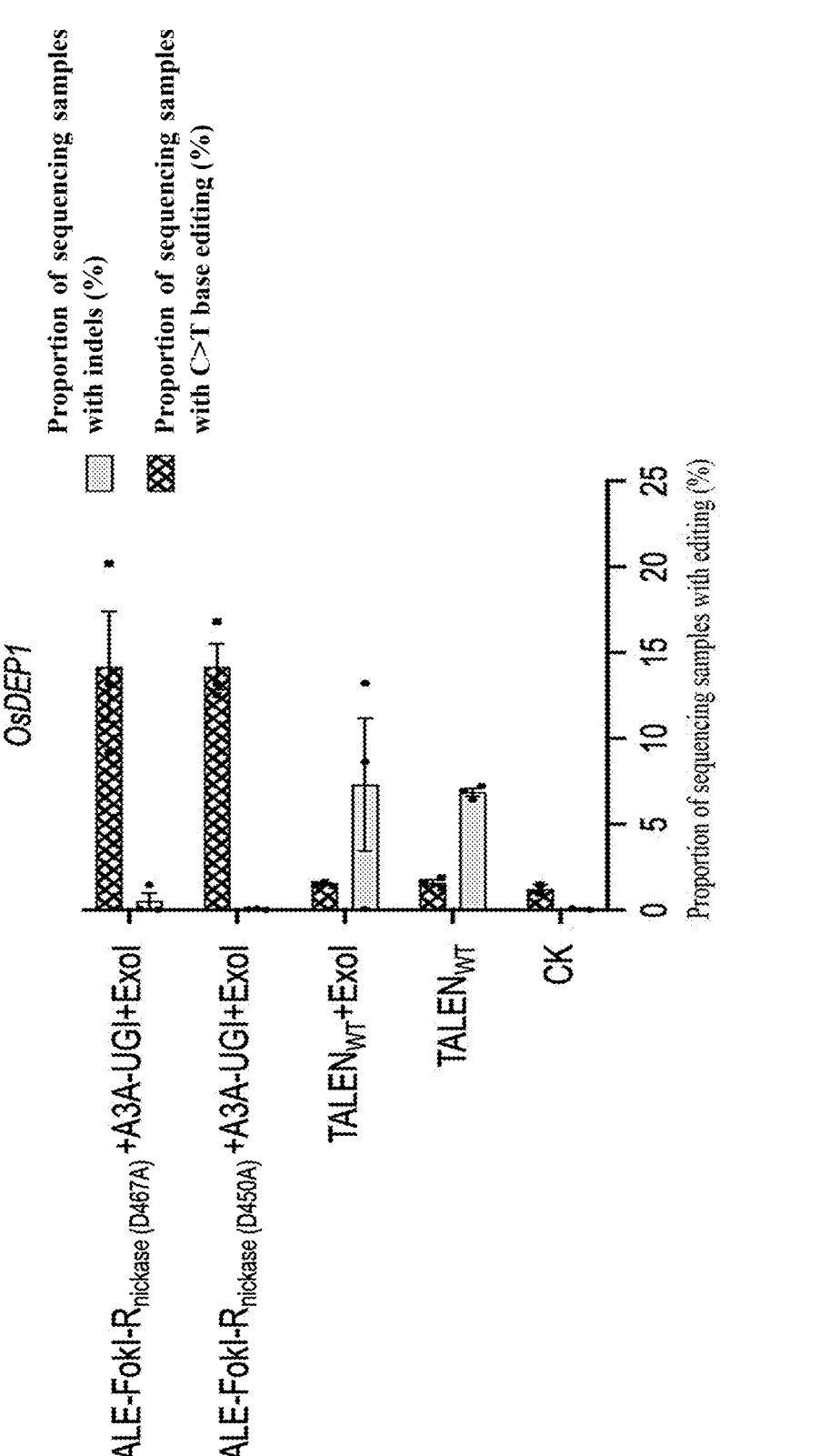

In order to verity the above-mentioned results, the inventors evaluated the nucleic acid base editor at another site (OsDEP1) of the present example, which comprised 5 C-bases (C1, C9, C13, C16 and C18) in strand A. Rice protoplasts were transformed with different construct combinations to target the OsDEP1 site, the NGS analysis results indicated that the base editing window was mainly located near the 5' region (C9 and C1) in strand A, although C13 and C16 were also slightly edited (as shown in FIG. 4A), which was caused by the generation of a transient 3' flap structure after nicking. Importantly, similar to the OsBADH2 site, indel byproducts merely appeared in the labeled products at the OsDEP1 site at an extremely low level (as shown in FIG. 4B). The above-mentioned results indicated that the novel base editor achieved the advantage of higher product purity.

In FIG. 4A and FIG. 4B, the experimental treatments or construct combinations involved in figures and the schematic diagrams of related vectors were as shown below.

| Experimental treatments or construct combinations involved in figures | Schematic diagrams of related vectors |
| --- | --- |
| CK | None |
| TALEN$_{WT}$ + mExoI | Exonuclease (mExoI) - nuclear localization signal fusion protein vector in FIG. 16A and FIG. 16C |
| TALE-FokI-R$_{nickase\ (D450A)}$ + A3A-UGI + mExoI | FIG. 16B, wherein the corresponding nickase was FokI-R$_{nickase\ (D450A)}$, the corresponding deaminase was hAPOBEC3A, and the corresponding exonuclease was mExoI. |
| TALE-FokI-R$_{nickase\ (D467A)}$ + A3A-UGI + mExoI | FIG. 16B, wherein the corresponding nickase was FokI-R$_{nickase\ (D467A)}$, the corresponding deaminase was hAPOBEC3A, and the corresponding exonuclease was mExoI. |
| TALEN$_{WT}$ | FIG. 16A |

Figure 5A:
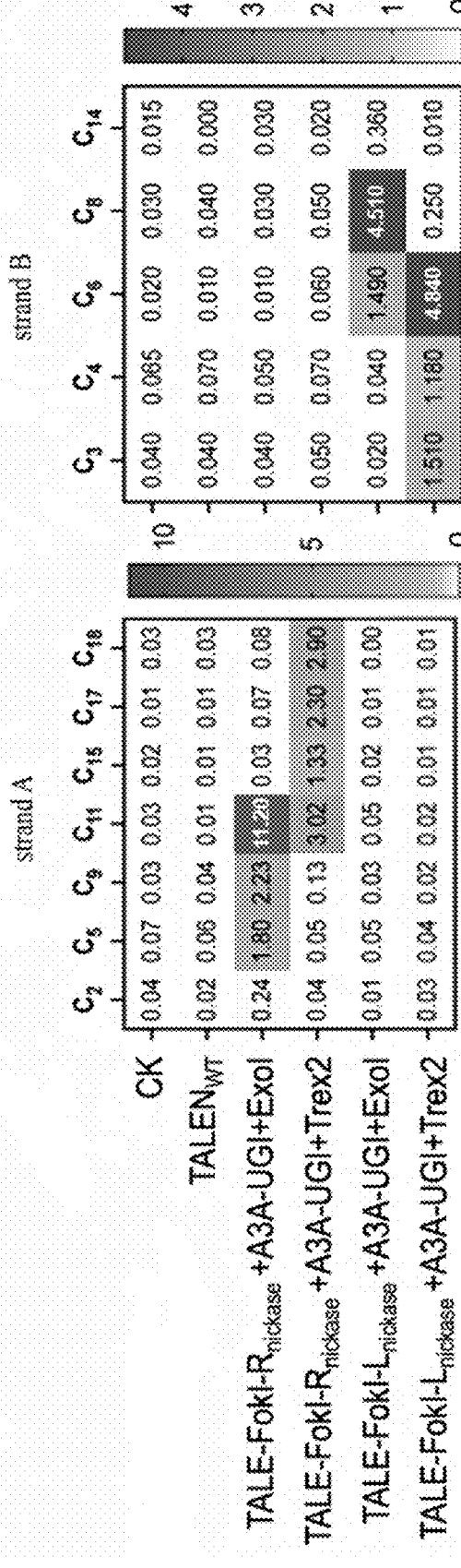
FIG. 5A and FIG. 5B show the application effects achieved by using base editors comprising combinations of different FokI nickases, different exonucleases and the cytidine deaminase. Different editing windows are generated when exonucleases with different digestion directions are used; and different DNA single strands at the target site are subjected to specific base editing when different nickases are used (FIG. 5A). The purity of the editing products and the frequency of generating byproducts of the base editor of the present disclosure achieved by different combinations are analyzed (FIG. 5B).
Figure 5B:
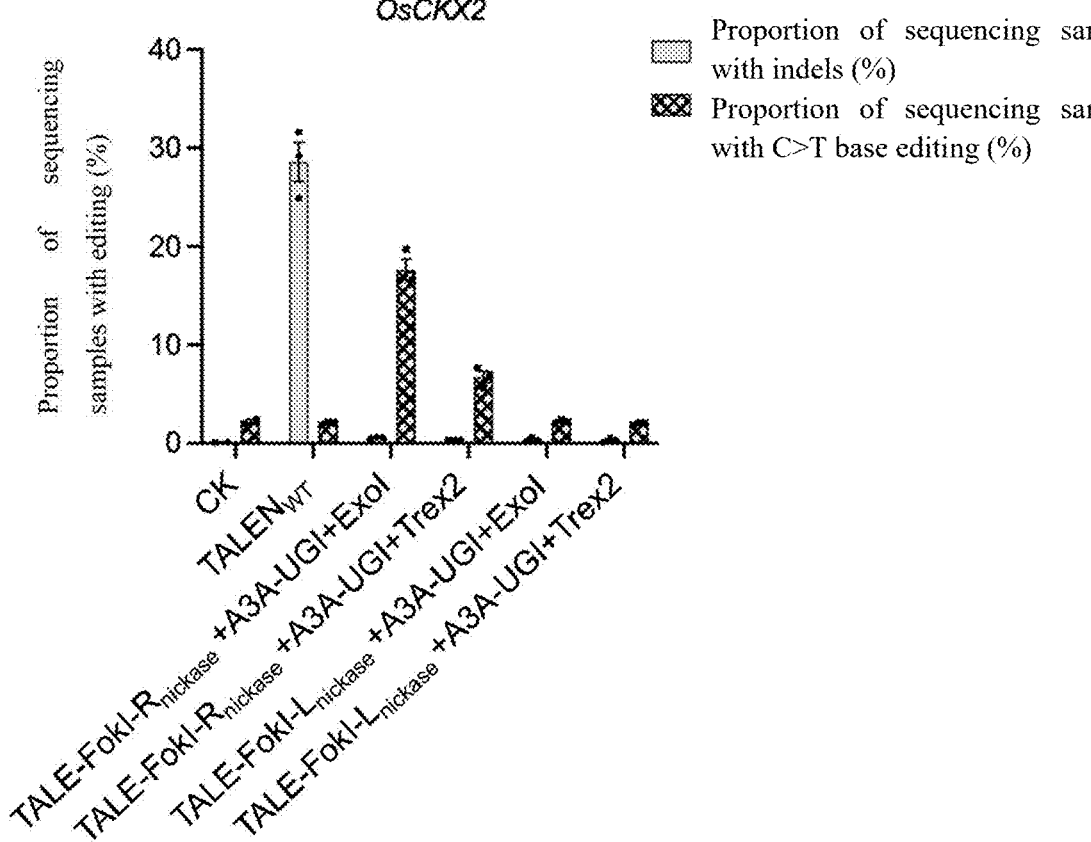

Example 3: Effects of Exonuclease Digestion Direction and the Preference of Nickase for Single Strand on Editing Results The exonuclease having 5'→3' digestion directionality (for example, rat exonuclease I (mExoI)) resulted in the exposure of the cytosine residues located near the 5' region of the target site in the complementary chain and the deamination of the cytosine residues by deaminase; while the 3' exonuclease resulted in the exposure of the cytosine residues located near the 3' region of the target site in the complementary chain and the deamination of the cytosine residues by deaminase. To verify the fact that the base editor disclosed in the present disclosure could achieve the expected effects for different exonuclease digestion directions, the inventors tested a 5' exonuclease (mExoI) and a 3' exonuclease (human-derived Trex2 exonuclease) at the OsCKX2 target simultaneously, and the editing window of the resulting base editor was analyzed by NGS. As shown by the experimental results, as for the FokI-R$_{nickase}$-mediated base editing, when the 5' exonuclease mExoI was used, the editing window was mainly located in the 5' region (C9 and C11) of strand A of the target site; on the contrary, when the 3' exonuclease Trex2 was used, the editing window was shifted to 3'-adjacent region (C11 and C15) of strand A of the OsCKX2 target site, and cytosine residues in strand B were not edited (as shown in FIG. 5A and FIG. 5B). Further, the inventors evaluated the impacts of the preference of nickase used for single strand on a single strand where base editing might occur. FokI-R$_{nickase}$ that preferred to nick strand B was replaced by FokI-L$_{nickase}$ that preferred to nick strand A. As expected, the single strand where base editing occurred was switched from strand A to strand B (FIG. 5A). Meanwhile, as for the editing window, when the 5' exonuclease mExoI was used, the editing window was the 5'-adjacent region (C6 and C8) of strand B of the OsCKX2 target site, correspondingly, when the 3' exonuclease Trex2 was used, the editing window could be shifted to the 3'-adjacent region (C3 and C6) of strand B of the OsCKX2 target site, and the cytosine residues in strand A were not edited (FIG. 5A). It could be seen that the base editor of the present disclosure could use exonucleases with different digestion directions and exert the digestion effect of the corresponding exonuclease, thereby editing the target site selectively.

Rice protoplasts were transformed with different construct combinations to target the OsCKX2 site, and the C>T base editing efficiency and the frequency of indel byproducts were determined by NGS. In FIG. 5A and FIG. 5B, the experimental treatments or construct combinations involved in figures and the schematic diagrams of related vectors were as shown below.

| Experimental treatments or construct combinations involved in figures | Schematic diagrams of related vectors |
| --- | --- |
| CK | None |
| TALE-FokI-R$_{nickase}$ + A3A-UGI + mExoI | FIG. 16B, wherein the corresponding nickase was FokI-R$_{nickase}$, the corresponding deaminase was hAPOBEC3A, and the corresponding exonuclease was mExoI. |
| TALE-FokI-R$_{nickase}$ + A3A-UGI + Trex2 | FIG. 16B, wherein the corresponding nickase was FokI-R$_{nickase}$, the corresponding deaminase was hAPOBEC3A, and the corresponding exonuclease was Trex2. |
| TALE-FokI-L$_{nickase}$ + A3A-UGI + mExoI | FIG. 16B, wherein the corresponding nickase was FokI-L$_{nickase}$, the corresponding deaminase was hAPOBEC3A, and the corresponding exonuclease was mExoI. |
| TALE-FokI-L$_{nickase}$ + A3A-UGI + Trex2 | FIG. 16B, wherein the corresponding nickase was FokI-L$_{nickase}$, the corresponding deaminase was hAPOBEC3A, and the corresponding exonuclease was Trex2. |
| TALEN$_{WT}$ | FIG. 16A |

US 12,612,651 B2

143
144

Example 4: Effects of Cytidine Deaminase Type

The novel base editor of the present disclosure had no dependence on the type of deaminase and was compatible with deaminases of different types. In order to exclude that the base editing ability of the novel base editor was deaminase hAPOBEC3A (A3A)-dependent, another cytidine deaminase rAPOBEC1 (APOBEC1) was tested by the inventor in this example. As indicated by NGS analysis results, in the presence of both an exonuclease, for example, mExoI (as shown in FIG. 6A) and Trex2 (as shown in FIG. 6B), targeted base editing was also achieved with high product purity after replacing hAPOBEC3A with rAPOBEC1 at the OsBADH2 site, indicating deaminases of different types were all suitable for the base editor of the present disclosure.

Figure 6A:
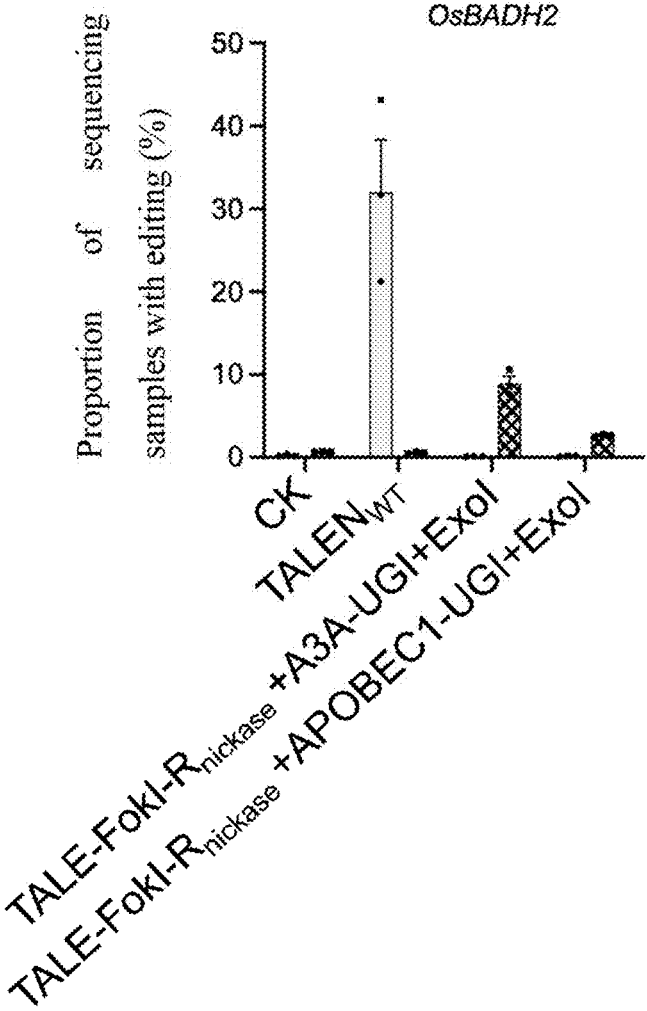
FIG. 6A and FIG. 6B show the base editing efficiency and the frequency of indel byproducts introduced into a target sequence (OsBADH2 in rice protoplast) by the base editor comprising a combination of a cytidine deaminase and an exonuclease of the present disclosure as determined by high-throughput sequencing, wherein the exonuclease is a 5' exonuclease or a 3' exonuclease.

In FIG. 6A, rice protoplasts were transformed with different construct combinations to target the OsBADH2 site, and the C>T base editing efficiency and the frequency of indel byproducts were determined by NGS. The experimental treatments or construct combinations involved in figures and the schematic diagrams of related vectors were as shown below.

| Experimental treatments or construct combinations involved in figures | Schematic diagrams of related vectors |
|---|---|
| CK | None |
| TALE-FokI-$R_{nickase}$ + A3A-UGI + mExoI | FIG. 16B, wherein the corresponding nickase was FokI-$R_{nickase}$, the corresponding deaminase was hAPOBEC3A, and the corresponding exonuclease was mExoI. |
| TALE-FokI-$R_{nickase}$ + APOBEC1-UGI + mExoI | FIG. 16B, wherein the corresponding nickase was FokI-$R_{nickase}$, the corresponding deaminase was rAPOBEC1, and the corresponding exonuclease was mExoI. |
| TALEN$_{WT}$ | FIG. 16A |

Figure 6B:
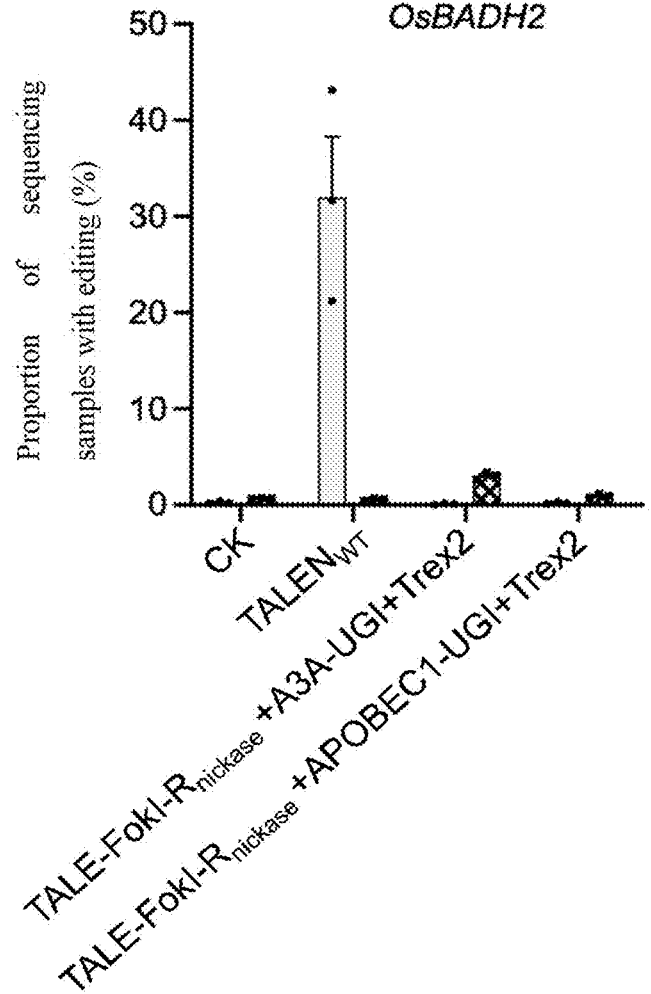

In FIG. 6B, rice protoplasts were transformed with different construct combinations to target the OsDEP1 site, and the C>T base editing efficiency and the frequency of indel byproducts were determined by NGS. The experimental treatments or construct combinations involved in figures and the schematic diagrams of related vectors were as shown below.

| Experimental treatments or construct combinations involved in figures | Schematic diagrams of related vectors |
|---|---|
| CK | None |
| TALE-FokI-$R_{nickase}$ + A3A-UGI + Trex2 | FIG. 16B, wherein the corresponding nickase was FokI-$R_{nickase}$, the corresponding deaminase was hAPOBEC3A, and the corresponding exonuclease was Trex2. |
| TALE-FokI-$R_{nickase}$ + APOBEC1-UGI + Trex2 | FIG. 16B, wherein the corresponding nickase was FokI-$R_{nickase}$, the corresponding deaminase was rAPOBEC1, and the corresponding exonuclease was Trex2. |
| TALEN$_{WT}$ | FIG. 16A |

Figure 7A:
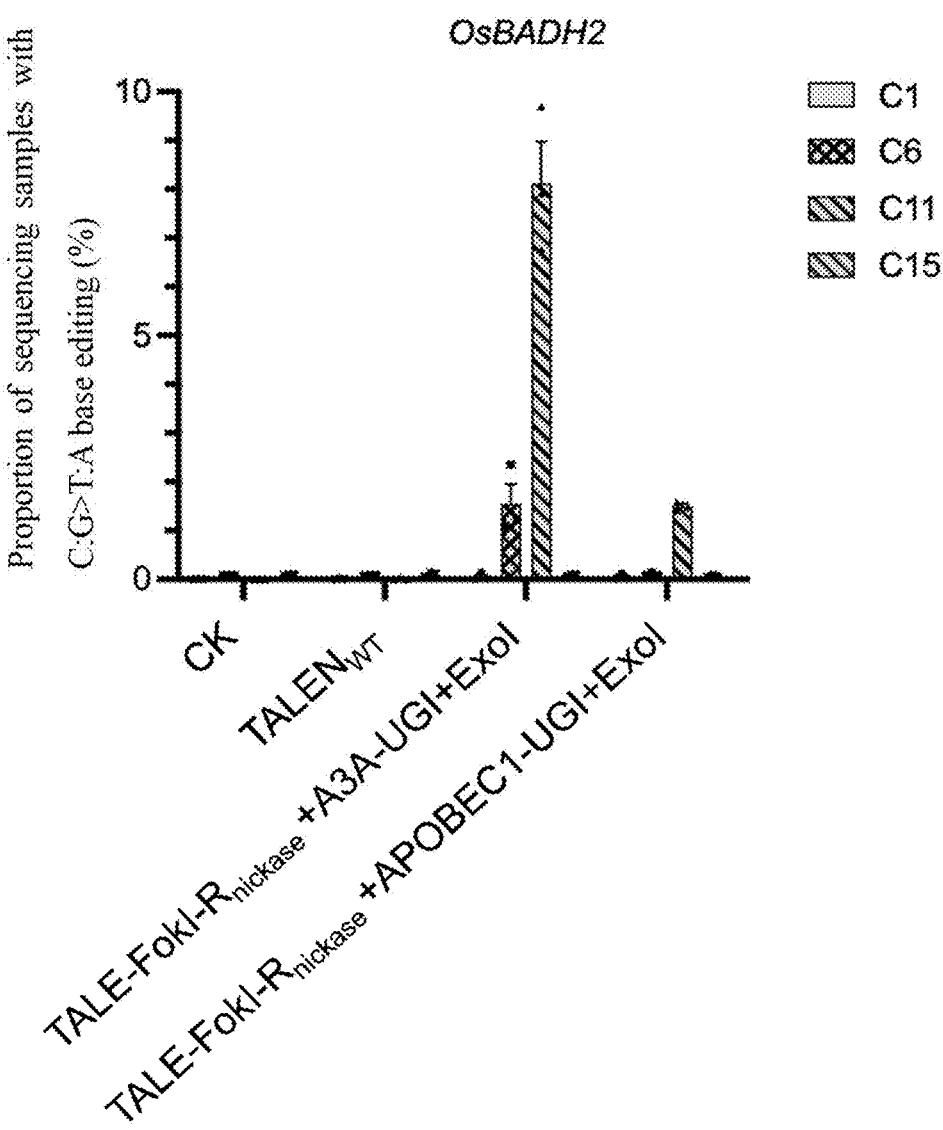
FIG. 7A and FIG. 7B show the base editing efficiency introduced into a target sequence (OsBADH2 in rice protoplast) by the base editor comprising a combination of a different cytidine deaminase and an exonuclease of the present disclosure as determined by high-throughput sequencing, and show the editing window.
Figure 7B:
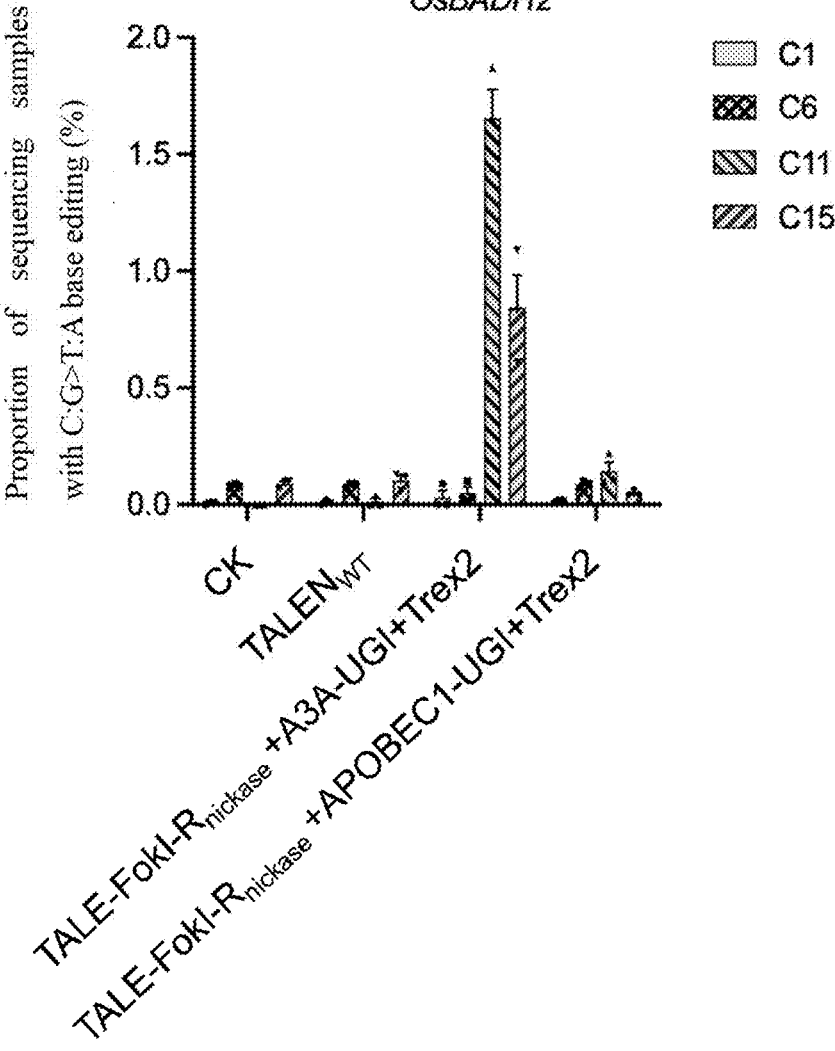

When the editing windows of these base editors were analyzed, cytosine residues located near the 5' region of the target site in the complementary strand of the nicked single strand were efficiently edited in the groups containing mExoI (as shown in FIG. 7A), while the cytosine residues located near the 3' region of the target site in the complementary chain were efficiently edited in the groups containing TREX2 (as shown in FIG. 7B), which were consistent with the results in the above-mentioned Example. These results indicated that the base editing method and the base editor disclosed in the present disclosure were compatible with different cytidine deaminases.

In FIG. 7A, the base editing window of the base editor was analyzed according to NGS results. The experimental treatments or construct combinations involved in figures and the schematic diagrams of related vectors were as shown below.

| Experimental treatments or construct combinations involved in figures | Schematic diagrams of related vectors |
|---|---|
| CK | None |
| TALE-FokI-R$_{nickase}$ + A3A-UGI + mExoI | FIG. 16B, wherein the corresponding nickase was FokI-R$_{nickase}$, the corresponding deaminase was hAPOBEC3A, and the corresponding exonuclease was mExoI. |
| TALE-FokI-R$_{nickase}$ + APOBEC1-UGI + mExoI | FIG. 16B, wherein the corresponding nickase was FokI-R$_{nickase}$, the corresponding deaminase was rAPOBEC1, and the corresponding exonuclease was mExoI. |
| TALEN$_{WT}$ | FIG. 16A |

In FIG. 7B, the base editing window of the base editor was analyzed according to NGS results. The experimental treatments or construct combinations involved in figures and the schematic diagrams of related vectors were as shown below.

| Experimental treatments or construct combinations involved in figures | Schematic diagrams of related vectors |
|---|---|
| CK | None |
| TALE-FokI-R$_{nickase}$ + A3A-UGI + Trex2 | FIG. 16B, wherein the corresponding nickase was FokI-R$_{nickase}$, the corresponding deaminase was hAPOBEC3A, and the corresponding exonuclease was Trex2. |
| TALE-FokI-R$_{nickase}$ + APOBEC1-UGI + Trex2 | FIG. 16B, wherein the corresponding nickase was FokI-R$_{nickase}$, the corresponding deaminase was Trex2, and the corresponding exonuclease was Trex2. |
| TALEN$_{WT}$ | FIG. 16A |

Example 5: Base Editor Comprising Adenosine Deaminase

Figure 8:
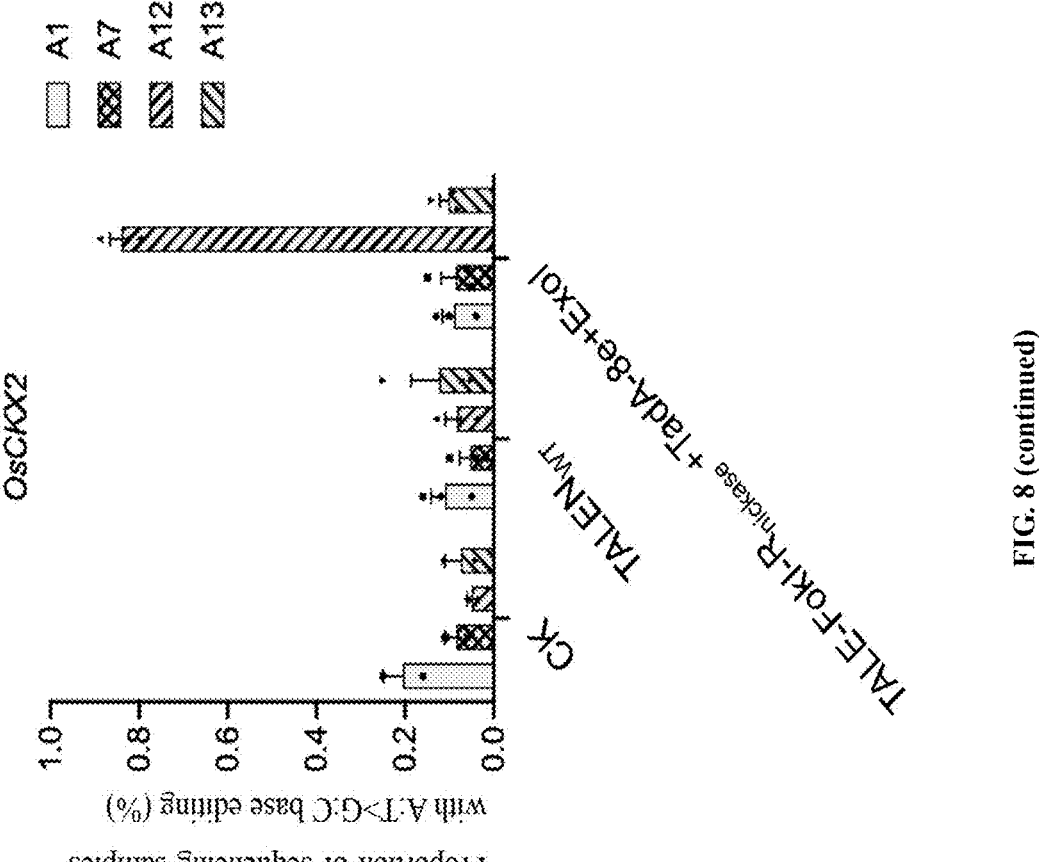
FIG. 8 shows the base editing efficiency introduced into a target sequence (OsCKX2 in rice protoplast) by the base editor comprising an adenosine deaminase of the present disclosure, as determined by high-throughput sequencing.

In order to expand the range of target sequences that could be edited by the base editor of the present disclosure, in this Example, an adenosine deaminase TadA-8e, which used deoxyadenosine (A) in single-stranded DNA as a substrate, was used as the deaminase to target A1, A7, A12 and A13 of the OsCKX2 site (as shown in FIG. 8). In this Example, UGI was not a necessary component of the base editor to be tested, since it was not essential for adenine base editing. The adenine base editing window of the base editor was analyzed according to NGS results. NGS analysis indicated that targeted A-to-G conversion occurred at the target site efficiently (FIG. 8), indicating that the base editor of the present disclosure was compatible with an adenosine deaminase for adenine base editing. Taken together, it could be seen from Examples 4 and 5 that the base editing method and the base editor disclosed in the present disclosure were compatible with different deaminases and were capable of exerting their corresponding editing effects.

In FIG. 8, the experimental treatments or construct combinations involved in figures and the schematic diagrams of related vectors were as shown below.

| Experimental treatments or construct combinations involved in figures | Schematic diagrams of related vectors |
|---|---|
| CK | None |
| TALE-FokI-R$_{nickase}$ + TadA-8e + mExoI | FIG. 16B, wherein the corresponding nickase was FokI-R$_{nickase}$, the corresponding deaminase was TadA-8e, the corresponding exonuclease was mExoI, and UGI was absent. |
| TALEN$_{WT}$ | FIG. 16A |

Figure 9:
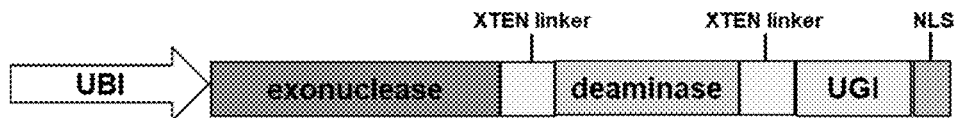
FIG. 9 is a schematic diagram of a base editor of the present disclosure, comprising a fusion protein of an exonuclease, a deaminase, a uracil DNA glycosylase inhibitor and a nuclear localization signal (NLS) separated by an XTEN linker peptide or a 48-amino acid linker peptide.
Figure 9:
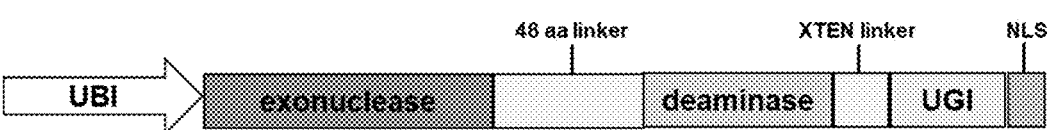

Example 6: Base Editors Comprising Fusion Proteins of Base Editing Components After the function and effect of the base editor of the present disclosure were demonstrated by the above-mentioned Examples, whether the transformation efficiency (and thus the editing efficiency) could be improved by fusing modular elements into a single vector were verified in this Example. The structures of two examples of such base editor comprising fused elements were as shown in FIG. 9, wherein the exonuclease was fused to the amino terminal of the deaminase-UGI fusion protein via an XTEN linker peptide or a 48-amino acid linker peptide (48aa) so as to target the OsDEP1 gene, that is, the deaminase was fused to the exonuclease.

Figure 10A:
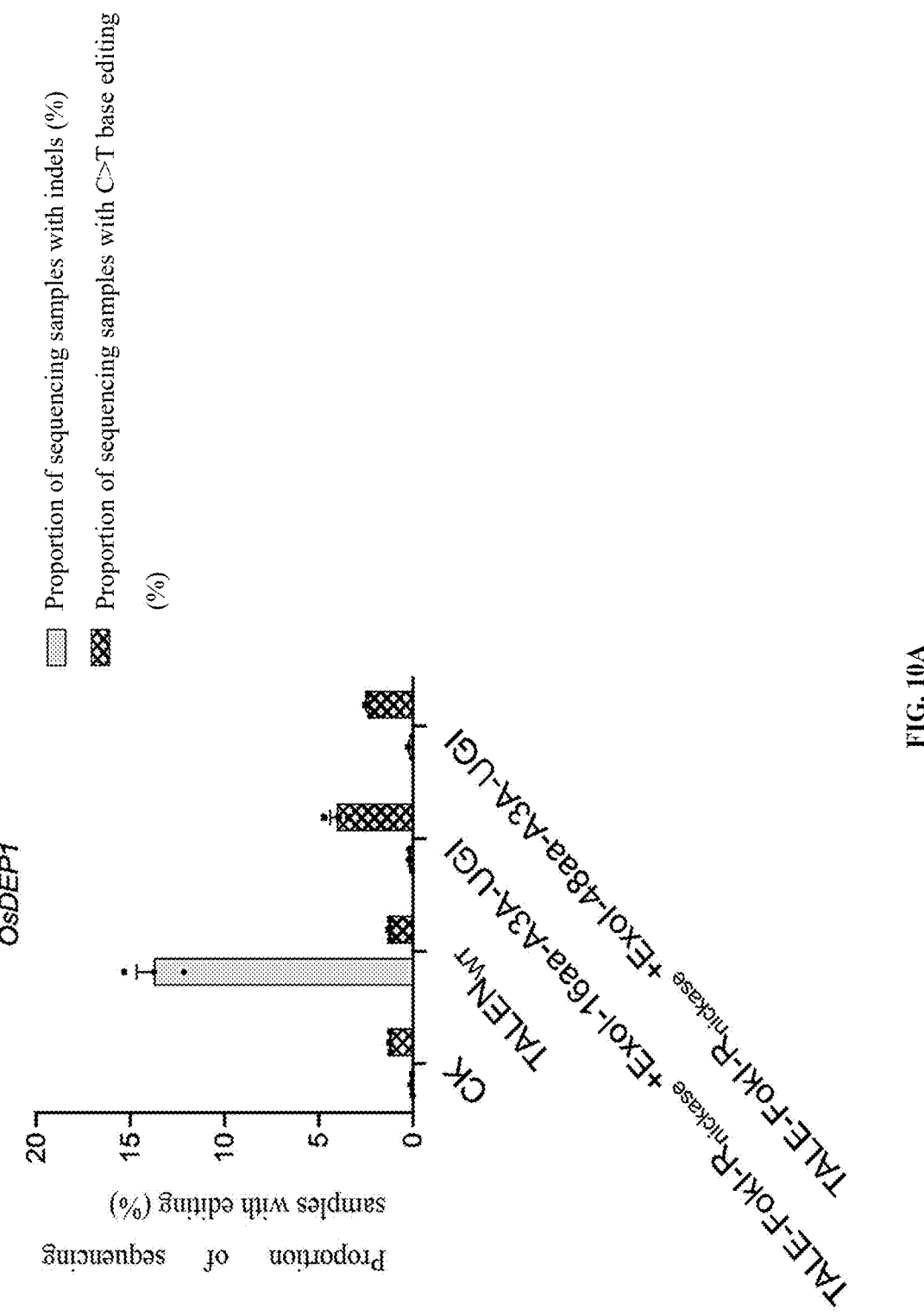
FIG. 10A and FIG. 10B show the base editing efficiency introduced into a target sequence (OsDEP1 in rice protoplast) by the base editors expressed by the different constructs of the present disclosure as determined by high-throughput sequencing (FIG. 10A) and show the editing windows of different base editors (FIG. 10B).

Rice protoplasts were transformed with different construct combinations to target the OsDEP1 site, and the C>T base editing efficiency and the frequency of indel byproducts were determined by NGS. The NGS analysis indicated that fusing an exonuclease to a deaminase could achieve targeted base editing while the efficiency achieved by such vector structure was similar to the efficiency achieved in a case where the exonuclease and the deaminase were expressed separately (as shown in FIG. 10A). When this base editor was used, C1 and C9 were preferred in the editing window (as shown in FIG. 10B), which was consistent with the catalytical direction of mExoI exonuclease.

Figure 10B:
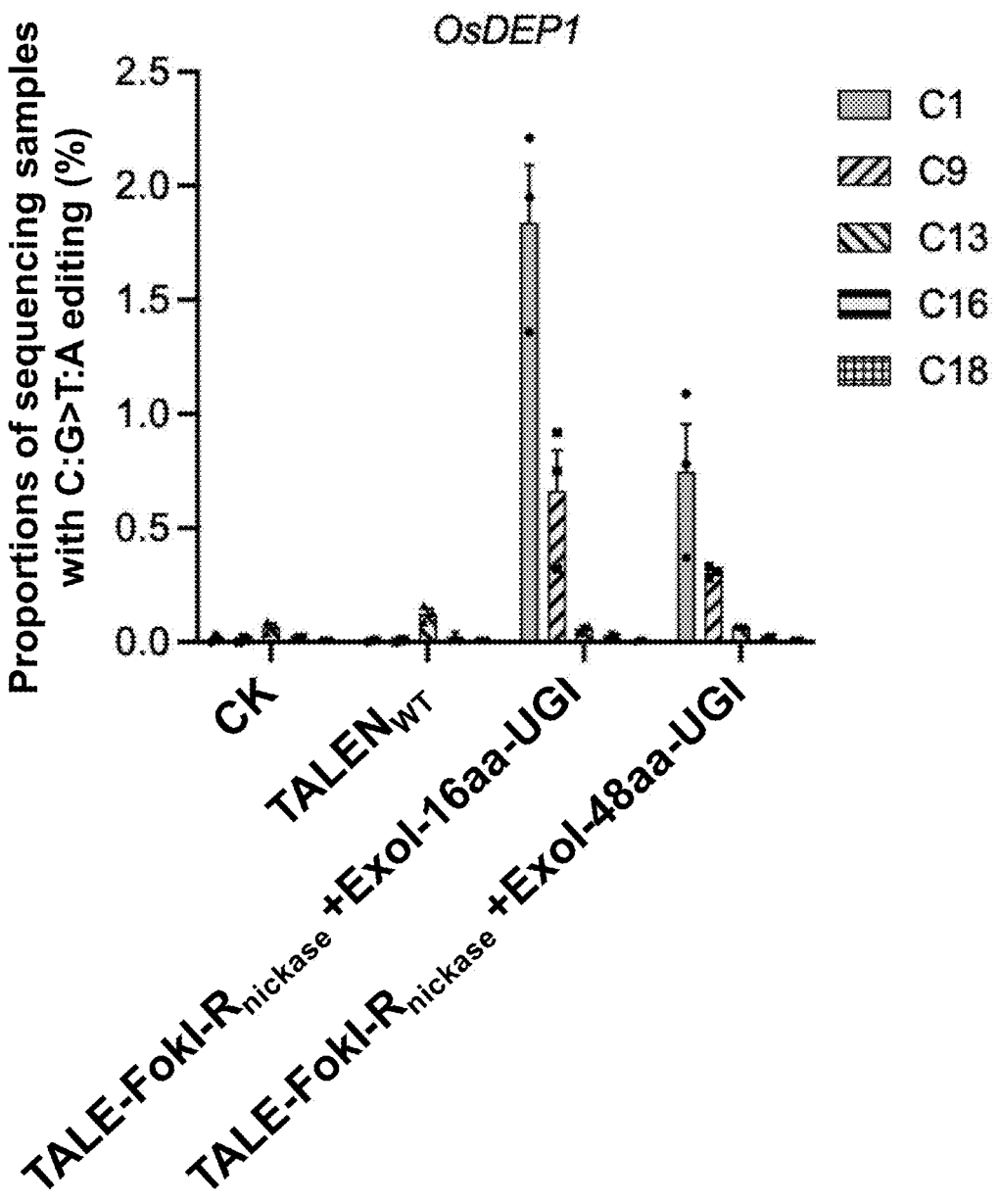

In FIG. 10A and FIG. 10B, the experimental treatments or construct combinations involved in figures and the schematic diagrams of related vectors were as shown below.

| Experimental treatments or construct combinations involved in figures | Schematic diagrams of related vectors |
| --- | --- |
| CK | None |
| TALE-FokI-R$_{nickase}$ + mExoI-16aa-A3A-UGI | FIG. 16B, wherein the corresponding nickase was FokI-R$_{nickase}$; FIG. 9, wherein the corresponding exonuclease was mExoI, the corresponding deaminase was hAPOBEC3A, and there was a 16-amino acid linker peptide (16aa) therebetween. |
| TALE-FokI-R$_{nickase}$ + mExoI-48aa-A3A-UGI | FIG. 16B, wherein the corresponding nickase was FokI-R$_{nickase}$; FIG. 9, wherein the corresponding exonuclease was mExoI, the corresponding deaminase was hAPOBEC3A, and there was a 48-amino acid linker peptide therebetween. |
| TALEN$_{WT}$ | FIG. 16A |

In addition, the inventors also tested other fusion protein structures. The structures of the above-mentioned base editors were shown in FIG. 11A and FIG. 11B, wherein the deaminase (hAPOBEC3A or rAPOBEC1) was fused to the amino terminal of TALE-L (FIG. 11A) or TALE-R (FIG. 11B) via a 48-amino acid linker peptide, UGI and the exonuclease were expressed by separate vectors, that is, the deaminase, the TALE protein and the nickase were fused.

Figure 12A:
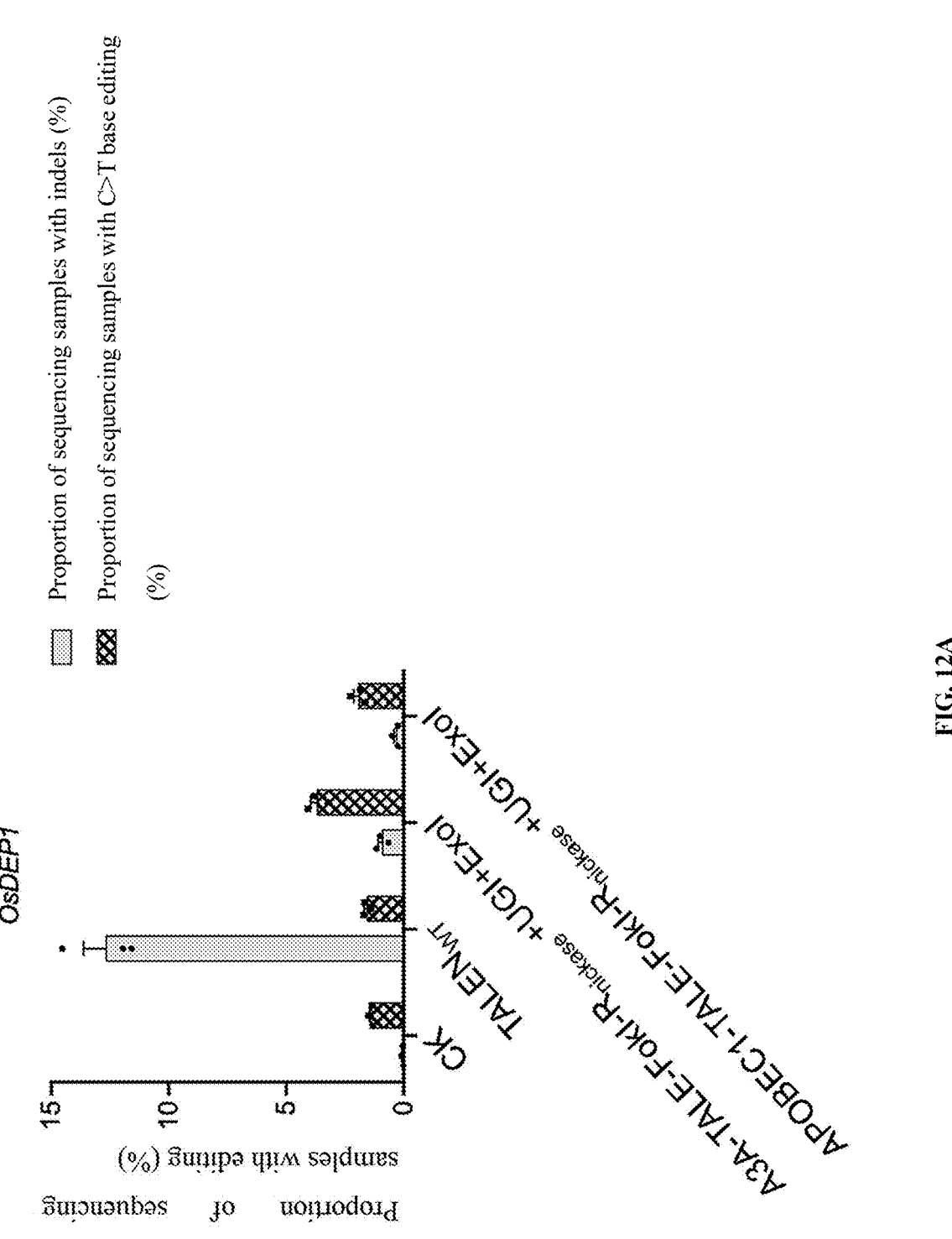
FIG. 12A and FIG. 12B are bar graphs showing the base editing rates and the indel rates introduced into target sequences (OsDEP1 in rice protoplast, FIG. 12A; OsCKX2 in rice protoplast, FIG. 12B) by the base editor (fusion protein) of the present disclosure. The results of the fusion protein of the deaminase-TALE-FokI-R$_{nickase}$ protein are as shown in FIG. 12A, and the results of the fusion protein of the deaminase-TALE-FokI-L$_{nickase}$ protein are as shown in FIG. 12B.

As for the deaminase-TALE-FokI-R$_{nickase}$, OsDEP1 was selected for characterization as the target gene to be tested (as shown in FIG. 12A), while for the deaminase-TALE-FokI-L$_{nickase}$, OsCKX2 was selected for characterization as the target gene to be tested (as shown in FIG. 123). The NGS analysis showed that both deaminase-TALE-FokI-L/R$_{nickase}$ achieved C-to-T conversion at the target site, indicating that deaminase could form a fusion body with the TALE protein and the nickase without interfering with the exertion of their respective functions. In addition, the experimental results also further indicated that base editing could occur in a case where the deaminase hAPOBEC3A was used and in a case where the deaminase rAPOBEC1 was used (as shown in FIG. 12A and FIG. 12).

In FIG. 12A, the experimental treatments or construct combinations involved in figures and the schematic diagrams of related vectors were as shown below.

Figure 11A:
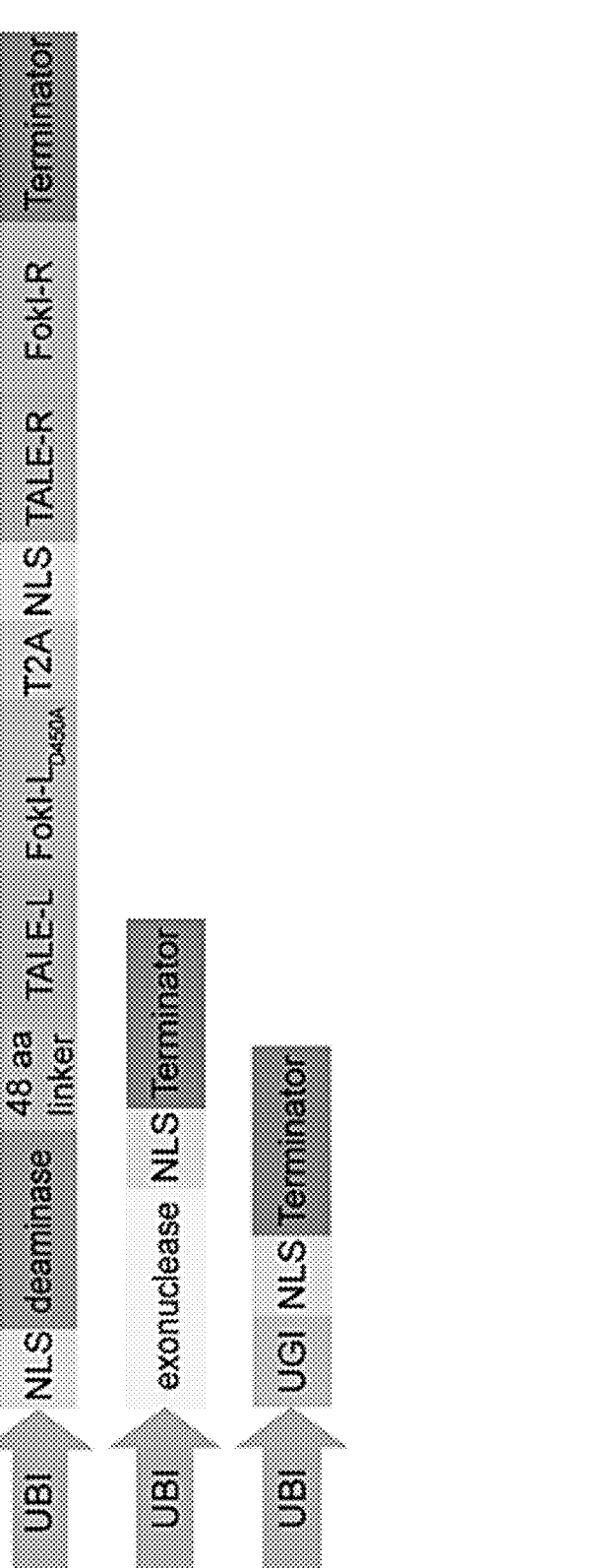
FIG. 11A and FIG. 11B are schematic diagrams of the base editors comprising a deaminase-TALE fusion protein as a vector of the present disclosure. In each embodiment, a fusion protein of an NLS-exonuclease and an NLS-uracil glycosylase inhibitor (UGI) are provided individually in separate vectors.
Figure 11B:
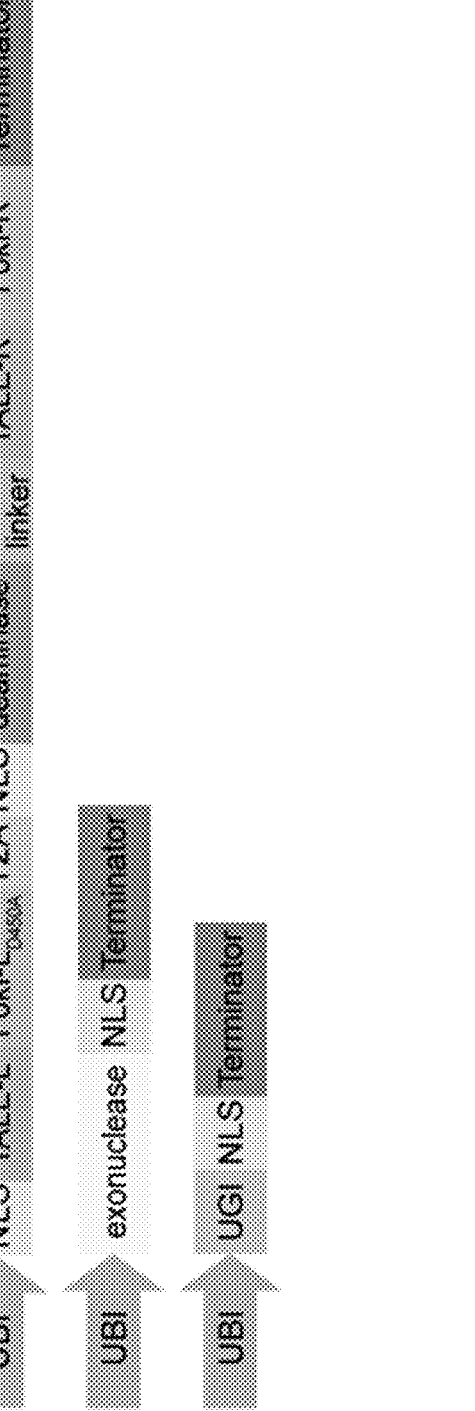

| Experimental treatments or construct combinations involved in figures | Schematic diagrams of related vectors |
| --- | --- |
| CK | None |
| A3A-TALE-FokI-R$_{nickase}$ + UGI + mExoI | FIG. 16C or FIG. 11A, wherein the corresponding nickase was FokI-R$_{nickase}$, and the corresponding exonuclease was mExoI, the corresponding deaminase was hAPOBEC3A. |
| APOBEC1-TALE-FokI-R$_{nickase}$ + UGI + mExoI | FIG. 16C or FIG. 11A, wherein the corresponding nickase was FokI-R$_{nickase}$, and the corresponding exonuclease was mExoI, the corresponding deaminase was APOBEC1. |
| TALEN$_{WT}$ | FIG. 16A |

Figure 12B:
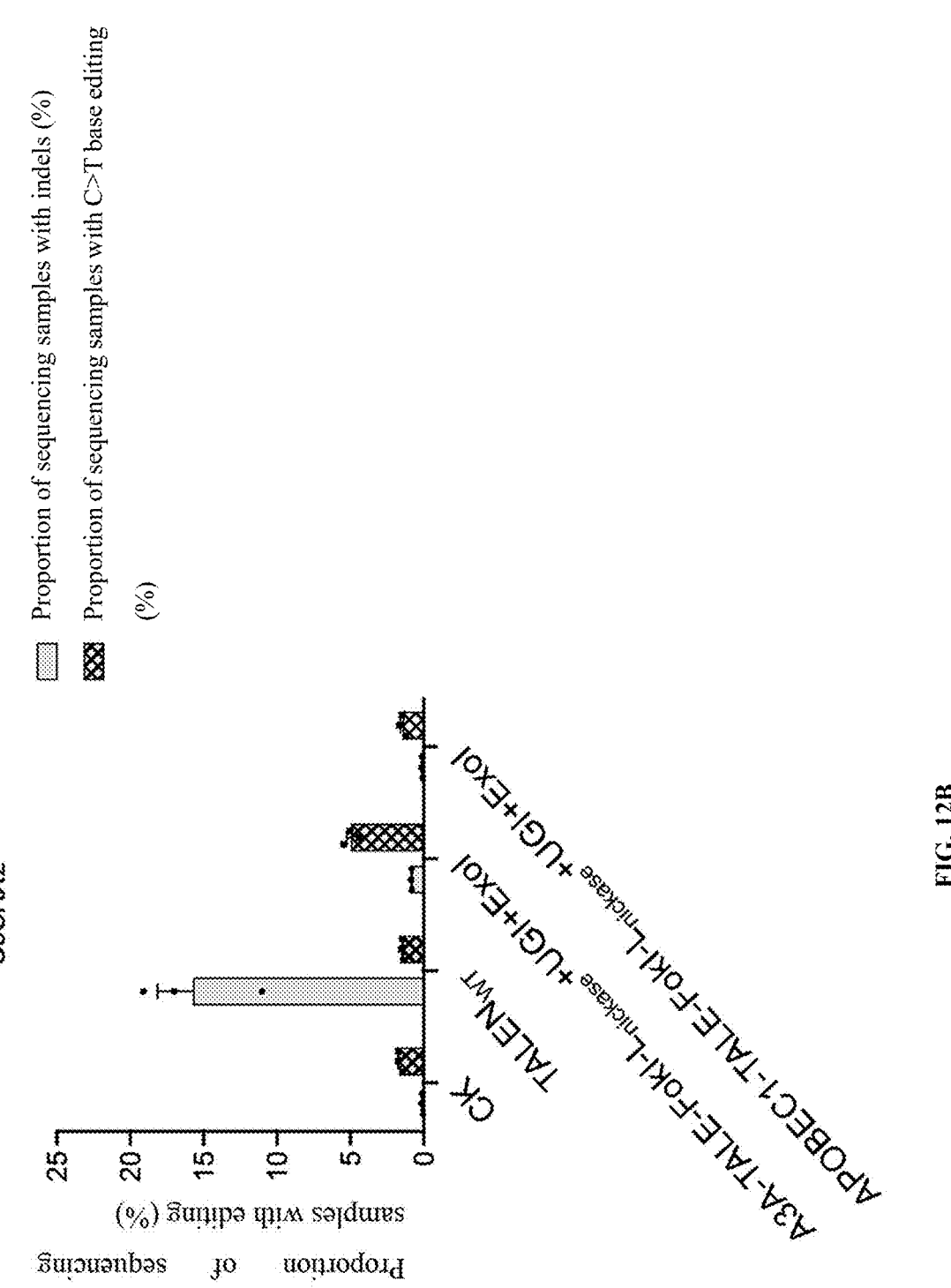

In FIG. 12B, the experimental treatments or construct combinations involved in figures and the schematic diagrams of related vectors were as shown below.

| Experimental treatments or construct combinations involved in figures | Schematic diagrams of related vectors |
|---|---|
| CK | None |
| A3A-TALE-FokI-L$_{nickase}$ + UGI + mExoI | FIG. 16C, wherein the corresponding nickase was FokI-L$_{nickase}$, and the corresponding exonuclease was mExoI, the corresponding deaminase was hAPOBEC3A. |
| APOBEC1-TALE-FokI-L$_{nickase}$ + UGI + mExoI | FIG. 16C, wherein the corresponding nickase was FokI-L$_{nickase}$, and the corresponding exonuclease was mExoI, the corresponding deaminase was rAPOBEC1. |
| TALEN$_{WT}$ | FIG. 16A |

Figure 13A:
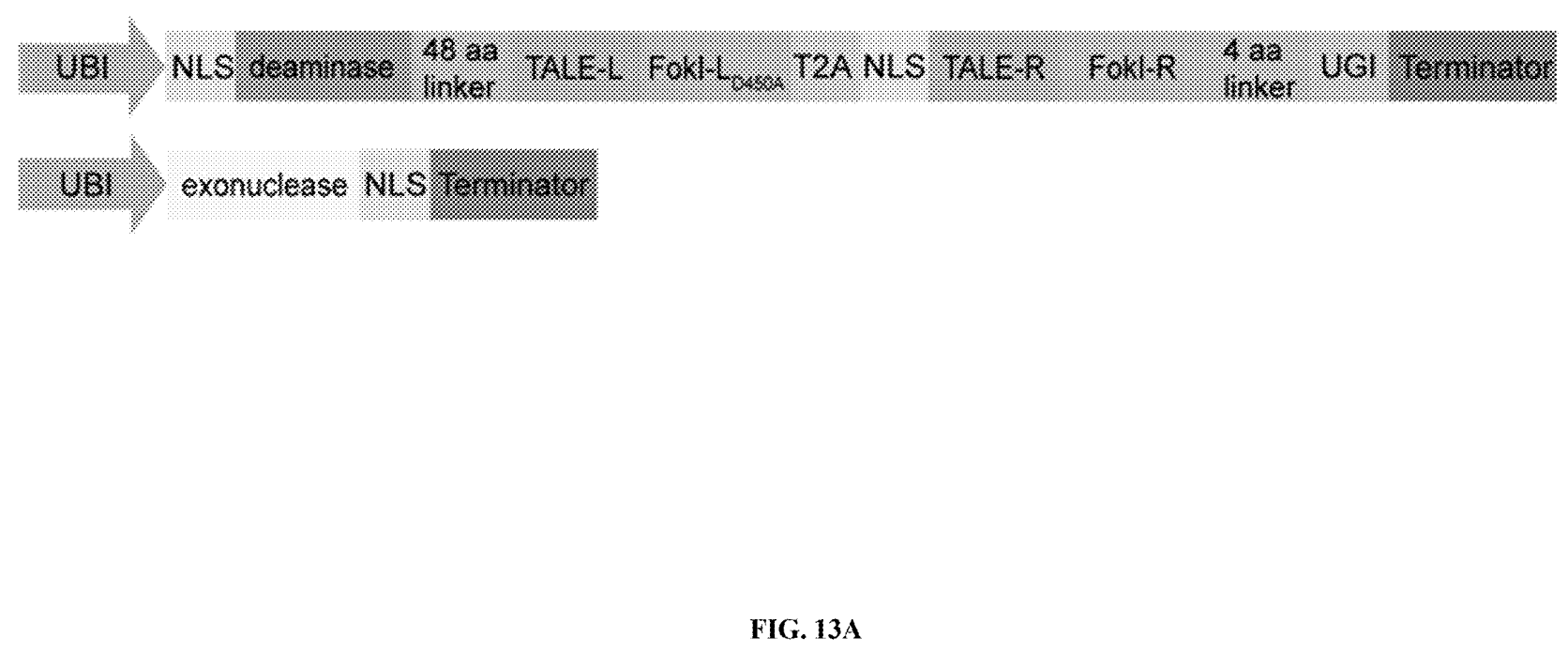
Figure 13B:
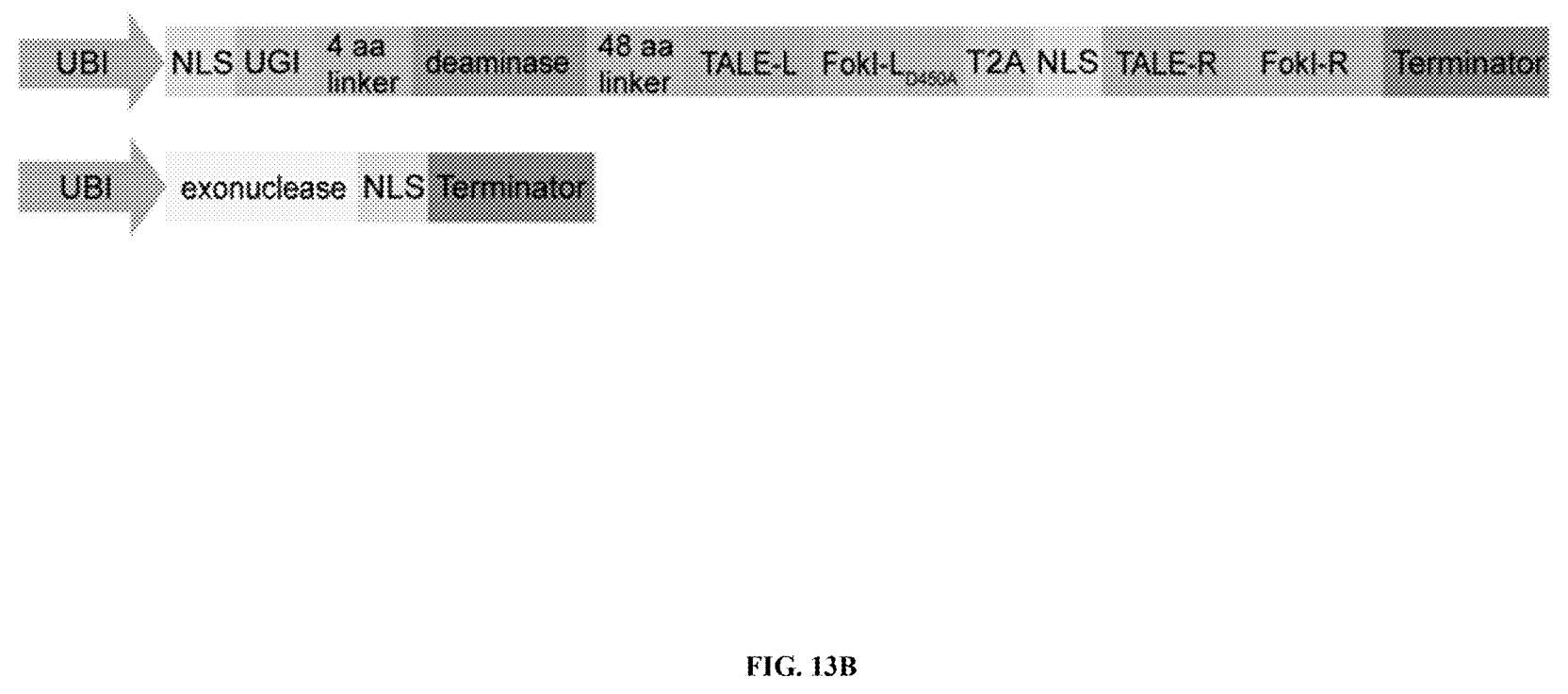
Figure 14:
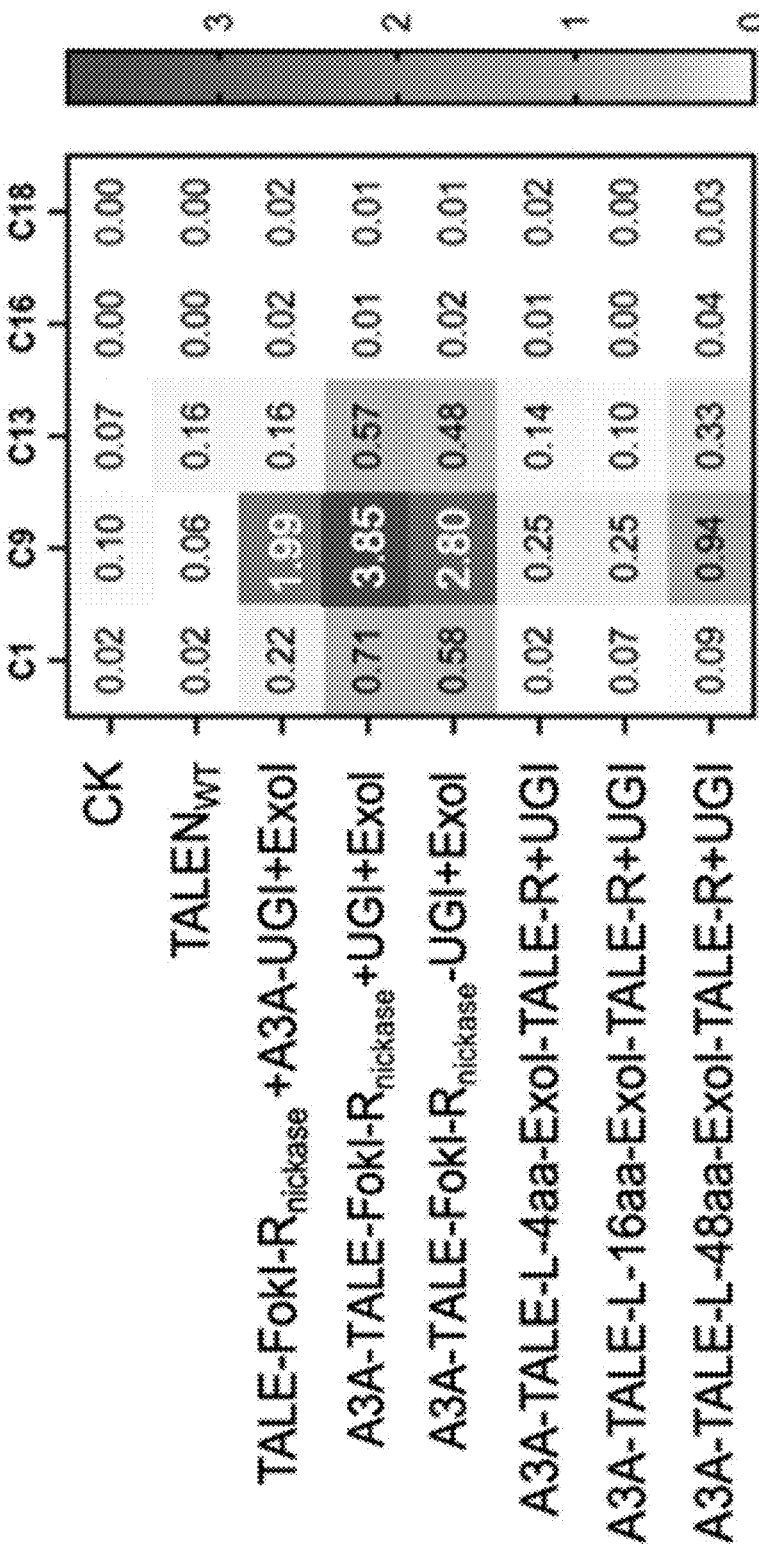
FIG. 14 shows the base editing efficiency in a target sequence (OsDEP1 in rice protoplast) resulted from using the fusion proteins as shown in FIG. 13A and FIG. 13B or expressing each component individually as the base editor of the present disclosure.

In order to investigate the influence of the fusion of UGI or exonuclease, in the deaminase-TALE-FokI-R$_{nickase}$ construct having the same target specificity as that of the present disclosure, the base editor had a UGI linked to the carboxy terminal of FokI-L$_{D450A}$ (as shown in FIG. 13A) or the amino terminal of the deaminase (as shown in FIG. 13B) via a 48-amino acid linker peptide or a 4-amino acid linker peptide. The NGS analysis indicated that the effect achieved by linking UGI to the fusion protein was similar to those of the embodiments in which UGI was separately expressed (FIG. 14). In addition, in the deaminase-TALE-FokI-R$_{nickase}$ construct, the embodiments in which an exonuclease was fused to the carboxy terminal of FokI-R via a 4-amino acid linker peptide, a 16-amino acid linker peptide or a 48-amino acid linker peptide also achieved similar editing efficiency (FIG. 14). As a result, both expressing UGI/exonuclease separately and fusing UGI/exonuclease to the vector for co-expression were technical solutions that could be adopted in the present disclosure.

In FIG. 14, rice protoplasts were transformed with different construct combinations to target the OsDEP1 site, and the DNA strand and the editing window where base editing occurred were analyzed via the results of high-throughput sequencing. The experimental treatments or construct combinations involved in figures and the schematic diagrams of related vectors were as shown below.

| Experimental treatments or construct combinations involved in figures | Schematic diagrams of related vectors or the elements used |
|---|---|
| CK | None |
| TALEN$_{WT}$ | FIG. 16A |
| TALE-FokI-R$_{nickase}$ + A3A-UGI + mExoI | FIG. 16B, wherein the corresponding nickase was FokI-R$_{nickase}$, the corresponding deaminase was hAPOBEC3A, and the corresponding exonuclease was mExoI. |
| A3A-TALE-FokI-R$_{nickase}$ + UGI + mExoI | FIG. 16C, wherein the corresponding nickase was FokI-R$_{nickase}$, the corresponding deaminase was hAPOBEC3A, and the corresponding exonuclease was mExoI. |
| A3A-TALE-FokI-R$_{nickase}$⁻ UGI + mExoI | FIG. 16D, wherein the corresponding nickase was FokI-R$_{nickase}$, the corresponding deaminase was hAPOBEC3A fused to the N-terminal of TALE-L, and the corresponding exonuclease was mExoI. |
| A3A-TALE-L-mExoI-4aa-TALE-R + UGI | the corresponding nickase was FokI-R$_{nickase}$, the corresponding deaminase was hAPOBEC3A fused to the N-terminal of TALE-L, the corresponding exonuclease was ExoI fused to the N-terminal of TALE-R, and there was a 4-amino acid linker peptide therebetween. |
| A3A-TALE-L-mExoI-16aa-TALE-R + UGI | the corresponding nickase was FokI-R$_{nickase}$, the corresponding deaminase was hAPOBEC3A fused to the N-terminal of TALE-L, the corresponding exonuclease was mExoI fused to the N-terminal of TALE-R, and there was a 16-amino acid linker peptide therebetween. |
| A3A-TALE-L-mExoI-48aa-TALE-R + UGI | the corresponding nickase was FokI-R$_{nickase}$, the corresponding deaminase was hAPOBEC3A fused to the N-terminal of TALE-L, the corresponding exonuclease was mExoI fused to the N-terminal of TALE-R, and there was a 48-amino acid linker peptide therebetween. |

Taken the above results together, each modular element of the base editor of the present disclosure could be expressed individually, or each element could form one or more fusion proteins with each other.

Example 7: Base Editing in Plant Nuclear Genome

In Examples above, the functions and characteristics of the base editor of the present disclosure were verified, that is, the composition of modular elements comprising a deaminase, an exonuclease, a nickase, a DNA-binding protein TALE could achieve efficient and precise DNA editing. For ease of description, the above-mentioned base editors were named DENT (Deaminase-Exonuclease-Nickase-TALE), and were respectively named CyDENT (Cytidine Deaminase-Exonuclease-Nickase-TALE) and AdDENT (Adenosine deaminase-Exonuclease-Nickase-TALE) according to the type of deaminase. In this Example, the applicable environments and scenarios of the base editor of the present disclosure were analyzed.

Figure 18:
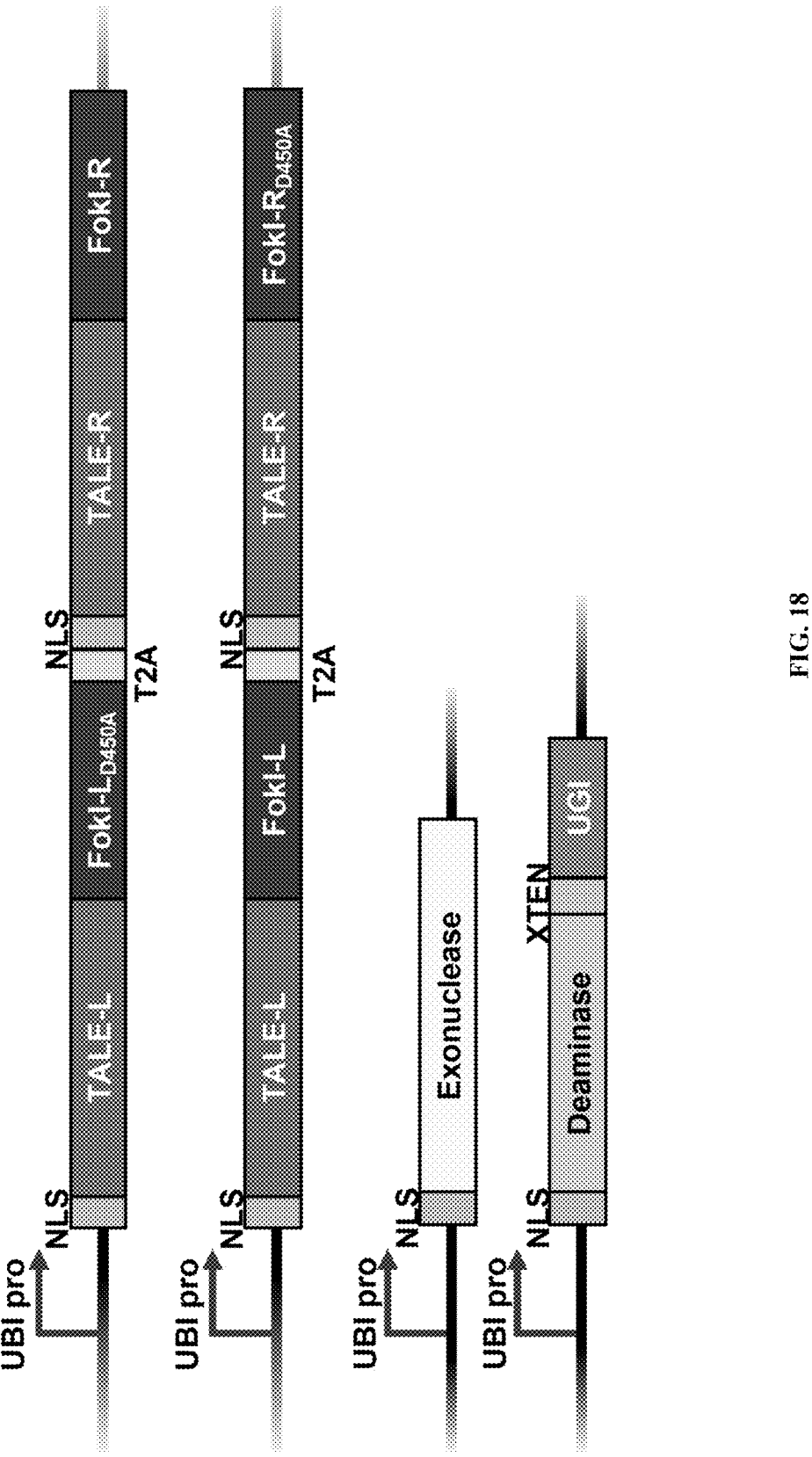
FIG. 18 is a schematic structural diagram of CyDENT for nuclear genome editing.
Figure 19A:
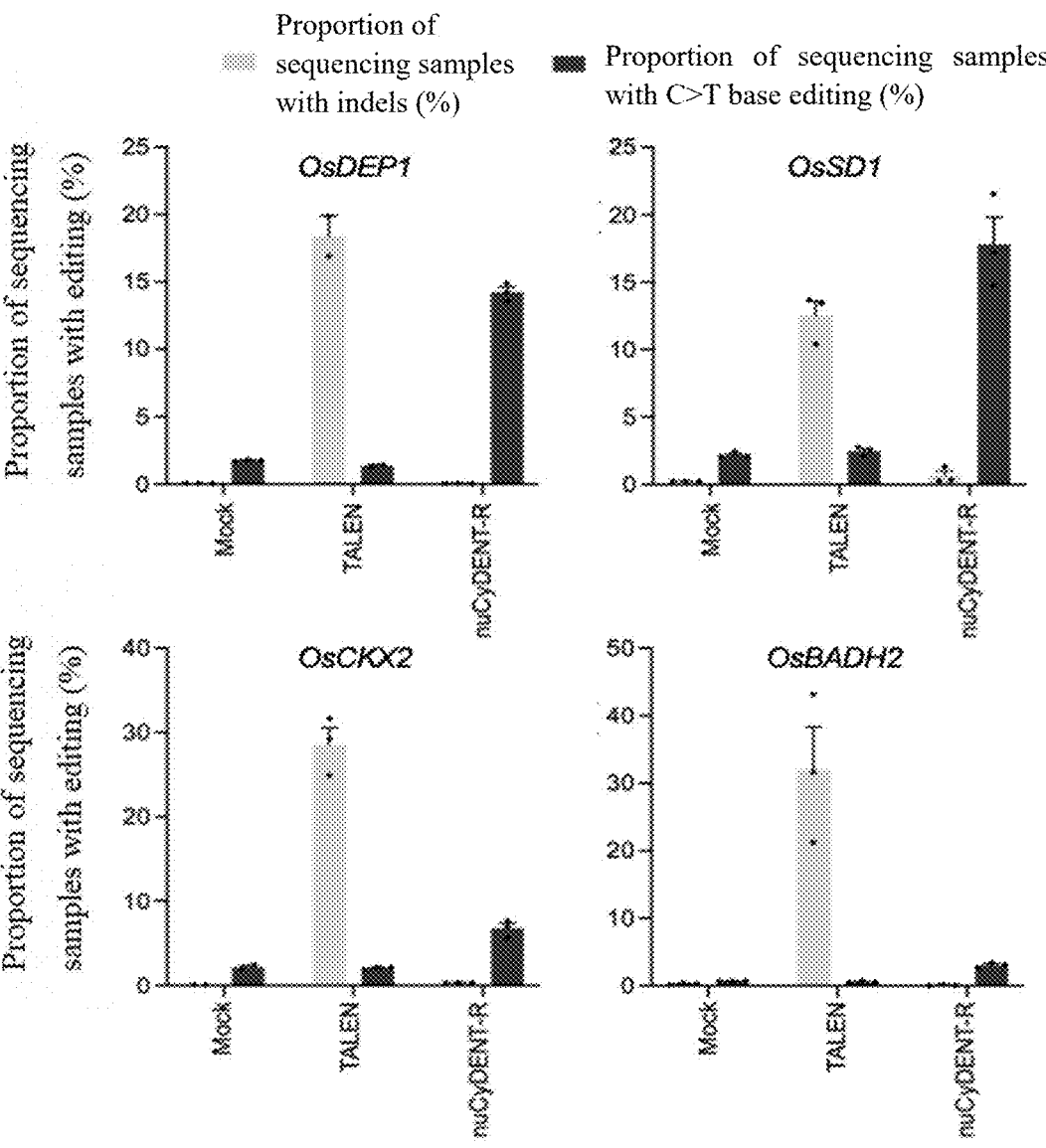
FIG. 19A shows the C-to-T conversion frequency and indel frequency achieved by nuCyDENT-R and TALEN at the OsDEP1, OsSD1, OsCKX2 and OsBADH2 sites in rice protoplast.
Figure 19B:
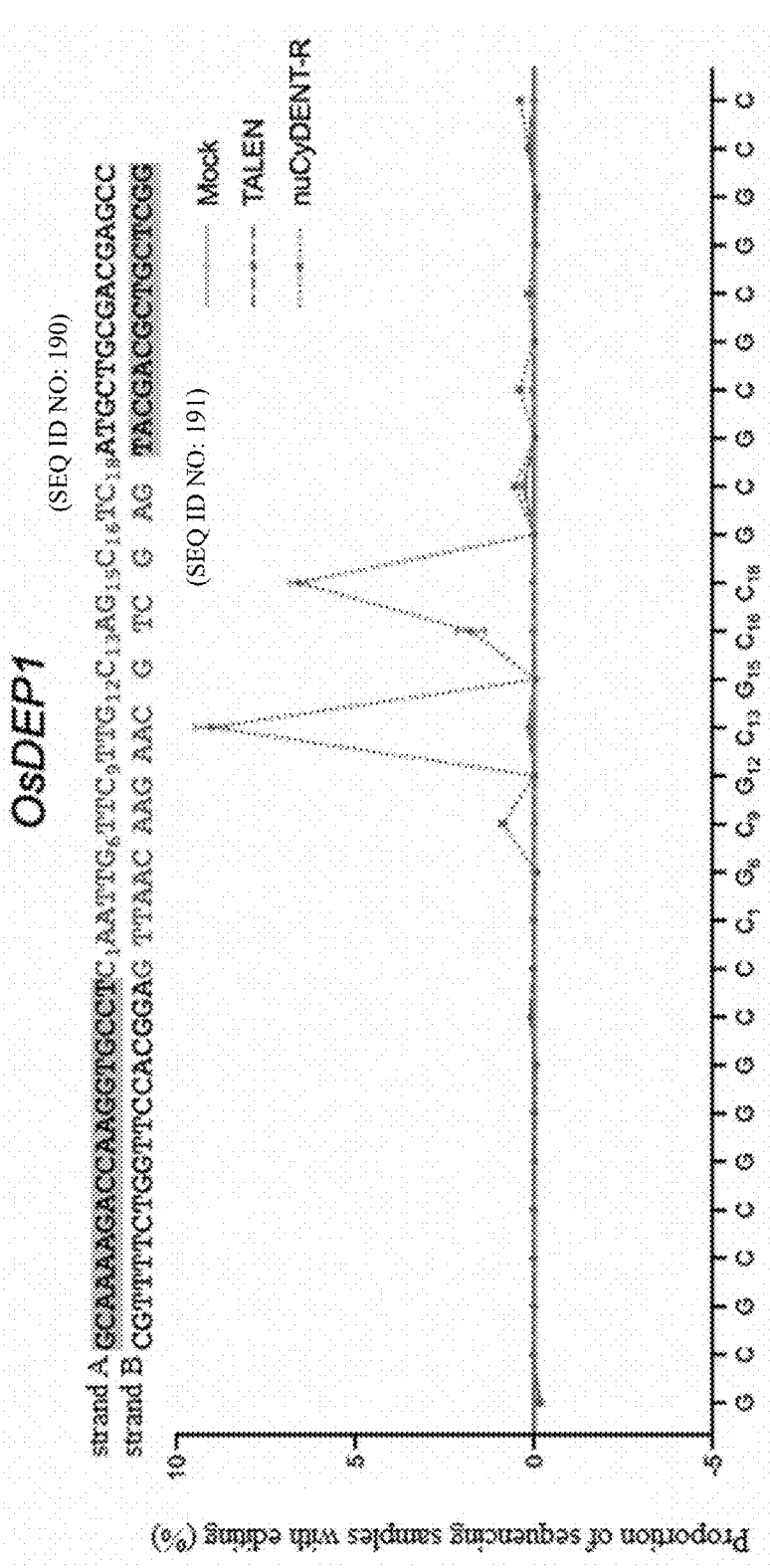
FIG. 19B shows the base editing windows of CyDENT at the OsDEP1, OsSD1, OsCKX2 and OsBADH2 sites in rice protoplast. In the figure, the gray regions represent the TALE binding sites, and the middle region is the spacer region.
Figure 19B:
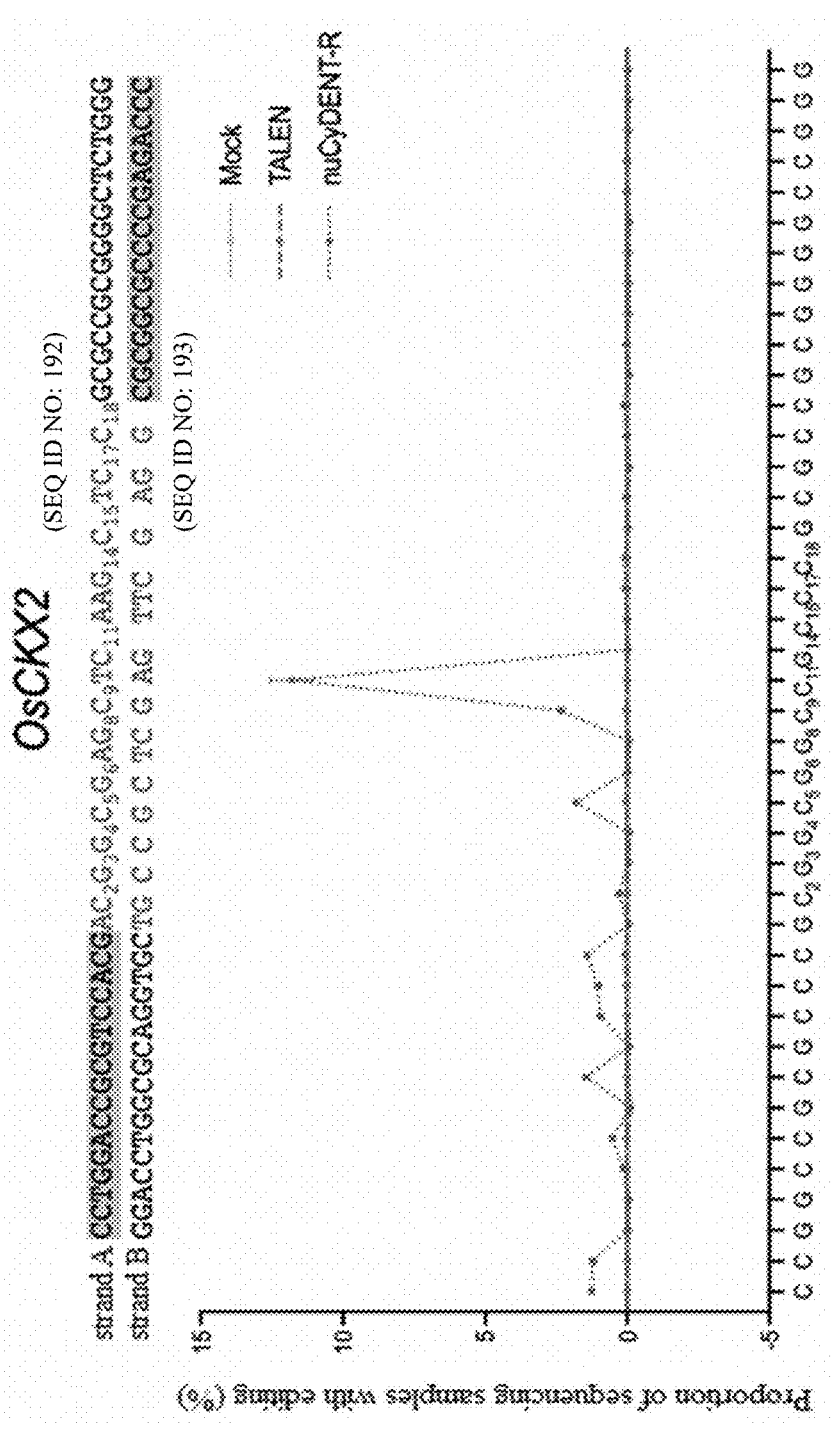
Figure 19B:
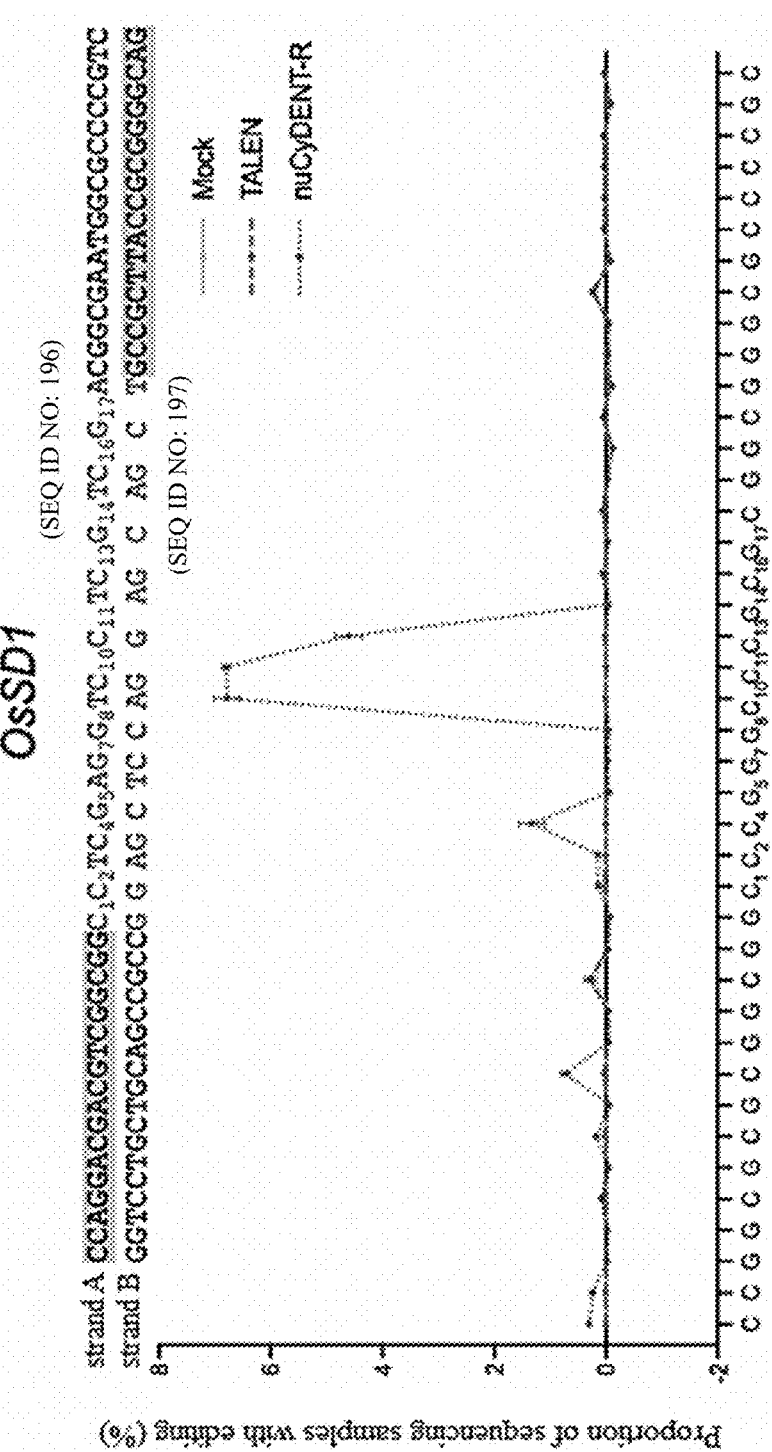
Figure 19B:
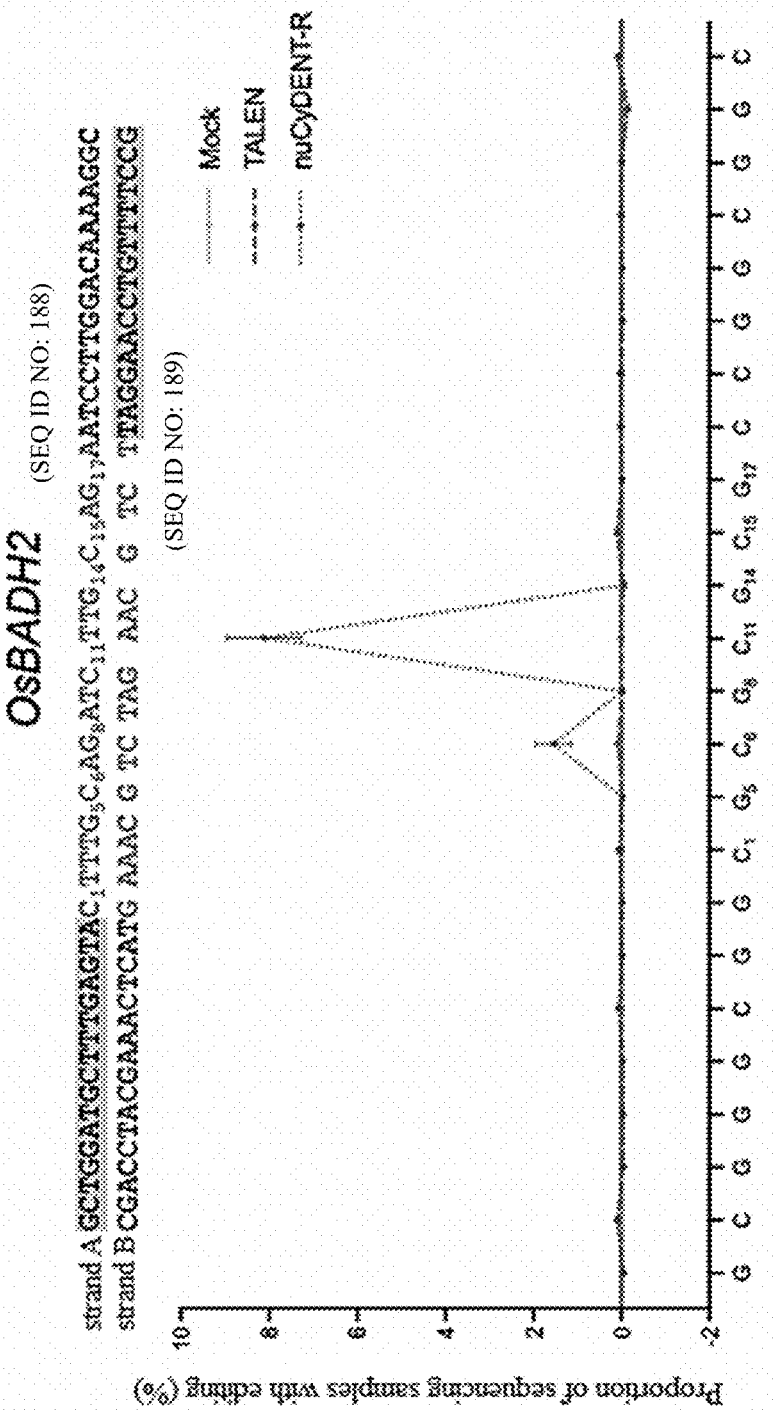

The inventors selected the nuclear genome of rice protoplast to evaluate the editing effect of the base editor of the present disclosure. In this Example, four pairs of TALE proteins were respectively designed for the endogenous gene loci of rice (i.e., OsDEP1, OsCKX2, OsBADH 2 and OsSD1). Exonucleases with 5'→3' (mExoI) cleavage preference or 3'→5' (Trex2) cleavage preference were used to evaluate the effect of fusing the exonuclease and the nickase to form an ssDNA intermediate. In this Example, an efficient cytidine deaminase hAPOBEC3A (hA3A) was selected to deaminate cytosine(s) in the ssDNA intermediate, a uracil glycosylase inhibitor (UGI) peptide was fused to its C-terminal, and the editing efficiency was further improved by minimizing the influence of DNA base excision repair. Nuclear localization signals (NLS) were fused to the N-terminal of each component, thereby editing the nuclear genome directly. Such combination of the base editors targeting the nuclear genome was referred to as nuCyDENT herein, and the schematic diagram of the exemplary construct was as shown in FIG. 18. The nuCyDENT that targeted the OsDEP1, OsCKX2, OsBADH2 and OsSD1 sites in rice was introduced into the rice protoplast, and the editing efficiency was evaluated after 2 days. Targeted cytosine base editing was assessed within the 18 bp spacing regions between the TALE binding sites of all four nuclear genomic sites by utilizing NGS analysis. An editing efficiency of 3% to 18% and lower indel frequency (compared to that of the corresponding wild-type TALEN system) were observed (FIG. 19A and FIG. 19B). These results indicated that the base editor of the present disclosure could achieve efficient base editing in the nuclear genome while merely resulting in indel byproducts at a low level.

Figure 20:
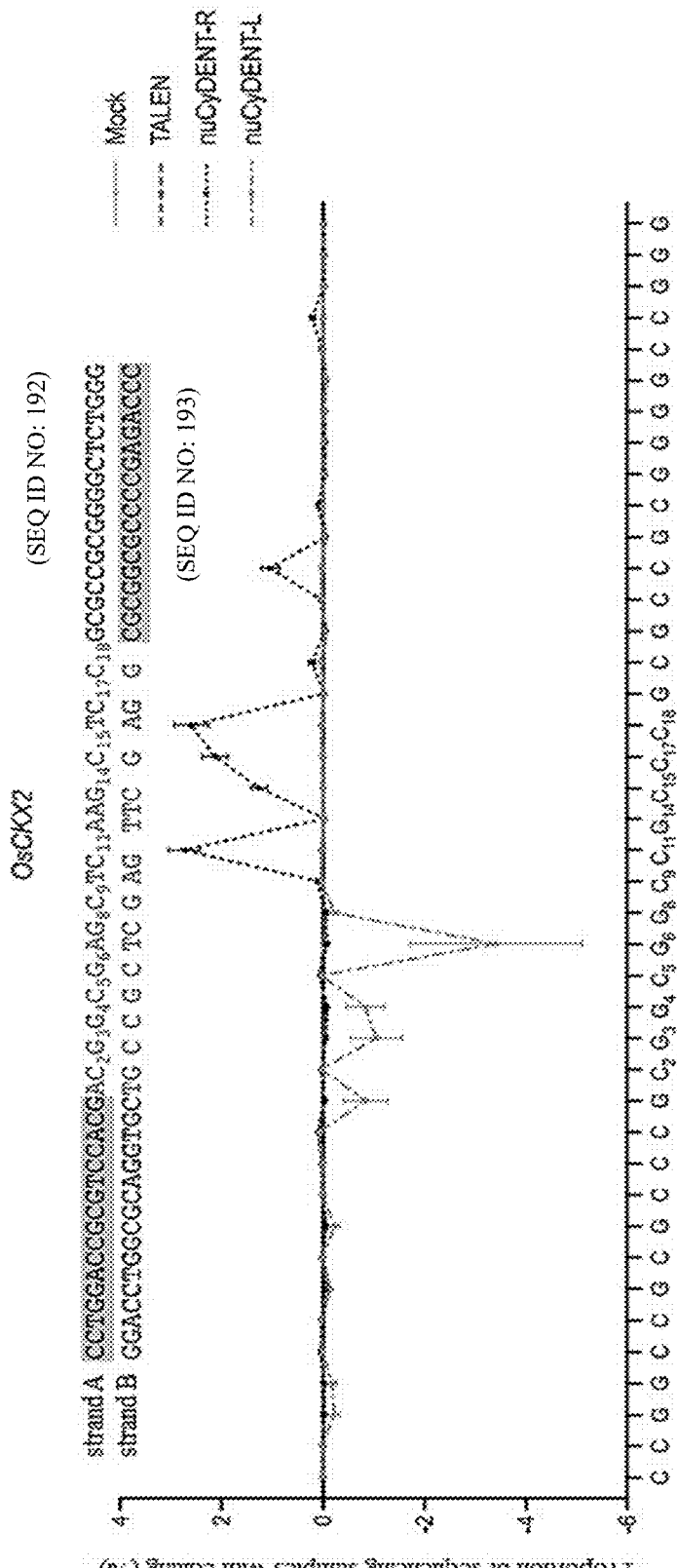
FIG. 20 shows the base editing of CyDENT at the OsCKX2 and OsSD1 sites in rice protoplast. The gray regions are the TALE binding sites.
Figure 20:
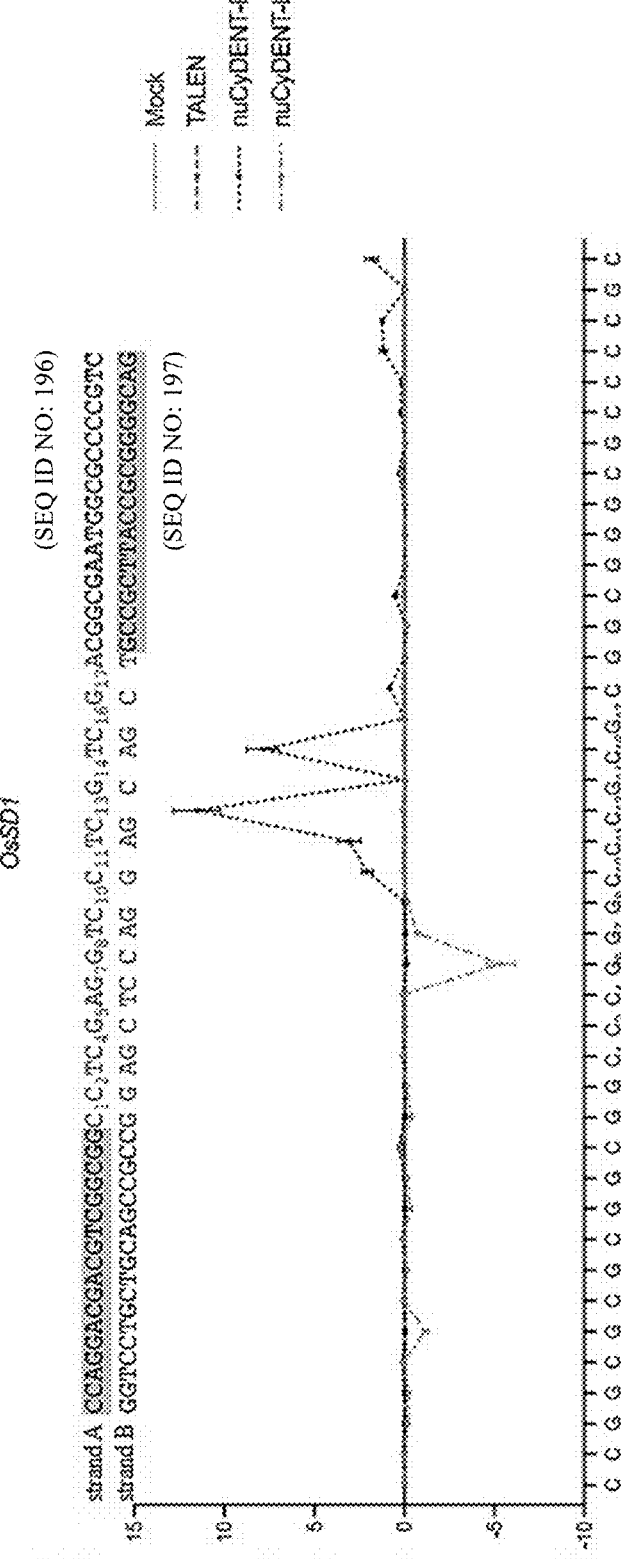

In terms of the single-strand editing performance, the inventors used nuCyDENT-L (nuCyDENT comprising an FokI-L$_{nickase}$ structure) and nuCyDENT-R (nuCyDENT comprising an FokI-R$_{nickase}$ structure) to perform respective base editing in rice genome loci OsCKX2 and OsSD1. As indicated by the results, the top strand of DNA was edited when using nuCyDENT-R for editing, and the bottom strand of DNA was edited when using nuCyDENT-L for editing (FIG. 20). This conclusion was the same as Example 2, which also showed the single-strand editing performance of CyDENT in the nuclear genome.

In FIG. 19A, FIG. 19B and FIG. 20, the experimental treatments or construct combinations involved in figures were as shown below.

| | Experimental treatments or construct combinations involved in figures |
|---|---|
| nuCyDENT for OsDEP1 target site | OsDEP1-NLS-TALE-L-FokI-L$_{D450A}$-T2A-NLS-TALE-R-FokI-R + NLS-A3A-UGI + NLS-mExoI |
| nuCyDENT-R for OsSD1 target site | OsSD1-NLS-TALE-L-FokI-L$_{D450A}$-T2A-NLS-TALE-R-FokI-R + NLS-A3A-UGI + NLS-mExoI |
| nuCyDENT-R for OsCKX2 target site | OsCKX2-NLS-TALE-L-FokI-L$_{D450A}$-T2A-NLS-TALE-R-FokI-R + NLS-A3A-UGI + NLS-mExoI |
| nuCyDENT for OsBADH2 target site | OsBADH2-NLS-TALE-L-FokI-L$_{D450A}$-T2A-NLS-TALE-R-FokI-R + NLS-A3A-UGI + NLS-mExoI |
| nuCyDENT-L for OsCKX2 target site | OsCKX2-NLS-TALE-L-FokI-L-T2A-NLS-TALE-R-FokI-R$_{D450A}$ + NLS-A3A-UGI + NLS-mExoI |
| nuCyDENT-L for OsSD1 target site | OsSD1-NLS-TALE-L-FokI-L-T2A-NLS-TALE-R-FokI-R$_{D450A}$ + NLS-A3A-UGI + NLS-Trex2 |
| TALEN | TALEN$_{WT}$ |
| Mock | None, i.e., blank control, the same applied to the subsequent Examples. |

Example 8: Base Editing in Animal Nuclear Genome

The effects of base editing of CyDENT and DdCBE at human SIRT6 gene (target site) were compared in this Example. The inventor designed a TALE protein for the SIRT6 target, designed and obtained nuCyDENT-L according to the method in Example 7, and designed and obtained a DddA-dependent DdCBE according to the method in the prior art (Nakazato, I. et al. Targeted base editing in the mitochondrial genome of *Arabidopsis thaliana*. Proc. Natl. Acad. Sci. USA. 119, e2121177119 (2022).). The experimental results showed that nuCyDENT-L had higher base editing efficiency than DdCBE at the target site (FIG. 21), indicating that the base editing system of the present disclosure had good base editing performance in the nuclear genome of animal cells.

Figure 21:
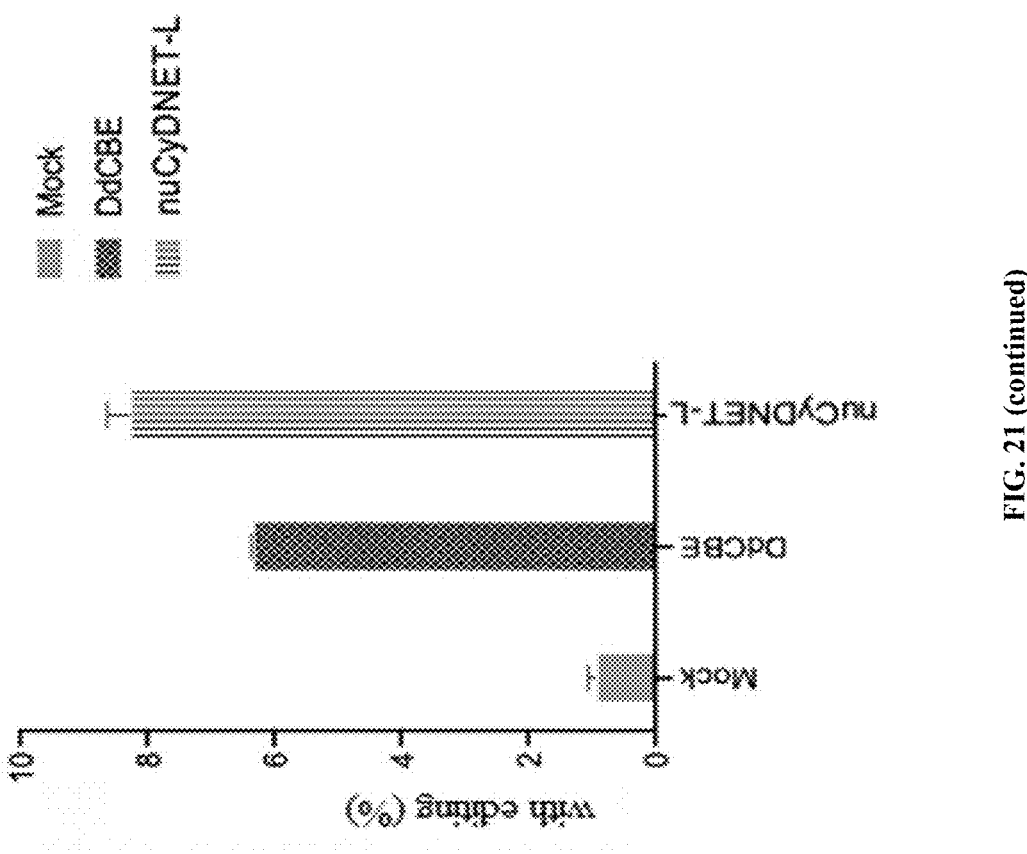
FIG. 21 shows the base editing of CyDENT at human SIRT6 site. The gray regions are the TALE binding sites.

In FIG. 21, the experimental treatments or construct combinations involved in figures were as shown below.

153

| Experimental treatments or construct combinations involved in figures | |
|---|---|
| nuCyDENT-L | SIRT6-NLS-TALE-L-FokI-L SIRT6-NLS-TALE-R-FokI-R$_{D450A}$ NLS-A3A NLS-UGI NLS-mExoI |
| DdCBE | SIRT6-NLS-TALE-L-DddA$_N$-UGI SIRT6-NLS-TALE-R-DddA$_C$-UGI |

Example 9: Base Editing of DNA in Organelle—Chloroplast

The base editor of the present disclosure could be used for mitochondrial DNA base editing and chloroplast DNA base editing, and had advantages over CRISPR base editors that needed to comprise nucleic acid components. The protein components in the base editor of the present disclosure could be translocated into mitochondria and chloroplasts via a mitochondrial targeting sequence (MTS) and a chloroplast translocation peptide (CTP) respectively. In these Examples, MTS or CTP could be selected to replace NLS according to the type of target organelle.

Figure 22A:
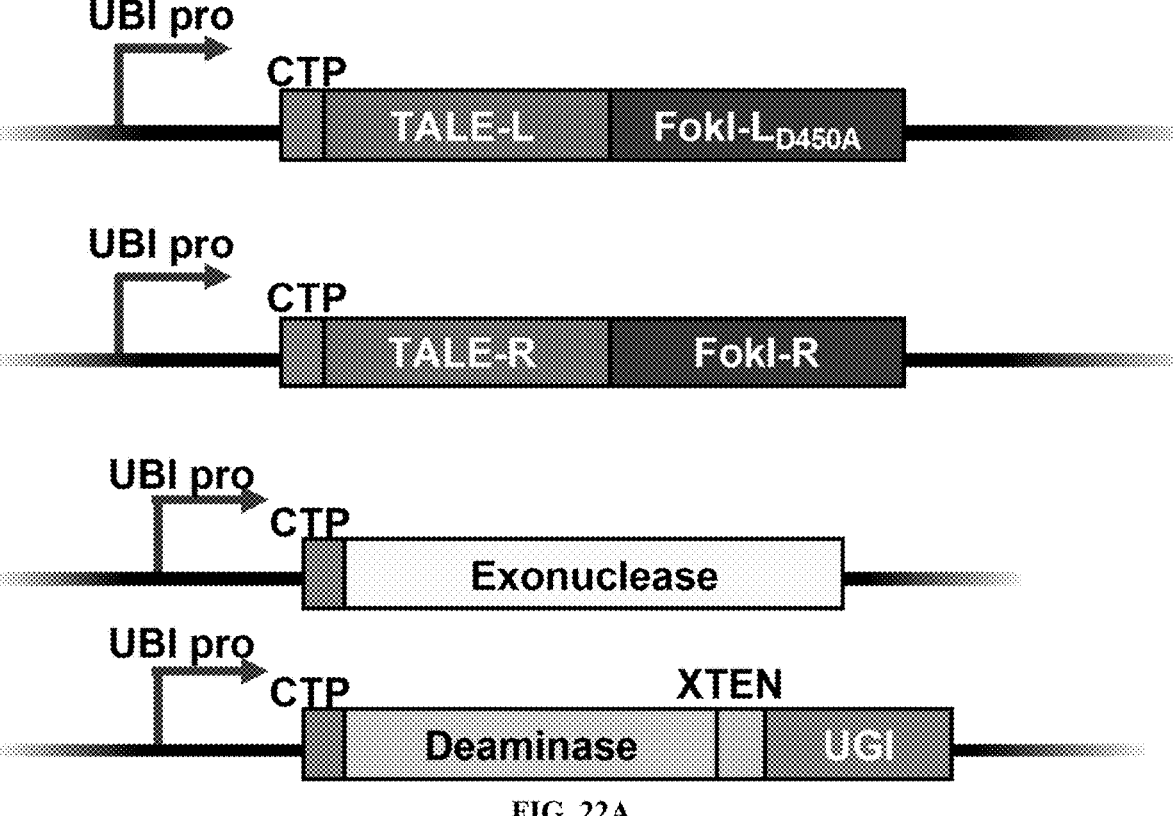
FIG. 22A is a schematic overview of the modular CyDENT construct used in chloroplast genome editing, and cpCyDENT-R is taken as an example.
Figure 22B:
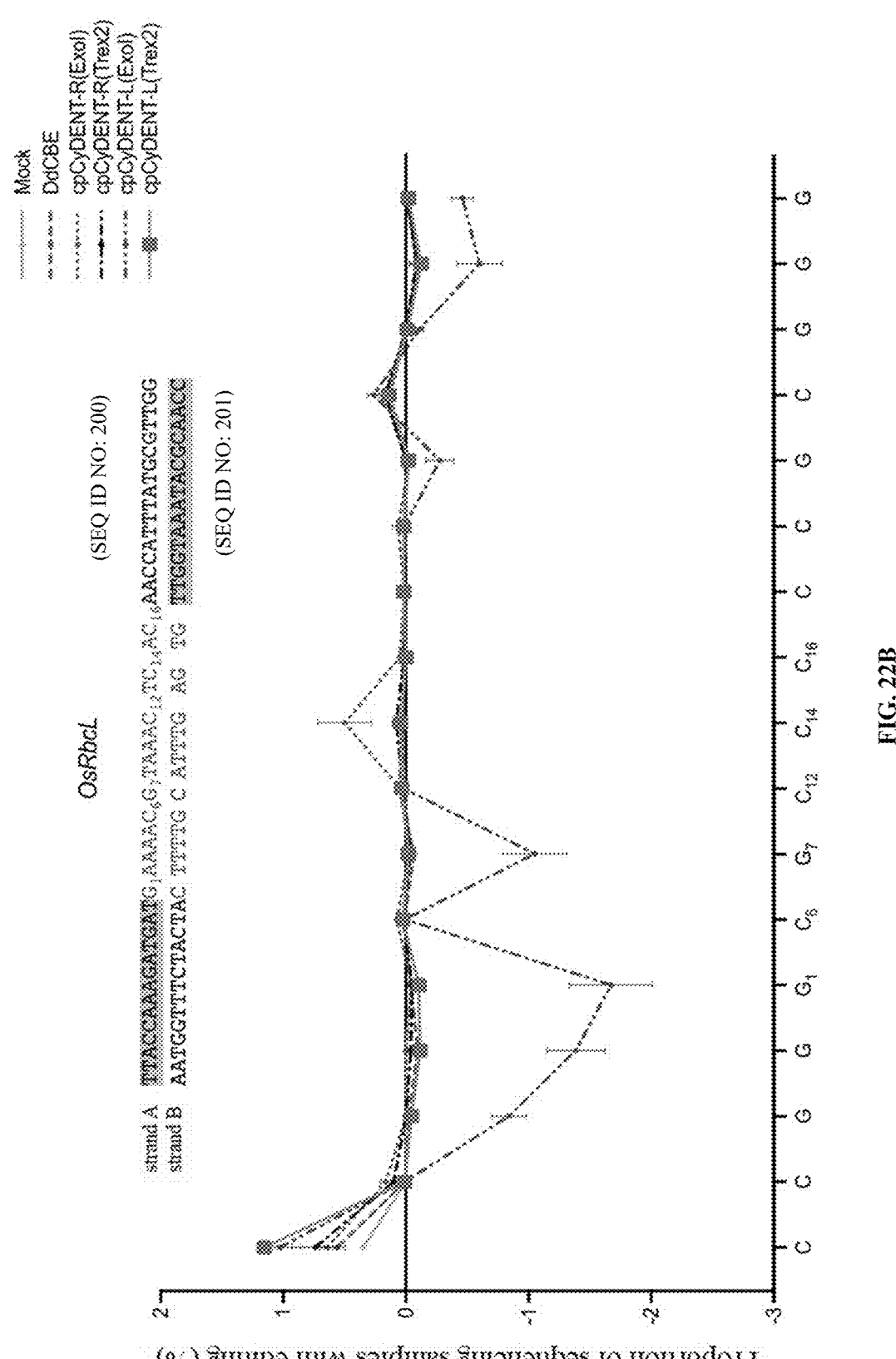
FIG. 22B shows the base editing window of CyDENT at the OsrbcL site in rice protoplast. The gray regions are the TALE binding sites.

First, the inventors attempted to perform base editing on plant chloroplast DNA using the base editing strategy of CyDENT. Plant chloroplast DNA was an important organelle specific to plants, had its own genomic DNA (cpDNA), and could not be edited by using CRISPR-derived base editors. The inventor replaced NLS with chloroplast translocation peptide (CTP) in nuCyDENT that was designed with reference to the method in Example 7 (Kang, B. C. et al. Chloroplast and mitochondrial DNA editing in plants. Nat Plants 7, 899-905 (2021).) (FIG. 22A), and the resultant was named cpCyDENT. Rice protoplasts were transformed by the inventors with cpCyDENT-L (comprising FokI-L$_{nickase}$) and cpCyDENT-R (comprising FokI-R$_{nickase}$), which comprised a TALE protein targeting the endogenous ribulose-1,5-bisphosphate carboxylase/oxygenase (RuBisCO) large subunit gene (rbcL). Base editing at the rbcL target was detected in cpCyDENT-L treatment (FIG. 22B). It is worth noting that the precise editing of specific bases could be achieved by regulating the type and direction of the nickase and the exonuclease in cpCyDENT. For example, as for Gi base (the most 5' nucleotide in the spacer region was designated as position 1, see FIG. 22B), this base could be edited efficiently with an editing efficiency of approximately 1.67% only when the cpCyDENT-L(mExoI) tool comprising FokI-L$_{nickase}$ and 5'→3' mExoI exonuclease was used.

This result conformed to the conclusion of the above-mentioned Examples. These results indicated that cpCyDENT was capable of performing base editing on the DNA strand in chloroplast genome selectively and precisely.

In FIG. 22B, the experimental treatments or construct combinations involved in figures were as shown below.

154

| Experimental treatments or construct combinations involved in figures | |
|---|---|
| cpCyDENT-R (mExoI) | OsRbcL-CTP-TALE-L-FokI-L$_{D450A}$A + OsRbcL-CTP-TALE-R-FokI-R + CTP-A3A-UGI + CTP-mExoI |
| cpCyDENT-R (Trex2) | OsRbcL-CTP-TALE-L-FokI-L$_{D450A}$A + OsRbcL-CTP-TALE-R-FokI-R + CTP-A3A-UGI + CTP-Trex2 |
| cpCyDENT-L (mExoI) | OsRbcL-CTP-TALE-L-FokI-L + OsRbcL-CTP-TALE-R-FokI-R$_{D450A}$ + CTP-A3A-UGI + CTP-mExoI |
| cpCyDENT-L (Trex2) | OsRbcL-CTP-TALE-L-FokI-L + OsRbcL-CTP-TALE-R-FokI-R$_{D450A}$ + CTP-A3A-UGI + CTP-Trex2 |

Example 10: Base Editing of DNA in Organelle—Mitochondrion

Figure 15A:
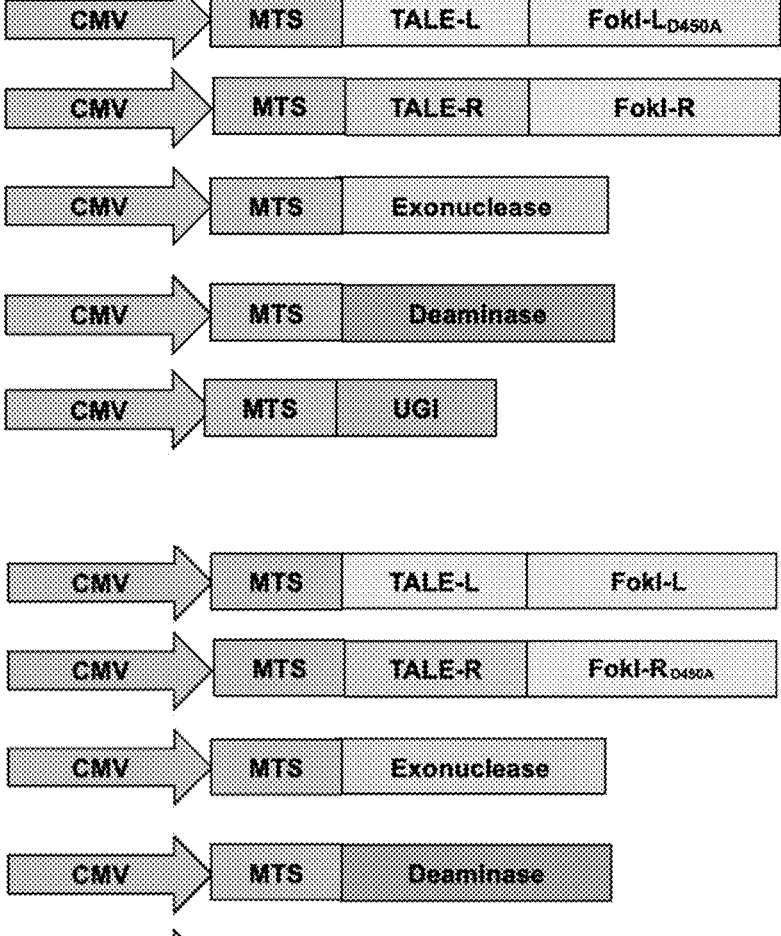
FIG. 15A is a schematic diagram of a vector used in the base editor of the present disclosure in mitochondrial editing, comprising constructs expressing MTS-deaminase, MTS-UGI, MTS-TALE-R-FokI-R (or MTS-TALE-R-FokI-R$_{D450A}$), MTS-TALE-L-FokI-L$_{D450A}$ (or MTS-TALE-L-FokI-L) nickase and MTS-exonuclease.
Figure 15B:
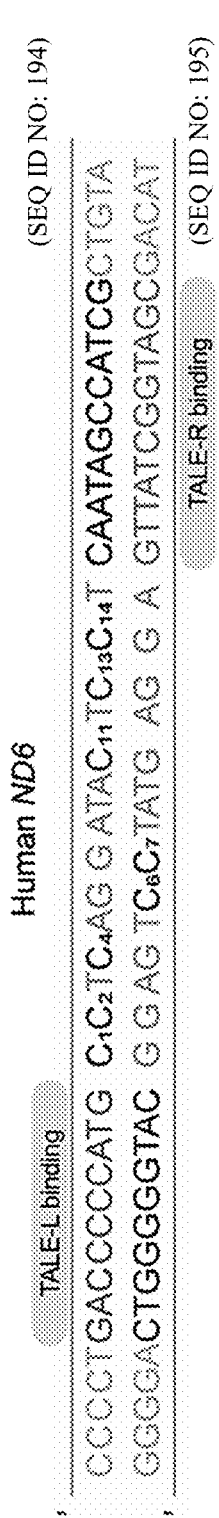
FIG. 15B is a schematic diagram showing a target sequence targeted by the base editor of the present disclosure using constructs as shown in FIG. 15A and showing the binding sites of TALE-R and TALE-L and cytosine residues targeted by certain nucleic acid base editors of the present disclosure, that is, a schematic diagram of mitochondrial ND6 target sequence and TALE binding sites.

In this Example, the inventors assessed the influence of CyDENT base editing in mitochondrial DNA (mtDNA) base editing in human cells, replaced NLS with mitochondrial targeting sequence (MTS) and selected promoters and terminators suitable for expression in HEK293T cells, thereby obtaining a base editor for mtDNA, referred to as mtCyDENT. The mtCyDENT construct generated in this Example was as shown in FIG. 15A (TALE-FokI-R$_{nickase}$ and TALE-FokI-L$_{nickase}$).

Figure 15C:
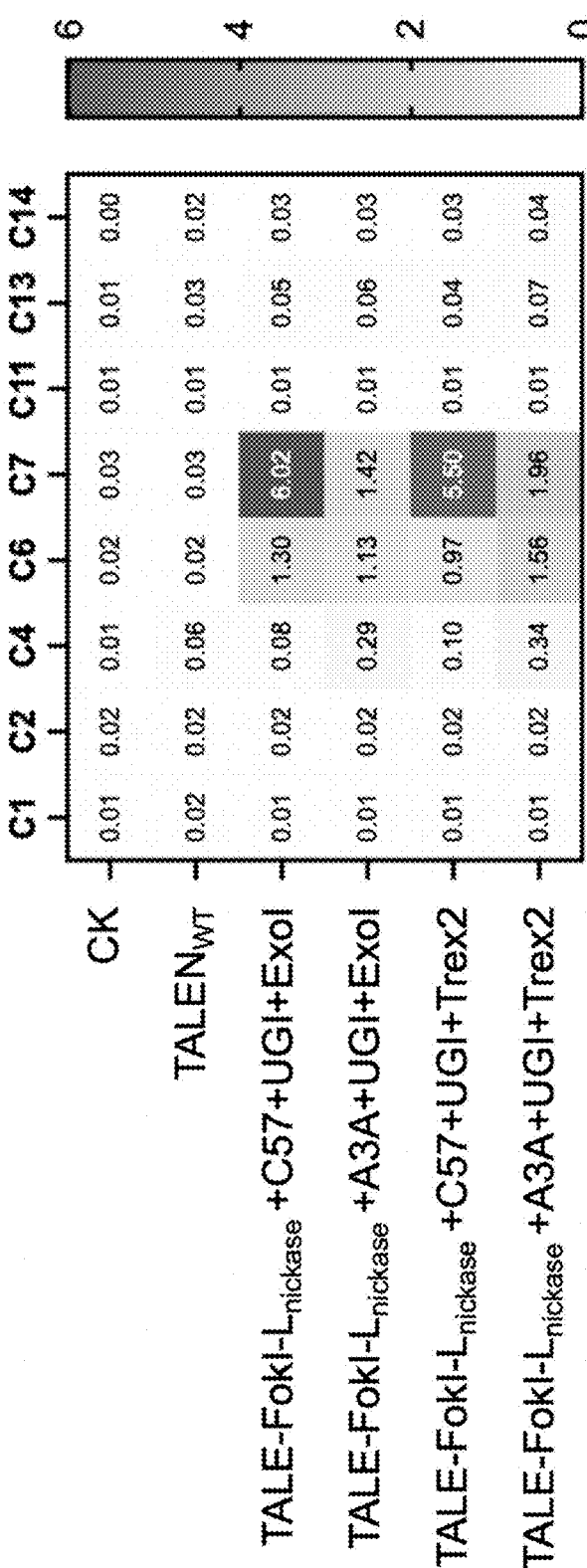
FIG. 15C shows the efficiency of the base mutations introduced into the target sequence by the base editor of the present disclosure using constructs as shown in FIG. 15A.

First, a target site in ND6 gene of human mitochondrial DNA was selected to construct TALE-FokI-R$_{nickase}$ and TALE-FokI-L$_{nickase}$ expression vectors in which the TALE proteins were modified to target the site, and said expression vectors were transfected into HEK293T cells together with the vectors expressing the deaminase (hAPOBEC3A or C57), the exonuclease (mExoI or Trex2) and UGI, wherein the mitochondrial targeting sequence (MTS) was fused to the terminal of the protein. NGS was used to determine the base editing frequency after the transfection by the base editor. The results indicated that targeted cytosine base editing was achieved with an efficiency of about 6.0% in the mitochondrial DNA target of human cells (FIG. 15C). The results indicated that the base editor of the present disclosure could be used for the base editing of organelle genome.

In FIG. 15C, HEK293T cells were transfected with different construct combinations to target the mitochondrial ND6 site, and the DNA strand and the editing window where base editing occurred were analyzed via the results of high-throughput sequencing. The experimental treatments or construct combinations involved in figures and the schematic diagrams of related vectors were as shown below.

| Experimental treatments or construct combinations involved in figures | Schematic diagrams of related vectors |
|---|---|
| CK | None |
| TALEN$_{WT}$ | FIG. 17A and FIG. 17B |
| TALE-FokI-L$_{nickase}$ + C57 + UGI + mExoI | FIGS. 17A, 17B, 17C, 17D and 17E, wherein the corresponding nickase was FokI-L$_{nickase}$, the corresponding exonuclease was mExoI, and the corresponding deaminase was C57. |
| TALE-FokI-L$_{nickase}$ + A3A + UGI + mExoI | FIGS. 17A, 17B, 17C, 17D and 17E, wherein the corresponding nickase was FokI-L$_{nickase}$, the |

-continued

| Experimental treatments or construct combinations involved in figures | Schematic diagrams of related vectors |
|---|---|
| | corresponding exonuclease was mExoI, and the corresponding deaminase was hAPOBEC3A. |
| TALE-FokI-L$_{nickase}$ + C57 + UGI + Trex2 | FIGS. 17A, 17B, 17C, 17D and 17E, wherein the corresponding nickase was FokI-L$_{nickase}$, the corresponding exonuclease was Trex2, and the corresponding deaminase was C57. |
| TALE-FokI-L$_{nickase}$ + A3A + UGI + Trex2 | FIGS. 17A, 17B, 17C, 17D and 17E, wherein the corresponding nickase was FokI-L$_{nickase}$, the corresponding exonuclease was Trex2, and the corresponding deaminase was hAPOBEC3A. |

Example 11: Effects of the Fusion State of Base Editor in Mitochondrial DNA Editing Next, the inventors verified the effects of the individually expressed deaminase, exonuclease, UGI and TALE-FokI nickase on mtDNA base editing efficiency.

Figure 23A:
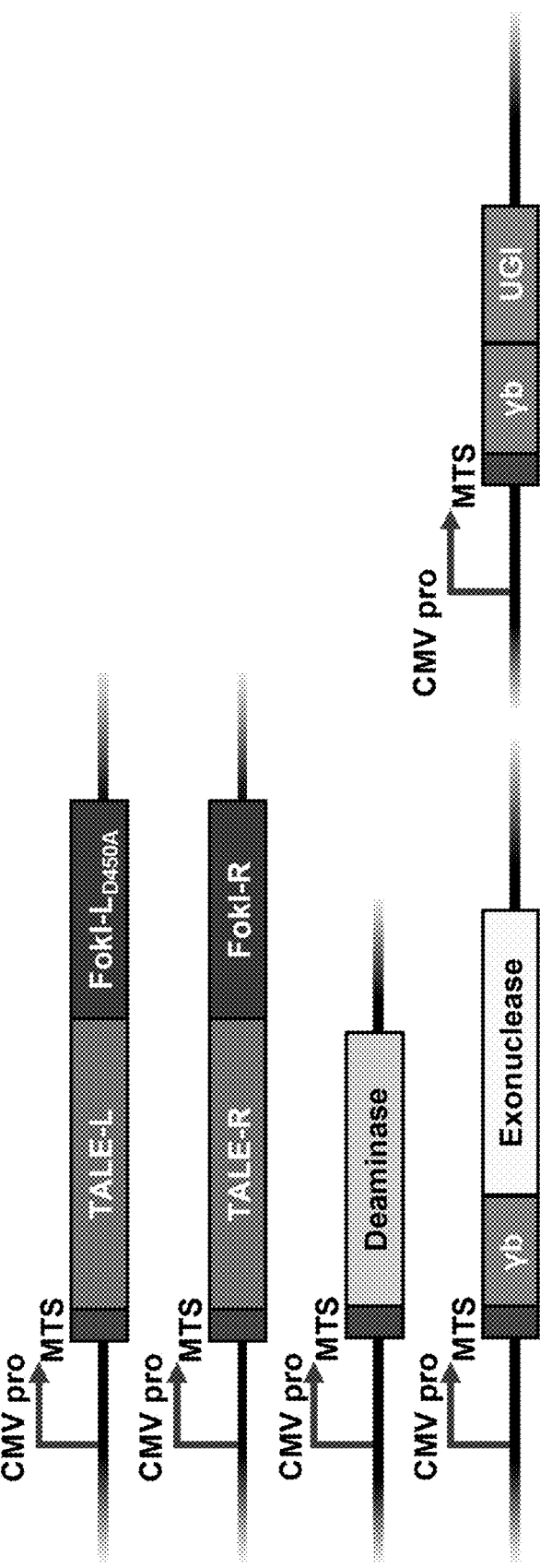
FIG. 23A is a schematic diagram of the structure of the modular CyDENT used in mitochondria. mtCyDENT-R is taken as an example.
Figure 23B:
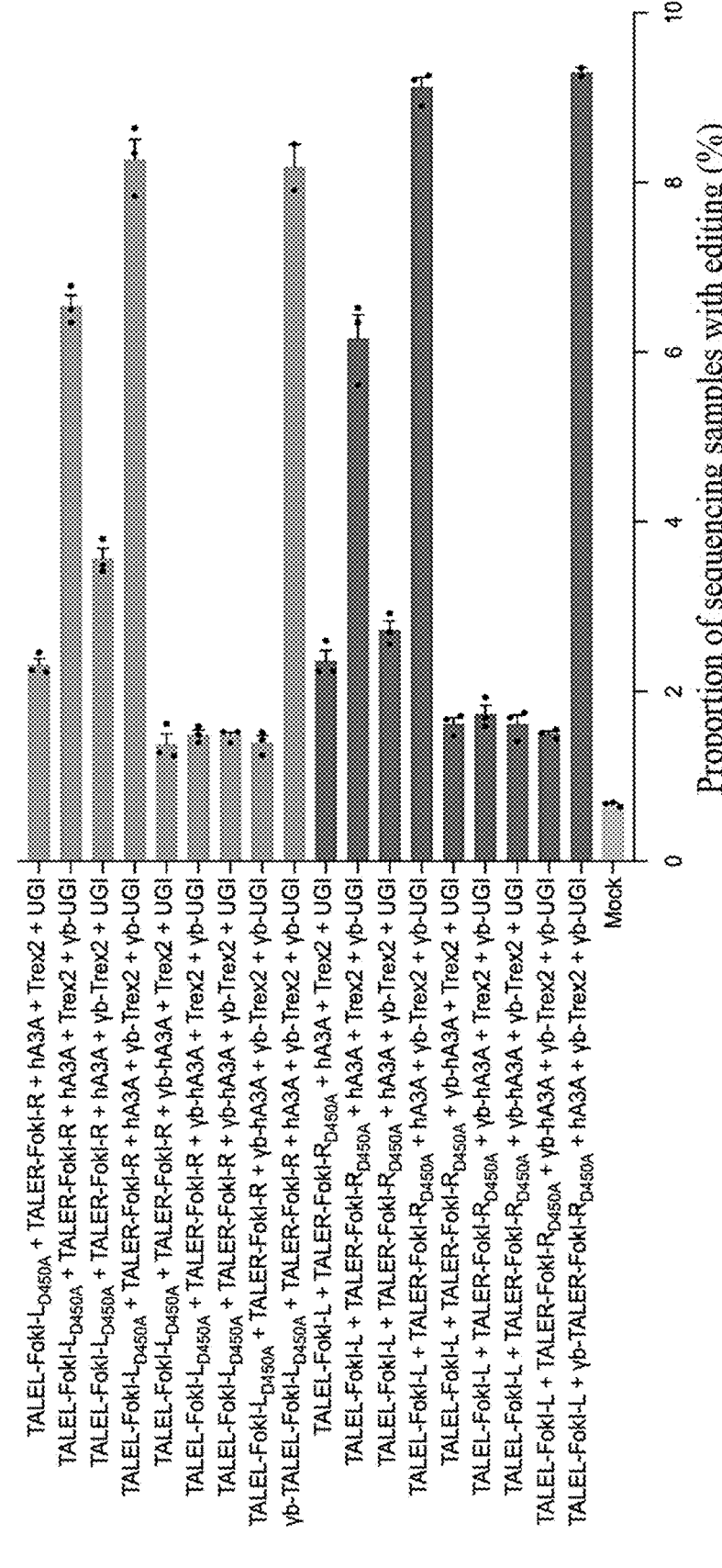
FIG. 23B shows the base editing at the mitochondrial ND6 site in HEK293T cells by mtCyDENT-L or mtCy-DENT-R in various fusion states with γb.

For this purpose, the inventors used a small peptide referred to as γb and γb was fused to the N-terminal of the domain of one or more modular components in mtCyDENT so as to drive the recruitment of each protein element (FIG. 23A). γb was an RNA silencing suppressor derived from barley stripe mosaic virus (BSMV) having self-interaction (Jiang, Z., Yang, M., Zhang, Y., Jackson, A. O. & Li, D. in Encyclopedia of Virology 420-429 (2021).). In this experiment, the exonuclease selected by the inventors was Trex2. The inventors designed a variety of schemes for the fusion between γb and each component, so as to screen out the base editor composition with optimal editing effect (FIG. 23B). Taking the size of the protein components entering mitochondria into consideration, a construct composition of five proteins/fusion proteins as shown in FIG. 23A was used for expression in this Example, and the proteins/fusion proteins were a fusion protein of TALE-L and FokI-L (simply referred to as TALE-L-FokI-L, TALEL-FL or TALEL-FokI-L), a fusion protein of TALE-R and FokI-R (simply referred to as TALE-R-FokI-R, TALEL-FR or TALER-FokI-R), hA3A deaminase protein, Trex2 exonuclease protein and UGI protein, respectively. Among them, the tail tag D450A represented a mutant, and WT represented "wild-type". The experimental results indicated that higher editing effect could be achieved when γb was merely fused with UGI and Trex2. The base editor composition having a structure in which γb was fused to UGI and Trex2 was named mtCyDENT1b.

Figure 24:
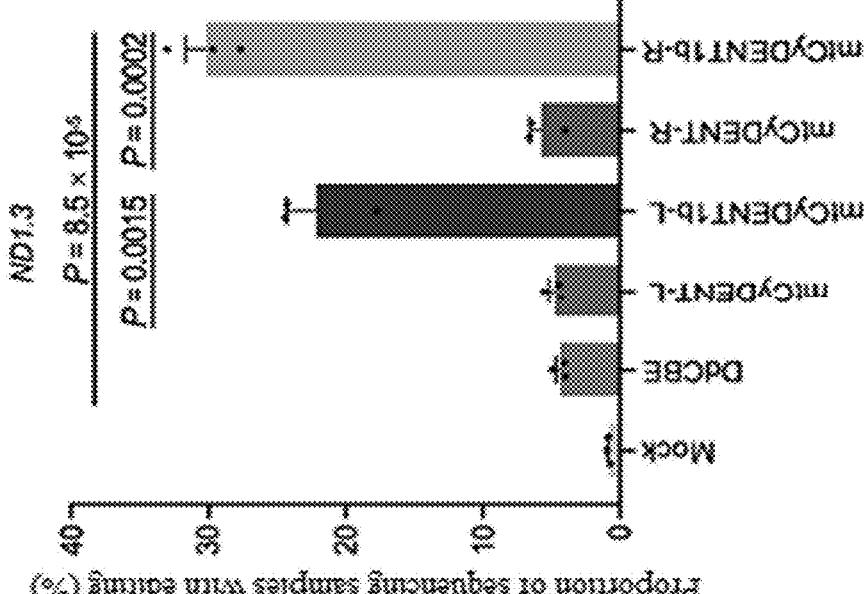
FIG. 24 shows the editing frequencies of DdCBE, mtCy-DENT-R, mtCyDENT1b-R, mtCyDENT-L and mtCyDENT1b-L at the ND1.2, ND1.3, ND3 and ND6.2 sites in the mitochondria in HEK293T cells.
Figure 24:
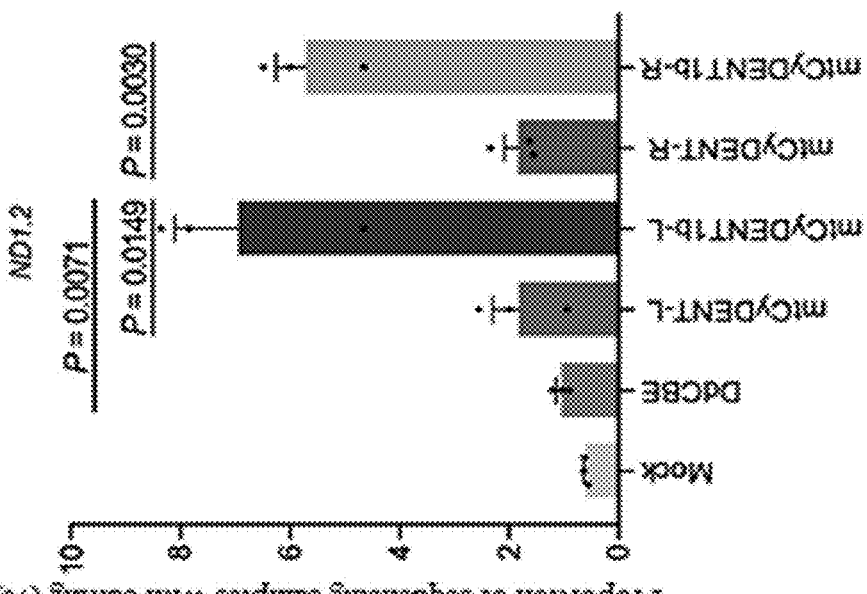
Figure 24:
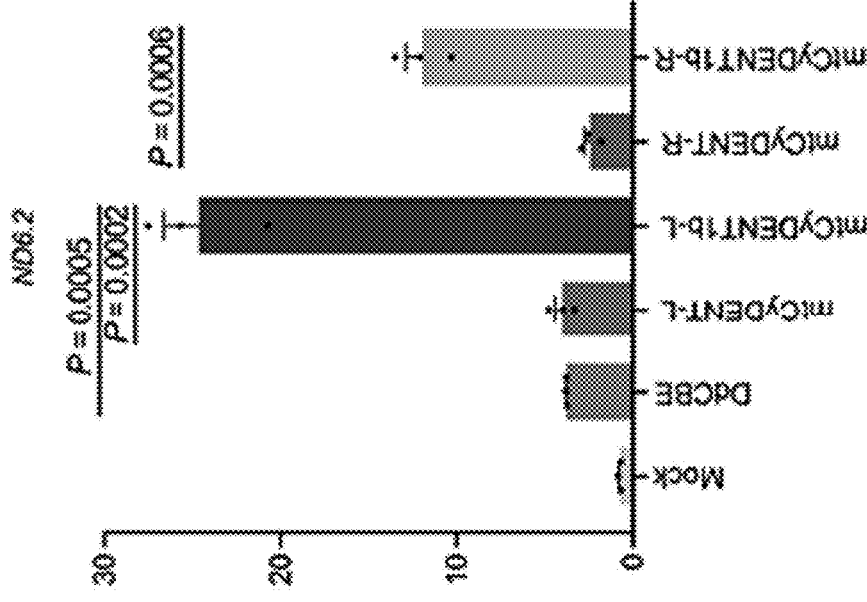
Figure 24:
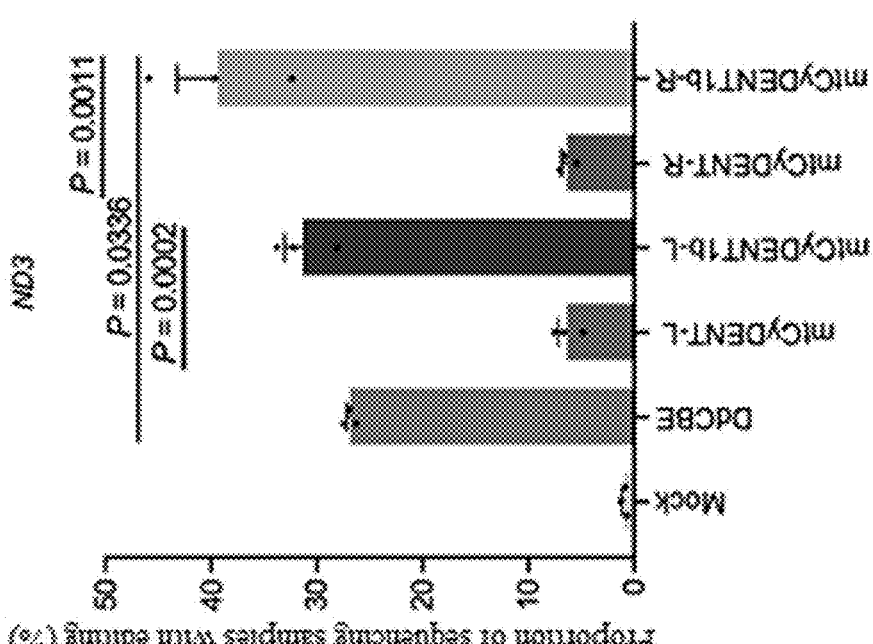
Figure 25:
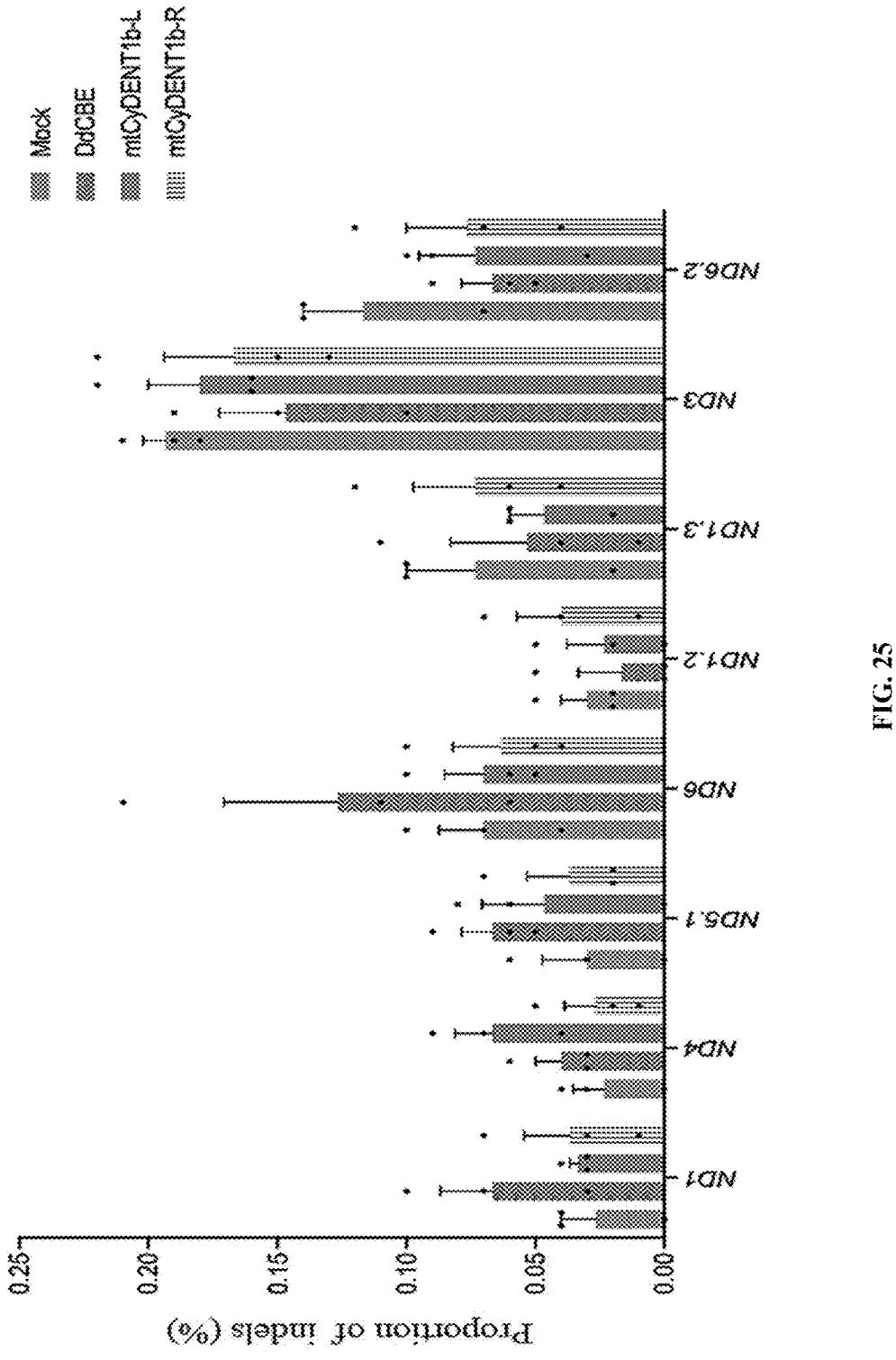
FIG. 25 shows the indel frequencies of DdCBE, mtCyDENT1b-R and mtCyDENT1b-L at different sites in the mitochondria of HEK293T cells.

Next, mtCyDENT and mtCyDENT1b were assessed at seven additional endogenous mtDNA genomic loci by the inventors. It was observed by the inventors that the average editing frequency of mtCyDENT was 1.16% to 11.7%, while mtCyDENT1b could achieve an average editing efficiency that was further increased by 2.42-fold to 6.18-fold and was up to 4.55% to 39.3% (FIG. 24). Also, the editing efficiency of mtCyDENT1b was higher than that of DdCBE at ND1.2, ND1.3, ND3 and ND6.2 targets having the same TALE sequence. In addition, the inventors also noticed that using CyDENT for base editing at mtDNA target site resulted in lower indel frequency as compared with DdCBE (FIG. 25). In summary, both mtCyDENT and mtCyDENT1b were capable of achieving efficient base editing in human mitochondrial DNA.

In FIG. 23B, the experimental treatments or construct combinations involved in figures were as shown below (from top to bottom).

| Experimental treatments or construct combinations involved in figures |
|---|
| ND6-MTS-TALE-L-FokI-L$_{D450A}$ + ND6-MTS-TALE-R-FokI-R + MTS-A3A + MTS-Trex2 + MTS-UGI |
| ND6-MTS-TALE-L-FokI-L$_{D450A}$ + ND6-MTS-TALE-R-FokI-R + MTS-A3A + MTS-Trex2 + MTS-γb-UGI |
| ND6-MTS-TALE-L-FokI-L$_{D450A}$ + ND6-MTS-TALE-R-FokI-R + MTS-A3A + MTS-γb-Trex2 + MTS-UGI |
| ND6-MTS-TALE-L-FokI-L$_{D450A}$ + ND6-MTS-TALE-R-FokI-R + MTS-A3A + MTS-γb-Trex2 + MTS-γb-UGI |
| ND6-MTS-TALE-L-FokI-L$_{D450A}$ + ND6-MTS-TALE-R-FokI-R + MTS-γb-A3A + MTS-Trex2 + MTS-UGI |
| ND6-MTS-TALE-L-FokI-L$_{D450A}$ + ND6-MTS-TALE-R-FokI-R + MTS-γb-A3A + MTS-Trex2 + MTS-γb-UGI |
| ND6-MTS-TALE-L-FokI-L$_{D450A}$ + ND6-MTS-TALE-R-FokI-R + MTS-γb-A3A + MTS-γb-Trex2 + MTS-UGI |
| ND6-MTS-TALE-L-FokI-L$_{D450A}$ + ND6-MTS-TALE-R-FokI-R + MTS-γb-A3A + MTS-γb-Trex2 + MTS-γb-UGI |
| ND6-MTS-γb-TALE-L-FokI-L$_{D450A}$ + ND6-MTS-TALE-R-FokI-R + MTS-A3A + MTS-γb-Trex2 + MTS-γb-UGI |
| ND6-MTS-TALE-L-FokI-L + ND6-MTS-TALE-R-FokI-R$_{D450A}$ + MTS-A3A + MTS-Trex2 + MTS-UGI |
| ND6-MTS-TALE-L-FokI-L + ND6-MTS-TALE-R-FokI-R$_{D450A}$ + MTS-A3A + MTS-Trex2 + MTS-γb-UGI |
| ND6-MTS-TALE-L-FokI-L + ND6-MTS-TALE-R-FokI-R$_{D450A}$ + MTS-A3A + MTS-γb-Trex2 + MTS-UGI |
| ND6-MTS-TALE-L-FokI-L + ND6-MTS-TALE-R-FokI-R$_{D450A}$ + MTS-A3A + MTS-γb-Trex2 + MTS-γb-UGI |
| ND6-MTS-TALE-L-FokI-L + ND6-MTS-TALE-R-FokI-R$_{D450A}$ + MTS-γb-A3A + MTS-Trex2 + MTS-UGI |
| ND6-MTS-TALE-L-FokI-L + ND6-MTS-TALE-R-FokI-R$_{D450A}$ + MTS-γb-A3A + MTS-Trex2 + MTS-γb-UGI |
| ND6-MTS-TALE-L-FokI-L + ND6-MTS-TALE-R-FokI-R$_{D450A}$ + MTS-γb-A3A + MTS-γb-Trex2 + MTS-UGI |
| ND6-MTS-TALE-L-FokI-L + ND6-MTS-TALE-R-FokI-R$_{D450A}$ + MTS-γb-A3A + MTS-γb-Trex2 + MTS-γb-UGI |
| ND6-MTS-TALE-L-FokI-L + ND6-MTS-γb-TALE-R-FokI-R$_{D450A}$ + MTS-A3A + MTS-γb-Trex2 + MTS-γb-UGI |
| blank control Mock |

In FIGS. 24 to 27, the experimental treatments or construct combinations involved in figures were as shown below.

| Experimental treatments or construct combinations involved in figures | |
|---|---|
| DdCBE for ND1.2 target site | ND1.2-MTS-TALE-L-DddA$_N$-UGI + ND1.2-MTS-TALE-R-DddA$_C$-UGI |

-continued

| | Experimental treatments or construct combinations involved in figures |
|---|---|
| DdCBE for ND1.3 target site | ND1.3-MTS-TALE-L-DddA$_N$-UGI + ND1.3-MTS-TALE-R-DddA$_C$-UGI |
| DdCBE for ND3 target site | ND3-MTS-TALE-L-DddA$_N$-UGI + ND3-MTS-TALE-R-DddA$_C$-UGI |
| DdCBE for ND6 target site | ND6-MTS-TALE-L-DddA$_N$-UGI + ND6-MTS-TALE-R-DddA$_C$-UGI |
| DdCBE for ND6.2 target site | ND6.2-MTS-TALE-L-DddA$_N$-UGI + ND6.2-MTS-TALE-R-DddA$_C$-UGI |
| mtCyDENT-L for ND1.2 target site | ND1.2-MTS-TALE-L-FokI-L + ND1.2-MTS-TALE-R-FokI-R$_{D450A}$ + MTS-A3A + MTS-Trex2 + MTS-UGI |
| mtCyDENT1b-L for ND1.2 target site | ND1.2-MTS-TALE-L-FokI-L + ND1.2-MTS-TALE-R-FokI-R$_{D450A}$ + MTS-A3A + MTS-γb-Trex2 + MTS-γb-UGI |
| mtCyDENT-R for ND1.2 target site | ND1.2-MTS-TALE-L-FokI-L$_{D450A}$ + ND1.2-MTS-TALE-R-FokI-R + MTS-A3A + MTS-Trex2 + MTS-UGI |
| mtCyDENT1b-R for ND1.2 target site | ND1.2-MTS-TALE-L-FokI-L$_{D450A}$ + ND1.2-MTS-TALE-R-FokI-R + MTS-A3A + MTS-γb-Trex2 + MTS-γb-UGI |
| mtCyDENT-L for ND1.3 target site | ND1.3-MTS-TALE-L-FokI-L + ND1.3-MTS-TALE-R-FokI-R$_{D450A}$ + MTS-A3A + MTS-Trex2 + MTS-UGI |
| mtCyDENT1b-L for ND1.3 target site | ND1.3-MTS-TALE-L-FokI-L + ND1.3-MTS-TALE-R-FokI-R$_{D450A}$ + MTS-A3A + MTS-γb-Trex2 + MTS-γb-UGI |
| mtCyDENT-R for ND1.3 target site | ND1.3-MTS-TALE-L-FokI-L$_{D450A}$ + ND1.3-MTS-TALE-R-FokI-R + MTS-A3A + MTS-Trex2 + MTS-UGI |
| mtCyDENT1b-R for ND1.3 target site | ND1.3-MTS-TALE-L-FokI-L$_{D450A}$ + ND1.2-MTS-TALE-R-FokI-R + MTS-A3A + MTS-γb-Trex2 + MTS-γb-UGI |
| mtCyDENT-L for ND3 target site | ND3-MTS-TALE-L-FokI-L + ND3-MTS-TALE-R-FokI-R$_{D450A}$ + MTS-A3A + MTS-Trex2 + MTS-UGI |
| mtCyDENT1b-L for ND3 target site | ND3-MTS-TALE-L-FokI-L + ND3-MTS-TALE-R-FokI-R$_{D450A}$ + MTS-A3A + MTS-γb-Trex2 + MTS-γb-UGI |
| mtCyDENT-R for ND3 target site | ND3-MTS-TALE-L-FokI-L$_{D450A}$ + ND3-MTS-TALE-R-FokI-R + MTS-A3A + MTS-Trex2 + MTS-UGI |
| mtCyDENT1b-R for ND3 target site | ND3-MTS-TALE-L-FokI-L$_{D450A}$ + ND3-MTS-TALE-R-FokI-R + MTS-A3A + MTS-γb-Trex2 + MTS-γb-UGI |
| mtCyDENT-L for ND6.2 target site | ND6.2-MTS-TALE-L-FokI-L + ND6.2-MTS-TALE-R-FokI-R$_{D450A}$ + MTS-A3A + MTS-Trex2 + MTS-UGI |
| mtCyDENT1b-L for ND6.2 target site | ND6.2-MTS-TALE-L-FokI-L + ND6.2-MTS-TALE-R-FokI-R$_{D450A}$ + MTS-A3A + MTS-γb-Trex2 + MTS-γb-UGI |
| mtCyDENT-R for ND6.2 target site | ND6.2-MTS-TALE-L-FokI-L$_{D450A}$ + ND6.2-MTS-TALE-R-FokI-R + MTS-A3A + MTS-Trex2 + MTS-UGI |
| mtCyDENT1b-R for ND6.2 target site | ND6.2-MTS-TALE-L-FokI-L$_{D450A}$ + ND6.2-MTS-TALE-R-FokI-R + MTS-A3A + MTS-γb-Trex2 + MTS-γb-UGI |
| mtCyDENT1b-L for ND1 target site | ND1-MTS-TALE-L-FokI-L + ND1-MTS-TALE-R-FokI-R$_{D450A}$ + MTS-A3A + MTS-γb-Trex2 + MTS-γb-UGI |
| mtCyDENT1b-R for ND1 target site | ND1-MTS-TALE-L-FokI-L$_{D450A}$ + ND1-MTS-TALE-R-FokI-R + MTS-A3A + MTS-γb-Trex2 + MTS-γb-UGI |
| mtCyDENT1b-L for ND4 target site | ND4-MTS-TALE-L-FokI-L + ND4-MTS-TALE-R-FokI-R$_{D450A}$ + MTS-A3A + MTS-γb-Trex2 + MTS-γb-UGI |
| mtCyDENT1b-R for ND4 target site | ND4-MTS-TALE-L-FokI-L$_{D450A}$ + ND4-MTS-TALE-R-FokI-R + MTS-A3A + MTS-γb-Trex2 + MTS-γb-UGI |
| mtCyDENT1b-L for ND5.1 target site | ND5.1-MTS-TALE-L-FokI-L + ND5.1-MTS-TALE-R-FokI-R$_{D450A}$ + MTS-A3A + MTS-γb-Trex2 + MTS-γb-UGI |
| mtCyDENT1b-R for ND5.1 target site | ND5.1-MTS-TALE-L-FokI-L$_{D450A}$ + ND5.1-MTS-TALE-R-FokI-R + MTS-A3A + MTS-γb-Trex2 + MTS-γb-UGI |
| mtCyDENT1b-L for ND6 target site | ND6-MTS-TALE-L-FokI-L + ND6-MTS-TALE-R-FokI-R$_{D450A}$ + MTS-A3A + MTS-γb-Trex2 + MTS-γb-UGI |

-continued

| Experimental treatments or construct combinations involved in figures |
| --- |
| mtCyDENT1b-R for ND6 target site    ND6-MTS-TALE-L-FokI-L$_{D450A}$ + ND6-MTS-TALE-R-FokI-R + MTS-A3A + MTS-γb-Trex2 + MTS-γb-UGI |

Example 12: Improving the Editing Efficiency and Precision of CyDENT

Figure 26:
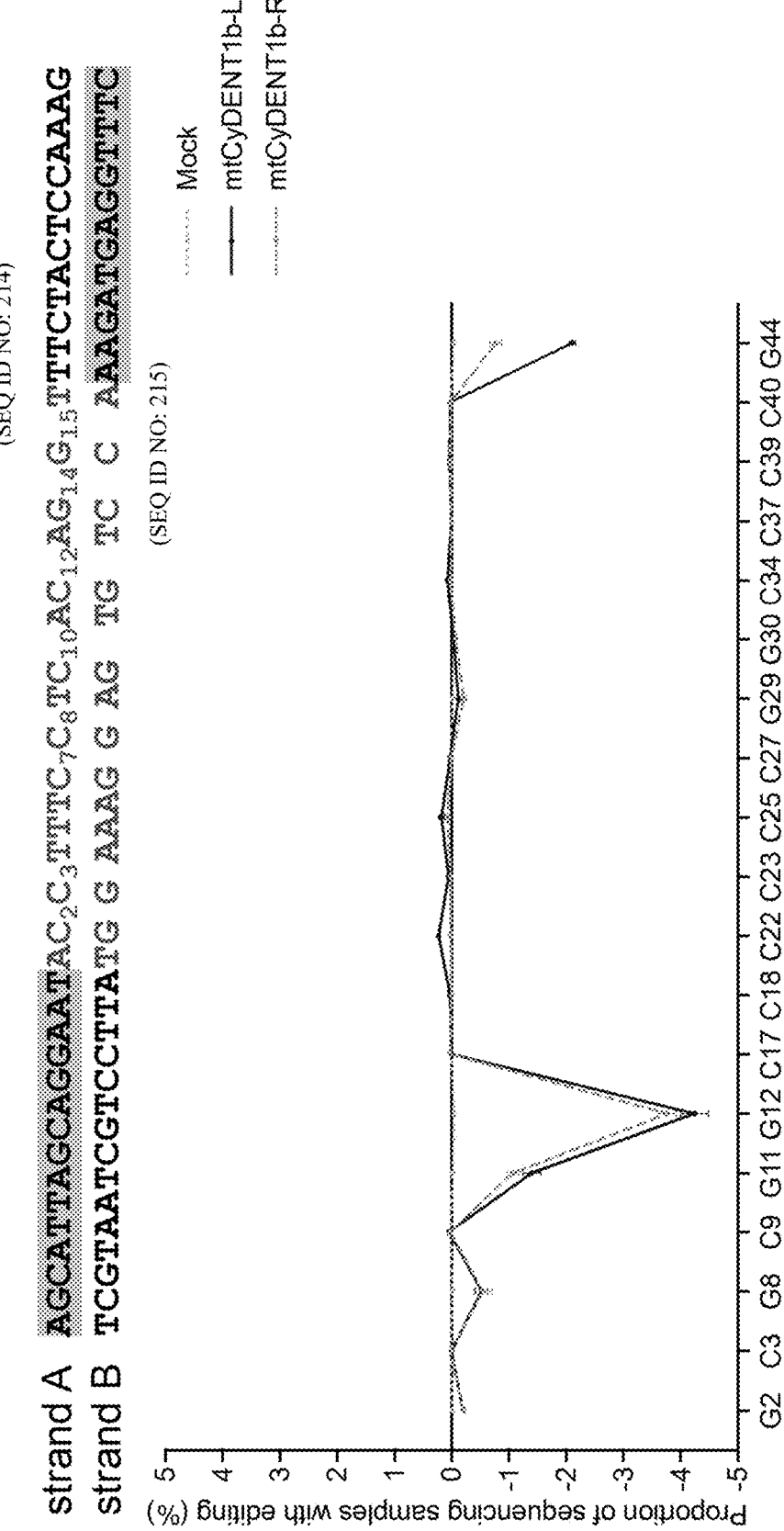
FIG. 26 shows the base editing sites of mtCyDENT at different sites in the mitochondria of HEK293T cells. The gray regions are the TALE binding sites.
Figure 26:
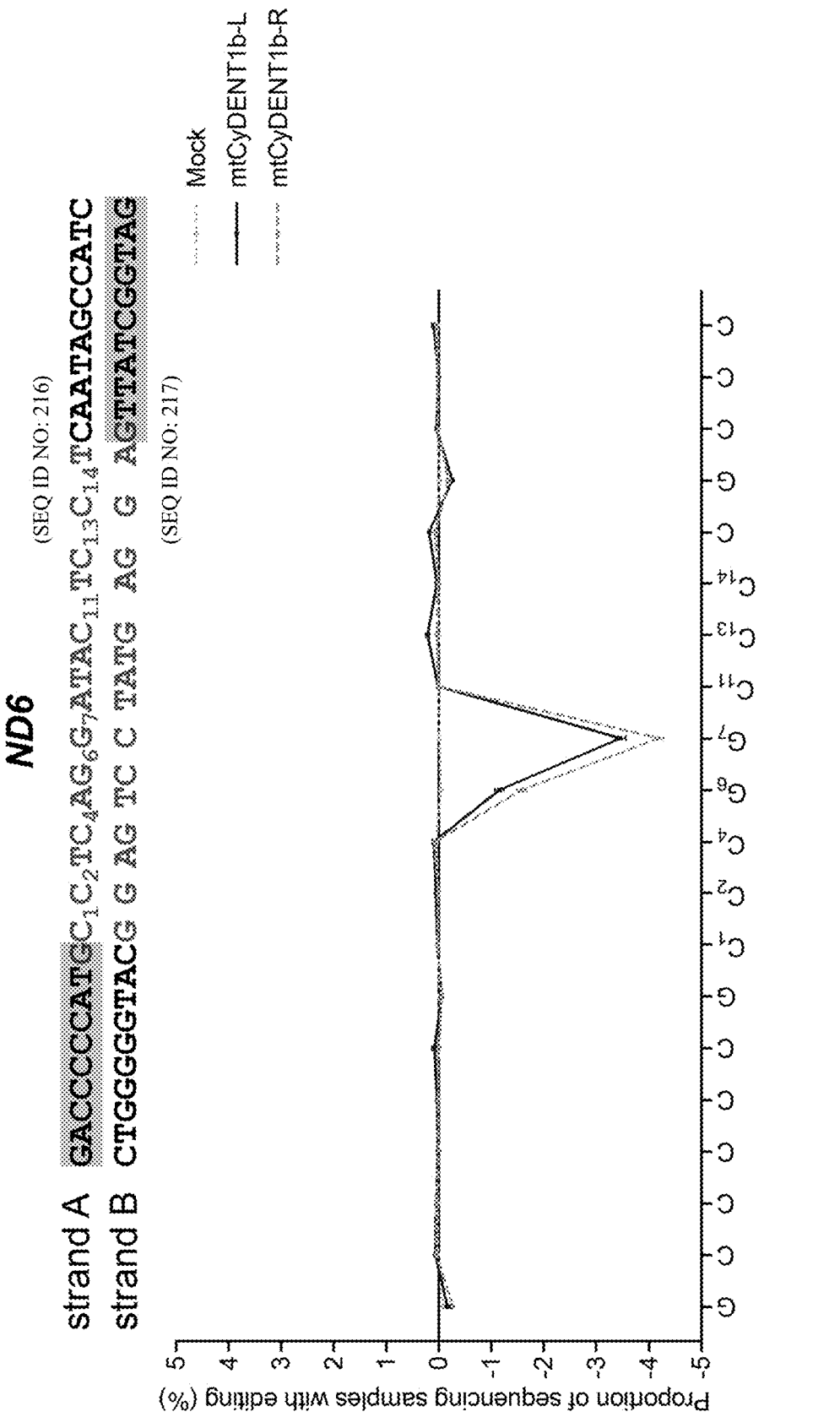
Figure 26:
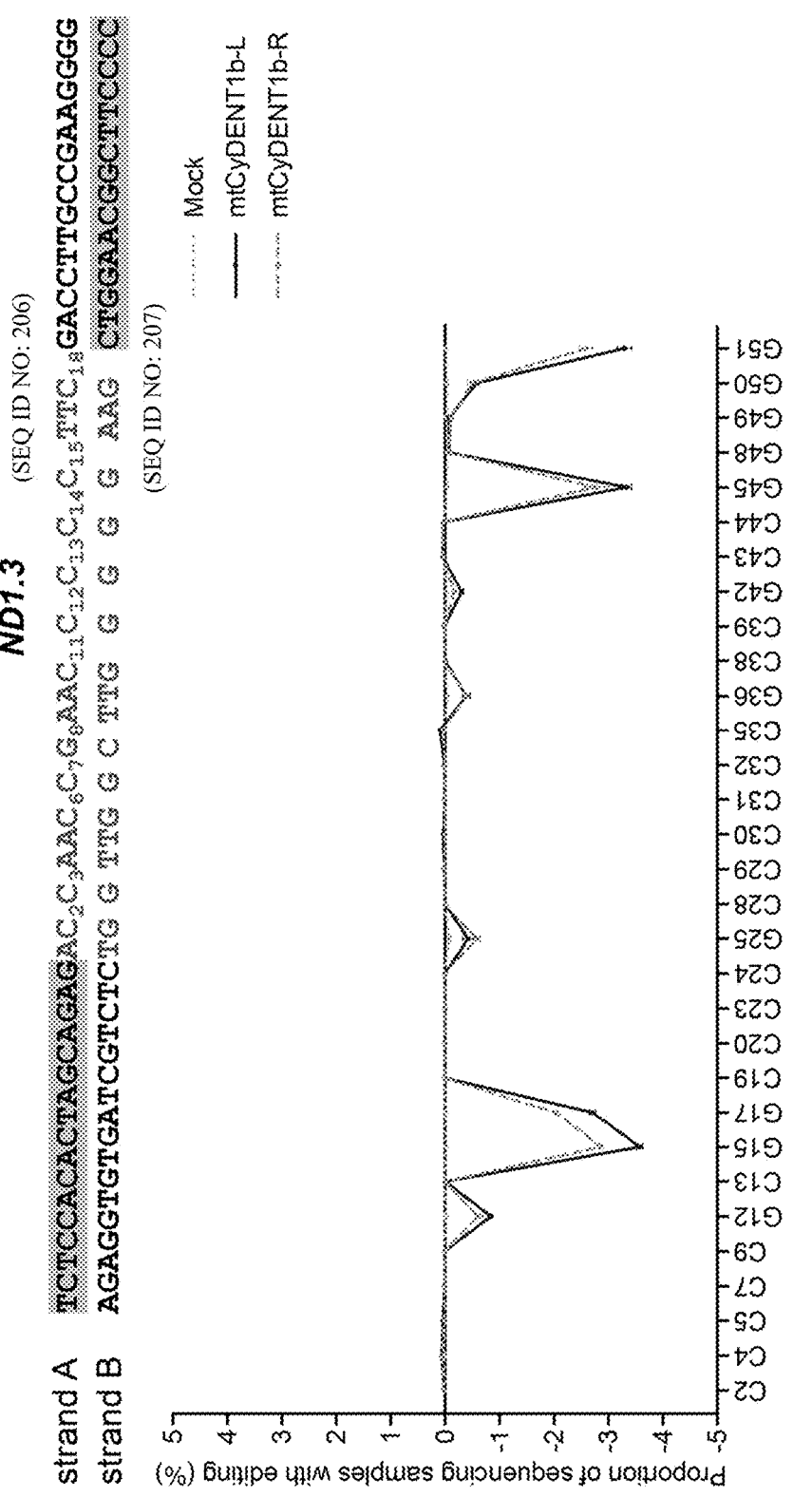
Figure 27:
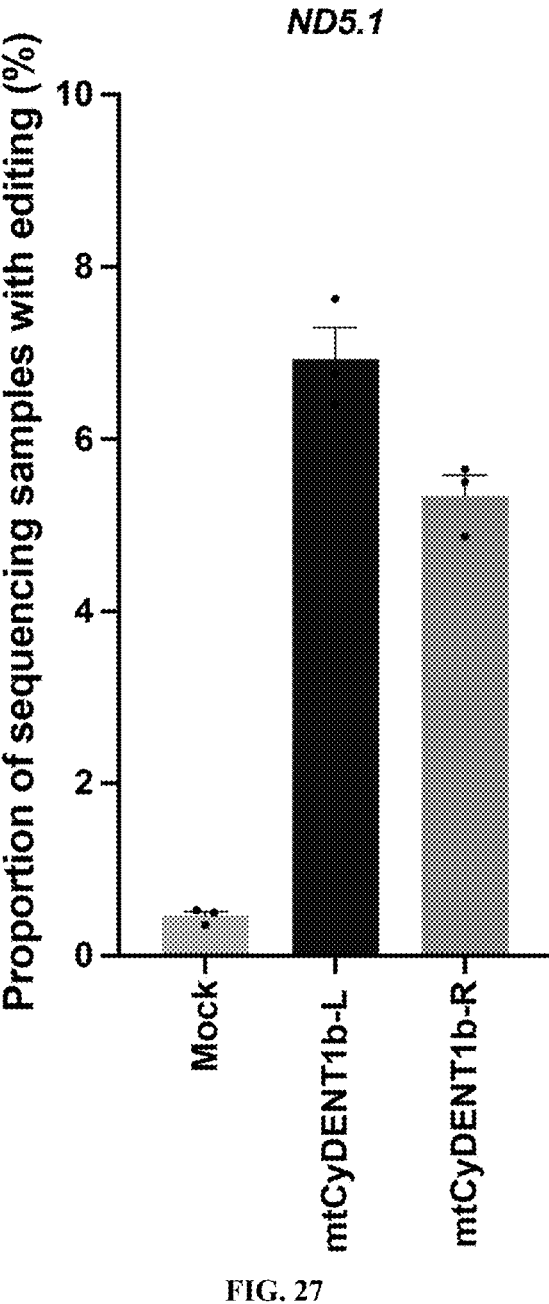
FIG. 27 shows the editing frequencies achieved by using Sdd7 deaminase mtCyDENT1b-L and mtCyDENT1b-R at the ND5.1, ND6 and ND1.3 sites in HEK293T cells.
Figure 27:
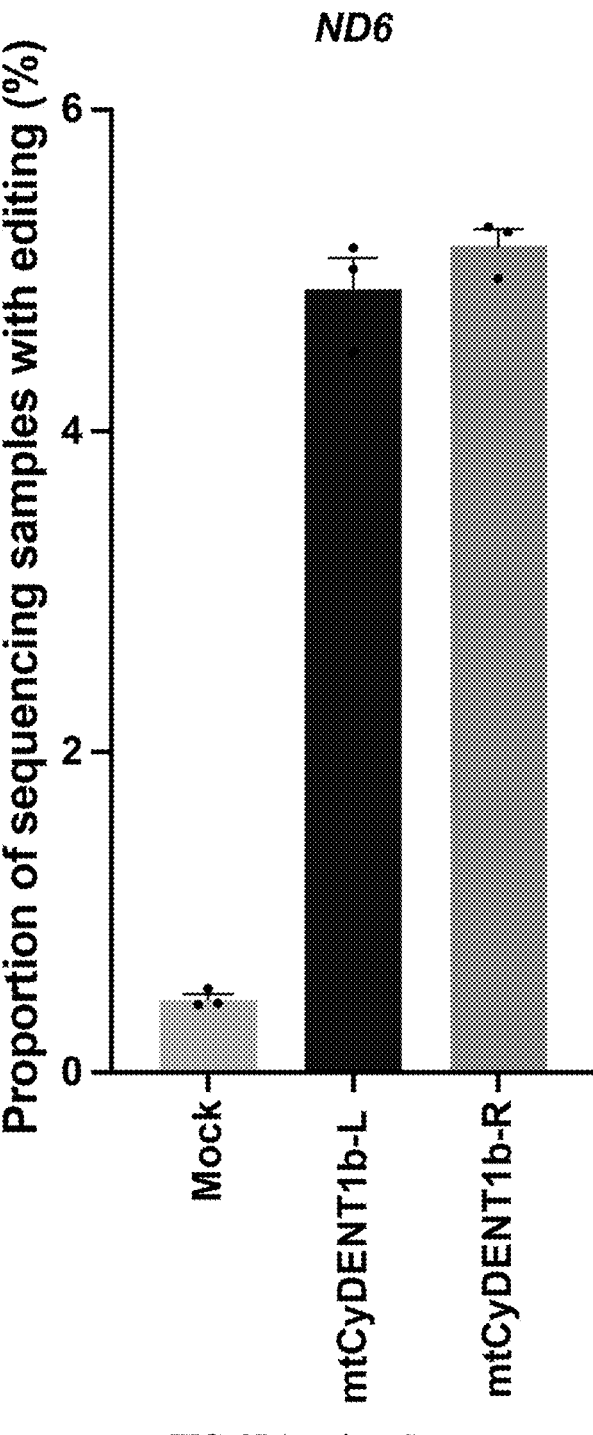
Figure 27:
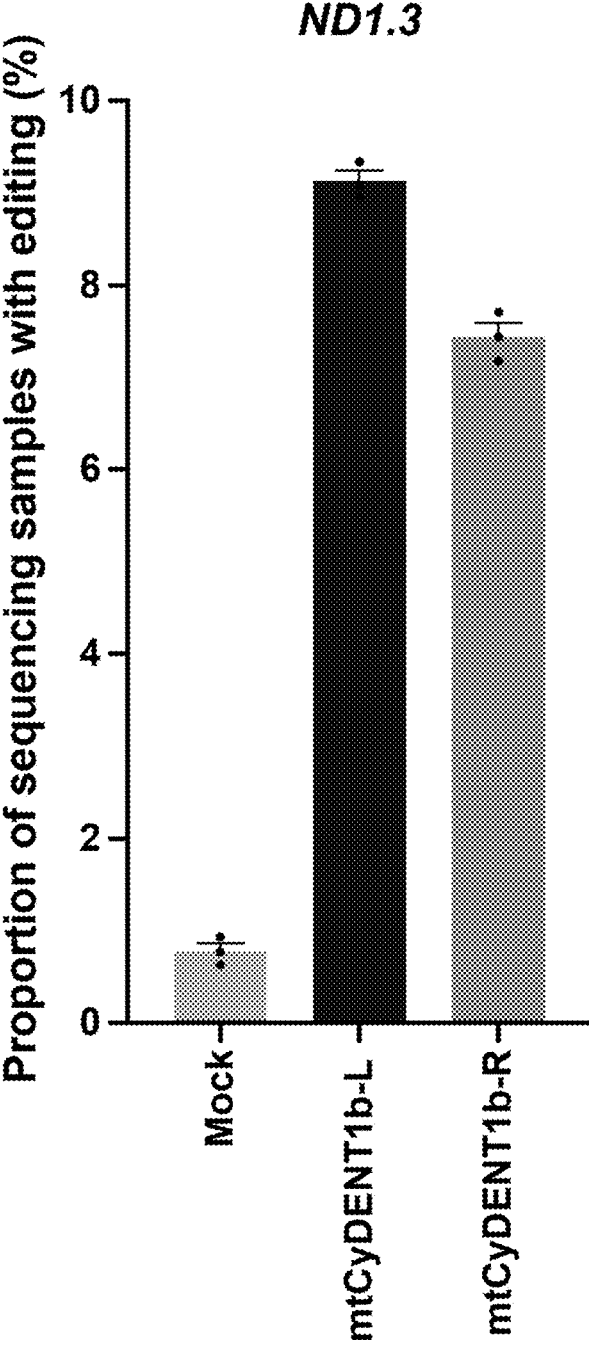

As mentioned in Example 4 above, the base editor of the present disclosure could be formed by the self-assembly of multiple functional modules and was compatible with deaminases of different types. Therefore, the deaminase domain in the base editor could be replaced with a deaminase known in the art to take advantage of the unique characteristics of each deaminase, thereby enhancing the activity or further improving the precision of editing in a strand. A newly discovered single-stranded DNA (ssDNA)-specific cytidine deaminase Sdd7 was found to have higher editing activity than other deaminases (Huang, J. et al. Discovery of new deaminase functions by structure-based protein clustering. bioRxiv (2023).). In this Example, the inventors took the mtCyDENT1b composition as an example and used Sdd7 as the deaminase of this editor, so as to evaluate the editing efficiency at the mtDNA targets ND5.1, ND6 and ND1.3. It was observed by the inventors that 87.5% of the base editing triggered by Sdd7-mtCyDENT1b-L merely occurred in one DNA strand and 93.0% of the base editing triggered by Sdd7-mtCyDENT1b-R merely occurred in one DNA strand. This result further demonstrated that CyDENT had superior strand specificity in base editing (FIG. 26). The average editing efficiency of these two editors on the target bottom strand of DNA ranged between 4.88% and 9.13% (FIG. 27).

These results further verified that the deaminase domain in the base editor of the present disclosure could be replaced during modular assembly.

Example 13: Improvements to Base Editors

In the above-mentioned Examples, the inventors had verified by experiments that the base editor composition of the present disclosure had technical advantages such as having single-strand editing specificity, being able to be formed by modular assembly, achieving efficient, precise and controllable base editing and resulting in low indel frequency. In subsequent Examples, the inventors further optimized the base editor so as to obtain a base editor composition having more superior functions.

Figure 28A:
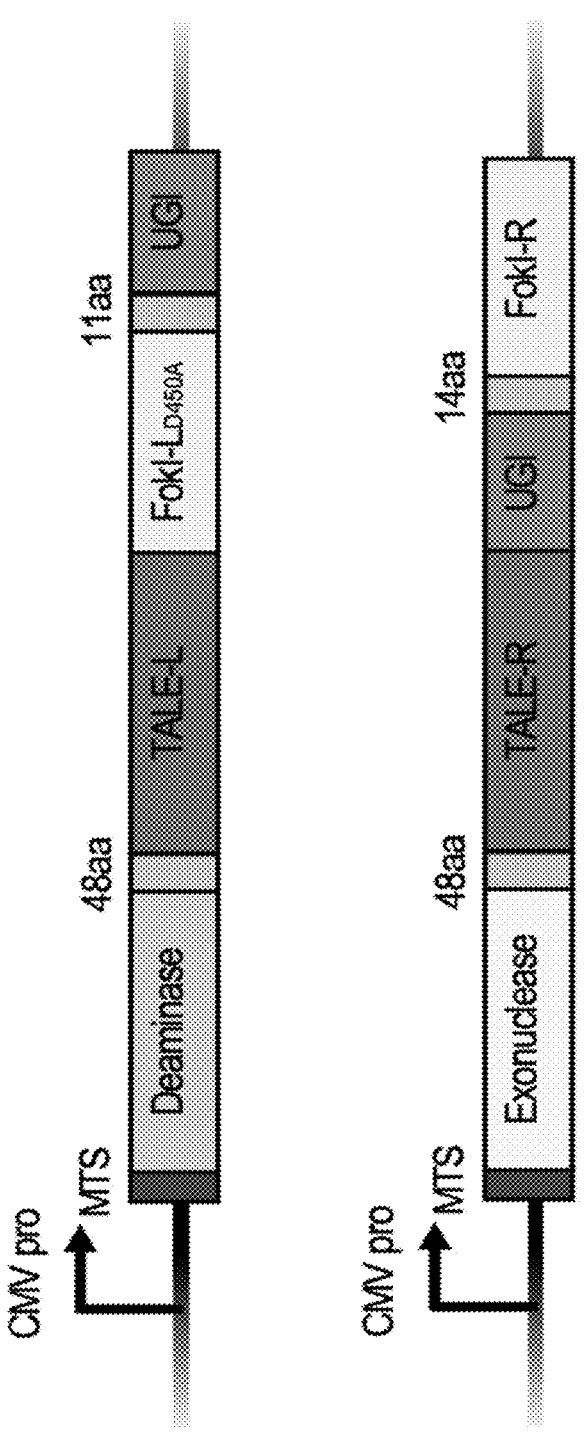
FIG. 28A is a schematic diagram of the mtCyDENT2 construct in the mitochondrial genome.

In this Example, the inventors fused the deaminase domain and the exonuclease domain to the N-termini of TALE-L and TALE-R via a 48-amino acid linker peptide (flexible linker), and UGI was fused to the C-terminal and the N-terminal of FokI-L and FokI-R, respectively. This construct architecture was referred to herein as mtCyDENT2 (FIG. 28A). The base editing effect of mtCyDENT2-L (comprising FokI-L$_{nickase}$) was determined on ND6 (FIG. 28B) and 94.5% of the base editing merely occurred in top strand, thereby reflecting good single-strand specific editing ability of CyDENT system.

Figure 28B:
FIG. 28B shows the base editing efficiency of DdCBE as well as mtCyDENT2-L and mtCyDENT2-R comprising different deaminases at the ND6 site in HEK293T cells and the ratio of various editing events.
Figure 28B:
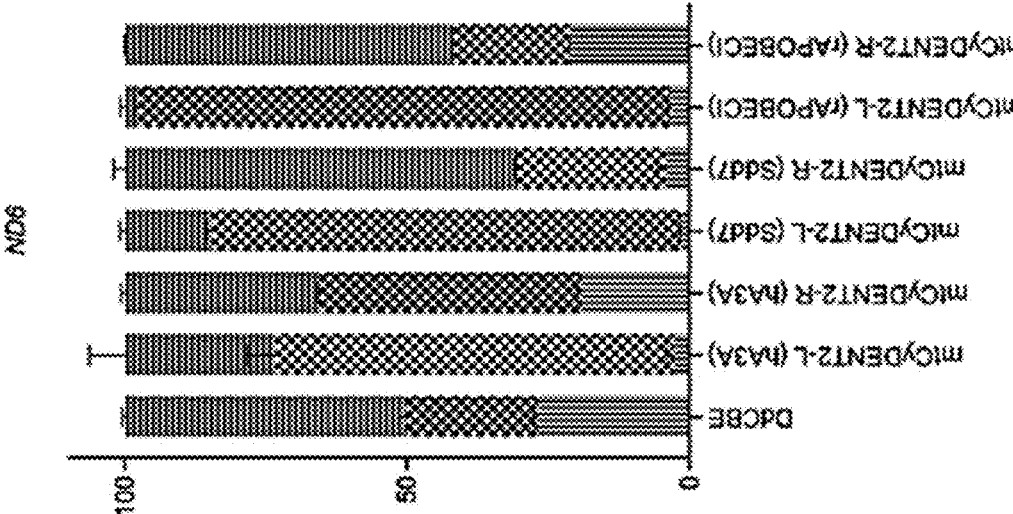
Figure 28B:
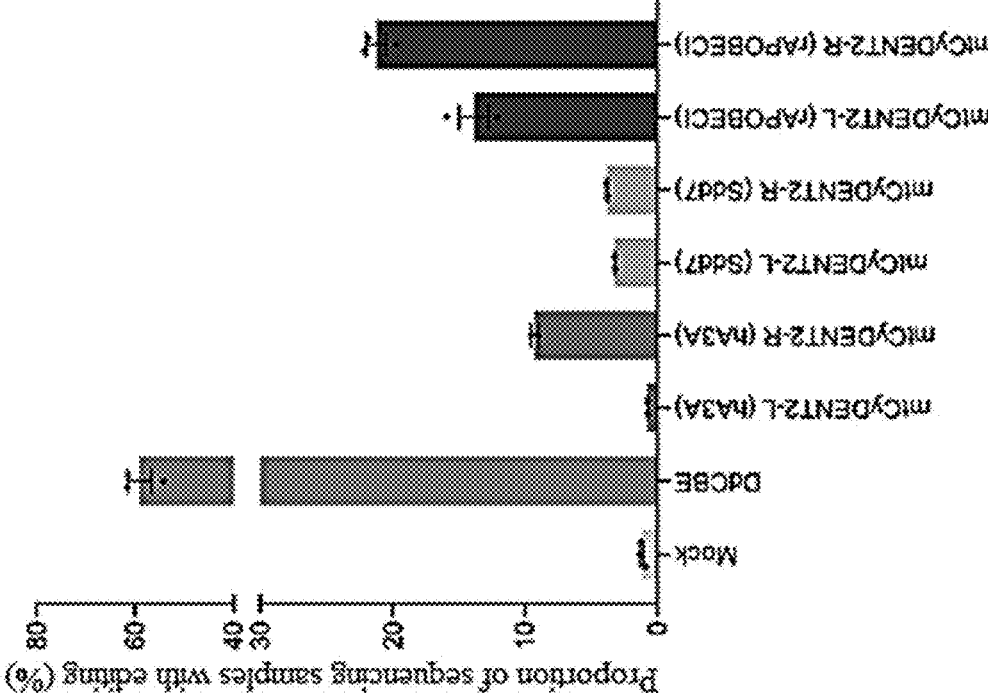

In FIGS. 28A to 28B, the experimental treatments or construct combinations involved in figures were as shown below.

| | Experimental treatments or construct combinations involved in figures |
| --- | --- |
| mtCyDENT2-L (hA3A) for ND6 target site | ND6-MTS-A3A-48aa-TALE-L-FokI-L-11aa-UGI + ND6-MTS-Trex2-48aa-TALE-R-UGI-14aa-FokI-R$_{D450A}$ |
| mtCyDENT2-L (hA3A) for ND6 target site | ND6-MTS-A3A-48aa-TALE-L-FokI-L$_{D450A}$-11aa-UGI + ND6-MTS-Trex2-48aa-TALE-R-UGI-14aa-FokI-R |
| mtCyDENT2-L (Sdd7) for ND6 target site | ND6-MTS-Sdd7-48aa-TALE-L-FokI-L-11aa-UGI + ND6-MTS-Trex2-48aa-TALE-R-UGI-14aa-FokI-R$_{D450A}$ |
| mtCyDENT2-R (Sdd7) for ND6 target site | ND6-MTS-Sdd7-48aa-TALE-L-FokI-L$_{D450A}$-11aa-UGI + ND6-MTS-Trex2-48aa-TALE-R-UGI-14aa-FokI-R |
| mtCyDENT2-L (rAPOBEC1) for ND6 target site | ND6-MTS-rAPOBEC1-48aa-TALE-L-FokI-L-11aa-UGI + ND6-MTS-Trex2-48aa-TALE-R-UGI-14aa-FokI-R$_{D450A}$ |
| mtCyDENT2-L (rAPOBEC1) for ND6 target site | ND6-MTS-rAPOBEC1-48aa-TALE-L-FokI-L$_{D450A}$-11aa-UGI + ND6-MTS-Trex2-48aa-TALE-R-UGI-14aa-FokI-R |

Example 14 Base Editing on GC-Motifs by mtCyDNET

A DddA-dependent DdCBE system had strict constraints on the context of TC-motifs for cytidine deamination, and researches had found that the frequency of occurrence of editing in the context of GC sequence was relatively low (Nakazato, I. et al. Targeted base editing in the mitochondrial genome of *Arabidopsis thaliana*. Proc. Natl. Acad. Sci. USA. 119, e2121177119 (2022).). Phage-assisted discontinuous and continuous evolution were used for the evolution of the "wild-type" DddA (Mok, B. Y et al. CRISPR-free base editors with enhanced activity and expanded targeting scope in mitochondrial and nuclear DNA. Nat. Biotechnol. 40, 1378-1387 (2022).), and the evolved DddA11 variant had better compatibility with AC and CC sequence motifs. However, there still remained challenge in the editing on GC sequence motifs by DddA11. In this Example, efficient and strand-selective editing on GC sequence motifs was achieved by using the modular replacement of the deaminase domain of CyDENT.

The inventors introduced a single-stranded DNA-specific cytidine deaminase having editing activity on GC sequence motifs, thereby developing a GC-compatible mtCyDENT base editor. Recently, a newly discovered single-stranded DNA-specific and GC- and AC-compatible cytidine deaminase Sdd3 exhibited higher editing activity on GC sequence motifs than other deaminases (Huang, J. et al. Discovery of new deaminase functions by structure-based protein clustering. bioRxiv (2023).).

Therefore, a TALE array (FIG. 29) was designed to target ND1.2 and ND6.2 sites in HEK293T cells in the present disclosure, so as to evaluate the editing preference of the sequence motifs that were difficult to edit with prior art. It was worth noting that the efficiency of strand-specific cytosine base editing on the GC sequence motifs at ND1.2 and ND6.2 sites reached 21.0% and 20.0% respectively, which was unachievable by the DdCBE in the prior art at the same target sites. At the ND1.2 site, 96.9% of the editing occurred selectively in the top strand of DNA, while at the ND6.2 site, 92.0% of the editing occurred selectively in the bottom strand of DNA (FIG. 29).

Figure 30:
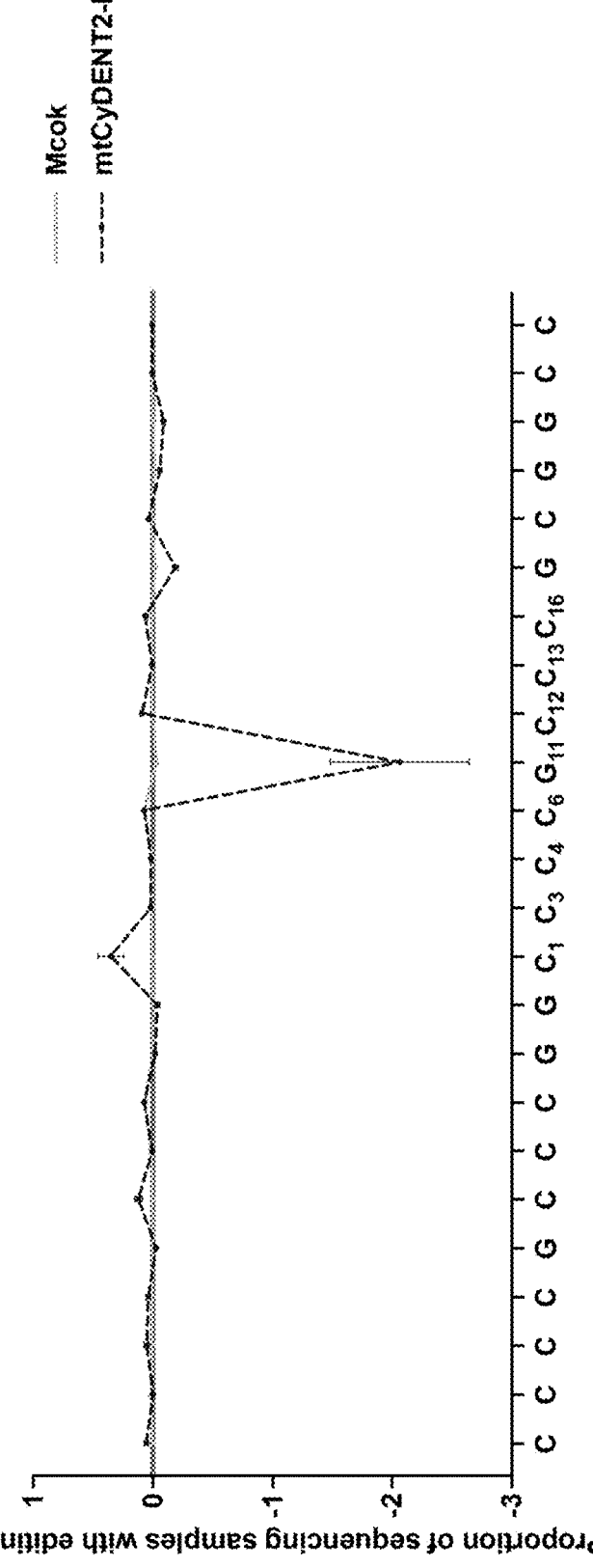
FIG. 30 shows the strand preferences in editing of mtCy-DENT2-L (Sdd3 deaminase+TALE-L1+TALE-R1) (designed for the pathogenic mutation of Leigh's syndrome at the ND6.2 site) at the ND6.2 site in HEK293T cells.

Subsequently, the inventors adjusted the TALE binding site, and observed that Sdd3-mtCyDENT had an editing efficiency of 2.06% at the ND6.2 site (FIG. 30). It was reported that such special mutation (m.14453G>A) was directly associated with the development of Leigh syndrome, and the DdCBE in the prior art, however, could not realize the editing in the context of this same target sequence. Therefore, mtCyDENT and its future optimized products could be used for a superior base editing method capable of performing precise editing on the pathogenic mutation in mtDNA.

Figure 29:
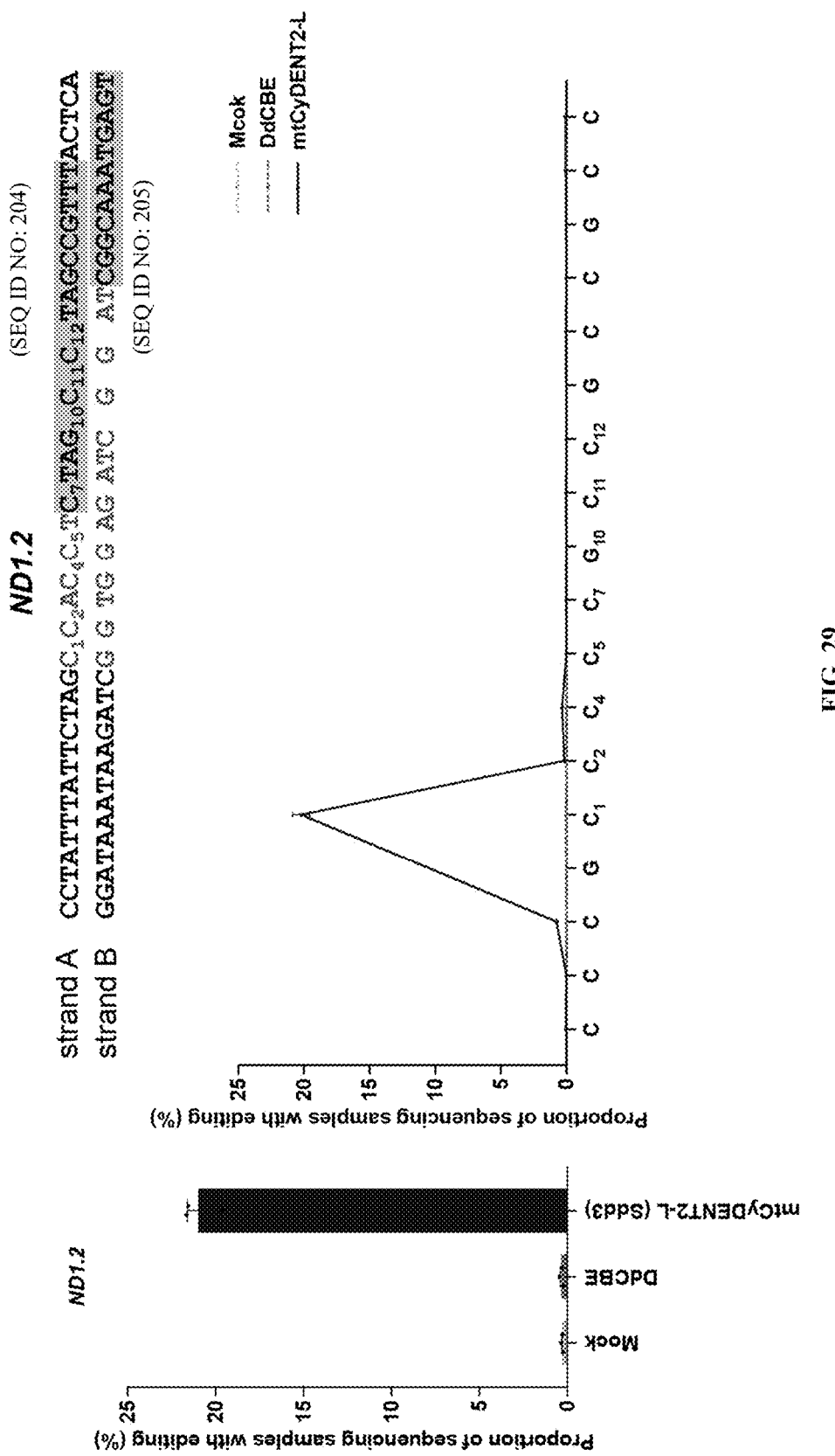
FIG. 29 shows the editing frequencies and the strand preferences in editing of DdCBE and mtCyDENT2-L comprising Sdd3 deaminase at the ND1.2 and ND6.2 sites in HEK293T cells, wherein the gray regions represent the TALE binding sites.
Figure 29:
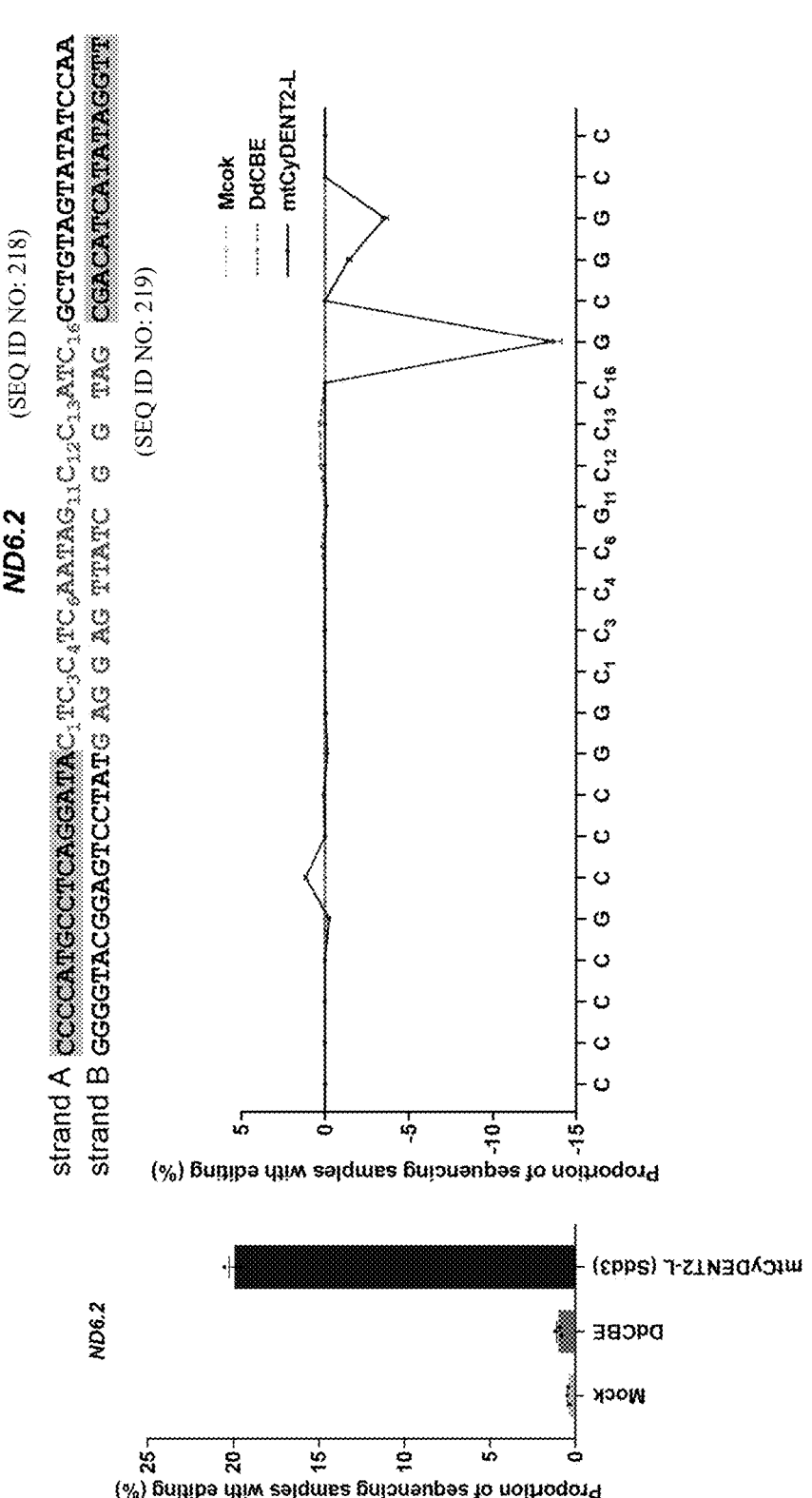

In FIGS. 29 and 30, the experimental treatments or construct combinations involved in figures were as shown below.

Example 15: Off-Target Analysis of mtCyDENT

The mitochondrial editing by DdCBE in the prior art could induce a large number of nuclear off-target editing. In order to evaluate the off-target rate of CyDENT in the entire nuclear genome and the entire mitochondrial genome, 2.25 Tb of clean bases were obtained in this Example, with an average of 281.13 Gb for each sample. The average depth of mitochondrial genome sequencing was approximately 6362 fold, and the human reference genome used was hg19.

Figure 31A:
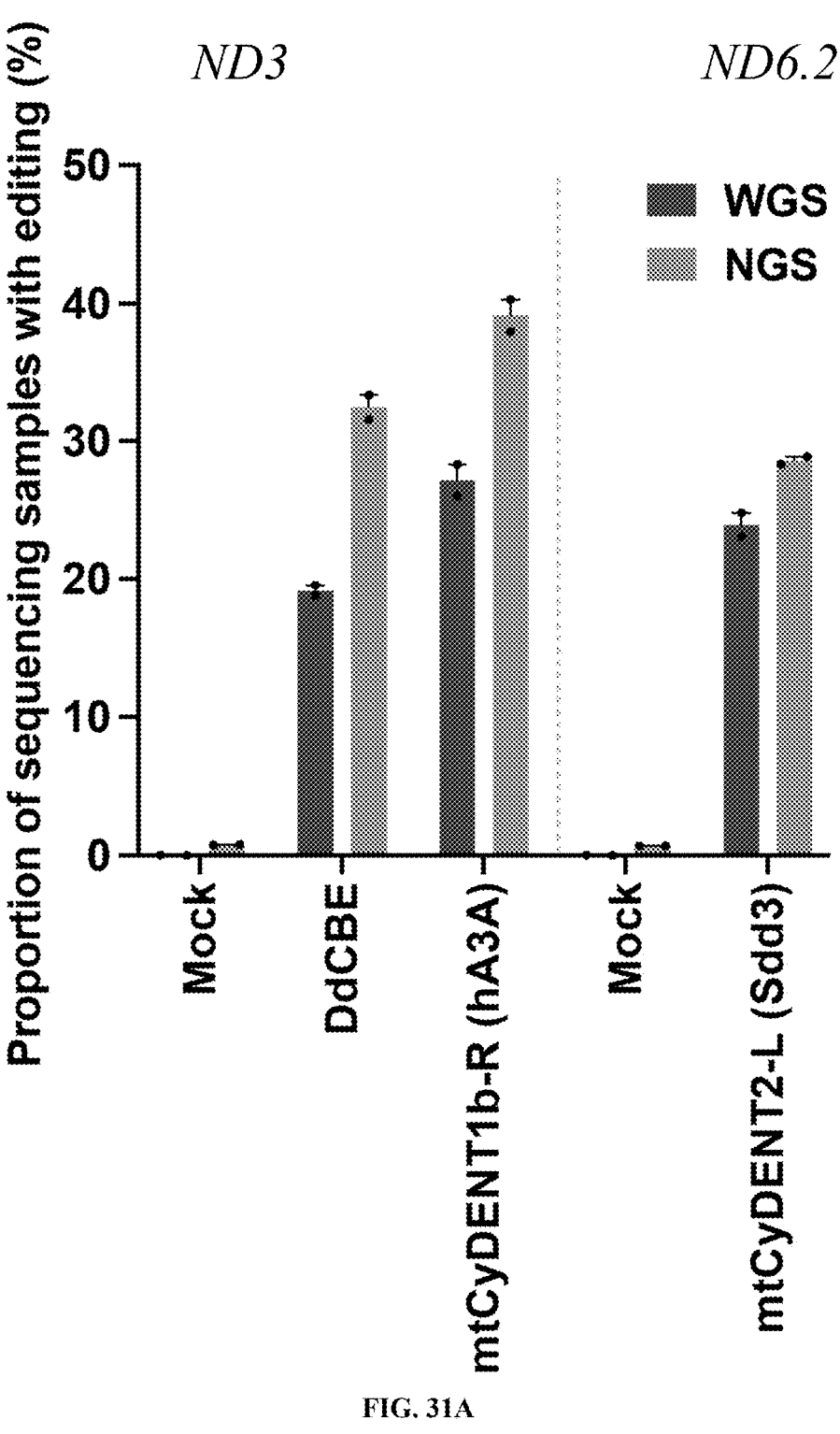
FIG. 31A shows the Whole-Genome Sequencing (WGS) analysis and Next-Generation Sequencing (NGS) analysis of the editing frequencies at the target sites ND3 and ND6.2.

In this Example, the DdCBE plasmid and the mtCyDENT1b-R (hA3A) plasmid targeting ND3 and the mtCyDENT2-L (Sdd3) plasmid targeting ND6.2 were designed to transfect HEK293T cells, and these plasmids were capable of perform editing on GC sequence motifs, as demonstrated by the whole genome sequencing (WGS) and NGS analysis (FIG. 31A). Subsequently, the off-target rates in the whole mitochondrial genome and the whole nuclear genome were analyzed. The results indicated that the average frequencies of C·G-to-T·A and G·C-to-A·T base conversion in the entire mitochondrial genome in the untreated negative control group, DdCBE treatment group, mtCyDENT1b-R (hA3A) treatment group and mtCyDENT2-L (Sdd3) treatment group were 4.8%, 6.9%, 16.5% and 5.9%, respectively. Compared with the control group, the inventors found an average of 32, 678 and 16 single nucleotide variations (SNVs) in the mitochondrial genome in DdCBE treatment group, mtCyDENT1b-R (hA3A) treatment group and mtCyDENT2-L (Sdd3) treatment group, respectively. By analyzing the 5-bp regions upstream and downstream of each potential off-target SNV, conserved TC-motifs were found inDdCBE group and mtCyDENT1b-R (hA3A) group, while conserved GC/AC-motifs were found in mtCyDENT2-L (Sdd3) group (FIG. 31B).

The inventors analyzed the TALE-dependent off-target effects in the nuclear genome. A total of 74963 potential off-target regions (comprising 0 to 3 regions that mismatched with the TALE binding site in ND3 and ND6.2) were identified. It was observed by the inventors that there was no difference in SNV allele frequency and indel frequency at ND3 site or ND6.2 site in the control group, DdCBE treatment group, mtCyDENT1b-R (hA3A) treatment group and mtCyDENT2-L (Sdd3) treatment group (FIG. 31C). These results indicated that the modular assembly and optimization of CyDENT were capable of reducing the off-target effects in mitochondrial and nuclear genomes to the largest extent. mtCyDENT was a valuable tool for mitochondrial genome editing.

Figure 31B:
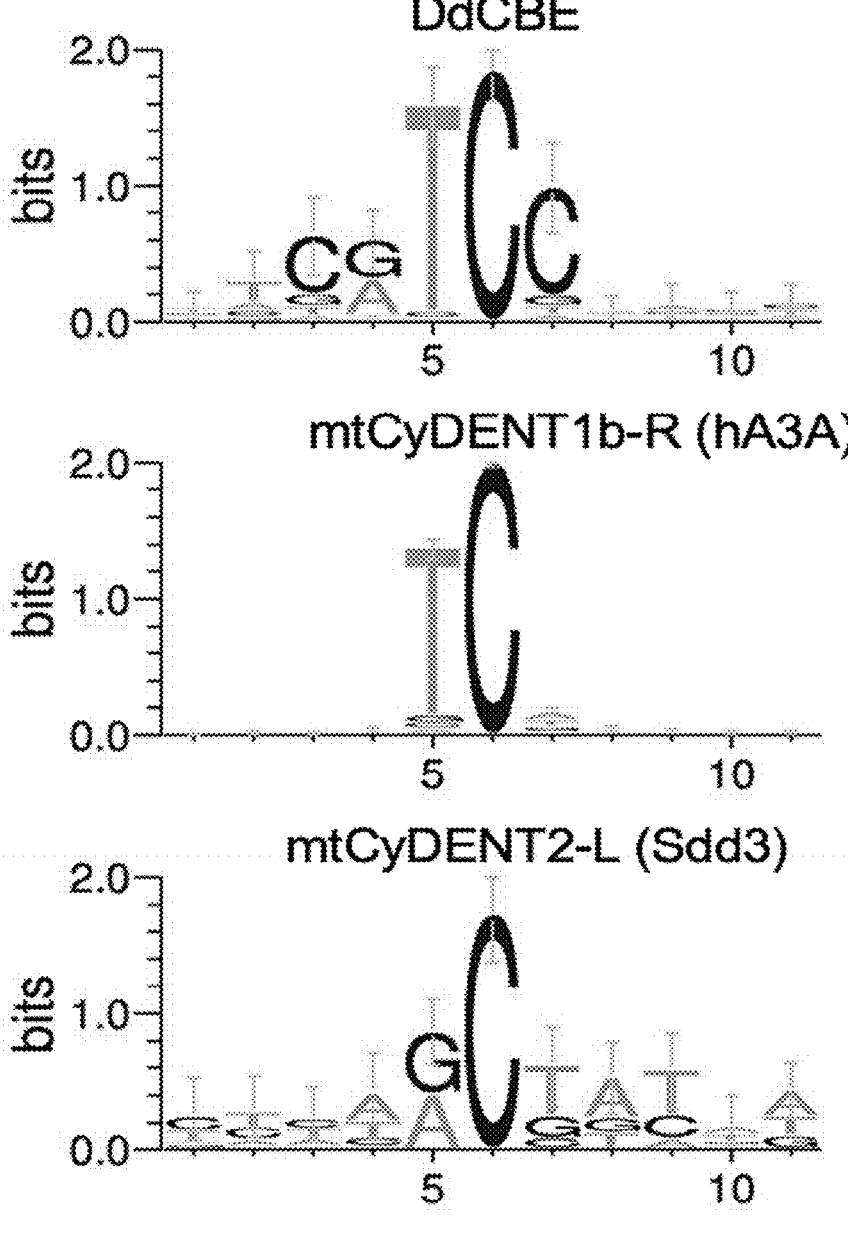
FIG. 31B shows the Logo diagram of the off-target C:G to T:A base conversion and G:C to A:T base conversion of each editor.
Figure 31C:
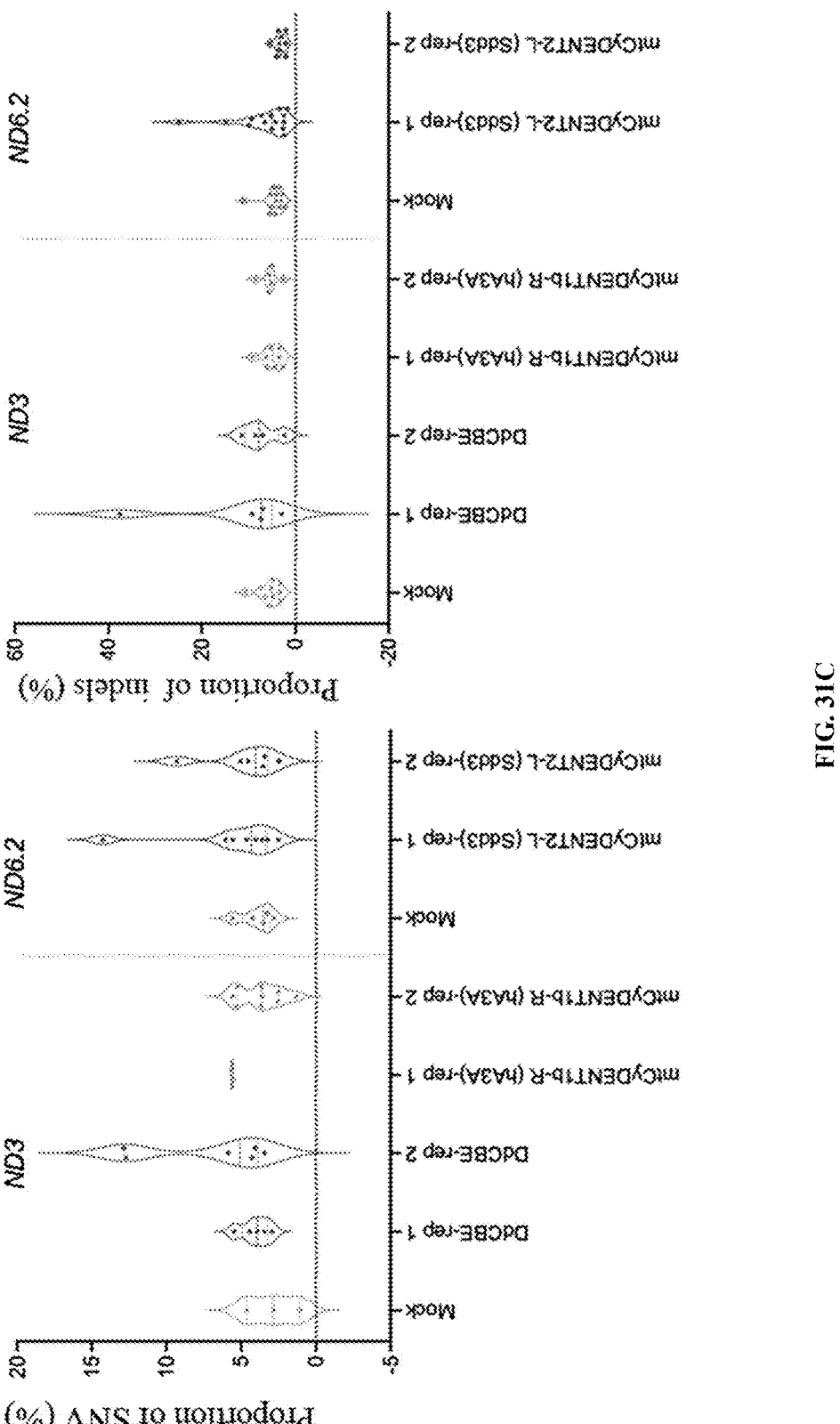
FIG. 31C shows the SNV frequency distribution and indel frequency distribution in potential TALE-dependent off-target sites.

In FIGS. 31A to 31C, the experimental treatments or construct combinations involved in figures were as shown below.

| | Experimental treatments or construct combinations involved in the Example |
|---|---|
| mtCyDENT2-L (Sdd3) for ND1.2 target site | ND1.2-MTS-Sdd3-48aa-TALE-L-FokI-L-11aa-UGI + ND1.2-MTS-Trex2-48aa-TALE-R-UGI-14aa-FokI-R$_{D450A}$ |
| mtCyDENT2-L (Sdd3) for ND6.2 target site | ND6.2-MTS-Sdd3-48aa-TALE-L-FokI-L-11aa-UGI + ND6.2-MTS-Trex2-48aa-TALE-R-UGI-14aa-FokI-R$_{D450A}$ |
| DdCBE for ND1.2 target site | ND1.2-MTS-TALE-L-DddA$_N$-UGI + ND1.2-MTS-TALE-R-DddA$_C$-UGI |
| DdCBE for ND6.2 target site | ND6.2-MTS-TALE-L-DddA$_N$-UGI + ND6.2-MTS-TALE-R-DddA$_C$-UGI |

| | Experimental treatments or construct combinations involved in figures |
| --- | --- |
| Mt CyDENT 1b-R (hA3A) for ND3 target site | ND3-MTS-TALE-L-FokI-L$_{D450A}$ + ND3-MTS-TALE-R-FokI-R + MTS-A3A + MTS-γb-Trex2 + MTS-γb-UGI |
| Mt CyDENT 2-L (Sdd3) for ND6.2 target site | ND6.2-MTS-Sdd3-48aa-TALE-L-FokI-L-11aa-UGI + ND6.2-MTS-Trex2-48aa-TALE-R-UGI-14aa-FokI-R$_{D450A}$ |
| DdCBE for ND3 target site | ND3-MTS-TALE-L-DddA$_N$-UGI + ND3-MTS-TALE-R-DddA$_C$-UGI |
| DdCBE for ND6.2 target site | ND6.2-MTS-TALE-L-DddA$_N$-UGI + ND6.2-MTS-TALE-R-DddA$_C$-UGI |

15

The illustration of the Examples above is merely intended to facilitate the understanding of the methods and the gists of the present disclosure. It should be noted that, a number of improvements and modifications may also be made to the present disclosure by those of ordinary skill in the art under the premise of not departing from the principles of the present disclosure, and these improvements and modifications also fall within the protection scope of the claims of the present disclosure.

What is claimed is:

1. A nucleic acid base editor system, comprising that comprises:
   a) a sequence-specific DNA binding protein;
   b) a nickase that nicks a DNA strand;
   c) an exonuclease;
   d) a base-specific deaminase; and
   e) γb;
   wherein the γb constitutes at least one fusion protein with other elements of the nucleic acid base editor system;
   wherein the nickase is a dimer of a cleavage domain monomer of FokI (FokICD) or a mutant of the dimer, wherein the dimer of the cleavage domain monomer of FokI (FokICD) or the mutant of the dimer comprises a pair of interacting cleavage domain monomers of FokI (FokICD), and wherein the dimer of the cleavage domain monomer of FokI (FokICD) or the mutant of the dimer has only a single cleavage domain monomer of FokI (FokICD) which has DNA endonuclease activity;
   wherein the cleavage domain monomer of FokI (FokICD) having DNA endonuclease activity is a FokI-L protein having a sequence identified as SEQ ID NO.87 or a FokI-R protein having a sequence identified as SEQ ID NO.88;
   wherein the cleavage domain monomer of FokI (FokICD) having no DNA endonuclease activity is a FokI-L$_{D450A}$ protein having a sequence identified as SEQ ID NO.60, a FokI-L$_{D467A}$ protein having a sequence identified as SEQ ID NO.61, a FokI-RD450A protein having a sequence identified as SEQ ID NO.62, or a FokI-RD467A protein having a sequence identified as SEQ ID NO.63;
   wherein the exonuclease digests the nicked DNA strand from the nick to produce a nicked single-stranded DNA; and
   wherein the base-specific deaminase catalyzes specifically on the single-stranded DNA that is complementary to the nicked single-stranded DNA.

2. The nucleic acid base editor system according to claim 1, wherein the sequence-specific DNA binding protein is one or more selected from the group consisting of a TALE protein, a ZFA protein, a Cas protein and a meganuclease.

3. The nucleic acid base editor system according to claim 2, wherein the sequence-specific DNA binding protein is a TALE protein.

4. The nucleic acid base editor system according to claim 1, wherein the FokICD having DNA endonuclease activity is SEQ ID NO. 87 and the FokICD having no DNA endonuclease activity is SEQ ID NO. 62 or SEQ ID NO. 63; or the FokICD having DNA endonuclease activity is SEQ ID NO. 88 and the FokICD having no DNA endonuclease activity is SEQ ID NO. 60 or SEQ ID NO. 61.

5. The nucleic acid base editor system according to claim 1, wherein the base-specific deaminase is a cytidine-specific deaminase or an adenosine-specific deaminase.

6. The nucleic acid base editor system according to claim 5, wherein the exonuclease is exonuclease V, mTrex2, mArtimes, or T5 exo.

7. The nucleic acid base editor system according to claim 1, wherein the base-specific deaminase is a cytidine-specific deaminase.

8. The nucleic acid base editor system according to claim 7, wherein the cytidine-specific deaminase is one or more selected from the group consisting of hAPOBEC3A, rAPOBEC1, hAID, and pmCDA1 and Sdd deaminase.

9. The nucleic acid base editor system according to claim 7, wherein the nucleic acid base editor system further comprises:
   f) a uracil glycosylase inhibitor (UGI);
   wherein the uracil glycosylase inhibitor exists alone or constitutes at least one fusion protein with other elements of the nucleic acid base editor system.

10. The nucleic acid base editor system according to claim 1, wherein the base-specific deaminase is an adenosine-specific deaminase.

11. The nucleic acid base editor system according to claim 10, wherein the adenosine-specific deaminase is TadA-8e.

12. The nucleic acid base editor system according to claim 1, wherein each element of the nucleic acid base editor system constitutes one or more fusion proteins.

13. The nucleic acid base editor system according to claim 12, wherein:
   (1) the one or more fusion proteins comprises:
   a first fusion protein comprising in linear order from the protein's amino terminus a mitochondrial targeting sequence (MTS); a TALE-L protein; the FokICD having the SEQ ID NO.87, SEQ ID NO.60, or SEQ ID NO.61;
   a second fusion protein comprising in linear order from the protein's amino terminus the mitochondrial targeting sequence (MTS); a TALE-R protein; and the FokICD having the SEQ ID NO.88, SEQ ID NO.62, or SEQ ID NO.63;
   a third fusion protein comprising in linear order from the protein's amino terminus the mitochondrial targeting sequence (MTS) and the exonuclease;
   a fourth fusion protein comprising in linear order from the protein's amino terminus the mitochondrial targeting sequence (MTS) and the base-specific deaminase; and
   a fifth fusion protein comprising in linear order from the protein's amino terminus the mitochondrial targeting sequence (MTS) and an uracil glycosylase inhibitor (UGI),
   wherein the γb is present in at least one of the first, second, third, fourth or fifth fusion proteins, wherein the TALE-L and TALE-R proteins are the sequence-specific DNA binding proteins;
   (2) the one or more fusion proteins comprises:
   a first fusion protein comprising in linear order from the protein's amino terminus a mitochondrial targeting sequence (MTS); a TALE-L protein; and the FokICD having the SEQ ID NO.87, SEQ ID NO.60, or SEQ ID NO.61;

a second fusion protein comprising in linear order from the protein's amino terminus the mitochondrial targeting sequence (MTS); a TALE-R protein; and the FokICD having the SEQ ID NO.88, SEQ ID NO.62, or SEQ ID NO.63;

a third fusion protein comprising in linear order from the protein's amino terminus the mitochondrial targeting sequence (MTS), the γb and the exonuclease;

a fourth fusion protein comprising in linear order from the protein's amino terminus the mitochondrial targeting sequence (MTS) and the base-specific deaminase; and a fifth fusion protein comprising in linear order from the protein's amino terminus the mitochondrial targeting sequence (MTS), the γb and an uracil glycosylase inhibitor (UGI), wherein the TALE-L and TALE-R proteins are the sequence-specific DNA binding proteins;

(3) the one or more fusion proteins comprises:

a first fusion protein comprising a mitochondrial targeting sequence (MTS); a sequence-specific DNA binding protein; and a nickase;

a second fusion protein comprising the exonuclease; and the mitochondrial targeting sequence (MTS); and a third fusion protein comprising the base-specific deaminase; a uracil glycosylase inhibitor (UGI); and the mitochondrial targeting sequence (MTS), wherein the γb is present in at least one of the first, second or third fusion proteins;

(4) the one or more fusion proteins comprises:

a first fusion protein comprising in linear order from the protein's amino terminus a mitochondrial targeting sequence (MTS); a TALE-L protein; the FokICD having the SEQ ID NO.60 or SEQ ID NO.61; a T2A sequence; the mitochondrial targeting sequence (MTS); a TALE-R protein; and the FokICD having the SEQ ID NO.88; or comprising in linear order from the protein's amino terminus the mitochondrial targeting sequence (MTS); a TALE-L protein; the FokICD having the SEQ ID NO.87; a T2A sequence; the MTS; a TALE-R protein; and the FokICD having the SEQ ID NO.62 or SEQ ID NO.63;

a second fusion protein comprising in linear order from the protein's amino terminus the mitochondrial targeting sequence (MTS); and the exonuclease;

and a third fusion protein comprising in linear order from the protein's amino terminus the mitochondrial targeting sequence (MTS); the base-specific deaminase; an XTEN linker peptide; and an uracil glycosylase inhibitor (UGI), wherein the γb is present in at least one of the first, second or third fusion proteins, wherein the TALE-L and TALE-R proteins are the sequence-specific DNA binding proteins; or (5) the one or more fusion proteins comprises:

a first fusion protein comprising in linear order from the protein's amino terminus a mitochondrial targeting sequence (MTS); the base-specific deaminase; a 48-amino acid linker peptide; a TALE-L protein; the FokICD having the SEQ ID NO.87, SEQ ID NO.60, or SEQ ID NO.61; an 11-amino acid linker peptide; and an uracil glycosylase inhibitor (UGI); and a second fusion protein comprising in linear order from the protein's amino terminus a mitochondrial targeting sequence (MTS); a 48-amino acid linker peptide; a TALE-R, the uracil glycosylase inhibitor (UGI); a 14-amino acid linker peptide; and the FokICD having the SEQ ID NO.88, SEQ ID NO.62, or SEQ ID NO.63, wherein the γb is present in at least one of the first and second fusion proteins, wherein the TALE-L and TALE-R proteins are the sequence-specific DNA binding proteins.

14. The nucleic acid base editor system according to claim 12, wherein the fusion proteins comprise:

a first fusion protein comprising in linear order from the protein's amino terminus a mitochondrial targeting sequence (MTS); a base-specific deaminase; a TALE-L protein; the FokICD having the SEQ ID NO.87, SEQ ID NO.60, or SEQ ID NO.61; a T2A sequence; a mitochondrial targeting sequence (MTS); a TALE-R protein; and the FokICD having the SEQ ID NO.88, SEQ ID NO.62, or SEQ ID NO.63;

a second fusion protein comprising an exonuclease and the mitochondrial targeting sequence (MTS); and a third fusion protein comprising an uracil glycosylase inhibitor (UGI) and the mitochondrial targeting sequence (MTS), wherein the γb is present in at least one of the first, second or third fusion proteins, wherein the TALE-L and TALE-R proteins are the sequence-specific DNA binding proteins.

15. A method of performing nucleic acid base editing in a mammalian cell, wherein the nucleic acid base editor system of claim 1 is introduced into the cell and a target gene is edited thereby.

16. The method of nucleic acid base editing according to claim 15, wherein the target gene is a mitochondrial genomic DNA.

17. The method of nucleic acid base editing according to claim 15, wherein the target gene is a mitochondrial genomic DNA, and the nucleic acid base editor system further comprises a mitochondrial targeting sequence (MTS).

18. The method of nucleic acid base editing according to claim 15, wherein the mammalian cell is a germ cell, a neuron, a muscle cell, an endocrine cell, an exocrine cell, an epithelial cell, a muscle cell, a tumor cell, an embryonic cell, a hematopoietic cell, an osteocyte, a germplasm cell, a somatic cell, a stem cell, a pluripotent stem cell, an induced pluripotent stem cell, a progenitor cell, a meiotic cell, or a mitotic cell of human.

19. A recombinant expression construct that comprises nucleic acids encoding a nucleic acid base editor system, wherein the nucleic acid base editor system comprises:

a) a sequence-specific DNA binding protein;

b) a nickase that nicks a DNA strand;

c) an exonuclease;

d) a base-specific deaminase; and e) γb;

wherein the γb constitutes at least one fusion protein with other elements of the nucleic acid base editor system wherein the nickase is a dimer of a cleavage domain monomer of FokI (FokICD) or a mutant of the dimer, wherein the dimer of the cleavage domain monomer of FokI (FokICD) or the mutant of the dimer comprises a pair of interacting cleavage domain monomers of FokI (FokICD), and wherein the dimer of the cleavage domain monomer of FokI (FokICD) or the mutant of the dimer has only a single cleavage domain monomer of FokI (FokICD) which has DNA endonuclease activity;

wherein the cleavage domain monomer of FokI (FokICD) having DNA endonuclease activity is a FokI-L protein having a sequence identified as SEQ ID NO.87 or a FokI-R protein having a sequence identified as SEQ ID NO.88;

wherein the cleavage domain monomer of FokI (FokICD) having no DNA endonuclease activity is a FokI-LD450A protein having a sequence identified as SEQ ID NO.60, a FokI-LD467A protein having a sequence identified as SEQ ID NO.61, a FokI-RD450A protein having a sequence identified as SEQ ID NO.62, or a FokI-RD467A protein having a sequence identified as SEQ ID NO.63;

wherein the exonuclease digests the nicked DNA strand from the nick to produce a nicked single-stranded DNA; and wherein the base-specific deaminase catalyzes specifically on the single-stranded DNA that is complementary to the nicked single-stranded DNA.

20. A non-human or isolated genetically engineered cell comprising the recombinant expression construct of claim 19.

\* \* \* \* \*

SEQUENCE LISTING

```
Sequence total quantity: 219
SEQ ID NO: 1            moltype = AA  length = 137
FEATURE                 Location/Qualifiers
source                  1..137
                        mol_type = protein
                        organism = synthetic construct
SEQUENCE: 1
MVDLRTLGYS QQQQEKIKPK VRSTVAQHHE ALVGHGFTHA HIVALSQHPA ALGTVAVTYQ  60
HIITALPEAT HEDIVGVGKQ WSGARALEAL LTDAGELRGP PLQLDTGQLV KIAKRGGVTA  120
MEAVHASRNA LTGAPLN                                                 137

SEQ ID NO: 2            moltype = AA  length = 63
FEATURE                 Location/Qualifiers
source                  1..63
                        mol_type = protein
                        organism = synthetic construct
SEQUENCE: 2
SIVAQLSRPD PALAALTNDH LVALACLGGR PAMDAVKKGL PHAPELIRRV NRRIGERTSH  60
RVA                                                               63

SEQ ID NO: 3            moltype = AA  length = 34
FEATURE                 Location/Qualifiers
source                  1..34
                        mol_type = protein
                        organism = synthetic construct
SEQUENCE: 3
LTPDQVVAIA SNNGGKQALE TVQRLLPVLC QDHG                              34

SEQ ID NO: 4            moltype = AA  length = 34
FEATURE                 Location/Qualifiers
source                  1..34
                        mol_type = protein
                        organism = synthetic construct
SEQUENCE: 4
LTPDQVVAIA SHDGGKQALE TVQRLLPVLC QDHG                              34

SEQ ID NO: 5            moltype = AA  length = 34
FEATURE                 Location/Qualifiers
source                  1..34
                        mol_type = protein
                        organism = synthetic construct
SEQUENCE: 5
LTPDQVVAIA SNGGGKQALE TVQRLLPVLC QDHG                              34

SEQ ID NO: 6            moltype = AA  length = 34
FEATURE                 Location/Qualifiers
source                  1..34
                        mol_type = protein
                        organism = synthetic construct
SEQUENCE: 6
LTPDQVVAIA SNNGGKQALE TVQRLLPVLC QDHG                              34
```

-continued

```
SEQ ID NO: 7            moltype = AA   length = 34
FEATURE                 Location/Qualifiers
source                  1..34
                        mol_type = protein
                        organism = synthetic construct
SEQUENCE: 7
LTPDQVVAIA SNNGGKQALE TVQRLLPVLC QDHG                                34

SEQ ID NO: 8            moltype = AA   length = 34
FEATURE                 Location/Qualifiers
source                  1..34
                        mol_type = protein
                        organism = synthetic construct
SEQUENCE: 8
LTPDQVVAIA SNIGGKQALE TVQRLLPVLC QDHG                                34

SEQ ID NO: 9            moltype = AA   length = 34
FEATURE                 Location/Qualifiers
source                  1..34
                        mol_type = protein
                        organism = synthetic construct
SEQUENCE: 9
LTPDQVVAIA SNGGGKQALE TVQRLLPVLC QDHG                                34

SEQ ID NO: 10           moltype = AA   length = 34
FEATURE                 Location/Qualifiers
source                  1..34
                        mol_type = protein
                        organism = synthetic construct
SEQUENCE: 10
LTPDQVVAIA SNNGGKQALE TVQRLLPVLC QDHG                                34

SEQ ID NO: 11           moltype = AA   length = 34
FEATURE                 Location/Qualifiers
source                  1..34
                        mol_type = protein
                        organism = synthetic construct
SEQUENCE: 11
LTPDQVVAIA SHDGGKQALE TVQRLLPVLC QDHG                                34

SEQ ID NO: 12           moltype = AA   length = 34
FEATURE                 Location/Qualifiers
source                  1..34
                        mol_type = protein
                        organism = synthetic construct
SEQUENCE: 12
LTPDQVVAIA SNGGGKQALE TVQRLLPVLC QDHG                                34

SEQ ID NO: 13           moltype = AA   length = 34
FEATURE                 Location/Qualifiers
source                  1..34
                        mol_type = protein
                        organism = synthetic construct
SEQUENCE: 13
LTPDQVVAIA SNGGGKQALE TVQRLLPVLC QDHG                                34

SEQ ID NO: 14           moltype = AA   length = 34
FEATURE                 Location/Qualifiers
source                  1..34
                        mol_type = protein
                        organism = synthetic construct
SEQUENCE: 14
LTPDQVVAIA SNGGGKQALE TVQRLLPVLC QDHG                                34

SEQ ID NO: 15           moltype = AA   length = 34
FEATURE                 Location/Qualifiers
source                  1..34
                        mol_type = protein
                        organism = synthetic construct
SEQUENCE: 15
LTPDQVVAIA SNNGGKQALE TVQRLLPVLC QDHG                                34

SEQ ID NO: 16           moltype = AA   length = 34
FEATURE                 Location/Qualifiers
source                  1..34
                        mol_type = protein
                        organism = synthetic construct
SEQUENCE: 16
LTPDQVVAIA SNIGGKQALE TVQRLLPVLC QDHG                                34
```

```
SEQ ID NO: 17            moltype = AA   length = 34
FEATURE                  Location/Qualifiers
source                   1..34
                         mol_type = protein
                         organism = synthetic construct
SEQUENCE: 17
LTPDQVVAIA SNNGGKQALE TVQRLLPVLC QDHG                                34

SEQ ID NO: 18            moltype = AA   length = 34
FEATURE                  Location/Qualifiers
source                   1..34
                         mol_type = protein
                         organism = synthetic construct
SEQUENCE: 18
LTPDQVVAIA SNGGGKQALE TVQRLLPVLC QDHG                                34

SEQ ID NO: 19            moltype = AA   length = 20
FEATURE                  Location/Qualifiers
source                   1..20
                         mol_type = protein
                         organism = synthetic construct
SEQUENCE: 19
LTPDQVVAIA SNIGGKQALE                                                20

SEQ ID NO: 20            moltype = AA   length = 34
FEATURE                  Location/Qualifiers
source                   1..34
                         mol_type = protein
                         organism = synthetic construct
SEQUENCE: 20
LTPDQVVAIA SNNGGKQALE TVQRLLPVLC QDHG                                34

SEQ ID NO: 21            moltype = AA   length = 34
FEATURE                  Location/Qualifiers
source                   1..34
                         mol_type = protein
                         organism = synthetic construct
SEQUENCE: 21
LTPDQVVAIA SHDGGKQALE TVQRLLPVLC QDHG                                34

SEQ ID NO: 22            moltype = AA   length = 34
FEATURE                  Location/Qualifiers
source                   1..34
                         mol_type = protein
                         organism = synthetic construct
SEQUENCE: 22
LTPDQVVAIA SHDGGKQALE TVQRLLPVLC QDHG                                34

SEQ ID NO: 23            moltype = AA   length = 34
FEATURE                  Location/Qualifiers
source                   1..34
                         mol_type = protein
                         organism = synthetic construct
SEQUENCE: 23
LTPDQVVAIA SNGGGKQALE TVQRLLPVLC QDHG                                34

SEQ ID NO: 24            moltype = AA   length = 34
FEATURE                  Location/Qualifiers
source                   1..34
                         mol_type = protein
                         organism = synthetic construct
SEQUENCE: 24
LTPDQVVAIA SNGGGKQALE TVQRLLPVLC QDHG                                34

SEQ ID NO: 25            moltype = AA   length = 34
FEATURE                  Location/Qualifiers
source                   1..34
                         mol_type = protein
                         organism = synthetic construct
SEQUENCE: 25
LTPDQVVAIA SNGGGKQALE TVQRLLPVLC QDHG                                34

SEQ ID NO: 26            moltype = AA   length = 34
FEATURE                  Location/Qualifiers
source                   1..34
                         mol_type = protein
                         organism = synthetic construct
SEQUENCE: 26
```

```
LTPDQVVAIA SNGGGKQALE TVQRLLPVLC QDHG                                   34

SEQ ID NO: 27           moltype = AA   length = 34
FEATURE                 Location/Qualifiers
source                  1..34
                        mol_type = protein
                        organism = synthetic construct
SEQUENCE: 27
LTPDQVVAIA SNNGGKQALE TVQRLLPVLC QDHG                                   34

SEQ ID NO: 28           moltype = AA   length = 34
FEATURE                 Location/Qualifiers
source                  1..34
                        mol_type = protein
                        organism = synthetic construct
SEQUENCE: 28
LTPDQVVAIA SNGGGKQALE TVQRLLPVLC QDHG                                   34

SEQ ID NO: 29           moltype = AA   length = 34
FEATURE                 Location/Qualifiers
source                  1..34
                        mol_type = protein
                        organism = synthetic construct
SEQUENCE: 29
LTPDQVVAIA SHDGGKQALE TVQRLLPVLC QDHG                                   34

SEQ ID NO: 30           moltype = AA   length = 34
FEATURE                 Location/Qualifiers
source                  1..34
                        mol_type = protein
                        organism = synthetic construct
SEQUENCE: 30
LTPDQVVAIA SHDGGKQALE TVQRLLPVLC QDHG                                   34

SEQ ID NO: 31           moltype = AA   length = 34
FEATURE                 Location/Qualifiers
source                  1..34
                        mol_type = protein
                        organism = synthetic construct
SEQUENCE: 31
LTPDQVVAIA SNIGGKQALE TVQRLLPVLC QDHG                                   34

SEQ ID NO: 32           moltype = AA   length = 34
FEATURE                 Location/Qualifiers
source                  1..34
                        mol_type = protein
                        organism = synthetic construct
SEQUENCE: 32
LTPDQVVAIA SNIGGKQALE TVQRLLPVLC QDHG                                   34

SEQ ID NO: 33           moltype = AA   length = 34
FEATURE                 Location/Qualifiers
source                  1..34
                        mol_type = protein
                        organism = synthetic construct
SEQUENCE: 33
LTPDQVVAIA SNNGGKQALE TVQRLLPVLC QDHG                                   34

SEQ ID NO: 34           moltype = AA   length = 34
FEATURE                 Location/Qualifiers
source                  1..34
                        mol_type = protein
                        organism = synthetic construct
SEQUENCE: 34
LTPDQVVAIA SNNGGKQALE TVQRLLPVLC QDHG                                   34

SEQ ID NO: 35           moltype = AA   length = 34
FEATURE                 Location/Qualifiers
source                  1..34
                        mol_type = protein
                        organism = synthetic construct
SEQUENCE: 35
LTPDQVVAIA SNIGGKQALE TVQRLLPVLC QDHG                                   34

SEQ ID NO: 36           moltype = AA   length = 229
FEATURE                 Location/Qualifiers
source                  1..229
                        mol_type = protein
                        organism = Rattus norvegicus
```

-continued

```
SEQUENCE: 36
MSSETGPVAV DPTLRRRIEP HEFEVFFDPR ELRKETCLLY EINWGGRHSI WRHTSQNTNK  60
HVEVNFIEKF TTERYFCPNT RCSITWFLSW SPCGECSRAI TEFLSRYPHV TLFIYIARLY  120
HHADPRNRQG LRDLISSGVT IQIMTEQESG YCWRNFVNYS PSNEAHWPRY PHLWVRLYVL  180
ELYCIILGLP PCLNILRRKQ PQLTFFTIAL QSCHYQRLPP HILWATGLK               229

SEQ ID NO: 37              moltype = AA   length = 199
FEATURE                    Location/Qualifiers
source                     1..199
                           mol_type = protein
                           organism = Homo sapiens
SEQUENCE: 37
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                                199

SEQ ID NO: 38              moltype = AA   length = 188
FEATURE                    Location/Qualifiers
source                     1..188
                           mol_type = protein
                           organism = Homo sapiens
SEQUENCE: 38
MDPPTFTFNF NNEPWVRGRH ETYLCYEVER MHNDTWVLLN QRRGFLCNQA PHKHGFLEGR  60
HAELCFLDVI PFWKLDLDQD YRVTCFTSWS PCFSCAQEMA KFISKNKHVS LCIFTARIYD  120
DQGRCQEGLR TLAEAGAKIS IMTYSEFKHC WDTFVDHQGC PFQPWDGLDE HSQDLSGRLR  180
AILQNQEN                                                           188

SEQ ID NO: 39              moltype = AA   length = 213
FEATURE                    Location/Qualifiers
source                     1..213
                           mol_type = protein
                           organism = Petromyzon marinus
SEQUENCE: 39
MTDAEYVRIH EKLDIYTFKK QFFNNKKSVS HRCYVLFELK RRGERRACFW GYAVNKPQSG  60
TERGIHAEIF SIRKVEEYLR DNPGQFTINW YSSWSPCADC AEKILEWYNQ ELRGNGHTLK  120
IWACKLYYEK NARNQIGLWN LRDNGVGLNV MVSEHYQCCR KIFIQSSHNQ LNENRWLEKT  180
LKRAEKRRSE LSIMIQVKIL HTTKSPAVSR GSG                               213

SEQ ID NO: 40              moltype = AA   length = 121
FEATURE                    Location/Qualifiers
source                     1..121
                           mol_type = protein
                           organism = synthetic construct
SEQUENCE: 40
SHRCYVLFEL KRRGERRACF WGYAVNKPQS GTERGIHAEI FSIRKVEEYL RDNPGQFTIN  60
WYSSWSPCAD CAEKILEWYN QELRGNGHTL KIEACKLYYE KNARNQIGLQ NLRDNGVGLN  120
V                                                                  121

SEQ ID NO: 41              moltype = AA   length = 198
FEATURE                    Location/Qualifiers
source                     1..198
                           mol_type = protein
                           organism = Homo sapiens
SEQUENCE: 41
MDSLLMNRRK FLYQFKNVRW AKGRRETYLC YVVKRRDSAT SFSLDFGYLR NKNGCHVELL  60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                                198

SEQ ID NO: 42              moltype = AA   length = 236
FEATURE                    Location/Qualifiers
source                     1..236
                           mol_type = protein
                           organism = Pongo pygmaeus
SEQUENCE: 42
MTSEKGPSTG DPTLRRRIES WEFDVFYDPR ELRKETCLLY EIKWGMSRKI WRSSGKNTTN  60
HVEVNFIKKF TSERRFHSSI SCSITWFLSW SPCWECSQAI REFLSQHPGV TLVIYVARLF  120
WHMDQRNRQG LRDLVNSGVT IQIMRASEYY HCWRNFVNYP PGDEAHWPQY PPLWMMLYAL  180
ELHCIILSLP PCLKISRRWQ NHLAFFRLHL QNCHYQTIPP HILLATGLIH PSVTWR       236

SEQ ID NO: 43              moltype = AA   length = 194
FEATURE                    Location/Qualifiers
source                     1..194
                           mol_type = protein
                           organism = Rhinopithecus roxellana
SEQUENCE: 43
MKPQIRDHRP NPMEAMYPHI FYFHFENLEK AYGRNETWLC FTVEIIKQYL PVPWKKGVFR  60
NQVDPETHCH AEKCFLSWFC NNTLSPKKNY QVTWYTSWSP CPECAGEVAE FLAEHSNVKL  120
```

```
TIYTARLYYF WDTDYQEGLR SLSEEGASVE IMDYEDFQYC WENFVYDDGE PFKRWKGLKY   180
NFQSLTRRLR EILQ                                                      194

SEQ ID NO: 44              moltype = AA   length = 192
FEATURE                    Location/Qualifiers
source                     1..192
                           mol_type = protein
                           organism = Alligator mississippiensis
SEQUENCE: 44
MADSSEKMRG QYISRDTFEK NYKPIDGTKE AHLLCEIKWG KYGKPWLHWC QNQRMNIHAE    60
DYFMNNIFKA KKHPVHCYVT WYLSWSPCAD CASKIVKFLE ERPYLKLTIY VAQLYYHTEE    120
ENRKGLRLLR SKKVIIRVMD ISDYNYCWKV FVSNQNGNED YWPLQFDPWV KENYSRLLDI    180
FWESKCRSPN PW                                                        192

SEQ ID NO: 45              moltype = AA   length = 280
FEATURE                    Location/Qualifiers
source                     1..280
                           mol_type = protein
                           organism = Sus scrofa
SEQUENCE: 45
MDPQRLRQWP GPGPASRGGY GQRPRIRNPE EWFHELSPRT FSFHFRNLRF ASGRNRSYIC    60
CQVEGKNCFF QGIFQNQVPP DPPCHAELCF LSWFQSWGLS PDEHYYVTWF ISWSPCCECA    120
AKVAQFLEEN RNVSLSLSAA RLYYFWKSES REGLRRLSDL GAQVGIMSFQ DFQHCWNNFV    180
HNLGMPFQPW KKLHKNYQRL VTELKQILRE EPATYGSPQA QGKVRIGSTA AGLRHSHSHT    240
RSEAHLRPNH SSRQHRILNP PREARARTCV LVDASWICYR                          280

SEQ ID NO: 46              moltype = AA   length = 382
FEATURE                    Location/Qualifiers
source                     1..382
                           mol_type = protein
                           organism = Homo sapiens
SEQUENCE: 46
MNPQIRNPME RMYRDTFYDN FENEPILYGR SYTWLCYEVK IKRGRSNLLW DTGVFRGQVY    60
FKPQYHAEMC FLSWFCGNQL PAYKCFQITW FVSWTPCPDC VAKLAEFLSE HPNVTLTISA    120
ARLYYYWERD YRRALCRLSQ AGARVKIMDY EEFAYCWENF VYNEGQQFMP WYKFDENYAF    180
LHRTLKEILR YLMDPDTFTF NFNNDPLVLR RRQTYLCYEV ERLDNGTWVL MDQHMGFLCN    240
EAKNLLCGFY GRHAELRFLD LVPSLQLDPA QIYRVTWFIS WSPCFSWGCA GEVRAFLQEN    300
THVRLRIFAA RIYDYDPLYK EALQMLRDAG AQVSIMTYDE FEYCWDTFVY RQGCPFQPWD    360
GLEEHSQALS GRLRAILQNQ GN                                             382

SEQ ID NO: 47              moltype = AA   length = 190
FEATURE                    Location/Qualifiers
source                     1..190
                           mol_type = protein
                           organism = Homo sapiens
SEQUENCE: 47
MNPQIRNPMK AMYPGTFYFQ FKNLWEANDR NETWLCFTVE GIKRRSVVSW KTGVFRNQVD    60
SETHCHAERC FLSWFCDDIL SPNTKYQVTW YTSWSPCPDC AGEVAEFLAR HSNVNLTIFT    120
ARLYYFQYPC YQEGLRSLSQ EGVAVEIMDY EDFKYCWENF VYNDNEPFKP WKGLKTNFRL    180
LKRRLRESLQ                                                           190

SEQ ID NO: 48              moltype = AA   length = 386
FEATURE                    Location/Qualifiers
source                     1..386
                           mol_type = protein
                           organism = Homo sapiens
SEQUENCE: 48
MNPQIRNPME RMYRDTFYDN FENEPILYGR SYTWLCYEVK IKRGRSNLLW DTGVFRGPVL    60
PKRQSNHRQE VYFRFENHAE MCFLSWFCGN RLPANRRFQI TWFVSWNPCL PCVVKVTKFL    120
AEHPNVTLTI SAARLYYYRD RDWRWVLLRL HKAGARVKIM DYEDFAYCWE NFVCNEGQPF    180
MPWYKFDDNY ASLHRTLKEI LRNPMEAMYP HIFYFHFKNL LKACGRNESW LCFTMEVTKH    240
HSAVFRKRGV FRNQVDPETH CHAERCFLSW FCDDILSPNT NYEVTWYTSW SPCPECAGEV    300
AEFLARHSNV NLTIFTARLC YFWDTDYQEG LCSLSQEGAS VKIMGYKDFV SCWKNFVYSD    360
DEPFKPWKGL QTNFRLLKRR LREILQ                                         386

SEQ ID NO: 49              moltype = AA   length = 373
FEATURE                    Location/Qualifiers
source                     1..373
                           mol_type = protein
                           organism = Homo sapiens
SEQUENCE: 49
MKPHFRNTVE RMYRDTFSYN FYNRPILSRR NTVWLCYEVK TKGPSRPRLD AKIFRGQVYS    60
QPEHHAEMCF LSWFCGNQLP AYKCFQITWF VSWTPCPDCV AKLAEFLAEH PNVTLTISAA    120
RLYYYWERDY RRALCRLSQA GARVKIMDDE EFAYCWENFV YSEGQPFMPW YKFDDNYAFL    180
HRTLKEILRN PMEAMYPHIF YFHFKNLRKA YGRNESWLCF TMEVVKHHSP VSWKRGVFRN    240
QVDPETHCHA ERCFLSWFCD DILSPNTNYE VTWYTSWSPC PECAGEVAEF LARHSNVNLT    300
IFTARLYYFW DTDYQEGLRS LSQEGASVEI MGYKDFKYCW ENFVYNDDEP FKPWKGLKYN    360
FLFLDSKLQE ILE                                                       373
```

```
SEQ ID NO: 50              moltype = AA   length = 384
FEATURE                    Location/Qualifiers
source                     1..384
                           mol_type = protein
                           organism = Homo sapiens
SEQUENCE: 50
MKPHFRNTVE RMYRDTFSYN FYNRPILSRR NTVWLCYEVK TKGPSRPPLD AKIFRGQVYS   60
ELKYHPEMRF FHWFSKWRKL HRDQEYEVTW YISWSPCTKC TRDMATFLAE DPKVTLTIFV  120
ARLYYFWDPD YQEALRSLCQ KRDGPRATMK IMNYDEFQHC WSKFVYSQRE LFEPWNNLPK  180
YYILLHIMLG EILRHSMDPP TFTFNFNNEP WVRGRHETYL CYEVERMHND TWVLLNQRRG  240
FLCNQAPHKH GFLEGRHAEL CFLDVIPFWK LDLDQDYRVT CFTSWSPCFS CAQEMAKFIS  300
KNKHVSLCIF TARIYDDQGR CQEGLRTLAE AGAKISIMTY SEFKHCWDTF VDHQGCPFQP  360
WDGLDEHSQD LSGRLRAILQ NQEN                                        384

SEQ ID NO: 51              moltype = AA   length = 182
FEATURE                    Location/Qualifiers
source                     1..182
                           mol_type = protein
                           organism = Homo sapiens
SEQUENCE: 51
MALLTAETFR LQFNNKRRLR RPYYPRKALL CYQLTPQNGS TPTRGYFENK KKCHAEICFI   60
NEIKSMGLDE TQCYQVTCYL TWSPCSSCAW ELVDFIKAHD HLNLRIFASR LYYHWCKPQQ  120
DGLRLLCGSQ VPVEVMGFPE FADCWENFVD HEKPLSFNPY KMLEELDKNS RAIKRRLDRI  180
KS                                                                182

SEQ ID NO: 52              moltype = AA   length = 197
FEATURE                    Location/Qualifiers
source                     1..197
                           mol_type = protein
                           organism = Homo sapiens
SEQUENCE: 52
MEILRYLMDP DTFTFNFNND PLVLRRRQTY LCYEVERLDN GTWVLMDQHM GFLCNEAKNL   60
LCGFYGRHAE LRFLDLVPSL QLDPAQIYRV TWFISWSPCF SWGCAGEVRA FLQENTHVRL  120
RIFAARIYDY DPLYKEALQM LRDAGAQVSI MTYDEFEYCW DTFVYRQGCP FQPWDGLEEH  180
SQALSGRLRA ILQNQGN                                                197

SEQ ID NO: 53              moltype = AA   length = 161
FEATURE                    Location/Qualifiers
source                     1..161
                           mol_type = protein
                           organism = synthetic construct
SEQUENCE: 53
FERNYDPREL RKETYLLYEI KWGKSGKLWR HWCQNNRTQH AEVYFLENIF NARRFNPSTH   60
CSITWYLSWS PCAECSQKIV DFLKEHPNVN LEIYVARLYY HEDERNRQGL RDLVNSGVTI  120
RIMDLPDYNY CWKTFVSDQG GDEDYWPGHF APWIKQYSLK L                      161

SEQ ID NO: 54              moltype = AA   length = 167
FEATURE                    Location/Qualifiers
source                     1..167
                           mol_type = protein
                           organism = Escherichia coli
SEQUENCE: 54
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTD                167

SEQ ID NO: 55              moltype = AA   length = 352
FEATURE                    Location/Qualifiers
source                     1..352
                           mol_type = protein
                           organism = Mus musculus
SEQUENCE: 55
MAQTPAFNKP KVELHVHLDG AIKPETILYF GKKRGIALPA DTVEELRNII GMDKPLSLPG   60
FLAKFDYYMP VIAGCREAIK RIAYEFVEMK AKEGVVYVEV RYSPHLLANS KVDPMPWNQT  120
EGDVTPDDVV DLVNQGLQEG EQAFGIKVRS ILCCMRHQPS WSLEVLELCK KYNQKTVVAM  180
DLAGDETIEG SSLFPGHVEA YEGAVKNGIH RTVHAGEVGS PEVVREAVDI LKTERVGHGY  240
HTIEDEALYN RLLKENMHFE VCPWSSYLTG AWDPKTTHAV VRFKNDKANY SLNTDDPLIF  300
KSTLDTDYQM TKKDMGFTEE EFKRLNINAA KSSFLPEEEK KELLERLYRE YQ          352

SEQ ID NO: 56              moltype = AA   length = 403
FEATURE                    Location/Qualifiers
source                     1..403
                           mol_type = protein
                           organism = Homo sapiens
SEQUENCE: 56
MHLDQTPSRQ PIPSEGLQLH LPQVLADAVS RLVLGKFGDL TDNFSSPHAR RKVLAGVVMT   60
TGTDVKDAKV ISVSTGTKCI NGEYMSDRGL ALNDCHAEII SRRSLLRFLY TQLELYLNNK  120
DDQKRSIFQK SERGGFRLKE NVQFHLYIST SPCGDARIFS PHEPILEEPA DRHPNRKARG  180
QLRTKIESGE GTIPVRSNAS IQTWDGVLQG ERLLTMSCSD KIARWNVVGI QGSLLSIFVE  240
```

-continued

```
PIYFSSIILG SLYHGDHLSR AMYQRISNIE DLPPLYTLNK PLLSGISNAE ARQPGKAPNF  300
SVNWTVGDSA IEVINATTGK DELGRASRLC KHALYCRWMR VHGKVPSHLL RSKITKPNVY  360
HESKLAAKEY QAAKARLFTA FIKAGLGAWV EKPTEQDQFS LTP                    403

SEQ ID NO: 57              moltype = AA  length = 191
FEATURE                    Location/Qualifiers
source                     1..191
                           mol_type = protein
                           organism = Homo sapiens
SEQUENCE: 57
MEAKAAPKPA ASGACSVSAE ETEKWMEEAM HMAKEALENT EVPVGCLMVY NNEVVGKGRN  60
EVNQTKNATR HAEMVAIDQV LDWCRQSGKS PSEVFEHTVL YVTVEPCIMC AAALRLMKIP  120
LVVYGCQNER FGGCGSVLNI ASADLPNTGR PFQCIPGYRA EEAVEMLKTF YKQENPNAPK  180
SKVRKKECQK S                                                      191

SEQ ID NO: 58              moltype = AA  length = 167
FEATURE                    Location/Qualifiers
source                     1..167
                           mol_type = protein
                           organism = Escherichia coli
SEQUENCE: 58
MSEVEFSHEY WMRHALTLAK RARDEREVPV GAVLVLNNRV IGEGWNRAIG LHDPTAHAEI  60
MALRQGGLVM QNYRLIDATL YVTFEPCVMC AGAMIHSRIG RVVFGVRNAK TGAAGSLMDV  120
LHYPGMNHRV EITEGILADE CAALLCYFFR MPRQVFNAQK KAQSSTD               167

SEQ ID NO: 59              moltype = AA  length = 167
FEATURE                    Location/Qualifiers
source                     1..167
                           mol_type = protein
                           organism = synthetic construct
SEQUENCE: 59
MSEVEFSHEY WMRHALTLAK RARDEREVPV GAVLVLNNRV IGEGWNRAIG LHDPTAHAEI  60
MALRQGGLVM QNYRLIDATL YVTFEPCVMC AGAMIHSRIG RVVFGVRNSK RGAAGSLMNV  120
LNYPGMNHRV EITEGILADE CAALLCDFYR MPRQVFNAQK KAQSSIN               167

SEQ ID NO: 60              moltype = AA  length = 196
FEATURE                    Location/Qualifiers
source                     1..196
                           mol_type = protein
                           organism = synthetic construct
SEQUENCE: 60
QLVKSELEEK KSELRHKLKY VPHEYIELIE IARNSTQDRI LEMKVMEFFM KVYGYRGKHL  60
GGSRKPAGAI YTVGSPIDYG VIVDTKAYSG GYNLPIGQAD EMQRYVKENQ TRNKHINPNE  120
WWKVYPSSVT EFKFLFVSGH FKGNYKAQLT RLNHKTNCNG AVLSVEELLI GGEMIKAGTL  180
TLEEVRRKFN NGEINF                                                 196

SEQ ID NO: 61              moltype = AA  length = 196
FEATURE                    Location/Qualifiers
source                     1..196
                           mol_type = protein
                           organism = synthetic construct
SEQUENCE: 61
QLVKSELEEK KSELRHKLKY VPHEYIELIE IARNSTQDRI LEMKVMEFFM KVYGYRGKHL  60
GGSRKPDGAI YTVGSPIDYG VIVATKAYSG GYNLPIGQAD EMQRYVKENQ TRNKHINPNE  120
WWKVYPSSVT EFKFLFVSGH FKGNYKAQLT RLNHKTNCNG AVLSVEELLI GGEMIKAGTL  180
TLEEVRRKFN NGEINF                                                 196

SEQ ID NO: 62              moltype = AA  length = 196
FEATURE                    Location/Qualifiers
source                     1..196
                           mol_type = protein
                           organism = synthetic construct
SEQUENCE: 62
QLVKSELEEK KSELRHKLKY VPHEYIELIE IARNSTQDRI LEMKVMEFFM KVYGYRGKHL  60
GGSRKPAGAI YTVGSPIDYG VIVDTKAYSG GYNLPIGQAD EMERYVEENQ TRNKHLNPNE  120
WWKVYPSSVT EFKFLFVSGH FKGNYKAQLT RLNHITNCNG AVLSVEELLI GGEMIKAGTL  180
TLEEVRRKFN NGEINF                                                 196

SEQ ID NO: 63              moltype = AA  length = 196
FEATURE                    Location/Qualifiers
source                     1..196
                           mol_type = protein
                           organism = synthetic construct
SEQUENCE: 63
QLVKSELEEK KSELRHKLKY VPHEYIELIE IARNSTQDRI LEMKVMEFFM KVYGYRGKHL  60
GGSRKPDGAI YTVGSPIDYG VIVATKAYSG GYNLPIGQAD EMERYVEENQ TRNKHLNPNE  120
WWKVYPSSVT EFKFLFVSGH FKGNYKAQLT RLNHITNCNG AVLSVEELLI GGEMIKAGTL  180
TLEEVRRKFN NGEINF                                                 196
```

US 12,612,651 B2

-continued

```
SEQ ID NO: 64            moltype = AA  length = 837
FEATURE                  Location/Qualifiers
source                   1..837
                         mol_type = protein
                         organism = Mus musculus
SEQUENCE: 64
MGIQGLLQFI QEASEPVNVK KYKGQAVAVD TYCWLHKGAI ACAEKLAKGE PTDRYVGFCM  60
KFVNMLLSYG VKPILIFDGC TLPSKKEVER SRRERRQSNL LKGKQLLREG KVSEARDCFA  120
RSINITHAMA HKVIKAARAL GVDCLVAPYE ADAQLAYLNK AGIVQAVITE DSDLLAFGCK  180
KVILKMDQFG NGLEVDQARL GMCKQLGDVF TEEKFRYMCI LSGCDYLASL RGIGLAKACK  240
VLRLANNPDI VKVIKKIGHY LRMNITVPED YITGFIRANN TFLYQLVFDP IQRKLVPLNA  300
YGDDVNPETL TYAGQYVGDS VALQIALGNR DVNTFEQIDD YSPDTMPAHS RSHSWNEKAG  360
QKPPGTNSIW HKNYCPRLEV NSVSHAPQLK EKPSTLGLKQ VISTKGLNLP RKSCVLKRPR  420
NEALAEDDLL SQYSSVSKKI KENGCGDGTS PNSSKMSKSC PDSGTAHKTD AHTPSKMRNK  480
FATFLQRRNE ESGAVVVPGT RSRFFCSSQD FDNFIPKKES GQPLNETVAT GKATTSLLGA  540
LDCPDTEGHK PVDANGTHNL SSQIPGNAAV SPEDEAQSSE TSKLLGAMSP PSLGTLRSCF  600
SWSGTLREFS RTPSPSASTT LQQFRRKSDP PACLPEASAV VTDRCDSKSE MLGETSQPLH  660
ELGCSSRSQE SMDSSCGLNT SSLSQPSSRD SGSEESDCNN KSLDNQGEQN SKQHLPHFSK  720
KDGLRRNKVP GLCRSSSMDS FSTTKIKPLV PARVSGLSKK SGSMQTRKHH DVENKPGLQT  780
KISELWKNFG FKKDSEKLPS CKKPLSPVKD NIQLTPETED EIFNKPECVR AQRAIFH     837

SEQ ID NO: 65            moltype = AA  length = 236
FEATURE                  Location/Qualifiers
source                   1..236
                         mol_type = protein
                         organism = Mus musculus
SEQUENCE: 65
MSEPPRAETF VFLDLEATGL PNMDPEIAEI SLFAVHRSSL ENPERDDSGS LVLPRVLDKL  60
TLCMCPERPF TAKASEITGL SSESLMHCGK AGFNGAVVRT LQGFLSRQEG PICLVAHNGF  120
DYDFPLLCTE LQRLGAHLPQ DTVCLDTLPA LRGLDRAHSH GTRAQGRKSY SLASLFHRYF  180
QAEPSAAHSA EGDVHTLLLI FLHRAPELLA WADEQARSWA HIEPMYVPPD GPSLEA      236

SEQ ID NO: 66            moltype = AA  length = 445
FEATURE                  Location/Qualifiers
source                   1..445
                         mol_type = protein
                         organism = Mus musculus
SEQUENCE: 66
MSSGMAYTSD RDRNKARAYS HCHKDHMKGR ASKRRCSKVY CSVTKTSKYR WNRTTTSVDA  60
SGKVVVTAGH CGSVMGSNGT VYTGDRAKGA SRMHSGGRVK DSVYDTTCDR YSRCRGVRSW  120
VTRSHHVVWN CKAAYGYYTN SGVVHVDKDM KNMDHHTTDR NTHACRHKAC WNKCGTSNKT  180
AHTSKSTMWG RTRKTNVVRT GSSYRACSHS SSKDSYCVNV YNVVGTVDKV MDVKCRSSVK  240
YKGKKRARTH DSDDDDDTRH KVYTSMKADR SGGCKASVWS SANDCSNSDS GTSGGGSTVN  300
ADDVDWVKRR DTGCHSSTGG SSKCSDSKCS DSKCSDSDGD STHSSNSSST HTDGSGWDSC  360
DTVSSKSGGD STSNKGAYKK KSSASDACDT HCDKSRAVNG ACVDTSGRKS KTSSTRADSS  420
SSDSTATHCY RKATGSVVKR KCSDS                                       445

SEQ ID NO: 67            moltype = AA  length = 291
FEATURE                  Location/Qualifiers
source                   1..291
                         mol_type = protein
                         organism = Escherichia phage
SEQUENCE: 67
MSKSWGKFIE EEEAEMASRR NLMIVDGTNL GFRFKHNNSK KPFASSYVST IQSLAKSYSA  60
RTTIVLGDKG KSVFRLEHLP EYKGNRDEKY AQRTEEEKAL DEQFFEYLKD APELCKTTFP  120
TFTIRGVEAD DMAAYIVKLI GHLYDHVWLI STDGDWDTLL TDKVSRFSFT TRREYHLRDM  180
YEHHNVDDVE QFISLKAIMG DLGDNIRGVE GIGAKRGYNI IREFGNVLDI IDQLPLPGKQ  240
KYIQNLNASE ELLFRNLILV DLPTYCVDAI AAVGQDVLDK FTKDILEIAE Q           291

SEQ ID NO: 68            moltype = AA  length = 83
FEATURE                  Location/Qualifiers
source                   1..83
                         mol_type = protein
                         organism = Bacillus subtilis bacteriophage PBS1
SEQUENCE: 68
TNLSDIIEKE TGKQLVIQES ILMLPEEVEE VIGNKPESDI LVHTAYDEST DENVMLLTSD  60
APEYKPWALV IQDSNGENKI KML                                         83

SEQ ID NO: 69            moltype = DNA  length = 1987
FEATURE                  Location/Qualifiers
source                   1..1987
                         mol_type = other DNA
                         organism = synthetic construct
SEQUENCE: 69
tgacccggtc gtgcccctct ctagagataa tgagcattgc atgtctaagt tataaaaaat  60
taccacatat ttttttttgtc acacttgttt gaagtgcagt ttatctatct ttatacatat  120
atttaaactt tactctacga ataatataat ctatagtact acaataatat cagtgtttta  180
gagaatcata taaatgaaca gttagacatg gtctaaagga caattgagta ttttgacaac  240
aggactctac agtttttatct ttttagtgtg catgtgttct cctttttttt tgcaaatagc  300
```

```
ttcacctata taatacttca tccattttat tagtacatcc atttagggtt taggggttaat  360
ggtttttata gactaatttt tttagtacat ctatttttatt ctattttagc ctctaaatta  420
agaaaactaa aactctattt tagttttttt atttaataat ttagatataa aatagaataa  480
aataaagtga ctaaaaatta aacaaatacc ctttaagaaa ttaaaaaaac taaggaaaca  540
tttttcttgt ttcgagtaga taatgccagc ctgttaaacg ccgtcgacga gtctaacgga  600
caccaaccag cgaaccagca gcgtcgcgtc gggccaagcg aagcagacgg cacggcatct  660
ctgtcgctgc ctctggaccc ctctcgatcg agagttccgc tccaccgttg gacttgctcc  720
gctgtcggca tccagaaatt gcgtggcgga gcggcagacg tgagccggca cggcaggcgg  780
cctcctcctc ctctcacggc accggcagct acggggggatt cctttcccac cgctccttcg  840
ctttcccttc ctcgcccgcc gtaatacaaata gacacccct ccacacccctc tttcccccaac  900
ctcgtgttgt tcggagcgca cacacacaca accagatctc ccccaaatcc acccgtcggc  960
acctccgctt caaggtacgc cgctcgtcct cccccccccc ccctctctac cttctctaga  1020
tcggcgttcc ggtccatggt tagggcccgg tagttctact tctgttcatg tttgtgttag  1080
atccgtgttt gtgttagatc cgtgctgcta gcgttcgtac acggatgcga cctgtacgtc  1140
agacacgttc tgattgctaa cttgccagtg tttctctttg gggaatcctg ggatggctct  1200
agccgttccg cagacgggat cgatttcatg atttttttttg tttcgttgca tagggtttgg  1260
tttgcccttt tccttttattt caatatatgc cgtgcacttg tttgtcgggt catcttttca  1320
tgcttttttt tgtcttggtt gtgatgatgt ggtctggttg ggcggtcgtt ctagatcgga  1380
gtagaattaa ttctgtttca aactacctgg tggatttatt aattttggat ctgtatgtgt  1440
gtgccataca tattcatagt tacgaattga agatgatgga tggaaaatatc gatctaggat  1500
aggtatacat gttgatgcgg gttttactga tgcatataca gagatgctttt ttgttcgctt  1560
ggttgtgatg atgtggtgtg gttagggcggt cgttcattcg ttctagatcg gagtagaata  1620
ctgtttcaaa ctacctggtg tatttattaa ttttggaact gtatgtgtgt gtcatacatc  1680
ttcatagtta cgagtttaag atggatggaa atatcgatct aggataggta tacatgttga  1740
tgtgggtttt actgatgcat atacatgatg gcatatgcag catctattca tatgctctaa  1800
ccttgagtac ctatctatta taataaacaa gtatgtttta taattattttt gatcttgata  1860
tacttggatg atggcatatg cagcagctat atgtggattt ttttagccct gccttcatac  1920
gctatttatt tgcttggtac tgtttctttt gtcgatgctc accctgttgt ttggtgttac  1980
ttctgca                                                             1987
```

SEQ ID NO: 70          moltype = DNA   length = 678
FEATURE                Location/Qualifiers
source                 1..678
                       mol_type = other DNA
                       organism = synthetic construct
SEQUENCE: 70

```
tgagactttt caacaaaggg taatatcggg aaacctcctc ggattccatt gcccagctat  60
ctgtcacttc atcaaaagga cagtagaaaa ggaaggtggc acctacaaat gccatcattg  120
cgataaagga aaggctatcg ttcaagatgc ctctgccgac agtggtccca aagatggacc  180
cccacccacg aggagcatcg tggaaaaaga agacgttcca accacgtctt caaagcaagt  240
ggattgatgt gataacatgg tggagcacga cactctcgtc tactccaaga atatcaaaga  300
tacagtctca gaagaccaaa gggctattga gacttttcaa caaagggtaa tatcgggaaa  360
cctcctcgga ttccattgcc cagctatctg tcacttctg tcacttctct aaaaggacag tagaaagga  420
aggtggcacc tacaaatgcc atcattgcga taaaggaaag gctatcgttc aagatgcctc  480
tgccgacagt ggtcccaaag atggaccccc acccacgagg agcatcgtgg aaaaagaaga  540
cgttccaacc acgtcttcaa agcaagtgga ttgatgtgat atctccactg acgtaaggga  600
tgacgcacaa tcccactatc cttcgcaaga ccttcctcta tataaggaag ttcatttcat  660
ttggagagga cacgctga                                                 678
```

SEQ ID NO: 71          moltype = DNA   length = 891
FEATURE                Location/Qualifiers
source                 1..891
                       mol_type = other DNA
                       organism = synthetic construct
SEQUENCE: 71

```
cctgcaggtc aacatggtgg agcacgacac acttgtctac tccaaaaata tcaaagatac  60
agtctcagaa gaccaaaggg caattgagac ttttcaacaa agggtaatat ccggaaacct  120
cctcggattc cattgcccag ctatctgtca ctttattgtg aagatagtgg aaaaggaagg  180
tggctcctac aaatgccatc attgcgataa aggaaaggc gctatcgttc aagatgcctc  240
tgccgacagt ggtcccaaag atggaccccc acccacgagg agcatcgtgg aaaaagaaga  300
tccaaccacg tcttcaaagc aagtggattg atgtgataac atggtggagc acgacacact  360
tgtctactcc aaaaatatca agatacagt ctcagaagac caaagggcaa ttgagactttt  420
tcaacaaagg gtaatatccg gaaacctcct cggattccat tgcccagcta tctgtcactt  480
tattgaag atagtggaaa aggaaggtgg ctcctacaaa tgccatcatt gcgataaagg  540
aaaggccatc gttgaagatg cctctgccga cagtggtccc aaagatggac ccccacccac  600
gaggagcatc gtgaaaaag aagacgttcc aaccacgtct tcaaagcaag tggattgatg  660
tgatatctcc actgacgtaa gggatgacgc acaatcccac tatccttcgc aagaccccttc  720
ctctatataa ggaagttcat ttcatttgga gaggacctcg acctcaacac aacatataca  780
aaacaaacga atctcaagca atcaagcatt ctacttctat tgcagcaatt taaatcatttt  840
cttttaaagc aaaagcaatt ttctgaaaat tttcaccatt tacgaacgat a            891
```

SEQ ID NO: 72          moltype = DNA   length = 204
FEATURE                Location/Qualifiers
source                 1..204
                       mol_type = other DNA
                       organism = synthetic construct
SEQUENCE: 72

```
gtgatgcggt tttggcagta catcaatggg cgtggatagc ggtttgactc acggggatttt  60
ccaagtctcc accccattga cgtcaatggg agtttgtttt ggcaccaaaa tcaacgggac  120
```

-continued

```
tttccaaaat gtcgtaacaa ctccgcccca ttgacgcaaa tgggcggtag gcgtgtacgg    180
tgggaggtct atataagcag agct                                          204

SEQ ID NO: 73          moltype = DNA   length = 258
FEATURE                Location/Qualifiers
source                 1..258
                       mol_type = other DNA
                       organism = synthetic construct
SEQUENCE: 73
gaatttcccc gatcgttcaa acatttggca ataaagtttc ttaagattga atcctgttgc    60
cggtcttgcg atgattatca tataatttct gttgaattac gttaagcatg taataattaa    120
catgtaatgc atgacgttat ttatgagatg ggtttttatg attagagtcc cgcaattata    180
catttaatac gcgatagaaa acaaaatata gcgcgcaaac taggataaat tatcgcgcgc    240
ggtgtcatct atgttact                                                 258

SEQ ID NO: 74          moltype = DNA   length = 635
FEATURE                Location/Qualifiers
source                 1..635
                       mol_type = other DNA
                       organism = synthetic construct
SEQUENCE: 74
agagctttcg ttcgtatcat cggtttcgac aacgttcgtc aagttcaatg catcagtttc    60
attgcgcaca caccagaatc ctactgagtt tgagtattat ggcattggga aaactgtttt    120
tcttgtacca tttgttgtgc ttgtaattta ctgtgttttt tattcggttt tcgctatcga    180
actgtgaaat ggaaatggat ggagaagagt taatgaatga tatggtcctt ttgttcattc    240
tcaaattaat attatttgtt ttttctctta tttgttgtgt gttgaatttg aaattataag    300
agatatgcaa acattttgtt ttgagtaaaa atgtgtcaaa tcgtggcctc taatgaccga    360
agttaatatg aggagtaaaa cacttgtagt tgtaccatta tgcttattca ctaggcaaca    420
aatatatttt cagacctaga aaagctgcaa atgttactga atacaagtat gtcctcttgt    480
gttttagaca tttatgaact ttcctttatg taattttcca gaatccttgt cagattctaa    540
tcattgcttt ataattatag ttatactcat ggatttgtag ttgagtatga aaatattttt    600
taatgcattt tatgacttgc caattgattg acaac                              635

SEQ ID NO: 75          moltype = DNA   length = 175
FEATURE                Location/Qualifiers
source                 1..175
                       mol_type = other DNA
                       organism = synthetic construct
SEQUENCE: 75
tttctccata ataatgtgtg agtagttccc agataaggga attagggttc ctatagggtt    60
tcgctcatgt gttgagcata taagaaaccc ttagtatgta tttgtatttg taaaatactt    120
ctatcaataa aatttctaat tcctaaaacc aaaatccagt actaaaatcc agatc         175

SEQ ID NO: 76          moltype = DNA   length = 225
FEATURE                Location/Qualifiers
source                 1..225
                       mol_type = other DNA
                       organism = synthetic construct
SEQUENCE: 76
ctgtgccttc tagttgccag ccatctgttg tttgcccctc ccccgtgcct tccttgaccc    60
tggaaggtgc cactcccact gtcctttcct aataaaatga ggaaattgca tcgcattgtc    120
tgagtaggtg tcattctatt ctggggggtg gggtggggca ggacagcaag ggggaggatt    180
gggaagacaa tagcaggcat gctggggatg cggtgggctc tatgg                   225

SEQ ID NO: 77          moltype = AA    length = 30
FEATURE                Location/Qualifiers
source                 1..30
                       mol_type = protein
                       organism = synthetic construct
SEQUENCE: 77
MLSRAVCGTS RQLAPVLGYL GSRQKHSLPD                                     30

SEQ ID NO: 78          moltype = AA    length = 25
FEATURE                Location/Qualifiers
source                 1..25
                       mol_type = protein
                       organism = synthetic construct
SEQUENCE: 78
MSVLTPLLLR GLTGSARRLP VPRAK                                          25

SEQ ID NO: 79          moltype = AA    length = 49
FEATURE                Location/Qualifiers
source                 1..49
                       mol_type = protein
                       organism = synthetic construct
SEQUENCE: 79
MAPTVMMASS ATAVAPFQGL KSAASLPVAR RSTRSLGNVS NGGRIRCMQ                49

SEQ ID NO: 80          moltype = AA    length = 144
```

```
FEATURE                 Location/Qualifiers
source                  1..144
                        mol_type = protein
                        organism = Sorangium cellulosum
SEQUENCE: 80
MAPDSLVWFD PLGLIVLQQV PYNDHPLFGA VSEFIQGKSR SDLRGRNVAA VLLDDGTVIV    60
RASEGGGNHA ERVLMGLSEV DPAKVVAVYT ERSPCTGRIN CHDLLDSSLG ADVPVYYTHE   120
MIRGQEGKTA QQIEADRNQF CRGG                                          144

SEQ ID NO: 81           moltype = AA  length = 208
FEATURE                 Location/Qualifiers
source                  1..208
                        mol_type = protein
                        organism = Stackebrandtia nassauensis
SEQUENCE: 81
MSASAQLNTY LAAIGNSTTT VEAQPEAAPP PAAAESLDST PRLPDGGIDF HALAKRLGLL    60
EARPTEQPPF DPRRFNPACW QGLKPYDQAG TAEGNLFIAP GKRWNTRPMQ ASKLEVGPQS   120
DLHPQWRSRK APWHIEGKIA AYMRQKGFTD GCVYLNARPC SGPDGCARNL PDLLPVGSTL   180
HVHARYIDRT GETRFYYREY RGTGKALT                                      208

SEQ ID NO: 82           moltype = AA  length = 212
FEATURE                 Location/Qualifiers
source                  1..212
                        mol_type = protein
                        organism = Stackebrandtia nassauensis
SEQUENCE: 82
MLDAMDAYLS EIAGGNAPAR AGPKAPEPKQ PGGSSSPRAR DGRIDFRALL ERLKAQGVVG    60
LEGRSDDPIP DFDPKKQNPA CYQGLAPRQK GKPVRGNLFF PDGRRWNDVA LESSRGEPAF   120
DLNIIKPEYR SLSPARGHLE GNVAAWMRST FHQEMVLYIN ESPCRKHGKG CLYTLEHFLP   180
RGYVLHVWSR NDRGEWRGNT FRGSGEAFTE GA                                 212

SEQ ID NO: 83           moltype = AA  length = 226
FEATURE                 Location/Qualifiers
source                  1..226
                        mol_type = protein
                        organism = Stackebrandtia nassauensis
SEQUENCE: 83
MVETRDKIIA AKSRSDAGLL AFQQATNGSI DSRPAEAIAN LQRAKTHLDE AQRLVANSDA    60
AVDNYINAIL GGASAATAQP SAVIPASKPS RFKPMRTDPA KADEIRPHVG KDRAVATLWD   120
ADGNRVLGLH SADDDGPAAT AAWKPPWRDY VRLRRHVEAH AAARMHQDGH KTMVMYINLP   180
PCKYFDGCKL NLEDILPKGS TLWMHRVFQN GGTKIYQFNG TGRAYV                  226

SEQ ID NO: 84           moltype = AA  length = 168
FEATURE                 Location/Qualifiers
source                  1..168
                        mol_type = protein
                        organism = Acionosynnema mirum
SEQUENCE: 84
MLEAVRARLI GEGGGPGAVP EGGDGPPAVP AEEVERLRGE LPPPVVPGTG QKTHGRWIGP    60
DGRVRAIVSG RDEDAALVHA QLAAKGIPDE PTRNSDVEQK LAAHMVANGI RHVTLVINHR   120
PCRGFDDSCD TLVPIILPEG CTLTVHGQTD KGMRVRVRYT GGARPWWS               168

SEQ ID NO: 85           moltype = AA  length = 166
FEATURE                 Location/Qualifiers
source                  1..166
                        mol_type = protein
                        organism = Acionosynnema mirum
SEQUENCE: 85
MLDAALGAVR RIIAALGTSG AERASPGANG SERVDELAER LPPTVVPNTS AKTHGWWFTG    60
QGAAQELISG EGPDARAAYE ALREEGYPRP GMPFVAMHVE IKLAAHMRRN DIEHATVVIN   120
NIPCPLVWGC ENLIGVVLPE GSSLTVHGSN GYERTFTGGR KPPWPR                  166

SEQ ID NO: 86           moltype = AA  length = 167
FEATURE                 Location/Qualifiers
source                  1..167
                        mol_type = protein
                        organism = Acionosynnema mirum
SEQUENCE: 86
MLLTPPPRPA APPTTRPKPL VARTGDAYPP GTEWALPLIV QPHPPVGGTV PVEGHVRALR    60
PESQISHVFH PGGGHWTEQA RARLRVLPGF GWAVNLGHHV ELQIAAWMTA CGIHHAELVL   120
NRPPCGERYG LGCHQALPVL LPRGYRLTVS STRGGPQPYQ HHYEGKA                 167

SEQ ID NO: 87           moltype = AA  length = 196
FEATURE                 Location/Qualifiers
source                  1..196
                        mol_type = protein
                        organism = Flavobacterium okeanokoites
SEQUENCE: 87
QLVKSELEEK KSELRHKLKY VPHEYIELIE IARNSTQDRI LEMKVMEFFM KVYGYRGKHL    60
```

-continued

```
GGSRKPDGAI YTVGSPIDYG VIVDTKAYSG GYNLPIGQAD EMQRYVKENQ TRNKHINPNE  120
WWKVYPSSVT EFKFLFVSGH FKGNYKAQLT RLNHKTNCNG AVLSVEELLI GGEMIKAGTL  180
TLEEVRRKFN NGEINF                                                   196

SEQ ID NO: 88            moltype = AA  length = 196
FEATURE                  Location/Qualifiers
source                   1..196
                         mol_type = protein
                         organism = Flavobacterium okeanokoites
SEQUENCE: 88
QLVKSELEEK KSELRHKLKY VPHEYIELIE IARNSTQDRI LEMKVMEFFM KVYGYRGKHL   60
GGSRKPDGAI YTVGSPIDYG VIVDTKAYSG GYNLPIGQAD EMERYVEENQ TRNKHLNPNE  120
WWKVYPSSVT EFKFLFVSGH FKGNYKAQLT RLNHITNCNG AVLSVEELLI GGEMIKAGTL  180
TLEEVRRKFN NGEINF                                                   196

SEQ ID NO: 89            moltype = AA  length = 564
FEATURE                  Location/Qualifiers
source                   1..564
                         mol_type = protein
                         organism = synthetic construct
SEQUENCE: 89
LTPDQVVAIA SNNGGKQALE TVQRLLPVLC QDHGLTPDQV VAIASHDGGK QALETVQRLL   60
PVLCQDHGLT PDQVVAIASN GGGKQALETV QRLLPVLCQD HGLTPDQVVA IASNNGGKQA  120
LETVQRLLPV LCQDHGLTPD QVVAIASNNG GKQALETVQR LLPVLCQDHG LTPDQVVAIA  180
SNIGGKQALE TVQRLLPVLC QDHGLTPDQV VAIASNGGGK QALETVQRLL PVLCQDHGLT  240
PDQVVAIASN NGGKQALETV QRLLPVLCQD HGLTPDQVVA IASHDGGKQA LETVQRLLPV  300
LCQDHGLTPD QVVAIASNGG GKQALETVQR LLPVLCQDHG LTPDQVVAIA SNGGGKQALE  360
TVQRLLPVLC QDHGLTPDQV VAIASNGGGK QALETVQRLL PVLCQDHGLT PDQVVAIASN  420
NGGKQALETV QRLLPVLCQD HGLTPDQVVA IASNIGGKQA LETVQRLLPV LCQDHGLTPD  480
QVVAIASNNG GKQALETVQR LLPVLCQDHG LTPDQVVAIA SNGGGKQALE TVQRLLPVLC  540
QDHGLTPDQV VAIASNIGGK QALE                                          564

SEQ ID NO: 90            moltype = AA  length = 564
FEATURE                  Location/Qualifiers
source                   1..564
                         mol_type = protein
                         organism = synthetic construct
SEQUENCE: 90
LTPDQVVAIA SNNGGKQALE TVQRLLPVLC QDHGLTPDQV VAIASHDGGK QALETVQRLL   60
PVLCQDHGLT PDQVVAIASH DGGKQALETV QRLLPVLCQD HGLTPDQVVA IASNGGGKQA  120
LETVQRLLPV LCQDHGLTPD QVVAIASNGG GKQALETVQR LLPVLCQDHG LTPDQVVAIA  180
SNGGGKQALE TVQRLLPVLC QDHGLTPDQV VAIASNGGGK QALETVQRLL PVLCQDHGLT  240
PDQVVAIASN NGGKQALETV QRLLPVLCQD HGLTPDQVVA IASNGGGKQA LETVQRLLPV  300
LCQDHGLTPD QVVAIASHDG GKQALETVQR LLPVLCQDHG LTPDQVVAIA SHDGGKQALE  360
TVQRLLPVLC QDHGLTPDQV VAIASNIGGK QALETVQRLL PVLCQDHGLT PDQVVAIASN  420
IGGKQALETV QRLLPVLCQD HGLTPDQVVA IASNNGGKQA LETVQRLLPV LCQDHGLTPD  480
QVVAIASNNG GKQALETVQR LLPVLCQDHG LTPDQVVAIA SNIGGKQALE TVQRLLPVLC  540
QDHGLTPDQV VAIASNGGGK QALE                                          564

SEQ ID NO: 91            moltype = AA  length = 632
FEATURE                  Location/Qualifiers
source                   1..632
                         mol_type = protein
                         organism = synthetic construct
SEQUENCE: 91
LTPDQVVAIA SNNGGKQALE TVQRLLPVLC QDHGLTPDQV VAIASHDGGK QALETVQRLL   60
PVLCQDHGLT PDQVVAIASN IGGKQALETV QRLLPVLCQD HGLTPDQVVA IASNIGGKQA  120
LETVQRLLPV LCQDHGLTPD QVVAIASNIG GKQALETVQR LLPVLCQDHG LTPDQVVAIA  180
SNIGGKQALE TVQRLLPVLC QDHGLTPDQV VAIASNNGGK QALETVQRLL PVLCQDHGLT  240
PDQVVAIASN IGGKQALETV QRLLPVLCQD HGLTPDQVVA IASHDGGKQA LETVQRLLPV  300
LCQDHGLTPD QVVAIASHDG GKQALETVQR LLPVLCQDHG LTPDQVVAIA SNIGGKQALE  360
TVQRLLPVLC QDHGLTPDQV VAIASNIGGK QALETVQRLL PVLCQDHGLT PDQVVAIASN  420
NGGKQALETV QRLLPVLCQD HGLTPDQVVA IASNNGGKQA LETVQRLLPV LCQDHGLTPD  480
QVVAIASNGG GKQALETVQR LLPVLCQDHG LTPDQVVAIA SNNGGKQALE TVQRLLPVLC  540
QDHGLTPDQV VAIASHDGGK QALETVQRLL PVLCQDHGLT PDQVVAIASH DGGKQALETV  600
QRLLPVLCQD HGLTPDQVVA IASNGGGKQA LE                                 632

SEQ ID NO: 92            moltype = AA  length = 496
FEATURE                  Location/Qualifiers
source                   1..496
                         mol_type = protein
                         organism = synthetic construct
SEQUENCE: 92
LTPDQVVAIA SNNGGKQALE TVQRLLPVLC QDHGLTPDQV VAIASNNGGK QALETVQRLL   60
PVLCQDHGLT PDQVVAIASH DGGKQALETV QRLLPVLCQD HGLTPDQVVA IASNGGGKQA  120
LETVQRLLPV LCQDHGLTPD QVVAIASHDG GKQALETVQR LLPVLCQDHG LTPDQVVAIA  180
SNNGGKQALE TVQRLLPVLC QDHGLTPDQV VAIASNGGGK QALETVQRLL PVLCQDHGLT  240
PDQVVAIASH DGGKQALETV QRLLPVLCQD HGLTPDQVVA IASNNGGKQA LETVQRLLPV  300
LCQDHGLTPD QVVAIASHDG GKQALETVQR LLPVLCQDHG LTPDQVVAIA SNIGGKQALE  360
```

```
TVQRLLPVLC QDHGLTPDQV VAIASNNGGK QALETVQRLL PVLCQDHGLT PDQVVAIASH   420
DGGKQALETV QRLLPVLCQD HGLTPDQVVA IASNIGGKQA LETVQRLLPV LCQDHGLTPD   480
QVVAIASNGG GKQALE                                                  496

SEQ ID NO: 93          moltype = AA  length = 530
FEATURE                Location/Qualifiers
source                 1..530
                       mol_type = protein
                       organism = synthetic construct
SEQUENCE: 93
LTPDQVVAIA SHDGGKQALE TVQRLLPVLC QDHGLTPDQV VAIASHDGGK QALETVQRLL   60
PVLCQDHGLT PDQVVAIASN GGGKQALETV QRLLPVLCQD HGLTPDQVVA IASNNGGKQA   120
LETVQRLLPV LCQDHGLTPD QVVAIASNNG GKQALETVQR LLPVLCQDHG LTPDQVVAIA   180
SHDGGKQALE TVQRLLPVLC QDHGLTPDQV VAIASHDGGK QALETVQRLL PVLCQDHGLT   240
PDQVVAIASN NGGKQALETV QRLLPVLCQD HGLTPDQVVA IASHDGGKQA LETVQRLLPV   300
LCQDHGLTPD QVVAIASNNG GKQALETVQR LLPVLCQDHG LTPDQVVAIA SNGGGKQALE   360
TVQRLLPVLC QDHGLTPDQV VAIASHDGGK QALETVQRLL PVLCQDHGLT PDQVVAIASH   420
DGGKQALETV QRLLPVLCQD HGLTPDQVVA IASNIGGKQA LETVQRLLPV LCQDHGLTPD   480
QVVAIASHDG GKQALETVQR LLPVLCQDHG LTPDQVVAIA SNNGGKQALE              530

SEQ ID NO: 94          moltype = AA  length = 598
FEATURE                Location/Qualifiers
source                 1..598
                       mol_type = protein
                       organism = synthetic construct
SEQUENCE: 94
LTPDQVVAIA SHDGGKQALE TVQRLLPVLC QDHGLTPDQV VAIASHDGGK QALETVQRLL   60
PVLCQDHGLT PDQVVAIASH DGGKQALETV QRLLPVLCQD HGLTPDQVVA IASNIGGKQA   120
LETVQRLLPV LCQDHGLTPD QVVAIASNNG GKQALETVQR LLPVLCQDHG LTPDQVVAIA   180
SNIGGKQALE TVQRLLPVLC QDHGLTPDQV VAIASNNGGK QALETVQRLL PVLCQDHGLT   240
PDQVVAIASH DGGKQALETV QRLLPVLCQD HGLTPDQVVA IASHDGGKQA LETVQRLLPV   300
LCQDHGLTPD QVVAIASHDG GKQALETVQR LLPVLCQDHG LTPDQVVAIA SHDGGKQALE   360
TVQRLLPVLC QDHGLTPDQV VAIASNNGGK QALETVQRLL PVLCQDHGLT PDQVVAIASH   420
DGGKQALETV QRLLPVLCQD HGLTPDQVVA IASNNGGKQA LETVQRLLPV LCQDHGLTPD   480
QVVAIASNNG GKQALETVQR LLPVLCQDHG LTPDQVVAIA SHDGGKQALE TVQRLLPVLC   540
QDHGLTPDQV VAIASNNGGK QALETVQRLL PVLCQDHGLT PDQVVAIASH DGGKQALE     598

SEQ ID NO: 95          moltype = AA  length = 598
FEATURE                Location/Qualifiers
source                 1..598
                       mol_type = protein
                       organism = synthetic construct
SEQUENCE: 95
LTPDQVVAIA SHDGGKQALE TVQRLLPVLC QDHGLTPDQV VAIASHDGGK QALETVQRLL   60
PVLCQDHGLT PDQVVAIASN IGGKQALETV QRLLPVLCQD HGLTPDQVVA IASNNGGKQA   120
LETVQRLLPV LCQDHGLTPD QVVAIASNNG GKQALETVQR LLPVLCQDHG LTPDQVVAIA   180
SNIGGKQALE TVQRLLPVLC QDHGLTPDQV VAIASHDGGK QALETVQRLL PVLCQDHGLT   240
PDQVVAIASN NGGKQALETV QRLLPVLCQD HGLTPDQVVA IASNIGGKQA LETVQRLLPV   300
LCQDHGLTPD QVVAIASHDG GKQALETVQR LLPVLCQDHG LTPDQVVAIA SNNGGKQALE   360
TVQRLLPVLC QDHGLTPDQV VAIASNNGGK QALETVQRLL PVLCQDHGLT PDQVVAIASH   420
DGGKQALETV QRLLPVLCQD HGLTPDQVVA IASNNGGKQA LETVQRLLPV LCQDHGLTPD   480
QVVAIASNNG GKQALETVQR LLPVLCQDHG LTPDQVVAIA SHDGGKQALE TVQRLLPVLC   540
QDHGLTPDQV VAIASNNGGK QALETVQRLL PVLCQDHGLT PDQVVAIASN NGGKQALE     598

SEQ ID NO: 96          moltype = AA  length = 632
FEATURE                Location/Qualifiers
source                 1..632
                       mol_type = protein
                       organism = synthetic construct
SEQUENCE: 96
LTPDQVVAIA SNNGGKQALE TVQRLLPVLC QDHGLTPDQV VAIASNIGGK QALETVQRLL   60
PVLCQDHGLT PDQVVAIASH DGGKQALETV QRLLPVLCQD HGLTPDQVVA IASNNGGKQA   120
LETVQRLLPV LCQDHGLTPD QVVAIASNNG GKQALETVQR LLPVLCQDHG LTPDQVVAIA   180
SNNGGKQALE TVQRLLPVLC QDHGLTPDQV VAIASNNGGK QALETVQRLL PVLCQDHGLT   240
PDQVVAIASH DGGKQALETV QRLLPVLCQD HGLTPDQVVA IASNNGGKQA LETVQRLLPV   300
LCQDHGLTPD QVVAIASHDG GKQALETVQR LLPVLCQDHG LTPDQVVAIA SHDGGKQALE   360
TVQRLLPVLC QDHGLTPDQV VAIASNIGGK QALETVQRLL PVLCQDHGLT PDQVVAIASN   420
GGGKQALETV QRLLPVLCQD HGLTPDQVVA IASNGGGKQA LETVQRLLPV LCQDHGLTPD   480
QVVAIASHDG GKQALETVQR LLPVLCQDHG LTPDQVVAIA SNNGGKQALE TVQRLLPVLC   540
QDHGLTPDQV VAIASHDGGK QALETVQRLL PVLCQDHGLT PDQVVAIASH DGGKQALETV   600
QRLLPVLCQD HGLTPDQVVA IASNNGGKQA LE                                632

SEQ ID NO: 97          moltype = AA  length = 564
FEATURE                Location/Qualifiers
source                 1..564
                       mol_type = protein
                       organism = synthetic construct
SEQUENCE: 97
LTPDQVVAIA SNGGGKQALE TVQRLLPVLC QDHGLTPEQV VAIASNIGGK QALETVQRLL   60
```

```
PVLCQAHGLT PDQVVAIASH DGGKQALETV QRLLPVLCQA HGLTPAQVVA IANNNGGKQA    120
LETVQRLLPV LCQDHGLTPD QVVAIASHDG GKQALETVQR LLPVLCQDHG LTPEQVVAIA    180
NNNGGKQALE TVQRLLPVLC QAHGLTPDQV VAIANNNGGK QALETVQRLL PVLCQAHGLT    240
PAQVVAIASH DGGKQALETV QRLLPVLCQD HGLTPDQVVA IANNNGGKQA LETVQRLLPV    300
LCQDHGLTPE QVVAIANNNG GKQALETVQR LLPVLCQAHG LTPDQVVAIA NNNGGKQALE    360
TVQRLLPVLC QAHGLTPAQV VAIANNNGGK QALETVQRLL PVLCQDHGLT PDQVVAIASH    420
DGGKQALETV QRLLPVLCQD HGLTPEQVVA IASNGGGKQA LETVQRLLPV LCQAHGLTPD    480
QVVAIANNNG GKQALETVQR LLPVLCQAHG LTPAQVVAIA SNGGGKQALE TVQRLLPVLC    540
QDHGLTPEQV VAIASHDGGR PALE                                          564

SEQ ID NO: 98              moltype = AA   length = 564
FEATURE                    Location/Qualifiers
source                     1..564
                           mol_type = protein
                           organism = synthetic construct
SEQUENCE: 98
LTPDQVVAIA SHDGGKQALE TVQRLLPVLC QDHGLTPEQV VAIASHDGGK QALETVQRLL    60
PVLCQAHGLT PDQVVAIANN NGGKQALETV QRLLPVLCQA HGLTPAQVVA IANNNGGKQA    120
LETVQRLLPV LCQDHGLTPD QVVAIANNNG GKQALETVQR LLPVLCQDHG LTPEQVVAIA    180
SNIGGKQALE TVQRLLPVLC QAHGLTPDQV VAIANNNGGK QALETVQRLL PVLCQAHGLT    240
PAQVVAIANN NGGKQALETV QRLLPVLCQD HGLTPDQVVA IASHDGGKQA LETVQRLLPV    300
LCQDHGLTPE QVVAIASHDG GKQALETVQR LLPVLCQAHG LTPDQVVAIA NNNGGKQALE    360
TVQRLLPVLC QAHGLTPAQV VAIASHDGGK QALETVQRLL PVLCQDHGLT PDQVVAIASN    420
IGGKQALETV QRLLPVLCQD HGLTPEQVVA IASHDGGKQA LETVQRLLPV LCQAHGLTPD    480
QVVAIASNGG GKQALETVQR LLPVLCQAHG LTPAQVVAIA SNGGGKQALE TVQRLLPVLC    540
QDHGLTPEQV VAIASNNGGR PALE                                          564

SEQ ID NO: 99              moltype = AA   length = 462
FEATURE                    Location/Qualifiers
source                     1..462
                           mol_type = protein
                           organism = synthetic construct
SEQUENCE: 99
LTPDQVVAIA SNGGGKQALE TVQRLLPVLC QDHGLTPDQV VAIASNGGGK QALETVQRLL    60
PVLCQDHGLT PDQVVAIASN IGGKQAVETV QRLLPVLCQA HGLTPAQVVA IASHDGGKQA    120
VETVQRLLPV LCQDHGLTPD QVVAIASHDG GKQAVETVQR LLPVLCQDHG LTPDQVVAIA    180
SNIGGKQALE TLQRLLPVLC QAHGLTPAQV VAIASNIGGK QALETVQRLL PVLCQDHGLT    240
PDQVVAIASN IGGKQALETV QRLLPVLCQD HGLTPDQVVA IASNNGGKQA LETVQRLLPV    300
LCQAHGLTPA QVVAIASNIG GKQALETVQR LLPVLCQAHG LTPDQVVAIA SNGGGKQAVE    360
TVQRLLPVLC QAHGLTPAQV VAIASNNGGK QAVETVQRLL PVLCQAHGLT PAQVVAIASN    420
IGGKQAVETV QRLLPVLCQD HGLTPEQVVA IASNGGGKQA LE                       462

SEQ ID NO: 100             moltype = AA   length = 564
FEATURE                    Location/Qualifiers
source                     1..564
                           mol_type = protein
                           organism = synthetic construct
SEQUENCE: 100
LTPAQVVAIA SHDGGKQALE TVQRLLPVLC QAHGLTPDQV VAIASHDGGK QAVETVQRLL    60
PVLCQDHGLT PDQVVAIASN IGGKQAVETV QRLLPVLCQA HGLTPAQVVA IASNIGGKQA    120
VETVQRLLPV LCQDHGLTPD QVVAIASHDG GKQALETLQR LLPVLCQDHG LTPDQVVAIA    180
SNNGGKQALE TVQRLLPVLC QAHGLTPAQV VAIASHDGGK QALETVQRLL PVLCQDHGLT    240
PDQVVAIASN IGGKQALETV QRLLPVLCQD HGLTPDQVVA IASNGGGKQA LETVQRLLPV    300
LCQDHGLTPD QVVAIASNIG GKQAVETVQR LLPVLCQDHG LTPDQVVAIA SNIGGKQAVE    360
TVQRLLPVLC QDHGLTPDQV VAIASNIGGK QAVETVQRLL PVLCQDHGLT PDQVVAIASN    420
GGGKQALETV QRLLPVLCQD HGLTPDQVVA IASNNGGKQA LETVQRLLPV LCQDHGLTPD    480
QVVAIASNNG GKQALETVQR LLPVLCQDHG LTPAQVVAIA SNGGGKQALE TVQRLLPVLC    540
QDHGLTPEQV VAIASNGGGK QALE                                          564

SEQ ID NO: 101             moltype = AA   length = 326
FEATURE                    Location/Qualifiers
source                     1..326
                           mol_type = protein
                           organism = synthetic construct
SEQUENCE: 101
LTPEQVVAIA SNNGGKQALE TVQRLLPVLC QAHGLTPEQV VAIASNIGGK QALETVQRLL    60
PVLCQAHGLT PEQVVAIASH DGGKQALETV QRLLPVLCQA HGLTPEQVVA IASHDGGKQA    120
LETVQRLLPV LCQAHGLTPE QVVAIASHDG GKQALETVQR LLPVLCQAHG LTPEQVVAIA    180
SHDGGKQALE TVQRLLPVLC QAHGLTPEQV VAIASHDGGK QALETVQRLL PVLCQAHGLT    240
PEQVVAIASN IGGKQALETV QRLLPVLCQA HGLTPEQVVA IASNGGGKQA LETVQRLLPV    300
LCQAHGLTPE QVVAIASNGG GRPALE                                        326

SEQ ID NO: 102             moltype = AA   length = 360
FEATURE                    Location/Qualifiers
source                     1..360
                           mol_type = protein
                           organism = synthetic construct
SEQUENCE: 102
LTPEQVVAIA SNNGGKQALE TVQRLLPVLC QAHGLTPEQV VAIASNIGGK QALETVQRLL    60
```

-continued

```
PVLCQAHGLT PEQVVAIASN GGGKQALETV QRLLPVLCQA HGLTPEQVVA IASNNGGKQA   120
LETVQRLLPV LCQAHGLTPE QVVAIASNNG GKQALETVQR LLPVLCQAHG LTPEQVVAIA   180
SHDGGKQALE TVQRLLPVLC QAHGLTPEQV VAIASNGGGK QALETVQRLL PVLCQAHGLT   240
PEQVVAIASN IGGKQALETV QRLLPVLCQA HGLTPEQVVA IASNGGGKQA LETVQRLLPV   300
LCQAHGLTPE QVVAIASNGG GKQALETVQR LLPVLCQAHG LTPEQVVAIA SNGGGRPALE   360

SEQ ID NO: 103          moltype = AA   length = 496
FEATURE                 Location/Qualifiers
source                  1..496
                        mol_type = protein
                        organism = synthetic construct
SEQUENCE: 103
LTPEQVVAIA SNIGGKQALE TVQRLLPVLC QAHGLTPEQV VAIASNNGGK QALETVQRLL   60
PVLCQAHGLT PEQVVAIASH DGGKQALETV QRLLPVLCQA HGLTPEQVVA IASNIGGKQA   120
LETVQRLLPV LCQAHGLTPE QVVAIASNGG GKQALETVQR LLPVLCQAHG LTPEQVVAIA   180
SNGGGKQALE TVQRLLPVLC QAHGLTPEQV VAIASNIGGK QALETVQRLL PVLCQAHGLT   240
PEQVVAIASN NGGKQALETV QRLLPVLCQA HGLTPEQVVA IASHDGGKQA LETVQRLLPV   300
LCQAHGLTPE QVVAIASNIG GKQALETVQR LLPVLCQAHG LTPEQVVAIA SNNGGKQALE   360
TVQRLLPVLC QAHGLTPEQV VAIASNNGGK QALETVQRLL PVLCQAHGLT PEQVVAIASN   420
IGGKQALETV QRLLPVLCQA HGLTPEQVVA IASNIGGKQA LETVQRLLPV LCQAHGLTPE   480
QVVAIASNGG GRPALE                                                   496

SEQ ID NO: 104          moltype = AA   length = 428
FEATURE                 Location/Qualifiers
source                  1..428
                        mol_type = protein
                        organism = synthetic construct
SEQUENCE: 104
LTPEQVVAIA SHDGGKQALE TVQRLLPVLC QAHGLTPEQV VAIASNGGGK QALETVQRLL   60
PVLCQAHGLT PEQVVAIASN GGGKQALETV QRLLPVLCQA HGLTPEQVVA IASNIGGKQA   120
LETVQRLLPV LCQAHGLTPE QVVAIASNNG GKQALETVQR LLPVLCQAHG LTPEQVVAIA   180
SNNGGKQALE TVQRLLPVLC QAHGLTPEQV VAIASNIGGK QALETVQRLL PVLCQAHGLT   240
PEQVVAIASN NGGKQALETV QRLLPVLCQA HGLTPEQVVA IASNGGGKQA LETVQRLLPV   300
LCQAHGLTPE QVVAIASNIG GKQALETVQR LLPVLCQAHG LTPEQVVAIA SNNGGKQALE   360
TVQRLLPVLC QAHGLTPEQV VAIASNIGGK QALETVQRLL PVLCQAHGLT PEQVVAIASN   420
IGGRPALE                                                            428

SEQ ID NO: 105          moltype = AA   length = 530
FEATURE                 Location/Qualifiers
source                  1..530
                        mol_type = protein
                        organism = synthetic construct
SEQUENCE: 105
LTPEQVVAIA SNIGGKQALE TVQALLPVLC QAHGLTPQQV VAIASHDGGK QALETVQRLL   60
PVLCQAHGLT PQQVVAIASN NGGKQALETV QRLLPVLCQA HGLTPEQVVA IASNIGGKQA   120
LETVQALLPV LCQAHGLTPE QVVAIASNNG GKQALETVQA LLPVLCQAHG LTPEQVVAIA   180
SNGGGKQALE TVQALLPVLC QAHGLTPEQV VAIASNGGGK QALETVQRLL PVLCQAHGLT   240
PEQVVAIASH DGGKQALETV QALLPVLCQA HGLTPEQVVA IASNNGGKQA LETVQRLLPV   300
LCQAHGLTPE QVVAIASNNG GKQALETVQA LLPVLCQAHG LTPEQVVAIA SHDGGKQALE   360
TVQALLPVLC QAHGLTPEQV VAIASNGGGK QALETVQALL PVLCQAHGLT PEQVVAIASN   420
GGGKQALETV QRLLPVLCQA HGLTPQQVVA IASHDGGKQA LETVQRLLPV LCQAHGLTPE   480
QVVAIASNNG GKQALETVQA LLPVLCQAHG LTPQQVVAIA SNIGGRPALE               530

SEQ ID NO: 106          moltype = AA   length = 529
FEATURE                 Location/Qualifiers
source                  1..529
                        mol_type = protein
                        organism = synthetic construct
SEQUENCE: 106
LTPEQVVAIA SNIGGKQALE TVQALLPVLC QAHGLTPQQV VAIASNGGGK QALETVQRLL   60
PVLCQAHGLT PQQVVAIASN NGGKQALETV QRLLPVLCQA HGLTPEQVVA IASNNGGKQA   120
LETVQALLPV LCQAHGLTPE QVVAIASNIG GKQALETVQA LLPVLCQAHG LTPEQVVAIA   180
SNGGGKQALE TVQALLPVLC QAHGLTPEQV VAIASNIGGK QALETVQRLL PVLCQAHGLT   240
PEQVVAIASN IGGKQALETV QALLPVLCQA HGLTPEQVVA IASNIGGKQA LETVQRLLPV   300
LCQAHGLTPE QVVAIASNNG GKQALETVQA LLPVLCQAHG LTPEQVVAIA SNNGGKQALE   360
TVQALLPVLC QAHGLTPEQV VAIASNNGGK QALETVQALL PVLCQAHGLT PEQVVAIASN   420
IGGKQLETVQ RLLPVLCQAH GLTPQQVVAI ASHDGGKQAL ETVQRLLPVL CQAHGLTPEQ   480
VVAIASNNGG KQALETVQAL LPVLCQAHGL TPQQVVAIAS HDGGRPALE                529

SEQ ID NO: 107          moltype = AA   length = 530
FEATURE                 Location/Qualifiers
source                  1..530
                        mol_type = protein
                        organism = synthetic construct
SEQUENCE: 107
LTPEQVVAIA SHDGGKQALE TVQALLPVLC QAHGLTPQQV VAIASNGGGK QALETVQRLL   60
PVLCQAHGLT PQQVVAIASH DGGKQALETV QRLLPVLCQA HGLTPEQVVA IASHDGGKQA   120
LETVQALLPV LCQAHGLTPE QVVAIASNIG GKQALETVQA LLPVLCQAHG LTPEQVVAIA   180
SHDGGKQALE TVQALLPVLC QAHGLTPEQV VAIASNIGGK QALETVQRLL PVLCQAHGLT   240
```

```
PEQVVAIASH DGGKQALETV QALLPVLCQA HGLTPEQVVA IASNGGGKQA LETVQRLLPV    300
LCQAHGLTPE QVVAIASNIG GKQALETVQA LLPVLCQAHG LTPEQVVAIA SNNGGKQALE    360
TVQALLPVLC QAHGLTPEQV VAIASHDGGK QALETVQALL PVLCQAHGLT PEQVVAIASN    420
IGGKQALETV QRLLPVLCQA HGLTPQQVVA IASNNGGKQA LETVQRLLPV LCQAHGLTPE    480
QVVAIASNIG GKQALETVQA LLPVLCQAHG LTPQQVVAIA SNNGGRPALE              530

SEQ ID NO: 108         moltype = AA   length = 564
FEATURE                Location/Qualifiers
source                 1..564
                       mol_type = protein
                       organism = synthetic construct
SEQUENCE: 108
LTPEQVVAIA SHDGGKQALE TVQALLPVLC QAHGLTPQQV VAIASHDGGK QALETVQRLL    60
PVLCQAHGLT PQQVVAIASH DGGKQALETV QRLLPVLCQA HGLTPEQVVA IASHDGGKQA    120
LETVQALLPV LCQAHGLTPE QVVAIASNGG GKQALETVQA LLPVLCQAHG LTPEQVVAIA    180
SNGGGKQALE TVQALLPVLC QAHGLTPEQV VAIASHDGGK QALETVQRLL PVLCQAHGLT    240
PEQVVAIASN NGGKQALETV QALLPVLCQA HGLTPEQVVA IASNNGGKQA LETVQRLLPV    300
LCQAHGLTPE QVVAIASHDG GKQALETVQA LLPVLCQAHG LTPEQVVAIA SNIGGKQALE    360
TVQALLPVLC QAHGLTPEQV VAIASNIGGK QALETVQALL PVLCQAHGLT PEQVVAIASN    420
NGGKQALETV QRLLPVLCQA HGLTPQQVVA IASNNGGKQA LETVQRLLPV LCQAHGLTPE    480
QVVAIASNGG GKQALETVQA LLPVLCQAHG LTPEQVVAIA SNGGGKQALE TVQALLPVLC    540
QAHGLTPQQV VAIASHDGGR PALE                                          564

SEQ ID NO: 109         moltype = AA   length = 462
FEATURE                Location/Qualifiers
source                 1..462
                       mol_type = protein
                       organism = synthetic construct
SEQUENCE: 109
LTPEQVVAIA SHDGGKQALE TVQALLPVLC QAHGLTPQQV VAIASHDGGK QALETVQRLL    60
PVLCQAHGLT PQQVVAIASN GGGKQALETV QRLLPVLCQA HGLTPEQVVA IASNIGGKQA    120
LETVQALLPV LCQAHGLTPE QVVAIASNGG GKQALETVQA LLPVLCQAHG LTPEQVVAIA    180
SNGGGKQALE TVQALLPVLC QAHGLTPEQV VAIASNGGGK QALETVQRLL PVLCQAHGLT    240
PEQVVAIASN IGGKQALETV QALLPVLCQA HGLTPEQVVA IASNGGGKQA LETVQRLLPV    300
LCQAHGLTPE QVVAIASNGG GKQALETVQA LLPVLCQAHG LTPEQVVAIA SHDGGKQALE    360
TVQALLPVLC QAHGLTPEQV VAIASNGGGK QALETVQALL PVLCQAHGLT PEQVVAIASN    420
IGGKQALETV QALLPVLCQA HGLTPQQVVA IASNNGGRPA LE                       462

SEQ ID NO: 110         moltype = AA   length = 394
FEATURE                Location/Qualifiers
source                 1..394
                       mol_type = protein
                       organism = synthetic construct
SEQUENCE: 110
LTPEQVVAIA SNGGGKQALE TVQALLPVLC QAHGLTPQQV VAIASNNGGK QALETVQRLL    60
PVLCQAHGLT PQQVVAIASN IGGKQALETV QRLLPVLCQA HGLTPEQVVA IASNNGGKQA    120
LETVQALLPV LCQAHGLTPE QVVAIASNGG GKQALETVQA LLPVLCQAHG LTPEQVVAIA    180
SNIGGKQALE TVQALLPVLC QAHGLTPEQV VAIASNIGGK QALETVQRLL PVLCQAHGLT    240
PEQVVAIASN IGGKQALETV QALLPVLCQA HGLTPEQVVA IASHDGGKQA LETVQRLLPV    300
LCQAHGLTPE QVVAIASNNG GKQALETVQA LLPVLCQAHG LTPEQVVAIA SNNGGKQALE    360
TVQALLPVLC QAHGLTPQQV VAIASHDGGR PALE                               394

SEQ ID NO: 111         moltype = AA   length = 530
FEATURE                Location/Qualifiers
source                 1..530
                       mol_type = protein
                       organism = synthetic construct
SEQUENCE: 111
LTPEQVVAIA SHDGGKQALE TVQALLPVLC QAHGLTPQQV VAIASHDGGK QALETVQRLL    60
PVLCQAHGLT PQQVVAIASH DGGKQALETV QRLLPVLCQA HGLTPEQVVA IASNIGGKQA    120
LETVQALLPV LCQAHGLTPE QVVAIASNGG GKQALETVQA LLPVLCQAHG LTPEQVVAIA    180
SNNGGKQALE TVQALLPVLC QAHGLTPEQV VAIASHDGGK QALETVQRLL PVLCQAHGLT    240
PEQVVAIASH DGGKQALETV QALLPVLCQA HGLTPEQVVA IASNGGGKQA LETVQRLLPV    300
LCQAHGLTPE QVVAIASHDG GKQALETVQA LLPVLCQAHG LTPEQVVAIA SNIGGKQALE    360
TVQALLPVLC QAHGLTPEQV VAIASNNGGK QALETVQALL PVLCQAHGLT PEQVVAIASN    420
NGGKQALETV QRLLPVLCQA HGLTPQQVVA IASNIGGKQA LETVQRLLPV LCQAHGLTPE    480
QVVAIASNGG GKQALETVQA LLPVLCQAHG LTPQQVVAIA SNIGGRPALE              530

SEQ ID NO: 112         moltype = AA   length = 530
FEATURE                Location/Qualifiers
source                 1..530
                       mol_type = protein
                       organism = synthetic construct
SEQUENCE: 112
LTPEQVVAIA SNGGGKQALE TVQALLPVLC QAHGLTPQQV VAIASNGGGK QALETVQRLL    60
PVLCQAHGLT PQQVVAIASN NGGKQALETV QRLLPVLCQA HGLTPEQVVA IASNNGGKQA    120
LETVQALLPV LCQAHGLTPE QVVAIASNIG GKQALETVQA LLPVLCQAHG LTPEQVVAIA    180
SNGGGKQALE TVQALLPVLC QAHGLTPEQV VAIASNIGGK QALETVQRLL PVLCQAHGLT    240
PEQVVAIASN GGGKQALETV QALLPVLCQA HGLTPEQVVA IASNIGGKQA LETVQRLLPV    300
```

-continued

```
LCQAHGLTPE QVVAIASHDG GKQALETVQA LLPVLCQAHG LTPEQVVAIA SNGGGKQALE   360
TVQALLPVLC QAHGLTPEQV VAIASNIGGK QALETVQALL PVLCQAHGLT PEQVVAIASH   420
DGGKQALETV QRLLPVLCQA HGLTPQQVVA IASNIGGKQA LETVQRLLPV LCQAHGLTPE   480
QVVAIASNNG GKQALETVQA LLPVLCQAHG LTPQQVVAIA SHDGGRPALE              530

SEQ ID NO: 113          moltype = AA   length = 17
FEATURE                 Location/Qualifiers
source                  1..17
                        mol_type = protein
                        organism = synthetic construct
SEQUENCE: 113
NSGSETPGTS ESATPES                                                  17

SEQ ID NO: 114          moltype = AA   length = 48
FEATURE                 Location/Qualifiers
source                  1..48
                        mol_type = protein
                        organism = synthetic construct
SEQUENCE: 114
SGSETPGTSE ATPESSGGS SGGSSGSETP GTSESATPES SGGSSGGS                 48

SEQ ID NO: 115          moltype = AA   length = 16
FEATURE                 Location/Qualifiers
source                  1..16
                        mol_type = protein
                        organism = synthetic construct
SEQUENCE: 115
SGSETPGTSE SATPES                                                   16

SEQ ID NO: 116          moltype = AA   length = 14
FEATURE                 Location/Qualifiers
source                  1..14
                        mol_type = protein
                        organism = synthetic construct
SEQUENCE: 116
SGGGSGGSGG SGGS                                                     14

SEQ ID NO: 117          moltype = AA   length = 11
FEATURE                 Location/Qualifiers
source                  1..11
                        mol_type = protein
                        organism = synthetic construct
SEQUENCE: 117
SGGSGGSGGS S                                                        11

SEQ ID NO: 118          moltype = AA   length = 4
FEATURE                 Location/Qualifiers
source                  1..4
                        mol_type = protein
                        organism = synthetic construct
SEQUENCE: 118
SGGS                                                                4

SEQ ID NO: 119          moltype = AA   length = 152
FEATURE                 Location/Qualifiers
source                  1..152
                        mol_type = protein
                        organism = Barley Stripe Mosaic Virus
SEQUENCE: 119
MMATFSCVCC GTLTTSTYCG KRCERKHVYS ETRNKRLELY KKYLLEPQKC ALNGIVGHSC   60
GMPCSIAEEA CDQLPIVSRF CGQKHADLYD SLLKRSEQEL LLEFLQKKMQ ELKLSHIVKM   120
AKLESEVNAI RKSVASSFED SVGCDDSSSV SK                                 152

SEQ ID NO: 120          moltype = AA   length = 2023
FEATURE                 Location/Qualifiers
source                  1..2023
                        mol_type = protein
                        organism = synthetic construct
SEQUENCE: 120
MDYKDHDGDY KDHDIDYKDD DDKMAPKKKR KVGIHGVPSR MVDLRTLGYS QQQQEKIKPK   60
VRSTVAQHHE ALVGHGFTHA HIVALSQHPA ALGTVAVTYQ HIITALPEAT HEDIVGVGKQ   120
WSGARALEAL LTDAGELRGP PLQLDTGQLV KIAKRGGVTA MEAVHASRNA LTGAPLNLTP   180
DQVVAIASNN GGKQALETVQ RLLPVLCQDH GLTPDQVVAI ASHDGGKQAL ETVQRLLPVL   240
CQDHGLTPDQ VVAIASNGGG KQALETVQRL LPVLCQDHGL TPDQVVAIAS NNGGKQALET   300
VQRLLPVLCQ DHGLTPDQVV AIASNNGGKQ ALETVQRLLP VLCQDHGLTP DQVVAIASNI   360
GGKQALETVQ RLLPVLCQDH GLTPDQVVAI ASNGGGKQAL ETVQRLLPVL CQDHGLTPDQ   420
VVAIASNNGG KQALETVQRL LPVLCQDHGL TPDQVVAIAS HDGGKQALET VQRLLPVLCQ   480
DHGLTPDQVV AIASNGGGKQ ALETVQRLLP VLCQDHGLTP DQVVAIASNG GGKQALETVQ   540
RLLPVLCQDH GLTPDQVVAI ASNGGGKQAL ETVQRLLPVL CQDHGLTPDQ VVAIASNNGG   600
```

```
KQALETVQRL LPVLCQDHGL TPDQVVAIAS NIGGKQALET VQRLLPVLCQ DHGLTPDQVV    660
AIASNNGGKQ ALETVQRLLP VLCQDHGLTP DQVVAIASNG GGKQALETVQ RLLPVLCQDH    720
GLTPDQVVAI ASNIGGKQAL ESIVAQLSRP DPALAALTND HLVALACLGG RPAMDAVKKG    780
LPHAPELIRR VNRRIGERTS HRVAGSQLVK SELEEKKSEL RHKLKYVPHE YIELIEIARN    840
STQDRILEMK VMEFFMKVYG YRGKHLGGSR KPDGAIYTVG SPIDYGVIVD TKAYSGGYNL    900
PIGQADEMQR YVKENQTRNK HINPNEWWKV YPSSVTEFKF LFVSGHFKGN YKAQLTRLNH    960
KTNCNGAVLS VEELLIGGEM IKAGTLTLEE VRRKFNNGEI NFEGRGSLLT CGDVEENPGP   1020
RMDYKDHDGD YKDHDIDYKD DDDKMAPKKK RKVGIHGVPA RMVDLRTLGY SQQQQEKIKP   1080
KVRSTVAQHH EALVGHGFTH AHIVALSQHP AALGTVAVTY QHIITALPEA THEDIVGVGK   1140
QWSGARALEA LLTDAGELRG PPLQLDTGQL VKIAKRGGVT AMEAVHASRN ALTGAPLNLT   1200
PDQVVAIASN NGGKQALETV QRLLPVLCQD HGLTPDQVVA IASHDGGKQA LETVQRLLPV   1260
LCQDHGLTPD QVVAIASHDG GKQALETVQR LLPVLCQDHG LTPDQVVAIA SNGGGKQALE   1320
TVQRLLPVLC QDHGLTPDQV VAIASNGGGK QALETVQRLL PVLCQDHGLT PDQVVAIASN   1380
GGGKQALETV QRLLPVLCQD HGLTPDQVVA IASNGGGKQA LETVQRLLPV LCQDHGLTPD   1440
QVVAIASNNG GKQALETVQR LLPVLCQDHG LTPDQVVAIA SNGGGKQALE TVQRLLPVLC   1500
QDHGLTPDQV VAIASHDGGK QALETVQRLL PVLCQDHGLT PDQVVAIASH DGGKQALETV   1560
QRLLPVLCQD HGLTPDQVVA IASNIGGKQA LETVQRLLPV LCQDHGLTPD QVVAIASNIG   1620
GKQALETVQR LLPVLCQDHG LTPDQVVAIA SNNGGKQALE TVQRLLPVLC QDHGLTPDQV   1680
VAIASNNGGK QALETVQRLL PVLCQDHGLT PDQVVAIASN IGGKQALETV QRLLPVLCQD   1740
HGLTPDQVVA IASNGGGKQA LESIVAQLSR PDPALAALTN DHLVALACLG GRPAMDAVKK   1800
GLPHAPELIR RVNRRIGERT SHRVAGSQLV KSELEEKKSE LRHKLKYVPH EYIELIEIAR   1860
NSTQDRILEM KVMEFFMKVY GYRGKHLGGS RKPDGAIYTV GSPIDYGVIV DTKAYSGGYN   1920
LPIGQADEME RYVEENQTRN KHLNPNEWWK VYPSSVTEFK FLFVSGHFKG NYKAQLTRLN   1980
HITNCNGAVL SVEELLIGGE MIKAGTLTLE EVRRKFNNGE INF                     2023

SEQ ID NO: 121         moltype = AA  length = 2023
FEATURE                Location/Qualifiers
source                 1..2023
                       mol_type = protein
                       organism = synthetic construct
SEQUENCE: 121
MDYKDHDGDY KDHDIDYKDD DDKMAPKKKR KVGIHGVPSR MVDLRTLGYS QQQQEKIKPK     60
VRSTVAQHHE ALVGHGFTHA HIVALSQHPA ALGTVAVTYQ HIITALPEAT HEDIVGVGKQ    120
WSGARALEAL LTDAGELRGP PLQLDTGQLV KIAKRGGVTA MEAVHASRNA LTGAPLNLTP    180
DQVVAIASNN GGKQALETVQ RLLPVLCQDH GLTPDQVVAI ASHDGGKQAL ETVQRLLPVL    240
CQDHGLTPDQ VVAIASNGGG KQALETVQRL LPVLCQDHGL TPDQVVAIAS NNGGKQALET    300
VQRLLPVLCQ DHGLTPDQVV AIASNNGGKQ ALETVQRLLP VLCQDHGLTP DQVVAIASNI    360
GGKQALETVQ RLLPVLCQDH GLTPDQVVAI ASNGGGKQAL ETVQRLLPVL CQDHGLTPDQ    420
VVAIASNNGG KQALETVQRL LPVLCQDHGL TPDQVVAIAS HDGGKQALET VQRLLPVLCQ    480
DHGLTPDQVV AIASNGGGKQ ALETVQRLLP VLCQDHGLTP DQVVAIASNG GGKQALETVQ    540
RLLPVLCQDH GLTPDQVVAI ASNGGGKQAL ETVQRLLPVL CQDHGLTPDQ VVAIASNNGG    600
KQALETVQRL LPVLCQDHGL TPDQVVAIAS NIGGKQALET VQRLLPVLCQ DHGLTPDQVV    660
AIASNNGGKQ ALETVQRLLP VLCQDHGLTP DQVVAIASNG GGKQALETVQ RLLPVLCQDH    720
GLTPDQVVAI ASNIGGKQAL ESIVAQLSRP DPALAALTND HLVALACLGG RPAMDAVKKG    780
LPHAPELIRR VNRRIGERTS HRVAGSQLVK SELEEKKSEL RHKLKYVPHE YIELIEIARN    840
STQDRILEMK VMEFFMKVYG YRGKHLGGSR KPDGAIYTVG SPIDYGVIVD TKAYSGGYNL    900
PIGQADEMQR YVKENQTRNK HINPNEWWKV YPSSVTEFKF LFVSGHFKGN YKAQLTRLNH    960
KTNCNGAVLS VEELLIGGEM IKAGTLTLEE VRRKFNNGEI NFEGRGSLLT CGDVEENPGP   1020
RMDYKDHDGD YKDHDIDYKD DDDKMAPKKK RKVGIHGVPA RMVDLRTLGY SQQQQEKIKP   1080
KVRSTVAQHH EALVGHGFTH AHIVALSQHP AALGTVAVTY QHIITALPEA THEDIVGVGK   1140
QWSGARALEA LLTDAGELRG PPLQLDTGQL VKIAKRGGVT AMEAVHASRN ALTGAPLNLT   1200
PDQVVAIASN NGGKQALETV QRLLPVLCQD HGLTPDQVVA IASHDGGKQA LETVQRLLPV   1260
LCQDHGLTPD QVVAIASHDG GKQALETVQR LLPVLCQDHG LTPDQVVAIA SNGGGKQALE   1320
TVQRLLPVLC QDHGLTPDQV VAIASNGGGK QALETVQRLL PVLCQDHGLT PDQVVAIASN   1380
GGGKQALETV QRLLPVLCQD HGLTPDQVVA IASNGGGKQA LETVQRLLPV LCQDHGLTPD   1440
QVVAIASNNG GKQALETVQR LLPVLCQDHG LTPDQVVAIA SNGGGKQALE TVQRLLPVLC   1500
QDHGLTPDQV VAIASHDGGK QALETVQRLL PVLCQDHGLT PDQVVAIASH DGGKQALETV   1560
QRLLPVLCQD HGLTPDQVVA IASNIGGKQA LETVQRLLPV LCQDHGLTPD QVVAIASNIG   1620
GKQALETVQR LLPVLCQDHG LTPDQVVAIA SNNGGKQALE TVQRLLPVLC QDHGLTPDQV   1680
VAIASNNGGK QALETVQRLL PVLCQDHGLT PDQVVAIASN IGGKQALETV QRLLPVLCQD   1740
HGLTPDQVVA IASNGGGKQA LESIVAQLSR PDPALAALTN DHLVALACLG GRPAMDAVKK   1800
GLPHAPELIR RVNRRIGERT SHRVAGSQLV KSELEEKKSE LRHKLKYVPH EYIELIEIAR   1860
NSTQDRILEM KVMEFFMKVY GYRGKHLGGS RKPAGAIYTV GSPIDYGVIV DTKAYSGGYN   1920
LPIGQADEME RYVEENQTRN KHLNPNEWWK VYPSSVTEFK FLFVSGHFKG NYKAQLTRLN   1980
HITNCNGAVL SVEELLIGGE MIKAGTLTLE EVRRKFNNGE INF                     2023

SEQ ID NO: 122         moltype = AA  length = 2023
FEATURE                Location/Qualifiers
source                 1..2023
                       mol_type = protein
                       organism = synthetic construct
SEQUENCE: 122
MDYKDHDGDY KDHDIDYKDD DDKMAPKKKR KVGIHGVPSR MVDLRTLGYS QQQQEKIKPK     60
VRSTVAQHHE ALVGHGFTHA HIVALSQHPA ALGTVAVTYQ HIITALPEAT HEDIVGVGKQ    120
WSGARALEAL LTDAGELRGP PLQLDTGQLV KIAKRGGVTA MEAVHASRNA LTGAPLNLTP    180
DQVVAIASNN GGKQALETVQ RLLPVLCQDH GLTPDQVVAI ASHDGGKQAL ETVQRLLPVL    240
CQDHGLTPDQ VVAIASNGGG KQALETVQRL LPVLCQDHGL TPDQVVAIAS NNGGKQALET    300
VQRLLPVLCQ DHGLTPDQVV AIASNNGGKQ ALETVQRLLP VLCQDHGLTP DQVVAIASNI    360
GGKQALETVQ RLLPVLCQDH GLTPDQVVAI ASNGGGKQAL ETVQRLLPVL CQDHGLTPDQ    420
```

-continued

```
VVAIASNNGG KQALETVQRL LPVLCQDHGL TPDQVVAIAS HDGGKQALET VQRLLPVLCQ 480
DHGLTPDQVV AIASNGGGKQ ALETVQRLLP VLCQDHGLTP DQVVAIASNG GGKQALETVQ 540
RLLPVLCQDH GLTPDQVVAI ASNGGGKQAL ETVQRLLPVL CQDHGLTPDQ VVAIASNNGG 600
KQALETVQRL LPVLCQDHGL TPDQVVAIAS NIGGKQALET VQRLLPVLCQ DHGLTPDQVV 660
AIASNNGGKQ ALETVQRLLP VLCQDHGLTP DQVVAIASNG GGKQALETVQ RLLPVLCQDH 720
GLTPDQVVAI ASNIGGKQAL ESIVAQLSRP DPALAALTND HLVALACLGG RPAMDAVKKG 780
LPHAPELIRR VNRRIGERTS HRVAGSQLVK SELEEKKSEL RHKLKYVPHE YIELIEIARN 840
STQDRILEMK VMEFFMKVYG YRGKHLGGSR KPAGAIYTVG SPIDYGVIVD TKAYSGGYNL 900
PIGQADEMQR YVKENQTRNK HINPNEWWKV YPSSVTEFKF LFVSGHFKGN YKAQLTRLNH 960
KTNCNGAVLS VEELLIGGEM IKAGTLTLEE VRRKFNNGEI NFEGRGSLLT CGDVEENPGP 1020
RMDYKDHDGD YKDHDIDYKD DDDKMAPKKK RKVGIHGVPA RMVDLRTLGY SQQQQEKIKP 1080
KVRSTVAQHH EALVGHGFTH AHIVALSQHP AALGTVAVTY QHIITALPEA THEDIVGVGK 1140
QWSGARALEA LLTDAGELRG PPLQLDTGQL VKIAKRGGVT AMEAVHASRN ALTGAPLNLT 1200
PDQVVAIASN NGGKQALETV QRLLPVLCQD HGLTPDQVVA IASHDGGKQA LETVQRLLPV 1260
LCQDHGLTPD QVVAIASHDG GKQALETVQR LLPVLCQDHG LTPDQVVAIA SNGGGKQALE 1320
TVQRLLPVLC QDHGLTPDQV VAIASNGGGK QALETVQRLL PVLCQDHGLT PDQVVAIASN 1380
GGGKQALETV QRLLPVLCQD HGLTPDQVVA IASNGGGKQA LETVQRLLPV LCQDHGLTPD 1440
QVVAIASNNG GKQALETVQR LLPVLCQDHG LTPDQVVAIA SNGGGKQALE TVQRLLPVLC 1500
QDHGLTPDQV VAIASHDGGK QALETVQRLL PVLCQDHGLT PDQVVAIASH DGGKQALETV 1560
QRLLPVLCQD HGLTPDQVVA IASNIGGKQA LETVQRLLPV LCQDHGLTPD QVVAIASNIG 1620
GKQALETVQR LLPVLCQDHG LTPDQVVAIA SNNGGKQALE TVQRLLPVLC QDHGLTPDQV 1680
VAIASNNGGK QALETVQRLL PVLCQDHGLT PDQVVAIASN IGGKQALETV QRLLPVLCQD 1740
HGLTPDQVVA IASNGGGKQA LESIVAQLSR PDPALAALTN DHLVALACLG GRPAMDAVKK 1800
GLPHAPELIR RVNRRIGERT SHRVAGSQLV KSELEEKKSE LRHKLKYVPH EYIELIEIAR 1860
NSTQDRILEM KVMEFFMKVY GYRGKHLGGS RKPDGAIYTV GSPIDYGVIV DTKAYSGGYN 1920
LPIGQADEME RYVEENQTRN KHLNPNEWWK VYPSSVTEFK FLFVSGHFKG NYKAQLTRLN 1980
HITNCNGAVL SVEELLIGGE MIKAGTLTLE EVRRKFNNGE INF 2023
```

```
SEQ ID NO: 123          moltype = AA   length = 317
FEATURE                 Location/Qualifiers
source                  1..317
                        mol_type = protein
                        organism = synthetic construct
SEQUENCE: 123
MKRTADGSEF ESPKKKRKVM EASPASGPRH LMDPHIFTSN FNNGIGRHKT YLCYEVERLD 60
NGTSVKMDQH RGFLHNQAKN LLCGFYGRHA ELRFLDLVPS LQLDPAQIYR VTWFISWSPC 120
FSWGCAGEVR AFLQENTHVR LRIFAARIYD YDPLYKEALQ MLRDAGAQVS IMTYDEFKHC 180
WDTFVDHQGC PFQPWDGLDE HSQALSGRLR AILQNQGNSG SETPGTSESA TPESTNLSDI 240
IEKETGKQLV IQESILMLPE EVEEVIGNKP ESDILVHTAY DESTDENVML LTSDAPEYKP 300
WALVIQDSNG ENKIKML 317
```

```
SEQ ID NO: 124          moltype = AA   length = 286
FEATURE                 Location/Qualifiers
source                  1..286
                        mol_type = protein
                        organism = synthetic construct
SEQUENCE: 124
MKRTADGSEF ESPKKKRKVL EAVRARLIGE GGGPGAVPEG GDGPPAVPAE EVERLRGELP 60
PPVVPGTGQK THGRWIGPDG RVRAIVSGRD EDAALVHAQL AAKGIPDEPT RNSDVEQKLA 120
AHMVANGIRH VTLVINHRPC RGFDDSCDTL VPIILPEGCT LTVHGQTDKG MRVRVRYTGG 180
ARPWWSNSGS ETPGTSESAT PESTNLSDII EKETGKQLVI QESILMLPEE VEEVIGNKPE 240
SDILVHTAYD ESTDENVMLL TSDAPEYKPW ALVIQDSNGE NKIKML 286
```

```
SEQ ID NO: 125          moltype = AA   length = 856
FEATURE                 Location/Qualifiers
source                  1..856
                        mol_type = protein
                        organism = synthetic construct
SEQUENCE: 125
MGIQGLLQFI QEASEPVNVK KYKGQAVAVD TYCWLHKGAI ACAEKLAKGE PTDRYVGFCM 60
KFVNMLLSYG VKPILIFDGC TLPSKKEVER SRRERRQSNL LKGKQLLREG KVSEARDCFA 120
RSINITHAMA HKVIKAARAL GVDCLVAPYE ADAQLAYLNK AGIVQAVITE DSDLLAFGCK 180
KVILKMDQFG NGLEVDQARL GMCKQLGDVF TEEKFRYMCI LSGCDYLASL RGIGLAKACK 240
VLRLANNPDI VKVIKKIGHY LRMNITVPED YITGFIRANN TFLYQLVFDP IQRKLVPLNA 300
YGDDVNPETL TYAGQYVGDS VALQIALGNR DVNTFEQIDD YSPDTMPAHS RSHSWNEKAG 360
QKPPGTNSIW HKNYCPRLEV NSVSHAPQLK EKPSTLGLKQ VISTKGLNLP RKSCVLKRPR 420
NEALAEDDLL SQYSSVSKKI KENGCGDGTS PNSSKMSKSC PDSGTAHKTD AHTPSKMRNK 480
FATFLQRRNE ESGAVVVPGT RSRFFCSSQD FDNFIPKKES GQPLNETVAT GKATTSLLGA 540
LDCPDTEGHK PVDANGTHNL SSQIPGNAAV SPEDEAQSSE TSKLLGAMSP PSLGTLRSCF 600
SWSGTLREFS RTPSPSASTT LQQFRRKSDP PACLPEASAV VTDRCDSKSE MLGETSQPLH 660
ELGCSSRSQE SMDSSCGLNT SSLSQPSSRD SGSEESDCNN KSLDNQGEQN SKQHLPHFSK 720
KDGLRRNKVP GLCRSSSMDS FSTTKIKPLV PARVSGLSKK SGSMQTRKHH DVENKPGLQT 780
KISELWKNFG FKKDSEKLPS CKKPLSPVKD NIQLTPETED EIFNKPECVR AQRAIFHMKR 840
TADGSEFESP KKKRKV 856
```

```
SEQ ID NO: 126          moltype = AA   length = 255
FEATURE                 Location/Qualifiers
source                  1..255
                        mol_type = protein
```

-continued

```
                         organism = synthetic construct
SEQUENCE: 126
MSEPPRAETF VFLDLEATGL PNMDPEIAEI SLFAVHRSSL ENPERDDSGS LVLPRVLDKL   60
TLCMCPERPF TAKASEITGL SSESLMHCGK AGFNGAVVRT LQGFLSRQEG PICLVAHNGF   120
DYDFPLLCTE LQRLGAHLPQ DTVCLDTLPA LRGLDRAHSH GTRAQGRKSY SLASLFHRYF   180
QAEPSAAHSA EGDVHTLLLI FLHRAPELLA WADEQARSWA HIEPMYVPPD GPSLEAMKRT   240
ADGSEFESPK KKRKV                                                    255

SEQ ID NO: 127          moltype = AA  length = 2269
FEATURE                 Location/Qualifiers
source                  1..2269
                        mol_type = protein
                        organism = synthetic construct
SEQUENCE: 127
MDYKDHDGDY KDHDIDYKDD DDKMAPKKKR KVEASPASGP RHLMDPHIFT SNFNNGIGRH   60
KTYLCYEVER LDNGTSVKMD QHRGFLHNQA KNLLCGFYGR HAELRFLDLV PSLQLDPAQI   120
YRVTWFISWS PCFSWGCAGE VRAFLQENTH VRLRIFAARI YDYDPLYKEA LQMLRDAGAQ   180
VSIMTYDEFK HCWDTFVDHQ GCPFQPWDGL DEHSQALSGR LRAILQNQGN SGSETPGTSE   240
SATPESSGGS SGGSSGSETP GTSESATPES SGGSSGGSGI HGVPSRMVDL RTLGYSQQQQ   300
EKIKPKVRST VAQHHEALVG HGFTHAHIVA LSQHPAALGT VAVTYQHIIT ALPEATHEDI   360
VGVGKQWSGA RALEALLTDA GELRGPPLQL DTGQLVKIAK RGGVTAMEAV HASRNALTGA   420
PLNLTPDQVV AIASNNGGKQ ALETVQRLLP VLCQDHGLTP DQVVAIASHD GGKQALETVQ   480
RLLPVLCQDH GLTPDQVVAI ASNGGGKQAL ETVQRLLPVL CQDHGLTPDQ VVAIASNNGG   540
KQALETVQRL LPVLCQDHGL TPDQVVAIAS NNGGKQALET VQRLLPVLCQ DHGLTPDQVV   600
AIASNIGGKQ ALETVQRLLP VLCQDHGLTP DQVVAIASNG GGKQALETVQ RLLPVLCQDH   660
GLTPDQVVAI ASNNGGKQAL ETVQRLLPVL CQDHGLTPDQ VVAIASHDGG KQALETVQRL   720
LPVLCQDHGL TPDQVVAIAS NGGGKQALET VQRLLPVLCQ DHGLTPDQVV AIASNGGGKQ   780
ALETVQRLLP VLCQDHGLTP DQVVAIASNG GGKQALETVQ RLLPVLCQDH GLTPDQVVAI   840
ASNNGGKQAL ETVQRLLPVL CQDHGLTPDQ VVAIASNIGG KQALETVQRL LPVLCQDHGL   900
TPDQVVAIAS NNGGKQALET VQRLLPVLCQ DHGLTPDQVV AIASNGGGKQ ALETVQRLLP   960
VLCQDHGLTP DQVVAIASNI GGKQALESIV AQLSRPDPAL AALTNDHLVA LACLGGRPAM   1020
DAVKKGLPHA PELIRRVNRR IGERTSHRVA GSQLVKSELE EKKSELRHKL KYVPHEYIEL   1080
IEIARNSTQD RILEMKVMEF FMKVYGYRGK HLGGSRKPDG AIYTVGSPID YGVIVDTKAY   1140
SGGYNLPIGQ ADEMQRYVKE NQTRNKHINP NEWWKVYPSS VTEFKFLFVS GHFKGNYKAQ   1200
LTRLNHKTNC NGAVLSVEEL LIGGEMIKAG TLTLEEVRRK FNNGEINFEG RGSLLTCGDV   1260
EENPGPRMDY KDHDGDYKDH DIDYKDDDDK MAPKKKRKVG IHGVPARMVD LRTLGYSQQQ   1320
QEKIKPKVRS TVAQHHEALV GHGFTHAHIV ALSQHPAALG TVAVTYQHII TALPEATHED   1380
IVGVGKQWSG ARALEALLTD AGELRGPPLQ LDTGQLVKIA KRGGVTAMEA VHASRNALTG   1440
APLNLTPDQV VAIASNNGGK QALETVQRLL PVLCQDHGLT PDQVVAIASH DGGKQALETV   1500
QRLLPVLCQD HGLTPDQVVA IASHDGGKQA LETVQRLLPV LCQDHGLTPD QVVAIASNGG   1560
GKQALETVQR LLPVLCQDHG LTPDQVVAIA SNGGGKQALE TVQRLLPVLC QDHGLTPDQV   1620
VAIASNGGGK QALETVQRLL PVLCQDHGLT PDQVVAIASN GGGKQALETV QRLLPVLCQD   1680
HGLTPDQVVA IASNNGGKQA LETVQRLLPV LCQDHGLTPD QVVAIASNGG KQALETVQLL   1740
LLPVLCQDHG LTPDQVVAIA SHDGGKQALE TVQRLLPVLC QDHGLTPDQV VAIASHDGGK   1800
QALETVQRLL PVLCQDHGLT PDQVVAIASN IGGKQALETV QRLLPVLCQD HGLTPDQVVA   1860
IASNIGGKQA LETVQRLLPV LCQDHGLTPD QVVAIASNNG GKQALETVQR LLPVLCQDHG   1920
LTPDQVVAIA SNGGGKQALE TVQRLLPVLC QDHGLTPDQV VAIASNIGGK QALETVQRLL   1980
PVLCQDHGLT PDQVVAIASN GGGKQALESI VAQLSRPDPA LAALTNDHLV ALACLGGRPA   2040
MDAVKKGLPH APELIRRVNR RIGERTSHRV AGSQLVKSEL EEKKSELRHK LKYVPHEYIE   2100
LIEIARNSTQ DRILEMKVME FFMKVYGYRG KHLGGSRKPA GAIYTVGSPI DYGVIVDTKA   2160
YSGGYNLPIG QADEMERYVE ENQTRNKHLN PNEWWKVYPS SVTEFKFLFV SGHFKGNYKA   2220
QLTRLNHITN CNGAVLSVEE LLIGGEMIKA GTLTLEEVRR KFNNGEINF                2269

SEQ ID NO: 128          moltype = AA  length = 2269
FEATURE                 Location/Qualifiers
source                  1..2269
                        mol_type = protein
                        organism = synthetic construct
SEQUENCE: 128
MDYKDHDGDY KDHDIDYKDD DDKMAPKKKR KVEASPASGP RHLMDPHIFT SNFNNGIGRH   60
KTYLCYEVER LDNGTSVKMD QHRGFLHNQA KNLLCGFYGR HAELRFLDLV PSLQLDPAQI   120
YRVTWFISWS PCFSWGCAGE VRAFLQENTH VRLRIFAARI YDYDPLYKEA LQMLRDAGAQ   180
VSIMTYDEFK HCWDTFVDHQ GCPFQPWDGL DEHSQALSGR LRAILQNQGN SGSETPGTSE   240
SATPESSGGS SGGSSGSETP GTSESATPES SGGSSGGSGI HGVPSRMVDL RTLGYSQQQQ   300
EKIKPKVRST VAQHHEALVG HGFTHAHIVA LSQHPAALGT VAVTYQHIIT ALPEATHEDI   360
VGVGKQWSGA RALEALLTDA GELRGPPLQL DTGQLVKIAK RGGVTAMEAV HASRNALTGA   420
PLNLTPDQVV AIASNNGGKQ ALETVQRLLP VLCQDHGLTP DQVVAIASHD GGKQALETVQ   480
RLLPVLCQDH GLTPDQVVAI ASNGGGKQAL ETVQRLLPVL CQDHGLTPDQ VVAIASNNGG   540
KQALETVQRL LPVLCQDHGL TPDQVVAIAS NNGGKQALET VQRLLPVLCQ DHGLTPDQVV   600
AIASNIGGKQ ALETVQRLLP VLCQDHGLTP DQVVAIASNG GGKQALETVQ RLLPVLCQDH   660
GLTPDQVVAI ASNNGGKQAL ETVQRLLPVL CQDHGLTPDQ VVAIASHDGG KQALETVQRL   720
LPVLCQDHGL TPDQVVAIAS NGGGKQALET VQRLLPVLCQ DHGLTPDQVV AIASNGGGKQ   780
ALETVQRLLP VLCQDHGLTP DQVVAIASNG GGKQALETVQ RLLPVLCQDH GLTPDQVVAI   840
ASNNGGKQAL ETVQRLLPVL CQDHGLTPDQ VVAIASNIGG KQALETVQRL LPVLCQDHGL   900
TPDQVVAIAS NNGGKQALET VQRLLPVLCQ DHGLTPDQVV AIASNGGGKQ ALETVQRLLP   960
VLCQDHGLTP DQVVAIASNI GGKQALESIV AQLSRPDPAL AALTNDHLVA LACLGGRPAM   1020
DAVKKGLPHA PELIRRVNRR IGERTSHRVA GSQLVKSELE EKKSELRHKL KYVPHEYIEL   1080
IEIARNSTQD RILEMKVMEF FMKVYGYRGK HLGGSRKPAG AIYTVGSPID YGVIVDTKAY   1140
SGGYNLPIGQ ADEMQRYVKE NQTRNKHINP NEWWKVYPSS VTEFKFLFVS GHFKGNYKAQ   1200
```

-continued

```
LTRLNHKTNC NGAVLSVEEL LIGGEMIKAG TLTLEEVRRK FNNGEINFEG RGSLLTCGDV   1260
EENPGPRMDY KDHDGDYKDH DIDYKDDDDK MAPKKKRKVG IHGVPARMVD LRTLGYSQQQ   1320
QEKIKPKVRS TVAQHHEALV GHGFTHAHIV ALSQHPAALG TVAVTYQHII TALPEATHED   1380
IVGVGKQWSG ARALEALLTD AGELRGPPLQ LDTGQLVKIA KRGGVTAMEA VHASRNALTG   1440
APLNLTPDQV VAIASNNGGK QALETVQRLL PVLCQDHGLT PDQVVAIASH DGGKQALETV   1500
QRLLPVLCQD HGLTPDQVVA IASHDGGKQA LETVQRLLPV LCQDHGLTPD QVVAIASNGG   1560
GKQALETVQR LLPVLCQDHG LTPDQVVAIA SNGGGKQALE TVQRLLPVLC QDHGLTPDQV   1620
VAIASNGGGK QALETVQRLL PVLCQDHGLT PDQVVAIASN GGGKQALETV QRLLPVLCQD   1680
HGLTPDQVVA IASNNGGKQA LETVQRLLPV LCQDHGLTPD QVVAIASNGG KGQALETVQR   1740
LLPVLCQDHG LTPDQVVAIA SHDGGKQALE TVQRLLPVLC QDHGLTPDQV VAIASHDGGK   1800
QALETVQRLL PVLCQDHGLT PDQVVAIASN IGGKQALETV QRLLPVLCQD HGLTPDQVVA   1860
IASNIGGKQA LETVQRLLPV LCQDHGLTPD QVVAIASNNG GKQALETVQR LLPVLCQDHG   1920
LTPDQVVAIA SNNGGKQALE TVQRLLPVLC QDHGLTPDQV VAIASNIGGK QALETVQRLL   1980
PVLCQDHGLT PDQVVAIASN GGGKQALESI VAQLSRPDPA LAALTNDHLV ALACLGGRPA   2040
MDAVKKGLPH APELIRRVNR RIGERTSHRV AGSQLVKSEL EEKKSELRHK LKYVPHEYIE   2100
LIEIARNSTQ DRILEMKVME FFMKVYGYRG KHLGGSRKPD GAIYTVGSPI DYGVIVDTKA   2160
YSGGYNLPIG QADEMERYVE ENQTRNKHLN PNEWWKVYPS SVTEFKFLFV SGHFKGNYKA   2220
QLTRLNHITN CNGAVLSVEE LLIGGEMIKA GTLTLEEVRR KFNNGEINF              2269

SEQ ID NO: 129              moltype = AA   length = 856
FEATURE                     Location/Qualifiers
source                      1..856
                            mol_type = protein
                            organism = synthetic construct
SEQUENCE: 129
MGIQGLLQFI QEASEPVNVK KYKGQAVAVD TYCWLHKGAI ACAEKLAKGE PTDRYVGFCM   60
KFVNMLLSYG VKPILIFDGC TLPSKKEVER SRRERRQSNL LKGKQLLREG KVSEARDCFA   120
RSINITHAMA HKVIKAARAL GVDCLVAPYE ADAQLAYLNK AGIVQAVITE DSDLLAFGCK   180
KVILKMDQFG NGLEVDQARL GMCKQLGDVF TEEKFRYMCI LSGCDYLASL RGIGLAKACK   240
VLRLANNPDI VKVIKKIGHY LRMNITVPED YITGFIRANN TFLYQLVFDP IQRKLVPLNA   300
YGDDVNPETL TYAGQYVGDS VALQIALGNR DVNTFEQIDD YSPDTMPAHS RSHSWNEKAG   360
QKPPGTNSIW HKNYCPRLEV NSVSHAPQLK EKPSTLGLKQ VISTKGLNLP RKSCVLKRPR   420
NEALAEDDLL SQYSSVSKKI KENGCGDGTS PNSSKMSKSC PDSGTAHKTD AHTPSKMRNK   480
FATFLQRRNE ESGAVVVPGT RSRFFCSSQD FDNFIPKKES GQPLNETVAT GKATTSLLGA   540
LDCPDTEGHK PVDANGTHNL SSQIPGNAAV SPEDEAQSSE TSKLLGAMSP PSLGTLRSCF   600
SWSGTLREFS RTPSPSASTT LQQFRRKSDP PACLPEASAV VTDRCDSKSE MLGETSQPLH   660
ELGCSSRSQE SMDSSCGLNT SSLSQPSSRD SGSEESDCNN KSLDNQGEQN SKQHLPHFSK   720
KDGLRRNKVP GLCRSSSMDS FSTTKIKPLV PARVSGLSKK SGSMQTRKHH DVENKPGLQT   780
KISELWKNFG FKKDSEKLPS CKKPLSPVKD NIQLTPETED EIFNKPECVR AQRAIFHMKR   840
TADGSEFESP KKKRKV                                                  856

SEQ ID NO: 130              moltype = AA   length = 255
FEATURE                     Location/Qualifiers
source                      1..255
                            mol_type = protein
                            organism = synthetic construct
SEQUENCE: 130
MSEPPRAETF VFLDLEATGL PNMDPEIAEI SLFAVHRSSL ENPERDDSGS LVLPRVLDKL   60
TLCMCPERPF TAKASEITGL SSESLMHCGK AGFNGAVVRT LQGFLSRQEG PICLVAHNGF   120
DYDFPLLCTE LQRLGAHLPQ DTVCLDTLPA LRGLDRAHSH GTRAQGRKSY SLASLFHRYF   180
QAEPSAAHSA EGDVHTLLLI FLHRAPELLA WADEQARSWA HIEPMYVPPD GPSLEAMKRT   240
ADGSEFESPK KKRKV                                                   255

SEQ ID NO: 131              moltype = AA   length = 102
FEATURE                     Location/Qualifiers
source                      1..102
                            mol_type = protein
                            organism = synthetic construct
SEQUENCE: 131
MKRTADGSEF ESPKKKRKVT NLSDIIEKET GKQLVIQESI LMLPEEVEEV IGNKPESDIL   60
VHTAYDESTD ENVMLLTSDA PEYKPWALVI QDSNGENKIK ML                     102

SEQ ID NO: 132              moltype = AA   length = 2362
FEATURE                     Location/Qualifiers
source                      1..2362
                            mol_type = protein
                            organism = synthetic construct
SEQUENCE: 132
MDYKDHDGDY KDHDIDYKDD DDKMAPKKKR KVEASPASGP RHLMDPHIFT SNFNNGIGRH   60
KTYLCYEVER LDNGTSVKMD QHRGFLHNQA KNLLCGFYGR HAELRFLDLV PSLQLDPAQI   120
YRVTWFISWS PCFSWGCAGE VRAFLQENTH VRLRIFAARI YDYDPLYKEA LQMLRDAGAQ   180
VSIMTYDEFK HCWDTFVDHQ GCPFQPWDGL DEHSQALSGR LRAILQNQGN SGSETPGTSE   240
SATPESSGGS SGGSSGSETP GTSESATPES SGGSSGGSGI HGVPSRMVDL RTLGYSQQQ    300
EKIKPKVRST VAQHHEALVG HGFTHAHIVA LSQHPAALGT VAVTYQHIIT ALPEATHEDI   360
VGVGKQWSGA RALEALLTDA GELRGPPLQL DTGQLVKIAK RGGVTAMEAV HASRNALTGA   420
PLNLTPDQVV AIASNNGGKQ ALETVQRLLP VLCQDHGLTP DQVVAIASHD GGKQALETVQ   480
RLLPVLCQDH GLTPDQVVAI ASNGGGKQAL ETVQRLLPVL CQDHGLTPDQ VVAIASNNGG   540
KQALETVQRL LPVLCQDHGL TPDQVVAIAS NNGGKQALET VQRLLPVLCQ DHGLTPDQVV   600
AIASNIGGKQ ALETVQRLLP VLCQDHGLTP DQVVAIASNG GGKQALETVQ RLLPVLCQDH   660
```

-continued

```
GLTPDQVVAI ASNNGGKQAL ETVQRLLPVL CQDHGLTPDQ VVAIASHDGG KQALETVQRL   720
LPVLCQDHGL TPDQVVAIAS NGGGKQALET VQRLLPVLCQ DHGLTPDQVV AIASNGGGKQ   780
ALETVQRLLP VLCQDHGLTP DQVVAIASNG GGKQALETVQ RLLPVLCQDH GLTPDQVVAI   840
ASNNGGKQAL ETVQRLLPVL CQDHGLTPDQ VVAIASNIGG KQALETVQRL LPVLCQDHGL   900
TPDQVVAIAS NNGGKQALET VQRLLPVLCQ DHGLTPDQVV AIASNGGGKQ ALETVQRLLP   960
VLCQDHGLTP DQVVAIASNI GGKQALESIV AQLSRPDPAL AALTNDHLVA LACLGGRPAM  1020
DAVKKGLPHA PELIRRVNRR IGERTSHRVA GSQLVKSELE EKKSELRHKL KYVPHEYIEL  1080
IEIARNSTQD RILEMKVMEF FMKVYGYRGK HLGGSRKPDG AIYTVGSPID YGVIVDTKAY  1140
SGGYNLPIGQ ADEMQRYVKE NQTRNKHINP NEWWKVYPSS VTEFKFLFVS GHFKGNYKAQ  1200
LTRLNHKTNC NGAVLSVEEL LIGGEMIKAG TLTLEEVRRK FNNGEINFEG RGSLLTCGDV  1260
EENPGPRMDY KDHDGDYKDH DIDYKDDDDK MAPKKKRKVG IHGVPARMVD LRTLGYSQQQ  1320
QEKIKPKVRS TVAQHHEALV GHGFTHAHIV ALSQHPAALG TVAVTYQHII TALPEATHED  1380
IVGVGKQWSG ARALEALLTD AGELRGPPLQ LDTGQLVKIA KRGGVTAMEA VHASRNALTG  1440
APLNLTPDQV VAIASNNGGK QALETVQRLL PVLCQDHGLT PDQVVAIASH DGGKQALETV  1500
QRLLPVLCQD HGLTPDQVVA IASHDGGKQA LETVQRLLPV LCQDHGLTPD QVVAIASNGG  1560
GKQALETVQR LLPVLCQDHG LTPDQVVAIA SNGGGKQALE TVQRLLPVLC QDHGLTPDQV  1620
VAIASNGGGK QALETVQRLL PVLCQDHGLT PDQVVAIASN GGGKQALETV QRLLPVLCQD  1680
HGLTPDQVVA IASNNGGKQA LETVQRLLPV LCQDHGLTPD QVVAIASNGG GKQALETVQR  1740
LLPVLCQDHG LTPDQVVAIA SHDGGKQALE TVQRLLPVLC QDHGLTPDQV VAIASHDGGK  1800
QALETVQRLL PVLCQDHGLT PDQVVAIASN IGGKQALETV QRLLPVLCQD HGLTPDQVVA  1860
IASNIGGKQA LETVQRLLPV LCQDHGLTPD QVVAIASNNG GKQALETVQR LLPVLCQDHG  1920
LTPDQVVAIA SNNGGKQALE TVQRLLPVLC QDHGLTPDQV VAIASNIGGK QALETVQRLL  1980
PVLCQDHGLT PDQVVAIASN GGGKQALESI VAQLSRPDPA LAALTNDHLV ALACLGGRPA  2040
MDAVKKGLPH APELIRRVNR RIGERTSHRV AGSQLVKSEL EEKKSELRHK LKYVPHEYIE  2100
LIEIARNSTQ DRILEMKVME FFMKVYGYRG KHLGGSRKPA GAIYTVGSPI DYGVIVDTKA  2160
YSGGYNLPIG QADEMERYVE ENQTRNKHLN PNEWWKVYPS SVTEFKFLFV SGHFKGNYKA  2220
QLTRLNHITN CNGAVLSVEE LLIGGEMIKA GTLTLEEVRR KFNNGEINFS GGSGGSGGST  2280
NLSDIIEKET GKQLVIQESI LMLPEEVEEV IGNKPESDIL VHTAYDESTD ENVMLLTSDA  2340
PEYKPWALVI QDSNGENKIK ML                                         2362
```

SEQ ID NO: 133          moltype = AA  length = 2362
FEATURE                 Location/Qualifiers
source                  1..2362
                        mol_type = protein
                        organism = synthetic construct
SEQUENCE: 133

```
MDYKDHDGDY KDHDIDYKDD DDKMAPKKKR KVEASPASGP RHLMDPHIFT SNFNNGIGRH   60
KTYLCYEVER LDNGTSVKMD QHRGFLHNQA KNLLCGFYGR HAELRFLDLV PSLQLDPAQI  120
YRVTWFISWS PCFSWGCAGE VRAFLQENTH VRLRIFAARI YDYDPLYKEA LQMLRDAGAQ  180
VSIMTYDEFK HCWDTFVDHQ GCPFQPWDGL DEHSQALSGR LRAILQNQGN SGSETPGTSE  240
SATPESSGGS SGGSSGSETP GTSESATPES SGGSSGGSGI HGVPSRMVDL RTLGYSQQQQ  300
EKIKPKVRST VAQHHEALVG HGFTHAHIVA LSQHPAALGT VAVTYQHIIT ALPEATHEDI  360
VGVGKQWSGA RALEALLTDA GELRGPPLQL DTGQLVKIAK RGGVTAMEAV HASRNALTGA  420
PLNLTPDQVV AIASNNGGKQ ALETVQRLLP VLCQDHGLTP DQVVAIASHD GGKQALETVQ  480
RLLPVLCQDH GLTPDQVVAI ASNGGGKQAL ETVQRLLPVL CQDHGLTPDQ VVAIASNNGG  540
KQALETVQRL LPVLCQDHGL TPDQVVAIAS NNGGKQALET VQRLLPVLCQ DHGLTPDQVV  600
AIASNIGGKQ ALETVQRLLP VLCQDHGLTP DQVVAIASNG GGKQALETVQ RLLPVLCQDH  660
GLTPDQVVAI ASNNGGKQAL ETVQRLLPVL CQDHGLTPDQ VVAIASHDGG KQALETVQRL  720
LPVLCQDHGL TPDQVVAIAS NGGGKQALET VQRLLPVLCQ DHGLTPDQVV AIASNGGGKQ  780
ALETVQRLLP VLCQDHGLTP DQVVAIASNG GGKQALETVQ RLLPVLCQDH GLTPDQVVAI  840
ASNNGGKQAL ETVQRLLPVL CQDHGLTPDQ VVAIASNGGG KQALETVQRL LPVLCQDHGL  900
TPDQVVAIAS NNGGKQALET VQRLLPVLCQ DHGLTPDQVV AIASNGGGKQ ALETVQRLLP  960
VLCQDHGLTP DQVVAIASNI GGKQALESIV AQLSRPDPAL AALTNDHLVA LACLGGRPAM  1020
DAVKKGLPHA PELIRRVNRR IGERTSHRVA GSQLVKSELE EKKSELRHKL KYVPHEYIEL  1080
IEIARNSTQD RILEMKVMEF FMKVYGYRGK HLGGSRKPDG AIYTVGSPID YGVIVDTKAY  1140
SGGYNLPIGQ ADEMQRYVKE NQTRNKHINP NEWWKVYPSS VTEFKFLFVS GHFKGNYKAQ  1200
LTRLNHKTNC NGAVLSVEEL LIGGEMIKAG TLTLEEVRRK FNNGEINFEG RGSLLTCGDV  1260
EENPGPRMDY KDHDGDYKDH DIDYKDDDDK MAPKKKRKVG IHGVPARMVD LRTLGYSQQQ  1320
QEKIKPKVRS TVAQHHEALV GHGFTHAHIV ALSQHPAALG TVAVTYQHII TALPEATHED  1380
IVGVGKQWSG ARALEALLTD AGELRGPPLQ LDTGQLVKIA KRGGVTAMEA VHASRNALTG  1440
APLNLTPDQV VAIASNNGGK QALETVQRLL PVLCQDHGLT PDQVVAIASH DGGKQALETV  1500
QRLLPVLCQD HGLTPDQVVA IASHDGGKQA LETVQRLLPV LCQDHGLTPD QVVAIASNGG  1560
GKQALETVQR LLPVLCQDHG LTPDQVVAIA SNGGGKQALE TVQRLLPVLC QDHGLTPDQV  1620
VAIASNGGGK QALETVQRLL PVLCQDHGLT PDQVVAIASN GGGKQALETV QRLLPVLCQD  1680
HGLTPDQVVA IASNNGGKQA LETVQRLLPV LCQDHGLTPD QVVAIASNGG GKQALETVQR  1740
LLPVLCQDHG LTPDQVVAIA SHDGGKQALE TVQRLLPVLC QDHGLTPDQV VAIASHDGGK  1800
QALETVQRLL PVLCQDHGLT PDQVVAIASN IGGKQALETV QRLLPVLCQD HGLTPDQVVA  1860
IASNIGGKQA LETVQRLLPV LCQDHGLTPD QVVAIASNNG GKQALETVQR LLPVLCQDHG  1920
LTPDQVVAIA SNNGGKQALE TVQRLLPVLC QDHGLTPDQV VAIASNIGGK QALETVQRLL  1980
PVLCQDHGLT PDQVVAIASN GGGKQALESI VAQLSRPDPA LAALTNDHLV ALACLGGRPA  2040
MDAVKKGLPH APELIRRVNR RIGERTSHRV AGSQLVKSEL EEKKSELRHK LKYVPHEYIE  2100
LIEIARNSTQ DRILEMKVME FFMKVYGYRG KHLGGSRKPD GAIYTVGSPI DYGVIVDTKA  2160
YSGGYNLPIG QADEMERYVE ENQTRNKHLN PNEWWKVYPS SVTEFKFLFV SGHFKGNYKA  2220
QLTRLNHITN CNGAVLSVEE LLIGGEMIKA GTLTLEEVRR KFNNGEINFS GGSGGSGGST  2280
NLSDIIEKET GKQLVIQESI LMLPEEVEEV IGNKPESDIL VHTAYDESTD ENVMLLTSDA  2340
PEYKPWALVI QDSNGENKIK ML                                         2362
```

SEQ ID NO: 134          moltype = AA  length = 856
FEATURE                 Location/Qualifiers -continued

```
source                 1..856
                       mol_type = protein
                       organism = synthetic construct
SEQUENCE: 134
MGIQGLLQFI QEASEPVNVK KYKGQAVAVD TYCWLHKGAI ACAEKLAKGE PTDRYVGFCM   60
KFVNMLLSYG VKPILIFDGC TLPSKKEVER SRRERRQSNL LKGKQLLREG KVSEARDCFA  120
RSINITHAMA HKVIKAARAL GVDCLVAPYE ADAQLAYLNK AGIVQAVITE DSDLLAFGCK  180
KVILKMDQFG NGLEVDQARL GMCKQLGDVF TEEKFRYMCI LSGCDYLASL RGIGLAKACK  240
VLRLANNPDI VKVIKKIGHY LRMNITVPED YITGFIRANN TFLYQLVFDP IQRKLVPLNA  300
YGDDVNPETL TYAGQYVGDS VALQIALGNR DVNTFEQIDD YSPDTMPAHS RSHSWNEKAG  360
QKPPGTNSIW HKNYCPRLEV NSVSHAPQLK EKPSTLGLKQ VISTKGLNLP RKSCVLKRPR  420
NEALAEDDLL SQYSSVSKKI KENGCGDGTS PNSSKMSKSC PDSGTAHKTD AHTPSKMRNK  480
FATFLQRRNE ESGAVVVPGT RSRFFCSSQD FDNFIPKKES GQPLNETVAT GKATTSLLGA  540
LDCPDTEGHK PVDANGTHNL SSQIPGNAAV SPEDEAQSSE TSKLLGAMSP PSLGTLRSCF  600
SWSGTLREFS RTPSPSASTT LQQFRRKSDP PACLPEASAV VTDRCDSKSE MLGETSQPLH  660
ELGCSSRSQE SMDSSCGLNT SSLSQPSSRD SGSEESDCNN KSLDNQGEQN SKQHLPHFSK  720
KDGLRRNKVP GLCRSSSMDS FSTTKIKPLV PARVSGLSKK SGSMQTRKHH DVENKPGLQT  780
KISELWKNFG FKKDSEKLPS CKKPLSPVKD NIQLTPETED EIFNKPECVR AQRAIFHMKR  840
TADGSEFESP KKKRKV                                                   856

SEQ ID NO: 135         moltype = AA   length = 255
FEATURE                Location/Qualifiers
source                 1..255
                       mol_type = protein
                       organism = synthetic construct
SEQUENCE: 135
MSEPPRAETF VFLDLEATGL PNMDPEIAEI SLFAVHRSSL ENPERDDSGS LVLPRVLDKL   60
TLCMCPERPF TAKASEITGL SSESLMHCGK AGFNGAVVRT LQGFLSRQEG PICLVAHNGF  120
DYDFPLLCTE LQRLGAHLPQ DTVCLDTLPA LRGLDRAHSH GTRAQGRKSY SLASLFHRYF  180
QAEPSAAHSA EGDVHTLLLI FLHRAPELLA WADEQARSWA HIEPMYVPPD GPSLEAMKRT  240
ADGSEFESPK KKRKV                                                   255

SEQ ID NO: 136         moltype = AA   length = 3218
FEATURE                Location/Qualifiers
source                 1..3218
                       mol_type = protein
                       organism = synthetic construct
REGION                 1..2362
                       note = cassette1
REGION                 2363..3218
                       note = cassette2
SEQUENCE: 136
MDYKDHDGDY KDHDIDYKDD DDKMAPKKKR KVEASPASGP RHLMDPHIFT SNFNNGIGRH   60
KTYLCYEVER LDNGTSVKMD QHRGFLHNQA KNLLCGFYGR HAELRFLDLV PSLQLDPAQI  120
YRVTWFISWS PCFSWGCAGE VRAFLQENTH VRLRIFAARI YDYDPLYKEA LQMLRDAGAQ  180
VSIMTYDEFK HCWDTFVDHQ GCPFQPWDGL DEHSQALSGR LRAILQNQGN SGSETPGTSE  240
SATPESSGGS SGGSSGSETP GTSESATPES SGGSSGGSGI HGVPSRMVDL RTLGYSQQQQ  300
EKIKPKVRST VAQHHEALVG HGFTHAHIVA LSQHPAALGT VAVTYQHIIT ALPEATHEDI  360
VGVGKQWSGA RALEALLTDA GELRGPPLQL DTGQLVKIAK RGGVTAMEAV HASRNALTGA  420
PLNLTPDQVV AIASNNGGKQ ALETVQRLLP VLCQDHGLTP DQVVAIASHD GGKQALETVQ  480
RLLPVLCQDH GLTPDQVVAI ASNGGGKQAL ETVQRLLPVL CQDHGLTPDQ VVAIASNGG  540
KQALETVQRL LPVLCQDHGL TPDQVVAIAS NNGGKQALET VQRLLPVLCQ DHGLTPDQVV  600
AIASNIGGKQ ALETVQRLLP VLCQDHGLTP DQVVAIASNG GGKQALETVQ RLLPVLCQDH  660
GLTPDQVVAI ASNNGGKQAL ETVQRLLPVL CQDHGLTPDQ VVAIASHDGG KQALETVQRL  720
LPVLCQDHGL TPDQVVAIAS NGGGKQALET VQRLLPVLCQ DHGLTPDQVV AIASNGGGKQ  780
ALETVQRLLP VLCQDHGLTP DQVVAIASNG GGKQALETVQ RLLPVLCQDH GLTPDQVVAI  840
ASNNGGKQAL ETVQRLLPVL CQDHGLTPDQ VVAIASNIGG KQALETVQRL LPVLCQDHGL  900
TPDQVVAIAS NNGGKQALET VQRLLPVLCQ DHGLTPDQVV AIASNGGGKQ ALETVQRLLP  960
VLCQDHGLTP DQVVAIASNI GGKQALESIV AQLSRPDPAL AALTNDHLVA LACLGGRPAM 1020
DAVKKGLPHA PELIRRVNRR IGERTSHRVA GSQLVKSELE EKKSELRHKL KYVPHEYIEL 1080
IEIARNSTQD RILEMKVMEF FMKVYGYRGK HLGGSRKPDG AIYTVGSPID YGVIVDTKAY 1140
SGGYNLPIGQ ADEMQRYVKE NQTRNKHINP NEWWKVYPSS VTEFKFLFVS GHFKGNYKAQ 1200
LTRLNHKTNC NGAVLSVEEL LIGGEMIKAG TLTLEEVRRK FNNGEINFEG RGSLLTCGSV 1260
EENPGPRMDY KDHDGDYKDH DIDYKDDDDK MAPKKKRKVG IHGVPARMVD LRTLGYSQQQ 1320
QEKIKPKVRS TVAQHHEALV GHGFTHAHIV ALSQHPAALG TVAVTYQHII TALPEATHED 1380
IVGVGKQWSG ARALEALLTD AGELRGPPLQ LDTGQLVKIA KRGGVTAMEA VHASRNALTG 1440
APLNLTPDQV VAIASNNGGK QALETVQRLL PVLCQDHGLT PDQVVAIASH DGGKQALETV 1500
QRLLPVLCQD HGLTPDQVVA IASHDGGKQA LETVQRLLPV LCQDHGLTPD QVVAIASNGG 1560
GKQALETVQR LLPVLCQDHG LTPDQVVAIA SNGGGKQALE TVQRLLPVLC QDHGLTPDQV 1620
VAIASNGGGK QALETVQRLL PVLCQDHGLT PDQVVAIASN GGGKQALETV QRLLPVLCQD 1680
HGLTPDQVVA IASNNGGKQA LETVQRLLPV LCQDHGLTPD QVVAIASNGG GKQALETVQR 1740
LLPVLCQDHG LTPDQVVAIA SHDGGKQALE TVQRLLPVLC QDHGLTPDQV VAIASHDGGK 1800
QALETVQRLL PVLCQDHGLT PDQVVAIASN IGGKQALETV QRLLPVLCQD HGLTPDQVVA 1860
IASNIGGKQA LETVQRLLPV LCQDHGLTPD QVVAIASNGG GKQALETVQR LLPVLCQDHG 1920
LTPDQVVAIA SNGGGKQALE TVQRLLPVLC QDHGLTPDQV VAIASNIGGK QALETVQRLL 1980
PVLCQDHGLT PDQVVAIASN GGGKQALESI VAQLSRPDPA LAALTNDHLV ALACLGGRPA 2040
MDAVKKGLPH APELIRRVNR RIGERTSHRV AGSQLVKSEL EEKKSELRHK LKYVPHEYIE 2100
LIEIARNSTQ DRILEMKVME FFMKVYGYRG KHLGGSRKPA GAIYTVGSPI DYGVIVDTKA 2160
YSGGYNLPIG QADEMERYVE ENQTRNKHLN PNEWWKVYPS SVTEFKFLFV SGHFKGNYKA 2220
```

-continued

```
QLTRLNHITN CNGAVLSVEE LLIGGEMIKA GTLTLEEVRR KFNNGEINFS GGSGGSGGST  2280
NLSDIIEKET GKQLVIQESI LMLPEEVEEV IGNKPESDIL VHTAYDESTD ENVMLLTSDA  2340
PEYKPWALVI QDSNGENKIK MLMGIQGLLQ FIQEASEPVN VKKYKGQAVA VDTYCWLHKG  2400
AIACAEKLAK GEPTDRYVGF CMKFVNMLLS YGVKPILIFD GCTLPSKKEV ERSRRERRQS  2460
NLLKGKQLLR EGKVSEARDC FARSINITHA MAHKVIKAAR ALGVDCLVAP YEADAQLAYL  2520
NKAGIVQAVI TEDSDLLAFG CKKVILKMDQ FGNGLEVDQA RLGMCKQLGD VFTEEKFRYM  2580
CILSGCDYLA SLRGIGLAKA CKVLRLANNP DIVKVIKKIG HYLRMNITVP EDYITGFIRA  2640
NNTFLYQLVF DPIQRKLVPL NAYGDDVNPE TLTYAGQYVG DSVALQIALG NRDVNTFEQI  2700
DDYSPDTMPA HSRSHSWNEK AGQKPPGTNS IWHKNYCPRL EVNSVSHAPQ LKEKPSTLGL  2760
KQVISTKGLN LPRKSCVLKR PRNEALAEDD LLSQYSSVSK KIKENGCGDG TSPNSSKMSK  2820
SCPDSGTAHK TDAHTPSKMR NKFATFLQRR NEESGAVVVP GTRSRFFCSS QDFDNFIPKK  2880
ESGQPLNETV ATGKATTSLL GALDCPDTEG HKPVDANGTH NLSSQIPGNA AVSPEDEAQS  2940
SETSKLLGAM SPPSLGTLRS CFSWSGTLRE FSRTPSPSAS TTLQQFRRKS DPPACLPEAS  3000
AVVTDRCDSK SEMLGETSQP LHELGCSSRS QESMDSSCGL NTSSLSQPSS RDSGSEESDC  3060
NNKSLDNQGE QNSKQHLPHF SKKDGLRRNK VPGLCRSSSM DSFSTTKIKP LVPARVSGLS  3120
KKSGSMQTRK HHDVENKPGL QTKISELWKN FGFKKDSEKL PSCKKPLSPV KDNIQLTPET  3180
EDEIFNKPEC VRAQRAIFHM KRTADGSEFE SPKKKRKV                          3218
```

```
SEQ ID NO: 137        moltype = AA   length = 3218
FEATURE               Location/Qualifiers
source                1..3218
                      mol_type = protein
                      organism = synthetic construct
REGION                1..2362
                      note = cassette1
REGION                2363..3218
                      note = cassette2
SEQUENCE: 137
MDYKDHDGDY KDHDIDYKDD DDKMAPKKKR KVEASPASGP RHLMDPHIFT SNFNNGIGRH  60
KTYLCYEVER LDNGTSVKMD QHRGFLHNQA KNLLCGFYGR HAELRFLDLV PSLQLDPAQI  120
YRVTWFISWS PCFSWGCAGE VRAFLQENTH VRLRIFAARI YDYDPLYKEA LQMLRDAGAQ  180
VSIMTYDEFK HCWDTFVDHQ GCPFQPWDGL DEHSQALSGR LRAILQNQGN SGGSETPGTSE  240
SATPESSGGS SGGSSGSETP GTSESATPES SGGSSGGSGI HGVPSRMVDL RTLGYSQQQQ  300
EKIKPKVRST VAQHHEALVG HGFTHAHIVA LSQHPAALGT VAVTYQHIIT ALPEATHEDI  360
VGVGKQWSGA RALEALLTDA GELRGPPLQL DTGQLVKIAK RGGVTAMEAV HASRNALTGA  420
PLNLTPDQVV AIASNNGGKQ ALETVQRLLP VLCQDHGLTP DQVVAIASHD GGKQALETVQ  480
RLLPVLCQDH GLTPDQVVAI ASNGGGKQAL ETVQRLLPVL CQDHGLTPDQ VVAIASNNGG  540
KQALETVQRL LPVLCQDHGL TPDQVVAIAS NNGGKQALET VQRLLPVLCQ DHGLTPDQVV  600
AIASNIGGKQ ALETVQRLLP VLCQDHGLTP DQVVAIASNG GGKQALETVQ RLLPVLCQDH  660
GLTPDQVVAI ASNNGGKQAL ETVQRLLPVL CQDHGLTPDQ VVAIASHDGG KQALETVQRL  720
LPVLCQDHGL TPDQVVAIAS NGGGKQALET VQRLLPVLCQ DHGLTPDQVV AIASNGGGKQ  780
ALETVQRLLP VLCQDHGLTP DQVVAIASNG GGKQALETVQ RLLPVLCQDH GLTPDQVVAI  840
ASNNGGKQAL ETVQRLLPVL CQDHGLTPDQ VVAIASNGGG KQALETVQRL LPVLCQDHGL  900
TPDQVVAIAS NNGGKQALET VQRLLPVLCQ DHGLTPDQVV AIASNGGGKQ ALETVQRLLP  960
VLCQDHGLTP DQVVAIASNI GGKQALESIV AQLSRPDPAL AALTNDHLVA LACLGGRPAM  1020
DAVKKGLPHA PELIRRVNRR IGERTSHRVA GSQLVKSELE EKKSELRHKL KYVPHEYIEL  1080
IEIARNSTQD RILEMKVMEF FMKVYGYRGK HLGGSRKPAG AIYTVGSPID YGVIVDTKAY  1140
SGGYNLPIGQ ADEMQRYVKE NQTRNKHINP NEWWKVYPSS VTEFKFLFVS GHFKGNYKAQ  1200
LTRLNHKTNC NGAVLSVEEL LIGGEMIKAG TLTLEEVRRK FNNGEINFEG RGSLLTCGDV  1260
EENPGPRMDY KDHDGDYKDH DIDYKDDDDK MAPKKKRKVG IHGVPARMVD LRTLGYSQQQ  1320
QEKIKPKVRS TVAQHHEALV GHGFTHAHIV ALSQHPAALG TVAVTYQHII TALPEATHED  1380
IVGVGKQWSG ARALEALLTD AGELRGPPLQ LDTGQLVKIA KRGGVTAMEA VHASRNALTG  1440
APLNLTPDQV VAIASNNGGK QALETVQRLL PVLCQDHGLT PDQVVAIASH DGGKQALETV  1500
QRLLPVLCQD HGLTPDQVVA IASHDGGKQA LETVQRLLPV LCQDHGLTPD QVVAIASNGG  1560
GKQALETVQR LLPVLCQDHG LTPDQVVAIA SNGGGKQALE TVQRLLPVLC QDHGLTPDQV  1620
VAIASNGGGK QALETVQRLL PVLCQDHGLT PDQVVAIASN GGGKQALETV QRLLPVLCQD  1680
HGLTPDQVVA IASNNGGKQA LETVQRLLPV LCQDHGLTPD QVVAIASNGG GKQALETVQR  1740
LLPVLCQDHG LTPDQVVAIA SHDGGKQALE TVQRLLPVLC QDHGLTPDQV VAIASHDGGK  1800
QALETVQRLL PVLCQDHGLT PDQVVAIASN IGGKQALETV QRLLPVLCQD HGLTPDQVVA  1860
IASNIGGKQA LETVQRLLPV LCQDHGLTPD QVVAIASNNG GKQALETVQR LLPVLCQDHG  1920
LTPDQVVAIA SNNGGKQALE TVQRLLPVLC QDHGLTPDQV VAIASNIGGK QALETVQRLL  1980
PVLCQDHGLT PDQVVAIASN GGGKQALESI VAQLSRPDPA LAALTNDHLV ALACLGGRPA  2040
MDAVKKGLPH APELIRRVNR RIGERTSHRV AGSQLVKSEL EEKKSELRHK LKYVPHEYIE  2100
LIEIARNSTQ DRILEMKVME FFMKVYGYRG KHLGGSRKPD GAIYTVGSPI DYGVIVDTKA  2160
YSGGYNLPIG QADEMERYVE ENQTRNKHLN PNEWWKVYPS SVTEFKFLFV SGHFKGNYKA  2220
QLTRLNHITN CNGAVLSVEE LLIGGEMIKA GTLTLEEVRR KFNNGEINFS GGSGGSGGST  2280
NLSDIIEKET GKQLVIQESI LMLPEEVEEV IGNKPESDIL VHTAYDESTD ENVMLLTSDA  2340
PEYKPWALVI QDSNGENKIK MLMGIQGLLQ FIQEASEPVN VKKYKGQAVA VDTYCWLHKG  2400
AIACAEKLAK GEPTDRYVGF CMKFVNMLLS YGVKPILIFD GCTLPSKKEV ERSRRERRQS  2460
NLLKGKQLLR EGKVSEARDC FARSINITHA MAHKVIKAAR ALGVDCLVAP YEADAQLAYL  2520
NKAGIVQAVI TEDSDLLAFG CKKVILKMDQ FGNGLEVDQA RLGMCKQLGD VFTEEKFRYM  2580
CILSGCDYLA SLRGIGLAKA CKVLRLANNP DIVKVIKKIG HYLRMNITVP EDYITGFIRA  2640
NNTFLYQLVF DPIQRKLVPL NAYGDDVNPE TLTYAGQYVG DSVALQIALG NRDVNTFEQI  2700
DDYSPDTMPA HSRSHSWNEK AGQKPPGTNS IWHKNYCPRL EVNSVSHAPQ LKEKPSTLGL  2760
KQVISTKGLN LPRKSCVLKR PRNEALAEDD LLSQYSSVSK KIKENGCGDG TSPNSSKMSK  2820
SCPDSGTAHK TDAHTPSKMR NKFATFLQRR NEESGAVVVP GTRSRFFCSS QDFDNFIPKK  2880
ESGQPLNETV ATGKATTSLL GALDCPDTEG HKPVDANGTH NLSSQIPGNA AVSPEDEAQS  2940
SETSKLLGAM SPPSLGTLRS CFSWSGTLRE FSRTPSPSAS TTLQQFRRKS DPPACLPEAS  3000
AVVTDRCDSK SEMLGETSQP LHELGCSSRS QESMDSSCGL NTSSLSQPSS RDSGSEESDC  3060
```

```
NNKSLDNQGE QNSKQHLPHF SKKDGLRRNK VPGLCRSSSM DSFSTTKIKP LVPARVSGLS   3120
KKSGSMQTRK HHDVENKPGL QTKISELWKN FGFKKDSEKL PSCKKPLSPV KDNIQLTPET   3180
EDEIFNKPEC VRAQRAIFHM KRTADGSEFE SPKKKRKV                           3218

SEQ ID NO: 138           moltype = AA  length = 764
FEATURE                  Location/Qualifiers
source                   1..764
                         mol_type = protein
                         organism = synthetic construct
SEQUENCE: 138
MALSRAVCGT SRQLAPVLGY LGSRQKHSLP DYPYDVPDYA GYPYDVPDYA GYPYDVPDYA   60
MDIADLRTLG YSQQQQEKIK PKVRSTVAQH HEALVGHGFT HAHIVALSQH PAALGTVAVK   120
YQDMIAALPE ATHEAIVGVG KQWSGARALE ALLTVAGELR GPPLQLDTGQ LLKIAKRGGV   180
TAVEAVHAWR NALTGAPLNL TPEQVVAIAS NNGGKQALET VQRLLPVLCQ AHGLTPEQVV   240
AIASNIGGKQ ALETVQRLLP VLCQAHGLTP EQVVAIASHD GGKQALETVQ RLLPVLCQAH   300
GLTPEQVVAI ASHDGGKQAL ETVQRLLPVL CQAHGLTPEQ VVAIASHDGG KQALETVQRL   360
LPVLCQAHGL TPEQVVAIAS HDGGKQALET VQRLLPVLCQ AHGLTPEQVV AIASHDGGKQ   420
ALETVQRLLP VLCQAHGLTP EQVVAIASNI GGKQALETVQ RLLPVLCQAH GLTPEQVVAI   480
ASNGGGKQAL ETVQRLLPVL CQAHGLTPEQ VVAIASNGGG RPALESIVAQ LSRPDPALAA   540
LTNDHLVALA CLGGRPALDA VKKGLGGSQL VKSELEEKKS ELRHKLKYVP HEYIELIEIA   600
RNSTQDRILE MKVMEFFMKV YGYRGKHLGG SRKPDGAIYT VGSPIDYGVI VDTKAYSGGY   660
NLPIGQADEM QRYVKENQTR NKHINPNEWW KVYPSSVTEF KPLFVSGHFK GNYKAQLTRL   720
NHKTNCNGAV LSVEELLIGG EMIKAGTLTL EEVRRKFNNG EINF                   764

SEQ ID NO: 139           moltype = AA  length = 790
FEATURE                  Location/Qualifiers
source                   1..790
                         mol_type = protein
                         organism = synthetic construct
SEQUENCE: 139
MASVLTPLLL RGLTGSARRL PVPRAKIHSL DYKDHDGDYK DHDIDYKDDD DKMDIADLRT   60
LGYSQQQQEK IKPKVRSTVA QHHEALVGHG FTHAHIVALS QHPAALGTVA VKYQDMIAAL   120
PEATHEAIVG VGKRGAGARA LEALLTVAGE LRGPPLQLDT GQLLKIAKRG GVTAVEAVHA   180
WRNALTGAPL NLTPEQVVAI ASNNGGKQAL ETVQRLLPVL CQAHGLTPEQ VVAIASNIGG   240
KQALETVQRL LPVLCQAHGL TPEQVVAIAS NGGGKQALET VQRLLPVLCQ AHGLTPEQVV   300
AIASNNGGKQ ALETVQRLLP VLCQAHGLTP EQVVAIASNN GGKQALETVQ RLLPVLCQAH   360
GLTPEQVVAI ASHDGGKQAL ETVQRLLPVL CQAHGLTPEQ VVAIASNGGG KQALETVQRL   420
LPVLCQAHGL TPEQVVAIAS NIGGKQALET VQRLLPVLCQ AHGLTPEQVV AIASNGGGKQ   480
ALETVQRLLP VLCQAHGLTP EQVVAIASNG GKQALETVQ RLLPVLCQAH GLTPEQVVAI   540
ASNGGGRPAL ESIVAQLSRP DPALAALTND HLVALACLGG RPALDAVKKG LGGSQLVKSE   600
LEEKKSELRH KLKYVPHEYI ELIEIARNST QDRILEMKVM EFFMKVYGYR GKHLGGSRKP   660
AGAIYTVGSP IDYGVIVDTK AYSGGYNLPI GQADEMERYV EENQTRNKHL NPNEWWKVYP   720
SSVTEFKFLF VSGHFKGNYK AQLTRLNHIT NCNGAVLSVE ELLIGGEMIK AGTLTLEEVR   780
RKFNNGEINF                                                         790

SEQ ID NO: 140           moltype = AA  length = 764
FEATURE                  Location/Qualifiers
source                   1..764
                         mol_type = protein
                         organism = synthetic construct
SEQUENCE: 140
MALSRAVCGT SRQLAPVLGY LGSRQKHSLP DYPYDVPDYA GYPYDVPDYA GYPYDVPDYA   60
MDIADLRTLG YSQQQQEKIK PKVRSTVAQH HEALVGHGFT HAHIVALSQH PAALGTVAVK   120
YQDMIAALPE ATHEAIVGVG KQWSGARALE ALLTVAGELR GPPLQLDTGQ LLKIAKRGGV   180
TAVEAVHAWR NALTGAPLNL TPEQVVAIAS NNGGKQALET VQRLLPVLCQ AHGLTPEQVV   240
AIASNIGGKQ ALETVQRLLP VLCQAHGLTP EQVVAIASHD GGKQALETVQ RLLPVLCQAH   300
GLTPEQVVAI ASHDGGKQAL ETVQRLLPVL CQAHGLTPEQ VVAIASHDGG KQALETVQRL   360
LPVLCQAHGL TPEQVVAIAS HDGGKQALET VQRLLPVLCQ AHGLTPEQVV AIASHDGGKQ   420
ALETVQRLLP VLCQAHGLTP EQVVAIASNI GGKQALETVQ RLLPVLCQAH GLTPEQVVAI   480
ASNGGGKQAL ETVQRLLPVL CQAHGLTPEQ VVAIASNGGG RPALESIVAQ LSRPDPALAA   540
LTNDHLVALA CLGGRPALDA VKKGLGGSQL VKSELEEKKS ELRHKLKYVP HEYIELIEIA   600
RNSTQDRILE MKVMEFFMKV YGYRGKHLGG SRKPAGAIYT VGSPIDYGVI VDTKAYSGGY   660
NLPIGQADEM QRYVKENQTR NKHINPNEWW KVYPSSVTEF KPLFVSGHFK GNYKAQLTRL   720
NHKTNCNGAV LSVEELLIGG EMIKAGTLTL EEVRRKFNNG EINF                   764

SEQ ID NO: 141           moltype = AA  length = 790
FEATURE                  Location/Qualifiers
source                   1..790
                         mol_type = protein
                         organism = synthetic construct
SEQUENCE: 141
MASVLTPLLL RGLTGSARRL PVPRAKIHSL DYKDHDGDYK DHDIDYKDDD DKMDIADLRT   60
LGYSQQQQEK IKPKVRSTVA QHHEALVGHG FTHAHIVALS QHPAALGTVA VKYQDMIAAL   120
PEATHEAIVG VGKRGAGARA LEALLTVAGE LRGPPLQLDT GQLLKIAKRG GVTAVEAVHA   180
WRNALTGAPL NLTPEQVVAI ASNNGGKQAL ETVQRLLPVL CQAHGLTPEQ VVAIASNIGG   240
KQALETVQRL LPVLCQAHGL TPEQVVAIAS NGGGKQALET VQRLLPVLCQ AHGLTPEQVV   300
AIASNNGGKQ ALETVQRLLP VLCQAHGLTP EQVVAIASNN GGKQALETVQ RLLPVLCQAH   360
GLTPEQVVAI ASHDGGKQAL ETVQRLLPVL CQAHGLTPEQ VVAIASNGGG KQALETVQRL   420
LPVLCQAHGL TPEQVVAIAS NIGGKQALET VQRLLPVLCQ AHGLTPEQVV AIASNGGGKQ   480
```

-continued

```
ALETVQRLLP VLCQAHGLTP EQVVAIASNG GGKQALETVQ RLLPVLCQAH GLTPEQVVAI   540
ASNGGGRPAL ESIVAQLSRP DPALAALTND HLVALACLGG RPALDAVKKG LGGSQLVKSE   600
LEEKKSELRH KLKYVPHEYI ELIEIARNST QDRILEMKVM EFFMKVYGYR GKHLGGSRKP   660
DGAIYTVGSP IDYGVIVDTK AYSGGYNLPI GQADEMERYV EENQTRNKHL NPNEWWKVYP   720
SSVTEFKFLF VSGHFKGNYK AQLTRLNHIT NCNGAVLSVE ELLIGGEMIK AGTLTLEEVR   780
RKFNNGEINF                                                          790

SEQ ID NO: 142          moltype = AA  length = 868
FEATURE                 Location/Qualifiers
source                  1..868
                        mol_type = protein
                        organism = synthetic construct
SEQUENCE: 142
MALSRAVCGT SRQLAPVLGY LGSRQKHSLP DMGIQGLLQF IQEASEPVNV KKYKGQAVAV   60
DTYCWLHKGA IACAEKLAKG EPTDRYVGFC MKFVNMLLSY GVKPILIFDG CTLPSKKEVE   120
RSRRERRQSN LLKGKQLLRE GKVSEARDCF ARSINITHAM AHKVIKAARA LGVDCLVAPY   180
EADAQLAYLN KAGIVQAVIT EDSDLLAFGC KKVILKMDQF GNGLEVDQAR LGMCKQLGDV   240
FTEEKFRYMC ILSGCDYLAS LRGIGLAKAC KVLRLANNPD IVKVIKKIGH YLRMNITVPE   300
DYITGFIRAN NTFLYQLVFD PIQRKLVPLN AYGDDVNPET LTYAGQYVGD SVALQIALGN   360
RDVNTFEQID DYSPDTMPAH SRSHSWNEKA GQKPPGTNSI WHKNYCPRLE VNSVSHAPQL   420
KEKPSTLGLK QVISTKGLNL PRKSCVLKRP RNEALAEDDL LSQYSSVSKK IKENGCGDGT   480
SPNSSKMSKS CPDSGTAHKT DAHTPSKMRN KFATFLQRRN EESGAVVVPG TRSRFFCSSQ   540
DFDNFIPKKE SGQPLNETVA TGKATTSLLG ALDCPDTEGH KPVDANGTHN LSSQIPGNAA   600
VSPEDEAQSS ETSKLLGAMS PPSLGTLRSC FSWSGTLREF SRTPSPSAST TLQQFRRKSD   660
PPACLPEASA VVTDRCDSKS EMLGETSQPL HELGCSSRSQ ESMDSSCGLN TSSLSQPSSR   720
DSGSEESDCN NKSLDNQGEQ NSKQHLPHFS KKDGLRRNKV PGLCRSSSMD SFSTTKIKPL   780
VPARVSGLSK KSGSMQTRKH HDVENKPGLQ TKISELWKNF GFKKDSEKLP SCKKPLSPVK   840
DNIQLTPETE DEIFNKPECV RAQRAIFH                                      868

SEQ ID NO: 143          moltype = AA  length = 267
FEATURE                 Location/Qualifiers
source                  1..267
                        mol_type = protein
                        organism = synthetic construct
SEQUENCE: 143
MALSRAVCGT SRQLAPVLGY LGSRQKHSLP DMSEPPRAET FVFLDLEATG LPNMDPEIAE   60
ISLFAVHRSS LENPERDDSG SLVLPRVLDK LTLCMCPERP FTAKASEITG LSSESLMHCG   120
KAGFNGAVVR TLQGFLSRQE GPICLVAHNG FDYDFPLLCT ELQRLGAHLP QDTVCLDTLP   180
ALRGLDRAHS HGTRAQGRKS YSLASLFHRY FQAEPSAAHS AEGDVHTLLL IFLHRAPELL   240
AWADEQARSW AHIEPMYVPP DGPSLEA                                       267

SEQ ID NO: 144          moltype = AA  length = 229
FEATURE                 Location/Qualifiers
source                  1..229
                        mol_type = protein
                        organism = synthetic construct
SEQUENCE: 144
MALSRAVCGT SRQLAPVLGY LGSRQKHSLP DEASPASGPR HLMDPHIFTS NFNNGIGRHK   60
TYLCYEVERL DNGTSVKMDQ HRGFLHNQAK NLLCGFYGRH AELRFLDLVP SLQLDPAQIY   120
RVTWFISWSP CFSWGCAGEV RAFLQENTHV RLRIFAARIY DYDPLYKEAL QMLRDAGAQV   180
SIMTYDEFKH CWDTFVDHQG CPFQPWDGLD EHSQALSGRL RAILQNQGN                229

SEQ ID NO: 145          moltype = AA  length = 198
FEATURE                 Location/Qualifiers
source                  1..198
                        mol_type = protein
                        organism = synthetic construct
SEQUENCE: 145
MALSRAVCGT SRQLAPVLGY LGSRQKHSLP DLEAVRARLI GEGGGPGAVP EGGDGPPAVP   60
AEEVERLRGE LPPPVVPGTG QKTHGRWIGP DGRVRAIVSG RDEDAALVHA QLAAKGIPDE   120
PTRNSDVEQK LAAHMVANGI RHVTLVINHR PCRGFDDSCD TLVPIILPEG CTLTVHGQTD   180
KGMRVRVRYT GGARPWWS                                                 198

SEQ ID NO: 146          moltype = AA  length = 120
FEATURE                 Location/Qualifiers
source                  1..120
                        mol_type = protein
                        organism = synthetic construct
SEQUENCE: 146
MALSRAVCGT SRQLAPVLGY LGSRQKHSLP DGSSGGSTNL SDIIEKETGK QLVIQESILM   60
LPEEVEEVIG NKPESDILVH TAYDESTDEN VMLLTSDAPE YKPWALVIQD SNGENKIKML   120

SEQ ID NO: 147          moltype = AA  length = 1010
FEATURE                 Location/Qualifiers
source                  1..1010
                        mol_type = protein
                        organism = synthetic construct
SEQUENCE: 147
MALSRAVCGT SRQLAPVLGY LGSRQKHSLP DYPYDVPDYA GYPYDVPDYA GYPYDVPDYA   60
```

```
EASPASGPRH LMDPHIFTSN FNNGIGRHKT YLCYEVERLD NGTSVKMDQH RGFLHNQAKN    120
LLCGFYGRHA ELRFLDLVPS LQLDPAQIYR VTWFISWSPC FSWGCAGEVR AFLQENTHVR    180
LRIFAARIYD YDPLYKEALQ MLRDAGAQVS IMTYDEFKHC WDTFVDHQGC PFQPWDGLDE    240
HSQALSGRLR AILQNQGNSG SETPGTSESA TPESSGGSSG GSSGSETPGT SESATPESSG    300
GSSGGSMDIA DLRTLGYSQQ QQEKIKPKVR STVAQHHEAL VGHGFTHAHI VALSQHPAAL    360
GTVAVKYQDM IAALPEATHE AIVGVGKQWS GARALEALLT VAGELRGPPL QLDTGQLLKI    420
AKRGGVTAVE AVHAWRNALT GAPLNLTPEQ VVAIASNNGG KQALETVQRL LPVLCQAHGL    480
TPEQVVAIAS NIGGKQALET VQRLLPVLCQ AHGLTPEQVV AIASHDGGKQ ALETVQRLLP    540
VLCQAHGLTP EQVVAIASHD GGKQALETVQ RLLPVLCQAH GLTPEQVVAI ASHDGGKQAL    600
ETVQRLLPVL CQAHGLTPEQ VVAIASHDGG KQALETVQRL LPVLCQAHGL TPEQVVAIAS    660
HDGGKQALET VQRLLPVLCQ AHGLTPEQVV AIASNIGGKQ ALETVQRLLP VLCQAHGLTP    720
EQVVAIASNG GGKQALETVQ RLLPVLCQAH GLTPEQVVAI ASNGGGRPAL ESIVAQLSRP    780
DPALAALTND HLVALACLGG RPALDAVKKG LGGSQLVKSE LEEKKSELRH KLKYVPHEYI    840
ELIEIARNST QDRILEMKVM EFFMKVYGYR GKHLGGSRKP DGAIYTVGSP IDYGVIVDTK    900
AYSGGYNLPI GQADEMQRYV KENQTRNKHI NPNEWWKVYP SSVTEFKFLF VSGHFKGNYK    960
AQLTRLNHKT NCNGAVLSVE ELLIGGEMIK AGTLTLEEVR RKFNNGEINF             1010
```

```
SEQ ID NO: 148          moltype = AA   length = 1074
FEATURE                 Location/Qualifiers
source                  1..1074
                        mol_type = protein
                        organism = synthetic construct
SEQUENCE: 148
MASVLTPLLL RGLTGSARRL PVPRAKIHSL DYKDHDGDYK DHDIDYKDDD DKMSEPPRAE     60
TFVFLDLEAT GLPNMDPEIA EISLFAVHRS SLENPERDDS GSLVLPRVLD KLTLCMCPER    120
PFTAKASEIT GLSSESLMHC GKAGFNGAVV RTLQGFLSRQ EGPICLVAHN GFDYDFPLLC    180
TELQRLGAHL PQDTVCLDTL PALRGLDRAH SHGTRAQGRK SYSLASLFHR YFQAEPSAAH    240
SAEGDVHTLL LIFLHRAPEL LAWADEQARS WAHIEPMYVP PDGPSLEASG SETPGTSESA    300
TPESSGGSSG GSSGSETPGT SESATPESSG GSSGGSMDIA DLRTLGYSQQ QQEKIKPKVR    360
STVAQHHEAL VGHGFTHAHI VALSQHPAAL GTVAVKYQDM IAALPEATHE AIVGVGKRGA    420
GARALEALLT VAGELRGPPL QLDTGQLLKI AKRGGVTAVE AVHAWRNALT GAPLNLTPEQ    480
VVAIASNNGG KQALETVQRL LPVLCQAHGL TPEQVVAIAS NIGGKQALET VQRLLPVLCQ    540
AHGLTPEQVV AIASNGGGKQ ALETVQRLLP VLCQAHGLTP EQVVAIASNN GGKQALETVQ    600
RLLPVLCQAH GLTPEQVVAI ASNNGGKQAL ETVQRLLPVL CQAHGLTPEQ VVAIASHDGG    660
KQALETVQRL LPVLCQAHGL TPEQVVAIAS NGGGKQALET VQRLLPVLCQ AHGLTPEQVV    720
AIASNIGGKQ ALETVQRLLP VLCQAHGLTP EQVVAIASNG GGKQALETVQ RLLPVLCQAH    780
GLTPEQVVAI ASNGGGKQAL ETVQRLLPVL CQAHGLTPEQ VVAIASNGGG RPALESIVAQ    840
LSRPDPALAA LTNDHLVALA CLGGRPALDA VKKGLGGSQL VKSELEEKKS ELRHKLKYVP    900
HEYIELIEIA RNSTQDRILE MKVMEFFMKV YGYRGKHLGG SRKPAGAIYT VGSPIDYGVI    960
VDTKAYSGGY NLPIGQADEM ERYVEENQTR NKHLNPNEWW KVYPSSVTEF KPLFVSGHFK   1020
GNYKAQLTRL NHITNCNGAV LSVEELLIGG EMIKAGTLTL EEVRRKFNNG EINF         1074
```

```
SEQ ID NO: 149          moltype = AA   length = 1167
FEATURE                 Location/Qualifiers
source                  1..1167
                        mol_type = protein
                        organism = synthetic construct
SEQUENCE: 149
MASVLTPLLL RGLTGSARRL PVPRAKIHSL DYKDHDGDYK DHDIDYKDDD DKTNLSDIIE     60
KETGKQLVIQ ESILMLPEEV EEVIGNKPES DILVHTAYDE STDENVMLLT SDAPEYKPWA    120
LVIQDSNGEN KIKMLSGGSG GSGGSMSEPP RAETFVFLDL EATGLPNMDP EIAEISLFAV    180
HRSSLENPER DDSGSLVLPR VLDKLTLCMC PERPFTAKAS EITGLSSESL MHCGKAGFNG    240
AVVRTLQGFL SRQEGPICLV AHNGFDYDFP LLCTELQRLG AHLPQDTVCL DTLPALRGLD    300
RAHSHGTRAQ GRKSYSLASL FHRYFQAEPS AAHSAEGDVH TLLLIFLHRA PELLAWADEQ    360
ARSWAHIEPM YVPPDGPSLE ASGSETPGTS ESATPESSGG SSGGSSGSET PGTSESATPE    420
SSGGSSGGSM DIADLRTLGY SQQQQEKIKP KVRSTVAQHH EALVGHGFTH AHIVALSQHP    480
AALGTVAVKY QDMIAALPEA THEAIVGVGK RGAGARALEA LLTVAGELRG PPLQLDTGQL    540
LKIAKRGGVT AVEAVHAWRN ALTGAPLNLT PEQVVAIASN NGGKQALETV QRLLPVLCQA    600
HGLTPEQVVA IASNIGGKQA LETVQRLLPV LCQAHGLTPE QVVAIASNGG GKQALETVQR    660
LLPVLCQAHG LTPEQVVAIA SNNGGKQALE TVQRLLPVLC QAHGLTPEQV VAIASNNGGK    720
QALETVQRLL PVLCQAHGLT PEQVVAIASH DGGKQALETV QRLLPVLCQA HGLTPEQVVA    780
IASNGGGKQA LETVQRLLPV LCQAHGLTPE QVVAIASNIG GKQALETVQR LLPVLCQAHG    840
LTPEQVVAIA SNGGGKQALE TVQRLLPVLC QAHGLTPEQV VAIASNGGGK QALETVQRLL    900
PVLCQAHGLT PEQVVAIASN GGGRPALESI VAQLSRPDPA LAALTNDHLV ALACLGGRPA    960
LDAVKKGLGG SQLVKSELEE KKSELRHKLK YVPHEYIELI EIARNSTQDR ILEMKVMEFF   1020
MKVYGYRGKH LGGSRKPAGA IYTVGSPIDY GVIVDTKAYS GGYNLPIGQA DEMERYVEEN   1080
QTRNKHLNPN EWWKVYPSSV TEFKFLFVSG HFKGNYKAQL TRLNHITNCN GAVLSVEELL   1140
IGGEMIKAGT LTLEEVRRKF NNGEINF                                       1167
```

```
SEQ ID NO: 150          moltype = AA   length = 5
FEATURE                 Location/Qualifiers
source                  1..5
                        mol_type = protein
                        organism = synthetic construct
SEQUENCE: 150
KKRKV                                                                  5
```

```
SEQ ID NO: 151          moltype = AA   length = 7
FEATURE                 Location/Qualifiers
```

-continued

```
source                  1..7
                        mol_type = protein
                        organism = synthetic construct
SEQUENCE: 151
PKKKRKV                                                          7

SEQ ID NO: 152          moltype = AA  length = 16
FEATURE                 Location/Qualifiers
source                  1..16
                        mol_type = protein
                        organism = synthetic construct
SEQUENCE: 152
KRPAATKKAG QAKKK                                                16

SEQ ID NO: 153          moltype = AA  length = 373
FEATURE                 Location/Qualifiers
source                  1..373
                        mol_type = protein
                        organism = Mus musculus
SEQUENCE: 153
MAETGEEETA SAEASGFSDL SDSELVEFLD LEEAKESAVS LSKPGPSAEL PGKDDKPVSL  60
QNWKGGLDVL SPMERFHLKY LYVTDLCTQN WCELQMVYGK ELPGSLTPEK AAVLDTGASI  120
HLAKELELHD LVTVPIATKE DAWAVKFLNI LAMIPALQSE GRVREFPVFG EVEGIFLVGV  180
IDELHYTSKG ELELAELKTR RRPVLPLPAQ KKKDYFQVSL YKYIFDAMVQ GKVTPASLIH  240
HTKLCLDKPL GPSVLRHARQ GGVSVKSLGD LMELVFLSLT LSDLPAIDTL KLEYIHQETA  300
TILGTEIVAF EEKEVKSKVQ HYVAYWMGHR DPQGVDVEEA WKCRTCDYVD ICEWRRGSGV  360
LSSSWEPKAK KFK                                                   373

SEQ ID NO: 154          moltype = AA  length = 2005
FEATURE                 Location/Qualifiers
source                  1..2005
                        mol_type = protein
                        organism = synthetic construct
SEQUENCE: 154
MAPKKKRKVG IHGVPSRMVD LRTLGYSQQQ QEKIKPKVRS TVAQHHEALV GHGFTHAHIV  60
ALSQHPAALG TVAVTYQHII TALPEATHED IVGVGKQWSG ARALEALLTD AGELRGPPLQ  120
LDTGQLVKIA KRGGVTAMEA VHASRNALTG APLNLTPDQV VAIASNNGGK QALETVQRLL  180
PVLCQDHGLT PDQVVAIASH DGGKQALETV QRLLPVLCQD HGLTPDQVVA IASNGGGKQA  240
LETVQRLLPV LCQDHGLTPD QVVAIASNNG GKQALETVQR LLPVLCQDHG LTPDQVVAIA  300
SNNGGKQALE TVQRLLPVLC QDHGLTPDQV VAIASNIGGK QALETVQRLL PVLCQDHGLT  360
PDQVVAIASN GGGKQALETV QRLLPVLCQD HGLTPDQVVA IASNNGGKQA LETVQRLLPV  420
LCQDHGLTPD QVVAIASHDG GKQALETVQR LLPVLCQDHG LTPDQVVAIA SNGGGKQALE  480
TVQRLLPVLC QDHGLTPDQV VAIASNGGGK QALETVQRLL PVLCQDHGLT PDQVVAIASN  540
GGGKQALETV QRLLPVLCQD HGLTPDQVVA IASNNGGKQA LETVQRLLPV LCQDHGLTPD  600
QVVAIASNIG GKQALETVQR LLPVLCQDHG LTPDQVVAIA SNNGGKQALE TVQRLLPVLC  660
QDHGLTPDQV VAIASNGGGK QALETVQRLL PVLCQDHGLT PDQVVAIASN IGGKQALESI  720
VAQLSRPDPA LAALTNDHLV ALACLGGRPA MDAVKKGLPH APELIRRVNR RIGERTSHRV  780
AGSQLVKSEL EEKKSELRHK LKYVPHEYIE LIEIARNSTQ DRILEMKVME FFMKVYGYRG  840
KHLGGSRKPD GAIYTVGSPI DYGVIVDTKA YSGGYNLPIG QADEMQRYVK ENQTRNKHIN  900
PNEWWKVYPS SVTEFKFLFV SGHFKGNYKA QLTRLNHKTN CNGAVLSVEE LLIGGEMIKA  960
GTLTLEEVRR KFNNGEINFR SGGGEGRGSL LTCGDVEENP GPRMDYKDHD GDYKDHDIDY  1020
KDDDDKMAPK KKRKVGIHGV PARMVDLRTL GYSQQQQEKI KPKVRSTVAQ HHEALVGHGF  1080
THAHIVALSQ HPAALGTVAV TYQHIITALP EATHEDIVGV GKQWSGARAL EALLTDAGEL  1140
RGPPLQLDTG QLVKIAKRGG VTAMEAVHAS RNALTGAPLN LTPDQVVAIA SNNGGKQALE  1200
TVQRLLPVLC QDHGLTPDQV VAIASHDGGK QALETVQRLL PVLCQDHGLT PDQVVAIASH  1260
DGGKQALETV QRLLPVLCQD HGLTPDQVVA IASNGGGKQA LETVQRLLPV LCQDHGLTPD  1320
QVVAIASNGG GKQALETVQR LLPVLCQDHG LTPDQVVAIA SNGGGKQALE TVQRLLPVLC  1380
QDHGLTPDQV VAIASNGGGK QALETVQRLL PVLCQDHGLT PDQVVAIASN NGGKQALETV  1440
QRLLPVLCQD HGLTPDQVVA IASNGGGKQA LETVQRLLPV LCQDHGLTPD QVVAIASHDG  1500
GKQALETVQR LLPVLCQDHG LTPDQVVAIA SHDGGKQALE TVQRLLPVLC QDHGLTPDQV  1560
VAIASNIGGK QALETVQRLL PVLCQDHGLT PDQVVAIASN IGGKQALETV QRLLPVLCQD  1620
HGLTPDQVVA IASNNGGKQA LETVQRLLPV LCQDHGLTPD QVVAIASNNG GKQALETVQR  1680
LLPVLCQDHG LTPDQVVAIA SNIGGKQALE TVQRLLPVLC QDHGLTPDQV VAIASNGGGK  1740
QALESIVAQL SRPDPALAAL TNDHLVALAC LGGRPAMDAV KKGLPHAPEL IRRVNRRIGE  1800
RTSHRVAGSQ LVKSELEEKK SELRHKLKYV PHEYIELIEI ARNSTQDRIL EMKVMEFFMK  1860
VYGYRGKHLG GSRKPDGAIY TVGSPIDYGV IVDTKAYSGG YNLPIGQADE MERYVEENQT  1920
RNKHLNPNEW WKVYPSSVTE FKFLFVSGHF KGNYKAQLTR LNHITNCNGA VLSVEELLIG  1980
GEMIKAGTLT LEEVRRKFNN GEINF                                      2005

SEQ ID NO: 155          moltype = AA  length = 2005
FEATURE                 Location/Qualifiers
source                  1..2005
                        mol_type = protein
                        organism = synthetic construct
SEQUENCE: 155
MAPKKKRKVG IHGVPSRMVD LRTLGYSQQQ QEKIKPKVRS TVAQHHEALV GHGFTHAHIV  60
ALSQHPAALG TVAVTYQHII TALPEATHED IVGVGKQWSG ARALEALLTD AGELRGPPLQ  120
LDTGQLVKIA KRGGVTAMEA VHASRNALTG APLNLTPDQV VAIASNNGGK QALETVQRLL  180
PVLCQDHGLT PDQVVAIASH DGGKQALETV QRLLPVLCQD HGLTPDQVVA IASNGGGKQA  240
```

```
LETVQRLLPV LCQDHGLTPD QVVAIASNNG GKQALETVQR LLPVLCQDHG LTPDQVVAIA    300
SNNGGKQALE TVQRLLPVLC QDHGLTPDQV VAIASNIGGK QALETVQRLL PVLCQDHGLT    360
PDQVVAIASN GGGKQALETV QRLLPVLCQD HGLTPDQVVA IASNNGGKQA LETVQRLLPV    420
LCQDHGLTPD QVVAIASHDG GKQALETVQR LLPVLCQDHG LTPDQVVAIA SNGGGKQALE    480
TVQRLLPVLC QDHGLTPDQV VAIASNGGGK QALETVQRLL PVLCQDHGLT PDQVVAIASN    540
GGGKQALETV QRLLPVLCQD HGLTPDQVVA IASNNGGKQA LETVQRLLPV LCQDHGLTPD    600
QVVAIASNIG GKQALETVQR LLPVLCQDHG LTPDQVVAIA SNNGGKQALE TVQRLLPVLC    660
QDHGLTPDQV VAIASNGGGK QALETVQRLL PVLCQDHGLT PDQVVAIASN IGGKQALESI    720
VAQLSRPDPA LAALTNDHLV ALACLGGRPA MDAVKKGLPH APELIRRVNR RIGERTSHRV    780
AGSQLVKSEL EEKKSELRHK LKYVPHEYIE LIEIARNSTQ DRILEMKVME FFMKVYGYRG    840
KHLGGSRKPA GAIYTVGSPI DYGVIVDTKA YSGGYNLPIG QADEMQRYVK ENQTRNKHIN    900
PNEWWKVYPS SVTEFKFLFV SGHFKGNYKA QLTRLNHKTN CNGAVLSVEE LLIGGEMIKA    960
GTLTLEEVRR KFNNGEINFR SGGGEGRGSL LTCGDVEENP GPRMDYKDHD GDYKDHDIDY   1020
KDDDDKMAPK KKRKVGIHGV PARMVDLRTL GYSQQQQEKI KPKVRSTVAQ HHEALVGHGF   1080
THAHIVALSQ HPAALGTVAV TYQHIITALP EATHEDIVGV GKQWSGARAL EALLTDAGEL   1140
RGPPLQLDTG QLVKIAKRGG VTAMEAVHAS RNALTGAPLN LTPDQVVAIA SNNGGKQALE   1200
TVQRLLPVLC QDHGLTPDQV VAIASHDGGK QALETVQRLL PVLCQDHGLT PDQVVAIASH   1260
DGGKQALETV QRLLPVLCQD HGLTPDQVVA IASNGGGKQA LETVQRLLPV LCQDHGLTPD   1320
QVVAIASNGG GKQALETVQR LLPVLCQDHG LTPDQVVAIA SNGGGKQALE TVQRLLPVLC   1380
QDHGLTPDQV VAIASNGGGK QALETVQRLL PVLCQDHGLT PDQVVAIASN NGGKQALETV   1440
QRLLPVLCQD HGLTPDQVVA IASNGGGKQA LETVQRLLPV LCQDHGLTPD QVVAIASHDG   1500
GKQALETVQR LLPVLCQDHG LTPDQVVAIA SHDGGKQALE TVQRLLPVLC QDHGLTPDQV   1560
VAIASNIGGK QALETVQRLL PVLCQDHGLT PDQVVAIASN IGGKQALETV QRLLPVLCQD   1620
HGLTPDQVVA IASNNGGKQA LETVQRLLPV LCQDHGLTPD QVVAIASNNG GKQALETVQR   1680
LLPVLCQDHG LTPDQVVAIA SNIGGKQALE TVQRLLPVLC QDHGLTPDQV VAIASNGGGK   1740
QALESIVAQL SRPDPALAAL TNDHLVALAC LGGRPAMDAV KKGLPHAPEL IRRVNRRIGE   1800
RTSHRVAGSQ LVKSELEEKK SELRHKLKYV PHEYIELIEI ARNSTQDRIL EMKVMEFFMK   1860
VYGYRGKHLG GSRKPDGAIY TVGSPIDYGV IVDTKAYSGG YNLPIGQADE MERYVEENQT   1920
RNKHLNPNEW WKVYPSSVTE FKFLFVSGHF KGNYKAQLTR LNHITNCNGA VLSVEELLIG   1980
GEMIKAGTLT LEEVRRKFNN GEINF                                        2005
```

```
SEQ ID NO: 156        moltype = AA  length = 2005
FEATURE               Location/Qualifiers
source                1..2005
                      mol_type = protein
                      organism = synthetic construct
SEQUENCE: 156
MAPKKKRKVG IHGVPSRMVD LRTLGYSQQQ QEKIKPKVRS TVAQHHEALV GHGFTHAHIV     60
ALSQHPAALG TVAVTYQHII TALPEATHED IVGVGKQWSG ARALEALLTD AGELRGPPLQ    120
LDTGQLVKIA KRGGVTAMEA VHASRNALTG APLNLTPDQV VAIASNNGGK QALETVQRLL    180
PVLCQDHGLT PDQVVAIASH DGGKQALETV QRLLPVLCQD HGLTPDQVVA IASNGGGKQA    240
LETVQRLLPV LCQDHGLTPD QVVAIASNNG GKQALETVQR LLPVLCQDHG LTPDQVVAIA    300
SNNGGKQALE TVQRLLPVLC QDHGLTPDQV VAIASNIGGK QALETVQRLL PVLCQDHGLT    360
PDQVVAIASN GGGKQALETV QRLLPVLCQD HGLTPDQVVA IASNNGGKQA LETVQRLLPV    420
LCQDHGLTPD QVVAIASHDG GKQALETVQR LLPVLCQDHG LTPDQVVAIA SNGGGKQALE    480
TVQRLLPVLC QDHGLTPDQV VAIASNGGGK QALETVQRLL PVLCQDHGLT PDQVVAIASN    540
GGGKQALETV QRLLPVLCQD HGLTPDQVVA IASNNGGKQA LETVQRLLPV LCQDHGLTPD    600
QVVAIASNIG GKQALETVQR LLPVLCQDHG LTPDQVVAIA SNNGGKQALE TVQRLLPVLC    660
QDHGLTPDQV VAIASNGGGK QALETVQRLL PVLCQDHGLT PDQVVAIASN IGGKQALESI    720
VAQLSRPDPA LAALTNDHLV ALACLGGRPA MDAVKKGLPH APELIRRVNR RIGERTSHRV    780
AGSQLVKSEL EEKKSELRHK LKYVPHEYIE LIEIARNSTQ DRILEMKVME FFMKVYGYRG    840
KHLGGSRKPD GAIYTVGSPI DYGVIVATKA YSGGYNLPIG QADEMQRYVK ENQTRNKHIN    900
PNEWWKVYPS SVTEFKFLFV SGHFKGNYKA QLTRLNHKTN CNGAVLSVEE LLIGGEMIKA    960
GTLTLEEVRR KFNNGEINFR SGGGEGRGSL LTCGDVEENP GPRMDYKDHD GDYKDHDIDY   1020
KDDDDKMAPK KKRKVGIHGV PARMVDLRTL GYSQQQQEKI KPKVRSTVAQ HHEALVGHGF   1080
THAHIVALSQ HPAALGTVAV TYQHIITALP EATHEDIVGV GKQWSGARAL EALLTDAGEL   1140
RGPPLQLDTG QLVKIAKRGG VTAMEAVHAS RNALTGAPLN LTPDQVVAIA SNNGGKQALE   1200
TVQRLLPVLC QDHGLTPDQV VAIASHDGGK QALETVQRLL PVLCQDHGLT PDQVVAIASH   1260
DGGKQALETV QRLLPVLCQD HGLTPDQVVA IASNGGGKQA LETVQRLLPV LCQDHGLTPD   1320
QVVAIASNGG GKQALETVQR LLPVLCQDHG LTPDQVVAIA SNGGGKQALE TVQRLLPVLC   1380
QDHGLTPDQV VAIASNGGGK QALETVQRLL PVLCQDHGLT PDQVVAIASN NGGKQALETV   1440
QRLLPVLCQD HGLTPDQVVA IASNGGGKQA LETVQRLLPV LCQDHGLTPD QVVAIASHDG   1500
GKQALETVQR LLPVLCQDHG LTPDQVVAIA SHDGGKQALE TVQRLLPVLC QDHGLTPDQV   1560
VAIASNIGGK QALETVQRLL PVLCQDHGLT PDQVVAIASN IGGKQALETV QRLLPVLCQD   1620
HGLTPDQVVA IASNNGGKQA LETVQRLLPV LCQDHGLTPD QVVAIASNNG GKQALETVQR   1680
LLPVLCQDHG LTPDQVVAIA SNIGGKQALE TVQRLLPVLC QDHGLTPDQV VAIASNGGGK   1740
QALESIVAQL SRPDPALAAL TNDHLVALAC LGGRPAMDAV KKGLPHAPEL IRRVNRRIGE   1800
RTSHRVAGSQ LVKSELEEKK SELRHKLKYV PHEYIELIEI ARNSTQDRIL EMKVMEFFMK   1860
VYGYRGKHLG GSRKPDGAIY TVGSPIDYGV IVDTKAYSGG YNLPIGQADE MERYVEENQT   1920
RNKHLNPNEW WKVYPSSVTE FKFLFVSGHF KGNYKAQLTR LNHITNCNGA VLSVEELLIG   1980
GEMIKAGTLT LEEVRRKFNN GEINF                                        2005
```

```
SEQ ID NO: 157        moltype = AA  length = 2005
FEATURE               Location/Qualifiers
source                1..2005
                      mol_type = protein
                      organism = synthetic construct
SEQUENCE: 157
MAPKKKRKVG IHGVPSRMVD LRTLGYSQQQ QEKIKPKVRS TVAQHHEALV GHGFTHAHIV     60
```

```
ALSQHPAALG TVAVTYQHII TALPEATHED IVGVGKQWSG ARALEALLTD AGELRGPPLQ  120
LDTGQLVKIA KRGGVTAMEA VHASRNALTG APLNLTPDQV VAIASNNGGK QALETVQRLL  180
PVLCQDHGLT PDQVVAIASH DGGKQALETV QRLLPVLCQD HGLTPDQVVA IASNIGGKQA  240
LETVQRLLPV LCQDHGLTPD QVVAIASNIG GKQALETVQR LLPVLCQDHG LTPDQVVAIA  300
SNIGGKQALE TVQRLLPVLC QDHGLTPDQV VAIASNIGGK QALETVQRLL PVLCQDHGLT  360
PDQVVAIASN NGGKQALETV QRLLPVLCQD HGLTPDQVVA IASNIGGKQA LETVQRLLPV  420
LCQDHGLTPD QVVAIASHDG GKQALETVQR LLPVLCQDHG LTPDQVVAIA SHDGGKQALE  480
TVQRLLPVLC QDHGLTPDQV VAIASNIGGK QALETVQRLL PVLCQDHGLT PDQVVAIASN  540
IGGKQALETV QRLLPVLCQD HGLTPDQVVA IASNNGGKQA LETVQRLLPV LCQDHGLTPD  600
QVVAIASNNG GKQALETVQR LLPVLCQDHG LTPDQVVAIA SNGGGKQALE TVQRLLPVLC  660
QDHGLTPDQV VAIASNNGGK QALETVQRLL PVLCQDHGLT PDQVVAIASH DGGKQALETV  720
QRLLPVLCQD HGLTPDQVVA IASHDGGKQA LETVQRLLPV LCQDHGLTPD QVVAIASNGG  780
GKQALESIVA QLSRPDPALA ALTNDHLVAL ACLGGRPAMD AVKKGLPHAP ELIRRVNRRI  840
GERTSHRVAG SQLVKSELEE KKSELRHKLK YVPHEYIELI EIARNSTQDR ILEMKVMEFF  900
MKVYGYRGKH LGGSRKPDGA IYTVGSPIDY GVIVDTKAYS GGYNLPIGQA DEMQRYVKEN  960
QTRNKHINPN EWWKVYPSSV TEFKFLFVSG HFKGNYKAQL TRLNHKTNCN GAVLSVEELL 1020
IGGEMIKAGT LTLEEVRRKF NNGEINFRSG GGEGRGSLLT CGDVEENPGP RMDYKDHDGD 1080
YKDHDIDYKD DDDKMAPKKK RKVGIHGVPA RMVDLRTLGY SQQQQEKIKP KVRSTVAQHH 1140
EALVGHGFTH AHIVALSQHP AALGTVAVTY QHIITALPEA THEDIVGVGK QWSGARALEA 1200
LLTDAGELRG PPLQLDTGQL VKIAKRGGVT AMEAVHASRN ALTGAPLNLT PDQVVAIASN 1260
NGGKQALETV QRLLPVLCQD HGLTPDQVVA IASNNGGKQA LETVQRLLPV LCQDHGLTPD 1320
QVVAIASHDG GKQALETVQR LLPVLCQDHG LTPDQVVAIA SNGGGKQALE TVQRLLPVLC 1380
QDHGLTPDQV VAIASHDGGK QALETVQRLL PVLCQDHGLT PDQVVAIASN NGGKQALETV 1440
QRLLPVLCQD HGLTPDQVVA IASNGGGKQA LETVQRLLPV LCQDHGLTPD QVVAIASHDG 1500
GKQALETVQR LLPVLCQDHG LTPDQVVAIA SNNGGKQALE TVQRLLPVLC QDHGLTPDQV 1560
VAIASHDGGK QALETVQRLL PVLCQDHGLT PDQVVAIASN IGGKQALETV QRLLPVLCQD 1620
HGLTPDQVVA IASNNGGKQA LETVQRLLPV LCQDHGLTPD QVVAIASHDG GKQALETVQR 1680
LLPVLCQDHG LTPDQVVAIA SNIGGKQALE TVQRLLPVLC QDHGLTPDQV VAIASNGGGK 1740
QALESIVAQL SRPDPALAAL TNDHLVALAC LGGRPAMDAV KKGLPHAPEL IRRVNRRIGE 1800
RTSHRVAGSQ LVKSELEIKK SELRHKLKYV PHEYIELIEI ARNSTQDRIL EMKVMEFFMK 1860
VYGYRGKHLG GSRKPDGAIY TVGSPIDYGV IVDTKAYSGG YNLPIGQADE MERYVEENQT 1920
RNKHLNPNEW WKVYPSSVTE FKFLFVSGHF KGNYKAQLTR LNHITNCNGA VLSVEELLIG 1980
GEMIKAGTLT LEEVRRKFNN GEINF                                      2005

SEQ ID NO: 158        moltype = AA  length = 2005
FEATURE               Location/Qualifiers
source                1..2005
                      mol_type = protein
                      organism = synthetic construct
SEQUENCE: 158
MAPKKKRKVG IHGVPSRMVD LRTLGYSQQQ QEKIKPKVRS TVAQHHEALV GHGFTHAHIV   60
ALSQHPAALG TVAVTYQHII TALPEATHED IVGVGKQWSG ARALEALLTD AGELRGPPLQ  120
LDTGQLVKIA KRGGVTAMEA VHASRNALTG APLNLTPDQV VAIASNNGGK QALETVQRLL  180
PVLCQDHGLT PDQVVAIASH DGGKQALETV QRLLPVLCQD HGLTPDQVVA IASNIGGKQA  240
LETVQRLLPV LCQDHGLTPD QVVAIASNIG GKQALETVQR LLPVLCQDHG LTPDQVVAIA  300
SNIGGKQALE TVQRLLPVLC QDHGLTPDQV VAIASNIGGK QALETVQRLL PVLCQDHGLT  360
PDQVVAIASN NGGKQALETV QRLLPVLCQD HGLTPDQVVA IASNIGGKQA LETVQRLLPV  420
LCQDHGLTPD QVVAIASHDG GKQALETVQR LLPVLCQDHG LTPDQVVAIA SHDGGKQALE  480
TVQRLLPVLC QDHGLTPDQV VAIASNIGGK QALETVQRLL PVLCQDHGLT PDQVVAIASN  540
IGGKQALETV QRLLPVLCQD HGLTPDQVVA IASNNGGKQA LETVQRLLPV LCQDHGLTPD  600
QVVAIASNNG GKQALETVQR LLPVLCQDHG LTPDQVVAIA SNGGGKQALE TVQRLLPVLC  660
QDHGLTPDQV VAIASNNGGK QALETVQRLL PVLCQDHGLT PDQVVAIASH DGGKQALETV  720
QRLLPVLCQD HGLTPDQVVA IASHDGGKQA LETVQRLLPV LCQDHGLTPD QVVAIASNGG  780
GKQALESIVA QLSRPDPALA ALTNDHLVAL ACLGGRPAMD AVKKGLPHAP ELIRRVNRRI  840
GERTSHRVAG SQLVKSELEE KKSELRHKLK YVPHEYIELI EIARNSTQDR ILEMKVMEFF  900
MKVYGYRGKH LGGSRKPAGA IYTVGSPIDY GVIVDTKAYS GGYNLPIGQA DEMQRYVKEN  960
QTRNKHINPN EWWKVYPSSV TEFKFLFVSG HFKGNYKAQL TRLNHKTNCN GAVLSVEELL 1020
IGGEMIKAGT LTLEEVRRKF NNGEINFRSG GGEGRGSLLT CGDVEENPGP RMDYKDHDGD 1080
YKDHDIDYKD DDDKMAPKKK RKVGIHGVPA RMVDLRTLGY SQQQQEKIKP KVRSTVAQHH 1140
EALVGHGFTH AHIVALSQHP AALGTVAVTY QHIITALPEA THEDIVGVGK QWSGARALEA 1200
LLTDAGELRG PPLQLDTGQL VKIAKRGGVT AMEAVHASRN ALTGAPLNLT PDQVVAIASN 1260
NGGKQALETV QRLLPVLCQD HGLTPDQVVA IASNNGGKQA LETVQRLLPV LCQDHGLTPD 1320
QVVAIASHDG GKQALETVQR LLPVLCQDHG LTPDQVVAIA SNGGGKQALE TVQRLLPVLC 1380
QDHGLTPDQV VAIASHDGGK QALETVQRLL PVLCQDHGLT PDQVVAIASN NGGKQALETV 1440
QRLLPVLCQD HGLTPDQVVA IASNGGGKQA LETVQRLLPV LCQDHGLTPD QVVAIASHDG 1500
GKQALETVQR LLPVLCQDHG LTPDQVVAIA SNNGGKQALE TVQRLLPVLC QDHGLTPDQV 1560
VAIASHDGGK QALETVQRLL PVLCQDHGLT PDQVVAIASN IGGKQALETV QRLLPVLCQD 1620
HGLTPDQVVA IASNNGGKQA LETVQRLLPV LCQDHGLTPD QVVAIASHDG GKQALETVQR 1680
LLPVLCQDHG LTPDQVVAIA SNIGGKQALE TVQRLLPVLC QDHGLTPDQV VAIASNGGGK 1740
QALESIVAQL SRPDPALAAL TNDHLVALAC LGGRPAMDAV KKGLPHAPEL IRRVNRRIGE 1800
RTSHRVAGSQ LVKSELEEKK SELRHKLKYV PHEYIELIEI ARNSTQDRIL EMKVMEFFMK 1860
VYGYRGKHLG GSRKPDGAIY TVGSPIDYGV IVDTKAYSGG YNLPIGQADE MERYVEENQT 1920
RNKHLNPNEW WKVYPSSVTE FKFLFVSGHF KGNYKAQLTR LNHITNCNGA VLSVEELLIG 1980
GEMIKAGTLT LEEVRRKFNN GEINF                                      2005

SEQ ID NO: 159        moltype = AA  length = 2005
FEATURE               Location/Qualifiers
source                1..2005
                      mol_type = protein
```

```
                       organism = synthetic construct
SEQUENCE: 159
MAPKKKRKVG IHGVPSRMVD LRTLGYSQQQ QEKIKPKVRS TVAQHHEALV GHGFTHAHIV    60
ALSQHPAALG TVAVTYQHII TALPEATHED IVGVGKQWSG ARALEALLTD AGELRGPPLQ   120
LDTGQLVKIA KRGGVTAMEA VHASRNALTG APLNLTPDQV VAIASNNGGK QALETVQRLL   180
PVLCQDHGLT PDQVVAIASH DGGKQALETV QRLLPVLCQD HGLTPDQVVA IASNIGGKQA   240
LETVQRLLPV LCQDHGLTPD QVVAIASNIG GKQALETVQR LLPVLCQDHG LTPDQVVAIA   300
SNIGGKQALE TVQRLLPVLC QDHGLTPDQV VAIASNIGGK QALETVQRLL PVLCQDHGLT   360
PDQVVAIASN NGGKQALETV QRLLPVLCQD HGLTPDQVVA IASNIGGKQA LETVQRLLPV   420
LCQDHGLTPD QVVAIASHDG GKQALETVQR LLPVLCQDHG LTPDQVVAIA SHDGGKQALE   480
TVQRLLPVLC QDHGLTPDQV VAIASNIGGK QALETVQRLL PVLCQDHGLT PDQVVAIASN   540
IGGKQALETV QRLLPVLCQD HGLTPDQVVA IASNNGGKQA LETVQRLLPV LCQDHGLTPD   600
QVVAIASNNG GKQALETVQR LLPVLCQDHG LTPDQVVAIA SNGGGKQALE TVQRLLPVLC   660
QDHGLTPDQV VAIASNNGGK QALETVQRLL PVLCQDHGLT PDQVVAIASH DGGKQALETV   720
QRLLPVLCQD HGLTPDQVVA IASHDGGKQA LETVQRLLPV LCQDHGLTPD QVVAIASNGG   780
GKQALESIVA QLSRPDPALA ALTNDHLVAL ACLGGRPAMD AVKKGLPHAP ELIRRVNRRI   840
GERTSHRVAG SQLVKSELEE KKSELRHKLK YVPHEYIELI EIARNSTQDR ILEMKVMEFF   900
MKVYGYRGKH LGGSRKPDGA IYTVGSPIDY GVIVATKAYS GGYNLPIGQA DEMQRYVKEN   960
QTRNKHINPN EWWKVYPSSV TEFKFLFVSG HFKGNYKAQL TRLNHKTNCN GAVLSVEELL  1020
IGGEMIKAGT LTLEEVRRKF NNGEINFRSG GGEGRGSLLT CGDVEENPGP RMDYKDHDGD  1080
YKDHDIDYKD DDDKMAPKKK RKVGIHGVPA RMVDLRTLGY SQQQQEKIKP KVRSTVAQHH  1140
EALVGHGFTH AHIVALSQHP AALGTVAVTY QHIITALPEA THEDIVGVGK QWSGARALEA  1200
LLTDAGELRG PPLQLDTGQL VKIAKRGGVT AMEAVHASRN ALTGAPLNLT PDQVVAIASN  1260
NGGKQALETV QRLLPVLCQD HGLTPDQVVA IASNNGGKQA LETVQRLLPV LCQDHGLTPD  1320
QVVAIASHDG GKQALETVQR LLPVLCQDHG LTPDQVVAIA SNGGGKQALE TVQRLLPVLC  1380
QDHGLTPDQV VAIASHDGGK QALETVQRLL PVLCQDHGLT PDQVVAIASN NGGKQALETV  1440
QRLLPVLCQD HGLTPDQVVA IASNGGGKQA LETVQRLLPV LCQDHGLTPD QVVAIASHDG  1500
GKQALETVQR LLPVLCQDHG LTPDQVVAIA SNNGGKQALE TVQRLLPVLC QDHGLTPDQV  1560
VAIASHDGGK QALETVQRLL PVLCQDHGLT PDQVVAIASN IGGKQALETV QRLLPVLCQD  1620
HGLTPDQVVA IASNNGGKQA LETVQRLLPV LCQDHGLTPD QVVAIASHDG GKQALETVQR  1680
LLPVLCQDHG LTPDQVVAIA SNIGGKQALE TVQRLLPVLC QDHGLTPDQV VAIASNGGGK  1740
QALESIVAQL SRPDPALAAL TNDHLVALAC LGGRPAMDAV KKGLPHAPEL IRRVNRRIGE  1800
RTSHRVAGSQ LVKSELEEKK SELRHKLKYV PHEYIELIEI ARNSTQDRIL EMKVMEFFMK  1860
VYGYRGKHLG GSRKPDGAIY TVGSPIDYGV IVDTKAYSGG YNLPIGQADE MERYVEENQT  1920
RNKHLNPNEW WKVYPSSVTE FKFLFVSGHF KGNYKAQLTR LNHITNCNGA VLSVEELLIG  1980
GEMIKAGTLT LEEVRRKFNN GEINF                                       2005

SEQ ID NO: 160           moltype = AA   length = 2311
FEATURE                  Location/Qualifiers
source                   1..2311
                         mol_type = protein
                         organism = synthetic construct
SEQUENCE: 160
MAPKKKRKVG IHGVPSRMVD LRTLGYSQQQ QEKIKPKVRS TVAQHHEALV GHGFTHAHIV    60
ALSQHPAALG TVAVTYQHII TALPEATHED IVGVGKQWSG ARALEALLTD AGELRGPPLQ   120
LDTGQLVKIA KRGGVTAMEA VHASRNALTG APLNLTPDQV VAIASHDGGK QALETVQRLL   180
PVLCQDHGLT PDQVVAIASH DGGKQALETV QRLLPVLCQD HGLTPDQVVA IASNGGGKQA   240
LETVQRLLPV LCQDHGLTPD QVVAIASNNG GKQALETVQR LLPVLCQDHG LTPDQVVAIA   300
SNNGGKQALE TVQRLLPVLC QDHGLTPDQV VAIASNIGGK QALETVQRLL PVLCQDHGLT   360
PDQVVAIASH DGGKQALETV QRLLPVLCQD HGLTPDQVVA IASHDGGKQA LETVQRLLPV   420
LCQDHGLTPD QVVAIASNNG GKQALETVQR LLPVLCQDHG LTPDQVVAIA SHDGGKQALE   480
TVQRLLPVLC QDHGLTPDQV VAIASNNGGK QALETVQRLL PVLCQDHGLT PDQVVAIASN   540
IGGKQALETV QRLLPVLCQD HGLTPDQVVA IASNIGGKQA LETVQRLLPV LCQDHGLTPD   600
QVVAIASNIG GKQALETVQR LLPVLCQDHG LTPDQVVAIA SNNGGKQALE TVQRLLPVLC   660
QDHGLTPDQV VAIASNIGGK QALETVQRLL PVLCQDHGLT PDQVVAIASH DGGKQALETV   720
QRLLPVLCQD HGLTPDQVVA IASHDGGKQA LETVQRLLPV LCQDHGLTPD QVVAIASNIG   780
GKQALETVQR LLPVLCQDHG LTPDQVVAIA SNGGGKQALE TVQRLLPVLC QDHGLTPDQV   840
VAIASHDGGK QALETVQRLL PVLCQDHGLT PDQVVAIASH DGGKQALETV QRLLPVLCQD   900
HGLTPDQVVA IASNIGGKQA LETVQRLLPV LCQDHGLTPD QVVAIASHDG GKQALETVQR   960
LLPVLCQDHG LTPDQVVAIA SNNGGKQALE SIVAQLSRPD PALAALTNDH LVALACLGGR  1020
PAMDAVKKGL PHAPELIRRV NRRIGERTSH RVAGSQLVKS ELEEKKSELR HKLKYVPHEY  1080
IELIEIARNS TQDRILEMKV MEFFMKVYGY RGKHLGGSRK PDGAIYTVGS PIDYGVIVDT  1140
KAYSGGYNLP IGQADEMQRY VKENQTRNKH INPNEWWKVY PSSVTEFKFL FVSGHFKGNY  1200
KAQLTRLNHK TNCNGAVLSV EELLIGGEMI KAGTLTLEEV RRKFNNGEIN FRSGGGEGRG  1260
SLLTCGDVEE NPGPRMDYKD HDGDYKDHDI DYKDDDDKMA PKKKRKVGIH GVPARMVDLR  1320
TLGYSQQQQE KIKPKVRSTV AQHHEALVGH GFTHAHIVAL SQHPAALGTV AVTYQHIITA  1380
LPEATHEDIV GVGKQWSGAR ALEALLTDAG ELRGPPLQLD TGQLVKIAKR GGVTAMEAVH  1440
ASRNALTGAP LNLTPDQVVA IASHDGGKQA LETVQRLLPV LCQDHGLTPD QVVAIASHDG  1500
GKQALETVQR LLPVLCQDHG LTPDQVVAIA SHDGGKQALE TVQRLLPVLC QDHGLTPDQV  1560
VAIASNIGGK QALETVQRLL PVLCQDHGLT PDQVVAIASN NGGKQALETV QRLLPVLCQD  1620
HGLTPDQVVA IASNIGGKQA LETVQRLLPV LCQDHGLTPD QVVAIASNNG GKQALETVQR  1680
LLPVLCQDHG LTPDQVVAIA SHDGGKQALE TVQRLLPVLC QDHGLTPDQV VAIASHDGGK  1740
QALETVQRLL PVLCQDHGLT PDQVVAIASH DGGKQALETV QRLLPVLCQD HGLTPDQVVA  1800
IASHDGGKQA LETVQRLLPV LCQDHGLTPD QVVAIASNNG GKQALETVQR LLPVLCQDHG  1860
LTPDQVVAIA SHDGGKQALE TVQRLLPVLC QDHGLTPDQV VAIASNNGGK QALETVQRLL  1920
PVLCQDHGLT PDQVVAIASN NGGKQALETV QRLLPVLCQD HGLTPDQVVA IASHDGGKQA  1980
LETVQRLLPV LCQDHGLTPD QVVAIASNNG GKQALETVQR LLPVLCQDHG LTPDQVVAIA  2040
SHDGGKQALE SIVAQLSRPD PALAALTNDH LVALACLGGR PAMDAVKKGL PHAPELIRRV  2100
NRRIGERTSH RVAGSQLVKS ELEEKKSELR HKLKYVPHEY IELIEIARNS TQDRILEMKV  2160
```

-continued

```
MEFFMKVYGY RGKHLGGSRK PDGAIYTVGS PIDYGVIVDT KAYSGGYNLP IGQADEMERY   2220
VEENQTRNKH LNPNEWWKVY PSSVTEFKFL FVSGHFKGNY KAQLTRLNHI TNCNGAVLSV   2280
EELLIGGEMI KAGTLTLEEV RRKFNNGEIN F                                  2311

SEQ ID NO: 161          moltype = AA   length = 2311
FEATURE                 Location/Qualifiers
source                  1..2311
                        mol_type = protein
                        organism = synthetic construct
SEQUENCE: 161
MAPKKKRKVG IHGVPSRMVD LRTLGYSQQQ QEKIKPKVRS TVAQHHEALV GHGFTHAHIV   60
ALSQHPAALG TVAVTYQHII TALPEATHED IVGVGKQWSG ARALEALLTD AGELRGPPLQ   120
LDTGQLVKIA KRGGVTAMEA VHASRNALTG APLNLTPDQV VAIASHDGGK QALETVQRLL   180
PVLCQDHGLT PDQVVAIASH DGGKQALETV QRLLPVLCQD HGLTPDQVVA IASNGGGKQA   240
LETVQRLLPV LCQDHGLTPD QVVAIASNNG GKQALETVQR LLPVLCQDHG LTPDQVVAIA   300
SNNGGKQALE TVQRLLPVLC QDHGLTPDQV VAIASNIGGK QALETVQRLL PVLCQDHGLT   360
PDQVVAIASH DGGKQALETV QRLLPVLCQD HGLTPDQVVA IASHDGGKQA LETVQRLLPV   420
LCQDHGLTPD QVVAIASNNG GKQALETVQR LLPVLCQDHG LTPDQVVAIA SHDGGKQALE   480
TVQRLLPVLC QDHGLTPDQV VAIASNNGGK QALETVQRLL PVLCQDHGLT PDQVVAIASN   540
IGGKQALETV QRLLPVLCQD HGLTPDQVVA IASNIGGKQA LETVQRLLPV LCQDHGLTPD   600
QVVAIASNIG GKQALETVQR LLPVLCQDHG LTPDQVVAIA SNNGGKQALE TVQRLLPVLC   660
QDHGLTPDQV VAIASNIGGK QALETVQRLL PVLCQDHGLT PDQVVAIASN DGGKQALETV   720
QRLLPVLCQD HGLTPDQVVA IASHDGGKQA LETVQRLLPV LCQDHGLTPD QVVAIASNIG   780
GKQALETVQR LLPVLCQDHG LTPDQVVAIA SNNGGKQALE TVQRLLPVLC QDHGLTPDQV   840
VAIASHDGGK QALETVQRLL PVLCQDHGLT PDQVVAIASH DGGKQALETV QRLLPVLCQD   900
HGLTPDQVVA IASNIGGKQA LETVQRLLPV LCQDHGLTPD QVVAIASHDG GKQALETVQR   960
LLPVLCQDHG LTPDQVVAIA SNNGGKQALE SIVAQLSRPD PALAALTNDH LVALACLGGR   1020
PAMDAVKKGL PHAPELIRRV NRRIGERTSH RVAGSQLVKS ELEEKKSELR HKLKYVPHEY   1080
IELIEIARNS TQDRILEMKV MEFFMKVYGY RGKHLGGSRK PAGAIYTVGS PIDYGVIVDT   1140
KAYSGGYNLP IGQADEMQRY VKENQTRNKH INPNEWWKVY PSSVTEFKFL FVSGHFKGNY   1200
KAQLTRLNHK TNCNGAVLSV EELLIGGEMI KAGTLTLEEV RRKFNNGEIN FRSGGGEGRG   1260
SLLTCGDVEE NPGPRMDYKD HDGDYKDHDI DYKDDDDKMA PKKKRKVGIH GVPARMVDLR   1320
TLGYSQQQE KIKPKVRSTV AQHHEALVGH GFTHAHIVAL SQHPAALGTV AVTYQHIITA   1380
LPEATHEDIV GVGKQWSGAR ALEALLTDAG ELRGPPLQTG DLVKIAKR GGVTAMEAVH   1440
ASRNALTGAP LNLTPDQVVA IASHDGGKQA LETVQRLLPV LCQDHGLTPD QVVAIASHDG   1500
GKQALETVQR LLPVLCQDHG LTPDQVVAIA SHDGGKQALE TVQRLLPVLC QDHGLTPDQV   1560
VAIASNIGGK QALETVQRLL PVLCQDHGLT PDQVVAIASN NGGKQALETV QRLLPVLCQD   1620
HGLTPDQVVA IASNIGGKQA LETVQRLLPV LCQDHGLTPD QVVAIASNNG GKQALETVQR   1680
LLPVLCQDHG LTPDQVVAIA SHDGGKQALE TVQRLLPVLC QDHGLTPDQV VAIASHDGGK   1740
QALETVQRLL PVLCQDHGLT PDQVVAIASH DGGKQALETV QRLLPVLCQD HGLTPDQVVA   1800
IASHDGGKQA LETVQRLLPV LCQDHGLTPD QVVAIASNNG GKQALETVQR LLPVLCQDHG   1860
LTPDQVVAIA SHDGGKQALE TVQRLLPVLC QDHGLTPDQV VAIASNNGGK QALETVQRLL   1920
PVLCQDHGLT PDQVVAIASN NGGKQALETV QRLLPVLCQD HGLTPDQVVA IASHDGGKQA   1980
LETVQRLLPV LCQDHGLTPD QVVAIASNNG GKQALETVQR LLPVLCQDHG LTPDQVVAIA   2040
SHDGGKQALE SIVAQLSRPD PALAALTNDH LVALACLGGR PAMDAVKKGL PHAPELIRRV   2100
NRRIGERTSH RVAGSQLVKS ELEEKKSELR HKLKYVPHEY IELIEIARNS TQDRILEMKV   2160
MEFFMKVYGY RGKHLGGSRK PDGAIYTVGS PIDYGVIVDT KAYSGGYNLP IGQADEMERY   2220
VEENQTRNKH LNPNEWWKVY PSSVTEFKFL FVSGHFKGNY KAQLTRLNHI TNCNGAVLSV   2280
EELLIGGEMI KAGTLTLEEV RRKFNNGEIN F                                  2311

SEQ ID NO: 162          moltype = AA   length = 2311
FEATURE                 Location/Qualifiers
source                  1..2311
                        mol_type = protein
                        organism = synthetic construct
SEQUENCE: 162
MAPKKKRKVG IHGVPSRMVD LRTLGYSQQQ QEKIKPKVRS TVAQHHEALV GHGFTHAHIV   60
ALSQHPAALG TVAVTYQHII TALPEATHED IVGVGKQWSG ARALEALLTD AGELRGPPLQ   120
LDTGQLVKIA KRGGVTAMEA VHASRNALTG APLNLTPDQV VAIASHDGGK QALETVQRLL   180
PVLCQDHGLT PDQVVAIASH DGGKQALETV QRLLPVLCQD HGLTPDQVVA IASNGGGKQA   240
LETVQRLLPV LCQDHGLTPD QVVAIASNNG GKQALETVQR LLPVLCQDHG LTPDQVVAIA   300
SNNGGKQALE TVQRLLPVLC QDHGLTPDQV VAIASNIGGK QALETVQRLL PVLCQDHGLT   360
PDQVVAIASH DGGKQALETV QRLLPVLCQD HGLTPDQVVA IASHDGGKQA LETVQRLLPV   420
LCQDHGLTPD QVVAIASNNG GKQALETVQR LLPVLCQDHG LTPDQVVAIA SHDGGKQALE   480
TVQRLLPVLC QDHGLTPDQV VAIASNNGGK QALETVQRLL PVLCQDHGLT PDQVVAIASN   540
IGGKQALETV QRLLPVLCQD HGLTPDQVVA IASNIGGKQA LETVQRLLPV LCQDHGLTPD   600
QVVAIASNIG GKQALETVQR LLPVLCQDHG LTPDQVVAIA SNNGGKQALE TVQRLLPVLC   660
QDHGLTPDQV VAIASNIGGK QALETVQRLL PVLCQDHGLT PDQVVAIASN DGGKQALETV   720
QRLLPVLCQD HGLTPDQVVA IASHDGGKQA LETVQRLLPV LCQDHGLTPD QVVAIASNIG   780
GKQALETVQR LLPVLCQDHG LTPDQVVAIA SNGGGKQALE TVQRLLPVLC QDHGLTPDQV   840
VAIASHDGGK QALETVQRLL PVLCQDHGLT PDQVVAIASH DGGKQALETV QRLLPVLCQD   900
HGLTPDQVVA IASNIGGKQA LETVQRLLPV LCQDHGLTPD QVVAIASHDG GKQALETVQR   960
LLPVLCQDHG LTPDQVVAIA SNNGGKQALE SIVAQLSRPD PALAALTNDH LVALACLGGR   1020
PAMDAVKKGL PHAPELIRRV NRRIGERTSH RVAGSQLVKS ELEEKKSELR HKLKYVPHEY   1080
IELIEIARNS TQDRILEMKV MEFFMKVYGY RGKHLGGSRK PDGAIYTVGS PIDYGVIVDT   1140
KAYSGGYNLP IGQADEMQRY VKENQTRNKH INPNEWWKVY PSSVTEFKFL FVSGHFKGNY   1200
KAQLTRLNHK TNCNGAVLSV EELLIGGEMI KAGTLTLEEV RRKFNNGEIN FRSGGGEGRG   1260
SLLTCGDVEE NPGPRMDYKD HDGDYKDHDI DYKDDDDKMA PKKKRKVGIH GVPARMVDLR   1320
TLGYSQQQE KIKPKVRSTV AQHHEALVGH GFTHAHIVAL SQHPAALGTV AVTYQHIITA   1380
```

-continued

```
LPEATHEDIV GVGKQWSGAR ALEALLTDAG ELRGPPLQLD TGQLVKIAKR GGVTAMEAVH    1440
ASRNALTGAP LNLTPDQVVA IASHDGGKQA LETVQRLLPV LCQDHGLTPD QVVAIASHDG    1500
GKQALETVQR LLPVLCQDHG LTPDQVVAIA SHDGGKQALE TVQRLLPVLC QDHGLTPDQV    1560
VAIASNIGGK QALETVQRLL PVLCQDHGLT PDQVVAIASN NGGKQALETV QRLLPVLCQD    1620
HGLTPDQVVA IASNIGGKQA LETVQRLLPV LCQDHGLTPD QVVAIASNNG GKQALETVQR    1680
LLPVLCQDHG LTPDQVVAIA SHDGGKQALE TVQRLLPVLC QDHGLTPDQV VAIASHDGGK    1740
QALETVQRLL PVLCQDHGLT PDQVVAIASH DGGKQALETV QRLLPVLCQD HGLTPDQVVA    1800
IASHDGGKQA LETVQRLLPV LCQDHGLTPD QVVAIASNNG GKQALETVQR LLPVLCQDHG    1860
LTPDQVVAIA SHDGGKQALE TVQRLLPVLC QDHGLTPDQV VAIASNNGGK QALETVQRLL    1920
PVLCQDHGLT PDQVVAIASN NGGKQALETV QRLLPVLCQD HGLTPDQVVA IASHDGGKQA    1980
LETVQRLLPV LCQDHGLTPD QVVAIASNNG GKQALETVQR LLPVLCQDHG LTPDQVVAIA    2040
SHDGGKQALE SIVAQLSRPD PALAALTNDH LVALACLGGR PAMDAVKKGL PHAPELIRRV    2100
NRRIGERTSH RVAGSQLVKS ELEEKKSELR HKLKYVPHEY IELIEIARNS TQDRILEMKV    2160
MEFFMKVYGY RGKHLGGSRK PAGAIYTVGS PIDYGVIVDT KAYSGGYNLP IGQADEMERY    2220
VEENQTRNKH LNPNEWWKVY PSSVTEFKFL FVSGHFKGNY KAQLTRLNHI TNCNGAVLSV    2280
EELLIGGEMI KAGTLTLEEV RRKFNNGEIN F                                  2311

SEQ ID NO: 163             moltype = AA   length = 103
FEATURE                    Location/Qualifiers
source                     1..103
                           mol_type = protein
                           organism = synthetic construct
SEQUENCE: 163
MTNLSDIIEK ETGKQLVIQE SILMLPEEVE EVIGNKPESD ILVHTAYDES TDENVMLLTS    60
DAPEYKPWAL VIQDSNGENK IKMLMKRTAD GSEFESPKKK RKV                      103

SEQ ID NO: 164             moltype = AA   length = 347
FEATURE                    Location/Qualifiers
source                     1..347
                           mol_type = protein
                           organism = synthetic construct
SEQUENCE: 164
MKRTADGSEF ESPKKKRKVS SETGPVAVDP TLRRRIEPHE FEVFFDPREL RKETCLLYEI    60
NWGGRHSIWR HTSQNTNKHV EVNFIEKFTT ERYFCPNTRC SITWFLSWSP CGECSRAITE    120
FLSRYPHVTL FIYIARLYHH ADPRNRQGLR DLISSGVTIQ IMTEQESGYC WRNFVNYSPS    180
NEAHWPRYPH LWVRLYVLEL YCIILGLPPC LNILRRKQPQ LTFFTIALQS CHYQRLPPHI    240
LWATGLKNSG SETPGTSESA TPESTNLSDI IEKETGKQLV IQESILMLPE EVEEVIGNKP    300
ESDILVHTAY DESTDENVML LTSDAPEYKP WALVIQDSNG ENKIKML                 347

SEQ ID NO: 165             moltype = AA   length = 392
FEATURE                    Location/Qualifiers
source                     1..392
                           mol_type = protein
                           organism = synthetic construct
SEQUENCE: 165
MAETGEEETA SAEASGFSDL SDSELVEFLD LEEAKESAVS LSKPGPSAEL PGKDDKPVSL    60
QNWKGGLDVL SPMERFHLKY LYVTDLCTQN WCELQMVYGK ELPGSLTPEK AAVLDTGASI    120
HLAKELELHD LVTVPIATKE DAWAVKFLNI LAMIPALQSE GRVREFPVFG EVEGIFLVGV    180
IDELHYTSKG ELELALKTR RRPVLPLPAQ KKKDYFQVSL YKYIFDAMVQ GKVTPASLIH    240
HTKLCLDKPL GPSVLRHARQ GGVSVKSLGD LMELVFLSLT LSDLPAIDTL KLEYIHQETA    300
TILGTEIVAF EEKEVSKVQ HYVAYWMGHR DPQGVDVEEA WKCRTCDYVD ICEWRRGSGV    360
LSSSWEPKAK KFKMKRTADG SEFESPKKK KV                                  392

SEQ ID NO: 166             moltype = AA   length = 190
FEATURE                    Location/Qualifiers
source                     1..190
                           mol_type = protein
                           organism = synthetic construct
SEQUENCE: 166
MSEVEFSHEY WMRHALTLAK RARDEREVPV GAVLVLNNRV IGEGWNRAIG LHDPTAHAEI    60
MALRQGGLVM QNYRLIDATL YVTFEPCVMC AGAMIHSRIG RVVFGVRNSK RGAAGSLMNV    120
LNYPGMNHRV EITEGILADE CAALLCDFYR MPRQVFNAQK KAQSSINSGG SMKRTADGSE    180
FESPKKKRKV                                                          190

SEQ ID NO: 167             moltype = AA   length = 1189
FEATURE                    Location/Qualifiers
source                     1..1189
                           mol_type = protein
                           organism = synthetic construct
SEQUENCE: 167
MKRTADGSEF ESPKKKRKVM GIQGLLQFIQ EASEPVNVKK YKGQAVAVDT YCWLHKGAIA    60
CAEKLAKGEP TDRYVGFCMK FVNMLLSYGV KPILIFDGCT LPSKKEVERS RRERRQSNLL    120
KGKQLLREGK VSEARDCFAR SINITHAMAH KVIKAARALG VDCLVAPYEA DAQLAYLNKA    180
GIVQAVITED SDLLAFGCKK VILKMDQFGN GLEVDQARLG MCKQLGDVFT EEKFRYMCIL    240
SGCDYLASLR GIGLAKACKV LRLANNPDIV KVIKKIGHYL RMNITVPEDY ITGFIRANNT    300
FLYQLVFDPI QRKLVPLNAY GDDVNPETLT YAGQYVGDSV ALQIALGNRD VNTFEQIDDY    360
SPDTMPAHSR SHSWNEKAGQ KPPGTNSIWH KNYCPRLEVN SVSHAPQLKE KPSTLGLKQV    420
ISTKGLNLPR KSCVLKRPRN EALAEDDLLS QYSSVSKKIK ENGCGDGTSP NSSKMSKSCP    480
DSGTAHKTDA HTPSKMRNKF ATFLQRRNEE SGAVVVPGTR SRFFCSSQDF DNFIPKKESG    540
```

-continued

```
QPLNETVATG KATTSLLGAL DCPDTEGHKP VDANGTHNLS SQIPGNAAVS PEDEAQSSET   600
SKLLGAMSPP SLGTLRSCFS WSGTLREFSR TPSPSASTTL QQFRRKSDPP ACLPEASAVV   660
TDRCDSKSEM LGETSQPLHE LGCSSRSQES MDSSCGLNTS SLSQPSSRDS GSEESDCNNK   720
SLDNQGEQNS KQHLPHFSKK DGLRRNKVPG LCRSSSMDSF STTKIKPLVP ARVSGLSKKS   780
GSMQTRKHHD VENKPGLQTK ISELWKNFGF KKDSEKLPSC KKPLSPVKDN IQLTPETEDE   840
IFNKPECVRA QRAIFHSGSE TPGTSESATP ESMKRTADGS EFESPKKKRK VMEASPASGP   900
RHLMDPHIFT SNFNNGIGRH KTYLCYEVER LDNGTSVKMD QHRGFLHNQA KNLLCGFYGR   960
HAELRFLDLV PSLQLDPAQI YRVTWFISWS PCFSWGCAGE VRAFLQENTH VRLRIFAARI  1020
YDYDPLYKEA LQMLRDAGAQ VSIMTYDEFK HCWDTFVDHQ GCPFQPWDGL DEHSQALSGR  1080
LRAILQNQGN SGSETPGTSE SATPESTNLS DIIEKETGKQ LVIQESILML PEEVEEVIGN  1140
KPESDILVHT AYDESTDENV MLLTSDAPEY KPWALVIQDS NGENKIKML              1189

SEQ ID NO: 168       moltype = AA  length = 1221
FEATURE              Location/Qualifiers
source               1..1221
                     mol_type = protein
                     organism = synthetic construct
SEQUENCE: 168
MKRTADGSEF ESPKKKRKVM GIQGLLQFIQ EASEPVNVKK YKGQAVAVDT YCWLHKGAIA   60
CAEKLAKGEP TDRYVGFCMK FVNMLLSYGV KPILIFDGCT LPSKKEVERS RRERRQSNLL  120
KGKQLLREGK VSEARDCFAR SINITHAMAH KVIKAARALG VDCLVAPYEA DAQLAYLNKA  180
GIVQAVITED SDLLAFGCKK VILKMDQFGN GLEVDQARLG MCKQLGDVFT EEKFRYMCIL  240
SGCDYLASLR GIGLAKACKV LRLANNPDIV KVIKKIGHYL RMNITVPEDY ITGFIRANNT  300
FLYQLVFDPI QRKLVPLNAY GDDVNPETLT YAGQYVGDSV ALQIALGNRD VNTFEQIDDY  360
SPDTMPAHSR SHSWNEKAGQ KPPGTNSIWH KNYCPRLEVN SVSHAPQLKE KPSTLGLKQV  420
ISTKGLNLPR KSCVLKRPRN EALAEDDLLS QYSSVSKKIK ENGCGDGTSP NSSKMSKSCP  480
DSGTAHKTDA HTPSKMRNKF ATFLQRRNEE SGAVVVPGTR SRFFCSSQDF DNFIPKKESG  540
QPLNETVATG KATTSLLGAL DCPDTEGHKP VDANGTHNLS SQIPGNAAVS PEDEAQSSET  600
SKLLGAMSPP SLGTLRSCFS WSGTLREFSR TPSPSASTTL QQFRRKSDPP ACLPEASAVV  660
TDRCDSKSEM LGETSQPLHE LGCSSRSQES MDSSCGLNTS SLSQPSSRDS GSEESDCNNK  720
SLDNQGEQNS KQHLPHFSKK DGLRRNKVPG LCRSSSMDSF STTKIKPLVP ARVSGLSKKS  780
GSMQTRKHHD VENKPGLQTK ISELWKNFGF KKDSEKLPSC KKPLSPVKDN IQLTPETEDE  840
IFNKPECVRA QRAIFHSGSE TPGTSESATP ESSGGSSGGS SGSETPGTSE SATPESSGGS  900
SGGSMKRTAD GSEFESPKKK RKVMEASPAS GPRHLMDPHI FTSNFNNGIG RHKTYLCYEV  960
ERLDNGTSVK MDQHRGFLHN QAKNLLCGFY GRHAELRFLD LVPSLQLDPA QIYRVTWFIS  1020
WSPCFSWGCA GEVRAFLQEN THVRLRIFAA RIYDYDPLYK EALQMLRDAG AQVSIMTYDE  1080
FKHCWDTFVD HQGCPFQPWD GLDEHSQALS GRLRAILQNQ GNSGSETPGT SESATPESTN  1140
LSDIIEKETG KQLVIQESIL MLPEEVEEVI GNKPESDILV HTAYDESTDE NVMLLTSDAP  1200
EYKPWALVIQ DSNGENKIKM L                                          1221

SEQ ID NO: 169       moltype = AA  length = 2251
FEATURE              Location/Qualifiers
source               1..2251
                     mol_type = protein
                     organism = synthetic construct
SEQUENCE: 169
MAPKKKRKVM EASPASGPRH LMDPHIFTSN FNNGIGRHKT YLCYEVERLD NGTSVKMDQH   60
RGFLHNQAKN LLCGFYGRHA ELRFLDLVPS LQLDPAQIYR VTWFISWSPC FSWGCAGEVR  120
AFLQENTHVR LRIFAARIYD YDPLYKEALQ MLRDAGAQVS IMTYDEFKHC WDTFVDHQGC  180
PFQPWDGLDE HSQALSGRLR AILQNQGSGS ETPGTSESAT PESSGGSSGG SSGSETPGTS  240
ESATPESSGG SSGGSGIHGV PSRMVDLRTL GYSQQQQEKI KPKVRSTVAQ HHEALVGHGF  300
THAHIVALSQ HPAALGTVAV TYQHIITALP EATHEDIVGV GKQWSGARAL EALLTDAGEL  360
RGPPLQLDTG QLVKIAKRGG VTAMEAVHAS RNALTGAPLN LTPDQVVAIA SNNGGKQALE  420
TVQRLLPVLC QDHGLTPDQV VAIASHDGGK QALETVQRLL PVLCQDHGLT PDQVVAIASN  480
IGGKQALETV QRLLPVLCQD HGLTPDQVVA IASNIGGKQA LETVQRLLPV LCQDHGLTPD  540
QVVAIASNIG GKQALETVQR LLPVLCQDHG LTPDQVVAIA SNIGGKQALE TVQRLLPVLC  600
QDHGLTPDQV VAIASNNGGK QALETVQRLL PVLCQDHGLT PDQVVAIASN IGGKQALETV  660
QRLLPVLCQD HGLTPDQVVA IASHDGGKQA LETVQRLLPV LCQDHGLTPD QVVAIASHDG  720
GKQALETVQR LLPVLCQDHG LTPDQVVAIA SNIGGKQALE TVQRLLPVLC QDHGLTPDQV  780
VAIASNIGGK QALETVQRLL PVLCQDHGLT PDQVVAIASN NGGKQALETV QRLLPVLCQD  840
HGLTPDQVVA IASNNGGKQA LETVQRLLPV LCQDHGLTPD QVVAIASNGG KQALETVQR   900
LLPVLCQDHG LTPDQVVAIA SNNGGKQALE TVQRLLPVLC QDHGLTPDQV VAIASHDGGK  960
QALETVQRLL PVLCQDHGLT PDQVVAIASH DGGKQALETV QRLLPVLCQD HGLTPDQVVA  1020
IASNGGGKQA LESIVAQLSR PDPALAALTN DHLVALACLG GRPAMDAVKK GLPHAPELIR  1080
RVNRRIGERT SHRVAGSQLV KSELEEKKSE LRHKLKYVPH EYIELIEIAR NSTQDRILEM  1140
KVMEFFMKVY GYRGKHLGGS RKPAGAIYTV GSPIDYGVIV DTKAYSGGYN LPIGQADEMQ  1200
RYVKENQTRN KHINPNEWWK VYPSSVTEFK FLFVSGHFKG NYKAQLTRLN HKTNCNGAVL  1260
SVEELLIGGE MIKAGTLTLE EVRRKFNNGE INFRSGGGEG RGSLLTCGDV EENPGPRMDY  1320
KDHDGDYKDH DIDYKDDDDK MAPKKKRKVG IHGVPARMVD LRTLGYSQQQ QEKIKPKVRS  1380
TVAQHHEALV GHGFTHAHIV ALSQHPAALG TVAVTYQHII TALPEATHED IVGVGKQWSG  1440
ARALEALLTD AGELRGPPLQ LDTGQLVKIA KRGGVTAMEA VHASRNALTG APLNLTPDQV  1500
VAIASNNGGK QALETVQRLL PVLCQDHGLT PDQVVAIASN NGGKQALETV QRLLPVLCQD  1560
HGLTPDQVVA IASHDGGKQA LETVQRLLPV LCQDHGLTPD QVVAIASNGG KQALETVQR   1620
LLPVLCQDHG LTPDQVVAIA SHDGGKQALE TVQRLLPVLC QDHGLTPDQV VAIASNNGGK  1680
QALETVQRLL PVLCQDHGLT PDQVVAIASN GGGKQALETV QRLLPVLCQD HGLTPDQVVA  1740
IASHDGGKQA LETVQRLLPV LCQDHGLTPD QVVAIASNNG GKQALETVQR LLPVLCQDHG  1800
LTPDQVVAIA SHDGGKQALE TVQRLLPVLC QDHGLTPDQV VAIASNIGGK QALETVQRLL  1860
PVLCQDHGLT PDQVVAIASN NGGKQALETV QRLLPVLCQD HGLTPDQVVA IASHDGGKQA  1920
LETVQRLLPV LCQDHGLTPD QVVAIASNIG GKQALETVQR LLPVLCQDHG LTPDQVVAIA  1980
```

-continued

```
SNGGGKQALE SIVAQLSRPD PALAALTNDH LVALACLGGR PAMDAVKKGL PHAPELIRRV   2040
NRRIGERTSH RVAGSQLVKS ELEEKKSELR HKLKYVPHEY IELIEIARNS TQDRILEMKV   2100
MEFFMKVYGY RGKHLGGSRK PDGAIYTVGS PIDYGVIVDT KAYSGGYNLP IGQADEMERY   2160
VEENQTRNKH LNPNEWWKVY PSSVTEFKFL FVSGHFKGNY KAQLTRLNHI TNCNGAVLSV   2220
EELLIGGEMI KAGTLTLEEV RRKFNNGEIN F                                 2251

SEQ ID NO: 170          moltype = AA  length = 2281
FEATURE                 Location/Qualifiers
source                  1..2281
                        mol_type = protein
                        organism = synthetic construct
SEQUENCE: 170
MAPKKKRKVS SETGPVAVDP TLRRRIEPHE FEVFFDPREL RKETCLLYEI NWGGRHSIWR   60
HTSQNTNKHV EVNFIEKFTT ERYFCPNTRC SITWFLSWSP CGECSRAITE FLSRYPHVTL   120
FIYIARLYHH ADPRNRQGLR DLISSGVTIQ IMTEQESGYC WRNFVNYSPS NEAHWPRYPH   180
LWVRLYVLEL YCIILGLPPC LNILRRKQPQ LTFFTIALQS CHYQRLPPHI LWATGLKSGS   240
ETPGTSESAT PESSGGSSGG SSGSETPGTS ESATPESSGG SSGGSGIHGV PSRMVDLRTL   300
GYSQQQQEKI KPKVRSTVAQ HHEALVGHGF THAHIVALSQ HPAALGTVAV TYQHIITALP   360
EATHEDIVGV GKQWSGARAL EALLTDAGEL RGPPLQLDTG QLVKIAKRGG VTAMEAVHAS   420
RNALTGAPLN LTPDQVVAIA SNNGGKQALE TVQRLLPVLC QDHGLTPDQV VAIASHDGGK   480
QALETVQRLL PVLCQDHGLT PDQVVAIASN IGGKQALETV QRLLPVLCQD HGLTPDQVVA   540
IASNIGGKQA LETVQRLLPV LCQDHGLTPD QVVAIASNIG GKQALETVQR LLPVLCQDHG   600
LTPDQVVAIA SNIGGKQALE TVQRLLPVLC QDHGLTPDQV VAIASNNGGK QALETVQRLL   660
PVLCQDHGLT PDQVVAIASN IGGKQALETV QRLLPVLCQD HGLTPDQVVA IASHDGGKQA   720
LETVQRLLPV LCQDHGLTPD QVVAIASHDG GKQALETVQR LLPVLCQDHG LTPDQVVAIA   780
SNIGGKQALE TVQRLLPVLC QDHGLTPDQV VAIASNIGGK QALETVQRLL PVLCQDHGLT   840
PDQVVAIASN NGGKQALETV QRLLPVLCQD HGLTPDQVVA IASNNGGKQA LETVQRLLPV   900
LCQDHGLTPD QVVAIASNGG GKQALETVQR LLPVLCQDHG LTPDQVVAIA SNNGGKQALE   960
TVQRLLPVLC QDHGLTPDQV VAIASHDGGK QALETVQRLL PVLCQDHGLT PDQVVAIASH   1020
DGGKQALETV QRLLPVLCQD HGLTPDQVVA IASNGGGKQA LESIVAQLSR PDPALAALTN   1080
DHLVALACLG GRPAMDAVKK GLPHAPELIR RVNRRIGERT SHRVAGSQLV KSELEEKKSE   1140
LRHKLKYVPH EYIELIEIAR NSTQDRILEM KVMEFFMKVY GYRGKHLGGS RKPAGAIYTV   1200
GSPIDYGVIV DTKAYSGGYN LPIGQADEMQ RYVKENQTRN KHINPNEWWK VYPSSVTEFK   1260
FLFVSGHFKG NYKAQLTRLN HKTNCNGAVL SVEELLIGGE MIKAGTLTLE EVRRKFNNGE   1320
INFRSGGGEG RGSLLTCGDV EENPGPRMDY KDHDGDYKDH DIDYKDDDDK MAPKKKRKVG   1380
IHGVPARMVD LRTLGYSQQQ QEKIKPKVRS TVAQHHEALV GHGFTHAHIV ALSQHPAALG   1440
TVAVTYQHII TALPEATHED IVGVGKQWSG ARALEALLTD AGELRGPPLQ LDTGQLVKIA   1500
KRGGVTAMEA VHASRNALTG APLNLTPDQV VAIASNNGGK QALETVQRLL PVLCQDHGLT   1560
PDQVVAIASN NGGKQALETV QRLLPVLCQD HGLTPDQVVA IASHDGGKQA LETVQRLLPV   1620
LCQDHGLTPD QVVAIASNGG GKQALETVQR LLPVLCQDHG LTPDQVVAIA SHDGGKQALE   1680
TVQRLLPVLC QDHGLTPDQV VAIASNNGGK QALETVQRLL PVLCQDHGLT PDQVVAIASN   1740
GGGKQALETV QRLLPVLCQD HGLTPDQVVA IASHDGGKQA LETVQRLLPV LCQDHGLTPD   1800
QVVAIASNGG GKQALETVQR LLPVLCQDHG LTPDQVVAIA SHDGGKQALE TVQRLLPVLC   1860
QDHGLTPDQV VAIASNIGGK QALETVQRLL PVLCQDHGLT PDQVVAIASN NGGKQALETV   1920
QRLLPVLCQD HGLTPDQVVA IASHDGGKQA LETVQRLLPV LCQDHGLTPD QVVAIASNIG   1980
GKQALETVQR LLPVLCQDHG LTPDQVVAIA SNGGGKQALE SIVAQLSRPD PALAALTNDH   2040
LVALACLGGR PAMDAVKKGL PHAPELIRRV NRRIGERTSH RVAGSQLVKS ELEEKKSELR   2100
HKLKYVPHEY IELIEIARNS TQDRILEMKV MEFFMKVYGY RGKHLGGSRK PDGAIYTVGS   2160
PIDYGVIVDT KAYSGGYNLP IGQADEMERY VEENQTRNKH LNPNEWWKVY PSSVTEFKFL   2220
FVSGHFKGNY KAQLTRLNHI TNCNGAVLSV EELLIGGEMI KAGTLTLEEV RRKFNNGEIN   2280
F                                                                 2281

SEQ ID NO: 171          moltype = AA  length = 2557
FEATURE                 Location/Qualifiers
source                  1..2557
                        mol_type = protein
                        organism = synthetic construct
SEQUENCE: 171
MAPKKKRKVM EASPASGPRH LMDPHIFTSN FNNGIGRHKT YLCYEVERLD NGTSVKMDQH   60
RGFLHNQAKN LLCGFYGRHA ELRFLDLVPS LQLDPAQIYR VTWFISWSPC FSWGCAGEVR   120
AFLQENTHVR LRIFAARIYD YDPLYKEALQ MLRDAGAQVS IMTYDEFKHC WDTFVDHQGC   180
PFQPWDGLDE HSQALSGRLR AILQNQGSGS ETPGTSESAT PESSGGSSGG SSGSETPGTS   240
ESATPESSGG SSGGSGIHGV PSRMVDLRTL GYSQQQQEKI KPKVRSTVAQ HHEALVGHGF   300
THAHIVALSQ HPAALGTVAV TYQHIITALP EATHEDIVGV GKQWSGARAL EALLTDAGEL   360
RGPPLQLDTG QLVKIAKRGG VTAMEAVHAS RNALTGAPLN LTPDQVVAIA SHDGGKQALE   420
TVQRLLPVLC QDHGLTPDQV VAIASHDGGK QALETVQRLL PVLCQDHGLT PDQVVAIASN   480
GGGKQALETV QRLLPVLCQD HGLTPDQVVA IASNNGGKQA LETVQRLLPV LCQDHGLTPD   540
QVVAIASNGG GKQALETVQR LLPVLCQDHG LTPDQVVAIA SNIGGKQALE TVQRLLPVLC   600
QDHGLTPDQV VAIASHDGGK QALETVQRLL PVLCQDHGLT PDQVVAIASH DGGKQALETV   660
QRLLPVLCQD HGLTPDQVVA IASNNGGKQA LETVQRLLPV LCQDHGLTPD QVVAIASHDG   720
GKQALETVQR LLPVLCQDHG LTPDQVVAIA SNNGGKQALE TVQRLLPVLC QDHGLTPDQV   780
VAIASNIGGK QALETVQRLL PVLCQDHGLT PDQVVAIASN IGGKQALETV QRLLPVLCQD   840
HGLTPDQVVA IASNIGGKQA LETVQRLLPV LCQDHGLTPD QVVAIASNNG GKQALETVQR   900
LLPVLCQDHG LTPDQVVAIA SNIGGKQALE TVQRLLPVLC QDHGLTPDQV VAIASHDGGK   960
QALETVQRLL PVLCQDHGLT PDQVVAIASH DGGKQALETV QRLLPVLCQD HGLTPDQVVA   1020
IASNIGGKQA LETVQRLLPV LCQDHGLTPD QVVAIASNGG GKQALETVQR LLPVLCQDHG   1080
LTPDQVVAIA SHDGGKQALE TVQRLLPVLC QDHGLTPDQV VAIASHDGGK QALETVQRLL   1140
PVLCQDHGLT PDQVVAIASN IGGKQALETV QRLLPVLCQD HGLTPDQVVA IASHDGGKQA   1200
LETVQRLLPV LCQDHGLTPD QVVAIASNNG GKQALESIVA QLSRPDPALA ALTNDHLVAL   1260
```

```
ACLGGRPAMD AVKKGLPHAP ELIRRVNRRI GERTSHRVAG SQLVKSELEE KKSELRHKLK   1320
YVPHEYIELI EIARNSTQDR ILEMKVMEFF MKVYGYRGKH LGGSRKPDGA IYTVGSPIDY   1380
GVIVDTKAYS GGYNLPIGQA DEMQRYVKEN QTRNKHINPN EWWKVYPSSV TEFKFLFVSG   1440
HFKGNYKAQL TRLNHKTNCN GAVLSVEELL IGGEMIKAGT LTLEEVRRKF NNGEINFRSG   1500
GGEGRGSLLT CGDVEENPGP RMDYKDHDGD YKDHDIDYKD DDDKMAPKKK RKVGIHGVPA   1560
RMVDLRTLGY SQQQQEKIKP KVRSTVAQHH EALVGHGFTH AHIVALSQHP AALGTVAVTY   1620
QHIITALPEA THEDIVGVGK QWSGARALEA LLTDAGELRG PPLQLDTGQL VKIAKRGGVT   1680
AMEAVHASRN ALTGAPLNLT PDQVVAIASH DGGKQALETV QRLLPVLCQD HGLTPDQVVA   1740
IASHDGGKQA LETVQRLLPV LCQDHGLTPD QVVAIASHDG GKQALETVQR LLPVLCQDHG   1800
LTPDQVVAIA SNIGGKQALE TVQRLLPVLC QDHGLTPDQV VAIASNNGGK QALETVQRLL   1860
PVLCQDHGLT PDQVVAIASN IGGKQALETV QRLLPVLCQD HGLTPDQVVA IASNNGGKQA   1920
LETVQRLLPV LCQDHGLTPD QVVAIASHDG GKQALETVQR LLPVLCQDHG LTPDQVVAIA   1980
SHDGGKQALE TVQRLLPVLC QDHGLTPDQV VAIASHDGGK QALETVQRLL PVLCQDHGLT   2040
PDQVVAIASH DGGKQALETV QRLLPVLCQD HGLTPDQVVA IASNNGGKQA LETVQRLLPV   2100
LCQDHGLTPD QVVAIASHDG GKQALETVQR LLPVLCQDHG LTPDQVVAIA SNNGGKQALE   2160
TVQRLLPVLC QDHGLTPDQV VAIASNNGGK QALETVQRLL PVLCQDHGLT PDQVVAIASH   2220
DGGKQALETV QRLLPVLCQD HGLTPDQVVA IASNNGGKQA LETVQRLLPV LCQDHGLTPD   2280
QVVAIASHDG GKQALESIVA QLSRPDPALA ALTNDHLVAL ACLGGRPAMD AVKKGLPHAP   2340
ELIRRVNRRI GERTSHRVAG SQLVKSELEE KKSELRHKLK YVPHEYIELI EIARNSTQDR   2400
ILEMKVMEFF MKVYGYRGKH LGGSRKPAGA IYTVGSPIDY GVIVDTKAYS GGYNLPIGQA   2460
DEMERYVEEN QTRNKHLNPN EWWKVYPSSV TEFKFLFVSG HFKGNYKAQL TRLNHITNCN   2520
GAVLSVEELL IGGEMIKAGT LTLEEVRRKF NNGEINF                            2557
```

SEQ ID NO: 172       moltype = AA  length = 2587
FEATURE               Location/Qualifiers
source                1..2587
                        mol_type = protein
                        organism = synthetic construct

SEQUENCE: 172

```
MAPKKKRKVS SETGPVAVDP TLRRRIEPHE FEVFFDPREL RKETCLLYEI NWGGRHSIWR    60
HTSQNTNKHV EVNFIEKFTT ERYFCPNTRC SITWFLSWSP CGECSRAITE FLSRYPHVTL   120
FIYIARLYHH ADPRNRQGLR DLISSGVTIQ IMTEQESGYC WRNFVNYSPS NEAHWPRYPH   180
LWVRLYVLEL YCIILGLPPC LNILRRKQPQ LTFFTIALQS CHYQRLPPHI LWATGLKSGS   240
ETPGTSESAT PESSGGSSGG SSGSETPGTS ESATPESSGG SSGGSSGSGI HGVPSRMVDLRTL   300
GYSQQQQEKI KPKVRSTVAQ HHEALVGHGF THAHIVALSQ HPAALGTVAV TYQHIITALP   360
EATHEDIVGV GKQWSGARAL EALLTDAGEL RGPPLQLDTG QLVKIAKRGG VTAMEAVHAS   420
RNALTGAPLN LTPDQVVAIA SHDGGKQALE TVQRLLPVLC QDHGLTPDQV VAIASHDGGK   480
QALETVQRLL PVLCQDHGLT PDQVVAIASN GGGKQALETV QRLLPVLCQD HGLTPDQVVA   540
IASNNGGKQA LETVQRLLPV LCQDHGLTPD QVVAIASNNG GKQALETVQR LLPVLCQDHG   600
LTPDQVVAIA SNIGGKQALE TVQRLLPVLC QDHGLTPDQV VAIASHDGGK QALETVQRLL   660
PVLCQDHGLT PDQVVAIASH DGGKQALETV QRLLPVLCQD HGLTPDQVVA IASNNGGKQA   720
LETVQRLLPV LCQDHGLTPD QVVAIASHDG GKQALETVQR LLPVLCQDHG LTPDQVVAIA   780
SNNGGKQALE TVQRLLPVLC QDHGLTPDQV VAIASNIGGK QALETVQRLL PVLCQDHGLT   840
PDQVVAIASN IGGKQALETV QRLLPVLCQD HGLTPDQVVA IASNIGGKQA LETVQRLLPV   900
LCQDHGLTPD QVVAIASNNG GKQALETVQR LLPVLCQDHG LTPDQVVAIA SNIGGKQALE   960
TVQRLLPVLC QDHGLTPDQV VAIASHDGGK QALETVQRLL PVLCQDHGLT PDQVVAIASH  1020
DGGKQALETV QRLLPVLCQD HGLTPDQVVA IASNIGGKQA LETVQRLLPV LCQDHGLTPD  1080
QVVAIASNGG GKQALETVQR LLPVLCQDHG LTPDQVVAIA SHDGGKQALE TVQRLLPVLC  1140
QDHGLTPDQV VAIASHDGGK QALETVQRLL PVLCQDHGLT PDQVVAIASN IGGKQALETV  1200
QRLLPVLCQD HGLTPDQVVA IASHDGGKQA LETVQRLLPV LCQDHGLTPD QVVAIASNNG  1260
GKQALESIVA QLSRPDPALA ALTNDHLVAL ACLGGRPAMD AVKKGLPHAP ELIRRVNRRI  1320
GERTSHRVAG SQLVKSELEE KKSELRHKLK YVPHEYIELI EIARNSTQDR ILEMKVMEFF  1380
MKVYGYRGKH LGGSRKPDGA IYTVGSPIDY GVIVDTKAYS GGYNLPIGQA DEMQRYVKEN  1440
QTRNKHINPN EWWKVYPSSV TEFKFLFVSG HFKGNYKAQL TRLNHKTNCN GAVLSVEELL  1500
IGGEMIKAGT LTLEEVRRKF NNGEINFRSG GGEGRGSLLT CGDVEENPGP RMDYKDHDGD  1560
YKDHDIDYKD DDDKMAPKKK RKVGIHGVPA RMVDLRTLGY SQQQQEKIKP KVRSTVAQHH  1620
EALVGHGFTH AHIVALSQHP AALGTVAVTY QHIITALPEA THEDIVGVGK QWSGARALEA  1680
LLTDAGELRG PPLQLDTGQL VKIAKRGGVT AMEAVHASRN ALTGAPLNLT PDQVVAIASH  1740
DGGKQALETV QRLLPVLCQD HGLTPDQVVA IASHDGGKQA LETVQRLLPV LCQDHGLTPD  1800
QVVAIASHDG GKQALETVQR LLPVLCQDHG LTPDQVVAIA SNIGGKQALE TVQRLLPVLC  1860
QDHGLTPDQV VAIASNNGGK QALETVQRLL PVLCQDHGLT PDQVVAIASN IGGKQALETV  1920
QRLLPVLCQD HGLTPDQVVA IASNNGGKQA LETVQRLLPV LCQDHGLTPD QVVAIASHDG  1980
GKQALETVQR LLPVLCQDHG LTPDQVVAIA SHDGGKQALE TVQRLLPVLC QDHGLTPDQV  2040
VAIASHDGGK QALETVQRLL PVLCQDHGLT PDQVVAIASH DGGKQALETV QRLLPVLCQD  2100
HGLTPDQVVA IASNNGGKQA LETVQRLLPV LCQDHGLTPD QVVAIASHDG GKQALETVQR  2160
LLPVLCQDHG LTPDQVVAIA SNNGGKQALE TVQRLLPVLC QDHGLTPDQV VAIASNNGGK  2220
QALETVQRLL PVLCQDHGLT PDQVVAIASH DGGKQALETV QRLLPVLCQD HGLTPDQVVA  2280
IASNNGGKQA LETVQRLLPV LCQDHGLTPD QVVAIASHDG GKQALESIVA QLSRPDPALA  2340
ALTNDHLVAL ACLGGRPAMD AVKKGLPHAP ELIRRVNRRI GERTSHRVAG SQLVKSELEE  2400
KKSELRHKLK YVPHEYIELI EIARNSTQDR ILEMKVMEFF MKVYGYRGKH LGGSRKPAGA  2460
IYTVGSPIDY GVIVDTKAYS GGYNLPIGQA DEMERYVEEN QTRNKHLNPN EWWKVYPSSV  2520
TEFKFLFVSG HFKGNYKAQL TRLNHITNCN GAVLSVEELL IGGEMIKAGT LTLEEVRRKF  2580
NNGEINF                                                           2587
```

SEQ ID NO: 173       moltype = AA  length = 1001
FEATURE               Location/Qualifiers
source                1..1001
                        mol_type = protein
                        organism = synthetic construct

```
SEQUENCE: 173
MALSRAVCGT SRQLAPVLGY LGSRQKHSLP DYPYDVPDYA GYPYDVPDYA GYPYDVPDYA   60
MDIADLRTLG YSQQQQEKIK PKVRSTVAQH HEALVGHGFT HAHIVALSQH PAALGTVAVK  120
YQDMIAALPE ATHEAIVGVG KQWSGARALE ALLTVAGELR GPPLQLDTGQ LLKIAKRGGV  180
TAVEAVHAWR NALTGAPLNL TPDQVVAIAS NGGGKQALET VQRLLPVLCQ DHGLTPEQVV  240
AIASNIGGKQ ALETVQRLLP VLCQAHGLTP DQVVAIASHD GGKQALETVQ RLLPVLCQAH  300
GLTPAQVVAI ANNNGGKQAL ETVQRLLPVL CQDHGLTPDQ VVAIASHDGG KQALETVQRL  360
LPVLCQDHGL TPEQVVAIAN NNGGKQALET VQRLLPVLCQ AHGLTPDQVV AIANNNGGKQ  420
ALETVQRLLP VLCQAHGLTP AQVVAIASHD GGKQALETVQ RLLPVLCQDH GLTPDQVVAI  480
ANNNGGKQAL ETVQRLLPVL CQDHGLTPEQ VVAIANNNGG KQALETVQRL LPVLCQAHGL  540
TPDQVVAIAN NNGGKQALET VQRLLPVLCQ AHGLTPAQVV AIANNNGGKQ ALETVQRLLP  600
VLCQDHGLTP DQVVAIASHD GGKQALETVQ RLLPVLCQDH GLTPEQVVAI ASNGGGKQAL  660
ETVQRLLPVL CQDHGLTPDQ VVAIANNNGG KQALETVQRL LPVLCQAHGL TPAQVVAIAS  720
NGGGKQALET VQRLLPVLCQ DHGLTPEQVV AIASHDGGRP ALESIVAQLS RPDPALAALT  780
NDHLVALACL GGRPALDAVK KGLGGSGSYA LGPYQISAPQ LPAYNGQTVG TFYYVNDAGG  840
LESKVFSSGG PTPYPNYANA GHVEGQSALF MRDNGISEGL VFHNNPEGTC GFCVNMTETL  900
LPENAKMTVV PPEGSGGSTN LSDIIEKETG KQLVIQESIL MLPEEVEEVI GNKPESDILV  960
HTAYDESTDE NVMLLTSDAP EYKPWALVIQ DSNGENKIKM L                     1001

SEQ ID NO: 174          moltype = AA  length = 915
FEATURE                 Location/Qualifiers
source                  1..915
                        mol_type = protein
                        organism = synthetic construct
SEQUENCE: 174
MASVLTPLLL RGLTGSARRL PVPRAKIHSL DYKDHDGDYK DHDIDYKDDD DKMDIADLRT   60
LGYSQQQQEK IKPKVRSTVA QHHEALVGHG FTHAHIVALS QHPAALGTVA VKYQDMIAAL  120
PEATHEAIVG VGKRGAGARA LEALLTVAGE LRGPPLQLDT GQLLKIAKRG GVTAVEAVHA  180
WRNALTGAPL NLTPDQVVAI ASHDGGKQAL ETVQRLLPVL CQDHGLTPEQ VVAIASHDGG  240
KQALETVQRL LPVLCQAHGL TPDQVVAIAN NNGGKQALET VQRLLPVLCQ AHGLTPAQVV  300
AIANNNGGKQ ALETVQRLLP VLCQDHGLTP DQVVAIANNN GGKQALETVQ RLLPVLCQDH  360
GLTPEQVVAI ASNIGGKQAL ETVQRLLPVL CQAHGLTPDQ VVAIANNNGG KQALETVQRL  420
LPVLCQAHGL TPAQVVAIAN NNGGKQALET VQRLLPVLCQ DHGLTPDQVV AIASHDGGKQ  480
ALETVQRLLP VLCQDHGLTP EQVVAIASHD GGKQALETVQ RLLPVLCQAH GLTPDQVVAI  540
ANNNGGKQAL ETVQRLLPVL CQAHGLTPAQ VVAIASHDGG KQALETVQRL LPVLCQDHGL  600
TPDQVVAIAS NIGGKQALET VQRLLPVLCQ DHGLTPEQVV AIASHDGGKQ ALETVQRLLP  660
VLCQAHGLTP DQVVAIASNG GGKQALETVQ RLLPVLCQAH GLTPAQVVAI ASNGGGKQAL  720
ETVQRLLPVL CQDHGLTPEQ VVAIASNNGG RPALESIVAQ LSRPDPALAA LTNDHLVALA  780
CLGGRPALDA VKKGLGGSAI PVKRGATGET KVFTGNSNSP KSPTKGGCSG GSTNLSDIIE  840
KETGKQLVIQ ESILMLPEEV EEVIGNKPES DILVHTAYDE STDENVMLLT SDAPEYKPWA  900
LVIQDSNGEN KIKML                                                  915

SEQ ID NO: 175          moltype = AA  length = 763
FEATURE                 Location/Qualifiers
source                  1..763
                        mol_type = protein
                        organism = synthetic construct
SEQUENCE: 175
MALSRAVCGT SRQLAPVLGY LGSRQKHSLP DYPYDVPDYA GYPYDVPDYA GYPYDVPDYA   60
MDIADLRTLG YSQQQQEKIK PKVRSTVAQH HEALVGHGFT HAHIVALSQH PAALGTVAVK  120
YQDMIAALPE ATHEAIVGVG KQWSGARALE ALLTVAGELR GPPLQLDTGQ LLKIAKRGGV  180
TAVEAVHAWR NALTGAPLNL TPEQVVAIAS NNGGKQALET VQRLLPVLCQ AHGLTPEQVV  240
AIASNIGGKQ ALETVQRLLP VLCQAHGLTP EQVVAIASHD GGKQALETVQ RLLPVLCQAH  300
GLTPEQVVAI ASHDGGKQAL ETVQRLLPVL CQAHGLTPEQ VVAIASHDGG KQALETVQRL  360
LPVLCQAHGL TPEQVVAIAS HDGGKQALET VQRLLPVLCQ AHGLTPEQVV AIASHDGGKQ  420
ALETVQRLLP VLCQAHGLTP EQVVAIASNI GGKQALETVQ RLLPVLCQAH GLTPEQVVAI  480
ASNGGGKQAL ETVQRLLPVL CQAHGLTPEQ VVAIASNGGG RPALESIVAQ LSRPDPALAA  540
LTNDHLVALA CLGGRPALDA VKKGLGGSGS YALGPYQISA PQLPAYNGQT VGTFYYVNDA  600
GGLESKVFSS GGPTPYPNYA NAGHVEGQSA LFMRDNGISE GLVFHNNPEG TCGFCVNMTE  660
TLLPENAKMT VVPPEGSGGS TNLSDIIEKE TGKQLVIQES ILMLPEEVEE VIGNKPESDI  720
LVHTAYDEST DENVMLLTSD APEYKPWALV IQDSNGENKI KML                   763

SEQ ID NO: 176          moltype = AA  length = 711
FEATURE                 Location/Qualifiers
source                  1..711
                        mol_type = protein
                        organism = synthetic construct
SEQUENCE: 176
MASVLTPLLL RGLTGSARRL PVPRAKIHSL DYKDHDGDYK DHDIDYKDDD DKMDIADLRT   60
LGYSQQQQEK IKPKVRSTVA QHHEALVGHG FTHAHIVALS QHPAALGTVA VKYQDMIAAL  120
PEATHEAIVG VGKRGAGARA LEALLTVAGE LRGPPLQLDT GQLLKIAKRG GVTAVEAVHA  180
WRNALTGAPL NLTPEQVVAI ASNNGKQAL ETVQRLLPVL CQAHGLTPEQ VVAIASNIGG  240
KQALETVQRL LPVLCQAHGL TPEQVVAIAS NGGGKQALET VQRLLPVLCQ AHGLTPEQVV  300
AIASNNGGKQ ALETVQRLLP VLCQAHGLTP EQVVAIASNN GGKQALETVQ RLLPVLCQAH  360
GLTPEQVVAI ASHDGGKQAL ETVQRLLPVL CQAHGLTPEQ VVAIASNGGG KQALETVQRL  420
LPVLCQAHGL TPEQVVAIAS NIGGKQALET VQRLLPVLCQ AHGLTPEQVV AIASNGGGKQ  480
ALETVQRLLP VLCQAHGLTP EQVVAIASNG GGKQALETVQ RLLPVLCQAH GLTPEQVVAI  540
ASNGGGRPAL ESIVAQLSRP DPALAALTND HLVALACLGG RPALDAVKKG LGGSAIPVKR  600
GATGETKVFT GNSNSPKSPT KGGCSGGSTN LSDIIEKETG KQLVIQESIL MLPEEVEEVI  660
```

```
GNKPESDILV HTAYDESTDE NVMLLTSDAP EYKPWALVIQ DSNGENKIKM L                  711

SEQ ID NO: 177          moltype = AA   length = 899
FEATURE                 Location/Qualifiers
source                  1..899
                        mol_type = protein
                        organism = synthetic construct
SEQUENCE: 177
MALSRAVCGT SRQLAPVLGY LGSRQKHSLP DYPYDVPDYA GYPYDVPDYA GYPYDVPDYA        60
MDIADLRTLG YSQQQQEKIK PKVRSTVAQH HEALVGHGFT HAHIVALSQH PAALGTVAVK        120
YQDMIAALPE ATHEAIVGVG KQWSGARALE ALLTVAGELR GPPLQLDTGQ LLKIAKRGGV        180
TAVEAVHAWR NALTGAPLNL TPEQVVAIAS HDGGKQALET VQALLPVLCQ AHGLTPQQVV        240
AIASHDGGKQ ALETVQRLLP VLCQAHGLTP QQVVAIASNG GGKQALETVQ RLLPVLCQAH        300
GLTPEQVVAI ASNIGGKQAL ETVQALLPVL CQAHGLTPEQ VVAIASNGGG KQALETVQAL        360
LPVLCQAHGL TPEQVVAIAS NGGGKQALET VQALLPVLCQ AHGLTPEQVV AIASNGGGKQ        420
ALETVQRLLP VLCQAHGLTP EQVVAIASNI GGKQALETVQ ALLPVLCQAH GLTPEQVVAI        480
ASNGGGKQAL ETVQRLLPVL CQAHGLTPEQ VVAIASNGGG KQALETVQAL LPVLCQAHGL        540
TPEQVVAIAS HDGGKQALET VQALLPVLCQ AHGLTPEQVV AIASNGGGKQ ALETVQALLP        600
VLCQAHGLTP EQVVAIASNI GGKQALETVQ ALLPVLCQAH GLTPQQVVAI ASNNGGRPAL        660
ESIVAQLSRP DPALAALTND HLVALACLGG RPALDAVKKG LGGSGSYALG PYQISAPQLP        720
AYNGQTVGTF YYVNDAGGLE SKVFSSGGPT PYPNYANAGH VEGQSALFMR DNGISEGLVF        780
HNNPEGTGCF CVNMTETLLP ENAKMTVVPP EGSGGSTNLS DIIEKETGKQ LVIQESILML        840
PEEVEEVIGN KPESDILVHT AYDESTDENV MLLTSDAPEY KPWALVIQDS NGENKIKML         899

SEQ ID NO: 178          moltype = AA   length = 725
FEATURE                 Location/Qualifiers
source                  1..725
                        mol_type = protein
                        organism = synthetic construct
SEQUENCE: 178
MASVLTPLLL RGLTGSARRL PVPRAKIHSL DYKDHDGDYK DHDIDYKDDD DKMDIADLRT        60
LGYSQQQQEK IKPKVRSTVA QHHEALVGHG FTHAHIVALS QHPAALGTVA VKYQDMIAAL        120
PEATHEAIVG VGKRGAGARA LEALLTVAGE LRGPPLQLDT GQLLKIAKRG GVTAVEAVHA        180
WRNALTGAPL NLTPEQVVAI ASNGGGKQAL ETVQALLPVL CQAHGLTPQQ VVAIASNNGG        240
KQALETVQRL LPVLCQAHGL TPQQVVAIAS NIGGKQALET VQRLLPVLCQ AHGLTPEQVV        300
AIASNNGGKQ ALETVQALLP VLCQAHGLTP EQVVAIASNG GGKQALETVQ ALLPVLCQAH        360
GLTPEQVVAI ASNIGGKQAL ETVQALLPVL CQAHGLTPEQ VVAIASNIGG KQALETVQRL        420
LPVLCQAHGL TPEQVVAIAS NIGGKQALET VQALLPVLCQ AHGLTPEQVV AIASHDGGKQ        480
ALETVQRLLP VLCQAHGLTP EQVVAIASNN GGKQALETVQ ALLPVLCQAH GLTPEQVVAI        540
ASNNGGKQAL ETVQALLPVL CQAHGSIVAQ LSRPDPALAA LTNDHLVALA CLGGRPALDA        600
VKKGLGGSAI PVKRGATGET KVFTGNSNSP KSPTKGGCSG GSTNLSDIIE KETGKQLVIQ        660
ESILMLPEEV EEVIGNKPES DILVHTAYDE STDENVMLLT SDAPEYKPWA LVIQDSNGEN        720
KIKML                                                                   725

SEQ ID NO: 179          moltype = AA   length = 967
FEATURE                 Location/Qualifiers
source                  1..967
                        mol_type = protein
                        organism = synthetic construct
SEQUENCE: 179
MALSRAVCGT SRQLAPVLGY LGSRQKHSLP DYPYDVPDYA GYPYDVPDYA GYPYDVPDYA        60
MDIADLRTLG YSQQQQEKIK PKVRSTVAQH HEALVGHGFT HAHIVALSQH PAALGTVAVK        120
YQDMIAALPE ATHEAIVGVG KQWSGARALE ALLTVAGELR GPPLQLDTGQ LLKIAKRGGV        180
TAVEAVHAWR NALTGAPLNL TPEQVVAIAS HDGGKQALET VQALLPVLCQ AHGLTPQQVV        240
AIASNGGGKQ ALETVQRLLP VLCQAHGLTP QQVVAIASND GGKQALETVQ RLLPVLCQAH        300
GLTPEQVVAI ASHDGGKQAL ETVQALLPVL CQAHGLTPEQ VVAIASNIGG KQALETVQAL        360
LPVLCQAHGL TPEQVVAIAS HDGGKQALET VQALLPVLCQ AHGLTPEQVV AIASNIGGKQ        420
ALETVQRLLP VLCQAHGLTP EQVVAIASHD GGKQALETVQ ALLPVLCQAH GLTPEQVVAI        480
ASNGGGKQAL ETVQRLLPVL CQAHGLTPEQ VVAIASNGGG KQALETVQAL LPVLCQAHGL        540
TPEQVVAIAS NNGGKQALET VQALLPVLCQ AHGLTPEQVV AIASHDGGKQ ALETVQALLP        600
VLCQAHGLTP EQVVAIASNI GGKQALETVQ RLLPVLCQAH GLTPQQVVAI ASNNGGKQAL        660
ETVQRLLPVL CQAHGLTPEQ VVAIASNIGG KQALETVQAL LPVLCQAHGL TPQQVVAIAS        720
NNGGRPALES IVAQLSRPDP ALAALTNDHL VALACLGGRP ALDAVKKGLG GSGSYALG         780
QISAPQLPAY NGQTVGTFYY VNDAGGLESK VFSSGGPTPY PNYANAGHVE GQSALFMRDN        840
GISEGLVFHN NPEGTGCFCV NMTETLLPEN AKMTVVPPEG SGGSTNLSDI IEKETGKQLV        900
IQESILMLPE EVEEVIGNKP ESDILVHTAY DESTDENVML LTSDAPEYKP WALVIQDSNG        960
ENKIKML                                                                 967

SEQ ID NO: 180          moltype = AA   length = 915
FEATURE                 Location/Qualifiers
source                  1..915
                        mol_type = protein
                        organism = synthetic construct
SEQUENCE: 180
MASVLTPLLL RGLTGSARRL PVPRAKIHSL DYKDHDGDYK DHDIDYKDDD DKMDIADLRT        60
LGYSQQQQEK IKPKVRSTVA QHHEALVGHG FTHAHIVALS QHPAALGTVA VKYQDMIAAL        120
PEATHEAIVG VGKRGAGARA LEALLTVAGE LRGPPLQLDT GQLLKIAKRG GVTAVEAVHA        180
WRNALTGAPL NLTPEQVVAI ASHDGGKQAL ETVQALLPVL CQAHGLTPQQ VVAIASHDGG        240
KQALETVQRL LPVLCQAHGL TPQQVVAIAS HDGGKQALET VQRLLPVLCQ AHGLTPEQVV        300
```

```
AIASHDGGKQ ALETVQALLP VLCQAHGLTP EQVVAIASNG GGKQALETVQ ALLPVLCQAH   360
GLTPEQVVAI ASNGGGKQAL ETVQALLPVL CQAHGLTPEQ VVAIASHDGG KQALETVQRL   420
LPVLCQAHGL TPEQVVAIAS NNGGKQALET VQALLPVLCQ AHGLTPEQVV AIASNNGGKQ   480
ALETVQRLLP VLCQAHGLTP EQVVAIASHD GGKQALETVQ ALLPVLCQAH GLTPEQVVAI   540
ASNIGGKQAL ETVQALLPVL CQAHGLTPEQ VVAIASNIGG KQALETVQAL LPVLCQAHGL   600
TPEQVVAIAS NNGGKQALET VQRLLPVLCQ AHGLTPQQVV AIASNNGGKQ ALETVQRLLP   660
VLCQAHGLTP EQVVAIASNG GGKQALETVQ ALLPVLCQAH GLTPEQVVAI ASNGGGKQAL   720
ETVQALLPVL CQAHGLTPQQ VVAIASHDGG RPALESIVAQ LSRPDPALAA LTNDHLVALA   780
CLGGRPALDA VKKGLGGSAI PVKRGATGET KVFTGNSNSP KSPTKGGCSG GSTNLSDIIE   840
KETGKQLVIQ ESILMLPEEV EEVIGNKPES DILVHTAYDE STDENVMLLT SDAPEYKPWA   900
LVIQDSNGEN KIKML                                                   915

SEQ ID NO: 181          moltype = AA  length = 967
FEATURE                 Location/Qualifiers
source                  1..967
                        mol_type = protein
                        organism = synthetic construct
SEQUENCE: 181
MALSRAVCGT SRQLAPVLGY LGSRQKHSLP DYPYDVPDYA GYPYDVPDYA GYPYDVPDYA   60
MDIADLRTLG YSQQQQEKIK PKVRSTVAQH HEALVGHGFT HAHIVALSQH PAALGTVAVK   120
YQDMIAALPE ATHEAIVGVG KQWSGARALE ALLTVAGELR GPPLQLDTGQ LLKIAKRGGV   180
TAVEAVHAWR NALTGAPLNL TPEQVVAIAS HDGGKQALET VQALLPVLCQ AHGLTPQQVV   240
AIASHDGGKQ ALETVQRLLP VLCQAHGLTP QQVVAIASHD GGKQALETVQ RLLPVLCQAH   300
GLTPEQVVAI ASNIGGKQAL ETVQALLPVL CQAHGLTPEQ VVAIASNGGG KQALETVQAL   360
LPVLCQAHGL TPEQVVAIAS NNGGKQALET VQALLPVLCQ AHGLTPEQVV AIASHDGGKQ   420
ALETVQRLLP VLCQAHGLTP EQVVAIASHD GGKQALETVQ ALLPVLCQAH GLTPEQVVAI   480
ASNGGGKQAL ETVQRLLPVL CQAHGLTPEQ VVAIASHDGG KQALETVQAL LPVLCQAHGL   540
TPEQVVAIAS NIGGKQALET VQALLPVLCQ AHGLTPEQVV AIASNNGGKQ ALETVQALLP   600
VLCQAHGLTP EQVVAIASNN GGKQALETVQ RLLPVLCQAH GLTPQQVVAI ASNIGGKQAL   660
ETVQRLLPVL CQAHGLTPEQ VVAIASNGGG KQALETVQAL LPVLCQAHGL TPQQVVAIAS   720
NIGGRPALES IVAQLSRPDP ALAALTNDHL VALACLGGRP ALDAVKKGLG GSGSYALGPY   780
QISAPQLPAY NGQTVGTFYY VNDAGGLESK VFSSGGPTPY PNYANAGHVE GQSALFMRDN   840
GISEGLVFHN NPEGTCGFCV NMTETLLPEN AKMTVVPPEG SGGSTNLSDI IEKETGKQLV   900
IQESILMLPE EVEEVIGNKP ESDILVHTAY DESTDENVML LTSDAPEYKP WALVIQDSNG   960
ENKIKML                                                            967

SEQ ID NO: 182          moltype = AA  length = 881
FEATURE                 Location/Qualifiers
source                  1..881
                        mol_type = protein
                        organism = synthetic construct
SEQUENCE: 182
MASVLTPLLL RGLTGSARRL PVPRAKIHSL DYKDHDGDYK DHDIDYKDDD DKMDIADLRT   60
LGYSQQQQEK IKPKVRSTVA QHHEALVGHG FTHAHIVALS QHPAALGTVA VKYQDMIAAL   120
PEATHEAIVG VGKRGAGARA LEALLTVAGE LRGPPLQLDT GQLLKIAKRG GVTAVEAVHA   180
WRNALTGAPL NLTPEQVVAI ASNGGGKQAL ETVQALLPVL CQAHGLTPQQ VVAIASNGGG   240
KQALETVQRL LPVLCQAHGL TPQQVVAIAS NNGGKQALET VQRLLPVLCQ AHGLTPEQVV   300
AIASNNGGKQ ALETVQALLP VLCQAHGLTP EQVVAIASNI GGKQALETVQ ALLPVLCQAH   360
GLTPEQVVAI ASNGGGKQAL ETVQALLPVL CQAHGLTPEQ VVAIASNIGG KQALETVQRL   420
LPVLCQAHGL TPEQVVAIAS NGGGKQALET VQALLPVLCQ AHGLTPEQVV AIASNIGGKQ   480
ALETVQRLLP VLCQAHGLTP EQVVAIASHD GGKQALETVQ ALLPVLCQAH GLTPEQVVAI   540
ASNGGGKQAL ETVQALLPVL CQAHGLTPEQ VVAIASNIGG KQALETVQAL LPVLCQAHGL   600
TPEQVVAIAS HDGGKQALET VQRLLPVLCQ AHGLTPQQVV AIASNIGGKQ ALETVQRLLP   660
VLCQAHGLTP EQVVAIASNN GGKQALETVQ ALLPVLCQAH GLTPQQVVAI ASHDGGRPAL   720
ESIVAQLSRP DPALAALTND HLVALACLGG RPALDAVKKG GATGETKVFT   780
GNSNSPKSPT KGGCSGGSTN LSDIIEKETG KQLVIQESIL MLPEEVEEVI GNKPESDILV   840
HTAYDESTDE NVMLLTSDAP EYKPWALVIQ DSNGENKIKM L                      881

SEQ ID NO: 183          moltype = AA  length = 967
FEATURE                 Location/Qualifiers
source                  1..967
                        mol_type = protein
                        organism = synthetic construct
SEQUENCE: 183
MALSRAVCGT SRQLAPVLGY LGSRQKHSLP DYPYDVPDYA GYPYDVPDYA GYPYDVPDYA   60
MDIADLRTLG YSQQQQEKIK PKVRSTVAQH HEALVGHGFT HAHIVALSQH PAALGTVAVK   120
YQDMIAALPE ATHEAIVGVG KQWSGARALE ALLTVAGELR GPPLQLDTGQ LLKIAKRGGV   180
TAVEAVHAWR NALTGAPLNL TPEQVVAIAS NIGGKQALET VQALLPVLCQ AHGLTPQQVV   240
AIASHDGGKQ ALETVQRLLP VLCQAHGLTP QQVVAIASNN GGKQALETVQ RLLPVLCQAH   300
GLTPEQVVAI ASNIGGKQAL ETVQALLPVL CQAHGLTPEQ VVAIASNNGG KQALETVQAL   360
LPVLCQAHGL TPEQVVAIAS NGGGKQALET VQALLPVLCQ AHGLTPEQVV AIASNNGGKQ   420
ALETVQRLLP VLCQAHGLTP EQVVAIASHD GGKQALETVQ ALLPVLCQAH GLTPEQVVAI   480
ASNNGGKQAL ETVQRLLPVL CQAHGLTPEQ VVAIASNNGG KQALETVQAL LPVLCQAHGL   540
TPEQVVAIAS HDGGKQALET VQALLPVLCQ AHGLTPEQVV AIASNGGGKQ ALETVQALLP   600
VLCQAHGLTP EQVVAIASNG GGKQALETVQ RLLPVLCQAH GLTPQQVVAI ASHDGGKQAL   660
ETVQRLLPVL CQAHGLTPEQ VVAIASNNGG KQALETVQAL LPVLCQAHGL TPQQVVAIAS   720
NIGGRPALES IVAQLSRPDP ALAALTNDHL VALACLGGRP ALDAVKKGLG GSGSYALGPY   780
QISAPQLPAY NGQTVGTFYY VNDAGGLESK VFSSGGPTPY PNYANAGHVE GQSALFMRDN   840
GISEGLVFHN NPEGTCGFCV NMTETLLPEN AKMTVVPPEG SGGSTNLSDI IEKETGKQLV   900
```

```
IQESILMLPE EVEEVIGNKP ESDILVHTAY DESTDENVML LTSDAPEYKP WALVIQDSNG   960
ENKIKML                                                            967

SEQ ID NO: 184          moltype = AA  length = 880
FEATURE                 Location/Qualifiers
source                  1..880
                        mol_type = protein
                        organism = synthetic construct
SEQUENCE: 184
MASVLTPLLL RGLTGSARRL PVPRAKIHSL DYKDHDGDYK DHDIDYKDDD DKMDIADLRT    60
LGYSQQQQEK IKPKVRSTVA QHHEALVGHG FTHAHIVALS QHPAALGTVA VKYQDMIAAL   120
PEATHEAIVG VGKRGAGARA LEALLTVAGE LRGPPLQLDT GQLLKIAKRG GVTAVEAVHA   180
WRNALTGAPL NLTPEQVVAI ASNIGGKQAL ETVQALLPVL CQAHGLTPQQ VVAIASNGGG   240
KQALETVQRL LPVLCQAHGL TPQQVVAIAS NNGGKQALET VQRLLPVLCQ AHGLTPEQVV   300
AIASNNGGKQ ALETVQALLP VLCQAHGLTP EQVVAIASNI GGKQALETVQ ALLPVLCQAH   360
GLTPEQVVAI ASNNGGKQAL ETVQALLPVL CQAHGLTPEQ VVAIASNIGG KQALETVQRL   420
LPVLCQAHGL TPEQVVAIAS NIGGKQALET VQALLPVLCQ AHGLTPEQVV AIASNIGGKQ   480
ALETVQRLLP VLCQAHGLTP EQVVAIASNN GGKQALETVQ ALLPVLCQAH GLTPEQVVAI   540
ASNNGGKQAL ETVQALLPVL CQAHGLTPEQ VVAIASNNGG KQALETVQAL LPVLCQAHGL   600
TPEQVVAIAS NIGGKQLETV QRLLPVLCQA HGLTPQQVVA IASHDGGKQA LETVQRLLPV   660
LCQAHGLTPE QVVAIASNNG GKQALETVQA LLPVLCQAHG LTPQQVVAIA SHDGGRPALE   720
SIVAQLSRPD PALAALTNDH LVALACLGGR PALDAVKKGL GGSAIPVKRG ATGETKVFTG   780
NSNSPKSPTK GGCSGGGSTNL SDIIEKETGK QLVIQESILM LPEEVEEVIG NKPESDILVH   840
TAYDESTDEN VMLLTSDAPE YKPWALVIQD SNGENKIKML                         880

SEQ ID NO: 185          moltype = AA  length = 340
FEATURE                 Location/Qualifiers
source                  1..340
                        mol_type = protein
                        organism = synthetic construct
SEQUENCE: 185
LTPDQVVAIA SNNGGKQALE TVQRLLPVLC QDHGLTPDQV VAIASNIGGK QALETVQRLL    60
PVLCQDHGLT PDQVVAIASH DGGKQALETV QRLLPVLCQD HGLTPDQVVA IASHDGGKQA   120
LETVQRLLPV LCQDHGLTPD QVVAIASHDG GKQALETVQR LLPVLCQDHG LTPDQVVAIA   180
SHDGGKQALE TVQRLLPVLC QDHGLTPDQV VAIASHDGGK QALETVQRLL PVLCQDHGLT   240
PDQVVAIASN IGGKQALETV QRLLPVLCQD HGLTPDQVVA IASNGGGKQA LETVQRLLPV   300
LCQDHGLTPD QVVAIASNNG GKQALETVQR LLPVLCQDHG                         340

SEQ ID NO: 186          moltype = AA  length = 578
FEATURE                 Location/Qualifiers
source                  1..578
                        mol_type = protein
                        organism = synthetic construct
SEQUENCE: 186
LTPDQVVAIA SNNGGKQALE TVQRLLPVLC QDHGLTPDQV VAIASHDGGK QALETVQRLL    60
PVLCQDHGLT PDQVVAIASH DGGKQALETV QRLLPVLCQD HGLTPDQVVA IASNGGGKQA   120
LETVQRLLPV LCQDHGLTPD QVVAIASHDG GKQALETVQR LLPVLCQDHG LTPDQVVAIA   180
SNIGGKQALE TVQRLLPVLC QDHGLTPDQV VAIASNNGGK QALETVQRLL PVLCQDHGLT   240
PDQVVAIASN NGGKQALETV QRLLPVLCQD HGLTPDQVVA IASNIGGKQA LETVQRLLPV   300
LCQDHGLTPD QVVAIASNGG GKQALETVQR LLPVLCQDHG LTPDQVVAIA SNIGGKQALE   360
TVQRLLPVLC QDHGLTPDQV VAIASHDGGK QALETVQRLL PVLCQDHGLT PDQVVAIASN   420
GGGKQALETV QRLLPVLCQD HGLTPDQVVA IASHDGGKQA LETVQRLLPV LCQDHGLTPD   480
QVVAIASHDG GKQALETVQR LLPVLCQDHG LTPDQVVAIA SNGGGKQALE TVQRLLPVLC   540
QDHGLTPDQV VAIASHDGGK QALETVQRLL PVLCQDHG                          578

SEQ ID NO: 187          moltype = AA  length = 408
FEATURE                 Location/Qualifiers
source                  1..408
                        mol_type = protein
                        organism = synthetic construct
SEQUENCE: 187
LTPDQVVAIA SHDGGKQALE TVQRLLPVLC QDHGLTPDQV VAIASNNGGK QALETVQRLL    60
PVLCQDHGLT PDQVVAIASN IGGKQALETV QRLLPVLCQD HGLTPDQVVA IASNGGGKQA   120
LETVQRLLPV LCQDHGLTPD QVVAIASNNG GKQALETVQR LLPVLCQDHG LTPDQVVAIA   180
SNNGGKQALE TVQRLLPVLC QDHGLTPDQV VAIASHDGGK QALETVQRLL PVLCQDHGLT   240
PDQVVAIASN GGGKQALETV QRLLPVLCQD HGLTPDQVVA IASNIGGKQA LETVQRLLPV   300
LCQDHGLTPD QVVAIASNGG GKQALETVQR LLPVLCQDHG LTPDQVVAIA SNGGGKQALE   360
TVQRLLPVLC QDHGLTPDQV VAIASNNGGK QALETVQRLL PVLCQDHG                408

SEQ ID NO: 188          moltype = DNA  length = 52
FEATURE                 Location/Qualifiers
source                  1..52
                        mol_type = other DNA
                        organism = Oryzasativa
SEQUENCE: 188
gctggatgct ttgagtactt tgcagatctt gcagaatcct tggacaaaag gc            52

SEQ ID NO: 189          moltype = DNA  length = 52
FEATURE                 Location/Qualifiers
```

-continued

```
source                     1..52
                           mol_type = other DNA
                           organism = Oryzasativa
SEQUENCE: 189
cgacctacga aactcatgaa acgtctagaa cgtcttagga acctgttttc cg          52

SEQ ID NO: 190        moltype = DNA   length = 52
FEATURE               Location/Qualifiers
source                     1..52
                           mol_type = other DNA
                           organism = Oryzasativa
SEQUENCE: 190
gcaaaagacc aaggtgcctc aattgttctt gcagctcatg ctgcgacgag cc          52

SEQ ID NO: 191        moltype = DNA   length = 52
FEATURE               Location/Qualifiers
source                     1..52
                           mol_type = other DNA
                           organism = Oryzasativa
SEQUENCE: 191
cgttttctgg ttccacggag ttaacaagaa cgtcgagtac gacgctgctc gg          52

SEQ ID NO: 192        moltype = DNA   length = 53
FEATURE               Location/Qualifiers
source                     1..53
                           mol_type = other DNA
                           organism = Oryzasativa
SEQUENCE: 192
cctggaccgc gtccacgacg gcgagctcaa gctccgcgcc gcggggctct ggg         53

SEQ ID NO: 193        moltype = DNA   length = 53
FEATURE               Location/Qualifiers
source                     1..53
                           mol_type = other DNA
                           organism = Oryzasativa
SEQUENCE: 193
ggacctggcg caggtgctgc cgctcgagtt cgaggcgcgg cgccccgaga ccc         53

SEQ ID NO: 194        moltype = DNA   length = 47
FEATURE               Location/Qualifiers
source                     1..47
                           mol_type = other DNA
                           organism = Homo sapiens
SEQUENCE: 194
cccctgaccc ccatgcctca ggatactcct caatagccat cgctgta              47

SEQ ID NO: 195        moltype = DNA   length = 47
FEATURE               Location/Qualifiers
source                     1..47
                           mol_type = other DNA
                           organism = Homo sapiens
SEQUENCE: 195
ggggactggg ggtacggagt cctatgagga gttatcggta gcgacat              47

SEQ ID NO: 196        moltype = DNA   length = 55
FEATURE               Location/Qualifiers
source                     1..55
                           mol_type = other DNA
                           organism = Oryzasativa
SEQUENCE: 196
ccaggacgac gtcggcggcc tcgaggtcct cgtcgacggc gaatggcgcc ccgtc       55

SEQ ID NO: 197        moltype = DNA   length = 55
FEATURE               Location/Qualifiers
source                     1..55
                           mol_type = other DNA
                           organism = Oryzasativa
SEQUENCE: 197
ggtcctgctg cagccgccgg agctccagga gcagctgccg cttaccgcgg ggcag       55

SEQ ID NO: 198        moltype = DNA   length = 52
FEATURE               Location/Qualifiers
source                     1..52
                           mol_type = other DNA
                           organism = Homo sapiens
SEQUENCE: 198
tacgcggcgg ggctgtcgcc gtacgcggac aagggcaagt gcggcctccc gg          52

SEQ ID NO: 199        moltype = DNA   length = 52
```

-continued

```
FEATURE                  Location/Qualifiers
source                   1..52
                         mol_type = other DNA
                         organism = Homo sapiens
SEQUENCE: 199
atgcgccgcc ccgacagcgg catgcgcctg ttcccgttca cgccggaggg cc          52

SEQ ID NO: 200           moltype = DNA   length = 47
FEATURE                  Location/Qualifiers
source                   1..47
                         mol_type = other DNA
                         organism = Oryzasativa
SEQUENCE: 200
ttaccaaaga tgatgaaaac gtaaactcac aaccatttat gcgttgg                47

SEQ ID NO: 201           moltype = DNA   length = 47
FEATURE                  Location/Qualifiers
source                   1..47
                         mol_type = other DNA
                         organism = Oryzasativa
SEQUENCE: 201
aatggtttct actacttttg catttgagtg ttggtaaata cgcaacc                47

SEQ ID NO: 202           moltype = DNA   length = 52
FEATURE                  Location/Qualifiers
source                   1..52
                         mol_type = other DNA
                         organism = Homo sapiens
SEQUENCE: 202
gacccccatg cctcaggata ctcctcaata gccatcgctg tagtatatcc aa          52

SEQ ID NO: 203           moltype = DNA   length = 52
FEATURE                  Location/Qualifiers
source                   1..52
                         mol_type = other DNA
                         organism = Homo sapiens
SEQUENCE: 203
ctgggggtac ggagtcctat gaggagttat cggtagcgac atcatatagg tt          52

SEQ ID NO: 204           moltype = DNA   length = 40
FEATURE                  Location/Qualifiers
source                   1..40
                         mol_type = other DNA
                         organism = Homo sapiens
SEQUENCE: 204
cctatttatt ctagccacct ctagcctagc cgtttactca                       40

SEQ ID NO: 205           moltype = DNA   length = 40
FEATURE                  Location/Qualifiers
source                   1..40
                         mol_type = other DNA
                         organism = Homo sapiens
SEQUENCE: 205
ggataaataa gatcggtgga gatcggatcg gcaaatgagt                       40

SEQ ID NO: 206           moltype = DNA   length = 51
FEATURE                  Location/Qualifiers
source                   1..51
                         mol_type = other DNA
                         organism = Homo sapiens
SEQUENCE: 206
tctccacact agcagagacc aaccgaaccc ccttcgacct tgccgaaggg g           51

SEQ ID NO: 207           moltype = DNA   length = 51
FEATURE                  Location/Qualifiers
source                   1..51
                         mol_type = other DNA
                         organism = Homo sapiens
SEQUENCE: 207
agaggtgtga tcgtctctgg ttggcttggg ggaagctgga acggcttccc c           51

SEQ ID NO: 208           moltype = DNA   length = 49
FEATURE                  Location/Qualifiers
source                   1..49
                         mol_type = other DNA
                         organism = Homo sapiens
SEQUENCE: 208
acgagtgcgg cttcgaccct atatcccccg cccgcgtccc tttctccat             49
```

```
SEQ ID NO: 209          moltype = DNA   length = 49
FEATURE                 Location/Qualifiers
source                  1..49
                        mol_type = other DNA
                        organism = Homo sapiens
SEQUENCE: 209
tgctcacgcc gaagctggga tataggggggc gggcgcaggg aaagaggta                    49

SEQ ID NO: 210          moltype = DNA   length = 49
FEATURE                 Location/Qualifiers
source                  1..49
                        mol_type = other DNA
                        organism = Homo sapiens
SEQUENCE: 210
ctagcctagc cgtttactca atcctctcat cagggtgagc atcaaactc                    49

SEQ ID NO: 211          moltype = DNA   length = 49
FEATURE                 Location/Qualifiers
source                  1..49
                        mol_type = other DNA
                        organism = Homo sapiens
SEQUENCE: 211
gatcggatcg gcaaatgagt taggagacta gtcccactcg tagtttgag                    49

SEQ ID NO: 212          moltype = DNA   length = 48
FEATURE                 Location/Qualifiers
source                  1..48
                        mol_type = other DNA
                        organism = Homo sapiens
SEQUENCE: 212
gctagtaacc acgttctcct gatcaaatat cactctccta cttacagg                     48

SEQ ID NO: 213          moltype = DNA   length = 48
FEATURE                 Location/Qualifiers
source                  1..48
                        mol_type = other DNA
                        organism = Homo sapiens
SEQUENCE: 213
cgatcattgg tgcaagagga ctagtttata gtgagaggat gaatgtcc                     48

SEQ ID NO: 214          moltype = DNA   length = 44
FEATURE                 Location/Qualifiers
source                  1..44
                        mol_type = other DNA
                        organism = Homo sapiens
SEQUENCE: 214
agcattagca ggaataccttt tcctcacagg tttctactcc aaag                        44

SEQ ID NO: 215          moltype = DNA   length = 44
FEATURE                 Location/Qualifiers
source                  1..44
                        mol_type = other DNA
                        organism = Homo sapiens
SEQUENCE: 215
tcgtaatcgt ccttatggaa aggagtgtcc aaagatgagg tttc                         44

SEQ ID NO: 216          moltype = DNA   length = 36
FEATURE                 Location/Qualifiers
source                  1..36
                        mol_type = other DNA
                        organism = synthetic construct
SEQUENCE: 216
gaccccatg cctcaggata ctcctcaata gccatc                                   36

SEQ ID NO: 217          moltype = DNA   length = 36
FEATURE                 Location/Qualifiers
source                  1..36
                        mol_type = other DNA
                        organism = synthetic construct
SEQUENCE: 217
ctgggggtac ggagtcctat gaggagttat cggtag                                  36

SEQ ID NO: 218          moltype = DNA   length = 49
FEATURE                 Location/Qualifiers
source                  1..49
                        mol_type = other DNA
                        organism = synthetic construct
SEQUENCE: 218
ccccatgcct caggatactc ctcaatagcc atcgctgtag tatatccaa                    49
```

-continued

```
SEQ ID NO: 219        moltype = DNA  length = 49
FEATURE               Location/Qualifiers
source                1..49
                      mol_type = other DNA
                      organism = synthetic construct
SEQUENCE: 219
ggggtacgga gtcctatgag gagttatcgg tagcgacatc atataggtt              49
```